(12) United States Patent
Scanlan et al.

(10) Patent No.: US 6,236,946 B1
(45) Date of Patent: May 22, 2001

(54) NUCLEAR RECEPTOR LIGANDS AND LIGAND BINDING DOMAINS

(76) Inventors: Thomas S. Scanlan, 2525 Moraga St., San Francisco, CA (US) 94122; John D. Baxter, 131 San Pablo Ave., San Francisco, CA (US) 94127; Robert J. Fletterick, 15 Christopher Ave., San Francisco, CA (US) 94131; Richard L. Wagner, 1704 Waller St., San Francisco, CA (US) 94117; Peter J. Kushner, 1362 6th Ave., San Francisco, CA (US) 94122; James Apriletti, 11 Virginia Gardens, Berkeley, CA (US) 94702; Brian West, 142 Anderson St., San Francisco, CA (US) 94110; Andrew K. Shiau, 34 Hugo St. #3, San Francisco, CA (US) 94122

( * ) Notice: Subject to any disclaimer, the term of this patent is extended or adjusted under 35 U.S.C. 154(b) by 0 days.

(21) Appl. No.: 08/764,870

(22) Filed: Dec. 13, 1996

Related U.S. Application Data

(60) Provisional application No. 60/008,540, filed on Dec. 13, 1995, provisional application No. 60/008,543, filed on Dec. 13, 1995, and provisional application No. 60/008,606, filed on Dec. 14, 1995.

(51) Int. Cl.[7] .............................. G06F 19/00; G06F 17/00; C07K 14/00
(52) U.S. Cl. ............................... 702/22; 702/19; 702/20; 530/350
(58) Field of Search ................................. 702/14, 21, 22; 530/350

(56) References Cited

U.S. PATENT DOCUMENTS

| | | | |
|---|---|---|---|
| 4,741,897 | 5/1988 | Andrews et al. | 424/1.1 |
| 4,766,121 | 8/1988 | Ellis et al. | 514/247 |
| 4,826,876 | 5/1989 | Ellis et al. | 514/535 |
| 4,910,305 | 3/1990 | Ellis et al. | 544/239 |
| 5,061,798 | 10/1991 | Emmett et al. | 544/239 |
| 5,116,828 | 5/1992 | Miura et al. | 514/171 |
| 5,171,671 | 12/1992 | Evans et al. | 435/69.1 |
| 5,284,999 | 2/1994 | Chin et al. | 435/252.7 |
| 5,312,732 | 5/1994 | Evans | 435/69.1 |
| 5,322,933 | 6/1994 | Davies et al. | 530/399 |
| 5,403,925 | 4/1995 | Ozato | 536/23.5 |
| 5,438,126 | 8/1995 | DeGroot et al. | 536/235 |
| 5,466,861 | 11/1995 | Dawson et al. | 560/100 |

FOREIGN PATENT DOCUMENTS

| | | |
|---|---|---|
| WO 97/21993 | 6/1997 | (WO) . |
| WO 98/07435 | 2/1998 | (WO) . |
| WO 98/57919 | 12/1998 | (WO) . |

OTHER PUBLICATIONS

Andrea, T.A., et al., "A Model for Thyroid Hormone–Receptor Interactions", *J. Med. Chem.*, vol.22:221–232 (1979).

Apriletti, J.W., et al., "Expression of the Rat α1 Thyroid Hormone Receptor Ligand Binding Domain in *Escherichia coli* and the Use of a Ligand–Induced Conformation Change as a Method for its Purification to Homogeneity", *Protein Expression and Purification*, vol.6:363–370 (1995).

Apriletti, J.W., et al., "Large Scale Purification of the Nuclear Thyroid Hormone Receptor From Rat Liver and Sequence–specific Binding of the Receptor to DNA", *J. Biol. Chem.*, vol.263:9409–9417 (1988).

Au–Fliegner, et al., "The Conserved Ninth C–Terminal Heptad in Thyroid Hormone and Retinoic Acid Receptors Mediates Diverse Responses by Affecting Heterodimer but Not Homodimer Formation", *Mol.Cell Biol.*, vol.13:5725–5737 (1993).

Baniahmad, A., et al."The τ4 Activation Domain of the Thyroid Hormone Receptor is Required for Release of a Putative Corepressor(s) Necessary for Transcriptional Silencing", *Mol.Cell Biol.*, vol. 15,:76–86 (1995).

Barettino, D., et al., "Characterization of the Ligand–dependent Transactivation Domain of Thyroid Hormone Receptor", *Embo.J.*, vol.13:3039–3049 (1994).

Barker, et al.,"Thyroxine Antagonism by Partially Iodinated Thyronines and Analogues", *Ann.N.Y.Acad.Sci.*, vol. 86:545–562 (1960).

Beck–Peccoz, P., et al., "Nomenclature of Thyroid Hormone Receptor β–Gene Mutations in Resistance to Thyroid Hormone: Consensus Statement from the First Workshop on Thyroid Hormone Resistance, Jul. 10–11, 1993 Cambridge, United Kingdom", *J.Clin.Endocrinol Metab.*, vol. 78:990–993 (1994).

Bhat, M.K., et al., "Interaction of Thyroid Hormone Nuclear Receptor With Antibody: Characterization of the Thyroid Hormone Binding Site", *Biochem.Biophys.Res.Commun.*, vol.210:464–471 (1995).

Blake, C.C. & Oatley, S.J., "Protein–DNA and Protein–Hormone Interactions in prealbumin: a Model of the Thyroid Hormone Nuclear Receptor?", *Nature*, vol.268:115–120 (1977).

Blake, C.C., et al., "Structure of Prealbumin: Secondary, Tertiary and Quarternary Interactions Determined by Fourier Refinement at 1 8 A", *J.Mol.Biol.*, vol.121:339–356 (1978).

(List continued on next page.)

*Primary Examiner*—Yvonne Eyler
*Assistant Examiner*—Nirmal S. Basi

(57) ABSTRACT

The present invention provides new methods, particularly computational methods, and compositions for the generation of nuclear receptor synthetic ligands based on the three dimensional structure of nuclear receptors, particularly the thyroid receptor (herein referred to as "TR"). Also provided are crystals, nuclear receptor synthetic ligands, and related methods.

22 Claims, 229 Drawing Sheets

OTHER PUBLICATIONS

Bourguet, W., et al., "Crystal Structure of the Ligand–Binding Domain of the Human Nuclear Receptor RXR–α", *Nature*, vol.375:377–382 (1995).

Brent, G.A., "The Moledular Basis of Thyroid Hormone Action", *N.Engl.J.Med.*, vol.331:847–853 (1994).

Brunger, A.T., et al., "Crystallographic R Factor Refinement by Molecular Dynamics", *Science*, vol.235:458–460 (1987).

Casanova, J., et al., "Functional Evidence for Ligand–Dependent Dissociation of Thyroid Hormone and Retinoic Acid Receptors from an Inhibitory Cellular Factor", *Mol. Cell.Biol.*, vol.14:5756–5765 (1994).

Cavailles, V. et al., "Nuclear Factor RIP140 Modulates Transcriptional Activation by the Estrogen Receptor", *Embo, J.*, vol.14:3741–3751 (1995).

Collaborative Computational Project, N. 4., "The CCP4 Suite: Programs for Protein Crystallography", *Acta Crystallogr.*, vol.D50:760–763 (1994).

Collingwood, T.N., et al., "Spectrum of Transcriptional, Dimerization, and Dominant Negative Properties of Twenty Different Mutant Thyroid Hormone β–Receptors in Thyroid Hormone Resistance Syndrome", *Mol.Endocrinol.*, vol.8:1262–1277 (1994).

Cowan, S.W., et al., "Improved Methods for Building Protein Models in Electron Density Maps and the Location of Errors in These Models", *Acta Crystallogr A*, vol.47:110–119 (1991).

Crowe et al, "6xHis–Ni–NTA Chromatography as a Superior Technique in Recombinant Protein Expression/Purification" *Methods in Molecular Biology*, vol.31:371–387 (1994).

Damm, K. & Evans, R.M., "Identification of a Domain Required for Oncogenic Activity and Transcription suppression by v–erbA and Thyroid–Hormone receptor α", *Proc. Natl.Acad.Sci.USA*, vol.90:10668–10672 (1993).

Danielian, P.S., et al., "Identification of a Conserved Region Required for Hormone Dependent Transcriptional Activation by Steroid Hormone Receptors", *Embo.J.*, vol. 11:1025–1033 (1992).

Dietrich, S.W., et al., "Thyroxine Analogues. 23. Quantitative Structure–Activity Correlation Studies of in Vivo and in Vitro Thyromimetic Activities", *J. Med.Chem.*, vol.20:863–880 (1977).

Durand, B., et al., "Activation Function 2 (AF–2) of Retinoic Acid Receptor and 9–cis Retinoic Acid Receptor: Presence of a Conserved Autonomous Constitutive Activating Domain and Influence of the Nature of the Response Element on AF–2 Activity", *Embo.J.*, vol.13:5370–5382 (1994).

Evans, R.M., "The Steroid and Thyroid Hormone Receptor Superfamily", *Science*, vol.240:889–895 (1988).

Fawell, S.E. et al., "Characterization and Colocalization of Steroid Binding and Dimerization Activities in the Mouse Estrogen Receptor", *Cell*, vol.60:953–962 (1990).

Forman, B.M. & Samuels, H.H., "Interactions Among a Subfamily of Nuclear Hormone Receptors: The Regulatory Zipper Model", *Mol.Endocrinol.*, vol.4:1293–1301 (1990).

Gewirth, D.T. & Sigler, P.B., "The Basis for Half–Site Specificity Explored Through a Non–Cognate Steroid Receptor–DNA Complex", *Nature Structural Biology*, vol.2:386–394 (1995).

Glass, C.K., "Differential Recognition of Target Genes by Nuclear Receptor Monomers, Dimers, and Heterodimers", *Enocr.Rev.*, vol.15:391–407 (1994).

Hayashi, Y. et al., "Mutations of CpG Dinucleotides Located in the Triiodothyronine ($T_3$)–Binding Domain of the Thyroid hormone Receptor (TR)β Gene That Appears to be Devoid of Natural Mutations may not be Detected Because They are Unlikely to Produce the Clinical Phenotype of Resistance to Thyroid Hormone", *J.Clin.Invest.*, vol.94:607–615 (1994).

Hollenberg, et al., "Ligand–Independent and –Dependent Functions of Thyroid Hormone Receptor Isoforms Depend Upon Their Distinct Amino Termini", *J.Biol.Chem.*, vol.270(24):14274–14280 (1995).

Horwitz, K.B., "The Molecular Biology of RU486. Is There a Role for Antiprogestins in the Treatment of Breast Cancer?", *Endocrine Rev.*, vol.13:146–163 (1992).

Janknecht R., "Rapid and Efficient Purification of Native Histidine–Tagged Protein Expressed by Recombinant Vaccinia Virus", *Proc.Natl.Acad.Sci.USA*, vol.88:8972–8976 (1991).

Jancarik & Kim, "Sparse Matrix Sampling: A Screening Method for Crystallization of Proteins", *J.Appl.Crystallogr.*, vol.24:409–411 (1991).

Jorgensen, E.C., "Thyroid Hormones and Analogs. II. Structure–Activity Relationships" *Hormonal Peptides and Proteins*, (eds. Li, C.H.) 107–204 (Academic Press, New York, 1978).

Kabsch, W.J., "Automatic Processing of Rotation Diffraction Data From Crystals of Initially Unknown Symmetry and Cell Constants", *Appl.Crystallogr.*, vol.26:795–800 (1993).

Kabsch, W. & Sander, C., "Dictionary of Protein Secondary Structure: Pattern Recognition of Hydrogen–Bonded and Geometrical Features", *Biopolymers*, vol.22:2577–2637 (1983).

Kediel S., et al., "Different Agonist–and Antagonist–Induced Conformational Changes in Retinoic Acid Receptors Analyzed by Protease Mapping", *Mol.Cell.Biol.*, vol.14:287–298 (1994).

Laskowski, R.A., et al., "Procheck: a Program to Check the Stereochemical Quality of Protein Structures", *J.Appl.Crystallogr.*, vol.26:283–291 (1993).

Latham, K.R., et al., "Development of Support Matrices for Affinity Chromatography of Thyroid Hormone Receptors", *J.Biol.Chem.*, vol.256:12088–12093 (1981).

Laudet, V., "Evolution of the Nuclear Receptor Gene Superfamily" *Embo.J.*, vol.11:1003–1013 (1992).

LeDouarin, B., et al. "The N–Terminal Part of T1F1, a Putative Mediator of the Ligand–Dependent Activiation Function (AF–2) of Nuclear Receptors, is fused to B–raf in the Oncogenic Protein T18", *Embo.J.*, vol.14:2020–2033 (1995).

Lee, J.W., "Interaction of Thyroid–Hormone Receptor With a Conserved Tanscriptional Mediator", *Nature*, vol.374:91–94 (1995).

Lee, J.W., et al., "Two Classes of Proteins Dependent on Either the Presence or Absence of Thyroid Hormone for Interaction With the Thyroid Hormone Receptor", *Molec.Endocrinol.*, vol.9:243–254 (1995).

Leeson, P.D., et al., "Selective Thyromimetics. Cardiac–Sparing Thyroid Hormone Analogues Containing 3'–Arylmethyl Substituents", *J.Med.Chem.*, vol.32:320–336 (1989).

Leeson, P.D., et al., "Thyroid Hormone Analogues. Synthesis of 3'-Substituted 3,5-Diiodo-L-Thyronines and Quantitative Structure-Activity Studies of in Vitro and in Vivo Thyromimetic Activities in Rat Liver and Heart", *J.Med. Chem.*, vol.31:37–54 (1987).

Leitman, D.C., et al., "Identification of a Tumor Necrosis Factor–Responsive Element in the Tumor Necrosis Factor α Gene", *J.Biol.Chem.*, vol.266:9343 (1991).

Leng, X., et al., "Ligand–Dependent Conformational Changes in Thyroid Hormone and Retinoic Acid Receptors are Potentially Enhanced by Heterodimerization With Retinoic X. Receptor", *J.Steroid Biochem. Molec.Biol.*, vol.46:643–661 (1993).

Leng, X., et al., "Mouse Retinoid X Receptor Contains a Separable Ligand–Binding and Transactivation Domain in its E Region", *Mol.and Cellular Biol.*, vol.15:255–263 (1995).

Lewis, N. and Wallbank, P., "Formation of Quinol Ethers Using (Diacetoxyiodo) Benzene", *Synthesis*, 1103 (1987).

Lin, K.H., et al., "An Essential Role of Domain D in the Hormone–Binding Activity of Human α1 Thyroid Hormone Nuclear Receptor", *Mol.Endocrinol.*, vol.5:485–492 (1991).

Luisi, B.F., et al., "Crystallographic Analysis of the Interaction of the Glucocorticoid Receptor with DNA", *Nature*, vol.352:497–505 (1991).

McGrath, M.E., et al., "Preliminary Crystallographic Studies of the Ligand–Binding Domain of the Thyroid Hormone Receptor Complexed With Triiodothyronine", *J.Mol.Biol.*, vol.237:236–239 (1994).

Meier, C.A., et al., "Variable Transcriptional Activity and Ligand Binding of Mutant β1 3,5,3'–Triiodothyronine Receptors From Four Families With Generalized Resistance to Thyroid Hormone", *Mol.Endocrinol.*, vol.6:248–258 (1992).

Monaco, Hugo et al., "Structure of a Complex of Two Plasma Proteins: Transthyretin and Retinol–Binding Protein", *Science*, vol.268:1039–1041 (1995).

Navaza, J., "AMoRe: an Automated Package for Molecular Replacement", *Acta Crytallographica Section A–Funamentals of Crystallography*, vol.50:157–63 (1994).

Nicholls, A., et al., "Protein Folding and Association: Insights From the Interfacial and Thermodynamic Properties of Hydrocarbons", *Proteins*, vol.11:281–296 (1991).

O'Donnell, A.L. et al. "Thyroid Hormone Receptor Mutations That Interfere With Transcriptional Activation Also Interfere With Receptor", *Mol.Endocrinol.*, vol.5:94–99 (1991).

Onate, S.A., et al., "Sequence and Characterization of a Coactivator for the Steroid Hormone Receptor Superfamily", *Science*, vol.270:1354–1357(1995).

Otwinoski, Z., "Oscillation Data Reduction Program", *Proceedings of the CCP4 Study Weekend: Data Collection and Processing*, 56–62 (1993).

Otwinoski, Z., "Maximum Likelihood Refinement of Heavy Atom Parameters", *Proceedings of the CCP4 Study Weekend*:80–86 (1991).

Rastinejad, R., et al., "Structural Determinants of Nuclear Receptor Assembly on DNA Direct Repeats", *Nature*, vol.375:203–211 (1995).

Raynaud, J.P. et al., "The Design and use of Sex–Steroid Antagonist", *J.Steroid Biochem,*, vol.25:811–833 (1986).

Refetoff, S., et al., "The Syndromes of Resistance to Thyroid Hormone", *Endocr.Rev.*, vol.14:348–399 (1993).

Ribeiro, R.C.J., et al., "The Molecular Biology of Thyroid Hormone Action", *Ann.N.Y.Acad.Sci.*, vol.758:366–389 (1995).

Ribeiro, R.C.J., et al., "Thyroid Hormone Alters in Vitro DNA Binding of Monomers and Dimers of Thyroid Hormone Receptors", *Mol.Endocrinol.*, vol.6:1142–1152 (1992).

Ribeiro, R.C.J., et al., "The Nuclear Hormone Receptor Gene Superfamily", *Annu.Rev.Med.*, vol.46:443–53 (1995).

Robsseau, G.G., et al., "Glucocorticoid Receptors: Relations Between Steroid Binding and Biological Effects", *J.Mol.Biol.*, vol.67:99–115 (1972).

Saatcioglu, F., et al., "A Conserved C–Terminal Sequence That is Deleted in v–ErbA is Essential for the Biological Activities of c–ErbA (the Thyroid Hormone Receptor)", *Mol.Cell Biol.*, vol.13:3675–3685 (1993).

Schwabe, J.W., et al., "The Crystal Structure of the Estrogen Receptor DNA–Binding Domain Bound to DNA: How Receptors Discriminate Between Their Response Elements", *Cell*, vol.75:567–578 (1993).

Seielstad, et al., "Molecular Characterization by Mass Spectrometry of the Human Estrogen Receptor Ligand–Binding Domain Expresses in *Escherichia coli*", *Molecular Endocrinology*, vol.9:647–658 (1995).

Selmi, S. & Samuels, H.H., "Thyroid Hormone Receptor/ and v–erbA", *J.Biol.Chem.*, vol.266:11589–11593 (1991).

Swaffield, J.C., et al., "A Highly Conserved ATPase Protein as a Mediator Between Acidic Activation Domains and the TATA–Binding Protein", *Nature*, vol.374:88–91 (1995).

Toney, J.H., et al., "Conformational Changes in Chicken Thyroid Hormone Receptor α1 Induced by Binding to Ligand or to DNA", *Biochemistry*, vol.32:2–6 (1993).

Tsai, M.J. & O'Malley, B.W., "Molecular Mechanisms of Action of Steroid/Thyroid Receptor Superfamily Members", *Annu.Rev.Biochem.*, vol.63:451–486 (1994).

Wagner, et al., "A Structural Role for Hormone in the Thyroid Hormone Receptor", *Nature*, vol.378(6558):670–697 (1995).

Westerfield, W.W., et al., "New Assay Procedure for Thyroxine Analogs", *Endocrinology*, vol.77:802 (1965).

Yokoyama et al., "Synthesis and Structure–Activity Relationships of Oxamic Acid and Acetic Acid Derivatives Related to L–Thyronine", *J.Med.Chem.*, vol.38:695–707 (1995).

Zenkie, M., et al., "v–erbA Oncogene Activation Entails the Loss of Hormone–Dependent Regulator Activity of c–erbA ", *Cell*, vol.61:1035–1049 (1990).

Bolger et al., "Molecular Interactions between Thyroid Hormone Analogs and the Rat Liver Nuclear Receptor," *Journal of Biological Chemistry*, 255(21):10271–10278, (1980).

Chiellini et al., "A High–Affinity Subtype–Selective Agonist for the Thyroid Hormone Receptor," *Chemistry and Biology*, 5(6):299–306, (1998).

Jorgenson et al., "The Nature of the Thyroid Hormone Receptor," *Thyroid Research*, 378:303–306, (1976).

Ribeiro et al., "Mechanisms of Thyroid Hormone Action: Insights from X–ray Crystallographic and Functional Studies," *Recent Progress in Hormone Research*, 53:351–394, (1998).

Bourguet et al., "Purification, functional characterization and crystallization of the ligand binding domain of the retinoid X receptor," Protein Expression and Purification, vol. 6:604–608 (1995).

McGrath et al., Preliminary crystallographic studies of the ligand–binding domain of the thyroid hormone receptor complexed with triiodothyronine. J. Mol. Biol., vol. 237:236–239 (1994).

Rastinejad et al., "Structural determinants of nuclear receptor assembly on DNA direct repeats," Nature, vol. 375:203–211 (May 18, 1995).

Wagner et al., "A structural role of hormone in the thyroid hormone receptor," Nature, vol. 378:690–697, (Dec. 1995).

Jorgensen et al., "Thyroxine Analogs. 22. Thyromimetic Activity of Halogen–Free Derivatives of 3,5–Dimethyl–L–thyronine," Journal of Medicinal Chemistry, vol. 17, No. 4, pp. 434–439, 1974.

|  |  | 1 |  |  |  |  | 60 |
|---|---|---|---|---|---|---|---|
| SEQ ID NO:1 | rTRalpha | ............ | ............ | ............ | ............ | ............ | ............ |
| SEQ ID NO:2 | hTRalpha | ............ | ............ | ............ | ............ | ............ | ............ |
| SEQ ID NO:3 | hTRbeta | ............ | ............ | ............ | ............ | ............ | ............ |
| SEQ ID NO:4 | hRARalpha | ............ | ............ | ............ | ............ | ............ | ............ |
| SEQ ID NO:5 | hRARgamma | ............ | ............ | ............ | ............ | ............ | ............ |
| SEQ ID NO:6 | hRXRalpha | ............ | ............ | ............ | ............ | ............ | ............ |
| SEQ ID NO:7 | hRXRbeta | ............ | ............ | ............ | ............ | ............ | ............ |
| SEQ ID NO:8 | hPPARalpha | ............ | ............ | ............ | ............ | ............ | ............ |
| SEQ ID NO:9 | hPPARbeta | ............ | ............ | ............ | ............ | ............ | ............ |
| SEQ ID NO:10 | hPPARgamma | ............ | ............ | ............ | ............ | ............ | ............ |
| SEQ ID NO:11 | hVDR | ............ | ............ | ............ | ............ | ............ | ............ |
| SEQ ID NO:12 | hER | ............ | ............ | ............ | ............ | ............ | ............ |
| SEQ ID NO:13 | hGR | ............ | ............ | ............ | ............ | ............ | ............ |
| SEQ ID NO:14 | hPR | MTELKAKGPR | APHVAGGPPS | PEVGSPLLCR | PAAGPFPGSQ | TSDTLPEVSA | IPISLDGLLF |
| SEQ ID NO:15 | hMR | ...METKGYH | SLPEGLDMER | RWGQVSQAVE | RSSLGPTERT | DENNYMEIVN | VSCVSGAIPN |
| SEQ ID NO:16 | hAR | ............ | ............ | ............ | ............ | ............ | ............ |

FIG.3A

| | 61 | | | | | 120 |
|---|---|---|---|---|---|---|
| rTRalpha | | | | | | |
| hTRalpha | | | | | | |
| hTRbeta | | | | | | |
| hRARalpha | | | | | | |
| hRARgamma | | | | | | |
| hRARgamma | | | | | | |
| hRXRalpha | | | | | | |
| hRXRbeta | | | | | | |
| hPPARalpha | | | | | | |
| hPPARbeta | | | | | | |
| hPPARgamma | | | | | | |
| hVDR | | | | ....MDSKE | SLTPGREENP | SSVLAQERGD VMDFYKTLRG |
| hER | | | | SDVEGAYSRA | EATRGAGGSS | SSPPEKDSGL LDSVLDTLLA |
| hGR | ........ | PRPCQGQDPS | DEKTQDQQSL | NNRPGILTSD | IKTELESKEL | SATVAESMGL YMDSVRDADY |
| hPR | PRPCQGQDPS | DEKTQDQQSL | | | | |
| hMR | NSTQGSSKEK | QELLPCLQQD | | | | |
| hAR | | | | | | |

FIG. 3B

```
           121                                                              180
rTRalpha    ............ ............ ............ ............ ............
hTRalpha    ............ ............ ............ ............ ............
hTRbeta     ............ ............ ............ ............ ............
hRARalpha   ............ ............ ............ ............ ............
hRARgamma   ............ ............ ............ ............ ............
hRXRalpha   ............ ............ ............ ............ ............
hRXRbeta    ............ ............ ............ ............ ............
hPPARalpha  ............ ............ ............ ............ ............
hPPARbeta   ............ ............ ............ ............ ............
hPPARgamma  ............ ............ ............ ............ ............
hVDR        ............ ............ ............ ............ ............
hER         ............ ............ ............ .DSKQRRLLV  DFPKGSVSNA
hGR         GATVKVSASS   PSLAVASQS.   ..........   ..........   ..........
hPR         PSGPGQSQPS   PPACEVTSSW   CLFGPELPED   PPAAPATQRV   LSPLMSRSGC   KVGDSSGTAA
hMR         SYEQQNQQGS   MSPAKIYQNV   EQLVKFYKGN   GHRPSTLSCV   NTPL..RSFM   SDSGSSVNGG
hAR         ............ ............ ............ ............ ............
```

FIG. 3C

```
            181                                                              240
rTRalpha    ........ ........ ........ ........ ........ ........ ........
hTRalpha    ........ ........ ........ ........ ........ ........ ........
hTRbeta     ........ ........ ........ ........ ........ ........ ........
hRARalpha   ........ ........ ........ ........ ........ ........ ........
hRARgamma   ........ ........ ........ ........ ........ ........ ........
hRXRalpha   ........ ........ ........ ........ ........ ........ ........
hRXRbeta    ........ ........ ........ ........ ........ ........ ........
hPPARalpha  ........ ........ ........ ........ ........ ........ ........
hPPARbeta   ........ ........ ........ ........ ........ ........ ........
hPPARgamma  ........ ........ ........ ........ ........ ........ ........
hVDR        ........ ........ ........ ........ ........ ........ ........
hER         ........ ........ ........ ........ ........ ........ ........
hGR         QQPDLSKAVS LSMGLYMGET ETKVMGNDLG FPQQGQISLS SGETDLKLLE ESIANLNRS.
hPR         AHKVLPRGLS PARQLLLPAS ESPHWSGAPV KPSPQAAAVE VEEEDSSESE ESAGPLLKGK
hMR         VMRAIVK..S PIMCHEKSPS VCSPLNMTSS VCSPAGINSV SSTTASFGSF PVHSPITQGT
hAR         ........ ........ ........ ........ ........ ........ ........
```

FIG.3D

```
          241                                                                                         300
rTRalpha   : ................................................................
hTRalpha   : ................................................................
hTRbeta    : ................................................................
hRARalpha  : ................................................................
hRARgamma  : ................................................................
hRXRalpha  : ................................................................
hRXRbeta   : ................................................................
hPPARalpha : ................................................................
hPPARbeta  : ................................................................
hPPARgamma : ................................................................
hVDR       : ................................................................
hER        : ................................................................
hGR        : ...TSVPEN PKSSASTAVS AAPTEKEFPK THSDVSSEQQ HLKGQTGTNG GNVKLYTT..
hPR        : PRALGGAAAC GGAAACPPGA AAGGVALVPK EDSRFSAPRV ALVEQDAPMA PGRSPLATTV
hMR        : PLTCSPNAEN RGSRSHSPAH ASNVGSPLSS PLSSMKSSIS SPPSHCSVKS PVSSPNNVTL
hAR        : ................................................................
```

FIG.3E

```
          301                                                           360
rTRalpha    ............ ............ ............ ............ ............
hTRalpha    ............ ............ ............ ............ ............
hTRbeta     ............ ............ ............ ............ ............
hRARalpha   ............ ............ ............ ............ ............
hRARgamma   ............ ............ ............ ............ ............
hRXRalpha   ............ ............ ............ ............ ............
hRXRbeta    ............ ............ ............ ............ ............
hPPARalpha  ............ ............ ............ ............ ............
hPPARbeta   ............ ............ ............ ............ ............
hPPARgamma  ............ ............ ............ ............ ............
hVDR        ............ ............ ............ ............ ............
hER         ............ ............ ............ ............ ............
hGR         ............ ......DQST   FDILQDLEFS   SGSPGK....   ............
hPR         MDFIHVPILP   LNHALLAART   RQLLEDESYD   GGAGAA....   .ET NESPWRSDLL
hMR         RSSVSSPANI   NNSRCSVSSP   SNTNNRSTLS   SPAASTVGSI   ...SA FAPPRTSPCA
hAR         ............ ............ ............ CSPVNNAFSY   TASGTSAGSS
```

FIG. 3F

|  | 361 |  |  |  |  | 420 |
|---|---|---|---|---|---|---|
| rTRalpha | . . . . . . . . . . | . . . . . . . . . . | . . . . . . . . . . | . . . . . . . . . . | . . . . . . . . . . | . . . . . . . . . . |
| hTRalpha | . . . . . . . . . . | . . . . . . . . . . | . . . . . . . . . . | . . . . . . . . . . | . . . . . . . . . . | . . . . . . . . . . |
| hTRbeta | . . . . . . . . . . | . . . . . . . . . . | . . . . . . . . . . | . . . . . . . . . . | . . . . . . . . . . | . . . . . . . . . . |
| hRARalpha | . . . . . . . . . . | . . . . . . . . . . | . . . . . . . . . . | . . . . . . . . . . | . . . . . . . . . . | . . . . . . . . . . |
| hRARgamma | . . . . . . . . . . | . . . . . . . . . . | . . . . . . . . . . | . . . . . . . . . . | . . . . . . . . . . | . . . . . . . . . . |
| hRXRalpha | . . . . . . . . . . | . . . . . . . . . . | . . . . . . . . . . | . . . . . . . . . . | . . . . . . . . . . | . . . . . . . . . . |
| hRXRbeta | . . . . . . . . . . | . . . . . . . . . . | . . . . . . . MSW | AARPPFLPQR | HAEGSVGRWG | . . . . . . . . . . |
| hPPARalpha | . . . . . . . . . . | . . . . . . . . . . | . . . . . . . . . . | . . . . . . . . . . | . . . . . . . . . . | . . . . . . . . . . |
| hPPARbeta | . . . . . . . . . . | . . . . . . . . . . | . . . . . . . . . . | . . . . . . . . . . | . . . . . . . . . . | . . . . . . . . . . |
| hPPARgamma | . . . . . . . . . . | . . . . . . . . . . | . . . . . . . . . . | . . . . . . . . . . | . . . . . . . . . . | . . . . . . . . . . |
| hVDR | . . . . . . . . . . | . . . . . . . . . . | . . . . . . . . . . | . . . . . . . . . . | . . . . . . . . . . | . . . . . . . . . . |
| hER | . . . . . . . . . . | . . . . . . . . . . | . . . . . . . . . . | . . . . . . . . . . | . . . . . . . . . . | . . . . . . . MTM |
| hGR | IDENCLLSPL | AGEDDSFLLE | GNSNEDCKPL | ILPDTKPKIK | DNGDLVLSSP | SNVTLPQVKT |
| hPR | SSTPVAVGDF | P..DCAYPPD | AEPKDDAYPL | YSDFQPPALK | IKEEEGAEA | SARSPRSYLV |
| hMR | TLRDVVPSPD | TQEKGAQEVP | FPKTEEVESA | ISNGVTGQLN | IVQYIKPEPD | GAFSSSCLGG |
| hAR | . . . . . . . . . . | . . . . . . . . . . | . . . . . . . . . . | . . . . . . . . . . | . . . . . . . . . . | . . . . . . . . . . |

FIG. 3G

```
                421                                                                                              480
rTRalpha        ..........  ..........  ..........  ..........  ..........  ..........
hTRalpha        ..........  ..........  ..........  ..........  ..........  ..........
hTRbeta         ..........  ..........  ..........  ..........  ..........  ..........
hRARalpha       ..........  ..........  ..........  ..........  ..........  ..........
hRARgamma       ..........  ..........  ..........  ..........  ..........  ..........
hRXRalpha       ..........  ..........  ..........  ..........  MDTKHFLPLD  FSTQVNSS..
hRXRbeta        AKECIVGSAT  ALAGSRSGGG  GGGGRRRTTN  PGAGARGWTG  RDGRH..GRD  SRSPDSSSPN
hPPARalpha      ..........  ..........  ..........  ..........  ..........  ..........
hPPARbeta       ..........  ..........  ..........  ..........  ..........  ..........
hPPARgamma      ..........  ..........  ..........  ..........  ..........  ..........
hVDR            ........M   DTEDLPANNA  PLTVNEQLLG  SCTLKFPAQD  AQVIVMSGQE  TIRVLEVEVD
hER             TLHTKASGMA  LLHQIQGNEL  EPLNRPQLKI  PLERPLGEVY  LDSSKPAVYN  YPEGAAYEFN
hGR             EKEDFIELCT  PGVIKQEKLG  TVYCQASFPG  ANIIG.....  .......NK   MSAISVHGVS
hPR             AGANPAAFPD  FPLGPPPPLP  PR.ATPSRPG  EAAVT.....  ..........  ..........
hMR             NSKINSDSSF  SVPIKQESTK  HSCSGTSFKG  NPTVNPFPFM  DGSYFSFMDD  KDYYSLSGIL
hAR             ..........  ..........  ..........  .......GG   GGGEA.....  ..GA VAPYGYTRP.
```

FIG.3H

```
         481                                                                            540
rTRalpha    ..........  ..........  ..........  ..........  ...MEQKPSK  VECGSDPEEN.
hTRalpha    ..........  ..........  ..........  ..........  ...MEQKPSK  VECGSDPEEN.
hTRbeta     ..........  ..........  ..MTPNSHTE  NGLTAWDKPK  HCPDREHDWK  LVGMSEACLH.
hRARalpha   ..........  ..........  ..........  ..........  ..........  ..........
hRARgamma   ..........  ..........  ..........  ..H  ATNKERLFAA  GALCPGSGYP.
hRXRalpha   .LTSPTGR..  GSMAAPSLHP  SLGPGIGSPG  .QLHSPISTL  SSPINGMGPP  FSVISSPMGP.
hRXRbeta    PLPQGVPP..  PSPPGPPLPP  STAPTLGGSG  .APPPP....  PMPPPPLGSP  FPVISSSHGS.
hPPARalpha  ..MVDTESPL  CPLSPLEAGD  LESPLSEEFL  QEMGNIQEIS  QSIGEDSSGS  FGFTEYQYLG.
hPPARbeta   ..........  ....MEQPQ   EEAP......  .EVREEEKE   EVAEAEGAPE  LNGGPQHALP.
hPPARgamma  ..........  ......MVD   TEMPFWPTNF  ....GISSVD  LSHMDDHSHS  FDIKPFTTVD.
hVDR        TALSSAGAAE  SGGDEEGSGQ  SLEATEEAQL  DGPVTTSSTT  AVTVEVSAPV  VQTVVSKAAI.
hER         AAAAANAQVY  GQTGLPYGPG  SEAAAFGSNG  LGGFPPLNSV  SPSPLMLLHP  PPQLSPFLQP.
hGR         TSGGQMYHYD  MNTASLSQQQ  DQ........  .KPIFNVIPP  IPVGSEN...  ..........
hPR         SSGSTLECIL  YKAEGAPPQQ  GPFAPPPCKA  PGASGCLLPR  DGLPSTS...  ..........
hMR         GPPVPGFDGN  CEGSGFPVGI  KQEPDDGSYY  PEASIPSSAI  VGVNSGGQSF  HYRIGAQGTI.
hAR         ..........  ..PQGLAGQE  SDFTAPDVWY  PGG...MVSR  VPYPSPT...  ..........
```

FIG. 31

```
             541                                                                    600
rTRalpha     SARSPDGKRK RKN.GQCP..  .....LKSSM  ..........  ..........  ......SGYI
hTRalpha     SARSPDGKRK RKN.GQCS..  .....LKTSM  ..........  ..........  ......SGYI
hTRbeta      RKSHSERRST LKN.EQSSPH  LIQTTWTSSI  FHLDHDDVND  QSVSSAQTFQ  TEEKKCKGYI
hRARalpha    .......... ..........  ........PN  SNHVASGAGE  AAIETQSSSS  EEIVPSPPSP
hRARgamma    GAGFPFAFPG ALR.GSPPFE  MLSPSFRGLG  QPDLPKEMAS  LSVETQSTSS  EEHVPSSPSP
hRXRalpha    HSMSVP.... .TTPTLGFST  GSPQLSS...  .PMNPVSSSE  DIKPPLGLNG  VLKVPAHPSG
hRXRbeta     PGLPPP.... .APPGFSGPV  SSPQINSTVS  LPGGGSGPPE  DVKPPVLGVR  GLHCPPPPGG
hPPARalpha   SCPGSDGSVI TDTLSPA...  ..........  ..........  .SSPS..SVT  YPVVPGSVDE
hPPARbeta    SSSYTD.... ...LSRS...  ..........  ..........  .SSPP..SLL  DQLQMGC.DG
hPPARgamma   FSSISAPHYE DIPFTRADPM  VADYKYDLKL  QEYQSAIKVE  PASPPYYSEK  AQLYNRPHEE
hVDR         SVSPAQQTSV PITVQACPQV  LTQDGLASLM  TGMLAQQSSL  GQPLLIPLSM  AGSVGGQGGL
hER          HGQQVPYYLE NEPSGYTVRE  AGPP....AF  YRPNSDNRRQ  GGRERLASTN  DKGSMAMESA
hGR          ..WNRCQGSG DDNLTSLGTL  NFPGRTVFSN  GYSSPSMRPD  V.........  .SSPPSSSST
hPR          ..ASAAAAGA APALYPALGL  NGLPQLGYQA  AVLKEGLPQV  YPPYLNYLRP  DSEASQSPQY
hMR          SLSRSARDQS FQHLSSFPPV  NTLVESWKSH  GDLSSRRSDG  YPVLEYIPEN  VSSSTLRSVS
hAR          ..CVKSEMGP WMDSYSG...  ......PYGD  MRLETARDHV  LP..IDYYFP  ..........
```

FIG.3J

|            | 601                                                          |      660 |
|------------|--------------------------------------------------------------|----------|
| rTRalpha   | PSYLDKDEQC VVCGDKATGY HYRCITCEGC KGFFRRTIQK NLHPTYSCKY DS.... |          |
| hTRalpha   | PSYLDKDEQC VVCGDKATGY HYRCITCEGC KGFFRRTIQK NLHPTYSCKY DS.... |          |
| hTRbeta    | PSYLDKDELC VVCGDKATGY HYRCITCEGC KGFFRRTIQK NLHPSYSCKY EG.... |          |
| hRARalpha  | PPLPRIYKPC FVCQDKSSGY HYGVSACEGC KGFFRRSIQK NM..VYTCHR DK.... |          |
| hRARgamma  | PPPPRVYKPC FVCNDKSSGY HYGVSSCEGC KGFFRRSIQK NM..VYTCHR DK.... |          |
| hRXRalpha  | NMASFTKHIC AICGDRSSGK HYGVYSCEGC KGFFKRTVRK DL..TYTCRD NK.... |          |
| hRXRbeta   | PGAG..KRLC AICGDRSSGK HYGVYSCEGC KGFFKRTIRK DL..TYSCRD NK.... |          |
| hPPARalpha | SPSGALNIEC RICGDKASGY HYGVHACEGC KGFFRRTIRL KLVYD...KC DR.... |          |
| hPPARbeta  | ASCGSLNMEC RVCGDKASGF HYGVHACEGC KGFFRRTIRM KLEYE...KC ER.... |          |
| hPPARgamma | PSNSLMAIEC RVCGDKASGF HYGVHACEGC KGFFRRTIRL KLIYD...RC DL.... |          |
| hVDR       | AVLTLPTATV ATLPGLAAAS PAGGLLKLPF AGLQAATVLN SVQTQLQAPA QAVLQPQMSA |      |
| hER        | KET....RYC AVCNDYASGY HYGVWSCEGC KAFFKRSIQG HN..DYHCPA TN.... |          |
| hGR        | ATTGPPPKLC LVCSDEASGC HYGVLTCGSC KVFFKRAVEG QHNYLCAGRN D..... |          |
| hPR        | SFESLPQKIC LICGDEASGC HYGVLTCGSC KVFFKRAMEG QHNYLCAGRN D..... |          |
| hMR        | TGSSRPSKIC LVCGDEASGC HYGVVTCGSC KVFFKRAVEG QHNYLCAGRN D..... |          |
| hAR        | .....PQKTC LICGDKASGC HYGALTCGSC KVFFKRAAEG KQKYLCASRN D..... |          |

FIG. 3K

|            | 661 |   |   |   |   | 720 |
|---|---|---|---|---|---|---|
| rTRalpha | .CCVIDKITR | NQCQLCRFKK | CIAVGMAMDL | VLDDSKRVAK | RKLIEQNRER | RRK..EEMIR |
| hTRalpha | .CCVIDKITR | NQCQLCRFKK | CIAVGMAMDL | VLDDSKRVAK | RKLIEQNRER | RRK..EEMIR |
| hTRbeta | .KCVIDKVTR | NQCQECRFKK | CIYVGMATDL | VLDDSKRLAK | RKLIEENREK | RRR..EELQK |
| hRARalpha | .NCIINKVTR | NRCQYCRLQK | CFEVGMSKES | VRND...... | ......RNK | KKK..EVPKP |
| hRARgamma | .NCIINKVTR | NRCQYCRLQK | CFEVGMSKEA | VRND...... | ......RNK | KKK..EVKEE |
| hRXRalpha | .DCLIDKRQR | NRCQYCRYQK | CLAMGMKREA | VQEERQRG.. | ....KDRNEN | EVE..STSSA |
| hRXRbeta | .DCTVDKRQR | NRCQYCRYQK | CLATGMKREA | VQEERQRG.. | ....KDK.DG | DGE..CAGGA |
| hPPARalpha | .SCKIQKKNR | NKCQYCRFHK | CLSVGMSHNA | IRFG...... | .RMPRSEKAK | LKA..EILTC |
| hPPARbeta | .SCKIQKKNR | NKCQYCRFQK | CLALGMSHNA | IRFG...... | .RMPEAEKRK | LVA..GLTAN |
| hPPARgamma | .NCRIHKKSR | NKCQYCRFQK | CLAVGMSHNA | IRFG...... | .RMPQAEKEK | LLA..EI.SS |
| hVDR | LQAMQQTQTT | AATTASIVQK | ASEPSVSVAT | LQTAGLSINP | AIISAASLGA | QPQFISSLTT |
| hER | .QCTIDKNRR | KSCQACRLRK | CYEVGMMKGG | IRKDRRGGRM | LKHKRQRDDG | EGR..GEVGS |
| hGR | ..CIIDKIRR | KNCPACRYRK | CLQAGMNLEA | .......... | RKTKK..KIK | GIQ..QATT. |
| hPR | ..CIVDKIRR | KNCPACRLRK | CCQAGMVLGG | .......... | RKFKFKNKVR | VVR..ALDAV |
| hMR | ..CIIDKIRR | KNCPACRLQK | CLQAGMNLGA | .......... | RKSKKLGKLK | GIH..EEQPQ |
| hAR | ..CTIDKFRR | KNCPSCRLRK | CYEAGMTLGA | .......... | RKLKKLGNLK | LQE..EGEAS |

FIG.3L

```
              721 ┌─ minimal start site 725                                                          780
rTRalpha          SLQQRPEPTP EEWDLIHVAT EAHRSTNAQG SHWKQRRKFL PDDIGQSPIV ..........
hTRalpha          SLQQRPEPTP EEWDLIHIAT EAHRSTNAQG SHWKQRRKFL PDDIGQSPIV ..........
hTRbeta           SIGHKPEPTD EEWELIKTVT EAHVATNAQG SHWKQKPKFL PEDIGQAPIV ..........
hRARalpha         ECSESYTLTP EVGELIEKVR KAHQETFPAL CQL...GKYT TNNSSEQRV. ..........
hRARgamma         GSPDSYELSP QLEELITKVS KAHQETFPSL CQL...GKYT TNSSADHRV. ..........
hRXRalpha         NEDMPVERIL EAELAVEPKT ETYVE..ANH GLNPS..... .......SP. ..........
hRXRbeta          PEEMPVDRIL EAELAVEQKS DQGVEGPGGT GGSGS..... .......SP. ..........
hPPARalpha        EHDIEDSETA DLKSLAKRIY EAYLKNFN.M NKVKARVILS GKASNNPPFV IHDMETLCMA
hPPARbeta         EGSQYNPQVA DLKAFSKHIY NAYLKNFN.M TKKKARSILT GKASHTAPFV IHDIETLWQA
hPPARgamma        DIDQLNPESA DLRALAKHLY DSYIKSFP.L TKAKARAILT GKTTDKSPFV IYDMNSLMMG
hVDR              TPIITSAMSN VAGLTSQLIT NAQGVIGTL PLLVNPASLA GAAAASA... ......LPA
hER               AGDMRAANLW PSPLMIKRSK KNSLALSLTA DQMVSALLDA EPPILYSE.. ..........
hGR               .....GVSQ ETSENPGNKT IVPATLPQLT PTLVS..... .......... LL........
hPR               ALPQPLGVPN ESQALSQRFT FSPGQDIQLI PPLIN..... .......... LL........
hMR               QQQPPPPPP PQSPEEGTTY IAPAKEPSVN TALVPQLSTI SRALTPSPVM VL........
hAR               STTSP..... .TEETTQKLT VSHIEGYECQ PIFLN..... .......... VL........

FIG. 3M
```

```
            781                                                                           840
rTRalpha    ............ ............ ............ ............ ............ ............
hTRalpha    ............ .SMPDGDKVD   LEAFSEFTKI   ITPAITRVVD   FAKKLPMFSE   LPCEDQILL
hTRbeta     ............ .SMPDGDKVD   LEAFSEFTKI   ITPAITRVVD   FAKKLPMFSE   LPCEDQILL
            ............ .NAPEGGKVD   LEAFSHFTKI   ITPAITRVVD   FAKKLPMFCE   LPCEDQILL hRARalpha   ............ .......SLD   IDLWDKFSEL   STKCIIKTVE   FAKQLPGFTT   LTIADQITLL
hRARgamma   ............ .......QLD   LGLWDKFSEL   ATKCIIKIVE   FAKRLPGFTG   LSIADQITLL
hRXRalpha   ............ .NDPVTNICQ   A.........   ADKQLFTLVE   WAKRIPHFSE   LPLDDQVILL
hRXRbeta    ............ .NDPVTNICQ   A.........   ADKQLFTLVE   WAKRIPHFSS   LPLDDQVILL hPPARalpha  EKTLVAKLVA   NGIQN.KEVE   VRIFHCCQCT   SVETVTELTE   FAKAIPAFAN   LDLNDQVTLL
hPPARbeta   EKGLVWKQLV   NGLPPYKEIS   VHVFYRCQCT   TVETVRELTE   FAKSIPSFSS   LFLNDQVTLL
hPPARgamma  EDKIKFKHIT   PLQEQSKEVA   IRIFQGCQFR   SVEAVQEITE   YAKNIPGFIN   LDLNDQVTLL hVDR        QGLQVQTVAP   QLLLNSQGQI   IATIGNGPTA   AIPSTASVLP   KATVPLTLTK   TTTQGPVGKV
hER         ...........  .YDPTRPFSE   ASMMGLLTNL   ADRELVHMIN   WAKRVPGFVD   LTLHDQVHLL
hGR         EVIEPEVLYA   GYDSSVPDST   WRIMTTLNML   GGRQVIAAVK   WAKAIPGFRN   LHLDDQMTLL
hPR         MSIEPDVIYA   GHDNTKPDTS   SSLLTSLNQL   GERQLLSVVK   WSKSLPGFRN   LHIDDQITLI
hMR         ENIEPEIVYA   GYDSSKPDTA   ENLLSTLNRL   AGKQMIQVVK   WAKVLPGFKN   LPLEDQITLI
hAR         EAIEPGVVCA   GHDNNQPDSF   AALLSSLNEL   GERQLVHVVK   WAKALPGFRN   LHVDDQMAVI
```

FIG.3N

|           | 841        |            |            |            |            | 900 |
|-----------|------------|------------|------------|------------|------------|-----|
| rTRalpha  | KGCCMEIMSL | RAAVRY..DP | ESDTLTLSGE | MTVKRKQLK. | ..N..GGLGV | VSDAIFELGK |
| hTRalpha  | KGCCMEIMSL | RAAVRY..DP | ESDTLTLSGE | MAVKREQLK. | ..N..GGLGV | VSDAIFELGK |
| hTRbeta   | KGCCMEIMSL | RAAVRY..DP | ESETLTLNGE | MAVIRGQLK. | ..N..GGLGV | VSDAIFDLGM |
| hRARalpha | KAACLDILIL | RICTRY..TP | EQDTMTFSDG | LTLNRTQMH. | ..N..AGFGP | LTDLVFAFAN |
| hRARgamma | KAACLDILML | RICTRY..TP | EQDTMTFSDG | LTLNRTQMH. | ..N..AGFGP | LTDLVFAFAG |
| hRXRalpha | RAGWNELLIA | SFSHRS...IA | VKDGILLATG | LHVHRNSAH. | ...S.AGVGAI | FDRVLTELVS |
| hRXRbeta  | RAGWNELLIA | SFSHRS...ID | VRDGILLATG | LHVHRNSAH. | ...S.AGVGAI | FDRVLTELVS |
| hPPARalpha | KYGVYEAIFA | MLSSVM..NK | DGMLVAYGNG | F.ITREFLK. | ..SLRKPFCD | IMEPKFDFAM |
| hPPARbeta | KYGVHEAIFA | MLASIV..NK | DGLLVANGSG | F.VTREFLR. | ..SLRKPFSD | IIEPKFEFAV |
| hPPARgamma | KYGVHEIIYT | MLASLM..NK | DGVLISEGQG | F.MTREFLK. | ..SLRKPFGD | FMEPKFEFAV |
| hVDR      | APSKVIIAPQ | PSVVKPVTSL | TAAGVIACGE | MPTVGQLVNK | PSAVKDEEAI | NLEEIREFAK |
| hER       | ECAWLEILMI | GLVWRS..ME | HPGKLLFAPN | LLLDRNQGK. | ..CVEGMVEI | FDMLLAT.SS |
| hGR       | QYSWMFLMAF | ALGWRSYRQS | SANLLCFAPD | LIINEQRMT. | ....LPCMYD | QCKHMLYVSS |
| hPR       | QYSWMSLMVF | GLGWRSYKHV | SGQMLYFAPD | LILNEQRMK. | ....ESSFYS | LCLTMWQIPQ |
| hMR       | QYSWMCLSSF | ALSWRSYKHT | NSQFLYFAPD | LVFNEEKMH. | ....QSAMYE | LCQGMHQISL |
| hAR       | QYSWMGLMVF | AMGWRSFTNV | NSRMLYFAPD | LVFNEYRMH. | ....KSRMYS | QCVRMRHLSQ |

FIG.30

```
                901                                                           960
rTRalpha     SLSAFNLDDT EVALLQAVLL MSTD...... ..RSGLLCVD KIEKSQEAYL LA...FEHYV
hTRalpha     SLSAFNLDDT EVALLQAVLL MSTD...... ..RSGLLCVD KIEKSQEAYL LA...FEHYV
hTRbeta      SLSSFNLDDT EVALLQAVLL MSSD...... ..RPGLACVE RIEKYQDSFL LA...FEHYI
hRARalpha    QLLPLEMDDA ETGILSAICL ICGD...... ..RQDLEQPD RVDMLQEPLL EA...LKVYV
hRARgamma    QLLPLEMDDT ETGLLSAICL ICGD...... ..RMDLEEPE KVDKLQEPLL EA...LRLYA
hRXRalpha    KMRDMQMDKT ELGCLRAIVL FNPDS..... ...KGLSNPA EVEALREKVY AS...LEAYC
hRXRbeta     KMRDMRMDKT ELGCLRAIIL FNPDA..... ...KGLSNPS EVEVLREKVY AS...LETYC
hPPARalpha   KFNALELDDS DISLFVAAII CCGD...... ..RPGLLNVG HIEKMQEGIV HV...LRLHL
hPPARbeta    KFNALELDDS DLALFIAAII LCGD...... ..RPGLMNVP RVEAIQDTIL RA...LEFHL
hPPARgamma   KFNALELDDS DLAIFIAVII LSGD...... ..RPGLLNVK PIEDIQDNLL QA...LELQL
hVDR         NFKIRRLSLG LTQTQVGQAL TATEGPAYSQ SAICRFEKLD ITPKSAQKLK PVLERWLAEA
hER          RFRMMNLQGE EFVCLKSIIL LNSGVYTFLS STLKSLEEKD HIHRVLDKIT DTLIHLMAKA
hGR          ELHRLQVSYE EYLCMKTLLL LSS....... VPKDGLKSQE LFDEIRMTYI KELGKAIVKR
hPR          EFVKLQVSQE EFLCMKVLLL LNT....... IPLEGLRSQT QFEEMRSSYI RELIKAIGLR
hMR          QFVRLQLTFE EYTIMKVLLL LST....... IPKDGLKSQA AFEEMRTNYI KELRKMVTKC
hAR          EFGWLQITPQ EFLCMKALLL FSI....... IPVDGLKNQK FFDELRMNYI KELDRIIACK
```

FIG. 3P

|            | 961             |             |            |             | 1020         |
|------------|-----------------|-------------|------------|-------------|--------------|
| rTRalpha   | NHRKHNIPHF      | WPKLL....M  | KVTDLRMIGA | CHASRFL..H  | MKVEC..PTE LFPPLFLEVF |
| hTRalpha   | NHRKHNIPHF      | WPKLL....M  | KVTDLRMIGA | CHASRFL..H  | MKVEC..PTE LFPPLFLEVF |
| hTRbeta    | NYRKHVTHF       | WPKLL....M  | KVTDLRMIGA | CHASRFL..H  | MKVEC..PTE LLPPLFLEVP |
| hRARalpha  | RKRRPSRPHM      | FPKML....M  | KITDLRSISA | KGAERVI..T  | LKMEI..PGS M.PPLIQEML |
| hRARgamma  | RRRRPSQPYM      | FPRML....M  | KITDLRGIST | KGAERAI..T  | LKMEI..PGP M.PPLIREML |
| hRXRalpha  | KHKYPEQPGR      | FAKLL....L  | RLPALRSIGL | KCLEHLF..F  | FKL.I..GDT PIDTFLMEML |
| hRXRbeta   | KQKYPEQQGR      | FAKLL....L  | RLPALRSIGL | KCLEHLF..F  | FKL.I..GDT PIDTFLMEML |
| hPPARalpha | QSNHPDDIFL      | FPKLL....Q  | KMADLRQLVT | EHAQLVQ..I  | IKKTE..SDA ALHPLLQEIY |
| hPPARbeta  | QANHPDAQYL      | FPKLL....Q  | KMADLRQLVT | EHAQMMQ..R  | IKKTE..TET SLHPLLQEIY |
| hPPARgamma | KLNHPESSQL      | FAKVL....Q  | KMTDLRQIVT | EHVQLLH..V  | IKKTE..TDM SLHPLLQEIY |
| hVDR       | ELWNQKGQQN      | LMEFVGGEPS  | KKRKRRTSFT | PQAIEVLNTY  | FEKNSLPTGQ EITEIAKELN |
| hER        | GLTLQQQHQR      | LAQLL....L  | ILSHIRHMSN | KGMEHLY..S  | MKC.K..NVV PLYDLLLEML |
| hGR        | EGNSSQNWQR      | FYQLT....K  | LLDSMHEVVE | NLLNYCFQTF  | LD.KT..MSI EFPEMLAEII |
| hPR        | QKGVVSSSQR      | FYQLT....K  | LLDNLHDLVK | QLHLYCLNTF  | IQSRA..LSV EFPEMMSEVI |
| hMR        | PNNSGQSWQR      | FYQLT....K  | LLDSMHDLVS | DLLEFCFYTF  | RESHA..LKV EFPAMLVEII |
| hAR        | RKNPTSCSRR      | FYQLT....K  | LLDSVQPIAR | ELHQFTFDLL  | IKSHM..VSV DFPEMMAEII |

FIG. 3Q

|  | 1021 | minimal end site 1025 |  |  |  |  | 1071 |
|---|---|---|---|---|---|---|---|
| rTRalpha | EDQEV | . . . . . . . . . . | . . . . . . . . . . | . . . . . . . . . . | . . . . . . . . . . | . . . . . . . . . . | . . . . . . . . . . |
| hTRalpha | EDQEV | . . . . . . . . . . | . . . . . . . . . . | . . . . . . . . . . | . . . . . . . . . . | . . . . . . . . . . | . . . . . . . . . . |
| hTRbeta | ED. . . | . . . . . . . . . . | . . . . . . . . . . | . . . . . . . . . . | . . . . . . . . . . | . . . . . . . . . . | . . . . . . . . . . |
| hRARalpha | ENSEGLDTLS | GQPGGGGRDG | GGLAPPPGSC | SPSLSPSSNR | SSPATHSP. . | . . . . . . . . . . | . . . . . . . . . . |
| hRARgamma | ENPEMFEDDS | SQPGPHPNAS | SEDEVPGGQG | KGGLKSPA. . | . . . . . . . . . . | . . . . . . . . . . | . . . . . . . . . . |
| hRXRalpha | EAPHQMT. . | . . . . . . . . . . | . . . . . . . . . . | . . . . . . . . . . | . . . . . . . . . . | . . . . . . . . . . | . . . . . . . . . . |
| hRXRbeta | EAPHQLA. . | . . . . . . . . . . | . . . . . . . . . . | . . . . . . . . . . | . . . . . . . . . . | . . . . . . . . . . | . . . . . . . . . . |
| hPPARalpha | RDMY. . . . | . . . . . . . . . . | . . . . . . . . . . | . . . . . . . . . . | . . . . . . . . . . | . . . . . . . . . . | . . . . . . . . . . |
| hPPARbeta | KDMY. . . . | . . . . . . . . . . | . . . . . . . . . . | . . . . . . . . . . | . . . . . . . . . . | . . . . . . . . . . | . . . . . . . . . . |
| hPPARgamma | KDLY. . . . | . . . . . . . . . . | . . . . . . . . . . | . . . . . . . . . . | . . . . . . . . . . | . . . . . . . . . . | . . . . . . . . . . |
| hVDR | YDREVVRVWF | CNRRQTLKNT | SKINVFQSQ. | . . . . . . . . . . | . . . . . . . . . . | . . . . . . . . . . | . . . . . . . . . . |
| hER | DAHRLHAPTS | RGGASVEETD | QSHLATAGST | SSHSLQKYYI | TGEAEGFPAT | V | |
| hGR | TNQIPKYSNG | NIKKLLFHQK | . . . . . . . . . . | . . . . . . . . . . | . . . . . . . . . . | . . . . . . . . . . | . . . . . . . . . . |
| hPR | AAQLPKILAG | MVKPLLFHKK | . . . . . . . . . . | . . . . . . . . . . | . . . . . . . . . . | . . . . . . . . . . | . . . . . . . . . . |
| hMR | SDQLPKVESG | NAKPLYFHRK | . . . . . . . . . . | . . . . . . . . . . | . . . . . . . . . . | . . . . . . . . . . | . . . . . . . . . . |
| hAR | SVQVPKILSG | KVKPIYFHTQ | . . . . . . . . . . | . . . . . . . . . . | . . . . . . . . . . | . . . . . . . . . . | . . . . . . . . . . | socr:<5>

FIG.3R

AGONISTS  ANTAGONISTS
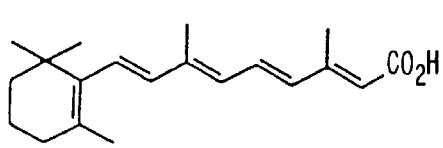
Retinoic Acid
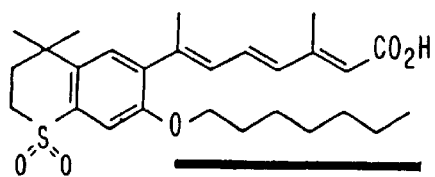
RO 46-8515
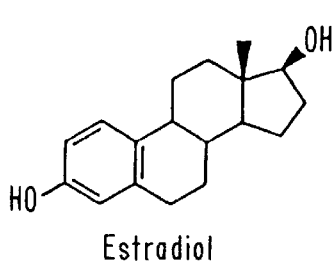
Estradiol
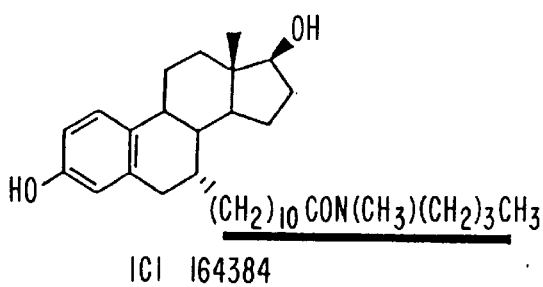
ICI 164384
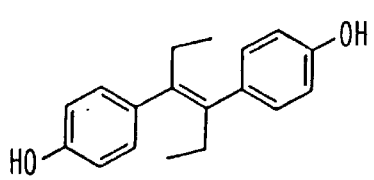
Diethylstilbestrol
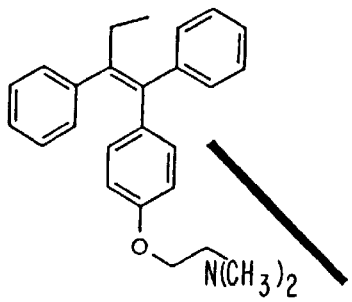
Tamoxifen
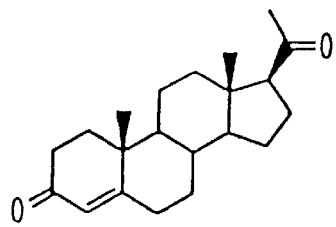
Progesterone
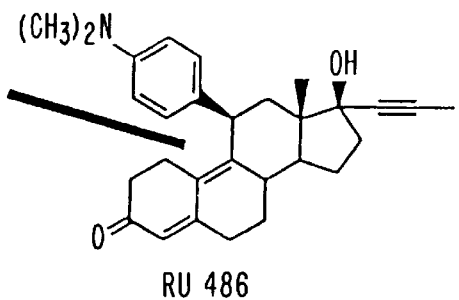
RU 486
FIG. 10 ——— shows position of extension group

| Compound | RCOX |
|---|---|
| TS1 | Ph$_2$CHCO$_2$NHS |
| TS2 | C$_{16}$H$_{33}$CO$_2$NHS |
| TS3 | FMOC-Cl |
| TS4 | tBOC$_2$O |
| TS5 | tBOC$_2$O |

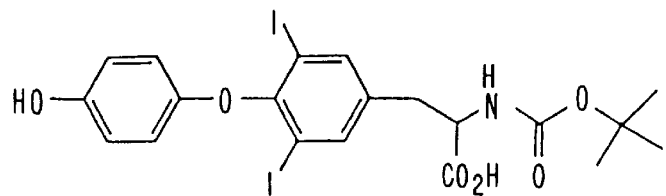
TS-5
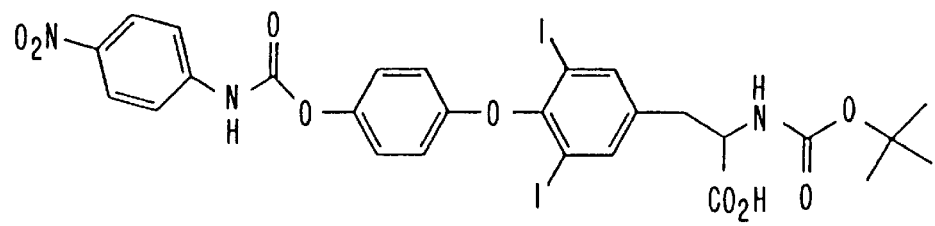
TS-6
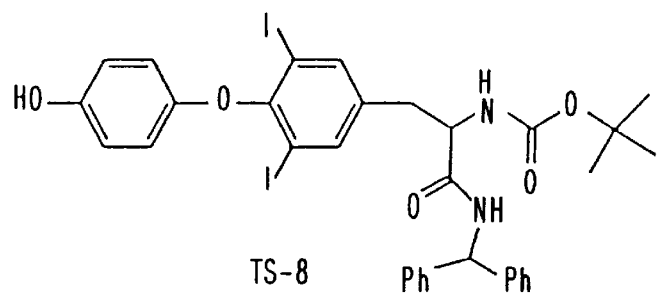
TS-8
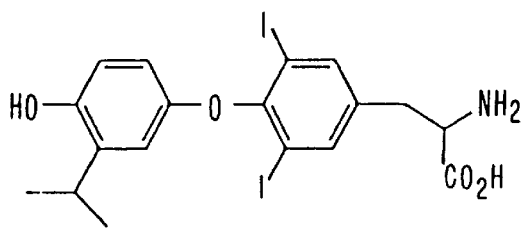
TS-9
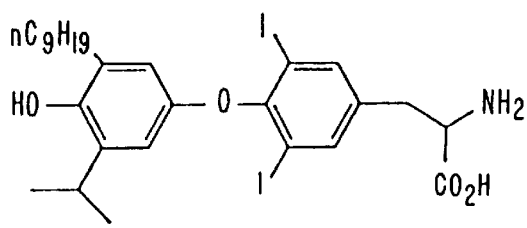
TS-10
FIG.15

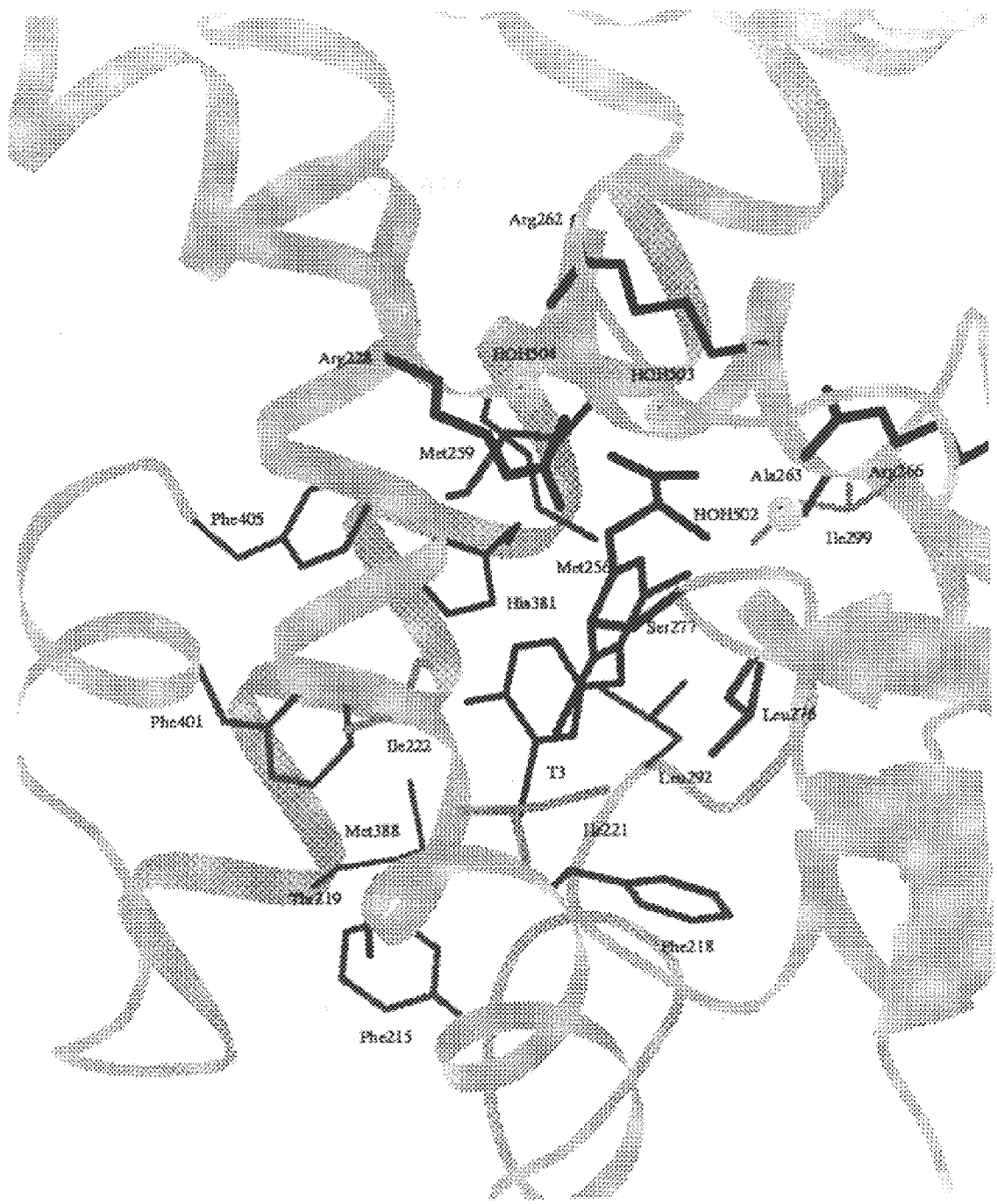
FIG.26.B

FIG. 27

| Dimit Atom[1] | Amino Acid in full length $\alpha$[2] | Amino Acid Atom[3] | Distance, Å[4] |
|---|---|---|---|
| C16 | 215-PHE | CD1 | 3.98 |
| C16 | 215-PHE | CE1 | 3.86 |
| C19 | 218-PHE | O | 3.69 |
| C16 | 218-PHE | CB | 3.89 |
| C18 | 218-PHE | CB | 3.92 |
| C19 | 218-PHE | CB | 4.13 |
| C18 | 218-PHE | CD2 | 3.77 |
| C16 | 219-THR | CG2 | 3.68 |
| C19 | 221-ILE | CG1 | 4.11 |
| C6 | 222-ILE | CD1 | 4.18 |
| C8 | 222-ILE | CD1 | 3.72 |
| C10 | 222-ILE | CD1 | 3.53 |
| C12 | 222-ILE | CD1 | 3.85 |
| O1 | 222-ILE | CD1 | 4.13 |
| C13 | 225-ALA | CB | 3.64 |
| O4 | 225-ALA | CB | 4.02 |
| O4 | 228-ARG | CZ | 3.96 |
| C17 | 228-ARG | NH2 | 3.36 |
| O3 | 228-ARG | NH2 | 3.58 |
| O4 | 228-ARG | NH2 | 2.86 |
| C10 | 256-MET | SD | 3.70 |
| C12 | 256-MET | SD | 3.89 |
| C10 | 256-MET | CE | 3.88 |
| C12 | 256-MET | CE | 3.83 |
| C11 | 259-MET | C | 4.03 |
| C11 | 259-MET | O | 3.66 |
| C15 | 259-MET | O | 3.42 |
| N1 | 259-MET | O | 3.71 |
| C1 | 259-MET | CB | 4.20 |
| C11 | 259-MET | CB | 3.87 |
| C13 | 259-MET | CB | 4.09 |
| C15 | 262-ARG | CB | 4.03 |
| C17 | 262-ARG | CB | 3.58 |
| O3 | 262-ARG | CB | 3.62 |
| O4 | 262-ARG | CB | 3.85 |
| C17 | 262-ARG | CD | 4.10 |
| O4 | 262-ARG | CD | 3.61 |
| N1 | 263-ALA | N | 3.71 |
| C17 | 263-ALA | CA | 3.69 |
| N1 | 263-ALA | CB | 3.46 |
| O3 | 266-ARG | NH1 | 3.93 |
| N1 | 275-THR | O | 3.62 |
| N1 | 276-LEU | CA | 3.51 |
| N1 | 276-LEU | C | 3.92 |
| C5 | 276-LEU | CD1 | 4.05 |
| C19 | 276-LEU | CD1 | 4.04 |
| C7 | 276-LEU | CD2 | 4.09 |
| C9 | 276-LEU | CD2 | 3.95 |
| C11 | 276-LEU | CD2 | 4.13 |
| N1 | 276-LEU | CD2 | 4.17 |
| C13 | 277-SER | N | 4.14 |
| C15 | 277-SER | N | 3.79 |

FIG. 27A-1

| Dimit Atom[1] | Amino Acid in full length α[2] | Amino Acid Atom[3] | Distance, Å[4] |
|---|---|---|---|
| C17 | 277-SER | N | 3.69 |
| N1 | 277-SER | N | 3.30 |
| O3 | 277-SER | N | 3.19 |
| C17 | 277-SER | CA | 3.92 |
| O3 | 277-SER | CA | 3.35 |
| C13 | 277-SER | OG | 3.92 |
| C7 | 287-LEU | CO2 | 3.90 |
| C18 | 290-GLY | C | 4.04 |
| C18 | 290-GLY | O | 3.54 |
| C18 | 291-GLY | CA | 4.04 |
| C18 | 292-LEU | N | 4.20 |
| C2 | 292-LEU | CG | 4.18 |
| C4 | 292-LEU | CG | 3.88 |
| C6 | 292-LEU | CG | 4.01 |
| C2 | 292-LEU | CD1 | 3.88 |
| C4 | 292-LEU | CD1 | 4.02 |
| O2 | 292-LEU | CD1 | 4.07 |
| C4 | 292-LEU | CD2 | 4.05 |
| C6 | 292-LEU | CD2 | 3.72 |
| C8 | 292-LEU | CD2 | 3.69 |
| C10 | 292-LEU | CD2 | 3.98 |
| O1 | 292-LEU | CD2 | 4.16 |
| C20 | 299-ILE | CD1 | 3.87 |
| C8 | 381-HIS | CD2 | 3.90 |
| C10 | 381-HIS | CD2 | 3.84 |
| O1 | 381-HIS | GO2 | 3.40 |
| O1 | 381-HIS | CE1 | 3.72 |
| C8 | 381-HIS | NE2 | 3.47 |
| C10 | 381-HIS | NE2 | 3.51 |
| O1 | 381-HIS | NE2 | 2.64 |
| C8 | 388-MET | CE | 3.90 |
| C8 | 401-PHE | CE1 | 4.19 |
| O1 | 401-PHE | CE1 | 3.37 |
| C16 | 401-PHE | CZ | 3.97 |
| O1 | 401-PHE | CZ | 3.28 |
| C17 | 3-$H_2O$ | O1 | 3.77 |
| O3 | 502-$H_2O$ | O1 | 3.13 |
| O4 | 3-$H_2O$ | O1 | 3.72 |
| C15 | 2-$H_2O$ | O1 | 4.04 |
| C17 | 2-$H_2O$ | O1 | 3.84 |
| N1 | 2-$H_2O$ | O1 | 3.35 |
| O3 | 503-$H_2O$ | O1 | 2.56 |
| C17 | 4-$H_2O$ | O1 | 3.92 |
| O4 | 504-$H_2O$ | O1 | 2.72 |

This table lists the interactions with Dimit (DMT). The column headings are as follows:
[1] The atom of Dimit that interacts with the amino acid of the receptor.
[2] The amino acid in the full length rTRα that interacts with the ligand.
[3] The name of the atom in the amino acid (standard nomenclature) where the interaction occurs.
[4] The distance in Å between Dimit and the protein atom.

FIG. 27A-2

| Triac Atom[1] | Amino Acid in full length α[2] | Amino Acid Atom[3] | Distance, Å[4] |
|---|---|---|---|
| I1 | 218-PHE | O | 3.52 |
| I1 | 221-ILE | CD1 | 4.16 |
| I1 | 222-ILE | CA | 4.15 |
| I1 | 222-ILE | CB | 4.03 |
| I1 | 221-ILE | CG1 | 3.92 |
| C8 | 222-ILE | CD1 | 4.12 |
| C10 | 222-ILE | CD1 | 3.77 |
| C12 | 222-ILE | CD1 | 3.79 |
| C13 | 225-ALA | CB | 4.17 |
| C3 | 225-ALA | CB | 3.86 |
| C10 | 256-MET | SD | 3.45 |
| C12 | 256-MET | SD | 3.73 |
| C10 | 256-MET | CE | 3.66 |
| C12 | 256-MET | CE | 3.77 |
| C11 | 256-MET | C | 3.68 |
| C11 | 256-MET | O | 3.24 |
| C1 | 259-MET | O | 3.93 |
| C11 | 259-MET | O | 3.24 |
| O3 | 259-MET | O | 4.09 |
| C1 | 259-MET | CB | 3.89 |
| C13 | 259-MET | O | 3.74 |
| C14 | 259-MET | O | 3.96 |
| C1 | 259-MET | CB | 3.89 |
| C11 | 259-MET | CB | 3.68 |
| C13 | 259-MET | CB | 4.01 |
| C14 | 262-ARG | CB | 4.07 |
| O4 | 262-ARG | CB | 3.60 |
| C17 | 282-ARG | CD | |
| O4 | 262-ARG | CD | |
| O3 | 263-ALA | N | 3.79 |
| O3 | 263-ALA | CA | 3.67 |
| O3 | 283-ALA | CB | 3.49 |
| C11 | 107-ALA | CB | 4.00 |
| O3 | 107-ALA | CB | 3.49 |
| O3 | 266-ARG | NH1 | 3.00 |
| O3 | 275-THR | O | 3.20 |
| O3 | 278-LEU | CA | 3.11 |
| N1 | 276-LEU | C | 3.52 |
| O3 | 120-LEU | N | 4.04 |
| C14 | 120-LEU | CA | 3.98 |
| O3 | 120-LEU | CA | 3.11 |
| C14 | 120-LEU | C | 3.98 |
| O3 | 120-LEU | CB | 3.95 |
| O2 | 276-LEU | CD1 | 4.03 |
| I1 | 276-LEU | CD1 | 4.10 |
| C7 | 276-LEU | CD2 | 3.84 |
| C9 | 276-LEU | CD2 | 3.73 |
| C11 | 276-LEU | CD2 | 4.06 |
| O2 | 276-LEU | CD2 | 4.10 |
| C13 | 277-SER | N | 4.06 |
| C14 | 277-SER | N | 3.13 |
| O4 | 277-SER | N | 3.28 |

FIG. 27A-3

| Triac Atom[1] | Amino Acid in full length α[2] | Amino Acid Atom[3] | Distance, Å[4] |
|---|---|---|---|
| O3 | 277-SER | N | 3.05 |
| C14 | 277-SER | CA | 3.76 |
| O4 | 277-SER | CA | 3.52 |
| C3 | 277-SER | OG | 3.87 |
| I2 | 290-GLY | O | 3.57 |
| I2 | 292-LEU | CG | 3.94 |
| C4 | 292-LEU | CG | 3.95 |
| C6 | 292-LEU | CG | 3.65 |
| C2 | 292-LEU | CD1 | 4.11 |
| C4 | 292-LEU | CD1 | 3.85 |
| I2 | 292-LEU | CD2 | 3.98 |
| C4 | 292-LEU | CD2 | 4.11 |
| C6 | 292-LEU | CD2 | 3.44 |
| C8 | 292-LEU | CD2 | 3.28 |
| C10 | 292-LEU | CD2 | 3.88 |
| O1 | 292-LEU | CD2 | 3.35 |
| I3 | 299-ILE | CD1 | 3.77 |
| C8 | 381-HIS | CD2 | 3.87 |
| C10 | 381-HIS | CD2 | 3.90 |
| O1 | 381-HIS | GO2 | 3.20 |
| O1 | 381-HIS | CE1 | 3.81 |
| C8 | 381-HIS | NE2 | 3.51 |
| C10 | 381-HIS | NE2 | 3.52 |
| O1 | 381-HIS | NE2 | 2.64 |
| O1 | 388-MET | CE | 4.03 |
| O1 | 401-PHE | CE1 | 3.86 |
| O1 | 401-PHE | CZ | 3.70 |

This table lists the interactions with Triac. The column headings are as follows:

1 The atom of Triac that interacts with the amino acid of the receptor.
2 The amino acid in the full length rTRα that interacts with the ligand.
3 The name of the atom in the amino acid (standard nomenclature) where the interaction occurs.
4 The distance in Å between Triac and the protein atom.

FIG. 27A-4

| IpBR$_2$ Atom[1] | Amino Acid in full length $\alpha$[2] | Amino Acid Atom[3] | Distance, Å[4] |
|---|---|---|---|
| C16 | 215-PHE | CD1 | 4.01 |
| C16 | 215-PHE | CE1 | 3.78 |
| BR1 | 218-PHE | O | 3.24 |
| BR1 | 218-PHE | C | 3.98 |
| C16 | 218-PHE | CB | 3.81 |
| C18 | 218-PHE | CB | 3.92 |
| BR1 | 218-PHE | CB | 4.08 |
| C18 | 218-PHE | CD2 | 3.92 |
| C18 | 219-THR | CG2 | 3.45 |
| BR1 | 221-ILE | CG1 | 3.81 |
| BR1 | 221-ILE | CD1 | 4.07 |
| C6 | 222-ILE | CD1 | 4.07 |
| C8 | 222-ILE | CD1 | 3.64 |
| C10 | 222-ILE | CD1 | 3.50 |
| C12 | 222-ILE | CD1 | 3.82 |
| O1 | 222-ILE | CD1 | 4.08 |
| C13 | 225-ALA | CB | 3.76 |
| O4 | 225-ALA | CB | 4.01 |
| O4 | 228-ARG | CZ | 3.92 |
| C17 | 228-ARG | NH2 | 3.26 |
| O3 | 228-ARG | NH2 | 3.43 |
| O4 | 228-ARG | NH2 | 2.79 |
| C10 | 256-MET | SD | 3.65 |
| C12 | 256-MET | SD | 3.71 |
| C10 | 256-MET | CE | 3.90 |
| C12 | 256-MET | CE | 3.75 |
| BR2 | 256-MET | CE | 4.03 |
| C11 | 259-MET | C | 3.98 |
| C11 | 259-MET | O | 3.52 |
| C15 | 259-MET | O | 3.44 |
| N1 | 259-MET | O | 3.76 |
| C11 | 259-MET | CB | 3.87 |
| C15 | 262-ARG | CB | 4.03 |

FIG. 27A-5

| IpBR$_2$ Atom[1] | Amino Acid in full length $\alpha$[2] | Amino Acid Atom[3] | Distance, Å[4] |
|---|---|---|---|
| C17 | 262-ARG | CB | 3.56 |
| O3 | 262-ARG | CB | 3.55 |
| O4 | 262-ARG | CB | 3.91 |
| C17 | 262-ARG | CD | 4.09 |
| O4 | 262-ARG | CD | 3.71 |
| N1 | 263-ALA | N | 3.61 |
| N1 | 263-ALA | CA | 3.59 |
| N1 | 263-ALA | CB | 3.54 |
| O3 | 268-ARG | NH1 | 3.93 |
| N1 | 275-THR | O | 3.43 |
| N1 | 276-LEU | CA | 3.46 |
| N1 | 276-LEU | C | 3.83 |
| C5 | 276-LEU | CD1 | 4.02 |
| C7 | 276-LEU | CD2 | 4.00 |
| C9 | 276-LEU | CD2 | 3.81 |
| C11 | 276-LEU | CD2 | 3.91 |
| C13 | 277-SER | N | 3.79 |
| C15 | 277-SER | N | 3.63 |
| C17 | 277-SER | N | 3.70 |
| N1 | 277-SER | N | 3.17 |
| O3 | 277-SER | N | 3.37 |
| C17 | 277-SER | CA | 3.89 |
| O3 | 277-SER | CA | 3.43 |
| C13 | 277-SER | OG | 3.66 |
| O2 | 287-LEU | CD1 | 4.05 |
| C18 | 290-GLY | C | 4.04 |
| C18 | 290-GLY | O | 3.48 |
| C18 | 291-GLY | CA | 4.02 |
| C4 | 292-LEU | CG | 3.89 |
| C6 | 292-LEU | CG | 4.02 |
| C2 | 292-LEU | CD1 | 3.79 |
| C4 | 292-LEU | CD1 | 3.96 |
| O2 | 292-LEU | CD1 | 3.97 |

FIG. 27A-6

| IpBR$_2$ Atom[1] | Amino Acid in full length α[2] | Amino Acid Atom[3] | Distance, Å[4] |
|---|---|---|---|
| C4 | 292-LEU | CD2 | 4.07 |
| C6 | 292-LEU | CD2 | 3.75 |
| C8 | 292-LEU | CD2 | 3.67 |
| C10 | 292-LEU | CD2 | 3.92 |
| BR2 | 299-ILE | CD1 | 3.68 |
| C8 | 361-HIS | CD2 | 3.67 |
| C10 | 381-HIS | CD2 | 3.92 |
| O1 | 381-HIS | GD2 | 3.50 |
| O1 | 381-HIS | CE1 | 3.62 |
| C8 | 381-HIS | NE2 | 3.36 |
| C10 | 381-HIS | NE2 | 3.34 |
| O1 | 381-HIS | NE2 | 2.62 |
| C8 | 401-PHE | CE1 | 4.02 |
| O1 | 401-PHE | CE1 | 3.19 |
| C16 | 401-PHE | CZ | 4.03 |
| O1 | 401-PHE | CZ | 3.06 |
| C17 | 3-H$_2$O | O1 | |
| O3 | 502H$_2$O | O1 | 3.40 |
| O4 | 3-H$_2$O | O1 | |
| C15 | 2-H$_2$O | O1 | |
| C17 | 2-H$_2$O | O1 | |
| N1 | 502H$_2$O | O1 | 3.12 |
| O3 | 503H$_2$O | O1 | 2.27 |
| C17 | 4-H$_2$O | O1 | |
| O4 | 504H$_2$O | O1 | 1.78 |

This table lists the interactions with IpBr2. The column headings are as follows:

1 The atom of IpBr2 that interacts with the amino acid of the receptor.
2 The amino acid in the full length rTRI that interacts with the ligand.
3 The name of the atom in the amino acid (standard nomenclature) where the interaction occurs.
4 The distance in A between IpBr2 and the protein atom.

FIG. 27A-7

| T3 Atom[1] | Amino Acid in full length α[2] | Amino Acid Atom[3] | Distance, Å[4] |
|---|---|---|---|
| I2 | 215-PHE | CD1 | 4.08 |
| I1 | 218-PHE | O | 3.19 |
| I1 | 218-PHE | CB | 3.99 |
| C4 | 218-PHE | CB | 4.04 |
| I1 | 218-PHE | CB | 3.99 |
| I1 | 221-ILE | CG1 | 4.01 |
| C8 | 222-ILE | CD1 | 3.99 |
| C10 | 222-ILE | CD1 | 3.99 |
| C12 | 222-ILE | CD1 | 3.57 |
| O1 | 222-ILE | CD1 | 3.68 |
| C13 | 225-ALA | CB | 3.66 |
| C3 | 225-ALA | CB | 4.04 |
| O4 | 228-ARG | NH1 | 3.23 |
| O4 | 228-ARG | CZ | 3.45 |
| C15 | 228-ARG | NH2 | 3.54 |
| O3 | 228-ARG | NH2 | 3.90 |
| O4 | 228-ARG | NH2 | 2.86 |
| C10 | 256-MET | SD | 3.73 |
| C12 | 256-MET | SD | 3.90 |
| C10 | 256-MET | CE | 3.97 |
| C12 | 256-MET | CE | 3.92 |
| C11 | 259-MET | C | 3.95 |
| C11 | 259-MET | O | 3.59 |
| C14 | 259-MET | O | 3.51 |
| N1 | 259-MET | O | 3.88 |
| C1 | 259-MET | CB | 4.06 |
| C11 | 259-MET | CB | 3.77 |
| C13 | 259-MET | CB | 3.96 |
| C15 | 262-ARG | CB | 3.61 |
| C14 | 262-ARG | CB | 4.02 |
| O3 | 262-ARG | CB | 3.65 |
| O4 | 262-ARG | CB | 3.92 |
| O4 | 282-ARG | CD | 3.72 |

FIG. 27A-8

| T3 Atom[1] | Amino Acid in full length α[2] | Amino Acid Atom[3] | Distance, Å[4] |
|---|---|---|---|
| N1 | 263-ALA | N | 3.81 |
| N1 | 263-ALA | CA | 3.81 |
| N1 | 263-ALA | CB | 3.63 |
| N1 | 275-THR | O | 3.54 |
| N1 | 276-LEU | CA | 3.38 |
| N1 | 276-LEU | C | 3.73 |
| C5 | 276-LEU | CD1 | 4.00 |
| C7 | 276-LEU | CD1 | 4.05 |
| C7 | 276-LEU | CD2 | 3.80 |
| C9 | 276-LEU | CD2 | 3.70 |
| C11 | 276-LEU | CD2 | 4.01 |
| C14 | 277-SER | N | 3.67 |
| C15 | 277-SER | N | 3.62 |
| O4 | 228-ARG | NH1 | 3.23 |
| N1 | 277-SER | N | 3.07 |
| O3 | 277-SSER | N | 3.24 |
| C15 | 277-SER | CA | 3.77 |
| O3 | 277-SER | CA | 3.34 |
| C13 | 277-SER | OG | 3.92 |
| I2 | 290-GLY | O | 3.50 |
| C4 | 292-LEU | CG | 3.95 |
| C8 | 292-LEU | CG | 3.83 |
| C2 | 292-LEU | CD1 | 4.07 |
| C4 | 292-LEU | CD1 | 3.99 |
| C4 | 292-LEU | CD2 | 4.09 |
| C6 | 292-LEU | CD2 | 3.58 |
| C8 | 292-LEU | CD2 | 3.50 |
| C10 | 292-LEU | CD2 | 3.96 |
| O1 | 292-LEU | CD2 | 3.71 |
| I3 | 299-ILE | CD1 | 3.74 |
| C8 | 381-HIS | CD2 | 3.94 |
| C10 | 381-HIS | CD2 | 3.97 |
| O1 | 381-HIS | CD2 | 3.39 |

FIG. 27A-9

| T3 Atom[1] | Amino Acid in full length α[2] | Amino Acid Atom[3] | Distance, Å[4] |
|---|---|---|---|
| O1 | 381-HIS | CD1 | 3.82 |
| C8 | 381-HIS | NE2 | 3.47 |
| C10 | 381-HIS | NE2 | 3.55 |
| O1 | 381-HIS | NE2 | 2.70 |
| O1 | 388-MET | CE | 3.88 |
| O1 | 401-PHE | CE1 | 3.52 |
| O1 | 401-PHE | CZ | 3.32 |
| O3 | 502 | O1 | 2.51 |
| O4 | 3-H$_2$O | O1 | |
| N1 | 2-H$_2$O | O1 | |
| O3 | 503 | O1 | 2.81 |
| O4 | 504 | O1 | 2.73 |

This table lists the interactions with T3. The column headings are as follows:

1  The atom of T3 that interacts with the amino acid of the receptor.
2  The amino acid in the full length rTRI that interacts with the ligand.
3  The name of the atom in the amino acid (standard nomenclature) where the interaction occurs.
4  The distance in A between T3 and the protein atom.

FIG. 27A-10

| Coordination Structure | $R_1$ | $R_2$ | $R_3$ | $R_5$ | $R_6$ | $R'_2$ | $R'_3$ | $R'_4$ | $R'_5$ | $R'_6$ | X |
|---|---|---|---|---|---|---|---|---|---|---|---|
| | $-CH_2-CH(NH_2)(CO_2)H$ | -H | $-CH_3$ | $-CH_3$ | -H | -H | $-CH(CH_3)_2$ | -OH | -H | -H | O |
| AA | | | | | | | 215 | | | | |
| SS | | | | | | | H3 | | | | |
| AA | | | 218 | | | | 218 | | | | |
| SS | | - | H3 | | | | H3 | | | | |
| AA | | | | | | | 219 | | | | |
| SS | | | | | | | H3 | | | | |
| AA | | | 221 | | | | | | | | |
| SS | | | H3 | | | | | | | | |
| AA | | | | | | | 222 | 222 | 222 | 222 | |
| SS | | | | | | | H3 | H3 | H3 | H3 | |
| AA | 225 | | | | | | | | | | |
| SS | H3 | | | | | | | | | | |
| AA | 228 | | | | | | | | | | |
| SS | H3 | | | | | | | | | | |
| AA | | | | | | | | | 256 | 256 | |
| SS | | | | | | | | | H5-H6 | H5-H6 | |
| AA | 259 | | | 259 | | | | | | | |
| SS | H5-H6 | | | H5-H6 | | | | | | | |
| AA | 262 | | | | | | | | | | |
| SS | H5-H6 | | | | | | | | | | |
| AA | 263 | | | | | | | | | | |
| SS | H5-H6 | | | | | | | | | | |
| AA | 266 | | | | | | | | | | |
| SS | loop | | | | | | | | | | |
| AA | 275 | | | | | | | | | | |
| SS | S3 | | | | | | | | | | |
| AA | 276 | | 276 | 276 | 276 | | | | | | |
| SS | S3 | | S3 | S3 | S3 | | | | | | |
| AA | 277 | | | | | | | | | | |
| SS | loop | | | | | | | | | | |
| AA | | | | | | | 290-291 | | | | |
| SS | | | | | | | loop | | | | |
| AA | | | | | | 292 | 292 | 292 | 292 | | 292 |
| SS | | | | | | loop | loop | loop | loop | | loop |
| AA | | | 299 | | | | | | | | |
| SS | | | H8 | | | | | | | | |
| AA | | | | | | | | | 381 | 381 | |
| SS | | | | | | | | | H11 | H11 | |
| AA | | | | | | | 388 | | | | |
| SS | | | | | | | H11 | | | | |
| AA | | | | | | | 401 | 401 | | | |
| SS | | | | | | | H12 | H12 | | | |
| AA | HOH502/HOH503 /HOH504 | | | | | | | | | | |
| SS | | | | | | | | | | | |

Abbreviations used:
AA = Amino Acid
SS = Secondary Structure

FIG. 27A-11

| Coordination Structure | $R_1$ | $R_2$ | $R_3$ | $R_5$ | $R_6$ | $R'_2$ | $R'_3$ | $R'_4$ | $R'_5$ | $R'_6$ | X |
|---|---|---|---|---|---|---|---|---|---|---|---|
| | -CH$_2$-COOH | -H | -I | -I | -H | -H | -I | -OH | -H | -H | O |
| AA | | | 218 | | | | | | | | |
| SS | | | H3 | | | | | | | | |
| AA | | | 221 | | | | | | | | |
| SS | | | H3 | | | | | | | | |
| AA | | | | | | | 222 | 222 | 222 | 222 | |
| SS | | | | | | | H3 | H3 | H3 | H3 | |
| AA | 225 | | | | | | | | | | |
| SS | H3 | | | | | | | | | | |
| AA | | | | 256 | | | | | 256 | 256 | |
| SS | | | | H5-H6 | | | | | H5-H6 | H5-H6 | |
| AA | 259 | | | | 259 | | | | | | |
| SS | H5-H6 | | | | H5-H6 | | | | | | |
| AA | 262 | | | | | | | | | | |
| SS | H5-H6 | | | | | | | | | | |
| AA | 263 | | | | | | | | | | |
| SS | H5-H6 | | | | | | | | | | |
| AA | 266 | | | | | | | | | | |
| SS | loop | | | | | | | | | | |
| AA | 275 | | | | | | | | | | |
| SS | S3 | | | | | | | | | | |
| AA | 276 | | 276 | 276 | 276 | | | | | | |
| SS | S3 | | S3 | S3 | S3 | | | | | | |
| AA | 277 | | | | | | | | | | |
| SS | loop | | | | | | | | | | |
| AA | | | | | | | 290 | | | | |
| SS | | | | | | | loop | | | | |
| AA | | | | | | 292 | 292 | 292 | 292 | | 292 |
| SS | | | | | | loop | loop | loop | loop | | loop |
| AA | | | | 299 | | | | | | | |
| SS | | | | H8 | | | | | | | |
| AA | | | | | | | | 381 | 381 | | |
| SS | | | | | | | | H11 | H11 | | |
| AA | | | | | | | | 388 | | | |
| SS | | | | | | | | H11 | | | |
| AA | | | | | | | | 401 | 401 | | |
| SS | | | | | | | | H12 | H12 | | |

Abbreviations used:
    AA = Amino Acid
    SS = Secondary Structure

FIG. 27A-12

| Coordination Structure | $R_1$ | $R_2$ | $R_3$ | $R_5$ | $R_6$ | $R'_2$ | $R'_3$ | $R'_4$ | $R'_5$ | $R'_6$ | X |
|---|---|---|---|---|---|---|---|---|---|---|---|
| | $-CH_2-CH(NH_2)(CO_2)H$ | -H | -Br | -Br | -H | -H | $-CH(CH_3)_2$ | -OH | -H | -H | O |
| AA | | | | | | | 215 | | | | |
| SS | | | | | | | H3 | | | | |
| AA | | | 218 | | | | 218 | | | | |
| SS | | | H3 | | | | H3 | | | | |
| AA | | | | | | | 219 | | | | |
| SS | | | | | | | H3 | | | | |
| AA | | | 221 | | | | | | | | |
| SS | | | H3 | | | | | | | | |
| AA | | | | | | | 222 | 222 | 222 | 222 | |
| SS | | | | | | | H3 | H3 | H3 | H3 | |
| AA | 225 | | | | | | | | | | |
| SS | H3 | | | | | | | | | | |
| AA | 228 | | | | | | | | | | |
| SS | H3 | | | | | | | | | | |
| AA | | | | 256 | | | | | 256 | 256 | |
| SS | | | | H5-H6 | | | | | H5-H6 | H5-H6 | |
| AA | 259 | | | | 259 | | | | | | |
| SS | H5-H6 | | | | H5-H6 | | | | | | |
| AA | 262 | | | | | | | | | | |
| SS | H5-H6 | | | | | | | | | | |
| AA | 263 | | | | | | | | | | |
| SS | H5-H6 | | | | | | | | | | |
| AA | 266 | | | | | | | | | | |
| SS | loop | | | | | | | | | | |
| AA | 275 | | | | | | | | | | |
| SS | S3 | | | | | | | | | | |
| AA | 276 | | 276 | 276 | 276 | | | | | | |
| SS | S3 | | S3 | S3 | S3 | | | | | | |
| AA | 277 | | | | | | | | | | |
| SS | | | | | | | | | | | |
| AA | | | | | | | 290-291 | | | | |
| SS | | | | | | | loop | | | | |
| AA | | | | | | 292 | 292 | 292 | 292 | | 292 |
| SS | | | | | | loop | loop | loop | loop | | loop |
| AA | | | 299 | | | | | | | | |
| SS | | | H8 | | | | | | | | |
| AA | | | | | | | | 381 | 381 | | |
| SS | | | | | | | | H11 | H11 | | |
| AA | | | | | | | | 401 | 401 | | |
| SS | | | | | | | | H12 | H12 | | |
| AA | HOH502/HOH503/HOH504 | | | | | | | | | | |
| SS | | | | | | | | | | | |

Abbreviations used:
AA = Amino Acid
SS = Secondary Structure

FIG. 27A-13

| Coordination Structure | $R_1$ | $R_2$ | $R_3$ | $R_5$ | $R_6$ | $R'_2$ | $R'_3$ | $R'_4$ | $R'_5$ | $R'_6$ | X |
|---|---|---|---|---|---|---|---|---|---|---|---|
| | $-CH_2-CH(NH_2)(CO_2)H$ | -H | -I | -I | -H | -H | -I | -OH | -H | -H | O |
| AA | | | | | | | 215 | | | | |
| SS | | | | | | | H3 | | | | |
| AA | | | 218 | | | | 218 | | | | |
| SS | | | H3 | | | | H3 | | | | |
| AA | | | 221 | | | | | | | | |
| SS | | | H3 | | | | | | | | |
| AA | | | | | | | 222 | 222 | 222 | 222 | |
| SS | | | | | | | H3 | H3 | H3 | H3 | |
| AA | 225 | | | | | | | | | | |
| SS | H3 | | | | | | | | | | |
| AA | 228 | | | | | | | | | | |
| SS | H3 | | | | | | | | | | |
| AA | | | | | 256 | | | | 256 | 256 | |
| SS | | | | | H5-H6 | | | | H5-H6 | H5-H6 | |
| AA | 259 | | | | 259 | | | | | | |
| SS | H5-H6 | | | | H5-H6 | | | | | | |
| AA | 262 | | | | | | | | | | |
| SS | H5-H6 | | | | | | | | | | |
| AA | 263 | | | | | | | | | | |
| SS | H5-H6 | | | | | | | | | | |
| AA | 275 | | | | | | | | | | |
| SS | S3 | | | | | | | | | | |
| AA | 276 | | 276 | 276 | 276 | | | | | | |
| SS | S3 | | S3 | S3 | S3 | | | | | | |
| AA | 277 | | | | | | | | | | |
| SS | | | | | | | | | | | |
| AA | | | | | | | 290 | | | | |
| SS | | | | | | | loop | | | | |
| AA | | | | | | 292 | 292 | 292 | 292 | | 292 |
| SS | | | | | | loop | loop | loop | loop | | loop |
| AA | | | | 299 | | | | | | | |
| SS | | | | H8 | | | | | | | |
| AA | | | | | | | | | 381 | 381 | |
| SS | | | | | | | | | H11 | H11 | |
| AA | | | | | | | | | 388 | | |
| SS | | | | | | | | | H11 | | |
| AA | | | | | | | | | 401 | 401 | |
| SS | | | | | | | | | H12 | H12 | |
| AA | HOH502/H0H503/ HOH504 | | | | | | | | | | |
| SS | | | | | | | | | | | |

Abbreviations used:
AA = Amino Acid
SS = Secondary Structure

FIG. 28

REMARK TR_dmt full length numbering
REMARK
REMARK Rfactor 0.205 Rfree 0.227
REMARK Resolution 15. 2.2 all reflections
REMARK
REMARK Three cacodylate-modified cysteines (CYA)
REMARK Cya334, Cya380, Cya392
REMARK cacodylate modeled as single arsenic atom
REMARK
REMARK side chain of certain residues modeled as ALA due to poor density;
REMARK however, residue name reflects true residue for clarity
REMARK
REMARK clone obtained from Murray et. al.
REMARK deposited sequence confirmed,
REMARK differing from that reported by Thompson et. al.
REMARK in the following codons:
REMARK 281 Thr - Ala
REMARK 285 Lys - Glu
REMARK identical to that reported by Mitsuhashi et. al.
REMARK gb:RNTRAVI X07409
JRNL      AUTH  M.B. MURRAY, N.D.ZILZ, N.L.MCCREARY,M.J.MACDONALD
JRNL      AUTH 2 H.C.TOWLE
JRNL         TITL   ISOLATION AND CHARACTERIZATION OF RAT CDNA CLONES FOR TWO
JRNL      TITL 2 DISTINCT THYROID HORMONE RECPTORS
JRNL      REF   JBC            V. 263 25  1988
JRNL      AUTH  C.C.THOMPSON, C.WEINBERGER, R.LEBO, R.M.EVANS
JRNL         TITL   IDENTIFICATION OF A NOVEL THYROID HORMONE RECEPTOR EXPRESSED
JRNL      TITL 2 IN THE MAMMALIAN CENTRAL NERVOUS SYSTEM
JRNL      REF   SCIENCE        V. 237     1987
JRNL      AUTH  T.MITSUHASHI,G.TENNYSON,V.NIKODEM
JRNL          TITL NUCLEOTIDE SEQUENCE OF NOVEL CDNAS GENERATED BY ALTERNATIVE
JRNL         TITL 2 SPLICING OF A RAT THYROID HORMONE RECEPTOR GENE TRANSCRIPT
JRNL      REF   NUC. ACIDS. RES.      V. 16 12 1988

| ATOM | 1 | N   | ARG | 157 | 68.504 | 8.445  | 5.651  | 1.00 | 68.93 |
|------|---|-----|-----|-----|--------|--------|--------|------|-------|
| ATOM | 2 | CA  | ARG | 157 | 67.886 | 9.543  | 6.398  | 1.00 | 56.98 |
| ATOM | 3 | CB  | ARG | 157 | 68.769 | 10.789 | 6.324  | 1.00 | 59.25 |
| ATOM | 4 | CG  | ARG | 157 | 70.147 | 10.632 | 6.932  | 1.00 | 58.90 |
| ATOM | 5 | CD  | ARG | 157 | 70.068 | 10.422 | 8.425  | 1.00 | 59.37 |
| ATOM | 6 | NE  | ARG | 157 | 71.392 | 10.446 | 9.036  | 1.00 | 63.94 |
| ATOM | 7 | CZ  | ARG | 157 | 71.613 | 10.329 | 10.341 | 1.00 | 64.39 |
| ATOM | 8 | NH1 | ARG | 157 | 70.596 | 10.182 | 11.179 | 1.00 | 62.14 |
| ATOM | 9 | NH2 | ARG | 157 | 72.855 | 10.365 | 10.808 | 1.00 | 65.56 |

FIG. 28A-1

| ATOM | 10 | C | ARG | 157 | 66.500 | 9.881 | 5.854 | 1.00 | 48.97 |
|---|---|---|---|---|---|---|---|---|---|
| ATOM | 11 | O | ARG | 157 | 66.351 | 10.203 | 4.674 | 1.00 | 48.61 |
| ATOM | 12 | N | PRO | 158 | 65.469 | 9.818 | 6.712 | 1.00 | 41.90 |
| ATOM | 13 | CD | PRO | 158 | 65.550 | 9.366 | 8.112 | 1.00 | 41.06 |
| ATOM | 14 | CA | PRO | 158 | 64.083 | 10.114 | 6.333 | 1.00 | 39.34 |
| ATOM | 15 | CB | PRO | 158 | 63.286 | 9.704 | 7.576 | 1.00 | 37.89 |
| ATOM | 16 | CG | PRO | 158 | 64.260 | 9.883 | 8.693 | 1.00 | 42.40 |
| ATOM | 17 | C | PRO | 158 | 63.814 | 11.573 | 5.930 | 1.00 | 37.10 |
| ATOM | 18 | O | PRO | 158 | 64.189 | 12.517 | 6.636 | 1.00 | 33.31 |
| ATOM | 19 | N | GLU | 159 | 63.171 | 11.733 | 4.778 | 1.00 | 30.56 |
| ATOM | 20 | CA | GLU | 159 | 62.821 | 13.038 | 4.231 | 1.00 | 24.26 |
| ATOM | 21 | CB | GLU | 159 | 62.553 | 12.904 | 2.727 | 1.00 | 19.19 |
| ATOM | 22 | CG | GLU | 159 | 63.788 | 12.677 | 1.874 | 1.00 | 20.60 |
| ATOM | 23 | CD | GLU | 159 | 64.407 | 13.971 | 1.390 | 1.00 | 26.54 |
| ATOM | 24 | OE1 | GLU | 159 | 63.649 | 14.929 | 1.115 | 1.00 | 30.85 |
| ATOM | 25 | OE2 | GLU | 159 | 65.649 | 14.027 | 1.268 | 1.00 | 28.35 |
| ATOM | 26 | C | GLU | 159 | 61.549 | 13.520 | 4.909 | 1.00 | 23.26 |
| ATOM | 27 | O | GLU | 159 | 60.906 | 12.765 | 5.643 | 1.00 | 26.86 |
| ATOM | 28 | N | PRO | 160 | 61.200 | 14.806 | 4.729 | 1.00 | 22.72 |
| ATOM | 29 | CD | PRO | 160 | 61.981 | 15.916 | 4.153 | 1.00 | 17.87 |
| ATOM | 30 | CA | PRO | 160 | 59.969 | 15.292 | 5.359 | 1.00 | 19.90 |
| ATOM | 31 | CB | PRO | 160 | 60.004 | 16.799 | 5.070 | 1.00 | 14.42 |
| ATOM | 32 | CG | PRO | 160 | 61.465 | 17.109 | 4.919 | 1.00 | 12.87 |
| ATOM | 33 | C | PRO | 160 | 58.747 | 14.623 | 4.701 | 1.00 | 23.68 |
| ATOM | 34 | O | PRO | 160 | 58.730 | 14.383 | 3.491 | 1.00 | 24.72 |
| ATOM | 35 | N | THR | 161 | 57.749 | 14.281 | 5.506 | 1.00 | 22.19 |
| ATOM | 36 | CA | THR | 161 | 56.542 | 13.660 | 4.985 | 1.00 | 19.50 |
| ATOM | 37 | CB | THR | 161 | 55.691 | 13.031 | 6.125 | 1.00 | 21.50 |
| ATOM | 38 | OG1 | THR | 161 | 55.163 | 14.062 | 6.972 | 1.00 | 20.33 |
| ATOM | 39 | CG2 | THR | 161 | 56.537 | 12.078 | 6.959 | 1.00 | 19.48 |
| ATOM | 40 | C | THR | 161 | 55.744 | 14.765 | 4.298 | 1.00 | 22.86 |
| ATOM | 41 | O | THR | 161 | 56.040 | 15.949 | 4.481 | 1.00 | 27.68 |
| ATOM | 42 | N | PRO | 162 | 54.720 | 14.403 | 3.504 | 1.00 | 20.36 |
| ATOM | 43 | CD | PRO | 162 | 54.280 | 13.050 | 3.113 | 1.00 | 16.55 |
| ATOM | 44 | CA | PRO | 162 | 53.924 | 15.435 | 2.830 | 1.00 | 21.97 |
| ATOM | 45 | CB | PRO | 162 | 52.780 | 14.633 | 2.210 | 1.00 | 18.17 |
| ATOM | 46 | CG | PRO | 162 | 53.422 | 13.316 | 1.905 | 1.00 | 18.01 |
| ATOM | 47 | C | PRO | 162 | 53.399 | 16.467 | 3.826 | 1.00 | 22.56 |
| ATOM | 48 | O | PRO | 162 | 53.461 | 17.675 | 3.567 | 1.00 | 21.73 |
| ATOM | 49 | N | GLU | 163 | 52.912 | 15.976 | 4.967 | 1.00 | 25.28 |
| ATOM | 50 | CA | GLU | 163 | 52.357 | 16.816 | 6.030 | 1.00 | 26.64 |
| ATOM | 51 | CB | GLU | 163 | 51.743 | 15.962 | 7.144 | 1.00 | 30.22 |
| ATOM | 52 | CG | GLU | 163 | 50.514 | 15.131 | 6.748 | 1.00 | 44.99 |
| ATOM | 53 | CD | GLU | 163 | 50.836 | 13.950 | 5.831 | 1.00 | 48.88 |
| ATOM | 54 | OE1 | GLU | 163 | 50.016 | 13.660 | 4.929 | 1.00 | 52.48 |
| ATOM | 55 | OE2 | GLU | 163 | 51.895 | 13.309 | 6.015 | 1.00 | 44.23 |

FIG. 28A-2

| ATOM | 56 | C | GLU | 163 | 53.414 | 17.731 | 6.634 | 1.00 | 27.65 |
| --- | --- | --- | --- | --- | --- | --- | --- | --- | --- |
| ATOM | 57 | O | GLU | 163 | 53.114 | 18.862 | 7.034 | 1.00 | 29.30 |
| ATOM | 58 | N | GLU | 164 | 54.646 | 17.235 | 6.712 | 1.00 | 21.89 |
| ATOM | 59 | CA | GLU | 164 | 55.741 | 18.015 | 7.265 | 1.00 | 18.29 |
| ATOM | 60 | CB | GLU | 164 | 56.901 | 17.109 | 7.657 | 1.00 | 14.78 |
| ATOM | 61 | CG | GLU | 164 | 56.552 | 16.196 | 8.825 | 1.00 | 21.11 |
| ATOM | 62 | CD | GLU | 164 | 57.669 | 15.249 | 9.198 | 1.00 | 20.35 |
| ATOM | 63 | OE1 | GLU | 164 | 58.605 | 15.071 | 8.392 | 1.00 | 28.55 |
| ATOM | 64 | OE2 | GLU | 164 | 57.610 | 14.677 | 10.302 | 1.00 | 28.25 |
| ATOM | 65 | C | GLU | 164 | 56.200 | 19.097 | 6.306 | 1.00 | 24.62 |
| ATOM | 66 | O | GLU | 164 | 56.574 | 20.183 | 6.741 | 1.00 | 32.05 |
| ATOM | 67 | N | TRP | 165 | 56.174 | 18.817 | 5.003 | 1.00 | 28.22 |
| ATOM | 68 | CA | TRP | 165 | 56.576 | 19.825 | 4.021 | 1.00 | 22.99 |
| ATOM | 69 | CB | TRP | 165 | 56.575 | 19.262 | 2.605 | 1.00 | 17.37 |
| ATOM | 70 | CG | TRP | 165 | 57.876 | 18.633 | 2.210 | 1.00 | 10.74 |
| ATOM | 71 | CD2 | TRP | 165 | 59.153 | 19.283 | 2.109 | 1.00 | 11.74 |
| ATOM | 72 | CE2 | TRP | 165 | 60.075 | 18.319 | 1.648 | 1.00 | 9.97 |
| ATOM | 73 | CE3 | TRP | 165 | 59.606 | 20.583 | 2.365 | 1.00 | 13.88 |
| ATOM | 74 | CD1 | TRP | 165 | 58.074 | 17.343 | 1.832 | 1.00 | 9.17 |
| ATOM | 75 | NE1 | TRP | 165 | 59.390 | 17.145 | 1.486 | 1.00 | 16.55 |
| ATOM | 76 | CZ2 | TRP | 165 | 61.427 | 18.613 | 1.436 | 1.00 | 13.37 |
| ATOM | 77 | CZ3 | TRP | 165 | 60.954 | 20.874 | 2.156 | 1.00 | 16.15 |
| ATOM | 78 | CH2 | TRP | 165 | 61.846 | 19.892 | 1.696 | 1.00 | 17.42 |
| ATOM | 79 | C | TRP | 165 | 55.634 | 21.015 | 4.115 | 1.00 | 21.44 |
| ATOM | 80 | O | TRP | 165 | 56.041 | 22.149 | 3.865 | 1.00 | 22.12 |
| ATOM | 81 | N | ASP | 166 | 54.373 | 20.747 | 4.456 | 1.00 | 21.29 |
| ATOM | 82 | CA | ASP | 166 | 53.369 | 21.796 | 4.621 | 1.00 | 25.77 |
| ATOM | 83 | CB | ASP | 166 | 51.972 | 21.196 | 4.808 | 1.00 | 26.02 |
| ATOM | 84 | CG | ASP | 166 | 51.428 | 20.559 | 3.539 | 1.00 | 33.01 |
| ATOM | 85 | OD1 | ASP | 166 | 51.874 | 20.932 | 2.434 | 1.00 | 29.48 |
| ATOM | 86 | OD2 | ASP | 166 | 50.537 | 19.692 | 3.649 | 1.00 | 34.47 |
| ATOM | 87 | C | ASP | 166 | 53.732 | 22.637 | 5.842 | 1.00 | 27.91 |
| ATOM | 88 | O | ASP | 166 | 53.744 | 23.865 | 5.767 | 1.00 | 31.28 |
| ATOM | 89 | N | LEU | 167 | 54.046 | 21.966 | 6.951 | 1.00 | 25.57 |
| ATOM | 90 | CA | LEU | 167 | 54.439 | 22.640 | 8.187 | 1.00 | 28.28 |
| ATOM | 91 | CB | LEU | 167 | 54.854 | 21.624 | 9.256 | 1.00 | 32.80 |
| ATOM | 92 | CG | LEU | 167 | 53.945 | 21.347 | 10.455 | 1.00 | 41.75 |
| ATOM | 93 | CD1 | LEU | 167 | 54.765 | 20.640 | 11.532 | 1.00 | 39.15 |
| ATOM | 94 | CD2 | LEU | 167 | 53.374 | 22.647 | 11.008 | 1.00 | 39.20 |
| ATOM | 95 | C | LEU | 167 | 55.636 | 23.532 | 7.902 | 1.00 | 22.19 |
| ATOM | 96 | O | LEU | 167 | 55.671 | 24.700 | 8.302 | 1.00 | 29.51 |
| ATOM | 97 | N | ILE | 168 | 56.610 | 22.957 | 7.206 | 1.00 | 15.01 |
| ATOM | 98 | CA | ILE | 168 | 57.846 | 23.632 | 6.833 | 1.00 | 18.03 |
| ATOM | 99 | CB | ILE | 168 | 58.756 | 22.668 | 6.040 | 1.00 | 11.37 |
| ATOM | 100 | CG2 | ILE | 168 | 59.890 | 23.413 | 5.367 | 1.00 | 16.36 |
| ATOM | 101 | CG1 | ILE | 168 | 59.289 | 21.580 | 6.975 | 1.00 | 21.63 |

FIG. 28A-3

| ATOM | 102 | CD1 | ILE | 168 | 60.095 | 20.501 | 6.287 | 1.00 | 21.03 |
|---|---|---|---|---|---|---|---|---|---|
| ATOM | 103 | C | ILE | 168 | 57.579 | 24.897 | 6.022 | 1.00 | 22.54 |
| ATOM | 104 | O | ILE | 168 | 58.155 | 25.948 | 6.300 | 1.00 | 24.88 |
| ATOM | 105 | N | HIS | 169 | 56.682 | 24.800 | 5.045 | 1.00 | 25.70 |
| ATOM | 106 | CA | HIS | 169 | 56.337 | 25.934 | 4.190 | 1.00 | 21.28 |
| ATOM | 107 | CB | HIS | 169 | 55.411 | 25.493 | 3.057 | 1.00 | 22.29 |
| ATOM | 108 | CG | HIS | 169 | 56.047 | 24.543 | 2.091 | 1.00 | 23.11 |
| ATOM | 109 | CD2 | HIS | 169 | 57.348 | 24.265 | 1.839 | 1.00 | 16.86 |
| ATOM | 110 | ND1 | HIS | 169 | 55.312 | 23.721 | 1.263 | 1.00 | 25.30 |
| ATOM | 111 | CE1 | HIS | 169 | 56.130 | 22.974 | 0.546 | 1.00 | 15.89 |
| ATOM | 112 | NE2 | HIS | 169 | 57.371 | 23.283 | 0.878 | 1.00 | 25.38 |
| ATOM | 113 | C | HIS | 169 | 55.664 | 27.048 | 4.976 | 1.00 | 18.32 |
| ATOM | 114 | O | HIS | 169 | 56.033 | 28.215 | 4.842 | 1.00 | 21.53 |
| ATOM | 115 | N | VAL | 170 | 54.679 | 26.685 | 5.795 | 1.00 | 17.13 |
| ATOM | 116 | CA | VAL | 170 | 53.957 | 27.661 | 6.607 | 1.00 | 21.29 |
| ATOM | 117 | CB | VAL | 170 | 52.808 | 26.991 | 7.399 | 1.00 | 24.33 |
| ATOM | 118 | CG1 | VAL | 170 | 52.164 | 27.985 | 8.354 | 1.00 | 23.78 |
| ATOM | 119 | CG2 | VAL | 170 | 51.760 | 26.439 | 6.435 | 1.00 | 18.87 |
| ATOM | 120 | C | VAL | 170 | 54.910 | 28.382 | 7.567 | 1.00 | 24.69 |
| ATOM | 121 | O | VAL | 170 | 54.912 | 29.616 | 7.637 | 1.00 | 28.77 |
| ATOM | 122 | N | ALA | 171 | 55.759 | 27.609 | 8.245 | 1.00 | 20.35 |
| ATOM | 123 | CA | ALA | 171 | 56.722 | 28.148 | 9.202 | 1.00 | 19.61 |
| ATOM | 124 | CB | ALA | 171 | 57.393 | 27.013 | 9.977 | 1.00 | 17.52 |
| ATOM | 125 | C | ALA | 171 | 57.775 | 29.026 | 8.531 | 1.00 | 20.91 |
| ATOM | 126 | O | ALA | 171 | 58.102 | 30.105 | 9.041 | 1.00 | 21.98 |
| ATOM | 127 | N | THR | 172 | 58.308 | 28.571 | 7.398 | 1.00 | 18.94 |
| ATOM | 128 | CA | THR | 172 | 59.313 | 29.342 | 6.668 | 1.00 | 19.55 |
| ATOM | 129 | CB | THR | 172 | 59.820 | 28.594 | 5.413 | 1.00 | 20.49 |
| ATOM | 130 | OG1 | THR | 172 | 60.394 | 27.336 | 5.795 | 1.00 | 20.66 |
| ATOM | 131 | CG2 | THR | 172 | 60.894 | 29.418 | 4.702 | 1.00 | 20.44 |
| ATOM | 132 | C | THR | 172 | 58.730 | 30.697 | 6.254 | 1.00 | 23.26 |
| ATOM | 133 | O | THR | 172 | 59.403 | 31.724 | 6.334 | 1.00 | 24.32 |
| ATOM | 134 | N | GLU | 173 | 57.468 | 30.694 | 5.836 | 1.00 | 27.42 |
| ATOM | 135 | CA | GLU | 173 | 56.797 | 31.922 | 5.434 | 1.00 | 27.68 |
| ATOM | 136 | CB | GLU | 173 | 55.477 | 31.605 | 4.728 | 1.00 | 24.51 |
| ATOM | 137 | CG | GLU | 173 | 54.652 | 32.836 | 4.338 | 1.00 | 39.69 |
| ATOM | 138 | CD | GLU | 173 | 55.396 | 33.814 | 3.426 | 1.00 | 47.72 |
| ATOM | 139 | OE1 | GLU | 173 | 55.019 | 35.009 | 3.417 | 1.00 | 48.26 |
| ATOM | 140 | OE2 | GLU | 173 | 56.344 | 33.398 | 2.717 | 1.00 | 49.61 |
| ATOM | 141 | C | GLU | 173 | 56.557 | 32.834 | 6.641 | 1.00 | 25.68 |
| ATOM | 142 | O | GLU | 173 | 56.773 | 34.046 | 6.559 | 1.00 | 23.39 |
| ATOM | 143 | N | ALA | 174 | 56.119 | 32.245 | 7.755 | 1.00 | 25.19 |
| ATOM | 144 | CA | ALA | 174 | 55.863 | 32.989 | 8.993 | 1.00 | 22.25 |
| ATOM | 145 | CB | ALA | 174 | 55.450 | 32.030 | 10.111 | 1.00 | 15.95 |
| ATOM | 146 | C | ALA | 174 | 57.125 | 33.747 | 9.391 | 1.00 | 23.22 |
| ATOM | 147 | O | ALA | 174 | 57.076 | 34.918 | 9.768 | 1.00 | 24.52 |

FIG. 28A-4

| ATOM | 148 | N   | HIS | 175 | 58.261 | 33.073 | 9.275  | 1.00 | 20.97 |
| ---- | --- | --- | --- | --- | ------ | ------ | ------ | ---- | ----- |
| ATOM | 149 | CA  | HIS | 175 | 59.544 | 33.665 | 9.606  | 1.00 | 19.55 |
| ATOM | 150 | CB  | HIS | 175 | 60.625 | 32.577 | 9.649  | 1.00 | 16.19 |
| ATOM | 151 | CG  | HIS | 175 | 62.016 | 33.104 | 9.835  | 1.00 | 18.89 |
| ATOM | 152 | CD2 | HIS | 175 | 63.148 | 32.901 | 9.119  | 1.00 | 16.05 |
| ATOM | 153 | ND1 | HIS | 175 | 62.359 | 33.962 | 10.859 | 1.00 | 13.83 |
| ATOM | 154 | CE1 | HIS | 175 | 63.642 | 34.265 | 10.765 | 1.00 | 15.87 |
| ATOM | 155 | NE2 | HIS | 175 | 64.143 | 33.635 | 9.718  | 1.00 | 19.19 |
| ATOM | 156 | C   | HIS | 175 | 59.934 | 34.757 | 8.617  | 1.00 | 21.28 |
| ATOM | 157 | O   | HIS | 175 | 60.274 | 35.869 | 9.014  | 1.00 | 25.12 |
| ATOM | 158 | N   | ARG | 176 | 59.891 | 34.436 | 7.329  | 1.00 | 26.73 |
| ATOM | 159 | CA  | ARG | 176 | 60.266 | 35.387 | 6.292  | 1.00 | 27.13 |
| ATOM | 160 | CB  | ARG | 176 | 60.156 | 34.748 | 4.914  | 1.00 | 36.00 |
| ATOM | 161 | CG  | ARG | 176 | 61.286 | 33.795 | 4.602  | 1.00 | 43.20 |
| ATOM | 162 | CD  | ARG | 176 | 61.197 | 33.334 | 3.170  | 1.00 | 50.07 |
| ATOM | 163 | NE  | ARG | 176 | 62.316 | 32.477 | 2.813  | 1.00 | 58.20 |
| ATOM | 164 | CZ  | ARG | 176 | 62.266 | 31.548 | 1.867  | 1.00 | 67.22 |
| ATOM | 165 | NH1 | ARG | 176 | 61.143 | 31.358 | 1.182  | 1.00 | 67.62 |
| ATOM | 166 | NH2 | ARG | 176 | 63.336 | 30.806 | 1.612  | 1.00 | 70.56 |
| ATOM | 167 | C   | ARG | 176 | 59.487 | 36.688 | 6.325  | 1.00 | 23.97 |
| ATOM | 168 | O   | ARG | 176 | 60.073 | 37.760 | 6.209  | 1.00 | 24.52 |
| ATOM | 169 | N   | SER | 177 | 58.177 | 36.598 | 6.515  | 1.00 | 23.60 |
| ATOM | 170 | CA  | SER | 177 | 57.341 | 37.789 | 6.565  | 1.00 | 26.36 |
| ATOM | 171 | CB  | SER | 177 | 55.865 | 37.407 | 6.439  | 1.00 | 21.93 |
| ATOM | 172 | OG  | SER | 177 | 55.495 | 36.459 | 7.423  | 1.00 | 25.97 |
| ATOM | 173 | C   | SER | 177 | 57.557 | 38.623 | 7.829  | 1.00 | 28.76 |
| ATOM | 174 | O   | SER | 177 | 57.084 | 39.761 | 7.907  | 1.00 | 33.09 |
| ATOM | 175 | N   | THR | 178 | 58.257 | 38.062 | 8.815  | 1.00 | 25.52 |
| ATOM | 176 | CA  | THR | 178 | 58.508 | 38.772 | 10.064 | 1.00 | 18.93 |
| ATOM | 177 | CB  | THR | 178 | 57.828 | 38.064 | 11.258 | 1.00 | 21.81 |
| ATOM | 178 | OG1 | THR | 178 | 58.348 | 36.736 | 11.394 | 1.00 | 24.18 |
| ATOM | 179 | CG2 | THR | 178 | 56.330 | 37.971 | 11.032 | 1.00 | 13.81 |
| ATOM | 180 | C   | THR | 178 | 59.993 | 38.967 | 10.358 | 1.00 | 20.69 |
| ATOM | 181 | O   | THR | 178 | 60.373 | 39.407 | 11.448 | 1.00 | 20.56 |
| ATOM | 182 | N   | ASN | 179 | 60.837 | 38.645 | 9.385  | 1.00 | 23.68 |
| ATOM | 183 | CA  | ASN | 179 | 62.275 | 38.802 | 9.555  | 1.00 | 28.22 |
| ATOM | 184 | CB  | ASN | 179 | 63.022 | 37.627 | 8.927  | 1.00 | 27.45 |
| ATOM | 185 | CG  | ASN | 179 | 64.460 | 37.529 | 9.402  | 1.00 | 33.98 |
| ATOM | 186 | OD1 | ASN | 179 | 65.342 | 37.131 | 8.644  | 1.00 | 42.72 |
| ATOM | 187 | ND2 | ASN | 179 | 64.702 | 37.865 | 10.667 | 1.00 | 31.14 |
| ATOM | 188 | C   | ASN | 179 | 62.689 | 40.115 | 8.902  | 1.00 | 34.47 |
| ATOM | 189 | O   | ASN | 179 | 62.832 | 40.200 | 7.678  | 1.00 | 36.54 |
| ATOM | 190 | N   | ALA | 180 | 62.874 | 41.135 | 9.735  | 1.00 | 37.39 |
| ATOM | 191 | CA  | ALA | 180 | 63.235 | 42.479 | 9.292  | 1.00 | 33.71 |
| ATOM | 192 | CB  | ALA | 180 | 63.555 | 43.352 | 10.494 | 1.00 | 31.57 |
| ATOM | 193 | C   | ALA | 180 | 64.375 | 42.545 | 8.284  | 1.00 | 37.87 |

FIG. 28A-5

| ATOM | 194 | O   | ALA | 180 | 65.458 | 42.018 | 8.525 | 1.00 | 35.26 |
|------|-----|-----|-----|-----|--------|--------|-------|------|-------|
| ATOM | 195 | N   | GLN | 181 | 64.095 | 43.187 | 7.150 | 1.00 | 40.55 |
| ATOM | 196 | CA  | GLN | 181 | 65.049 | 43.391 | 6.057 | 1.00 | 42.95 |
| ATOM | 197 | CB  | GLN | 181 | 66.344 | 44.043 | 6.570 | 1.00 | 45.47 |
| ATOM | 198 | CG  | GLN | 181 | 66.144 | 45.326 | 7.383 | 1.00 | 52.70 |
| ATOM | 199 | CD  | GLN | 181 | 65.351 | 46.399 | 6.650 | 1.00 | 55.03 |
| ATOM | 200 | OE1 | GLN | 181 | 65.270 | 46.412 | 5.421 | 1.00 | 59.56 |
| ATOM | 201 | NE2 | GLN | 181 | 64.757 | 47.308 | 7.411 | 1.00 | 54.39 |
| ATOM | 202 | C   | GLN | 181 | 65.391 | 42.176 | 5.197 | 1.00 | 44.27 |
| ATOM | 203 | O   | GLN | 181 | 66.181 | 42.291 | 4.251 | 1.00 | 46.47 |
| ATOM | 204 | N   | GLY | 182 | 64.797 | 41.025 | 5.508 | 1.00 | 42.17 |
| ATOM | 205 | CA  | GLY | 182 | 65.054 | 39.815 | 4.742 | 1.00 | 42.63 |
| ATOM | 206 | C   | GLY | 182 | 66.522 | 39.584 | 4.427 | 1.00 | 47.40 |
| ATOM | 207 | O   | GLY | 182 | 67.382 | 39.691 | 5.306 | 1.00 | 49.38 |
| ATOM | 208 | N   | SER | 183 | 66.816 | 39.297 | 3.163 | 1.00 | 49.46 |
| ATOM | 209 | CA  | SER | 183 | 68.189 | 39.061 | 2.733 | 1.00 | 54.13 |
| ATOM | 210 | CB  | SER | 183 | 68.208 | 38.225 | 1.449 | 1.00 | 55.08 |
| ATOM | 211 | OG  | SER | 183 | 67.197 | 38.647 | 0.546 | 1.00 | 63.54 |
| ATOM | 212 | C   | SER | 183 | 68.949 | 40.369 | 2.532 | 1.00 | 54.84 |
| ATOM | 213 | O   | SER | 183 | 70.175 | 40.373 | 2.407 | 1.00 | 56.90 |
| ATOM | 214 | N   | HIS | 184 | 68.223 | 41.482 | 2.535 | 1.00 | 55.77 |
| ATOM | 215 | CA  | HIS | 184 | 68.854 | 42.775 | 2.342 | 1.00 | 57.78 |
| ATOM | 216 | C   | HIS | 184 | 69.605 | 43.296 | 3.556 | 1.00 | 59.09 |
| ATOM | 217 | O   | HIS | 184 | 70.312 | 44.301 | 3.454 | 1.00 | 60.34 |
| ATOM | 218 | N   | TRP | 185 | 69.502 | 42.597 | 4.686 | 1.00 | 55.60 |
| ATOM | 219 | CA  | TRP | 185 | 70.159 | 43.020 | 5.923 | 1.00 | 53.73 |
| ATOM | 220 | CB  | TRP | 185 | 69.973 | 41.973 | 7.030 | 1.00 | 50.40 |
| ATOM | 221 | CG  | TRP | 185 | 70.746 | 40.694 | 6.837 | 1.00 | 48.09 |
| ATOM | 222 | CD2 | TRP | 185 | 72.091 | 40.419 | 7.269 | 1.00 | 47.38 |
| ATOM | 223 | CE2 | TRP | 185 | 72.390 | 39.094 | 6.888 | 1.00 | 40.29 |
| ATOM | 224 | CE3 | TRP | 185 | 73.071 | 41.169 | 7.937 | 1.00 | 45.43 |
| ATOM | 225 | CD1 | TRP | 185 | 70.301 | 39.554 | 6.234 | 1.00 | 49.87 |
| ATOM | 226 | NE1 | TRP | 185 | 71.280 | 38.589 | 6.262 | 1.00 | 48.02 |
| ATOM | 227 | CZ2 | TRP | 185 | 73.628 | 38.496 | 7.154 | 1.00 | 38.65 |
| ATOM | 228 | CZ3 | TRP | 185 | 74.304 | 40.573 | 8.201 | 1.00 | 43.26 |
| ATOM | 229 | CH2 | TRP | 185 | 74.570 | 39.250 | 7.807 | 1.00 | 40.00 |
| ATOM | 230 | C   | TRP | 185 | 71.638 | 43.386 | 5.800 | 1.00 | 55.99 |
| ATOM | 231 | O   | TRP | 185 | 72.089 | 44.359 | 6.401 | 1.00 | 52.84 |
| ATOM | 232 | N   | LYS | 186 | 72.389 | 42.614 | 5.021 | 1.00 | 59.15 |
| ATOM | 233 | CA  | LYS | 186 | 73.818 | 42.863 | 4.843 | 1.00 | 64.01 |
| ATOM | 234 | CB  | LYS | 186 | 74.466 | 41.688 | 4.091 | 1.00 | 64.67 |
| ATOM | 235 | CG  | LYS | 186 | 75.943 | 41.868 | 3.729 | 1.00 | 65.58 |
| ATOM | 236 | CD  | LYS | 186 | 76.817 | 42.181 | 4.946 | 1.00 | 62.03 |
| ATOM | 237 | CE  | LYS | 186 | 78.238 | 42.512 | 4.515 | 1.00 | 61.52 |
| ATOM | 238 | NZ  | LYS | 186 | 78.988 | 43.243 | 5.579 | 1.00 | 61.67 |
| ATOM | 239 | C   | LYS | 186 | 74.131 | 44.203 | 4.160 | 1.00 | 67.49 |

FIG. 28A-6

| ATOM | 240 | O | LYS | 186 | 75.164 | 44.816 | 4.432 | 1.00 | 68.66 |
|---|---|---|---|---|---|---|---|---|---|
| ATOM | 241 | N | GLN | 187 | 73.221 | 44.678 | 3.316 | 1.00 | 68.99 |
| ATOM | 242 | CA | GLN | 187 | 73.431 | 45.939 | 2.612 | 1.00 | 69.65 |
| ATOM | 243 | CB | GLN | 187 | 72.880 | 45.867 | 1.180 | 1.00 | 73.76 |
| ATOM | 244 | CG | GLN | 187 | 73.632 | 44.935 | 0.237 | 1.00 | 78.61 |
| ATOM | 245 | CD | GLN | 187 | 73.368 | 43.471 | 0.525 | 1.00 | 84.96 |
| ATOM | 246 | OE1 | GLN | 187 | 74.203 | 42.782 | 1.109 | 1.00 | 87.73 |
| ATOM | 247 | NE2 | GLN | 187 | 72.197 | 42.989 | 0.122 | 1.00 | 84.98 |
| ATOM | 248 | C | GLN | 187 | 72.817 | 47.141 | 3.323 | 1.00 | 69.16 |
| ATOM | 249 | O | GLN | 187 | 73.379 | 48.235 | 3.299 | 1.00 | 71.39 |
| ATOM | 250 | N | ARG | 188 | 71.666 | 46.936 | 3.953 | 1.00 | 65.82 |
| ATOM | 251 | CA | ARG | 188 | 70.961 | 48.014 | 4.639 | 1.00 | 65.00 |
| ATOM | 252 | CB | ARG | 188 | 69.458 | 47.739 | 4.591 | 1.00 | 66.20 |
| ATOM | 253 | CG | ARG | 188 | 68.957 | 47.483 | 3.181 | 1.00 | 70.30 |
| ATOM | 254 | CD | ARG | 188 | 67.463 | 47.212 | 3.132 | 1.00 | 78.59 |
| ATOM | 255 | NE | ARG | 188 | 67.003 | 47.008 | 1.760 | 1.00 | 87.71 |
| ATOM | 256 | CZ | ARG | 188 | 67.011 | 47.946 | 0.814 | 1.00 | 94.10 |
| ATOM | 257 | NH1 | ARG | 188 | 67.453 | 49.171 | 1.081 | 1.00 | 97.26 |
| ATOM | 258 | NH2 | ARG | 188 | 66.589 | 47.657 | -0.409 | 1.00 | 94.07 |
| ATOM | 259 | C | ARG | 188 | 71.409 | 48.286 | 6.077 | 1.00 | 65.39 |
| ATOM | 260 | O | ARG | 188 | 70.900 | 49.201 | 6.727 | 1.00 | 65.20 |
| ATOM | 261 | N | ARG | 189 | 72.372 | 47.506 | 6.561 | 1.00 | 64.28 |
| ATOM | 262 | CA | ARG | 189 | 72.882 | 47.654 | 7.922 | 1.00 | 60.75 |
| ATOM | 263 | CB | ARG | 189 | 73.691 | 46.409 | 8.321 | 1.00 | 56.87 |
| ATOM | 264 | CG | ARG | 189 | 75.050 | 46.308 | 7.630 | 1.00 | 59.52 |
| ATOM | 265 | CD | ARG | 189 | 75.580 | 44.891 | 7.589 | 1.00 | 55.86 |
| ATOM | 266 | NE | ARG | 189 | 75.874 | 44.348 | 8.907 | 1.00 | 55.48 |
| ATOM | 267 | CZ | ARG | 189 | 77.055 | 43.849 | 9.257 | 1.00 | 61.38 |
| ATOM | 268 | NH1 | ARG | 189 | 78.057 | 43.832 | 8.388 | 1.00 | 62.54 |
| ATOM | 269 | NH2 | ARG | 189 | 77.225 | 43.328 | 10.465 | 1.00 | 62.20 |
| ATOM | 270 | C | ARG | 189 | 73.747 | 48.907 | 8.082 | 1.00 | 60.91 |
| ATOM | 271 | O | ARG | 189 | 74.548 | 49.245 | 7.207 | 1.00 | 60.67 |
| ATOM | 272 | N | LYS | 190 | 73.575 | 49.591 | 9.207 | 1.00 | 59.06 |
| ATOM | 273 | CA | LYS | 190 | 74.340 | 50.790 | 9.521 | 1.00 | 55.00 |
| ATOM | 274 | CB | LYS | 190 | 73.423 | 52.008 | 9.582 | 1.00 | 55.45 |
| ATOM | 275 | C | LYS | 190 | 74.991 | 50.542 | 10.875 | 1.00 | 51.52 |
| ATOM | 276 | O | LYS | 190 | 74.320 | 50.144 | 11.830 | 1.00 | 51.68 |
| ATOM | 277 | N | PHE | 191 | 76.304 | 50.721 | 10.944 | 1.00 | 50.49 |
| ATOM | 278 | CA | PHE | 191 | 77.037 | 50.508 | 12.186 | 1.00 | 50.17 |
| ATOM | 279 | CB | PHE | 191 | 78.546 | 50.571 | 11.943 | 1.00 | 48.38 |
| ATOM | 280 | CG | PHE | 191 | 79.090 | 49.423 | 11.142 | 1.00 | 49.66 |
| ATOM | 281 | CD1 | PHE | 191 | 78.873 | 49.348 | 9.768 | 1.00 | 51.03 |
| ATOM | 282 | CD2 | PHE | 191 | 79.845 | 48.429 | 11.759 | 1.00 | 46.28 |
| ATOM | 283 | CE1 | PHE | 191 | 79.403 | 48.298 | 9.018 | 1.00 | 51.35 |
| ATOM | 284 | CE2 | PHE | 191 | 80.379 | 47.377 | 11.021 | 1.00 | 47.26 |
| ATOM | 285 | CZ | PHE | 191 | 80.158 | 47.311 | 9.646 | 1.00 | 48.48 |

FIG. 28A-7

| ATOM | 286 | C | PHE | 191 | 76.663 | 51.534 | 13.248 | 1.00 | 48.61 |
|---|---|---|---|---|---|---|---|---|---|
| ATOM | 287 | O | PHE | 191 | 76.507 | 52.720 | 12.952 | 1.00 | 50.38 |
| ATOM | 288 | N | LEU | 192 | 76.488 | 51.068 | 14.479 | 1.00 | 47.31 |
| ATOM | 289 | CA | LEU | 192 | 76.169 | 51.958 | 15.584 | 1.00 | 42.72 |
| ATOM | 290 | CB | LEU | 192 | 75.845 | 51.151 | 16.844 | 1.00 | 36.66 |
| ATOM | 291 | CG | LEU | 192 | 75.397 | 51.949 | 18.068 | 1.00 | 31.01 |
| ATOM | 292 | CD1 | LEU | 192 | 74.048 | 52.590 | 17.786 | 1.00 | 28.37 |
| ATOM | 293 | CD2 | LEU | 192 | 75.318 | 51.043 | 19.289 | 1.00 | 29.60 |
| ATOM | 294 | C | LEU | 192 | 77.447 | 52.760 | 15.800 | 1.00 | 42.28 |
| ATOM | 295 | O | LEU | 192 | 78.528 | 52.179 | 15.932 | 1.00 | 39.71 |
| ATOM | 296 | N | PRO | 193 | 77.350 | 54.104 | 15.781 | 1.00 | 45.15 |
| ATOM | 297 | CD | PRO | 193 | 76.095 | 54.865 | 15.617 | 1.00 | 43.82 |
| ATOM | 298 | CA | PRO | 193 | 78.493 | 55.006 | 15.973 | 1.00 | 43.14 |
| ATOM | 299 | CB | PRO | 193 | 77.820 | 56.306 | 16.400 | 1.00 | 44.37 |
| ATOM | 300 | CG | PRO | 193 | 76.571 | 56.308 | 15.565 | 1.00 | 41.66 |
| ATOM | 301 | C | PRO | 193 | 79.476 | 54.498 | 17.028 | 1.00 | 43.34 |
| ATOM | 302 | O | PRO | 193 | 79.103 | 54.296 | 18.182 | 1.00 | 45.18 |
| ATOM | 303 | N | ASP | 194 | 80.732 | 54.317 | 16.628 | 1.00 | 44.22 |
| ATOM | 304 | CA | ASP | 194 | 81.781 | 53.804 | 17.512 | 1.00 | 47.20 |
| ATOM | 305 | CB | ASP | 194 | 83.108 | 53.732 | 16.761 | 1.00 | 41.89 |
| ATOM | 306 | C | ASP | 194 | 81.962 | 54.511 | 18.866 | 1.00 | 51.99 |
| ATOM | 307 | O | ASP | 194 | 82.636 | 53.986 | 19.752 | 1.00 | 54.04 |
| ATOM | 308 | N | ASP | 195 | 81.381 | 55.698 | 19.025 | 1.00 | 55.21 |
| ATOM | 309 | CA | ASP | 195 | 81.489 | 56.428 | 20.288 | 1.00 | 57.50 |
| ATOM | 310 | CB | ASP | 195 | 81.423 | 57.948 | 20.061 | 1.00 | 60.04 |
| ATOM | 311 | CG | ASP | 195 | 80.123 | 58.398 | 19.406 | 1.00 | 68.39 |
| ATOM | 312 | OD1 | ASP | 195 | 79.211 | 58.847 | 20.136 | 1.00 | 69.46 |
| ATOM | 313 | OD2 | ASP | 195 | 80.020 | 58.322 | 18.162 | 1.00 | 72.91 |
| ATOM | 314 | C | ASP | 195 | 80.410 | 55.976 | 21.280 | 1.00 | 58.05 |
| ATOM | 315 | O | ASP | 195 | 80.540 | 56.180 | 22.491 | 1.00 | 58.97 |
| ATOM | 316 | N | ILE | 196 | 79.349 | 55.363 | 20.759 | 1.00 | 56.06 |
| ATOM | 317 | CA | ILE | 196 | 78.247 | 54.863 | 21.580 | 1.00 | 50.48 |
| ATOM | 318 | CB | ILE | 196 | 76.930 | 54.762 | 20.766 | 1.00 | 45.82 |
| ATOM | 319 | CG2 | ILE | 196 | 75.818 | 54.166 | 21.621 | 1.00 | 44.04 |
| ATOM | 320 | CG1 | ILE | 196 | 76.517 | 56.147 | 20.261 | 1.00 | 44.27 |
| ATOM | 321 | CD1 | ILE | 196 | 75.179 | 56.171 | 19.541 | 1.00 | 45.25 |
| ATOM | 322 | C | ILE | 196 | 78.603 | 53.484 | 22.135 | 1.00 | 47.66 |
| ATOM | 323 | O | ILE | 196 | 79.138 | 52.636 | 21.419 | 1.00 | 43.96 |
| ATOM | 324 | N | GLY | 197 | 78.309 | 53.269 | 23.414 | 1.00 | 46.29 |
| ATOM | 325 | CA | GLY | 197 | 78.608 | 51.995 | 24.045 | 1.00 | 48.03 |
| ATOM | 326 | C | GLY | 197 | 79.978 | 51.963 | 24.692 | 1.00 | 50.42 |
| ATOM | 327 | O | GLY | 197 | 80.463 | 50.902 | 25.070 | 1.00 | 46.66 |
| ATOM | 328 | N | GLN | 198 | 80.583 | 53.137 | 24.854 | 1.00 | 56.94 |
| ATOM | 329 | CA | GLN | 198 | 81.910 | 53.259 | 25.454 | 1.00 | 59.51 |
| ATOM | 330 | CB | GLN | 198 | 82.751 | 54.257 | 24.649 | 1.00 | 62.53 |
| ATOM | 331 | CG | GLN | 198 | 83.232 | 53.718 | 23.316 | 1.00 | 69.39 |

FIG. 28A-8

| ATOM | 332 | CD  | GLN | 198 | 84.088 | 52.484 | 23.483 | 1.00 | 76.76 |
| --- | --- | --- | --- | --- | --- | --- | --- | --- | --- |
| ATOM | 333 | OE1 | GLN | 198 | 83.745 | 51.399 | 22.996 | 1.00 | 81.73 |
| ATOM | 334 | NE2 | GLN | 198 | 85.205 | 52.632 | 24.192 | 1.00 | 78.09 |
| ATOM | 335 | C   | GLN | 198 | 81.915 | 53.678 | 26.922 | 1.00 | 57.56 |
| ATOM | 336 | O   | GLN | 198 | 82.946 | 53.584 | 27.588 | 1.00 | 57.71 |
| ATOM | 337 | N   | SER | 199 | 80.770 | 54.128 | 27.425 | 1.00 | 54.11 |
| ATOM | 338 | CA  | SER | 199 | 80.676 | 54.600 | 28.800 | 1.00 | 46.28 |
| ATOM | 339 | CB  | SER | 199 | 80.243 | 56.067 | 28.777 | 1.00 | 50.28 |
| ATOM | 340 | OG  | SER | 199 | 80.935 | 56.776 | 27.757 | 1.00 | 50.95 |
| ATOM | 341 | C   | SER | 199 | 79.776 | 53.805 | 29.757 | 1.00 | 40.19 |
| ATOM | 342 | O   | SER | 199 | 78.680 | 54.252 | 30.102 | 1.00 | 39.26 |
| ATOM | 343 | N   | PRO | 200 | 80.236 | 52.629 | 30.214 | 1.00 | 35.63 |
| ATOM | 344 | CD  | PRO | 200 | 81.530 | 52.011 | 29.904 | 1.00 | 34.88 |
| ATOM | 345 | CA  | PRO | 200 | 79.464 | 51.789 | 31.139 | 1.00 | 37.54 |
| ATOM | 346 | CB  | PRO | 200 | 80.223 | 50.457 | 31.124 | 1.00 | 29.86 |
| ATOM | 347 | CG  | PRO | 200 | 81.207 | 50.570 | 29.995 | 1.00 | 34.29 |
| ATOM | 348 | C   | PRO | 200 | 79.521 | 52.416 | 32.532 | 1.00 | 44.63 |
| ATOM | 349 | O   | PRO | 200 | 80.443 | 52.137 | 33.300 | 1.00 | 47.80 |
| ATOM | 350 | N   | ILE | 201 | 78.532 | 53.241 | 32.867 | 1.00 | 49.57 |
| ATOM | 351 | CA  | ILE | 201 | 78.525 | 53.924 | 34.158 | 1.00 | 49.15 |
| ATOM | 352 | CB  | ILE | 201 | 78.213 | 55.426 | 33.990 | 1.00 | 49.19 |
| ATOM | 353 | CG2 | ILE | 201 | 78.429 | 56.150 | 35.306 | 1.00 | 53.37 |
| ATOM | 354 | CG1 | ILE | 201 | 79.137 | 56.037 | 32.934 | 1.00 | 52.55 |
| ATOM | 355 | CD1 | ILE | 201 | 78.811 | 57.471 | 32.586 | 1.00 | 55.26 |
| ATOM | 356 | C   | ILE | 201 | 77.625 | 53.352 | 35.254 | 1.00 | 49.88 |
| ATOM | 357 | O   | ILE | 201 | 78.044 | 53.250 | 36.408 | 1.00 | 50.20 |
| ATOM | 358 | N   | VAL | 202 | 76.384 | 53.014 | 34.920 | 1.00 | 47.85 |
| ATOM | 359 | CA  | VAL | 202 | 75.468 | 52.474 | 35.927 | 1.00 | 45.76 |
| ATOM | 360 | CB  | VAL | 202 | 74.015 | 52.415 | 35.400 | 1.00 | 39.98 |
| ATOM | 361 | CG1 | VAL | 202 | 73.072 | 51.896 | 36.482 | 1.00 | 35.94 |
| ATOM | 362 | CG2 | VAL | 202 | 73.574 | 53.799 | 34.944 | 1.00 | 29.43 |
| ATOM | 363 | C   | VAL | 202 | 75.954 | 51.093 | 36.373 | 1.00 | 50.57 |
| ATOM | 364 | O   | VAL | 202 | 76.296 | 50.249 | 35.545 | 1.00 | 49.50 |
| ATOM | 365 | N   | SER | 203 | 76.009 | 50.876 | 37.683 | 1.00 | 54.82 |
| ATOM | 366 | CA  | SER | 203 | 76.490 | 49.609 | 38.223 | 1.00 | 59.26 |
| ATOM | 367 | CB  | SER | 203 | 77.067 | 49.809 | 39.628 | 1.00 | 64.88 |
| ATOM | 368 | OG  | SER | 203 | 76.127 | 50.428 | 40.492 | 1.00 | 75.47 |
| ATOM | 369 | C   | SER | 203 | 75.457 | 48.491 | 38.244 | 1.00 | 55.78 |
| ATOM | 370 | O   | SER | 203 | 74.285 | 48.712 | 38.544 | 1.00 | 57.50 |
| ATOM | 371 | N   | MET | 204 | 75.923 | 47.283 | 37.958 | 1.00 | 52.29 |
| ATOM | 372 | CA  | MET | 204 | 75.076 | 46.103 | 37.948 | 1.00 | 50.42 |
| ATOM | 373 | CB  | MET | 204 | 75.032 | 45.487 | 36.548 | 1.00 | 47.74 |
| ATOM | 374 | CG  | MET | 204 | 74.243 | 46.297 | 35.541 | 1.00 | 43.40 |
| ATOM | 375 | SD  | MET | 204 | 72.491 | 46.348 | 35.953 | 1.00 | 40.93 |
| ATOM | 376 | CE  | MET | 204 | 71.947 | 44.785 | 35.241 | 1.00 | 39.19 |
| ATOM | 377 | C   | MET | 204 | 75.670 | 45.107 | 38.925 | 1.00 | 49.42 |

FIG. 28A-9

| ATOM | 378 | O | MET | 204 | 76.892 | 45.020 | 39.062 | 1.00 | 52.25 |
|------|-----|-----|-----|-----|--------|--------|--------|------|-------|
| ATOM | 379 | N | PRO | 205 | 74.816 | 44.329 | 39.605 | 1.00 | 47.73 |
| ATOM | 380 | CD | PRO | 205 | 73.344 | 44.414 | 39.549 | 1.00 | 48.94 |
| ATOM | 381 | CA | PRO | 205 | 75.250 | 43.326 | 40.580 | 1.00 | 47.34 |
| ATOM | 382 | CB | PRO | 205 | 73.982 | 42.513 | 40.810 | 1.00 | 49.44 |
| ATOM | 383 | CG | PRO | 205 | 72.907 | 43.562 | 40.725 | 1.00 | 50.62 |
| ATOM | 384 | C | PRO | 205 | 76.431 | 42.442 | 40.168 | 1.00 | 47.12 |
| ATOM | 385 | O | PRO | 205 | 77.299 | 42.160 | 40.990 | 1.00 | 51.21 |
| ATOM | 386 | N | ASP | 206 | 76.487 | 42.023 | 38.909 | 1.00 | 48.81 |
| ATOM | 387 | CA | ASP | 206 | 77.583 | 41.160 | 38.465 | 1.00 | 49.88 |
| ATOM | 388 | CB | ASP | 206 | 77.128 | 40.223 | 37.330 | 1.00 | 54.06 |
| ATOM | 389 | CG | ASP | 206 | 76.598 | 40.967 | 36.107 | 1.00 | 57.34 |
| ATOM | 390 | OD1 | ASP | 206 | 77.056 | 42.095 | 35.811 | 1.00 | 52.21 |
| ATOM | 391 | OD2 | ASP | 206 | 75.719 | 40.397 | 35.423 | 1.00 | 59.16 |
| ATOM | 392 | C | ASP | 206 | 78.902 | 41.843 | 38.093 | 1.00 | 48.70 |
| ATOM | 393 | O | ASP | 206 | 79.862 | 41.171 | 37.715 | 1.00 | 49.75 |
| ATOM | 394 | N | GLY | 207 | 78.946 | 43.168 | 38.161 | 1.00 | 47.54 |
| ATOM | 395 | CA | GLY | 207 | 80.174 | 43.869 | 37.820 | 1.00 | 49.23 |
| ATOM | 396 | C | GLY | 207 | 80.169 | 44.585 | 36.482 | 1.00 | 51.96 |
| ATOM | 397 | O | GLY | 207 | 80.783 | 45.645 | 36.348 | 1.00 | 56.32 |
| ATOM | 398 | N | ASP | 208 | 79.510 | 44.005 | 35.481 | 1.00 | 52.50 |
| ATOM | 399 | CA | ASP | 208 | 79.435 | 44.624 | 34.157 | 1.00 | 48.00 |
| ATOM | 400 | CB | ASP | 208 | 78.968 | 43.609 | 33.115 | 1.00 | 53.23 |
| ATOM | 401 | CG | ASP | 208 | 80.038 | 42.592 | 32.774 | 1.00 | 53.17 |
| ATOM | 402 | OD1 | ASP | 208 | 81.130 | 43.006 | 32.335 | 1.00 | 57.42 |
| ATOM | 403 | OD2 | ASP | 208 | 79.787 | 41.380 | 32.942 | 1.00 | 55.64 |
| ATOM | 404 | C | ASP | 208 | 78.497 | 45.823 | 34.187 | 1.00 | 46.68 |
| ATOM | 405 | O | ASP | 208 | 77.283 | 45.671 | 34.332 | 1.00 | 45.81 |
| ATOM | 406 | N | LYS | 209 | 79.075 | 47.014 | 34.077 | 1.00 | 45.95 |
| ATOM | 407 | CA | LYS | 209 | 78.313 | 48.257 | 34.115 | 1.00 | 45.87 |
| ATOM | 408 | CB | LYS | 209 | 79.235 | 49.418 | 34.478 | 1.00 | 46.90 |
| ATOM | 409 | C | LYS | 209 | 77.561 | 48.546 | 32.812 | 1.00 | 41.17 |
| ATOM | 410 | O | LYS | 209 | 77.951 | 48.074 | 31.745 | 1.00 | 39.51 |
| ATOM | 411 | N | VAL | 210 | 76.500 | 49.344 | 32.916 | 1.00 | 39.35 |
| ATOM | 412 | CA | VAL | 210 | 75.652 | 49.713 | 31.782 | 1.00 | 38.03 |
| ATOM | 413 | CB | VAL | 210 | 74.136 | 49.584 | 32.140 | 1.00 | 32.13 |
| ATOM | 414 | CG1 | VAL | 210 | 73.269 | 49.926 | 30.937 | 1.00 | 27.92 |
| ATOM | 415 | CG2 | VAL | 210 | 73.818 | 48.183 | 32.627 | 1.00 | 29.43 |
| ATOM | 416 | C | VAL | 210 | 75.895 | 51.134 | 31.263 | 1.00 | 38.68 |
| ATOM | 417 | O | VAL | 210 | 76.090 | 52.079 | 32.038 | 1.00 | 39.57 |
| ATOM | 418 | N | ASP | 211 | 75.848 | 51.272 | 29.942 | 1.00 | 39.19 |
| ATOM | 419 | CA | ASP | 211 | 76.019 | 52.544 | 29.254 | 1.00 | 38.39 |
| ATOM | 420 | CB | ASP | 211 | 76.794 | 52.327 | 27.946 | 1.00 | 40.36 |
| ATOM | 421 | CG | ASP | 211 | 77.051 | 53.620 | 27.177 | 1.00 | 36.85 |
| ATOM | 422 | OD1 | ASP | 211 | 76.193 | 54.528 | 27.167 | 1.00 | 37.95 |
| ATOM | 423 | OD2 | ASP | 211 | 78.121 | 53.716 | 26.553 | 1.00 | 33.87 |

FIG. 28A-10

| ATOM | 424 | C | ASP | 211 | 74.601 | 53.040 | 28.958 | 1.00 | 40.60 |
|---|---|---|---|---|---|---|---|---|---|
| ATOM | 425 | O | ASP | 211 | 73.919 | 52.517 | 28.073 | 1.00 | 40.36 |
| ATOM | 426 | N | LEU | 212 | 74.185 | 54.074 | 29.680 | 1.00 | 41.55 |
| ATOM | 427 | CA | LEU | 212 | 72.854 | 54.664 | 29.552 | 1.00 | 38.39 |
| ATOM | 428 | CB | LEU | 212 | 72.759 | 55.883 | 30.467 | 1.00 | 40.93 |
| ATOM | 429 | CG | LEU | 212 | 71.575 | 55.979 | 31.428 | 1.00 | 45.32 |
| ATOM | 430 | CD1 | LEU | 212 | 71.271 | 54.626 | 32.047 | 1.00 | 43.83 |
| ATOM | 431 | CD2 | LEU | 212 | 71.900 | 57.007 | 32.502 | 1.00 | 44.93 |
| ATOM | 432 | C | LEU | 212 | 72.448 | 55.050 | 28.133 | 1.00 | 37.61 |
| ATOM | 433 | O | LEU | 212 | 71.318 | 54.805 | 27.719 | 1.00 | 33.71 |
| ATOM | 434 | N | GLU | 213 | 73.360 | 55.670 | 27.393 | 1.00 | 41.23 |
| ATOM | 435 | CA | GLU | 213 | 73.068 | 56.084 | 26.023 | 1.00 | 43.48 |
| ATOM | 436 | CB | GLU | 213 | 74.181 | 56.986 | 25.481 | 1.00 | 47.66 |
| ATOM | 437 | CG | GLU | 213 | 73.919 | 57.494 | 24.065 | 1.00 | 56.87 |
| ATOM | 438 | CD | GLU | 213 | 75.121 | 58.180 | 23.433 | 1.00 | 60.87 |
| ATOM | 439 | OE1 | GLU | 213 | 76.258 | 57.996 | 23.924 | 1.00 | 60.37 |
| ATOM | 440 | OE2 | GLU | 213 | 74.921 | 58.894 | 22.423 | 1.00 | 61.13 |
| ATOM | 441 | C | GLU | 213 | 72.889 | 54.880 | 25.102 | 1.00 | 39.29 |
| ATOM | 442 | O | GLU | 213 | 71.965 | 54.841 | 24.290 | 1.00 | 36.66 |
| ATOM | 443 | N | ALA | 214 | 73.785 | 53.906 | 25.233 | 1.00 | 36.33 |
| ATOM | 444 | CA | ALA | 214 | 73.739 | 52.693 | 24.422 | 1.00 | 34.89 |
| ATOM | 445 | CB | ALA | 214 | 74.946 | 51.817 | 24.711 | 1.00 | 30.70 |
| ATOM | 446 | C | ALA | 214 | 72.454 | 51.938 | 24.718 | 1.00 | 31.96 |
| ATOM | 447 | O | ALA | 214 | 71.739 | 51.523 | 23.804 | 1.00 | 33.93 |
| ATOM | 448 | N | PHE | 215 | 72.151 | 51.798 | 26.003 | 1.00 | 28.47 |
| ATOM | 449 | CA | PHE | 215 | 70.947 | 51.116 | 26.445 | 1.00 | 29.74 |
| ATOM | 450 | CB | PHE | 215 | 70.819 | 51.223 | 27.962 | 1.00 | 23.73 |
| ATOM | 451 | CG | PHE | 215 | 69.589 | 50.568 | 28.515 | 1.00 | 22.71 |
| ATOM | 452 | CD1 | PHE | 215 | 69.603 | 49.220 | 28.858 | 1.00 | 22.53 |
| ATOM | 453 | CD2 | PHE | 215 | 68.423 | 51.301 | 28.712 | 1.00 | 19.74 |
| ATOM | 454 | CE1 | PHE | 215 | 68.477 | 48.606 | 29.391 | 1.00 | 20.75 |
| ATOM | 455 | CE2 | PHE | 215 | 67.290 | 50.698 | 29.245 | 1.00 | 21.02 |
| ATOM | 456 | CZ | PHE | 215 | 67.318 | 49.346 | 29.586 | 1.00 | 19.50 |
| ATOM | 457 | C | PHE | 215 | 69.730 | 51.742 | 25.771 | 1.00 | 34.64 |
| ATOM | 458 | O | PHE | 215 | 68.872 | 51.034 | 25.239 | 1.00 | 39.86 |
| ATOM | 459 | N | SER | 216 | 69.677 | 53.071 | 25.771 | 1.00 | 34.78 |
| ATOM | 460 | CA | SER | 216 | 68.572 | 53.801 | 25.160 | 1.00 | 36.01 |
| ATOM | 461 | CB | SER | 216 | 68.762 | 55.302 | 25.366 | 1.00 | 37.36 |
| ATOM | 462 | OG | SER | 216 | 67.537 | 55.987 | 25.193 | 1.00 | 48.33 |
| ATOM | 463 | C | SER | 216 | 68.458 | 53.475 | 23.664 | 1.00 | 37.06 |
| ATOM | 464 | O | SER | 216 | 67.358 | 53.250 | 23.148 | 1.00 | 33.23 |
| ATOM | 465 | N | GLU | 217 | 69.601 | 53.410 | 22.986 | 1.00 | 36.25 |
| ATOM | 466 | CA | GLU | 217 | 69.645 | 53.091 | 21.562 | 1.00 | 36.99 |
| ATOM | 467 | CB | GLU | 217 | 71.092 | 53.104 | 21.064 | 1.00 | 37.10 |
| ATOM | 468 | CG | GLU | 217 | 71.682 | 54.491 | 20.912 | 1.00 | 44.30 |
| ATOM | 469 | CD | GLU | 217 | 71.016 | 55.284 | 19.802 | 1.00 | 51.30 |

FIG. 28A-11

| ATOM | 470 | OE1 | GLU | 217 | 71.439 | 55.142 | 18.633 | 1.00 | 57.25 |
|---|---|---|---|---|---|---|---|---|---|
| ATOM | 471 | OE2 | GLU | 217 | 70.070 | 56.046 | 20.096 | 1.00 | 52.50 |
| ATOM | 472 | C | GLU | 217 | 69.019 | 51.726 | 21.286 | 1.00 | 36.93 |
| ATOM | 473 | O | GLU | 217 | 68.191 | 51.577 | 20.381 | 1.00 | 41.06 |
| ATOM | 474 | N | PHE | 218 | 69.395 | 50.740 | 22.093 | 1.00 | 30.27 |
| ATOM | 475 | CA | PHE | 218 | 68.875 | 49.388 | 21.947 | 1.00 | 27.20 |
| ATOM | 476 | CB | PHE | 218 | 69.679 | 48.421 | 22.814 | 1.00 | 28.10 |
| ATOM | 477 | CG | PHE | 218 | 71.124 | 48.330 | 22.428 | 1.00 | 24.84 |
| ATOM | 478 | CD1 | PHE | 218 | 72.117 | 48.286 | 23.398 | 1.00 | 21.78 |
| ATOM | 479 | CD2 | PHE | 218 | 71.495 | 48.301 | 21.087 | 1.00 | 24.78 |
| ATOM | 480 | CE1 | PHE | 218 | 73.458 | 48.215 | 23.040 | 1.00 | 24.08 |
| ATOM | 481 | CE2 | PHE | 218 | 72.834 | 48.230 | 20.719 | 1.00 | 25.33 |
| ATOM | 482 | CZ | PHE | 218 | 73.818 | 48.187 | 21.697 | 1.00 | 25.04 |
| ATOM | 483 | C | PHE | 218 | 67.381 | 49.281 | 22.261 | 1.00 | 28.23 |
| ATOM | 484 | O | PHE | 218 | 66.639 | 48.605 | 21.543 | 1.00 | 33.52 |
| ATOM | 485 | N | THR | 219 | 66.927 | 49.961 | 23.310 | 1.00 | 27.24 |
| ATOM | 486 | CA | THR | 219 | 65.515 | 49.913 | 23.666 | 1.00 | 29.28 |
| ATOM | 487 | CB | THR | 219 | 65.238 | 50.533 | 25.052 | 1.00 | 30.97 |
| ATOM | 488 | OG1 | THR | 219 | 65.724 | 51.880 | 25.090 | 1.00 | 35.50 |
| ATOM | 489 | CG2 | THR | 219 | 65.901 | 49.712 | 26.149 | 1.00 | 30.78 |
| ATOM | 490 | C | THR | 219 | 64.660 | 50.612 | 22.615 | 1.00 | 33.29 |
| ATOM | 491 | O | THR | 219 | 63.473 | 50.317 | 22.474 | 1.00 | 36.85 |
| ATOM | 492 | N | LYS | 220 | 65.276 | 51.515 | 21.860 | 1.00 | 35.23 |
| ATOM | 493 | CA | LYS | 220 | 64.579 | 52.253 | 20.816 | 1.00 | 38.97 |
| ATOM | 494 | CB | LYS | 220 | 65.506 | 53.334 | 20.236 | 1.00 | 44.67 |
| ATOM | 495 | CG | LYS | 220 | 64.805 | 54.491 | 19.513 | 1.00 | 58.02 |
| ATOM | 496 | CD | LYS | 220 | 64.406 | 54.130 | 18.079 | 1.00 | 68.57 |
| ATOM | 497 | CE | LYS | 220 | 63.732 | 55.296 | 17.347 | 1.00 | 70.50 |
| ATOM | 498 | NZ | LYS | 220 | 62.395 | 55.668 | 17.905 | 1.00 | 66.08 |
| ATOM | 499 | C | LYS | 220 | 64.112 | 51.289 | 19.721 | 1.00 | 38.48 |
| ATOM | 500 | O | LYS | 220 | 63.021 | 51.446 | 19.173 | 1.00 | 37.18 |
| ATOM | 501 | N | ILE | 221 | 64.917 | 50.270 | 19.432 | 1.00 | 36.19 |
| ATOM | 502 | CA | ILE | 221 | 64.563 | 49.305 | 18.394 | 1.00 | 36.77 |
| ATOM | 503 | CB | ILE | 221 | 65.756 | 48.996 | 17.457 | 1.00 | 34.41 |
| ATOM | 504 | CG2 | ILE | 221 | 66.270 | 50.276 | 16.814 | 1.00 | 38.54 |
| ATOM | 505 | CG1 | ILE | 221 | 66.864 | 48.267 | 18.221 | 1.00 | 32.93 |
| ATOM | 506 | CD1 | ILE | 221 | 67.984 | 47.752 | 17.338 | 1.00 | 31.12 |
| ATOM | 507 | C | ILE | 221 | 64.002 | 47.971 | 18.888 | 1.00 | 38.22 |
| ATOM | 508 | O | ILE | 221 | 63.499 | 47.181 | 18.089 | 1.00 | 38.90 |
| ATOM | 509 | N | ILE | 222 | 64.048 | 47.719 | 20.191 | 1.00 | 35.75 |
| ATOM | 510 | CA | ILE | 222 | 63.557 | 46.446 | 20.702 | 1.00 | 31.77 |
| ATOM | 511 | CB | ILE | 222 | 64.086 | 46.152 | 22.130 | 1.00 | 33.14 |
| ATOM | 512 | CG2 | ILE | 222 | 63.203 | 46.813 | 23.183 | 1.00 | 24.60 |
| ATOM | 513 | CG1 | ILE | 222 | 64.147 | 44.638 | 22.350 | 1.00 | 32.60 |
| ATOM | 514 | CD1 | ILE | 222 | 64.860 | 44.226 | 23.609 | 1.00 | 34.52 |
| ATOM | 515 | C | ILE | 222 | 62.042 | 46.240 | 20.624 | 1.00 | 32.56 |

FIG. 28A-12

| ATOM | 516 | O | ILE | 222 | 61.581 | 45.109 | 20.452 | 1.00 | 35.74 |
| --- | --- | --- | --- | --- | --- | --- | --- | --- | --- |
| ATOM | 517 | N | THR | 223 | 61.262 | 47.313 | 20.720 | 1.00 | 29.43 |
| ATOM | 518 | CA | THR | 223 | 59.806 | 47.170 | 20.651 | 1.00 | 33.57 |
| ATOM | 519 | CB | THR | 223 | 59.075 | 48.514 | 20.903 | 1.00 | 38.99 |
| ATOM | 520 | OG1 | THR | 223 | 59.422 | 49.010 | 22.205 | 1.00 | 41.23 |
| ATOM | 521 | CG2 | THR | 223 | 57.558 | 48.325 | 20.836 | 1.00 | 36.98 |
| ATOM | 522 | C | THR | 223 | 59.355 | 46.528 | 19.325 | 1.00 | 31.45 |
| ATOM | 523 | O | THR | 223 | 58.571 | 45.571 | 19.334 | 1.00 | 26.77 |
| ATOM | 524 | N | PRO | 224 | 59.824 | 47.054 | 18.173 | 1.00 | 31.35 |
| ATOM | 525 | CD | PRO | 224 | 60.570 | 48.306 | 17.950 | 1.00 | 30.11 |
| ATOM | 526 | CA | PRO | 224 | 59.424 | 46.462 | 16.891 | 1.00 | 30.38 |
| ATOM | 527 | CB | PRO | 224 | 60.149 | 47.336 | 15.865 | 1.00 | 30.09 |
| ATOM | 528 | CG | PRO | 224 | 60.200 | 48.659 | 16.530 | 1.00 | 31.86 |
| ATOM | 529 | C | PRO | 224 | 59.882 | 45.007 | 16.795 | 1.00 | 29.51 |
| ATOM | 530 | O | PRO | 224 | 59.147 | 44.153 | 16.295 | 1.00 | 32.52 |
| ATOM | 531 | N | ALA | 225 | 61.090 | 44.734 | 17.285 | 1.00 | 22.63 |
| ATOM | 532 | CA | ALA | 225 | 61.650 | 43.385 | 17.268 | 1.00 | 20.88 |
| ATOM | 533 | CB | ALA | 225 | 63.046 | 43.386 | 17.862 | 1.00 | 20.57 |
| ATOM | 534 | C | ALA | 225 | 60.752 | 42.416 | 18.026 | 1.00 | 23.53 |
| ATOM | 535 | O | ALA | 225 | 60.455 | 41.323 | 17.544 | 1.00 | 25.07 |
| ATOM | 536 | N | ILE | 226 | 60.296 | 42.828 | 19.202 | 1.00 | 22.61 |
| ATOM | 537 | CA | ILE | 226 | 59.420 | 41.989 | 20.007 | 1.00 | 19.46 |
| ATOM | 538 | CB | ILE | 226 | 59.120 | 42.644 | 21.360 | 1.00 | 20.25 |
| ATOM | 539 | CG2 | ILE | 226 | 58.071 | 41.843 | 22.105 | 1.00 | 16.75 |
| ATOM | 540 | CG1 | ILE | 226 | 60.401 | 42.772 | 22.182 | 1.00 | 19.30 |
| ATOM | 541 | CD1 | ILE | 226 | 60.240 | 43.645 | 23.413 | 1.00 | 20.92 |
| ATOM | 542 | C | ILE | 226 | 58.112 | 41.768 | 19.251 | 1.00 | 21.28 |
| ATOM | 543 | O | ILE | 226 | 57.553 | 40.670 | 19.256 | 1.00 | 23.75 |
| ATOM | 544 | N | THR | 227 | 57.629 | 42.821 | 18.598 | 1.00 | 24.46 |
| ATOM | 545 | CA | THR | 227 | 56.393 | 42.752 | 17.826 | 1.00 | 25.81 |
| ATOM | 546 | CB | THR | 227 | 56.020 | 44.136 | 17.260 | 1.00 | 31.00 |
| ATOM | 547 | OG1 | THR | 227 | 55.772 | 45.039 | 18.345 | 1.00 | 35.43 |
| ATOM | 548 | CG2 | THR | 227 | 54.776 | 44.049 | 16.388 | 1.00 | 29.01 |
| ATOM | 549 | C | THR | 227 | 56.508 | 41.728 | 16.691 | 1.00 | 22.85 |
| ATOM | 550 | O | THR | 227 | 55.589 | 40.939 | 16.469 | 1.00 | 22.84 |
| ATOM | 551 | N | ARG | 228 | 57.647 | 41.713 | 16.004 | 1.00 | 16.09 |
| ATOM | 552 | CA | ARG | 228 | 57.862 | 40.765 | 14.919 | 1.00 | 16.97 |
| ATOM | 553 | CB | ARG | 228 | 59.161 | 41.064 | 14.174 | 1.00 | 14.71 |
| ATOM | 554 | CG | ARG | 228 | 59.137 | 42.369 | 13.391 | 1.00 | 16.22 |
| ATOM | 555 | CD | ARG | 228 | 60.309 | 42.447 | 12.422 | 1.00 | 20.90 |
| ATOM | 556 | NE | ARG | 228 | 61.595 | 42.207 | 13.078 | 1.00 | 24.94 |
| ATOM | 557 | CZ | ARG | 228 | 62.243 | 43.113 | 13.805 | 1.00 | 35.06 |
| ATOM | 558 | NH1 | ARG | 228 | 61.729 | 44.328 | 13.973 | 1.00 | 36.35 |
| ATOM | 559 | NH2 | ARG | 228 | 63.404 | 42.807 | 14.370 | 1.00 | 32.78 |
| ATOM | 560 | C | ARG | 228 | 57.866 | 39.326 | 15.431 | 1.00 | 21.63 |
| ATOM | 561 | O | ARG | 228 | 57.477 | 38.407 | 14.704 | 1.00 | 24.47 |

FIG. 28A-13

| ATOM | 562 | N   | VAL | 229 | 58.304 | 39.128 | 16.675 | 1.00 | 20.00 |
|------|-----|-----|-----|-----|--------|--------|--------|------|-------|
| ATOM | 563 | CA  | VAL | 229 | 58.319 | 37.793 | 17.266 | 1.00 | 18.39 |
| ATOM | 564 | CB  | VAL | 229 | 59.103 | 37.745 | 18.606 | 1.00 | 19.20 |
| ATOM | 565 | CG1 | VAL | 229 | 58.938 | 36.382 | 19.265 | 1.00 | 14.19 |
| ATOM | 566 | CG2 | VAL | 229 | 60.581 | 38.001 | 18.356 | 1.00 | 14.81 |
| ATOM | 567 | C   | VAL | 229 | 56.875 | 37.367 | 17.501 | 1.00 | 20.00 |
| ATOM | 568 | O   | VAL | 229 | 56.499 | 36.227 | 17.212 | 1.00 | 20.04 |
| ATOM | 569 | N   | VAL | 230 | 56.058 | 38.291 | 18.003 | 1.00 | 19.60 |
| ATOM | 570 | CA  | VAL | 230 | 54.651 | 37.996 | 18.247 | 1.00 | 18.72 |
| ATOM | 571 | CB  | VAL | 230 | 53.930 | 39.185 | 18.912 | 1.00 | 22.15 |
| ATOM | 572 | CG1 | VAL | 230 | 52.452 | 38.862 | 19.113 | 1.00 | 15.66 |
| ATOM | 573 | CG2 | VAL | 230 | 54.592 | 39.522 | 20.248 | 1.00 | 21.05 |
| ATOM | 574 | C   | VAL | 230 | 53.967 | 37.660 | 16.917 | 1.00 | 26.17 |
| ATOM | 575 | O   | VAL | 230 | 53.188 | 36.704 | 16.836 | 1.00 | 28.01 |
| ATOM | 576 | N   | ASP | 231 | 54.288 | 38.426 | 15.873 | 1.00 | 25.07 |
| ATOM | 577 | CA  | ASP | 231 | 53.714 | 38.216 | 14.542 | 1.00 | 26.10 |
| ATOM | 578 | CB  | ASP | 231 | 54.169 | 39.309 | 13.568 | 1.00 | 22.15 |
| ATOM | 579 | CG  | ASP | 231 | 53.620 | 40.684 | 13.921 | 1.00 | 29.49 |
| ATOM | 580 | OD1 | ASP | 231 | 52.587 | 40.767 | 14.624 | 1.00 | 30.93 |
| ATOM | 581 | OD2 | ASP | 231 | 54.223 | 41.687 | 13.481 | 1.00 | 31.74 |
| ATOM | 582 | C   | ASP | 231 | 54.087 | 36.842 | 13.989 | 1.00 | 27.35 |
| ATOM | 583 | O   | ASP | 231 | 53.245 | 36.154 | 13.408 | 1.00 | 25.89 |
| ATOM | 584 | N   | PHE | 232 | 55.347 | 36.451 | 14.175 | 1.00 | 24.29 |
| ATOM | 585 | CA  | PHE | 232 | 55.825 | 35.154 | 13.714 | 1.00 | 22.90 |
| ATOM | 586 | CB  | PHE | 232 | 57.302 | 34.956 | 14.090 | 1.00 | 20.56 |
| ATOM | 587 | CG  | PHE | 232 | 57.762 | 33.525 | 14.007 | 1.00 | 24.20 |
| ATOM | 588 | CD1 | PHE | 232 | 57.952 | 32.910 | 12.772 | 1.00 | 23.44 |
| ATOM | 589 | CD2 | PHE | 232 | 57.959 | 32.776 | 15.167 | 1.00 | 19.41 |
| ATOM | 590 | CE1 | PHE | 232 | 58.329 | 31.567 | 12.689 | 1.00 | 19.53 |
| ATOM | 591 | CE2 | PHE | 232 | 58.336 | 31.431 | 15.100 | 1.00 | 21.09 |
| ATOM | 592 | CZ  | PHE | 232 | 58.520 | 30.824 | 13.858 | 1.00 | 21.61 |
| ATOM | 593 | C   | PHE | 232 | 54.984 | 34.047 | 14.341 | 1.00 | 24.18 |
| ATOM | 594 | O   | PHE | 232 | 54.481 | 33.160 | 13.645 | 1.00 | 22.26 |
| ATOM | 595 | N   | ALA | 233 | 54.810 | 34.127 | 15.656 | 1.00 | 23.90 |
| ATOM | 596 | CA  | ALA | 233 | 54.048 | 33.128 | 16.397 | 1.00 | 22.60 |
| ATOM | 597 | CB  | ALA | 233 | 54.088 | 33.435 | 17.890 | 1.00 | 15.34 |
| ATOM | 598 | C   | ALA | 233 | 52.609 | 33.040 | 15.917 | 1.00 | 22.04 |
| ATOM | 599 | O   | ALA | 233 | 52.084 | 31.948 | 15.697 | 1.00 | 22.86 |
| ATOM | 600 | N   | LYS | 234 | 51.978 | 34.195 | 15.743 | 1.00 | 25.04 |
| ATOM | 601 | CA  | LYS | 234 | 50.593 | 34.248 | 15.298 | 1.00 | 27.68 |
| ATOM | 602 | CB  | LYS | 234 | 50.096 | 35.691 | 15.292 | 1.00 | 31.41 |
| ATOM | 603 | CG  | LYS | 234 | 49.845 | 36.248 | 16.682 | 1.00 | 40.37 |
| ATOM | 604 | CD  | LYS | 234 | 49.212 | 37.626 | 16.604 | 1.00 | 57.53 |
| ATOM | 605 | CE  | LYS | 234 | 48.772 | 38.112 | 17.974 | 1.00 | 64.28 |
| ATOM | 606 | NZ  | LYS | 234 | 48.164 | 39.473 | 17.904 | 1.00 | 67.19 |
| ATOM | 607 | C   | LYS | 234 | 50.358 | 33.588 | 13.939 | 1.00 | 26.42 |

FIG. 28A-14

| ATOM | 608 | O | LYS | 234 | 49.269 | 33.067 | 13.674 | 1.00 | 31.34 |
|---|---|---|---|---|---|---|---|---|---|
| ATOM | 609 | N | LYS | 235 | 51.382 | 33.588 | 13.093 | 1.00 | 24.38 |
| ATOM | 610 | CA | LYS | 235 | 51.278 | 32.985 | 11.770 | 1.00 | 26.42 |
| ATOM | 611 | CB | LYS | 235 | 52.244 | 33.664 | 10.805 | 1.00 | 24.92 |
| ATOM | 612 | CG | LYS | 235 | 51.908 | 35.127 | 10.583 | 1.00 | 22.41 |
| ATOM | 613 | CD | LYS | 235 | 52.843 | 35.775 | 9.588 | 1.00 | 29.38 |
| ATOM | 614 | CE | LYS | 235 | 52.481 | 37.234 | 9.395 | 1.00 | 33.49 |
| ATOM | 615 | NZ | LYS | 235 | 53.354 | 37.869 | 8.376 | 1.00 | 40.13 |
| ATOM | 616 | C | LYS | 235 | 51.470 | 31.469 | 11.759 | 1.00 | 30.02 |
| ATOM | 617 | O | LYS | 235 | 51.417 | 30.838 | 10.699 | 1.00 | 30.37 |
| ATOM | 618 | N | LEU | 236 | 51.722 | 30.889 | 12.930 | 1.00 | 32.39 |
| ATOM | 619 | CA | LEU | 236 | 51.878 | 29.443 | 13.053 | 1.00 | 36.24 |
| ATOM | 620 | CB | LEU | 236 | 52.944 | 29.080 | 14.089 | 1.00 | 29.91 |
| ATOM | 621 | CG | LEU | 236 | 54.373 | 29.516 | 13.765 | 1.00 | 24.69 |
| ATOM | 622 | CD1 | LEU | 236 | 55.299 | 29.054 | 14.877 | 1.00 | 22.71 |
| ATOM | 623 | CD2 | LEU | 236 | 54.811 | 28.942 | 12.427 | 1.00 | 24.48 |
| ATOM | 624 | C | LEU | 236 | 50.520 | 28.891 | 13.470 | 1.00 | 41.22 |
| ATOM | 625 | O | LEU | 236 | 49.936 | 29.333 | 14.467 | 1.00 | 41.45 |
| ATOM | 626 | N | PRO | 237 | 50.012 | 27.895 | 12.729 | 1.00 | 47.86 |
| ATOM | 627 | CD | PRO | 237 | 50.739 | 27.190 | 11.657 | 1.00 | 49.32 |
| ATOM | 628 | CA | PRO | 237 | 48.713 | 27.262 | 12.992 | 1.00 | 50.28 |
| ATOM | 629 | CB | PRO | 237 | 48.669 | 26.128 | 11.962 | 1.00 | 55.25 |
| ATOM | 630 | CG | PRO | 237 | 50.135 | 25.818 | 11.706 | 1.00 | 54.08 |
| ATOM | 631 | C | PRO | 237 | 48.495 | 26.751 | 14.422 | 1.00 | 47.94 |
| ATOM | 632 | O | PRO | 237 | 47.533 | 27.134 | 15.087 | 1.00 | 42.48 |
| ATOM | 633 | N | MET | 238 | 49.415 | 25.927 | 14.906 | 1.00 | 49.51 |
| ATOM | 634 | CA | MET | 238 | 49.306 | 25.354 | 16.245 | 1.00 | 53.49 |
| ATOM | 635 | CB | MET | 238 | 50.379 | 24.275 | 16.424 | 1.00 | 52.52 |
| ATOM | 636 | CG | MET | 238 | 50.028 | 22.959 | 15.728 | 1.00 | 56.00 |
| ATOM | 637 | SD | MET | 238 | 51.443 | 21.961 | 15.204 | 1.00 | 50.16 |
| ATOM | 638 | CE | MET | 238 | 50.896 | 21.440 | 13.552 | 1.00 | 55.71 |
| ATOM | 639 | C | MET | 238 | 49.352 | 26.362 | 17.395 | 1.00 | 54.20 |
| ATOM | 640 | O | MET | 238 | 48.930 | 26.058 | 18.515 | 1.00 | 54.72 |
| ATOM | 641 | N | PHE | 239 | 49.803 | 27.578 | 17.101 | 1.00 | 50.11 |
| ATOM | 642 | CA | PHE | 239 | 49.917 | 28.619 | 18.117 | 1.00 | 41.11 |
| ATOM | 643 | CB | PHE | 239 | 51.089 | 29.552 | 17.788 | 1.00 | 34.80 |
| ATOM | 644 | CG | PHE | 239 | 51.336 | 30.607 | 18.826 | 1.00 | 30.25 |
| ATOM | 645 | CD1 | PHE | 239 | 52.127 | 30.332 | 19.937 | 1.00 | 25.66 |
| ATOM | 646 | CD2 | PHE | 239 | 50.786 | 31.878 | 18.690 | 1.00 | 26.30 |
| ATOM | 647 | CE1 | PHE | 239 | 52.368 | 31.307 | 20.896 | 1.00 | 30.28 |
| ATOM | 648 | CE2 | PHE | 239 | 51.019 | 32.862 | 19.644 | 1.00 | 30.49 |
| ATOM | 649 | CZ | PHE | 239 | 51.813 | 32.576 | 20.750 | 1.00 | 29.00 |
| ATOM | 650 | C | PHE | 239 | 48.647 | 29.434 | 18.337 | 1.00 | 35.65 |
| ATOM | 651 | O | PHE | 239 | 48.151 | 29.521 | 19.457 | 1.00 | 30.27 |
| ATOM | 652 | N | SER | 240 | 48.133 | 30.037 | 17.272 | 1.00 | 36.49 |
| ATOM | 653 | CA | SER | 240 | 46.936 | 30.866 | 17.359 | 1.00 | 36.37 |

FIG. 28A-15

| ATOM | 654 | CB  | SER | 240 | 46.622 | 31.466 | 15.994 | 1.00 | 35.87 |
| ---- | --- | --- | --- | --- | ------ | ------ | ------ | ---- | ----- |
| ATOM | 655 | C   | SER | 240 | 45.707 | 30.145 | 17.936 | 1.00 | 40.37 |
| ATOM | 656 | O   | SER | 240 | 44.784 | 30.789 | 18.438 | 1.00 | 37.47 |
| ATOM | 657 | N   | GLU | 241 | 45.713 | 28.814 | 17.889 | 1.00 | 43.00 |
| ATOM | 658 | CA  | GLU | 241 | 44.605 | 28.004 | 18.404 | 1.00 | 46.31 |
| ATOM | 659 | CB  | GLU | 241 | 44.714 | 26.566 | 17.881 | 1.00 | 55.84 |
| ATOM | 660 | CG  | GLU | 241 | 44.750 | 26.422 | 16.360 | 1.00 | 69.03 |
| ATOM | 661 | CD  | GLU | 241 | 45.141 | 25.015 | 15.900 | 1.00 | 74.99 |
| ATOM | 662 | OE1 | GLU | 241 | 45.835 | 24.299 | 16.658 | 1.00 | 77.81 |
| ATOM | 663 | OE2 | GLU | 241 | 44.765 | 24.629 | 14.770 | 1.00 | 70.58 |
| ATOM | 664 | C   | GLU | 241 | 44.587 | 27.961 | 19.933 | 1.00 | 42.60 |
| ATOM | 665 | O   | GLU | 241 | 43.541 | 27.740 | 20.545 | 1.00 | 43.23 |
| ATOM | 666 | N   | LEU | 242 | 45.762 | 28.125 | 20.535 | 1.00 | 39.31 |
| ATOM | 667 | CA  | LEU | 242 | 45.926 | 28.086 | 21.987 | 1.00 | 34.54 |
| ATOM | 668 | CB  | LEU | 242 | 47.417 | 28.109 | 22.344 | 1.00 | 28.35 |
| ATOM | 669 | CG  | LEU | 242 | 48.311 | 26.974 | 21.853 | 1.00 | 27.59 |
| ATOM | 670 | CD1 | LEU | 242 | 49.750 | 27.307 | 22.180 | 1.00 | 20.72 |
| ATOM | 671 | CD2 | LEU | 242 | 47.902 | 25.661 | 22.500 | 1.00 | 24.97 |
| ATOM | 672 | C   | LEU | 242 | 45.242 | 29.240 | 22.711 | 1.00 | 32.23 |
| ATOM | 673 | O   | LEU | 242 | 44.956 | 30.282 | 22.119 | 1.00 | 31.50 |
| ATOM | 674 | N   | PRO | 243 | 44.954 | 29.060 | 24.010 | 1.00 | 34.39 |
| ATOM | 675 | CD  | PRO | 243 | 45.118 | 27.843 | 24.827 | 1.00 | 31.68 |
| ATOM | 676 | CA  | PRO | 243 | 44.309 | 30.134 | 24.773 | 1.00 | 34.39 |
| ATOM | 677 | CB  | PRO | 243 | 44.092 | 29.498 | 26.154 | 1.00 | 32.34 |
| ATOM | 678 | CG  | PRO | 243 | 44.081 | 28.026 | 25.892 | 1.00 | 33.80 |
| ATOM | 679 | C   | PRO | 243 | 45.300 | 31.303 | 24.873 | 1.00 | 35.56 |
| ATOM | 680 | O   | PRO | 243 | 46.517 | 31.082 | 24.897 | 1.00 | 34.99 |
| ATOM | 681 | N   | CYS | 244 | 44.791 | 32.532 | 24.946 | 1.00 | 34.23 |
| ATOM | 682 | CA  | CYS | 244 | 45.648 | 33.714 | 25.062 | 1.00 | 37.03 |
| ATOM | 683 | CB  | CYS | 244 | 44.820 | 34.960 | 25.376 | 1.00 | 43.49 |
| ATOM | 684 | SG  | CYS | 244 | 43.820 | 35.531 | 24.007 | 1.00 | 71.28 |
| ATOM | 685 | C   | CYS | 244 | 46.716 | 33.555 | 26.135 | 1.00 | 34.99 |
| ATOM | 686 | O   | CYS | 244 | 47.894 | 33.802 | 25.882 | 1.00 | 37.49 |
| ATOM | 687 | N   | GLU | 245 | 46.305 | 33.125 | 27.326 | 1.00 | 33.03 |
| ATOM | 688 | CA  | GLU | 245 | 47.249 | 32.944 | 28.424 | 1.00 | 35.72 |
| ATOM | 689 | CB  | GLU | 245 | 46.559 | 32.469 | 29.716 | 1.00 | 37.85 |
| ATOM | 690 | CG  | GLU | 245 | 45.294 | 31.633 | 29.549 | 1.00 | 46.81 |
| ATOM | 691 | CD  | GLU | 245 | 44.029 | 32.478 | 29.480 | 1.00 | 44.81 |
| ATOM | 692 | OE1 | GLU | 245 | 43.606 | 33.012 | 30.527 | 1.00 | 33.05 |
| ATOM | 693 | OE2 | GLU | 245 | 43.454 | 32.599 | 28.377 | 1.00 | 48.22 |
| ATOM | 694 | C   | GLU | 245 | 48.414 | 32.035 | 28.047 | 1.00 | 32.29 |
| ATOM | 695 | O   | GLU | 245 | 49.558 | 32.319 | 28.399 | 1.00 | 35.92 |
| ATOM | 696 | N   | ASP | 246 | 48.134 | 30.975 | 27.295 | 1.00 | 30.64 |
| ATOM | 697 | CA  | ASP | 246 | 49.182 | 30.058 | 26.855 | 1.00 | 28.23 |
| ATOM | 698 | CB  | ASP | 246 | 48.575 | 28.809 | 26.208 | 1.00 | 30.51 |
| ATOM | 699 | CG  | ASP | 246 | 48.213 | 27.737 | 27.222 | 1.00 | 33.18 |

FIG. 28A-16

| ATOM | 700 | OD1 | ASP | 246 | 48.265 | 28.006 | 28.439 | 1.00 | 31.26 |
|---|---|---|---|---|---|---|---|---|---|
| ATOM | 701 | OD2 | ASP | 246 | 47.884 | 26.613 | 26.796 | 1.00 | 33.85 |
| ATOM | 702 | C | ASP | 246 | 50.104 | 30.757 | 25.860 | 1.00 | 30.10 |
| ATOM | 703 | O | ASP | 246 | 51.330 | 30.651 | 25.950 | 1.00 | 27.08 |
| ATOM | 704 | N | GLN | 247 | 49.500 | 31.477 | 24.918 | 1.00 | 30.39 |
| ATOM | 705 | CA | GLN | 247 | 50.249 | 32.208 | 23.901 | 1.00 | 29.08 |
| ATOM | 706 | CB | GLN | 247 | 49.295 | 32.949 | 22.964 | 1.00 | 27.34 |
| ATOM | 707 | CG | GLN | 247 | 48.390 | 32.034 | 22.147 | 1.00 | 28.95 |
| ATOM | 708 | CD | GLN | 247 | 47.531 | 32.796 | 21.153 | 1.00 | 30.74 |
| ATOM | 709 | OE1 | GLN | 247 | 47.850 | 33.918 | 20.767 | 1.00 | 33.23 |
| ATOM | 710 | NE2 | GLN | 247 | 46.439 | 32.185 | 20.729 | 1.00 | 35.19 |
| ATOM | 711 | C | GLN | 247 | 51.190 | 33.196 | 24.575 | 1.00 | 27.51 |
| ATOM | 712 | O | GLN | 247 | 52.377 | 33.261 | 24.256 | 1.00 | 28.70 |
| ATOM | 713 | N | ILE | 248 | 50.661 | 33.921 | 25.552 | 1.00 | 27.81 |
| ATOM | 714 | CA | ILE | 248 | 51.431 | 34.908 | 26.295 | 1.00 | 29.41 |
| ATOM | 715 | CB | ILE | 248 | 50.525 | 35.662 | 27.303 | 1.00 | 28.96 |
| ATOM | 716 | CG2 | ILE | 248 | 51.356 | 36.476 | 28.279 | 1.00 | 28.67 |
| ATOM | 717 | CG1 | ILE | 248 | 49.555 | 36.571 | 26.543 | 1.00 | 28.83 |
| ATOM | 718 | CD1 | ILE | 248 | 48.514 | 37.236 | 27.420 | 1.00 | 30.76 |
| ATOM | 719 | C | ILE | 248 | 52.618 | 34.259 | 27.006 | 1.00 | 28.39 |
| ATOM | 720 | O | ILE | 248 | 53.759 | 34.715 | 26.869 | 1.00 | 27.88 |
| ATOM | 721 | N | ILE | 249 | 52.356 | 33.177 | 27.732 | 1.00 | 26.07 |
| ATOM | 722 | CA | ILE | 249 | 53.413 | 32.474 | 28.454 | 1.00 | 27.37 |
| ATOM | 723 | CB | ILE | 249 | 52.839 | 31.294 | 29.281 | 1.00 | 30.32 |
| ATOM | 724 | CG2 | ILE | 249 | 53.958 | 30.425 | 29.840 | 1.00 | 31.29 |
| ATOM | 725 | CG1 | ILE | 249 | 51.987 | 31.831 | 30.429 | 1.00 | 30.31 |
| ATOM | 726 | CD1 | ILE | 249 | 51.295 | 30.753 | 31.230 | 1.00 | 31.30 |
| ATOM | 727 | C | ILE | 249 | 54.510 | 31.974 | 27.509 | 1.00 | 28.63 |
| ATOM | 728 | O | ILE | 249 | 55.701 | 32.100 | 27.808 | 1.00 | 29.59 |
| ATOM | 729 | N | LEU | 250 | 54.110 | 31.442 | 26.357 | 1.00 | 29.03 |
| ATOM | 730 | CA | LEU | 250 | 55.068 | 30.934 | 25.380 | 1.00 | 22.44 |
| ATOM | 731 | CB | LEU | 250 | 54.351 | 30.166 | 24.266 | 1.00 | 24.30 |
| ATOM | 732 | CG | LEU | 250 | 53.665 | 28.866 | 24.687 | 1.00 | 23.20 |
| ATOM | 733 | CD1 | LEU | 250 | 52.951 | 28.273 | 23.502 | 1.00 | 20.36 |
| ATOM | 734 | CD2 | LEU | 250 | 54.685 | 27.880 | 25.238 | 1.00 | 19.45 |
| ATOM | 735 | C | LEU | 250 | 55.919 | 32.055 | 24.794 | 1.00 | 18.97 |
| ATOM | 736 | O | LEU | 250 | 57.133 | 31.903 | 24.648 | 1.00 | 18.37 |
| ATOM | 737 | N | LEU | 251 | 55.291 | 33.180 | 24.468 | 1.00 | 20.63 |
| ATOM | 738 | CA | LEU | 251 | 56.026 | 34.318 | 23.915 | 1.00 | 27.43 |
| ATOM | 739 | CB | LEU | 251 | 55.065 | 35.412 | 23.449 | 1.00 | 22.92 |
| ATOM | 740 | CG | LEU | 251 | 54.364 | 35.093 | 22.128 | 1.00 | 24.72 |
| ATOM | 741 | CD1 | LEU | 251 | 53.342 | 36.167 | 21.821 | 1.00 | 32.13 |
| ATOM | 742 | CD2 | LEU | 251 | 55.389 | 34.981 | 21.009 | 1.00 | 22.46 |
| ATOM | 743 | C | LEU | 251 | 57.026 | 34.875 | 24.930 | 1.00 | 27.23 |
| ATOM | 744 | O | LEU | 251 | 58.202 | 35.078 | 24.614 | 1.00 | 26.48 |
| ATOM | 745 | N | LYS | 252 | 56.561 | 35.094 | 26.156 | 1.00 | 27.34 |

FIG. 28A-17

| ATOM | 746 | CA  | LYS | 252 | 57.425 | 35.598 | 27.215 | 1.00 | 28.95 |
| ---- | --- | --- | --- | --- | ------ | ------ | ------ | ---- | ----- |
| ATOM | 747 | CB  | LYS | 252 | 56.649 | 35.715 | 28.527 | 1.00 | 32.89 |
| ATOM | 748 | CG  | LYS | 252 | 55.570 | 36.783 | 28.530 | 1.00 | 35.06 |
| ATOM | 749 | CD  | LYS | 252 | 55.084 | 37.028 | 29.943 | 1.00 | 42.82 |
| ATOM | 750 | CE  | LYS | 252 | 54.124 | 38.191 | 30.003 | 1.00 | 53.05 |
| ATOM | 751 | NZ  | LYS | 252 | 53.677 | 38.451 | 31.398 | 1.00 | 64.03 |
| ATOM | 752 | C   | LYS | 252 | 58.605 | 34.647 | 27.405 | 1.00 | 27.66 |
| ATOM | 753 | O   | LYS | 252 | 59.734 | 35.076 | 27.646 | 1.00 | 33.16 |
| ATOM | 754 | N   | GLY | 253 | 58.344 | 33.357 | 27.243 | 1.00 | 24.50 |
| ATOM | 755 | CA  | GLY | 253 | 59.386 | 32.364 | 27.402 | 1.00 | 22.33 |
| ATOM | 756 | C   | GLY | 253 | 60.423 | 32.273 | 26.297 | 1.00 | 23.99 |
| ATOM | 757 | O   | GLY | 253 | 61.589 | 32.016 | 26.581 | 1.00 | 30.77 |
| ATOM | 758 | N   | CYS | 254 | 60.041 | 32.526 | 25.049 | 1.00 | 22.66 |
| ATOM | 759 | CA  | CYS | 254 | 60.986 | 32.405 | 23.934 | 1.00 | 20.75 |
| ATOM | 760 | CB  | CYS | 254 | 60.386 | 31.494 | 22.868 | 1.00 | 24.86 |
| ATOM | 761 | SG  | CYS | 254 | 58.996 | 32.276 | 22.014 | 1.00 | 25.55 |
| ATOM | 762 | C   | CYS | 254 | 61.399 | 33.702 | 23.242 | 1.00 | 23.79 |
| ATOM | 763 | O   | CYS | 254 | 62.262 | 33.685 | 22.357 | 1.00 | 22.18 |
| ATOM | 764 | N   | CYS | 255 | 60.788 | 34.814 | 23.625 | 1.00 | 19.49 |
| ATOM | 765 | CA  | CYS | 255 | 61.084 | 36.085 | 22.981 | 1.00 | 21.08 |
| ATOM | 766 | CB  | CYS | 255 | 60.336 | 37.220 | 23.669 | 1.00 | 18.21 |
| ATOM | 767 | SG  | CYS | 255 | 60.264 | 38.713 | 22.677 | 1.00 | 22.96 |
| ATOM | 768 | C   | CYS | 255 | 62.570 | 36.413 | 22.842 | 1.00 | 21.87 |
| ATOM | 769 | O   | CYS | 255 | 63.050 | 36.641 | 21.729 | 1.00 | 22.23 |
| ATOM | 770 | N   | MET | 256 | 63.310 | 36.397 | 23.947 | 1.00 | 20.82 |
| ATOM | 771 | CA  | MET | 256 | 64.741 | 36.706 | 23.895 | 1.00 | 20.50 |
| ATOM | 772 | CB  | MET | 256 | 65.322 | 36.801 | 25.312 | 1.00 | 22.50 |
| ATOM | 773 | CG  | MET | 256 | 66.808 | 37.139 | 25.354 | 1.00 | 16.67 |
| ATOM | 774 | SD  | MET | 256 | 67.205 | 38.732 | 24.605 | 1.00 | 24.46 |
| ATOM | 775 | CE  | MET | 256 | 69.027 | 38.764 | 24.791 | 1.00 | 19.21 |
| ATOM | 776 | C   | MET | 256 | 65.510 | 35.667 | 23.072 | 1.00 | 18.38 |
| ATOM | 777 | O   | MET | 256 | 66.401 | 36.005 | 22.293 | 1.00 | 17.68 |
| ATOM | 778 | N   | GLU | 257 | 65.149 | 34.404 | 23.248 | 1.00 | 20.33 |
| ATOM | 779 | CA  | GLU | 257 | 65.779 | 33.308 | 22.526 | 1.00 | 21.08 |
| ATOM | 780 | CB  | GLU | 257 | 65.148 | 31.982 | 22.943 | 1.00 | 22.28 |
| ATOM | 781 | CG  | GLU | 257 | 65.374 | 31.640 | 24.411 | 1.00 | 34.68 |
| ATOM | 782 | CD  | GLU | 257 | 64.515 | 30.486 | 24.907 | 1.00 | 43.20 |
| ATOM | 783 | OE1 | GLU | 257 | 63.823 | 29.836 | 24.091 | 1.00 | 42.14 |
| ATOM | 784 | OE2 | GLU | 257 | 64.530 | 30.230 | 26.128 | 1.00 | 50.15 |
| ATOM | 785 | C   | GLU | 257 | 65.650 | 33.503 | 21.018 | 1.00 | 19.26 |
| ATOM | 786 | O   | GLU | 257 | 66.632 | 33.360 | 20.276 | 1.00 | 18.09 |
| ATOM | 787 | N   | ILE | 258 | 64.446 | 33.850 | 20.566 | 1.00 | 16.30 |
| ATOM | 788 | CA  | ILE | 258 | 64.199 | 34.065 | 19.141 | 1.00 | 18.09 |
| ATOM | 789 | CB  | ILE | 258 | 62.677 | 34.150 | 18.825 | 1.00 | 18.61 |
| ATOM | 790 | CG2 | ILE | 258 | 62.441 | 34.653 | 17.395 | 1.00 | 16.23 |
| ATOM | 791 | CG1 | ILE | 258 | 62.032 | 32.771 | 19.021 | 1.00 | 13.80 |

FIG. 28A-18

| ATOM | 792 | CD1 | ILE | 258 | 60.544 | 32.714 | 18.695 | 1.00 | 13.21 |
|---|---|---|---|---|---|---|---|---|---|
| ATOM | 793 | C | ILE | 258 | 64.948 | 35.297 | 18.638 | 1.00 | 20.12 |
| ATOM | 794 | O | ILE | 258 | 65.605 | 35.242 | 17.593 | 1.00 | 19.17 |
| ATOM | 795 | N | MET | 259 | 64.903 | 36.387 | 19.404 | 1.00 | 22.71 |
| ATOM | 796 | CA | MET | 259 | 65.602 | 37.611 | 19.015 | 1.00 | 17.09 |
| ATOM | 797 | CB | MET | 259 | 65.249 | 38.772 | 19.941 | 1.00 | 18.80 |
| ATOM | 798 | CG | MET | 259 | 63.782 | 39.159 | 19.894 | 1.00 | 17.66 |
| ATOM | 799 | SD | MET | 259 | 63.457 | 40.748 | 20.678 | 1.00 | 25.77 |
| ATOM | 800 | CE | MET | 259 | 63.774 | 40.377 | 22.374 | 1.00 | 16.65 |
| ATOM | 801 | C | MET | 259 | 67.111 | 37.397 | 18.973 | 1.00 | 19.51 |
| ATOM | 802 | O | MET | 259 | 67.797 | 37.913 | 18.080 | 1.00 | 25.53 |
| ATOM | 803 | N | SER | 260 | 67.625 | 36.605 | 19.908 | 1.00 | 19.58 |
| ATOM | 804 | CA | SER | 260 | 69.056 | 36.324 | 19.947 | 1.00 | 16.90 |
| ATOM | 805 | CB | SER | 260 | 69.434 | 35.631 | 21.251 | 1.00 | 15.56 |
| ATOM | 806 | OG | SER | 260 | 69.093 | 36.455 | 22.352 | 1.00 | 22.98 |
| ATOM | 807 | C | SER | 260 | 69.471 | 35.487 | 18.746 | 1.00 | 14.52 |
| ATOM | 808 | O | SER | 260 | 70.496 | 35.761 | 18.129 | 1.00 | 22.82 |
| ATOM | 809 | N | LEU | 261 | 68.663 | 34.490 | 18.397 | 1.00 | 16.50 |
| ATOM | 810 | CA | LEU | 261 | 68.948 | 33.642 | 17.241 | 1.00 | 17.78 |
| ATOM | 811 | CB | LEU | 261 | 67.878 | 32.552 | 17.092 | 1.00 | 18.38 |
| ATOM | 812 | CG | LEU | 261 | 67.890 | 31.708 | 15.812 | 1.00 | 14.47 |
| ATOM | 813 | CD1 | LEU | 261 | 69.159 | 30.877 | 15.728 | 1.00 | 16.76 |
| ATOM | 814 | CD2 | LEU | 261 | 66.672 | 30.806 | 15.793 | 1.00 | 14.06 |
| ATOM | 815 | C | LEU | 261 | 68.959 | 34.519 | 15.992 | 1.00 | 20.40 |
| ATOM | 816 | O | LEU | 261 | 69.885 | 34.450 | 15.181 | 1.00 | 22.00 |
| ATOM | 817 | N | ARG | 262 | 67.934 | 35.356 | 15.854 | 1.00 | 21.02 |
| ATOM | 818 | CA | ARG | 262 | 67.821 | 36.249 | 14.705 | 1.00 | 22.84 |
| ATOM | 819 | CB | ARG | 262 | 66.530 | 37.067 | 14.782 | 1.00 | 20.29 |
| ATOM | 820 | CG | ARG | 262 | 65.311 | 36.267 | 14.364 | 1.00 | 23.33 |
| ATOM | 821 | CD | ARG | 262 | 64.007 | 37.026 | 14.509 | 1.00 | 19.05 |
| ATOM | 822 | NE | ARG | 262 | 62.959 | 36.321 | 13.775 | 1.00 | 21.32 |
| ATOM | 823 | CZ | ARG | 262 | 61.780 | 36.837 | 13.441 | 1.00 | 23.44 |
| ATOM | 824 | NH1 | ARG | 262 | 61.465 | 38.081 | 13.780 | 1.00 | 22.99 |
| ATOM | 825 | NH2 | ARG | 262 | 60.933 | 36.116 | 12.713 | 1.00 | 22.09 |
| ATOM | 826 | C | ARG | 262 | 69.035 | 37.154 | 14.561 | 1.00 | 22.66 |
| ATOM | 827 | O | ARG | 262 | 69.434 | 37.483 | 13.445 | 1.00 | 22.41 |
| ATOM | 828 | N | ALA | 263 | 69.625 | 37.545 | 15.689 | 1.00 | 23.52 |
| ATOM | 829 | CA | ALA | 263 | 70.820 | 38.386 | 15.677 | 1.00 | 22.37 |
| ATOM | 830 | CB | ALA | 263 | 70.986 | 39.089 | 17.018 | 1.00 | 22.76 |
| ATOM | 831 | C | ALA | 263 | 72.052 | 37.530 | 15.366 | 1.00 | 22.85 |
| ATOM | 832 | O | ALA | 263 | 72.882 | 37.897 | 14.529 | 1.00 | 25.50 |
| ATOM | 833 | N | ALA | 264 | 72.131 | 36.365 | 16.005 | 1.00 | 21.68 |
| ATOM | 834 | CA | ALA | 264 | 73.242 | 35.438 | 15.826 | 1.00 | 20.26 |
| ATOM | 835 | CB | ALA | 264 | 73.092 | 34.256 | 16.763 | 1.00 | 15.97 |
| ATOM | 836 | C | ALA | 264 | 73.401 | 34.957 | 14.382 | 1.00 | 23.11 |
| ATOM | 837 | O | ALA | 264 | 74.523 | 34.831 | 13.892 | 1.00 | 24.87 |

FIG. 28A-19

| ATOM | 838 | N | VAL | 265 | 72.293 | 34.679 | 13.697 | 1.00 | 22.94 |
|------|-----|------|-----|-----|--------|--------|--------|------|-------|
| ATOM | 839 | CA | VAL | 265 | 72.380 | 34.226 | 12.306 | 1.00 | 28.98 |
| ATOM | 840 | CB | VAL | 265 | 71.072 | 33.547 | 11.797 | 1.00 | 25.97 |
| ATOM | 841 | CG1 | VAL | 265 | 70.751 | 32.330 | 12.638 | 1.00 | 26.27 |
| ATOM | 842 | CG2 | VAL | 265 | 69.907 | 34.527 | 11.797 | 1.00 | 26.64 |
| ATOM | 843 | C | VAL | 265 | 72.761 | 35.373 | 11.369 | 1.00 | 28.81 |
| ATOM | 844 | O | VAL | 265 | 72.966 | 35.160 | 10.176 | 1.00 | 31.92 |
| ATOM | 845 | N | ARG | 266 | 72.830 | 36.587 | 11.915 | 1.00 | 31.83 |
| ATOM | 846 | CA | ARG | 266 | 73.210 | 37.774 | 11.150 | 1.00 | 33.19 |
| ATOM | 847 | CB | ARG | 266 | 72.141 | 38.861 | 11.258 | 1.00 | 31.67 |
| ATOM | 848 | CG | ARG | 266 | 70.986 | 38.623 | 10.320 | 1.00 | 26.82 |
| ATOM | 849 | CD | ARG | 266 | 69.913 | 39.668 | 10.454 | 1.00 | 33.95 |
| ATOM | 850 | NE | ARG | 266 | 68.955 | 39.532 | 9.361 | 1.00 | 38.15 |
| ATOM | 851 | CZ | ARG | 266 | 67.688 | 39.927 | 9.410 | 1.00 | 37.39 |
| ATOM | 852 | NH1 | ARG | 266 | 67.198 | 40.491 | 10.509 | 1.00 | 29.92 |
| ATOM | 853 | NH2 | ARG | 266 | 66.918 | 39.770 | 8.340 | 1.00 | 31.24 |
| ATOM | 854 | C | ARG | 266 | 74.565 | 38.307 | 11.604 | 1.00 | 36.31 |
| ATOM | 855 | O | ARG | 266 | 74.821 | 39.516 | 11.575 | 1.00 | 38.56 |
| ATOM | 856 | N | TYR | 267 | 75.416 | 37.393 | 12.056 | 1.00 | 34.21 |
| ATOM | 857 | CA | TYR | 267 | 76.755 | 37.733 | 12.502 | 1.00 | 35.24 |
| ATOM | 858 | CB | TYR | 267 | 77.283 | 36.640 | 13.440 | 1.00 | 32.37 |
| ATOM | 859 | CG | TYR | 267 | 78.774 | 36.699 | 13.703 | 1.00 | 35.07 |
| ATOM | 860 | CD1 | TYR | 267 | 79.303 | 37.555 | 14.669 | 1.00 | 33.94 |
| ATOM | 861 | CE1 | TYR | 267 | 80.677 | 37.609 | 14.905 | 1.00 | 36.60 |
| ATOM | 862 | CD2 | TYR | 267 | 79.658 | 35.894 | 12.979 | 1.00 | 34.68 |
| ATOM | 863 | CE2 | TYR | 267 | 81.029 | 35.940 | 13.208 | 1.00 | 36.07 |
| ATOM | 864 | CZ | TYR | 267 | 81.533 | 36.797 | 14.170 | 1.00 | 37.14 |
| ATOM | 865 | OH | TYR | 267 | 82.889 | 36.835 | 14.396 | 1.00 | 41.52 |
| ATOM | 866 | C | TYR | 267 | 77.639 | 37.831 | 11.263 | 1.00 | 37.68 |
| ATOM | 867 | O | TYR | 267 | 77.609 | 36.943 | 10.410 | 1.00 | 36.48 |
| ATOM | 868 | N | ASP | 268 | 78.400 | 38.915 | 11.150 | 1.00 | 39.58 |
| ATOM | 869 | CA | ASP | 268 | 79.301 | 39.096 | 10.016 | 1.00 | 42.77 |
| ATOM | 870 | CB | ASP | 268 | 79.170 | 40.511 | 9.434 | 1.00 | 44.38 |
| ATOM | 871 | CG | ASP | 268 | 80.145 | 40.770 | 8.290 | 1.00 | 50.31 |
| ATOM | 872 | OD1 | ASP | 268 | 80.290 | 39.901 | 7.400 | 1.00 | 55.79 |
| ATOM | 873 | OD2 | ASP | 268 | 80.773 | 41.847 | 8.280 | 1.00 | 50.24 |
| ATOM | 874 | C | ASP | 268 | 80.737 | 38.846 | 10.466 | 1.00 | 42.51 |
| ATOM | 875 | O | ASP | 268 | 81.305 | 39.645 | 11.208 | 1.00 | 42.75 |
| ATOM | 876 | N | PRO | 269 | 81.346 | 37.733 | 10.020 | 1.00 | 44.56 |
| ATOM | 877 | CD | PRO | 269 | 80.770 | 36.697 | 9.146 | 1.00 | 42.66 |
| ATOM | 878 | CA | PRO | 269 | 82.725 | 37.395 | 10.393 | 1.00 | 45.98 |
| ATOM | 879 | CB | PRO | 269 | 82.991 | 36.111 | 9.607 | 1.00 | 44.04 |
| ATOM | 880 | CG | PRO | 269 | 81.631 | 35.506 | 9.458 | 1.00 | 43.33 |
| ATOM | 881 | C | PRO | 269 | 83.710 | 38.492 | 10.004 | 1.00 | 50.31 |
| ATOM | 882 | O | PRO | 269 | 84.630 | 38.800 | 10.761 | 1.00 | 49.83 |
| ATOM | 883 | N | ALA | 270 | 83.486 | 39.100 | 8.840 | 1.00 | 53.62 |

FIG. 28A-20

| ATOM | 884 | CA  | ALA | 270 | 84.348 | 40.165 | 8.329  | 1.00 | 54.54 |
|------|-----|-----|-----|-----|--------|--------|--------|------|-------|
| ATOM | 885 | CB  | ALA | 270 | 83.892 | 40.585 | 6.929  | 1.00 | 51.24 |
| ATOM | 886 | C   | ALA | 270 | 84.449 | 41.389 | 9.248  | 1.00 | 55.69 |
| ATOM | 887 | O   | ALA | 270 | 85.488 | 42.045 | 9.294  | 1.00 | 57.92 |
| ATOM | 888 | N   | SER | 271 | 83.384 | 41.685 | 9.989  | 1.00 | 54.71 |
| ATOM | 889 | CA  | SER | 271 | 83.378 | 42.838 | 10.889 | 1.00 | 51.26 |
| ATOM | 890 | CB  | SER | 271 | 82.182 | 43.740 | 10.575 | 1.00 | 49.92 |
| ATOM | 891 | OG  | SER | 271 | 82.065 | 43.976 | 9.183  | 1.00 | 60.09 |
| ATOM | 892 | C   | SER | 271 | 83.305 | 42.443 | 12.360 | 1.00 | 50.78 |
| ATOM | 893 | O   | SER | 271 | 83.482 | 43.288 | 13.240 | 1.00 | 52.11 |
| ATOM | 894 | N   | ASP | 272 | 83.051 | 41.162 | 12.619 | 1.00 | 48.96 |
| ATOM | 895 | CA  | ASP | 272 | 82.898 | 40.643 | 13.978 | 1.00 | 45.53 |
| ATOM | 896 | CB  | ASP | 272 | 84.206 | 40.765 | 14.776 | 1.00 | 44.82 |
| ATOM | 897 | CG  | ASP | 272 | 84.142 | 40.064 | 16.131 | 1.00 | 47.66 |
| ATOM | 898 | OD1 | ASP | 272 | 84.750 | 40.581 | 17.091 | 1.00 | 48.64 |
| ATOM | 899 | OD2 | ASP | 272 | 83.495 | 38.999 | 16.238 | 1.00 | 43.85 |
| ATOM | 900 | C   | ASP | 272 | 81.765 | 41.437 | 14.636 | 1.00 | 44.46 |
| ATOM | 901 | O   | ASP | 272 | 81.904 | 41.958 | 15.747 | 1.00 | 42.41 |
| ATOM | 902 | N   | THR | 273 | 80.652 | 41.551 | 13.915 | 1.00 | 39.79 |
| ATOM | 903 | CA  | THR | 273 | 79.492 | 42.282 | 14.401 | 1.00 | 38.82 |
| ATOM | 904 | CB  | THR | 273 | 79.334 | 43.648 | 13.670 | 1.00 | 39.73 |
| ATOM | 905 | OG1 | THR | 273 | 79.288 | 43.439 | 12.254 | 1.00 | 39.36 |
| ATOM | 906 | CG2 | THR | 273 | 80.496 | 44.578 | 13.991 | 1.00 | 41.31 |
| ATOM | 907 | C   | THR | 273 | 78.203 | 41.485 | 14.211 | 1.00 | 38.36 |
| ATOM | 908 | O   | THR | 273 | 78.151 | 40.546 | 13.408 | 1.00 | 33.79 |
| ATOM | 909 | N   | LEU | 274 | 77.187 | 41.835 | 14.995 | 1.00 | 36.91 |
| ATOM | 910 | CA  | LEU | 274 | 75.869 | 41.212 | 14.912 | 1.00 | 34.49 |
| ATOM | 911 | CB  | LEU | 274 | 75.342 | 40.822 | 16.297 | 1.00 | 30.37 |
| ATOM | 912 | CG  | LEU | 274 | 75.948 | 39.651 | 17.069 | 1.00 | 32.97 |
| ATOM | 913 | CD1 | LEU | 274 | 75.297 | 39.593 | 18.440 | 1.00 | 28.23 |
| ATOM | 914 | CD2 | LEU | 274 | 75.749 | 38.341 | 16.318 | 1.00 | 26.86 |
| ATOM | 915 | C   | LEU | 274 | 74.956 | 42.289 | 14.352 | 1.00 | 35.35 |
| ATOM | 916 | O   | LEU | 274 | 75.171 | 43.478 | 14.601 | 1.00 | 37.47 |
| ATOM | 917 | N   | THR | 275 | 73.942 | 41.890 | 13.599 | 1.00 | 34.05 |
| ATOM | 918 | CA  | THR | 275 | 73.020 | 42.868 | 13.052 | 1.00 | 32.62 |
| ATOM | 919 | CB  | THR | 275 | 72.824 | 42.674 | 11.542 | 1.00 | 35.14 |
| ATOM | 920 | OG1 | THR | 275 | 74.108 | 42.590 | 10.909 | 1.00 | 39.50 |
| ATOM | 921 | CG2 | THR | 275 | 72.064 | 43.851 | 10.952 | 1.00 | 30.94 |
| ATOM | 922 | C   | THR | 275 | 71.699 | 42.746 | 13.793 | 1.00 | 30.92 |
| ATOM | 923 | O   | THR | 275 | 71.100 | 41.670 | 13.845 | 1.00 | 36.53 |
| ATOM | 924 | N   | LEU | 276 | 71.291 | 43.835 | 14.434 | 1.00 | 28.10 |
| ATOM | 925 | CA  | LEU | 276 | 70.051 | 43.868 | 15.192 | 1.00 | 27.78 |
| ATOM | 926 | CB  | LEU | 276 | 70.205 | 44.780 | 16.420 | 1.00 | 22.51 |
| ATOM | 927 | CG  | LEU | 276 | 71.383 | 44.532 | 17.373 | 1.00 | 25.89 |
| ATOM | 928 | CD1 | LEU | 276 | 71.225 | 45.408 | 18.608 | 1.00 | 20.70 |
| ATOM | 929 | CD2 | LEU | 276 | 71.456 | 43.069 | 17.782 | 1.00 | 20.79 |

FIG. 28A-21

| ATOM | 930 | C   | LEU | 276 | 68.930 | 44.376 | 14.296 | 1.00 | 27.27 |
|------|-----|-----|-----|-----|--------|--------|--------|------|-------|
| ATOM | 931 | O   | LEU | 276 | 69.068 | 45.430 | 13.672 | 1.00 | 29.06 |
| ATOM | 932 | N   | SER | 277 | 67.854 | 43.598 | 14.187 | 1.00 | 25.97 |
| ATOM | 933 | CA  | SER | 277 | 66.697 | 43.957 | 13.366 | 1.00 | 28.63 |
| ATOM | 934 | CB  | SER | 277 | 65.990 | 45.177 | 13.967 | 1.00 | 27.78 |
| ATOM | 935 | OG  | SER | 277 | 65.561 | 44.905 | 15.290 | 1.00 | 22.65 |
| ATOM | 936 | C   | SER | 277 | 67.067 | 44.209 | 11.897 | 1.00 | 30.31 |
| ATOM | 937 | O   | SER | 277 | 66.374 | 44.939 | 11.181 | 1.00 | 28.52 |
| ATOM | 938 | N   | GLY | 278 | 68.168 | 43.597 | 11.465 | 1.00 | 31.24 |
| ATOM | 939 | CA  | GLY | 278 | 68.638 | 43.754 | 10.101 | 1.00 | 39.59 |
| ATOM | 940 | C   | GLY | 278 | 68.999 | 45.178 | 9.706  | 1.00 | 44.55 |
| ATOM | 941 | O   | GLY | 278 | 69.104 | 45.479 | 8.517  | 1.00 | 46.66 |
| ATOM | 942 | N   | GLU | 279 | 69.234 | 46.046 | 10.686 | 1.00 | 43.47 |
| ATOM | 943 | CA  | GLU | 279 | 69.566 | 47.435 | 10.387 | 1.00 | 43.87 |
| ATOM | 944 | CB  | GLU | 279 | 68.314 | 48.312 | 10.515 | 1.00 | 44.28 |
| ATOM | 945 | CG  | GLU | 279 | 67.703 | 48.322 | 11.908 | 1.00 | 52.30 |
| ATOM | 946 | CD  | GLU | 279 | 66.440 | 49.159 | 12.001 | 1.00 | 60.23 |
| ATOM | 947 | OE1 | GLU | 279 | 66.398 | 50.074 | 12.853 | 1.00 | 63.06 |
| ATOM | 948 | OE2 | GLU | 279 | 65.485 | 48.894 | 11.238 | 1.00 | 65.67 |
| ATOM | 949 | C   | GLU | 279 | 70.700 | 48.038 | 11.216 | 1.00 | 42.40 |
| ATOM | 950 | O   | GLU | 279 | 71.330 | 49.001 | 10.787 | 1.00 | 43.89 |
| ATOM | 951 | N   | MET | 280 | 70.977 | 47.472 | 12.388 | 1.00 | 40.86 |
| ATOM | 952 | CA  | MET | 280 | 72.027 | 48.009 | 13.248 | 1.00 | 32.80 |
| ATOM | 953 | CB  | MET | 280 | 71.435 | 48.415 | 14.603 | 1.00 | 29.25 |
| ATOM | 954 | CG  | MET | 280 | 72.384 | 49.193 | 15.506 | 1.00 | 31.64 |
| ATOM | 955 | SD  | MET | 280 | 71.830 | 49.235 | 17.232 | 1.00 | 34.02 |
| ATOM | 956 | CE  | MET | 280 | 70.566 | 50.495 | 17.197 | 1.00 | 26.56 |
| ATOM | 957 | C   | MET | 280 | 73.172 | 47.033 | 13.465 | 1.00 | 32.77 |
| ATOM | 958 | O   | MET | 280 | 72.983 | 45.971 | 14.058 | 1.00 | 34.61 |
| ATOM | 959 | N   | ALA | 281 | 74.351 | 47.375 | 12.959 | 1.00 | 31.87 |
| ATOM | 960 | CA  | ALA | 281 | 75.523 | 46.526 | 13.147 | 1.00 | 34.71 |
| ATOM | 961 | CB  | ALA | 281 | 76.519 | 46.727 | 12.023 | 1.00 | 34.42 |
| ATOM | 962 | C   | ALA | 281 | 76.125 | 46.950 | 14.482 | 1.00 | 36.76 |
| ATOM | 963 | O   | ALA | 281 | 76.416 | 48.129 | 14.693 | 1.00 | 34.59 |
| ATOM | 964 | N   | VAL | 282 | 76.275 | 45.993 | 15.390 | 1.00 | 37.16 |
| ATOM | 965 | CA  | VAL | 282 | 76.798 | 46.263 | 16.721 | 1.00 | 37.83 |
| ATOM | 966 | CB  | VAL | 282 | 75.692 | 46.023 | 17.780 | 1.00 | 37.58 |
| ATOM | 967 | CG1 | VAL | 282 | 76.219 | 46.271 | 19.175 | 1.00 | 48.99 |
| ATOM | 968 | CG2 | VAL | 282 | 74.514 | 46.939 | 17.514 | 1.00 | 43.59 |
| ATOM | 969 | C   | VAL | 282 | 78.017 | 45.400 | 17.046 | 1.00 | 39.04 |
| ATOM | 970 | O   | VAL | 282 | 78.081 | 44.230 | 16.660 | 1.00 | 39.16 |
| ATOM | 971 | N   | LYS | 283 | 78.989 | 45.993 | 17.735 | 1.00 | 38.75 |
| ATOM | 972 | CA  | LYS | 283 | 80.205 | 45.287 | 18.136 | 1.00 | 42.18 |
| ATOM | 973 | CB  | LYS | 283 | 81.428 | 46.208 | 18.045 | 1.00 | 47.46 |
| ATOM | 974 | CG  | LYS | 283 | 81.803 | 46.617 | 16.632 | 1.00 | 51.71 |
| ATOM | 975 | CD  | LYS | 283 | 83.092 | 47.416 | 16.618 | 1.00 | 59.26 |

FIG. 28A-22

| ATOM | 976 | CE | LYS | 283 | 83.481 | 47.813 | 15.202 | 1.00 | 62.52 |
| --- | --- | --- | --- | --- | --- | --- | --- | --- | --- |
| ATOM | 977 | NZ | LYS | 283 | 82.492 | 48.742 | 14.588 | 1.00 | 66.27 |
| ATOM | 978 | C | LYS | 283 | 80.075 | 44.746 | 19.559 | 1.00 | 38.78 |
| ATOM | 979 | O | LYS | 283 | 79.283 | 45.257 | 20.356 | 1.00 | 40.63 |
| ATOM | 980 | N | ARG | 284 | 80.900 | 43.753 | 19.881 | 1.00 | 36.01 |
| ATOM | 981 | CA | ARG | 284 | 80.908 | 43.104 | 21.189 | 1.00 | 38.62 |
| ATOM | 982 | CB | ARG | 284 | 82.150 | 42.224 | 21.327 | 1.00 | 38.83 |
| ATOM | 983 | CG | ARG | 284 | 82.220 | 41.091 | 20.333 | 1.00 | 41.87 |
| ATOM | 984 | CD | ARG | 284 | 83.521 | 40.335 | 20.451 | 1.00 | 39.60 |
| ATOM | 985 | NE | ARG | 284 | 83.506 | 39.120 | 19.644 | 1.00 | 45.18 |
| ATOM | 986 | CZ | ARG | 284 | 83.259 | 37.905 | 20.128 | 1.00 | 44.79 |
| ATOM | 987 | NH1 | ARG | 284 | 83.005 | 37.739 | 21.421 | 1.00 | 41.84 |
| ATOM | 988 | NH2 | ARG | 284 | 83.271 | 36.852 | 19.319 | 1.00 | 42.27 |
| ATOM | 989 | C | ARG | 284 | 80.829 | 44.051 | 22.385 | 1.00 | 41.18 |
| ATOM | 990 | O | ARG | 284 | 79.995 | 43.867 | 23.274 | 1.00 | 44.38 |
| ATOM | 991 | N | GLU | 285 | 81.703 | 45.052 | 22.416 | 1.00 | 38.71 |
| ATOM | 992 | CA | GLU | 285 | 81.724 | 46.002 | 23.525 | 1.00 | 37.18 |
| ATOM | 993 | CB | GLU | 285 | 82.950 | 46.906 | 23.422 | 1.00 | 36.65 |
| ATOM | 994 | C | GLU | 285 | 80.444 | 46.838 | 23.614 | 1.00 | 35.71 |
| ATOM | 995 | O | GLU | 285 | 79.921 | 47.074 | 24.704 | 1.00 | 33.00 |
| ATOM | 996 | N | GLN | 286 | 79.920 | 47.245 | 22.463 | 1.00 | 32.01 |
| ATOM | 997 | CA | GLN | 286 | 78.714 | 48.061 | 22.425 | 1.00 | 32.31 |
| ATOM | 998 | CB | GLN | 286 | 78.440 | 48.525 | 20.997 | 1.00 | 38.24 |
| ATOM | 999 | CG | GLN | 286 | 79.565 | 49.352 | 20.392 | 1.00 | 42.42 |
| ATOM | 1000 | CD | GLN | 286 | 79.277 | 49.761 | 18.964 | 1.00 | 44.79 |
| ATOM | 1001 | OE1 | GLN | 286 | 79.103 | 48.910 | 18.089 | 1.00 | 42.21 |
| ATOM | 1002 | NE2 | GLN | 286 | 79.215 | 51.063 | 18.719 | 1.00 | 47.53 |
| ATOM | 1003 | C | GLN | 286 | 77.484 | 47.355 | 23.002 | 1.00 | 33.08 |
| ATOM | 1004 | O | GLN | 286 | 76.770 | 47.929 | 23.827 | 1.00 | 30.95 |
| ATOM | 1005 | N | LEU | 287 | 77.245 | 46.114 | 22.579 | 1.00 | 31.49 |
| ATOM | 1006 | CA | LEU | 287 | 76.095 | 45.350 | 23.068 | 1.00 | 31.01 |
| ATOM | 1007 | CB | LEU | 287 | 75.892 | 44.073 | 22.242 | 1.00 | 24.63 |
| ATOM | 1008 | CG | LEU | 287 | 74.498 | 43.780 | 21.661 | 1.00 | 27.34 |
| ATOM | 1009 | CD1 | LEU | 287 | 74.382 | 42.282 | 21.359 | 1.00 | 20.50 |
| ATOM | 1010 | CD2 | LEU | 287 | 73.393 | 44.205 | 22.616 | 1.00 | 14.41 |
| ATOM | 1011 | C | LEU | 287 | 76.298 | 44.986 | 24.538 | 1.00 | 32.80 |
| ATOM | 1012 | O | LEU | 287 | 75.351 | 45.014 | 25.334 | 1.00 | 32.10 |
| ATOM | 1013 | N | LYS | 288 | 77.536 | 44.641 | 24.885 | 1.00 | 32.54 |
| ATOM | 1014 | CA | LYS | 288 | 77.897 | 44.280 | 26.251 | 1.00 | 30.70 |
| ATOM | 1015 | CB | LYS | 288 | 79.376 | 43.893 | 26.315 | 1.00 | 31.24 |
| ATOM | 1016 | CG | LYS | 288 | 79.834 | 43.382 | 27.662 | 1.00 | 34.69 |
| ATOM | 1017 | CD | LYS | 288 | 81.227 | 42.784 | 27.574 | 1.00 | 37.69 |
| ATOM | 1018 | CE | LYS | 288 | 81.638 | 42.177 | 28.904 | 1.00 | 42.86 |
| ATOM | 1019 | NZ | LYS | 288 | 82.883 | 41.369 | 28.786 | 1.00 | 49.63 |
| ATOM | 1020 | C | LYS | 288 | 77.611 | 45.448 | 27.189 | 1.00 | 28.74 |
| ATOM | 1021 | O | LYS | 288 | 76.827 | 45.319 | 28.129 | 1.00 | 34.45 |

FIG. 28A-23

| ATOM | 1022 | N   | ASN | 289 | 78.190 | 46.602 | 26.882 | 1.00 | 26.57 |
| ATOM | 1023 | CA  | ASN | 289 | 78.011 | 47.803 | 27.691 | 1.00 | 30.84 |
| ATOM | 1024 | CB  | ASN | 289 | 79.012 | 48.879 | 27.274 | 1.00 | 26.04 |
| ATOM | 1025 | CG  | ASN | 289 | 80.437 | 48.485 | 27.570 | 1.00 | 35.16 |
| ATOM | 1026 | OD1 | ASN | 289 | 80.700 | 47.718 | 28.499 | 1.00 | 42.54 |
| ATOM | 1027 | ND2 | ASN | 289 | 81.371 | 48.998 | 26.784 | 1.00 | 32.82 |
| ATOM | 1028 | C   | ASN | 289 | 76.602 | 48.371 | 27.620 | 1.00 | 35.05 |
| ATOM | 1029 | O   | ASN | 289 | 76.154 | 49.039 | 28.550 | 1.00 | 36.94 |
| ATOM | 1030 | N   | GLY | 290 | 75.909 | 48.113 | 26.515 | 1.00 | 32.43 |
| ATOM | 1031 | CA  | GLY | 290 | 74.556 | 48.614 | 26.345 | 1.00 | 28.66 |
| ATOM | 1032 | C   | GLY | 290 | 73.525 | 48.024 | 27.289 | 1.00 | 28.48 |
| ATOM | 1033 | O   | GLY | 290 | 72.377 | 48.467 | 27.308 | 1.00 | 28.17 |
| ATOM | 1034 | N   | GLY | 291 | 73.908 | 47.002 | 28.047 | 1.00 | 28.66 |
| ATOM | 1035 | CA  | GLY | 291 | 72.969 | 46.408 | 28.980 | 1.00 | 29.19 |
| ATOM | 1036 | C   | GLY | 291 | 72.976 | 44.894 | 29.075 | 1.00 | 29.76 |
| ATOM | 1037 | O   | GLY | 291 | 72.595 | 44.340 | 30.105 | 1.00 | 34.44 |
| ATOM | 1038 | N   | LEU | 292 | 73.399 | 44.213 | 28.017 | 1.00 | 29.69 |
| ATOM | 1039 | CA  | LEU | 292 | 73.410 | 42.755 | 28.036 | 1.00 | 30.64 |
| ATOM | 1040 | CB  | LEU | 292 | 73.421 | 42.194 | 26.611 | 1.00 | 27.07 |
| ATOM | 1041 | CG  | LEU | 292 | 72.113 | 42.348 | 25.833 | 1.00 | 23.27 |
| ATOM | 1042 | CD1 | LEU | 292 | 72.202 | 41.580 | 24.532 | 1.00 | 22.24 |
| ATOM | 1043 | CD2 | LEU | 292 | 70.950 | 41.827 | 26.661 | 1.00 | 23.80 |
| ATOM | 1044 | C   | LEU | 292 | 74.530 | 42.125 | 28.861 | 1.00 | 29.22 |
| ATOM | 1045 | O   | LEU | 292 | 74.365 | 41.033 | 29.404 | 1.00 | 31.02 |
| ATOM | 1046 | N   | GLY | 293 | 75.671 | 42.800 | 28.945 | 1.00 | 30.26 |
| ATOM | 1047 | CA  | GLY | 293 | 76.788 | 42.259 | 29.700 | 1.00 | 28.37 |
| ATOM | 1048 | C   | GLY | 293 | 77.307 | 40.995 | 29.040 | 1.00 | 29.85 |
| ATOM | 1049 | O   | GLY | 293 | 77.460 | 40.951 | 27.820 | 1.00 | 32.37 |
| ATOM | 1050 | N   | VAL | 294 | 77.537 | 39.953 | 29.832 | 1.00 | 30.08 |
| ATOM | 1051 | CA  | VAL | 294 | 78.041 | 38.687 | 29.308 | 1.00 | 31.62 |
| ATOM | 1052 | CB  | VAL | 294 | 78.466 | 37.716 | 30.442 | 1.00 | 29.11 |
| ATOM | 1053 | CG1 | VAL | 294 | 79.649 | 38.292 | 31.191 | 1.00 | 31.37 |
| ATOM | 1054 | CG2 | VAL | 294 | 77.304 | 37.443 | 31.396 | 1.00 | 26.69 |
| ATOM | 1055 | C   | VAL | 294 | 77.079 | 37.978 | 28.351 | 1.00 | 32.81 |
| ATOM | 1056 | O   | VAL | 294 | 77.496 | 37.095 | 27.591 | 1.00 | 33.00 |
| ATOM | 1057 | N   | VAL | 295 | 75.801 | 38.356 | 28.380 | 1.00 | 30.45 |
| ATOM | 1058 | CA  | VAL | 295 | 74.814 | 37.752 | 27.487 | 1.00 | 28.02 |
| ATOM | 1059 | CB  | VAL | 295 | 73.378 | 38.232 | 27.793 | 1.00 | 29.96 |
| ATOM | 1060 | CG1 | VAL | 295 | 72.380 | 37.575 | 26.838 | 1.00 | 22.55 |
| ATOM | 1061 | CG2 | VAL | 295 | 73.016 | 37.903 | 29.232 | 1.00 | 20.10 |
| ATOM | 1062 | C   | VAL | 295 | 75.203 | 38.115 | 26.057 | 1.00 | 29.90 |
| ATOM | 1063 | O   | VAL | 295 | 75.047 | 37.312 | 25.140 | 1.00 | 34.47 |
| ATOM | 1064 | N   | SER | 296 | 75.762 | 39.309 | 25.886 | 1.00 | 29.11 |
| ATOM | 1065 | CA  | SER | 296 | 76.215 | 39.771 | 24.581 | 1.00 | 30.96 |
| ATOM | 1066 | CB  | SER | 296 | 76.785 | 41.184 | 24.702 | 1.00 | 27.26 |
| ATOM | 1067 | OG  | SER | 296 | 77.300 | 41.648 | 23.469 | 1.00 | 22.93 |

FIG. 28A-24

| ATOM | 1068 | C   | SER | 296 | 77.294 | 38.811 | 24.080 | 1.00 | 36.41 |
|------|------|-----|-----|-----|--------|--------|--------|------|-------|
| ATOM | 1069 | O   | SER | 296 | 77.238 | 38.341 | 22.939 | 1.00 | 38.84 |
| ATOM | 1070 | N   | ASP | 297 | 78.254 | 38.501 | 24.954 | 1.00 | 35.29 |
| ATOM | 1071 | CA  | ASP | 297 | 79.346 | 37.585 | 24.629 | 1.00 | 32.14 |
| ATOM | 1072 | CB  | ASP | 297 | 80.245 | 37.356 | 25.851 | 1.00 | 36.57 |
| ATOM | 1073 | CG  | ASP | 297 | 80.958 | 38.616 | 26.307 | 1.00 | 41.75 |
| ATOM | 1074 | OD1 | ASP | 297 | 81.492 | 39.352 | 25.447 | 1.00 | 45.45 |
| ATOM | 1075 | OD2 | ASP | 297 | 80.999 | 38.861 | 27.532 | 1.00 | 45.15 |
| ATOM | 1076 | C   | ASP | 297 | 78.768 | 36.249 | 24.191 | 1.00 | 29.61 |
| ATOM | 1077 | O   | ASP | 297 | 79.242 | 35.644 | 23.231 | 1.00 | 32.90 |
| ATOM | 1078 | N   | ALA | 298 | 77.738 | 35.804 | 24.903 | 1.00 | 27.85 |
| ATOM | 1079 | CA  | ALA | 298 | 77.071 | 34.544 | 24.608 | 1.00 | 27.89 |
| ATOM | 1080 | CB  | ALA | 298 | 75.998 | 34.258 | 25.657 | 1.00 | 21.67 |
| ATOM | 1081 | C   | ALA | 298 | 76.462 | 34.539 | 23.202 | 1.00 | 28.26 |
| ATOM | 1082 | O   | ALA | 298 | 76.648 | 33.579 | 22.446 | 1.00 | 30.19 |
| ATOM | 1083 | N   | ILE | 299 | 75.744 | 35.606 | 22.853 | 1.00 | 25.20 |
| ATOM | 1084 | CA  | ILE | 299 | 75.119 | 35.708 | 21.537 | 1.00 | 23.46 |
| ATOM | 1085 | CB  | ILE | 299 | 74.200 | 36.944 | 21.427 | 1.00 | 21.63 |
| ATOM | 1086 | CG2 | ILE | 299 | 73.491 | 36.946 | 20.078 | 1.00 | 22.20 |
| ATOM | 1087 | CG1 | ILE | 299 | 73.145 | 36.914 | 22.536 | 1.00 | 19.79 |
| ATOM | 1088 | CD1 | ILE | 299 | 72.245 | 38.139 | 22.578 | 1.00 | 18.33 |
| ATOM | 1089 | C   | ILE | 299 | 76.181 | 35.752 | 20.444 | 1.00 | 26.28 |
| ATOM | 1090 | O   | ILE | 299 | 76.043 | 35.095 | 19.414 | 1.00 | 31.72 |
| ATOM | 1091 | N   | PHE | 300 | 77.247 | 36.512 | 20.675 | 1.00 | 29.35 |
| ATOM | 1092 | CA  | PHE | 300 | 78.338 | 36.613 | 19.709 | 1.00 | 29.01 |
| ATOM | 1093 | CB  | PHE | 300 | 79.386 | 37.622 | 20.182 | 1.00 | 29.53 |
| ATOM | 1094 | CG  | PHE | 300 | 79.239 | 38.978 | 19.562 | 1.00 | 27.60 |
| ATOM | 1095 | CD1 | PHE | 300 | 78.481 | 39.964 | 20.179 | 1.00 | 24.86 |
| ATOM | 1096 | CD2 | PHE | 300 | 79.853 | 39.266 | 18.350 | 1.00 | 27.39 |
| ATOM | 1097 | CE1 | PHE | 300 | 78.337 | 41.218 | 19.597 | 1.00 | 25.66 |
| ATOM | 1098 | CE2 | PHE | 300 | 79.715 | 40.518 | 17.761 | 1.00 | 25.97 |
| ATOM | 1099 | CZ  | PHE | 300 | 78.956 | 41.495 | 18.384 | 1.00 | 21.03 |
| ATOM | 1100 | C   | PHE | 300 | 78.988 | 35.248 | 19.496 | 1.00 | 30.34 |
| ATOM | 1101 | O   | PHE | 300 | 79.309 | 34.873 | 18.367 | 1.00 | 29.35 |
| ATOM | 1102 | N   | GLU | 301 | 79.181 | 34.507 | 20.582 | 1.00 | 31.04 |
| ATOM | 1103 | CA  | GLU | 301 | 79.775 | 33.178 | 20.499 | 1.00 | 33.60 |
| ATOM | 1104 | CB  | GLU | 301 | 80.012 | 32.607 | 21.898 | 1.00 | 31.64 |
| ATOM | 1105 | C   | GLU | 301 | 78.851 | 32.265 | 19.696 | 1.00 | 33.90 |
| ATOM | 1106 | O   | GLU | 301 | 79.315 | 31.473 | 18.872 | 1.00 | 33.33 |
| ATOM | 1107 | N   | LEU | 302 | 77.546 | 32.386 | 19.935 | 1.00 | 31.13 |
| ATOM | 1108 | CA  | LEU | 302 | 76.556 | 31.581 | 19.227 | 1.00 | 27.57 |
| ATOM | 1109 | CB  | LEU | 302 | 75.150 | 31.842 | 19.776 | 1.00 | 25.24 |
| ATOM | 1110 | CG  | LEU | 302 | 73.994 | 31.131 | 19.059 | 1.00 | 28.59 |
| ATOM | 1111 | CD1 | LEU | 302 | 74.066 | 29.634 | 19.299 | 1.00 | 25.52 |
| ATOM | 1112 | CD2 | LEU | 302 | 72.660 | 31.682 | 19.532 | 1.00 | 19.30 |
| ATOM | 1113 | C   | LEU | 302 | 76.601 | 31.904 | 17.739 | 1.00 | 26.80 |

FIG. 28A-25

| ATOM | 1114 | O | LEU | 302 | 76.682 | 31.003 | 16.904 | 1.00 | 27.81 |
|---|---|---|---|---|---|---|---|---|---|
| ATOM | 1115 | N | GLY | 303 | 76.576 | 33.195 | 17.416 | 1.00 | 26.47 |
| ATOM | 1116 | CA | GLY | 303 | 76.611 | 33.624 | 16.030 | 1.00 | 26.99 |
| ATOM | 1117 | C | GLY | 303 | 77.845 | 33.133 | 15.295 | 1.00 | 33.46 |
| ATOM | 1118 | O | GLY | 303 | 77.757 | 32.646 | 14.164 | 1.00 | 32.33 |
| ATOM | 1119 | N | LYS | 304 | 78.994 | 33.232 | 15.956 | 1.00 | 34.63 |
| ATOM | 1120 | CA | LYS | 304 | 80.269 | 32.813 | 15.383 | 1.00 | 36.20 |
| ATOM | 1121 | CB | LYS | 304 | 81.399 | 33.115 | 16.372 | 1.00 | 41.96 |
| ATOM | 1122 | CG | LYS | 304 | 82.779 | 33.179 | 15.757 | 1.00 | 47.05 |
| ATOM | 1123 | CD | LYS | 304 | 83.800 | 33.610 | 16.796 | 1.00 | 59.47 |
| ATOM | 1124 | CE | LYS | 304 | 85.179 | 33.791 | 16.181 | 1.00 | 65.89 |
| ATOM | 1125 | NZ | LYS | 304 | 85.182 | 34.863 | 15.144 | 1.00 | 71.01 |
| ATOM | 1126 | C | LYS | 304 | 80.276 | 31.332 | 14.992 | 1.00 | 33.17 |
| ATOM | 1127 | O | LYS | 304 | 80.752 | 30.974 | 13.913 | 1.00 | 34.44 |
| ATOM | 1128 | N | SER | 305 | 79.739 | 30.482 | 15.861 | 1.00 | 31.40 |
| ATOM | 1129 | CA | SER | 305 | 79.687 | 29.048 | 15.594 | 1.00 | 33.10 |
| ATOM | 1130 | CB | SER | 305 | 79.513 | 28.266 | 16.900 | 1.00 | 34.10 |
| ATOM | 1131 | OG | SER | 305 | 78.391 | 28.727 | 17.633 | 1.00 | 40.61 |
| ATOM | 1132 | C | SER | 305 | 78.597 | 28.664 | 14.589 | 1.00 | 33.02 |
| ATOM | 1133 | O | SER | 305 | 78.771 | 27.718 | 13.816 | 1.00 | 35.32 |
| ATOM | 1134 | N | LEU | 306 | 77.488 | 29.404 | 14.580 | 1.00 | 32.14 |
| ATOM | 1135 | CA | LEU | 306 | 76.391 | 29.121 | 13.653 | 1.00 | 31.02 |
| ATOM | 1136 | CB | LEU | 306 | 75.138 | 29.936 | 13.996 | 1.00 | 22.76 |
| ATOM | 1137 | CG | LEU | 306 | 74.361 | 29.487 | 15.235 | 1.00 | 24.42 |
| ATOM | 1138 | CD1 | LEU | 306 | 73.094 | 30.311 | 15.380 | 1.00 | 23.13 |
| ATOM | 1139 | CD2 | LEU | 306 | 74.016 | 28.009 | 15.126 | 1.00 | 25.53 |
| ATOM | 1140 | C | LEU | 306 | 76.780 | 29.354 | 12.198 | 1.00 | 33.11 |
| ATOM | 1141 | O | LEU | 306 | 76.161 | 28.796 | 11.293 | 1.00 | 32.60 |
| ATOM | 1142 | N | SER | 307 | 77.821 | 30.153 | 11.975 | 1.00 | 36.12 |
| ATOM | 1143 | CA | SER | 307 | 78.296 | 30.448 | 10.624 | 1.00 | 38.80 |
| ATOM | 1144 | CB | SER | 307 | 79.514 | 31.373 | 10.677 | 1.00 | 41.64 |
| ATOM | 1145 | OG | SER | 307 | 79.224 | 32.556 | 11.401 | 1.00 | 54.66 |
| ATOM | 1146 | C | SER | 307 | 78.650 | 29.182 | 9.845 | 1.00 | 36.98 |
| ATOM | 1147 | O | SER | 307 | 78.302 | 29.055 | 8.669 | 1.00 | 42.87 |
| ATOM | 1148 | N | ALA | 308 | 79.315 | 28.239 | 10.509 | 1.00 | 35.72 |
| ATOM | 1149 | CA | ALA | 308 | 79.719 | 26.983 | 9.879 | 1.00 | 32.70 |
| ATOM | 1150 | CB | ALA | 308 | 80.683 | 26.227 | 10.782 | 1.00 | 33.88 |
| ATOM | 1151 | C | ALA | 308 | 78.531 | 26.093 | 9.521 | 1.00 | 34.83 |
| ATOM | 1152 | O | ALA | 308 | 78.620 | 25.278 | 8.600 | 1.00 | 39.61 |
| ATOM | 1153 | N | PHE | 309 | 77.424 | 26.250 | 10.244 | 1.00 | 31.54 |
| ATOM | 1154 | CA | PHE | 309 | 76.226 | 25.453 | 9.999 | 1.00 | 32.43 |
| ATOM | 1155 | CB | PHE | 309 | 75.259 | 25.558 | 11.182 | 1.00 | 30.89 |
| ATOM | 1156 | CG | PHE | 309 | 75.718 | 24.826 | 12.415 | 1.00 | 33.73 |
| ATOM | 1157 | CD1 | PHE | 309 | 76.769 | 25.314 | 13.183 | 1.00 | 40.48 |
| ATOM | 1158 | CD2 | PHE | 309 | 75.091 | 23.654 | 12.816 | 1.00 | 35.96 |
| ATOM | 1159 | CE1 | PHE | 309 | 77.189 | 24.643 | 14.334 | 1.00 | 37.87 |

FIG. 28A-26

| | | | | | | | | |
|---|---|---|---|---|---|---|---|---|
| ATOM | 1160 | CE2 | PHE | 309 | 75.502 | 22.975 | 13.962 | 1.00 | 38.44 |
| ATOM | 1161 | CZ | PHE | 309 | 76.553 | 23.471 | 14.722 | 1.00 | 37.34 |
| ATOM | 1162 | C | PHE | 309 | 75.507 | 25.809 | 8.693 | 1.00 | 34.76 |
| ATOM | 1163 | O | PHE | 309 | 74.810 | 24.969 | 8.118 | 1.00 | 36.18 |
| ATOM | 1164 | N | ASN | 310 | 75.693 | 27.040 | 8.218 | 1.00 | 35.80 |
| ATOM | 1165 | CA | ASN | 310 | 75.060 | 27.506 | 6.980 | 1.00 | 41.00 |
| ATOM | 1166 | CB | ASN | 310 | 75.705 | 26.852 | 5.755 | 1.00 | 51.94 |
| ATOM | 1167 | CG | ASN | 310 | 77.053 | 27.452 | 5.419 | 1.00 | 67.92 |
| ATOM | 1168 | OD1 | ASN | 310 | 77.139 | 28.439 | 4.687 | 1.00 | 77.32 |
| ATOM | 1169 | ND2 | ASN | 310 | 78.116 | 26.869 | 5.962 | 1.00 | 72.62 |
| ATOM | 1170 | C | ASN | 310 | 73.560 | 27.245 | 6.985 | 1.00 | 38.15 |
| ATOM | 1171 | O | ASN | 310 | 73.034 | 26.515 | 6.141 | 1.00 | 35.87 |
| ATOM | 1172 | N | LEU | 311 | 72.885 | 27.819 | 7.971 | 1.00 | 33.94 |
| ATOM | 1173 | CA | LEU | 311 | 71.450 | 27.651 | 8.111 | 1.00 | 32.09 |
| ATOM | 1174 | CB | LEU | 311 | 71.011 | 28.009 | 9.533 | 1.00 | 28.06 |
| ATOM | 1175 | CG | LEU | 311 | 71.656 | 27.301 | 10.724 | 1.00 | 26.38 |
| ATOM | 1176 | CD1 | LEU | 311 | 71.092 | 27.883 | 12.012 | 1.00 | 23.56 |
| ATOM | 1177 | CD2 | LEU | 311 | 71.409 | 25.801 | 10.651 | 1.00 | 21.24 |
| ATOM | 1178 | C | LEU | 311 | 70.705 | 28.542 | 7.124 | 1.00 | 33.00 |
| ATOM | 1179 | O | LEU | 311 | 71.173 | 29.630 | 6.782 | 1.00 | 35.47 |
| ATOM | 1180 | N | ASP | 312 | 69.569 | 28.057 | 6.638 | 1.00 | 27.78 |
| ATOM | 1181 | CA | ASP | 312 | 68.749 | 28.841 | 5.733 | 1.00 | 27.06 |
| ATOM | 1182 | CB | ASP | 312 | 68.385 | 28.049 | 4.456 | 1.00 | 25.84 |
| ATOM | 1183 | CG | ASP | 312 | 67.580 | 26.778 | 4.724 | 1.00 | 25.67 |
| ATOM | 1184 | OD1 | ASP | 312 | 67.124 | 26.541 | 5.860 | 1.00 | 28.20 |
| ATOM | 1185 | OD2 | ASP | 312 | 67.387 | 26.008 | 3.762 | 1.00 | 27.62 |
| ATOM | 1186 | C | ASP | 312 | 67.517 | 29.314 | 6.514 | 1.00 | 28.51 |
| ATOM | 1187 | O | ASP | 312 | 67.371 | 28.990 | 7.703 | 1.00 | 25.35 |
| ATOM | 1188 | N | ASP | 313 | 66.633 | 30.060 | 5.855 | 1.00 | 22.16 |
| ATOM | 1189 | CA | ASP | 313 | 65.430 | 30.589 | 6.494 | 1.00 | 21.37 |
| ATOM | 1190 | CB | ASP | 313 | 64.625 | 31.431 | 5.499 | 1.00 | 25.11 |
| ATOM | 1191 | CG | ASP | 313 | 65.380 | 32.666 | 5.025 | 1.00 | 31.54 |
| ATOM | 1192 | OD1 | ASP | 313 | 65.119 | 33.115 | 3.890 | 1.00 | 35.35 |
| ATOM | 1193 | OD2 | ASP | 313 | 66.225 | 33.193 | 5.783 | 1.00 | 35.37 |
| ATOM | 1194 | C | ASP | 313 | 64.524 | 29.535 | 7.120 | 1.00 | 21.11 |
| ATOM | 1195 | O | ASP | 313 | 63.904 | 29.783 | 8.158 | 1.00 | 23.68 |
| ATOM | 1196 | N | THR | 314 | 64.440 | 28.367 | 6.489 | 1.00 | 22.88 |
| ATOM | 1197 | CA | THR | 314 | 63.591 | 27.281 | 6.981 | 1.00 | 22.81 |
| ATOM | 1198 | CB | THR | 314 | 63.472 | 26.155 | 5.927 | 1.00 | 26.00 |
| ATOM | 1199 | OG1 | THR | 314 | 62.873 | 26.679 | 4.732 | 1.00 | 20.14 |
| ATOM | 1200 | CG2 | THR | 314 | 62.629 | 25.010 | 6.457 | 1.00 | 17.51 |
| ATOM | 1201 | C | THR | 314 | 64.086 | 26.706 | 8.310 | 1.00 | 19.46 |
| ATOM | 1202 | O | THR | 314 | 63.312 | 26.529 | 9.247 | 1.00 | 19.33 |
| ATOM | 1203 | N | GLU | 315 | 65.381 | 26.431 | 8.392 | 1.00 | 17.49 |
| ATOM | 1204 | CA | GLU | 315 | 65.965 | 25.885 | 9.611 | 1.00 | 20.62 |
| ATOM | 1205 | CB | GLU | 315 | 67.426 | 25.514 | 9.358 | 1.00 | 14.39 |

FIG. 28A-27

| | | | | | | | | | |
|---|---|---|---|---|---|---|---|---|---|
| ATOM | 1206 | CG | GLU | 315 | 67.539 | 24.339 | 8.400 | 1.00 | 13.07 |
| ATOM | 1207 | CD | GLU | 315 | 68.923 | 24.125 | 7.835 | 1.00 | 14.98 |
| ATOM | 1208 | OE1 | GLU | 315 | 69.634 | 25.116 | 7.552 | 1.00 | 17.71 |
| ATOM | 1209 | OE2 | GLU | 315 | 69.287 | 22.948 | 7.651 | 1.00 | 17.88 |
| ATOM | 1210 | C | GLU | 315 | 65.810 | 26.883 | 10.762 | 1.00 | 20.57 |
| ATOM | 1211 | O | GLU | 315 | 65.368 | 26.518 | 11.854 | 1.00 | 18.43 |
| ATOM | 1212 | N | VAL | 316 | 66.096 | 28.154 | 10.488 | 1.00 | 19.19 |
| ATOM | 1213 | CA | VAL | 316 | 65.955 | 29.203 | 11.490 | 1.00 | 16.53 |
| ATOM | 1214 | CB | VAL | 316 | 66.418 | 30.567 | 10.933 | 1.00 | 17.42 |
| ATOM | 1215 | CG1 | VAL | 316 | 66.149 | 31.687 | 11.940 | 1.00 | 13.89 |
| ATOM | 1216 | CG2 | VAL | 316 | 67.900 | 30.506 | 10.594 | 1.00 | 14.31 |
| ATOM | 1217 | C | VAL | 316 | 64.488 | 29.291 | 11.927 | 1.00 | 19.53 |
| ATOM | 1218 | O | VAL | 316 | 64.191 | 29.448 | 13.110 | 1.00 | 19.86 |
| ATOM | 1219 | N | ALA | 317 | 63.575 | 29.159 | 10.970 | 1.00 | 19.02 |
| ATOM | 1220 | CA | ALA | 317 | 62.145 | 29.215 | 11.254 | 1.00 | 16.95 |
| ATOM | 1221 | CB | ALA | 317 | 61.357 | 29.239 | 9.951 | 1.00 | 17.68 |
| ATOM | 1222 | C | ALA | 317 | 61.674 | 28.047 | 12.126 | 1.00 | 14.13 |
| ATOM | 1223 | O | ALA | 317 | 60.875 | 28.228 | 13.045 | 1.00 | 15.34 |
| ATOM | 1224 | N | LEU | 318 | 62.154 | 26.847 | 11.819 | 1.00 | 17.41 |
| ATOM | 1225 | CA | LEU | 318 | 61.769 | 25.653 | 12.569 | 1.00 | 19.10 |
| ATOM | 1226 | CB | LEU | 318 | 62.186 | 24.398 | 11.802 | 1.00 | 18.21 |
| ATOM | 1227 | CG | LEU | 318 | 61.443 | 24.209 | 10.473 | 1.00 | 19.02 |
| ATOM | 1228 | CD1 | LEU | 318 | 62.105 | 23.128 | 9.646 | 1.00 | 16.10 |
| ATOM | 1229 | CD2 | LEU | 318 | 59.987 | 23.875 | 10.735 | 1.00 | 11.32 |
| ATOM | 1230 | C | LEU | 318 | 62.399 | 25.685 | 13.954 | 1.00 | 22.38 |
| ATOM | 1231 | O | LEU | 318 | 61.782 | 25.278 | 14.945 | 1.00 | 21.64 |
| ATOM | 1232 | N | LEU | 319 | 63.619 | 26.207 | 14.016 | 1.00 | 20.97 |
| ATOM | 1233 | CA | LEU | 319 | 64.338 | 26.344 | 15.270 | 1.00 | 19.71 |
| ATOM | 1234 | CB | LEU | 319 | 65.715 | 26.951 | 15.005 | 1.00 | 20.56 |
| ATOM | 1235 | CG | LEU | 319 | 66.722 | 27.036 | 16.152 | 1.00 | 32.05 |
| ATOM | 1236 | CD1 | LEU | 319 | 66.704 | 25.760 | 16.963 | 1.00 | 33.15 |
| ATOM | 1237 | CD2 | LEU | 319 | 68.109 | 27.303 | 15.590 | 1.00 | 28.25 |
| ATOM | 1238 | C | LEU | 319 | 63.496 | 27.254 | 16.164 | 1.00 | 20.66 |
| ATOM | 1239 | O | LEU | 319 | 63.215 | 26.920 | 17.313 | 1.00 | 24.47 |
| ATOM | 1240 | N | GLN | 320 | 63.026 | 28.365 | 15.604 | 1.00 | 19.25 |
| ATOM | 1241 | CA | GLN | 320 | 62.191 | 29.307 | 16.346 | 1.00 | 19.02 |
| ATOM | 1242 | CB | GLN | 320 | 61.842 | 30.526 | 15.488 | 1.00 | 19.11 |
| ATOM | 1243 | CG | GLN | 320 | 63.032 | 31.377 | 15.101 | 1.00 | 20.02 |
| ATOM | 1244 | CD | GLN | 320 | 62.665 | 32.562 | 14.224 | 1.00 | 23.65 |
| ATOM | 1245 | OE1 | GLN | 320 | 63.487 | 33.445 | 13.997 | 1.00 | 22.68 |
| ATOM | 1246 | NE2 | GLN | 320 | 61.440 | 32.574 | 13.704 | 1.00 | 20.77 |
| ATOM | 1247 | C | GLN | 320 | 60.905 | 28.635 | 16.811 | 1.00 | 20.52 |
| ATOM | 1248 | O | GLN | 320 | 60.465 | 28.845 | 17.938 | 1.00 | 22.04 |
| ATOM | 1249 | N | ALA | 321 | 60.306 | 27.825 | 15.942 | 1.00 | 21.01 |
| ATOM | 1250 | CA | ALA | 321 | 59.069 | 27.128 | 16.280 | 1.00 | 16.83 |
| ATOM | 1251 | CB | ALA | 321 | 58.556 | 26.358 | 15.079 | 1.00 | 16.58 |

FIG. 28A-28

| ATOM | 1252 | C | ALA | 321 | 59.288 | 26.185 | 17.462 | 1.00 | 18.15 |
|------|------|---|-----|-----|--------|--------|--------|------|-------|
| ATOM | 1253 | O | ALA | 321 | 58.427 | 26.069 | 18.344 | 1.00 | 13.03 |
| ATOM | 1254 | N | VAL | 322 | 60.442 | 25.523 | 17.481 | 1.00 | 14.89 |
| ATOM | 1255 | CA | VAL | 322 | 60.774 | 24.599 | 18.559 | 1.00 | 19.05 |
| ATOM | 1256 | CB | VAL | 322 | 62.051 | 23.779 | 18.233 | 1.00 | 21.50 |
| ATOM | 1257 | CG1 | VAL | 322 | 62.510 | 22.990 | 19.457 | 1.00 | 21.49 |
| ATOM | 1258 | CG2 | VAL | 322 | 61.773 | 22.819 | 17.073 | 1.00 | 15.42 |
| ATOM | 1259 | C | VAL | 322 | 60.947 | 25.375 | 19.867 | 1.00 | 19.89 |
| ATOM | 1260 | O | VAL | 322 | 60.478 | 24.940 | 20.919 | 1.00 | 21.58 |
| ATOM | 1261 | N | LEU | 323 | 61.591 | 26.537 | 19.788 | 1.00 | 20.25 |
| ATOM | 1262 | CA | LEU | 323 | 61.804 | 27.387 | 20.959 | 1.00 | 19.32 |
| ATOM | 1263 | CB | LEU | 323 | 62.683 | 28.586 | 20.597 | 1.00 | 12.95 |
| ATOM | 1264 | CG | LEU | 323 | 64.129 | 28.273 | 20.217 | 1.00 | 20.70 |
| ATOM | 1265 | CD1 | LEU | 323 | 64.805 | 29.503 | 19.641 | 1.00 | 13.23 |
| ATOM | 1266 | CD2 | LEU | 323 | 64.883 | 27.767 | 21.438 | 1.00 | 22.91 |
| ATOM | 1267 | C | LEU | 323 | 60.468 | 27.884 | 21.497 | 1.00 | 20.25 |
| ATOM | 1268 | O | LEU | 323 | 60.251 | 27.918 | 22.706 | 1.00 | 25.88 |
| ATOM | 1269 | N | LEU | 324 | 59.571 | 28.251 | 20.587 | 1.00 | 23.08 |
| ATOM | 1270 | CA | LEU | 324 | 58.248 | 28.753 | 20.944 | 1.00 | 21.24 |
| ATOM | 1271 | CB | LEU | 324 | 57.555 | 29.333 | 19.707 | 1.00 | 18.45 |
| ATOM | 1272 | CG | LEU | 324 | 56.119 | 29.847 | 19.868 | 1.00 | 17.07 |
| ATOM | 1273 | CD1 | LEU | 324 | 56.083 | 31.092 | 20.752 | 1.00 | 15.39 |
| ATOM | 1274 | CD2 | LEU | 324 | 55.545 | 30.162 | 18.498 | 1.00 | 17.90 |
| ATOM | 1275 | C | LEU | 324 | 57.342 | 27.706 | 21.598 | 1.00 | 21.54 |
| ATOM | 1276 | O | LEU | 324 | 56.742 | 27.967 | 22.642 | 1.00 | 23.41 |
| ATOM | 1277 | N | MET | 325 | 57.249 | 26.521 | 21.003 | 1.00 | 24.63 |
| ATOM | 1278 | CA | MET | 325 | 56.380 | 25.476 | 21.545 | 1.00 | 25.35 |
| ATOM | 1279 | CB | MET | 325 | 55.901 | 24.536 | 20.430 | 1.00 | 25.53 |
| ATOM | 1280 | CG | MET | 325 | 55.235 | 25.220 | 19.232 | 1.00 | 21.89 |
| ATOM | 1281 | SD | MET | 325 | 53.871 | 26.337 | 19.649 | 1.00 | 25.50 |
| ATOM | 1282 | CE | MET | 325 | 52.705 | 25.250 | 20.397 | 1.00 | 17.66 |
| ATOM | 1283 | C | MET | 325 | 57.031 | 24.676 | 22.675 | 1.00 | 27.58 |
| ATOM | 1284 | O | MET | 325 | 56.988 | 23.450 | 22.690 | 1.00 | 28.61 |
| ATOM | 1285 | N | SER | 326 | 57.613 | 25.376 | 23.638 | 1.00 | 27.98 |
| ATOM | 1286 | CA | SER | 326 | 58.265 | 24.718 | 24.757 | 1.00 | 31.60 |
| ATOM | 1287 | CB | SER | 326 | 59.527 | 25.493 | 25.155 | 1.00 | 35.80 |
| ATOM | 1288 | OG | SER | 326 | 60.123 | 24.966 | 26.327 | 1.00 | 43.74 |
| ATOM | 1289 | C | SER | 326 | 57.313 | 24.624 | 25.939 | 1.00 | 32.12 |
| ATOM | 1290 | O | SER | 326 | 56.590 | 25.574 | 26.240 | 1.00 | 30.91 |
| ATOM | 1291 | N | THR | 327 | 57.276 | 23.464 | 26.583 | 1.00 | 35.41 |
| ATOM | 1292 | CA | THR | 327 | 56.420 | 23.278 | 27.747 | 1.00 | 39.61 |
| ATOM | 1293 | CB | THR | 327 | 55.777 | 21.890 | 27.758 | 1.00 | 38.84 |
| ATOM | 1294 | OG1 | THR | 327 | 56.784 | 20.890 | 27.538 | 1.00 | 42.53 |
| ATOM | 1295 | CG2 | THR | 327 | 54.716 | 21.802 | 26.679 | 1.00 | 40.78 |
| ATOM | 1296 | C | THR | 327 | 57.232 | 23.471 | 29.022 | 1.00 | 43.86 |
| ATOM | 1297 | O | THR | 327 | 56.785 | 23.133 | 30.118 | 1.00 | 42.40 |

FIG. 28A-29

| ATOM | 1298 | N   | ASP | 328 | 58.417 | 24.054 | 28.869 | 1.00 | 47.35 |
|------|------|-----|-----|-----|--------|--------|--------|------|-------|
| ATOM | 1299 | CA  | ASP | 328 | 59.309 | 24.308 | 29.987 | 1.00 | 49.43 |
| ATOM | 1300 | CB  | ASP | 328 | 60.750 | 24.358 | 29.482 | 1.00 | 58.03 |
| ATOM | 1301 | CG  | ASP | 328 | 61.718 | 23.687 | 30.425 | 1.00 | 72.16 |
| ATOM | 1302 | OD1 | ASP | 328 | 61.816 | 24.117 | 31.595 | 1.00 | 82.32 |
| ATOM | 1303 | OD2 | ASP | 328 | 62.378 | 22.720 | 29.994 | 1.00 | 81.63 |
| ATOM | 1304 | C   | ASP | 328 | 58.951 | 25.625 | 30.676 | 1.00 | 47.99 |
| ATOM | 1305 | O   | ASP | 328 | 59.830 | 26.373 | 31.093 | 1.00 | 53.33 |
| ATOM | 1306 | N   | ARG | 329 | 57.657 | 25.910 | 30.780 | 1.00 | 48.33 |
| ATOM | 1307 | CA  | ARG | 329 | 57.177 | 27.135 | 31.413 | 1.00 | 47.67 |
| ATOM | 1308 | CB  | ARG | 329 | 56.562 | 28.091 | 30.379 | 1.00 | 47.64 |
| ATOM | 1309 | CG  | ARG | 329 | 57.550 | 28.802 | 29.450 | 1.00 | 47.87 |
| ATOM | 1310 | CD  | ARG | 329 | 57.893 | 27.968 | 28.226 | 1.00 | 44.00 |
| ATOM | 1311 | NE  | ARG | 329 | 58.759 | 28.682 | 27.288 | 1.00 | 41.17 |
| ATOM | 1312 | CZ  | ARG | 329 | 60.087 | 28.605 | 27.283 | 1.00 | 48.58 |
| ATOM | 1313 | NH1 | ARG | 329 | 60.719 | 27.848 | 28.172 | 1.00 | 52.94 |
| ATOM | 1314 | NH2 | ARG | 329 | 60.784 | 29.257 | 26.362 | 1.00 | 43.16 |
| ATOM | 1315 | C   | ARG | 329 | 56.126 | 26.778 | 32.457 | 1.00 | 48.01 |
| ATOM | 1316 | O   | ARG | 329 | 55.573 | 25.677 | 32.437 | 1.00 | 50.22 |
| ATOM | 1317 | N   | SER | 330 | 55.832 | 27.716 | 33.351 | 1.00 | 47.37 |
| ATOM | 1318 | CA  | SER | 330 | 54.848 | 27.490 | 34.402 | 1.00 | 47.64 |
| ATOM | 1319 | CB  | SER | 330 | 55.376 | 28.021 | 35.736 | 1.00 | 46.62 |
| ATOM | 1320 | C   | SER | 330 | 53.506 | 28.139 | 34.074 | 1.00 | 46.40 |
| ATOM | 1321 | O   | SER | 330 | 53.460 | 29.252 | 33.548 | 1.00 | 48.49 |
| ATOM | 1322 | N   | GLY | 331 | 52.421 | 27.424 | 34.359 | 1.00 | 44.16 |
| ATOM | 1323 | CA  | GLY | 331 | 51.090 | 27.956 | 34.123 | 1.00 | 41.44 |
| ATOM | 1324 | C   | GLY | 331 | 50.424 | 27.660 | 32.790 | 1.00 | 42.83 |
| ATOM | 1325 | O   | GLY | 331 | 49.478 | 28.351 | 32.413 | 1.00 | 45.88 |
| ATOM | 1326 | N   | LEU | 332 | 50.889 | 26.643 | 32.075 | 1.00 | 40.10 |
| ATOM | 1327 | CA  | LEU | 332 | 50.288 | 26.300 | 30.789 | 1.00 | 39.27 |
| ATOM | 1328 | CB  | LEU | 332 | 51.301 | 25.596 | 29.885 | 1.00 | 37.42 |
| ATOM | 1329 | CG  | LEU | 332 | 52.436 | 26.426 | 29.291 | 1.00 | 35.35 |
| ATOM | 1330 | CD1 | LEU | 332 | 53.374 | 25.505 | 28.530 | 1.00 | 31.61 |
| ATOM | 1331 | CD2 | LEU | 332 | 51.875 | 27.511 | 28.376 | 1.00 | 31.82 |
| ATOM | 1332 | C   | LEU | 332 | 49.058 | 25.415 | 30.951 | 1.00 | 39.32 |
| ATOM | 1333 | O   | LEU | 332 | 49.060 | 24.467 | 31.738 | 1.00 | 42.74 |
| ATOM | 1334 | N   | LEU | 333 | 48.009 | 25.730 | 30.202 | 1.00 | 37.62 |
| ATOM | 1335 | CA  | LEU | 333 | 46.778 | 24.953 | 30.241 | 1.00 | 41.30 |
| ATOM | 1336 | CB  | LEU | 333 | 45.586 | 25.835 | 29.852 | 1.00 | 43.52 |
| ATOM | 1337 | CG  | LEU | 333 | 45.125 | 26.904 | 30.848 | 1.00 | 49.39 |
| ATOM | 1338 | CD1 | LEU | 333 | 44.296 | 27.970 | 30.142 | 1.00 | 46.19 |
| ATOM | 1339 | CD2 | LEU | 333 | 44.330 | 26.248 | 31.968 | 1.00 | 51.29 |
| ATOM | 1340 | C   | LEU | 333 | 46.859 | 23.762 | 29.285 | 1.00 | 41.39 |
| ATOM | 1341 | O   | LEU | 333 | 46.565 | 22.628 | 29.657 | 1.00 | 43.41 |
| ATOM | 1342 | N   | CYA | 334 | 47.317 | 24.024 | 28.067 | 1.00 | 42.18 |
| ATOM | 1343 | CA  | CYA | 334 | 47.409 | 23.003 | 27.029 | 1.00 | 39.56 |

FIG. 28A-30

| ATOM | 1344 | CB | CYA | 334 | 47.004 | 23.616 | 25.691 | 1.00 | 45.48 |
| ATOM | 1345 | SG | CYA | 334 | 45.517 | 24.616 | 25.785 | 1.00 | 51.57 |
| ATOM | 1346 | AS | CYA | 334 | 44.187 | 22.808 | 25.555 | 1.00 | 90.90 |
| ATOM | 1347 | C | CYA | 334 | 48.776 | 22.347 | 26.891 | 1.00 | 38.28 |
| ATOM | 1348 | O | CYA | 334 | 49.273 | 22.178 | 25.778 | 1.00 | 40.95 |
| ATOM | 1349 | N | VAL | 335 | 49.345 | 21.913 | 28.009 | 1.00 | 36.05 |
| ATOM | 1350 | CA | VAL | 335 | 50.661 | 21.278 | 28.006 | 1.00 | 35.78 |
| ATOM | 1351 | CB | VAL | 335 | 50.996 | 20.679 | 29.399 | 1.00 | 35.53 |
| ATOM | 1352 | CG1 | VAL | 335 | 52.413 | 20.123 | 29.407 | 1.00 | 32.76 |
| ATOM | 1353 | CG2 | VAL | 335 | 50.822 | 21.729 | 30.490 | 1.00 | 28.87 |
| ATOM | 1354 | C | VAL | 335 | 50.776 | 20.170 | 26.950 | 1.00 | 36.41 |
| ATOM | 1355 | O | VAL | 335 | 51.756 | 20.104 | 26.202 | 1.00 | 34.26 |
| ATOM | 1356 | N | ASP | 336 | 49.756 | 19.323 | 26.880 | 1.00 | 38.42 |
| ATOM | 1357 | CA | ASP | 336 | 49.736 | 18.209 | 25.942 | 1.00 | 39.71 |
| ATOM | 1358 | CB | ASP | 336 | 48.485 | 17.359 | 26.179 | 1.00 | 51.53 |
| ATOM | 1359 | CG | ASP | 336 | 48.534 | 16.028 | 25.452 | 1.00 | 65.98 |
| ATOM | 1360 | OD1 | ASP | 336 | 49.240 | 15.114 | 25.934 | 1.00 | 70.75 |
| ATOM | 1361 | OD2 | ASP | 336 | 47.858 | 15.891 | 24.406 | 1.00 | 72.15 |
| ATOM | 1362 | C | ASP | 336 | 49.794 | 18.668 | 24.486 | 1.00 | 37.72 |
| ATOM | 1363 | O | ASP | 336 | 50.686 | 18.259 | 23.733 | 1.00 | 32.08 |
| ATOM | 1364 | N | LYS | 337 | 48.858 | 19.532 | 24.100 | 1.00 | 33.78 |
| ATOM | 1365 | CA | LYS | 337 | 48.797 | 20.040 | 22.731 | 1.00 | 28.00 |
| ATOM | 1366 | CB | LYS | 337 | 47.626 | 21.022 | 22.574 | 1.00 | 22.46 |
| ATOM | 1367 | C | LYS | 337 | 50.116 | 20.704 | 22.334 | 1.00 | 29.06 |
| ATOM | 1368 | O | LYS | 337 | 50.607 | 20.512 | 21.220 | 1.00 | 28.41 |
| ATOM | 1369 | N | ILE | 338 | 50.705 | 21.449 | 23.267 | 1.00 | 27.56 |
| ATOM | 1370 | CA | ILE | 338 | 51.964 | 22.138 | 23.022 | 1.00 | 25.03 |
| ATOM | 1371 | CB | ILE | 338 | 52.274 | 23.149 | 24.144 | 1.00 | 19.49 |
| ATOM | 1372 | CG2 | ILE | 338 | 53.577 | 23.876 | 23.859 | 1.00 | 19.00 |
| ATOM | 1373 | CG1 | ILE | 338 | 51.135 | 24.167 | 24.232 | 1.00 | 21.97 |
| ATOM | 1374 | CD1 | ILE | 338 | 51.277 | 25.175 | 25.348 | 1.00 | 26.67 |
| ATOM | 1375 | C | ILE | 338 | 53.119 | 21.153 | 22.826 | 1.00 | 29.97 |
| ATOM | 1376 | O | ILE | 338 | 53.935 | 21.328 | 21.914 | 1.00 | 31.00 |
| ATOM | 1377 | N | GLU | 339 | 53.165 | 20.100 | 23.642 | 1.00 | 33.52 |
| ATOM | 1378 | CA | GLU | 339 | 54.213 | 19.080 | 23.516 | 1.00 | 35.34 |
| ATOM | 1379 | CB | GLU | 339 | 54.136 | 18.062 | 24.659 | 1.00 | 39.97 |
| ATOM | 1380 | CG | GLU | 339 | 54.653 | 18.585 | 25.986 | 1.00 | 53.23 |
| ATOM | 1381 | CD | GLU | 339 | 54.549 | 17.579 | 27.126 | 1.00 | 61.16 |
| ATOM | 1382 | OE1 | GLU | 339 | 53.602 | 16.759 | 27.131 | 1.00 | 64.30 |
| ATOM | 1383 | OE2 | GLU | 339 | 55.412 | 17.622 | 28.031 | 1.00 | 57.76 |
| ATOM | 1384 | C | GLU | 339 | 54.091 | 18.353 | 22.178 | 1.00 | 31.63 |
| ATOM | 1385 | O | GLU | 339 | 55.086 | 18.123 | 21.491 | 1.00 | 28.96 |
| ATOM | 1386 | N | LYS | 340 | 52.861 | 18.006 | 21.810 | 1.00 | 30.95 |
| ATOM | 1387 | CA | LYS | 340 | 52.602 | 17.313 | 20.554 | 1.00 | 31.58 |
| ATOM | 1388 | CB | LYS | 340 | 51.121 | 16.966 | 20.438 | 1.00 | 31.83 |
| ATOM | 1389 | C | LYS | 340 | 53.057 | 18.159 | 19.358 | 1.00 | 29.84 |

FIG. 28A-31

| ATOM | 1390 | O | LYS | 340 | 53.696 | 17.640 | 18.438 | 1.00 | 31.58 |
|---|---|---|---|---|---|---|---|---|---|
| ATOM | 1391 | N | SER | 341 | 52.765 | 19.460 | 19.388 | 1.00 | 25.33 |
| ATOM | 1392 | CA | SER | 341 | 53.165 | 20.351 | 18.297 | 1.00 | 23.92 |
| ATOM | 1393 | CB | SER | 341 | 52.468 | 21.707 | 18.400 | 1.00 | 24.02 |
| ATOM | 1394 | OG | SER | 341 | 52.700 | 22.302 | 19.657 | 1.00 | 48.88 |
| ATOM | 1395 | C | SER | 341 | 54.677 | 20.533 | 18.240 | 1.00 | 24.39 |
| ATOM | 1396 | O | SER | 341 | 55.254 | 20.593 | 17.150 | 1.00 | 24.71 |
| ATOM | 1397 | N | GLN | 342 | 55.324 | 20.606 | 19.405 | 1.00 | 25.45 |
| ATOM | 1398 | CA | GLN | 342 | 56.777 | 20.751 | 19.437 | 1.00 | 26.66 |
| ATOM | 1399 | CB | GLN | 342 | 57.311 | 20.975 | 20.853 | 1.00 | 22.77 |
| ATOM | 1400 | CG | GLN | 342 | 58.805 | 21.307 | 20.840 | 1.00 | 25.76 |
| ATOM | 1401 | CD | GLN | 342 | 59.427 | 21.371 | 22.214 | 1.00 | 28.46 |
| ATOM | 1402 | OE1 | GLN | 342 | 59.342 | 20.422 | 22.990 | 1.00 | 34.22 |
| ATOM | 1403 | NE2 | GLN | 342 | 60.080 | 22.483 | 22.517 | 1.00 | 30.01 |
| ATOM | 1404 | C | GLN | 342 | 57.425 | 19.504 | 18.843 | 1.00 | 23.37 |
| ATOM | 1405 | O | GLN | 342 | 58.414 | 19.598 | 18.106 | 1.00 | 23.65 |
| ATOM | 1406 | N | GLU | 343 | 56.864 | 18.340 | 19.162 | 1.00 | 21.48 |
| ATOM | 1407 | CA | GLU | 343 | 57.370 | 17.076 | 18.641 | 1.00 | 20.74 |
| ATOM | 1408 | CB | GLU | 343 | 56.599 | 15.902 | 19.247 | 1.00 | 22.09 |
| ATOM | 1409 | C | GLU | 343 | 57.225 | 17.094 | 17.119 | 1.00 | 19.18 |
| ATOM | 1410 | O | GLU | 343 | 58.156 | 16.743 | 16.393 | 1.00 | 21.11 |
| ATOM | 1411 | N | ALA | 344 | 56.077 | 17.570 | 16.648 | 1.00 | 19.93 |
| ATOM | 1412 | CA | ALA | 344 | 55.803 | 17.662 | 15.217 | 1.00 | 20.20 |
| ATOM | 1413 | CB | ALA | 344 | 54.411 | 18.216 | 14.989 | 1.00 | 16.46 |
| ATOM | 1414 | C | ALA | 344 | 56.850 | 18.539 | 14.528 | 1.00 | 20.75 |
| ATOM | 1415 | O | ALA | 344 | 57.432 | 18.140 | 13.514 | 1.00 | 25.13 |
| ATOM | 1416 | N | TYR | 345 | 57.105 | 19.722 | 15.088 | 1.00 | 21.31 |
| ATOM | 1417 | CA | TYR | 345 | 58.107 | 20.631 | 14.531 | 1.00 | 15.93 |
| ATOM | 1418 | CB | TYR | 345 | 58.127 | 21.969 | 15.282 | 1.00 | 17.29 |
| ATOM | 1419 | CG | TYR | 345 | 57.049 | 22.927 | 14.833 | 1.00 | 16.11 |
| ATOM | 1420 | CD1 | TYR | 345 | 56.017 | 23.296 | 15.689 | 1.00 | 9.93 |
| ATOM | 1421 | CE1 | TYR | 345 | 54.999 | 24.138 | 15.263 | 1.00 | 16.95 |
| ATOM | 1422 | CD2 | TYR | 345 | 57.041 | 23.431 | 13.531 | 1.00 | 19.84 |
| ATOM | 1423 | CE2 | TYR | 345 | 56.026 | 24.276 | 13.094 | 1.00 | 17.13 |
| ATOM | 1424 | CZ | TYR | 345 | 55.005 | 24.622 | 13.963 | 1.00 | 18.12 |
| ATOM | 1425 | OH | TYR | 345 | 53.980 | 25.430 | 13.530 | 1.00 | 26.25 |
| ATOM | 1426 | C | TYR | 345 | 59.493 | 20.008 | 14.554 | 1.00 | 20.65 |
| ATOM | 1427 | O | TYR | 345 | 60.240 | 20.129 | 13.583 | 1.00 | 20.75 |
| ATOM | 1428 | N | LEU | 346 | 59.832 | 19.337 | 15.655 | 1.00 | 22.14 |
| ATOM | 1429 | CA | LEU | 346 | 61.134 | 18.684 | 15.803 | 1.00 | 19.43 |
| ATOM | 1430 | CB | LEU | 346 | 61.267 | 18.041 | 17.186 | 1.00 | 19.92 |
| ATOM | 1431 | CG | LEU | 346 | 61.683 | 18.945 | 18.347 | 1.00 | 25.56 |
| ATOM | 1432 | CD1 | LEU | 346 | 61.440 | 18.244 | 19.677 | 1.00 | 22.06 |
| ATOM | 1433 | CD2 | LEU | 346 | 63.147 | 19.332 | 18.197 | 1.00 | 17.62 |
| ATOM | 1434 | C | LEU | 346 | 61.359 | 17.635 | 14.723 | 1.00 | 19.30 |
| ATOM | 1435 | O | LEU | 346 | 62.441 | 17.560 | 14.142 | 1.00 | 22.84 |

FIG. 28A-32

| ATOM | 1436 | N   | LEU | 347 | 60.337 | 16.826 | 14.456 | 1.00 | 25.17 |
|------|------|-----|-----|-----|--------|--------|--------|------|-------|
| ATOM | 1437 | CA  | LEU | 347 | 60.423 | 15.790 | 13.427 | 1.00 | 24.55 |
| ATOM | 1438 | CB  | LEU | 347 | 59.187 | 14.892 | 13.453 | 1.00 | 25.47 |
| ATOM | 1439 | CG  | LEU | 347 | 59.256 | 13.654 | 14.345 | 1.00 | 30.65 |
| ATOM | 1440 | CD1 | LEU | 347 | 57.941 | 12.890 | 14.258 | 1.00 | 34.28 |
| ATOM | 1441 | CD2 | LEU | 347 | 60.416 | 12.765 | 13.908 | 1.00 | 28.26 |
| ATOM | 1442 | C   | LEU | 347 | 60.584 | 16.400 | 12.042 | 1.00 | 24.00 |
| ATOM | 1443 | O   | LEU | 347 | 61.399 | 15.932 | 11.245 | 1.00 | 29.74 |
| ATOM | 1444 | N   | ALA | 348 | 59.809 | 17.443 | 11.761 | 1.00 | 22.72 |
| ATOM | 1445 | CA  | ALA | 348 | 59.875 | 18.125 | 10.475 | 1.00 | 19.19 |
| ATOM | 1446 | CB  | ALA | 348 | 58.789 | 19.188 | 10.388 | 1.00 | 22.73 |
| ATOM | 1447 | C   | ALA | 348 | 61.246 | 18.762 | 10.316 | 1.00 | 20.34 |
| ATOM | 1448 | O   | ALA | 348 | 61.881 | 18.633 | 9.274  | 1.00 | 23.94 |
| ATOM | 1449 | N   | PHE | 349 | 61.707 | 19.402 | 11.388 | 1.00 | 22.19 |
| ATOM | 1450 | CA  | PHE | 349 | 63.001 | 20.078 | 11.435 | 1.00 | 19.41 |
| ATOM | 1451 | CB  | PHE | 349 | 63.185 | 20.701 | 12.832 | 1.00 | 17.45 |
| ATOM | 1452 | CG  | PHE | 349 | 64.371 | 21.632 | 12.963 | 1.00 | 18.70 |
| ATOM | 1453 | CD1 | PHE | 349 | 65.183 | 21.943 | 11.874 | 1.00 | 19.09 |
| ATOM | 1454 | CD2 | PHE | 349 | 64.669 | 22.203 | 14.199 | 1.00 | 21.81 |
| ATOM | 1455 | CE1 | PHE | 349 | 66.270 | 22.811 | 12.012 | 1.00 | 21.49 |
| ATOM | 1456 | CE2 | PHE | 349 | 65.753 | 23.072 | 14.351 | 1.00 | 18.58 |
| ATOM | 1457 | CZ  | PHE | 349 | 66.555 | 23.376 | 13.256 | 1.00 | 18.67 |
| ATOM | 1458 | C   | PHE | 349 | 64.110 | 19.071 | 11.136 | 1.00 | 20.96 |
| ATOM | 1459 | O   | PHE | 349 | 64.967 | 19.311 | 10.283 | 1.00 | 25.19 |
| ATOM | 1460 | N   | GLU | 350 | 64.076 | 17.935 | 11.824 | 1.00 | 23.96 |
| ATOM | 1461 | CA  | GLU | 350 | 65.077 | 16.888 | 11.642 | 1.00 | 27.98 |
| ATOM | 1462 | CB  | GLU | 350 | 64.794 | 15.721 | 12.591 | 1.00 | 28.90 |
| ATOM | 1463 | CG  | GLU | 350 | 65.738 | 14.542 | 12.413 | 1.00 | 39.36 |
| ATOM | 1464 | CD  | GLU | 350 | 65.603 | 13.497 | 13.505 | 1.00 | 41.62 |
| ATOM | 1465 | OE1 | GLU | 350 | 64.475 | 13.260 | 13.988 | 1.00 | 43.67 |
| ATOM | 1466 | OE2 | GLU | 350 | 66.636 | 12.908 | 13.876 | 1.00 | 49.64 |
| ATOM | 1467 | C   | GLU | 350 | 65.100 | 16.385 | 10.203 | 1.00 | 27.12 |
| ATOM | 1468 | O   | GLU | 350 | 66.158 | 16.288 | 9.577  | 1.00 | 27.44 |
| ATOM | 1469 | N   | HIS | 351 | 63.918 | 16.088 | 9.678  | 1.00 | 27.36 |
| ATOM | 1470 | CA  | HIS | 351 | 63.787 | 15.591 | 8.318  | 1.00 | 23.97 |
| ATOM | 1471 | CB  | HIS | 351 | 62.366 | 15.087 | 8.090  | 1.00 | 22.89 |
| ATOM | 1472 | CG  | HIS | 351 | 61.991 | 13.945 | 8.986  | 1.00 | 24.58 |
| ATOM | 1473 | CD2 | HIS | 351 | 62.736 | 13.209 | 9.846  | 1.00 | 25.83 |
| ATOM | 1474 | ND1 | HIS | 351 | 60.709 | 13.448 | 9.073  | 1.00 | 26.50 |
| ATOM | 1475 | CE1 | HIS | 351 | 60.677 | 12.460 | 9.948  | 1.00 | 24.81 |
| ATOM | 1476 | NE2 | HIS | 351 | 61.896 | 12.295 | 10.431 | 1.00 | 28.42 |
| ATOM | 1477 | C   | HIS | 351 | 64.200 | 16.635 | 7.278  | 1.00 | 24.22 |
| ATOM | 1478 | O   | HIS | 351 | 64.757 | 16.287 | 6.236  | 1.00 | 25.79 |
| ATOM | 1479 | N   | TYR | 352 | 63.969 | 17.912 | 7.572  | 1.00 | 21.04 |
| ATOM | 1480 | CA  | TYR | 352 | 64.363 | 18.974 | 6.654  | 1.00 | 18.98 |
| ATOM | 1481 | CB  | TYR | 352 | 63.770 | 20.321 | 7.067  | 1.00 | 17.08 |

FIG. 28A-33

| ATOM | 1482 | CG | TYR | 352 | 64.127 | 21.413 | 6.090 | 1.00 | 21.83 |
|---|---|---|---|---|---|---|---|---|---|
| ATOM | 1483 | CD1 | TYR | 352 | 63.537 | 21.467 | 4.828 | 1.00 | 20.07 |
| ATOM | 1484 | CE1 | TYR | 352 | 63.941 | 22.411 | 3.883 | 1.00 | 23.51 |
| ATOM | 1485 | CD2 | TYR | 352 | 65.121 | 22.339 | 6.388 | 1.00 | 19.94 |
| ATOM | 1486 | CE2 | TYR | 352 | 65.531 | 23.284 | 5.452 | 1.00 | 20.85 |
| ATOM | 1487 | CZ | TYR | 352 | 64.942 | 23.313 | 4.203 | 1.00 | 24.80 |
| ATOM | 1488 | OH | TYR | 352 | 65.380 | 24.221 | 3.269 | 1.00 | 26.74 |
| ATOM | 1489 | C | TYR | 352 | 65.889 | 19.055 | 6.624 | 1.00 | 20.58 |
| ATOM | 1490 | O | TYR | 352 | 66.492 | 19.276 | 5.570 | 1.00 | 22.72 |
| ATOM | 1491 | N | VAL | 353 | 66.508 | 18.877 | 7.789 | 1.00 | 28.34 |
| ATOM | 1492 | CA | VAL | 353 | 67.967 | 18.892 | 7.904 | 1.00 | 22.38 |
| ATOM | 1493 | CB | VAL | 353 | 68.419 | 18.755 | 9.389 | 1.00 | 26.46 |
| ATOM | 1494 | CG1 | VAL | 353 | 69.915 | 18.527 | 9.478 | 1.00 | 20.92 |
| ATOM | 1495 | CG2 | VAL | 353 | 68.053 | 20.009 | 10.165 | 1.00 | 22.46 |
| ATOM | 1496 | C | VAL | 353 | 68.518 | 17.725 | 7.078 | 1.00 | 23.51 |
| ATOM | 1497 | O | VAL | 353 | 69.535 | 17.865 | 6.391 | 1.00 | 24.73 |
| ATOM | 1498 | N | ASN | 354 | 67.850 | 16.575 | 7.158 | 1.00 | 20.93 |
| ATOM | 1499 | CA | ASN | 354 | 68.252 | 15.392 | 6.397 | 1.00 | 27.25 |
| ATOM | 1500 | CB | ASN | 354 | 67.320 | 14.210 | 6.680 | 1.00 | 28.43 |
| ATOM | 1501 | CG | ASN | 354 | 67.521 | 13.607 | 8.058 | 1.00 | 31.50 |
| ATOM | 1502 | OD1 | ASN | 354 | 68.565 | 13.787 | 8.692 | 1.00 | 37.79 |
| ATOM | 1503 | ND2 | ASN | 354 | 66.521 | 12.867 | 8.524 | 1.00 | 26.44 |
| ATOM | 1504 | C | ASN | 354 | 68.182 | 15.721 | 4.908 | 1.00 | 31.27 |
| ATOM | 1505 | O | ASN | 354 | 69.066 | 15.347 | 4.134 | 1.00 | 34.22 |
| ATOM | 1506 | N | HIS | 355 | 67.124 | 16.429 | 4.520 | 1.00 | 30.49 |
| ATOM | 1507 | CA | HIS | 355 | 66.917 | 16.826 | 3.132 | 1.00 | 26.88 |
| ATOM | 1508 | CB | HIS | 355 | 65.548 | 17.494 | 2.975 | 1.00 | 27.27 |
| ATOM | 1509 | CG | HIS | 355 | 65.319 | 18.103 | 1.625 | 1.00 | 37.76 |
| ATOM | 1510 | CD2 | HIS | 355 | 65.439 | 19.382 | 1.196 | 1.00 | 35.28 |
| ATOM | 1511 | ND1 | HIS | 355 | 64.913 | 17.369 | 0.532 | 1.00 | 34.93 |
| ATOM | 1512 | CE1 | HIS | 355 | 64.789 | 18.169 | -0.513 | 1.00 | 34.84 |
| ATOM | 1513 | NE2 | HIS | 355 | 65.104 | 19.394 | -0.135 | 1.00 | 33.13 |
| ATOM | 1514 | C | HIS | 355 | 68.016 | 17.748 | 2.610 | 1.00 | 24.66 |
| ATOM | 1515 | O | HIS | 355 | 68.420 | 17.630 | 1.456 | 1.00 | 26.62 |
| ATOM | 1516 | N | ARG | 356 | 68.487 | 18.670 | 3.448 | 1.00 | 25.86 |
| ATOM | 1517 | CA | ARG | 356 | 69.536 | 19.608 | 3.040 | 1.00 | 26.94 |
| ATOM | 1518 | CB | ARG | 356 | 69.620 | 20.791 | 3.996 | 1.00 | 20.57 |
| ATOM | 1519 | CG | ARG | 356 | 68.453 | 21.727 | 3.899 | 1.00 | 19.69 |
| ATOM | 1520 | CD | ARG | 356 | 68.866 | 23.110 | 4.340 | 1.00 | 23.81 |
| ATOM | 1521 | NE | ARG | 356 | 69.768 | 23.746 | 3.388 | 1.00 | 23.14 |
| ATOM | 1522 | CZ | ARG | 356 | 70.641 | 24.697 | 3.702 | 1.00 | 24.11 |
| ATOM | 1523 | NH1 | ARG | 356 | 70.755 | 25.129 | 4.949 | 1.00 | 26.29 |
| ATOM | 1524 | NH2 | ARG | 356 | 71.384 | 25.242 | 2.754 | 1.00 | 32.79 |
| ATOM | 1525 | C | ARG | 356 | 70.921 | 19.002 | 2.875 | 1.00 | 29.38 |
| ATOM | 1526 | O | ARG | 356 | 71.795 | 19.607 | 2.257 | 1.00 | 32.91 |
| ATOM | 1527 | N | LYS | 357 | 71.133 | 17.848 | 3.498 | 1.00 | 33.39 |

FIG. 28A-34

| ATOM | 1528 | CA  | LYS | 357 | 72.401 | 17.128 | 3.417  | 1.00 | 35.97 |
| ---- | ---- | --- | --- | --- | ------ | ------ | ------ | ---- | ----- |
| ATOM | 1529 | CB  | LYS | 357 | 72.479 | 16.363 | 2.089  | 1.00 | 40.55 |
| ATOM | 1530 | CG  | LYS | 357 | 71.327 | 15.381 | 1.891  | 1.00 | 44.03 |
| ATOM | 1531 | CD  | LYS | 357 | 71.360 | 14.722 | 0.523  | 1.00 | 52.31 |
| ATOM | 1532 | CE  | LYS | 357 | 70.171 | 13.787 | 0.343  | 1.00 | 56.99 |
| ATOM | 1533 | NZ  | LYS | 357 | 70.208 | 13.085 | -0.970 | 1.00 | 64.78 |
| ATOM | 1534 | C   | LYS | 357 | 73.657 | 17.981 | 3.629  | 1.00 | 38.55 |
| ATOM | 1535 | O   | LYS | 357 | 74.518 | 18.079 | 2.748  | 1.00 | 42.50 |
| ATOM | 1536 | N   | HIS | 358 | 73.751 | 18.601 | 4.802  | 1.00 | 35.00 |
| ATOM | 1537 | CA  | HIS | 358 | 74.906 | 19.418 | 5.155  | 1.00 | 32.94 |
| ATOM | 1538 | CB  | HIS | 358 | 74.732 | 20.018 | 6.552  | 1.00 | 27.62 |
| ATOM | 1539 | CG  | HIS | 358 | 73.669 | 21.067 | 6.643  | 1.00 | 26.64 |
| ATOM | 1540 | CD2 | HIS | 358 | 72.330 | 20.968 | 6.819  | 1.00 | 20.85 |
| ATOM | 1541 | ND1 | HIS | 358 | 73.950 | 22.416 | 6.587  | 1.00 | 24.71 |
| ATOM | 1542 | CE1 | HIS | 358 | 72.831 | 23.103 | 6.724  | 1.00 | 21.02 |
| ATOM | 1543 | NE2 | HIS | 358 | 71.834 | 22.248 | 6.865  | 1.00 | 21.42 |
| ATOM | 1544 | C   | HIS | 358 | 76.140 | 18.520 | 5.176  | 1.00 | 36.60 |
| ATOM | 1545 | O   | HIS | 358 | 76.072 | 17.379 | 5.635  | 1.00 | 38.73 |
| ATOM | 1546 | N   | ASN | 359 | 77.267 | 19.037 | 4.702  | 1.00 | 41.40 |
| ATOM | 1547 | CA  | ASN | 359 | 78.515 | 18.277 | 4.689  | 1.00 | 45.02 |
| ATOM | 1548 | CB  | ASN | 359 | 79.441 | 18.799 | 3.587  | 1.00 | 42.57 |
| ATOM | 1549 | C   | ASN | 359 | 79.193 | 18.386 | 6.058  | 1.00 | 46.59 |
| ATOM | 1550 | O   | ASN | 359 | 80.405 | 18.588 | 6.150  | 1.00 | 52.31 |
| ATOM | 1551 | N   | ILE | 360 | 78.400 | 18.254 | 7.117  | 1.00 | 45.14 |
| ATOM | 1552 | CA  | ILE | 360 | 78.896 | 18.348 | 8.487  | 1.00 | 43.69 |
| ATOM | 1553 | CB  | ILE | 360 | 78.330 | 19.597 | 9.207  | 1.00 | 40.08 |
| ATOM | 1554 | CG2 | ILE | 360 | 78.824 | 19.657 | 10.645 | 1.00 | 32.11 |
| ATOM | 1555 | CG1 | ILE | 360 | 78.733 | 20.864 | 8.452  | 1.00 | 41.47 |
| ATOM | 1556 | CD1 | ILE | 360 | 78.057 | 22.115 | 8.954  | 1.00 | 44.93 |
| ATOM | 1557 | C   | ILE | 360 | 78.452 | 17.101 | 9.242  | 1.00 | 43.63 |
| ATOM | 1558 | O   | ILE | 360 | 77.257 | 16.797 | 9.313  | 1.00 | 45.20 |
| ATOM | 1559 | N   | PRO | 361 | 79.413 | 16.337 | 9.780  | 1.00 | 43.91 |
| ATOM | 1560 | CD  | PRO | 361 | 80.871 | 16.540 | 9.699  | 1.00 | 47.07 |
| ATOM | 1561 | CA  | PRO | 361 | 79.087 | 15.118 | 10.526 | 1.00 | 41.66 |
| ATOM | 1562 | CB  | PRO | 361 | 80.462 | 14.495 | 10.782 | 1.00 | 43.73 |
| ATOM | 1563 | CG  | PRO | 361 | 81.383 | 15.679 | 10.830 | 1.00 | 45.45 |
| ATOM | 1564 | C   | PRO | 361 | 78.332 | 15.403 | 11.832 | 1.00 | 36.42 |
| ATOM | 1565 | O   | PRO | 361 | 78.679 | 16.325 | 12.572 | 1.00 | 35.74 |
| ATOM | 1566 | N   | HIS | 362 | 77.291 | 14.610 | 12.088 | 1.00 | 33.14 |
| ATOM | 1567 | CA  | HIS | 362 | 76.462 | 14.726 | 13.292 | 1.00 | 34.09 |
| ATOM | 1568 | CB  | HIS | 362 | 77.288 | 14.413 | 14.547 | 1.00 | 33.82 |
| ATOM | 1569 | CG  | HIS | 362 | 78.132 | 13.181 | 14.424 | 1.00 | 36.04 |
| ATOM | 1570 | CD2 | HIS | 362 | 77.793 | 11.885 | 14.224 | 1.00 | 34.77 |
| ATOM | 1571 | ND1 | HIS | 362 | 79.509 | 13.212 | 14.482 | 1.00 | 37.16 |
| ATOM | 1572 | CE1 | HIS | 362 | 79.983 | 11.990 | 14.325 | 1.00 | 37.16 |
| ATOM | 1573 | NE2 | HIS | 362 | 78.962 | 11.165 | 14.167 | 1.00 | 40.13 |

FIG. 28A-35

| ATOM | 1574 | C   | HIS | 362 | 75.829 | 16.110 | 13.417 | 1.00 | 31.00 |
|------|------|-----|-----|-----|--------|--------|--------|------|-------|
| ATOM | 1575 | O   | HIS | 362 | 75.617 | 16.608 | 14.525 | 1.00 | 30.22 |
| ATOM | 1576 | N   | PHE | 363 | 75.478 | 16.690 | 12.272 | 1.00 | 33.06 |
| ATOM | 1577 | CA  | PHE | 363 | 74.878 | 18.021 | 12.200 | 1.00 | 28.08 |
| ATOM | 1578 | CB  | PHE | 363 | 74.503 | 18.355 | 10.747 | 1.00 | 25.26 |
| ATOM | 1579 | CG  | PHE | 363 | 73.923 | 19.733 | 10.567 | 1.00 | 24.91 |
| ATOM | 1580 | CD1 | PHE | 363 | 74.750 | 20.817 | 10.320 | 1.00 | 27.60 |
| ATOM | 1581 | CD2 | PHE | 363 | 72.552 | 19.948 | 10.664 | 1.00 | 25.52 |
| ATOM | 1582 | CE1 | PHE | 363 | 74.221 | 22.100 | 10.175 | 1.00 | 29.70 |
| ATOM | 1583 | CE2 | PHE | 363 | 72.014 | 21.227 | 10.522 | 1.00 | 25.88 |
| ATOM | 1584 | CZ  | PHE | 363 | 72.850 | 22.304 | 10.278 | 1.00 | 21.49 |
| ATOM | 1585 | C   | PHE | 363 | 73.659 | 18.201 | 13.099 | 1.00 | 23.79 |
| ATOM | 1586 | O   | PHE | 363 | 73.587 | 19.164 | 13.863 | 1.00 | 24.48 |
| ATOM | 1587 | N   | TRP | 364 | 72.707 | 17.277 | 13.012 | 1.00 | 23.13 |
| ATOM | 1588 | CA  | TRP | 364 | 71.484 | 17.369 | 13.805 | 1.00 | 25.06 |
| ATOM | 1589 | CB  | TRP | 364 | 70.536 | 16.201 | 13.494 | 1.00 | 21.17 |
| ATOM | 1590 | CG  | TRP | 364 | 69.247 | 16.220 | 14.271 | 1.00 | 23.14 |
| ATOM | 1591 | CD2 | TRP | 364 | 68.261 | 17.266 | 14.296 | 1.00 | 27.68 |
| ATOM | 1592 | CE2 | TRP | 364 | 67.229 | 16.845 | 15.165 | 1.00 | 28.31 |
| ATOM | 1593 | CE3 | TRP | 364 | 68.149 | 18.517 | 13.671 | 1.00 | 26.46 |
| ATOM | 1594 | CD1 | TRP | 364 | 68.784 | 15.241 | 15.096 | 1.00 | 23.76 |
| ATOM | 1595 | NE1 | TRP | 364 | 67.576 | 15.607 | 15.637 | 1.00 | 32.12 |
| ATOM | 1596 | CZ2 | TRP | 364 | 66.100 | 17.628 | 15.427 | 1.00 | 25.63 |
| ATOM | 1597 | CZ3 | TRP | 364 | 67.028 | 19.294 | 13.931 | 1.00 | 25.55 |
| ATOM | 1598 | CH2 | TRP | 364 | 66.017 | 18.845 | 14.803 | 1.00 | 29.79 |
| ATOM | 1599 | C   | TRP | 364 | 71.715 | 17.531 | 15.312 | 1.00 | 27.80 |
| ATOM | 1600 | O   | TRP | 364 | 71.212 | 18.486 | 15.904 | 1.00 | 26.96 |
| ATOM | 1601 | N   | PRO | 365 | 72.458 | 16.605 | 15.955 | 1.00 | 30.69 |
| ATOM | 1602 | CD  | PRO | 365 | 72.974 | 15.308 | 15.481 | 1.00 | 31.45 |
| ATOM | 1603 | CA  | PRO | 365 | 72.687 | 16.757 | 17.397 | 1.00 | 27.97 |
| ATOM | 1604 | CB  | PRO | 365 | 73.506 | 15.512 | 17.752 | 1.00 | 26.50 |
| ATOM | 1605 | CG  | PRO | 365 | 73.057 | 14.509 | 16.757 | 1.00 | 33.47 |
| ATOM | 1606 | C   | PRO | 365 | 73.457 | 18.043 | 17.709 | 1.00 | 27.10 |
| ATOM | 1607 | O   | PRO | 365 | 73.154 | 18.736 | 18.681 | 1.00 | 26.88 |
| ATOM | 1608 | N   | LYS | 366 | 74.440 | 18.365 | 16.873 | 1.00 | 26.99 |
| ATOM | 1609 | CA  | LYS | 366 | 75.230 | 19.577 | 17.061 | 1.00 | 30.69 |
| ATOM | 1610 | CB  | LYS | 366 | 76.275 | 19.708 | 15.957 | 1.00 | 28.53 |
| ATOM | 1611 | CG  | LYS | 366 | 77.481 | 18.804 | 16.106 | 1.00 | 28.89 |
| ATOM | 1612 | CD  | LYS | 366 | 78.430 | 19.027 | 14.939 | 1.00 | 32.51 |
| ATOM | 1613 | CE  | LYS | 366 | 79.743 | 18.294 | 15.116 | 1.00 | 38.52 |
| ATOM | 1614 | NZ  | LYS | 366 | 80.632 | 18.506 | 13.939 | 1.00 | 45.28 |
| ATOM | 1615 | C   | LYS | 366 | 74.349 | 20.831 | 17.079 | 1.00 | 36.18 |
| ATOM | 1616 | O   | LYS | 366 | 74.472 | 21.672 | 17.972 | 1.00 | 39.82 |
| ATOM | 1617 | N   | LEU | 367 | 73.464 | 20.950 | 16.091 | 1.00 | 37.54 |
| ATOM | 1618 | CA  | LEU | 367 | 72.557 | 22.092 | 15.994 | 1.00 | 36.14 |
| ATOM | 1619 | CB  | LEU | 367 | 71.803 | 22.070 | 14.659 | 1.00 | 32.20 |

FIG. 28A-36

| ATOM | 1620 | CG | LEU | 367 | 70.764 | 23.179 | 14.447 | 1.00 | 36.16 |
| --- | --- | --- | --- | --- | --- | --- | --- | --- | --- |
| ATOM | 1621 | CD1 | LEU | 367 | 71.402 | 24.567 | 14.618 | 1.00 | 20.60 |
| ATOM | 1622 | CD2 | LEU | 367 | 70.139 | 23.030 | 13.065 | 1.00 | 34.30 |
| ATOM | 1623 | C | LEU | 367 | 71.561 | 22.060 | 17.143 | 1.00 | 36.84 |
| ATOM | 1624 | O | LEU | 367 | 71.231 | 23.091 | 17.729 | 1.00 | 36.94 |
| ATOM | 1625 | N | LEU | 368 | 71.083 | 20.866 | 17.459 | 1.00 | 37.81 |
| ATOM | 1626 | CA | LEU | 368 | 70.130 | 20.683 | 18.536 | 1.00 | 34.83 |
| ATOM | 1627 | CB | LEU | 368 | 69.763 | 19.205 | 18.622 | 1.00 | 36.98 |
| ATOM | 1628 | CG | LEU | 368 | 68.421 | 18.777 | 19.205 | 1.00 | 40.34 |
| ATOM | 1629 | CD1 | LEU | 368 | 67.276 | 19.595 | 18.619 | 1.00 | 36.28 |
| ATOM | 1630 | CD2 | LEU | 368 | 68.241 | 17.299 | 18.908 | 1.00 | 39.39 |
| ATOM | 1631 | C | LEU | 368 | 70.755 | 21.182 | 19.843 | 1.00 | 38.32 |
| ATOM | 1632 | O | LEU | 368 | 70.059 | 21.711 | 20.707 | 1.00 | 41.87 |
| ATOM | 1633 | N | MET | 369 | 72.075 | 21.057 | 19.962 | 1.00 | 39.46 |
| ATOM | 1634 | CA | MET | 369 | 72.790 | 21.515 | 21.154 | 1.00 | 40.12 |
| ATOM | 1635 | CB | MET | 369 | 74.219 | 20.971 | 21.168 | 1.00 | 41.26 |
| ATOM | 1636 | CG | MET | 369 | 74.307 | 19.493 | 21.521 | 1.00 | 47.83 |
| ATOM | 1637 | SD | MET | 369 | 75.961 | 18.810 | 21.289 | 1.00 | 55.72 |
| ATOM | 1638 | CE | MET | 369 | 76.809 | 19.474 | 22.727 | 1.00 | 54.37 |
| ATOM | 1639 | C | MET | 369 | 72.805 | 23.039 | 21.251 | 1.00 | 42.81 |
| ATOM | 1640 | O | MET | 369 | 72.990 | 23.601 | 22.335 | 1.00 | 47.81 |
| ATOM | 1641 | N | LYS | 370 | 72.622 | 23.708 | 20.115 | 1.00 | 40.09 |
| ATOM | 1642 | CA | LYS | 370 | 72.588 | 25.165 | 20.080 | 1.00 | 33.65 |
| ATOM | 1643 | CB | LYS | 370 | 72.751 | 25.677 | 18.650 | 1.00 | 30.83 |
| ATOM | 1644 | CG | LYS | 370 | 74.138 | 25.435 | 18.078 | 1.00 | 30.98 |
| ATOM | 1645 | CD | LYS | 370 | 75.188 | 26.198 | 18.867 | 1.00 | 37.82 |
| ATOM | 1646 | CE | LYS | 370 | 76.591 | 25.938 | 18.351 | 1.00 | 36.05 |
| ATOM | 1647 | NZ | LYS | 370 | 77.034 | 24.562 | 18.667 | 1.00 | 48.68 |
| ATOM | 1648 | C | LYS | 370 | 71.293 | 25.684 | 20.702 | 1.00 | 33.32 |
| ATOM | 1649 | O | LYS | 370 | 71.218 | 26.842 | 21.112 | 1.00 | 34.75 |
| ATOM | 1650 | N | VAL | 371 | 70.277 | 24.826 | 20.779 | 1.00 | 31.90 |
| ATOM | 1651 | CA | VAL | 371 | 69.006 | 25.197 | 21.395 | 1.00 | 31.77 |
| ATOM | 1652 | CB | VAL | 371 | 67.933 | 24.092 | 21.214 | 1.00 | 30.28 |
| ATOM | 1653 | CG1 | VAL | 371 | 66.673 | 24.429 | 21.995 | 1.00 | 30.02 |
| ATOM | 1654 | CG2 | VAL | 371 | 67.596 | 23.933 | 19.746 | 1.00 | 32.23 |
| ATOM | 1655 | C | VAL | 371 | 69.277 | 25.417 | 22.885 | 1.00 | 34.44 |
| ATOM | 1656 | O | VAL | 371 | 68.722 | 26.331 | 23.499 | 1.00 | 33.35 |
| ATOM | 1657 | N | THR | 372 | 70.161 | 24.590 | 23.443 | 1.00 | 33.15 |
| ATOM | 1658 | CA | THR | 372 | 70.551 | 24.675 | 24.847 | 1.00 | 32.47 |
| ATOM | 1659 | CB | THR | 372 | 71.541 | 23.556 | 25.207 | 1.00 | 32.11 |
| ATOM | 1660 | OG1 | THR | 372 | 70.955 | 22.288 | 24.891 | 1.00 | 35.33 |
| ATOM | 1661 | CG2 | THR | 372 | 71.894 | 23.603 | 26.688 | 1.00 | 32.54 |
| ATOM | 1662 | C | THR | 372 | 71.226 | 26.020 | 25.108 | 1.00 | 34.49 |
| ATOM | 1663 | O | THR | 372 | 70.936 | 26.696 | 26.099 | 1.00 | 34.07 |
| ATOM | 1664 | N | ASP | 373 | 72.120 | 26.405 | 24.202 | 1.00 | 32.77 |
| ATOM | 1665 | CA | ASP | 373 | 72.830 | 27.671 | 24.315 | 1.00 | 28.08 |

FIG. 28A-37

| ATOM | 1666 | CB  | ASP | 373 | 73.803 | 27.841 | 23.147 | 1.00 | 31.59 |
| ATOM | 1667 | CG  | ASP | 373 | 74.910 | 26.789 | 23.142 | 1.00 | 37.29 |
| ATOM | 1668 | OD1 | ASP | 373 | 75.170 | 26.169 | 24.196 | 1.00 | 40.82 |
| ATOM | 1669 | OD2 | ASP | 373 | 75.531 | 26.586 | 22.079 | 1.00 | 40.81 |
| ATOM | 1670 | C   | ASP | 373 | 71.830 | 28.821 | 24.353 | 1.00 | 29.21 |
| ATOM | 1671 | O   | ASP | 373 | 71.931 | 29.709 | 25.200 | 1.00 | 31.85 |
| ATOM | 1672 | N   | LEU | 374 | 70.843 | 28.775 | 23.463 | 1.00 | 24.71 |
| ATOM | 1673 | CA  | LEU | 374 | 69.813 | 29.802 | 23.403 | 1.00 | 25.25 |
| ATOM | 1674 | CB  | LEU | 374 | 68.906 | 29.587 | 22.188 | 1.00 | 25.61 |
| ATOM | 1675 | CG  | LEU | 374 | 69.480 | 30.084 | 20.858 | 1.00 | 25.51 |
| ATOM | 1676 | CD1 | LEU | 374 | 68.741 | 29.469 | 19.677 | 1.00 | 23.53 |
| ATOM | 1677 | CD2 | LEU | 374 | 69.405 | 31.596 | 20.820 | 1.00 | 21.92 |
| ATOM | 1678 | C   | LEU | 374 | 68.994 | 29.827 | 24.686 | 1.00 | 26.84 |
| ATOM | 1679 | O   | LEU | 374 | 68.591 | 30.895 | 25.151 | 1.00 | 28.96 |
| ATOM | 1680 | N   | ARG | 375 | 68.746 | 28.651 | 25.254 | 1.00 | 31.00 |
| ATOM | 1681 | CA  | ARG | 375 | 67.996 | 28.554 | 26.502 | 1.00 | 32.86 |
| ATOM | 1682 | CB  | ARG | 375 | 67.831 | 27.090 | 26.924 | 1.00 | 36.80 |
| ATOM | 1683 | CG  | ARG | 375 | 66.861 | 26.297 | 26.071 | 1.00 | 44.91 |
| ATOM | 1684 | CD  | ARG | 375 | 65.433 | 26.731 | 26.338 | 1.00 | 58.99 |
| ATOM | 1685 | NE  | ARG | 375 | 64.501 | 26.210 | 25.342 | 1.00 | 72.26 |
| ATOM | 1686 | CZ  | ARG | 375 | 63.909 | 25.020 | 25.404 | 1.00 | 77.46 |
| ATOM | 1687 | NH1 | ARG | 375 | 64.147 | 24.201 | 26.422 | 1.00 | 80.94 |
| ATOM | 1688 | NH2 | ARG | 375 | 63.062 | 24.657 | 24.447 | 1.00 | 75.58 |
| ATOM | 1689 | C   | ARG | 375 | 68.771 | 29.317 | 27.570 | 1.00 | 32.27 |
| ATOM | 1690 | O   | ARG | 375 | 68.199 | 30.125 | 28.304 | 1.00 | 33.75 |
| ATOM | 1691 | N   | MET | 376 | 70.084 | 29.098 | 27.602 | 1.00 | 32.65 |
| ATOM | 1692 | CA  | MET | 376 | 70.967 | 29.753 | 28.560 | 1.00 | 35.83 |
| ATOM | 1693 | CB  | MET | 376 | 72.392 | 29.210 | 28.434 | 1.00 | 39.25 |
| ATOM | 1694 | CG  | MET | 376 | 72.526 | 27.751 | 28.839 | 1.00 | 54.45 |
| ATOM | 1695 | SD  | MET | 376 | 74.245 | 27.212 | 28.944 | 1.00 | 73.93 |
| ATOM | 1696 | CE  | MET | 376 | 74.421 | 26.270 | 27.434 | 1.00 | 67.01 |
| ATOM | 1697 | C   | MET | 376 | 70.960 | 31.267 | 28.378 | 1.00 | 35.38 |
| ATOM | 1698 | O   | MET | 376 | 70.882 | 32.015 | 29.353 | 1.00 | 34.73 |
| ATOM | 1699 | N   | ILE | 377 | 71.038 | 31.716 | 27.129 | 1.00 | 32.51 |
| ATOM | 1700 | CA  | ILE | 377 | 71.016 | 33.142 | 26.816 | 1.00 | 26.55 |
| ATOM | 1701 | CB  | ILE | 377 | 71.182 | 33.370 | 25.299 | 1.00 | 24.84 |
| ATOM | 1702 | CG2 | ILE | 377 | 70.817 | 34.797 | 24.923 | 1.00 | 26.63 |
| ATOM | 1703 | CG1 | ILE | 377 | 72.616 | 33.038 | 24.890 | 1.00 | 20.66 |
| ATOM | 1704 | CD1 | ILE | 377 | 72.872 | 33.104 | 23.409 | 1.00 | 20.74 |
| ATOM | 1705 | C   | ILE | 377 | 69.706 | 33.755 | 27.313 | 1.00 | 25.47 |
| ATOM | 1706 | O   | ILE | 377 | 69.696 | 34.848 | 27.881 | 1.00 | 29.99 |
| ATOM | 1707 | N   | GLY | 378 | 68.608 | 33.033 | 27.127 | 1.00 | 25.11 |
| ATOM | 1708 | CA  | GLY | 378 | 67.321 | 33.522 | 27.580 | 1.00 | 27.82 |
| ATOM | 1709 | C   | GLY | 378 | 67.279 | 33.613 | 29.095 | 1.00 | 30.90 |
| ATOM | 1710 | O   | GLY | 378 | 66.749 | 34.579 | 29.651 | 1.00 | 31.19 |
| ATOM | 1711 | N   | ALA | 379 | 67.851 | 32.611 | 29.761 | 1.00 | 31.62 |

FIG. 28A-38

| ATOM | 1712 | CA | ALA | 379 | 67.896 | 32.547 | 31.223 | 1.00 | 30.74 |
|------|------|-----|-----|-----|--------|--------|--------|------|-------|
| ATOM | 1713 | CB | ALA | 379 | 68.433 | 31.198 | 31.671 | 1.00 | 30.82 |
| ATOM | 1714 | C | ALA | 379 | 68.756 | 33.668 | 31.801 | 1.00 | 30.07 |
| ATOM | 1715 | O | ALA | 379 | 68.327 | 34.384 | 32.708 | 1.00 | 31.05 |
| ATOM | 1716 | N | CYA | 380 | 69.966 | 33.817 | 31.273 | 1.00 | 29.72 |
| ATOM | 1717 | CA | CYA | 380 | 70.873 | 34.866 | 31.723 | 1.00 | 33.36 |
| ATOM | 1718 | CB | CYA | 380 | 72.201 | 34.809 | 30.963 | 1.00 | 38.31 |
| ATOM | 1719 | SG | CYA | 380 | 73.249 | 33.407 | 31.386 | 1.00 | 50.99 |
| ATOM | 1720 | AS | CYA | 380 | 74.982 | 33.655 | 29.929 | 1.00 | 70.37 |
| ATOM | 1721 | C | CYA | 380 | 70.226 | 36.232 | 31.535 | 1.00 | 33.40 |
| ATOM | 1722 | O | CYA | 380 | 70.246 | 37.062 | 32.442 | 1.00 | 36.41 |
| ATOM | 1723 | N | HIS | 381 | 69.615 | 36.456 | 30.374 | 1.00 | 32.55 |
| ATOM | 1724 | CA | HIS | 381 | 68.965 | 37.734 | 30.114 | 1.00 | 26.41 |
| ATOM | 1725 | CB | HIS | 381 | 68.434 | 37.811 | 28.681 | 1.00 | 20.89 |
| ATOM | 1726 | CG | HIS | 381 | 67.593 | 39.023 | 28.423 | 1.00 | 15.78 |
| ATOM | 1727 | CD2 | HIS | 381 | 67.928 | 40.277 | 28.041 | 1.00 | 12.67 |
| ATOM | 1728 | ND1 | HIS | 381 | 66.226 | 39.031 | 28.605 | 1.00 | 17.88 |
| ATOM | 1729 | CE1 | HIS | 381 | 65.756 | 40.239 | 28.353 | 1.00 | 16.27 |
| ATOM | 1730 | NE2 | HIS | 381 | 66.768 | 41.013 | 28.008 | 1.00 | 17.18 |
| ATOM | 1731 | C | HIS | 381 | 67.839 | 38.023 | 31.102 | 1.00 | 26.73 |
| ATOM | 1732 | O | HIS | 381 | 67.621 | 39.176 | 31.464 | 1.00 | 30.46 |
| ATOM | 1733 | N | ALA | 382 | 67.111 | 36.991 | 31.521 | 1.00 | 26.68 |
| ATOM | 1734 | CA | ALA | 382 | 66.010 | 37.176 | 32.464 | 1.00 | 27.90 |
| ATOM | 1735 | CB | ALA | 382 | 65.237 | 35.878 | 32.642 | 1.00 | 25.29 |
| ATOM | 1736 | C | ALA | 382 | 66.511 | 37.697 | 33.810 | 1.00 | 31.23 |
| ATOM | 1737 | O | ALA | 382 | 65.927 | 38.617 | 34.378 | 1.00 | 37.67 |
| ATOM | 1738 | N | SER | 383 | 67.596 | 37.114 | 34.316 | 1.00 | 34.15 |
| ATOM | 1739 | CA | SER | 383 | 68.174 | 37.550 | 35.588 | 1.00 | 37.23 |
| ATOM | 1740 | CB | SER | 383 | 69.294 | 36.605 | 36.027 | 1.00 | 40.21 |
| ATOM | 1741 | OG | SER | 383 | 68.785 | 35.324 | 36.361 | 1.00 | 53.99 |
| ATOM | 1742 | C | SER | 383 | 68.727 | 38.958 | 35.417 | 1.00 | 33.67 |
| ATOM | 1743 | O | SER | 383 | 68.532 | 39.827 | 36.268 | 1.00 | 40.73 |
| ATOM | 1744 | N | ARG | 384 | 69.411 | 39.171 | 34.298 | 1.00 | 29.95 |
| ATOM | 1745 | CA | ARG | 384 | 70.000 | 40.458 | 33.957 | 1.00 | 29.77 |
| ATOM | 1746 | CB | ARG | 384 | 70.684 | 40.350 | 32.594 | 1.00 | 30.79 |
| ATOM | 1747 | CG | ARG | 384 | 71.481 | 41.558 | 32.167 | 1.00 | 31.34 |
| ATOM | 1748 | CD | ARG | 384 | 72.781 | 41.638 | 32.918 | 1.00 | 33.62 |
| ATOM | 1749 | NE | ARG | 384 | 73.657 | 42.660 | 32.358 | 1.00 | 41.68 |
| ATOM | 1750 | CZ | ARG | 384 | 74.584 | 43.310 | 33.052 | 1.00 | 41.20 |
| ATOM | 1751 | NH1 | ARG | 384 | 74.756 | 43.047 | 34.339 | 1.00 | 42.11 |
| ATOM | 1752 | NH2 | ARG | 384 | 75.349 | 44.213 | 32.455 | 1.00 | 37.27 |
| ATOM | 1753 | C | ARG | 384 | 68.910 | 41.536 | 33.911 | 1.00 | 35.72 |
| ATOM | 1754 | O | ARG | 384 | 69.090 | 42.635 | 34.439 | 1.00 | 41.66 |
| ATOM | 1755 | N | PHE | 385 | 67.768 | 41.196 | 33.318 | 1.00 | 34.30 |
| ATOM | 1756 | CA | PHE | 385 | 66.646 | 42.119 | 33.199 | 1.00 | 32.40 |
| ATOM | 1757 | CB | PHE | 385 | 65.527 | 41.502 | 32.356 | 1.00 | 29.02 |

FIG. 28A-39

| ATOM | 1758 | CG | PHE | 385 | 64.344 | 42.407 | 32.163 | 1.00 | 26.56 |
| --- | --- | --- | --- | --- | --- | --- | --- | --- | --- |
| ATOM | 1759 | CD1 | PHE | 385 | 64.317 | 43.320 | 31.119 | 1.00 | 26.59 |
| ATOM | 1760 | CD2 | PHE | 385 | 63.263 | 42.355 | 33.037 | 1.00 | 24.69 |
| ATOM | 1761 | CE1 | PHE | 385 | 63.231 | 44.173 | 30.947 | 1.00 | 31.70 |
| ATOM | 1762 | CE2 | PHE | 385 | 62.174 | 43.202 | 32.875 | 1.00 | 26.79 |
| ATOM | 1763 | CZ | PHE | 385 | 62.158 | 44.115 | 31.827 | 1.00 | 31.59 |
| ATOM | 1764 | C | PHE | 385 | 66.121 | 42.492 | 34.578 | 1.00 | 32.98 |
| ATOM | 1765 | O | PHE | 385 | 65.822 | 43.659 | 34.839 | 1.00 | 33.91 |
| ATOM | 1766 | N | LEU | 386 | 66.003 | 41.499 | 35.456 | 1.00 | 33.91 |
| ATOM | 1767 | CA | LEU | 386 | 65.533 | 41.736 | 36.818 | 1.00 | 38.66 |
| ATOM | 1768 | CB | LEU | 386 | 65.547 | 40.440 | 37.633 | 1.00 | 43.79 |
| ATOM | 1769 | CG | LEU | 386 | 64.327 | 39.521 | 37.525 | 1.00 | 49.81 |
| ATOM | 1770 | CD1 | LEU | 386 | 64.652 | 38.147 | 38.099 | 1.00 | 51.12 |
| ATOM | 1771 | CD2 | LEU | 386 | 63.135 | 40.148 | 38.246 | 1.00 | 49.17 |
| ATOM | 1772 | C | LEU | 386 | 66.445 | 42.761 | 37.475 | 1.00 | 38.95 |
| ATOM | 1773 | O | LEU | 386 | 65.979 | 43.682 | 38.146 | 1.00 | 42.16 |
| ATOM | 1774 | N | HIS | 387 | 67.745 | 42.613 | 37.248 | 1.00 | 33.62 |
| ATOM | 1775 | CA | HIS | 387 | 68.723 | 43.531 | 37.808 | 1.00 | 39.73 |
| ATOM | 1776 | CB | HIS | 387 | 70.138 | 42.980 | 37.639 | 1.00 | 40.71 |
| ATOM | 1777 | CG | HIS | 387 | 70.403 | 41.749 | 38.449 | 1.00 | 52.03 |
| ATOM | 1778 | CD2 | HIS | 387 | 69.573 | 40.967 | 39.181 | 1.00 | 53.85 |
| ATOM | 1779 | ND1 | HIS | 387 | 71.657 | 41.189 | 38.566 | 1.00 | 54.79 |
| ATOM | 1780 | CE1 | HIS | 387 | 71.590 | 40.114 | 39.334 | 1.00 | 56.55 |
| ATOM | 1781 | NE2 | HIS | 387 | 70.336 | 39.958 | 39.720 | 1.00 | 57.48 |
| ATOM | 1782 | C | HIS | 387 | 68.594 | 44.913 | 37.175 | 1.00 | 42.08 |
| ATOM | 1783 | O | HIS | 387 | 68.712 | 45.926 | 37.865 | 1.00 | 44.12 |
| ATOM | 1784 | N | MET | 388 | 68.318 | 44.957 | 35.874 | 1.00 | 42.38 |
| ATOM | 1785 | CA | MET | 388 | 68.154 | 46.229 | 35.175 | 1.00 | 38.00 |
| ATOM | 1786 | CB | MET | 388 | 67.840 | 46.006 | 33.692 | 1.00 | 40.21 |
| ATOM | 1787 | CG | MET | 388 | 69.009 | 45.555 | 32.829 | 1.00 | 41.26 |
| ATOM | 1788 | SD | MET | 388 | 68.500 | 45.427 | 31.089 | 1.00 | 45.51 |
| ATOM | 1789 | CE | MET | 388 | 69.089 | 43.802 | 30.645 | 1.00 | 42.40 |
| ATOM | 1790 | C | MET | 388 | 67.025 | 47.044 | 35.810 | 1.00 | 38.11 |
| ATOM | 1791 | O | MET | 388 | 67.155 | 48.255 | 35.997 | 1.00 | 38.41 |
| ATOM | 1792 | N | LYS | 389 | 65.926 | 46.374 | 36.144 | 1.00 | 39.67 |
| ATOM | 1793 | CA | LYS | 389 | 64.773 | 47.036 | 36.750 | 1.00 | 44.96 |
| ATOM | 1794 | CB | LYS | 389 | 63.570 | 46.087 | 36.818 | 1.00 | 49.52 |
| ATOM | 1795 | CG | LYS | 389 | 62.674 | 46.102 | 35.588 | 1.00 | 56.74 |
| ATOM | 1796 | CD | LYS | 389 | 62.145 | 47.509 | 35.278 | 1.00 | 68.05 |
| ATOM | 1797 | CE | LYS | 389 | 61.287 | 48.100 | 36.403 | 1.00 | 71.47 |
| ATOM | 1798 | NZ | LYS | 389 | 60.038 | 47.330 | 36.661 | 1.00 | 71.98 |
| ATOM | 1799 | C | LYS | 389 | 65.041 | 47.604 | 38.141 | 1.00 | 46.60 |
| ATOM | 1800 | O | LYS | 389 | 64.516 | 48.661 | 38.499 | 1.00 | 47.25 |
| ATOM | 1801 | N | VAL | 390 | 65.832 | 46.893 | 38.935 | 1.00 | 47.15 |
| ATOM | 1802 | CA | VAL | 390 | 66.129 | 47.353 | 40.284 | 1.00 | 50.75 |
| ATOM | 1803 | CB | VAL | 390 | 66.686 | 46.202 | 41.182 | 1.00 | 50.42 |

FIG. 28A-40

| ATOM | 1804 | CG1 | VAL | 390 | 68.095 | 45.802 | 40.770 | 1.00 | 47.93 |
|---|---|---|---|---|---|---|---|---|---|
| ATOM | 1805 | CG2 | VAL | 390 | 66.650 | 46.612 | 42.640 | 1.00 | 56.67 |
| ATOM | 1806 | C | VAL | 390 | 67.072 | 48.558 | 40.286 | 1.00 | 49.82 |
| ATOM | 1807 | O | VAL | 390 | 66.971 | 49.426 | 41.152 | 1.00 | 52.44 |
| ATOM | 1808 | N | GLU | 391 | 67.926 | 48.651 | 39.272 | 1.00 | 46.14 |
| ATOM | 1809 | CA | GLU | 391 | 68.888 | 49.741 | 39.173 | 1.00 | 43.84 |
| ATOM | 1810 | CB | GLU | 391 | 70.150 | 49.268 | 38.449 | 1.00 | 41.44 |
| ATOM | 1811 | CG | GLU | 391 | 70.837 | 48.074 | 39.095 | 1.00 | 51.12 |
| ATOM | 1812 | CD | GLU | 391 | 71.218 | 48.325 | 40.540 | 1.00 | 57.29 |
| ATOM | 1813 | OE1 | GLU | 391 | 71.970 | 49.287 | 40.802 | 1.00 | 58.15 |
| ATOM | 1814 | OE2 | GLU | 391 | 70.764 | 47.559 | 41.416 | 1.00 | 62.51 |
| ATOM | 1815 | C | GLU | 391 | 68.386 | 51.015 | 38.501 | 1.00 | 45.94 |
| ATOM | 1816 | O | GLU | 391 | 68.567 | 52.114 | 39.033 | 1.00 | 51.14 |
| ATOM | 1817 | N | CYA | 392 | 67.727 | 50.872 | 37.354 | 1.00 | 45.84 |
| ATOM | 1818 | CA | CYA | 392 | 67.255 | 52.029 | 36.598 | 1.00 | 41.60 |
| ATOM | 1819 | CB | CYA | 392 | 67.681 | 51.889 | 35.140 | 1.00 | 42.06 |
| ATOM | 1820 | SG | CYA | 392 | 69.452 | 52.008 | 34.968 | 1.00 | 44.47 |
| ATOM | 1821 | AS | CYA | 392 | 69.867 | 50.812 | 33.150 | 1.00 | 54.22 |
| ATOM | 1822 | C | CYA | 392 | 65.779 | 52.395 | 36.683 | 1.00 | 42.27 |
| ATOM | 1823 | O | CYA | 392 | 64.937 | 51.564 | 37.029 | 1.00 | 43.91 |
| ATOM | 1824 | N | PRO | 393 | 65.451 | 53.674 | 36.414 | 1.00 | 42.79 |
| ATOM | 1825 | CD | PRO | 393 | 66.384 | 54.774 | 36.106 | 1.00 | 38.59 |
| ATOM | 1826 | CA | PRO | 393 | 64.067 | 54.159 | 36.459 | 1.00 | 44.20 |
| ATOM | 1827 | CB | PRO | 393 | 64.218 | 55.667 | 36.238 | 1.00 | 39.88 |
| ATOM | 1828 | CG | PRO | 393 | 65.487 | 55.789 | 35.459 | 1.00 | 35.88 |
| ATOM | 1829 | C | PRO | 393 | 63.178 | 53.513 | 35.398 | 1.00 | 45.29 |
| ATOM | 1830 | O | PRO | 393 | 63.600 | 53.308 | 34.257 | 1.00 | 43.97 |
| ATOM | 1831 | N | THR | 394 | 61.935 | 53.238 | 35.782 | 1.00 | 48.20 |
| ATOM | 1832 | CA | THR | 394 | 60.959 | 52.607 | 34.901 | 1.00 | 53.71 |
| ATOM | 1833 | CB | THR | 394 | 59.605 | 52.429 | 35.629 | 1.00 | 59.59 |
| ATOM | 1834 | OG1 | THR | 394 | 58.690 | 51.717 | 34.787 | 1.00 | 66.50 |
| ATOM | 1835 | CG2 | THR | 394 | 59.013 | 53.787 | 36.004 | 1.00 | 61.00 |
| ATOM | 1836 | C | THR | 394 | 60.752 | 53.358 | 33.581 | 1.00 | 51.35 |
| ATOM | 1837 | O | THR | 394 | 60.419 | 52.751 | 32.563 | 1.00 | 54.39 |
| ATOM | 1838 | N | GLU | 395 | 61.008 | 54.664 | 33.595 | 1.00 | 47.65 |
| ATOM | 1839 | CA | GLU | 395 | 60.845 | 55.509 | 32.414 | 1.00 | 44.43 |
| ATOM | 1840 | CB | GLU | 395 | 60.988 | 56.978 | 32.804 | 1.00 | 43.85 |
| ATOM | 1841 | C | GLU | 395 | 61.788 | 55.175 | 31.250 | 1.00 | 42.93 |
| ATOM | 1842 | O | GLU | 395 | 61.589 | 55.649 | 30.129 | 1.00 | 41.39 |
| ATOM | 1843 | N | LEU | 396 | 62.818 | 54.375 | 31.517 | 1.00 | 39.38 |
| ATOM | 1844 | CA | LEU | 396 | 63.782 | 53.989 | 30.486 | 1.00 | 35.70 |
| ATOM | 1845 | CB | LEU | 396 | 65.185 | 53.867 | 31.090 | 1.00 | 34.96 |
| ATOM | 1846 | CG | LEU | 396 | 65.854 | 55.141 | 31.609 | 1.00 | 36.47 |
| ATOM | 1847 | CD1 | LEU | 396 | 67.234 | 54.807 | 32.150 | 1.00 | 34.21 |
| ATOM | 1848 | CD2 | LEU | 396 | 65.959 | 56.164 | 30.491 | 1.00 | 32.74 |
| ATOM | 1849 | C | LEU | 396 | 63.407 | 52.671 | 29.803 | 1.00 | 34.60 |

FIG. 28A-41

| ATOM | 1850 | O   | LEU | 396 | 64.086 | 52.223 | 28.873 | 1.00 | 30.36 |
| ---- | ---- | --- | --- | --- | ------ | ------ | ------ | ---- | ----- |
| ATOM | 1851 | N   | PHE | 397 | 62.325 | 52.059 | 30.269 | 1.00 | 33.02 |
| ATOM | 1852 | CA  | PHE | 397 | 61.868 | 50.792 | 29.725 | 1.00 | 33.39 |
| ATOM | 1853 | CB  | PHE | 397 | 61.615 | 49.782 | 30.852 | 1.00 | 34.30 |
| ATOM | 1854 | CG  | PHE | 397 | 62.834 | 49.439 | 31.665 | 1.00 | 32.62 |
| ATOM | 1855 | CD1 | PHE | 397 | 63.296 | 50.301 | 32.654 | 1.00 | 32.35 |
| ATOM | 1856 | CD2 | PHE | 397 | 63.504 | 48.241 | 31.461 | 1.00 | 31.28 |
| ATOM | 1857 | CE1 | PHE | 397 | 64.407 | 49.976 | 33.426 | 1.00 | 27.01 |
| ATOM | 1858 | CE2 | PHE | 397 | 64.616 | 47.905 | 32.229 | 1.00 | 33.34 |
| ATOM | 1859 | CZ  | PHE | 397 | 65.067 | 48.775 | 33.213 | 1.00 | 31.29 |
| ATOM | 1860 | C   | PHE | 397 | 60.580 | 50.961 | 28.934 | 1.00 | 33.17 |
| ATOM | 1861 | O   | PHE | 397 | 59.540 | 51.318 | 29.498 | 1.00 | 31.99 |
| ATOM | 1862 | N   | PRO | 398 | 60.636 | 50.752 | 27.606 | 1.00 | 32.45 |
| ATOM | 1863 | CD  | PRO | 398 | 61.821 | 50.493 | 26.768 | 1.00 | 28.15 |
| ATOM | 1864 | CA  | PRO | 398 | 59.429 | 50.885 | 26.786 | 1.00 | 30.02 |
| ATOM | 1865 | CB  | PRO | 398 | 59.921 | 50.483 | 25.394 | 1.00 | 28.15 |
| ATOM | 1866 | CG  | PRO | 398 | 61.352 | 50.923 | 25.397 | 1.00 | 24.89 |
| ATOM | 1867 | C   | PRO | 398 | 58.384 | 49.900 | 27.326 | 1.00 | 28.39 |
| ATOM | 1868 | O   | PRO | 398 | 58.735 | 48.810 | 27.789 | 1.00 | 28.00 |
| ATOM | 1869 | N   | PRO | 399 | 57.092 | 50.262 | 27.267 | 1.00 | 32.45 |
| ATOM | 1870 | CD  | PRO | 399 | 56.577 | 51.511 | 26.672 | 1.00 | 34.93 |
| ATOM | 1871 | CA  | PRO | 399 | 55.989 | 49.421 | 27.753 | 1.00 | 32.54 |
| ATOM | 1872 | CB  | PRO | 399 | 54.755 | 50.122 | 27.188 | 1.00 | 34.47 |
| ATOM | 1873 | CG  | PRO | 399 | 55.159 | 51.564 | 27.196 | 1.00 | 31.37 |
| ATOM | 1874 | C   | PRO | 399 | 56.044 | 47.946 | 27.338 | 1.00 | 32.18 |
| ATOM | 1875 | O   | PRO | 399 | 55.950 | 47.054 | 28.188 | 1.00 | 32.58 |
| ATOM | 1876 | N   | LEU | 400 | 56.195 | 47.689 | 26.041 | 1.00 | 30.15 |
| ATOM | 1877 | CA  | LEU | 400 | 56.259 | 46.314 | 25.541 | 1.00 | 32.32 |
| ATOM | 1878 | CB  | LEU | 400 | 56.211 | 46.297 | 24.011 | 1.00 | 28.67 |
| ATOM | 1879 | CG  | LEU | 400 | 56.028 | 44.927 | 23.351 | 1.00 | 28.77 |
| ATOM | 1880 | CD1 | LEU | 400 | 54.802 | 44.234 | 23.919 | 1.00 | 22.73 |
| ATOM | 1881 | CD2 | LEU | 400 | 55.897 | 45.096 | 21.846 | 1.00 | 27.89 |
| ATOM | 1882 | C   | LEU | 400 | 57.496 | 45.561 | 26.051 | 1.00 | 32.27 |
| ATOM | 1883 | O   | LEU | 400 | 57.437 | 44.358 | 26.307 | 1.00 | 32.87 |
| ATOM | 1884 | N   | PHE | 401 | 58.602 | 46.279 | 26.215 | 1.00 | 32.27 |
| ATOM | 1885 | CA  | PHE | 401 | 59.847 | 45.695 | 26.710 | 1.00 | 32.39 |
| ATOM | 1886 | CB  | PHE | 401 | 60.946 | 46.769 | 26.711 | 1.00 | 31.38 |
| ATOM | 1887 | CG  | PHE | 401 | 62.290 | 46.286 | 27.194 | 1.00 | 35.12 |
| ATOM | 1888 | CD1 | PHE | 401 | 62.835 | 45.089 | 26.729 | 1.00 | 34.68 |
| ATOM | 1889 | CD2 | PHE | 401 | 63.030 | 47.051 | 28.097 | 1.00 | 34.57 |
| ATOM | 1890 | CE1 | PHE | 401 | 64.100 | 44.662 | 27.155 | 1.00 | 30.27 |
| ATOM | 1891 | CE2 | PHE | 401 | 64.291 | 46.635 | 28.526 | 1.00 | 33.57 |
| ATOM | 1892 | CZ  | PHE | 401 | 64.828 | 45.438 | 28.054 | 1.00 | 35.74 |
| ATOM | 1893 | C   | PHE | 401 | 59.599 | 45.169 | 28.129 | 1.00 | 32.21 |
| ATOM | 1894 | O   | PHE | 401 | 60.002 | 44.056 | 28.478 | 1.00 | 33.36 |
| ATOM | 1895 | N   | LEU | 402 | 58.902 | 45.967 | 28.929 | 1.00 | 31.85 |

FIG. 28A-42

| ATOM | 1896 | CA | LEU | 402 | 58.582 | 45.602 | 30.302 | 1.00 | 35.06 |
|---|---|---|---|---|---|---|---|---|---|
| ATOM | 1897 | CB | LEU | 402 | 57.948 | 46.789 | 31.029 | 1.00 | 34.76 |
| ATOM | 1898 | CG | LEU | 402 | 58.878 | 47.852 | 31.591 | 1.00 | 33.48 |
| ATOM | 1899 | CD1 | LEU | 402 | 58.060 | 49.010 | 32.152 | 1.00 | 32.58 |
| ATOM | 1900 | CD2 | LEU | 402 | 59.753 | 47.217 | 32.662 | 1.00 | 26.27 |
| ATOM | 1901 | C | LEU | 402 | 57.626 | 44.426 | 30.393 | 1.00 | 36.80 |
| ATOM | 1902 | O | LEU | 402 | 57.793 | 43.545 | 31.239 | 1.00 | 35.43 |
| ATOM | 1903 | N | GLU | 403 | 56.600 | 44.443 | 29.547 | 1.00 | 38.50 |
| ATOM | 1904 | CA | GLU | 403 | 55.581 | 43.401 | 29.540 | 1.00 | 40.24 |
| ATOM | 1905 | CB | GLU | 403 | 54.435 | 43.792 | 28.605 | 1.00 | 44.03 |
| ATOM | 1906 | CG | GLU | 403 | 53.239 | 42.850 | 28.666 | 1.00 | 55.53 |
| ATOM | 1907 | CD | GLU | 403 | 52.180 | 43.159 | 27.618 | 1.00 | 66.67 |
| ATOM | 1908 | OE1 | GLU | 403 | 52.151 | 44.299 | 27.095 | 1.00 | 70.81 |
| ATOM | 1909 | OE2 | GLU | 403 | 51.370 | 42.255 | 27.315 | 1.00 | 73.80 |
| ATOM | 1910 | C | GLU | 403 | 56.096 | 42.018 | 29.162 | 1.00 | 38.00 |
| ATOM | 1911 | O | GLU | 403 | 55.745 | 41.029 | 29.805 | 1.00 | 38.78 |
| ATOM | 1912 | N | VAL | 404 | 56.934 | 41.955 | 28.132 | 1.00 | 37.39 |
| ATOM | 1913 | CA | VAL | 404 | 57.475 | 40.686 | 27.652 | 1.00 | 37.05 |
| ATOM | 1914 | CB | VAL | 404 | 58.180 | 40.855 | 26.286 | 1.00 | 35.57 |
| ATOM | 1915 | CG1 | VAL | 404 | 58.677 | 39.513 | 25.776 | 1.00 | 36.85 |
| ATOM | 1916 | CG2 | VAL | 404 | 57.222 | 41.451 | 25.287 | 1.00 | 42.03 |
| ATOM | 1917 | C | VAL | 404 | 58.438 | 40.000 | 28.609 | 1.00 | 38.69 |
| ATOM | 1918 | O | VAL | 404 | 58.436 | 38.774 | 28.727 | 1.00 | 40.71 |
| ATOM | 1919 | N | PHE | 405 | 59.267 | 40.785 | 29.286 | 1.00 | 39.34 |
| ATOM | 1920 | CA | PHE | 405 | 60.250 | 40.221 | 30.198 | 1.00 | 39.33 |
| ATOM | 1921 | CB | PHE | 405 | 61.620 | 40.840 | 29.913 | 1.00 | 33.87 |
| ATOM | 1922 | CG | PHE | 405 | 62.107 | 40.609 | 28.509 | 1.00 | 32.17 |
| ATOM | 1923 | CD1 | PHE | 405 | 62.355 | 41.683 | 27.660 | 1.00 | 31.34 |
| ATOM | 1924 | CD2 | PHE | 405 | 62.315 | 39.317 | 28.032 | 1.00 | 31.98 |
| ATOM | 1925 | CE1 | PHE | 405 | 62.801 | 41.476 | 26.352 | 1.00 | 30.79 |
| ATOM | 1926 | CE2 | PHE | 405 | 62.759 | 39.099 | 26.730 | 1.00 | 26.06 |
| ATOM | 1927 | CZ | PHE | 405 | 63.004 | 40.182 | 25.889 | 1.00 | 27.98 |
| ATOM | 1928 | C | PHE | 405 | 59.905 | 40.322 | 31.682 | 1.00 | 42.64 |
| ATOM | 1929 | O | PHE | 405 | 60.785 | 40.188 | 32.534 | 1.00 | 45.10 |
| ATOM | 1930 | N | GLU | 406 | 58.630 | 40.536 | 31.988 | 1.00 | 48.95 |
| ATOM | 1931 | CA | GLU | 406 | 58.181 | 40.641 | 33.373 | 1.00 | 56.93 |
| ATOM | 1932 | CB | GLU | 406 | 56.820 | 41.324 | 33.432 | 1.00 | 56.94 |
| ATOM | 1933 | C | GLU | 406 | 58.116 | 39.263 | 34.040 | 1.00 | 61.92 |
| ATOM | 1934 | O | GLU | 406 | 57.988 | 38.256 | 33.308 | 1.00 | 67.61 |
| ATOM | 1 | O1 | HOH | 501 | 67.588 | 36.828 | 11.225 | 1.00 | 27.32 |
| ATOM | 2 | O1 | HOH | 502 | 68.647 | 41.203 | 12.940 | 1.00 | 39.54 |
| ATOM | 3 | O1 | HOH | 503 | 64.072 | 40.115 | 12.407 | 1.00 | 32.47 |
| ATOM | 4 | O1 | HOH | 504 | 62.312 | 39.659 | 16.075 | 1.00 | 17.39 |
| ATOM | 5 | O1 | HOH | 505 | 63.449 | 46.468 | 15.530 | 1.00 | 30.46 |
| ATOM | 6 | O1 | HOH | 506 | 67.191 | 15.561 | -0.279 | 1.00 | 35.96 |
| ATOM | 7 | O1 | HOH | 507 | 67.100 | 11.855 | 0.295 | 1.00 | 20.00 |

FIG. 28A-43

| | | | | | | | | |
|---|---|---|---|---|---|---|---|---|
| ATOM | 8 | O1 | HOH | 508 | 61.004 | 15.510 | 0.047 | 1.00 | 20.00 |
| ATOM | 9 | O1 | HOH | 509 | 59.851 | 10.761 | 6.050 | 1.00 | 20.00 |
| ATOM | 10 | O1 | HOH | 510 | 57.553 | 11.824 | 10.360 | 1.00 | 44.63 |
| ATOM | 11 | O1 | HOH | 511 | 54.101 | 13.545 | 8.720 | 1.00 | 20.00 |
| ATOM | 12 | O1 | HOH | 512 | 55.923 | 15.916 | 12.205 | 1.00 | 29.31 |
| ATOM | 13 | O1 | HOH | 513 | 50.900 | 19.934 | 8.193 | 1.00 | 20.00 |
| ATOM | 14 | O1 | HOH | 514 | 50.474 | 22.912 | 7.942 | 1.00 | 45.34 |
| ATOM | 15 | O1 | HOH | 515 | 49.737 | 20.631 | 11.530 | 1.00 | 20.00 |
| ATOM | 16 | O1 | HOH | 516 | 50.829 | 25.467 | 13.330 | 1.00 | 20.00 |
| ATOM | 17 | O1 | HOH | 517 | 53.818 | 25.833 | 10.682 | 1.00 | 42.12 |
| ATOM | 18 | O1 | HOH | 518 | 52.591 | 31.216 | 7.313 | 1.00 | 35.55 |
| ATOM | 19 | O1 | HOH | 519 | 58.510 | 31.667 | 2.158 | 1.00 | 20.00 |
| ATOM | 20 | O1 | HOH | 520 | 58.235 | 36.751 | 2.232 | 1.00 | 20.00 |
| ATOM | 21 | O1 | HOH | 521 | 62.484 | 37.992 | 5.537 | 1.00 | 20.00 |
| ATOM | 22 | O1 | HOH | 522 | 68.184 | 36.969 | 5.889 | 1.00 | 50.08 |
| ATOM | 23 | O1 | HOH | 523 | 66.889 | 33.781 | 8.584 | 1.00 | 20.00 |
| ATOM | 24 | O1 | HOH | 524 | 67.217 | 30.836 | 3.085 | 1.00 | 34.44 |
| ATOM | 25 | O1 | HOH | 525 | 64.336 | 28.325 | 3.098 | 1.00 | 20.00 |
| ATOM | 26 | O1 | HOH | 526 | 67.667 | 26.625 | 1.519 | 1.00 | 20.00 |
| ATOM | 27 | O1 | HOH | 527 | 76.757 | 22.883 | 5.467 | 1.00 | 36.94 |
| ATOM | 28 | O1 | HOH | 528 | 72.250 | 17.936 | 6.950 | 1.00 | 36.00 |
| ATOM | 29 | O1 | HOH | 529 | 71.760 | 14.791 | 8.058 | 1.00 | 40.18 |
| ATOM | 30 | O1 | HOH | 530 | 72.884 | 14.751 | 11.484 | 1.00 | 41.44 |
| ATOM | 31 | O1 | HOH | 531 | 69.235 | 12.986 | 11.709 | 1.00 | 39.38 |
| ATOM | 32 | O1 | HOH | 532 | 69.402 | 12.036 | 14.891 | 1.00 | 40.68 |
| ATOM | 33 | O1 | HOH | 533 | 64.560 | 10.910 | 15.076 | 1.00 | 20.00 |
| ATOM | 34 | O1 | HOH | 534 | 63.169 | 10.413 | 11.722 | 1.00 | 20.00 |
| ATOM | 35 | O1 | HOH | 535 | 66.042 | 11.455 | 11.077 | 1.00 | 41.05 |
| ATOM | 36 | O1 | HOH | 536 | 76.285 | 12.458 | 10.677 | 1.00 | 20.00 |
| ATOM | 37 | O1 | HOH | 537 | 81.094 | 22.520 | 13.435 | 1.00 | 48.70 |
| ATOM | 38 | O1 | HOH | 538 | 80.505 | 25.457 | 14.849 | 1.00 | 46.30 |
| ATOM | 39 | O1 | HOH | 539 | 77.669 | 21.932 | 18.119 | 1.00 | 43.79 |
| ATOM | 40 | O1 | HOH | 540 | 77.187 | 28.903 | 21.137 | 1.00 | 40.22 |
| ATOM | 41 | O1 | HOH | 541 | 76.420 | 30.760 | 23.658 | 1.00 | 29.63 |
| ATOM | 42 | O1 | HOH | 542 | 83.028 | 32.743 | 20.922 | 1.00 | 38.14 |
| ATOM | 43 | O1 | HOH | 543 | 82.842 | 43.133 | 17.983 | 1.00 | 39.36 |
| ATOM | 44 | O1 | HOH | 544 | 77.484 | 34.040 | 9.664 | 1.00 | 36.37 |
| ATOM | 45 | O1 | HOH | 545 | 75.904 | 32.986 | 12.256 | 1.00 | 34.93 |
| ATOM | 46 | O1 | HOH | 546 | 74.185 | 29.689 | 9.761 | 1.00 | 38.60 |
| ATOM | 47 | O1 | HOH | 547 | 64.936 | 20.644 | 23.365 | 1.00 | 36.83 |
| ATOM | 48 | O1 | HOH | 548 | 61.750 | 22.313 | 25.288 | 1.00 | 34.81 |
| ATOM | 49 | O1 | HOH | 549 | 59.544 | 21.463 | 26.162 | 1.00 | 20.00 |
| ATOM | 50 | O1 | HOH | 550 | 62.300 | 27.528 | 24.386 | 1.00 | 35.89 |
| ATOM | 51 | O1 | HOH | 551 | 58.228 | 29.424 | 24.603 | 1.00 | 25.47 |
| ATOM | 52 | O1 | HOH | 552 | 57.368 | 32.196 | 30.527 | 1.00 | 45.27 |
| ATOM | 53 | O1 | HOH | 553 | 62.063 | 36.304 | 30.245 | 1.00 | 42.26 |

FIG. 28A-44

| ATOM | 54 | O1 | HOH | 554 | 64.722 | 36.725 | 28.906 | 1.00 | 24.66 |
|---|---|---|---|---|---|---|---|---|---|
| ATOM | 55 | O1 | HOH | 555 | 62.207 | 35.851 | 26.642 | 1.00 | 30.36 |
| ATOM | 56 | O1 | HOH | 556 | 63.608 | 33.715 | 25.707 | 1.00 | 42.74 |
| ATOM | 57 | O1 | HOH | 557 | 62.979 | 38.422 | 32.977 | 1.00 | 49.93 |
| ATOM | 58 | O1 | HOH | 558 | 66.911 | 33.364 | 34.901 | 1.00 | 50.02 |
| ATOM | 59 | O1 | HOH | 559 | 72.608 | 29.636 | 31.674 | 1.00 | 37.60 |
| ATOM | 60 | O1 | HOH | 560 | 76.967 | 40.633 | 32.514 | 1.00 | 44.81 |
| ATOM | 61 | O1 | HOH | 561 | 73.613 | 41.817 | 36.847 | 1.00 | 31.79 |
| ATOM | 62 | O1 | HOH | 562 | 75.773 | 46.227 | 30.514 | 1.00 | 29.06 |
| ATOM | 63 | O1 | HOH | 563 | 79.903 | 46.178 | 30.800 | 1.00 | 41.67 |
| ATOM | 64 | O1 | HOH | 564 | 69.746 | 51.175 | 33.564 | 1.00 | 20.00 |
| ATOM | 65 | O1 | HOH | 565 | 74.320 | 52.047 | 39.438 | 1.00 | 20.00 |
| ATOM | 66 | O1 | HOH | 566 | 65.900 | 53.647 | 27.404 | 1.00 | 40.45 |
| ATOM | 67 | O1 | HOH | 567 | 68.848 | 53.076 | 17.895 | 1.00 | 39.25 |
| ATOM | 68 | O1 | HOH | 568 | 63.507 | 48.672 | 13.581 | 1.00 | 43.77 |
| ATOM | 69 | O1 | HOH | 569 | 64.625 | 46.825 | 10.331 | 1.00 | 20.00 |
| ATOM | 70 | O1 | HOH | 570 | 55.882 | 41.431 | 11.148 | 1.00 | 20.00 |
| ATOM | 71 | O1 | HOH | 571 | 52.830 | 43.513 | 20.032 | 1.00 | 35.18 |
| ATOM | 72 | O1 | HOH | 572 | 56.990 | 49.485 | 24.052 | 1.00 | 37.30 |
| ATOM | 73 | O1 | HOH | 573 | 54.188 | 47.024 | 30.900 | 1.00 | 52.93 |
| ATOM | 74 | O1 | HOH | 574 | 57.823 | 44.590 | 34.025 | 1.00 | 53.64 |
| ATOM | 75 | O1 | HOH | 575 | 47.827 | 29.597 | 30.690 | 1.00 | 37.61 |
| ATOM | 76 | O1 | HOH | 576 | 53.030 | 24.901 | 32.732 | 1.00 | 45.06 |
| ATOM | 77 | O1 | HOH | 577 | 47.569 | 19.105 | 28.647 | 1.00 | 38.88 |
| ATOM | 78 | O1 | HOH | 578 | 47.232 | 20.282 | 25.561 | 1.00 | 20.00 |
| ATOM | 79 | O1 | HOH | 579 | 51.960 | 14.869 | 25.534 | 1.00 | 49.45 |
| ATOM | 80 | O1 | HOH | 580 | 52.831 | 23.395 | 1.634 | 1.00 | 20.00 |
| ATOM | 81 | O1 | HOH | 581 | 51.472 | 22.968 | -0.900 | 1.00 | 25.10 |
| ATOM | 82 | O1 | HOH | 582 | 77.238 | 52.503 | 8.906 | 1.00 | 47.05 |
| END | | | | | | | | | |
| ATOM | 2004 | C1 | DMT | 1 | 67.320 | 42.326 | 18.648 | 1.00 | 28.58 |
| ATOM | 2005 | C2 | DMT | 1 | 68.927 | 43.263 | 23.318 | 1.00 | 29.26 |
| ATOM | 2006 | C3 | DMT | 1 | 67.236 | 43.583 | 19.236 | 1.00 | 24.54 |
| ATOM | 2007 | C4 | DMT | 1 | 69.268 | 44.313 | 24.111 | 1.00 | 28.48 |
| ATOM | 2008 | C5 | DMT | 1 | 68.003 | 43.859 | 20.363 | 1.00 | 28.76 |
| ATOM | 2009 | C6 | DMT | 1 | 68.654 | 44.389 | 25.458 | 1.00 | 28.16 |
| ATOM | 2010 | C7 | DMT | 1 | 68.811 | 42.902 | 20.875 | 1.00 | 26.80 |
| ATOM | 2011 | C8 | DMT | 1 | 67.803 | 43.410 | 25.793 | 1.00 | 29.83 |
| ATOM | 2012 | C9 | DMT | 1 | 68.921 | 41.665 | 20.324 | 1.00 | 26.77 |
| ATOM | 2013 | C10 | DMT | 1 | 67.464 | 42.358 | 24.989 | 1.00 | 28.60 |
| ATOM | 2014 | C11 | DMT | 1 | 68.165 | 41.349 | 19.185 | 1.00 | 25.29 |
| ATOM | 2015 | C12 | DMT | 1 | 68.059 | 42.281 | 23.675 | 1.00 | 26.74 |
| ATOM | 2016 | C13 | DMT | 1 | 66.475 | 42.038 | 17.456 | 1.00 | 21.51 |
| ATOM | 2017 | C14 | DMT | 1 | 68.916 | 45.478 | 26.380 | 1.00 | 21.05 |
| ATOM | 2018 | C15 | DMT | 1 | 66.989 | 40.910 | 16.417 | 1.00 | 22.84 |
| ATOM | 2019 | C16 | DMT | 1 | 68.090 | 46.870 | 26.009 | 1.00 | 19.41 |

FIG. 28A-45

| ATOM | 2020 | C17 | DMT | 1 | 65.982 | 40.730 | 15.243 | 1.00 | 27.07 |
|------|------|-----|-----|---|--------|--------|--------|------|-------|
| ATOM | 2021 | C18 | DMT | 1 | 70.279 | 46.131 | 26.085 | 1.00 | 16.03 |
| ATOM | 2022 | C19 | DMT | 1 | 67.903 | 45.249 | 20.974 | 1.00 | 19.56 |
| ATOM | 2023 | C20 | DMT | 1 | 69.853 | 40.599 | 20.901 | 1.00 | 4.52 |
| ATOM | 2024 | N1  | DMT | 1 | 68.280 | 41.070 | 16.042 | 1.00 | 17.57 |
| ATOM | 2025 | O1  | DMT | 1 | 67.209 | 43.465 | 27.087 | 1.00 | 25.94 |
| ATOM | 2026 | O2  | DMT | 1 | 69.547 | 43.191 | 22.015 | 1.00 | 30.23 |
| ATOM | 2027 | O3  | DMT | 1 | 66.449 | 40.778 | 14.118 | 1.00 | 29.45 |
| ATOM | 2028 | O4  | DMT | 1 | 64.820 | 40.564 | 15.546 | 1.00 | 26.46 |

END

FIG. 29

REMARK
REMARK TR_triac full length numbering
REMARK Rfactor 0.236 Rfree 0.241
REMARK Resolution 25. 2.5 all reflections
REMARK
REMARK Three cacodylate-modified cysteines:
REMARK Cys334, Cys380, Cys392
REMARK modeled as free arsenic atoms
REMARK
REMARK conserved polar HOH numbered as in TR_t3.pdb
REMARK rearrangements start 600
REMARK
REMARK side chain of certain residues modeled as ALA due to poor density;
REMARK however, residue name reflects true residue for clarity
REMARK
REMARK clone obtained from Murray et. al.
REMARK deposited sequence confirmed,
REMARK differing from that reported by Thompson et. al.
REMARK in the following codons:
REMARK 281 Thr - Ala
REMARK 285 Lys - Glu
REMARK identical to that reported by Mitsuhashi et. al.
REMARK gb:RNTRAVI X07409
JRNL      AUTH  M.B. MURRAY, N.D.ZILZ, N.L.MCCREARY,M.J.MACDONALD
JRNL      AUTH 2 H.C.TOWLE
JRNL      TITL  ISOLATION AND CHARACTERIZATION OF RAT CDNA CLONES FOR TWO
JRNL      TITL 2 DISTINCT THYROID HORMONE RECPTORS
JRNL      REF   JBC           V. 263 25 1988
JRNL      AUTH  C.C.THOMPSON, C.WEINBERGER, R.LEBO, R.M.EVANS
JRNL      TITL  IDENTIFICATION OF A NOVEL THYROID HORMONE RECEPTOR EXPRESSED
JRNL      TITL 2 IN THE MAMMALIAN CENTRAL NERVOUS SYSTEM
JRNL      REF   SCIENCE       V. 237 1987
JRNL      AUTH  T.MITSUHASHI,G.TENNYSON,V.NIKODEM
JRNL      TITL  NUCLEOTIDE SEQUENCE OF NOVEL CDNAS GENERATED BY ALTERNATIVE
JRNL      TITL 2 SPLICING OF A RAT THYROID HORMONE RECEPTOR GENE TRANSCRIPT
JRNL      REF   NUC. ACIDS. RES.     V. 16 12 1988
REMARK
ATOM   1   CB   ARG  157    9.880   -24.199    7.196   1.00   57.79
ATOM   2   CG   ARG  157   11.380   -24.411    7.340   1.00   57.79
ATOM   3   CD   ARG  157   11.960   -23.602    8.486   1.00   57.79
ATOM   4   NE   ARG  157   11.492   -24.098    9.778   1.00   57.79
ATOM   5   CZ   ARG  157   12.284   -24.379   10.809   1.00   57.79
ATOM   6   NH1  ARG  157   13.598   -24.212   10.714   1.00   57.79
ATOM   7   NH2  ARG  157   11.762   -24.854   11.932   1.00   57.79
ATOM   8   C    ARG  157    7.774   -24.838    5.974   1.00   38.50
ATOM   9   O    ARG  157    7.553   -24.416    4.840   1.00   57.79

FIG. 29A-1

| ATOM | 10 | N   | ARG | 157 | 9.929  | -25.500 | 5.089 | 1.00 | 38.50 |
|------|----|-----|-----|-----|--------|---------|-------|------|-------|
| ATOM | 11 | CA  | ARG | 157 | 9.183  | -25.276 | 6.360 | 1.00 | 38.50 |
| ATOM | 12 | N   | PRO | 158 | 6.802  | -24.951 | 6.895 | 1.00 | 23.08 |
| ATOM | 13 | CD  | PRO | 158 | 6.945  | -25.424 | 8.282 | 1.00 | 28.38 |
| ATOM | 14 | CA  | PRO | 158 | 5.415  | -24.562 | 6.617 | 1.00 | 23.08 |
| ATOM | 15 | CB  | PRO | 158 | 4.704  | -24.824 | 7.948 | 1.00 | 28.38 |
| ATOM | 16 | CG  | PRO | 158 | 5.801  | -24.735 | 8.966 | 1.00 | 28.38 |
| ATOM | 17 | C   | PRO | 158 | 5.210  | -23.124 | 6.132 | 1.00 | 23.08 |
| ATOM | 18 | O   | PRO | 158 | 5.678  | -22.167 | 6.753 | 1.00 | 28.38 |
| ATOM | 19 | N   | GLU | 159 | 4.504  | -23.000 | 5.012 | 1.00 | 19.26 |
| ATOM | 20 | CA  | GLU | 159 | 4.191  | -21.717 | 4.389 | 1.00 | 19.26 |
| ATOM | 21 | CB  | GLU | 159 | 4.022  | -21.912 | 2.878 | 1.00 | 24.58 |
| ATOM | 22 | CG  | GLU | 159 | 5.317  | -22.009 | 2.086 | 1.00 | 24.58 |
| ATOM | 23 | CD  | GLU | 159 | 5.849  | -20.651 | 1.659 | 1.00 | 24.58 |
| ATOM | 24 | OE1 | GLU | 159 | 5.034  | -19.722 | 1.476 | 1.00 | 24.58 |
| ATOM | 25 | OE2 | GLU | 159 | 7.080  | -20.513 | 1.490 | 1.00 | 24.58 |
| ATOM | 26 | C   | GLU | 159 | 2.879  | -21.193 | 4.968 | 1.00 | 19.26 |
| ATOM | 27 | O   | GLU | 159 | 2.152  | -21.931 | 5.636 | 1.00 | 24.58 |
| ATOM | 28 | N   | PRO | 160 | 2.579  | -19.899 | 4.765 | 1.00 | 17.44 |
| ATOM | 29 | CD  | PRO | 160 | 3.442  | -18.817 | 4.259 | 1.00 | 13.94 |
| ATOM | 30 | CA  | PRO | 160 | 1.323  | -19.360 | 5.299 | 1.00 | 17.44 |
| ATOM | 31 | CB  | PRO | 160 | 1.414  | -17.872 | 4.956 | 1.00 | 13.94 |
| ATOM | 32 | CG  | PRO | 160 | 2.880  | -17.604 | 4.952 | 1.00 | 13.94 |
| ATOM | 33 | C   | PRO | 160 | 0.098  | -20.006 | 4.639 | 1.00 | 17.44 |
| ATOM | 34 | O   | PRO | 160 | 0.067  | -20.207 | 3.423 | 1.00 | 13.94 |
| ATOM | 35 | N   | THR | 161 | -0.895 | -20.352 | 5.450 | 1.00 | 17.00 |
| ATOM | 36 | CA  | THR | 161 | -2.119 | -20.957 | 4.941 | 1.00 | 17.00 |
| ATOM | 37 | CB  | THR | 161 | -2.958 | -21.587 | 6.086 | 1.00 | 20.43 |
| ATOM | 38 | OG1 | THR | 161 | -3.441 | -20.557 | 6.959 | 1.00 | 20.43 |
| ATOM | 39 | CG2 | THR | 161 | -2.121 | -22.576 | 6.888 | 1.00 | 20.43 |
| ATOM | 40 | C   | THR | 161 | -2.929 | -19.843 | 4.284 | 1.00 | 17.00 |
| ATOM | 41 | O   | THR | 161 | -2.691 | -18.660 | 4.547 | 1.00 | 20.43 |
| ATOM | 42 | N   | PRO | 162 | -3.918 | -20.200 | 3.449 | 1.00 | 12.94 |
| ATOM | 43 | CD  | PRO | 162 | -4.311 | -21.559 | 3.038 | 1.00 | 17.56 |
| ATOM | 44 | CA  | PRO | 162 | -4.743 | -19.190 | 2.780 | 1.00 | 12.94 |
| ATOM | 45 | CB  | PRO | 162 | -5.846 | -20.029 | 2.143 | 1.00 | 17.56 |
| ATOM | 46 | CG  | PRO | 162 | -5.147 | -21.303 | 1.816 | 1.00 | 17.56 |
| ATOM | 47 | C   | PRO | 162 | -5.317 | -18.171 | 3.763 | 1.00 | 12.94 |
| ATOM | 48 | O   | PRO | 162 | -5.305 | -16.964 | 3.503 | 1.00 | 17.56 |
| ATOM | 49 | N   | GLU | 163 | -5.790 | -18.668 | 4.903 | 1.00 | 19.45 |
| ATOM | 50 | CA  | GLU | 163 | -6.374 | -17.828 | 5.943 | 1.00 | 19.45 |
| ATOM | 51 | CB  | GLU | 163 | -6.994 | -18.690 | 7.047 | 1.00 | 49.96 |
| ATOM | 52 | CG  | GLU | 163 | -8.178 | -19.558 | 6.606 | 1.00 | 49.96 |
| ATOM | 53 | CD  | GLU | 163 | -7.782 | -20.720 | 5.697 | 1.00 | 49.96 |
| ATOM | 54 | OE1 | GLU | 163 | -6.735 | -21.361 | 5.951 | 1.00 | 49.96 |
| ATOM | 55 | OE2 | GLU | 163 | -8.527 | -20.999 | 4.731 | 1.00 | 49.96 |
| ATOM | 56 | C   | GLU | 163 | -5.330 | -16.897 | 6.548 | 1.00 | 19.45 |
| ATOM | 57 | O   | GLU | 163 | -5.614 | -15.731 | 6.832 | 1.00 | 49.96 |
| ATOM | 58 | N   | GLU | 164 | -4.120 | -17.417 | 6.734 | 1.00 | 22.03 |
| ATOM | 59 | CA  | GLU | 164 | -3.033 | -16.634 | 7.305 | 1.00 | 22.03 |

FIG. 29A-2

| ATOM | 60 | CB | GLU | 164 | -1.875 | -17.541 | 7.725 | 1.00 | 17.15 |
|---|---|---|---|---|---|---|---|---|---|
| ATOM | 61 | CG | GLU | 164 | -2.198 | -18.414 | 8.937 | 1.00 | 17.15 |
| ATOM | 62 | CD | GLU | 164 | -1.114 | -19.434 | 9.249 | 1.00 | 17.15 |
| ATOM | 63 | OE1 | GLU | 164 | -0.283 | -19.710 | 8.361 | 1.00 | 17.15 |
| ATOM | 64 | OE2 | GLU | 164 | -1.099 | -19.968 | 10.379 | 1.00 | 17.15 |
| ATOM | 65 | C | GLU | 164 | -2.559 | -15.542 | 6.354 | 1.00 | 22.03 |
| ATOM | 66 | O | GLU | 164 | -2.160 | -14.470 | 6.802 | 1.00 | 17.15 |
| ATOM | 67 | N | TRP | 165 | -2.607 | -15.805 | 5.048 | 1.00 | 10.72 |
| ATOM | 68 | CA | TRP | 165 | -2.205 | -14.803 | 4.063 | 1.00 | 10.72 |
| ATOM | 69 | CB | TRP | 165 | -2.223 | -15.377 | 2.644 | 1.00 | 2.00 |
| ATOM | 70 | CG | TRP | 165 | -0.928 | -16.003 | 2.227 | 1.00 | 2.00 |
| ATOM | 71 | CD2 | TRP | 165 | 0.350 | -15.358 | 2.131 | 1.00 | 2.00 |
| ATOM | 72 | CE2 | TRP | 165 | 1.275 | -16.326 | 1.685 | 1.00 | 2.00 |
| ATOM | 73 | CE3 | TRP | 165 | 0.804 | -14.054 | 2.379 | 1.00 | 2.00 |
| ATOM | 74 | CD1 | TRP | 165 | -0.731 | -17.298 | 1.848 | 1.00 | 2.00 |
| ATOM | 75 | NE1 | TRP | 165 | 0.587 | -17.500 | 1.521 | 1.00 | 2.00 |
| ATOM | 76 | CZ2 | TRP | 165 | 2.627 | -16.036 | 1.479 | 1.00 | 2.00 |
| ATOM | 77 | CZ3 | TRP | 165 | 2.152 | -13.764 | 2.174 | 1.00 | 2.00 |
| ATOM | 78 | CH2 | TRP | 165 | 3.046 | -14.754 | 1.729 | 1.00 | 2.00 |
| ATOM | 79 | C | TRP | 165 | -3.137 | -13.601 | 4.149 | 1.00 | 10.72 |
| ATOM | 80 | O | TRP | 165 | -2.717 | -12.463 | 3.925 | 1.00 | 2.00 |
| ATOM | 81 | N | ASP | 166 | -4.408 | -13.861 | 4.441 | 1.00 | 14.80 |
| ATOM | 82 | CA | ASP | 166 | -5.397 | -12.796 | 4.580 | 1.00 | 14.80 |
| ATOM | 83 | CB | ASP | 166 | -6.812 | -13.370 | 4.698 | 1.00 | 28.74 |
| ATOM | 84 | CG | ASP | 166 | -7.298 | -13.999 | 3.403 | 1.00 | 28.74 |
| ATOM | 85 | OD1 | ASP | 166 | -6.909 | -13.511 | 2.320 | 1.00 | 28.74 |
| ATOM | 86 | OD2 | ASP | 166 | -8.071 | -14.978 | 3.466 | 1.00 | 28.74 |
| ATOM | 87 | C | ASP | 166 | -5.063 | -11.981 | 5.819 | 1.00 | 14.80 |
| ATOM | 88 | O | ASP | 166 | -5.056 | -10.749 | 5.775 | 1.00 | 28.74 |
| ATOM | 89 | N | LEU | 167 | -4.745 | -12.682 | 6.906 | 1.00 | 11.01 |
| ATOM | 90 | CA | LEU | 167 | -4.383 | -12.044 | 8.166 | 1.00 | 11.01 |
| ATOM | 91 | CB | LEU | 167 | -4.036 | -13.103 | 9.214 | 1.00 | 31.53 |
| ATOM | 92 | CG | LEU | 167 | -4.672 | -12.975 | 10.601 | 1.00 | 31.53 |
| ATOM | 93 | CD1 | LEU | 167 | -3.806 | -13.709 | 11.619 | 1.00 | 31.53 |
| ATOM | 94 | CD2 | LEU | 167 | -4.820 | -11.507 | 10.989 | 1.00 | 31.53 |
| ATOM | 95 | C | LEU | 167 | -3.161 | -11.159 | 7.933 | 1.00 | 11.01 |
| ATOM | 96 | O | LEU | 167 | -3.120 | -10.006 | 8.367 | 1.00 | 31.53 |
| ATOM | 97 | N | ILE | 168 | -2.180 | -11.714 | 7.228 | 1.00 | 13.18 |
| ATOM | 98 | CA | ILE | 168 | -0.937 | -11.027 | 6.900 | 1.00 | 13.18 |
| ATOM | 99 | CB | ILE | 168 | 0.015 | -11.968 | 6.113 | 1.00 | 18.30 |
| ATOM | 100 | CG2 | ILE | 168 | 1.118 | -11.182 | 5.414 | 1.00 | 18.30 |
| ATOM | 101 | CG1 | ILE | 168 | 0.604 | -13.013 | 7.063 | 1.00 | 18.30 |
| ATOM | 102 | CD1 | ILE | 168 | 1.379 | -14.111 | 6.373 | 1.00 | 18.30 |
| ATOM | 103 | C | ILE | 168 | -1.185 | -9.747 | 6.107 | 1.00 | 13.18 |
| ATOM | 104 | O | ILE | 168 | -0.637 | -8.697 | 6.437 | 1.00 | 18.30 |
| ATOM | 105 | N | HIS | 169 | -2.032 | -9.831 | 5.084 | 1.00 | 12.99 |
| ATOM | 106 | CA | HIS | 169 | -2.342 | -8.674 | 4.245 | 1.00 | 12.99 |
| ATOM | 107 | CB | HIS | 169 | -3.218 | -9.087 | 3.062 | 1.00 | 13.09 |
| ATOM | 108 | CG | HIS | 169 | -2.553 | -10.045 | 2.126 | 1.00 | 13.09 |
| ATOM | 109 | CD2 | HIS | 169 | -1.247 | -10.223 | 1.811 | 1.00 | 13.09 |

FIG. 29A-3

| ATOM | 110 | ND1 | HIS | 169 | -3.249 | -11.000 | 1.416 | 1.00 | 13.09 |
|---|---|---|---|---|---|---|---|---|---|
| ATOM | 111 | CE1 | HIS | 169 | -2.403 | -11.728 | 0.710 | 1.00 | 13.09 |
| ATOM | 112 | NE2 | HIS | 169 | -1.181 | -11.277 | 0.936 | 1.00 | 13.09 |
| ATOM | 113 | C | HIS | 169 | -3.017 | -7.550 | 5.017 | 1.00 | 12.99 |
| ATOM | 114 | O | HIS | 169 | -2.680 | -6.377 | 4.839 | 1.00 | 13.09 |
| ATOM | 115 | N | VAL | 170 | -3.978 | -7.909 | 5.862 | 1.00 | 13.36 |
| ATOM | 116 | CA | VAL | 170 | -4.696 | -6.926 | 6.664 | 1.00 | 13.36 |
| ATOM | 117 | CB | VAL | 170 | -5.863 | -7.572 | 7.443 | 1.00 | 20.12 |
| ATOM | 118 | CG1 | VAL | 170 | -6.541 | -6.540 | 8.340 | 1.00 | 20.12 |
| ATOM | 119 | CG2 | VAL | 170 | -6.869 | -8.165 | 6.471 | 1.00 | 20.12 |
| ATOM | 120 | C | VAL | 170 | -3.741 | -6.246 | 7.639 | 1.00 | 13.36 |
| ATOM | 121 | O | VAL | 170 | -3.728 | -5.019 | 7.744 | 1.00 | 20.12 |
| ATOM | 122 | N | ALA | 171 | -2.920 | -7.043 | 8.320 | 1.00 | 11.04 |
| ATOM | 123 | CA | ALA | 171 | -1.953 | -6.515 | 9.277 | 1.00 | 11.04 |
| ATOM | 124 | CB | ALA | 171 | -1.249 | -7.653 | 10.005 | 1.00 | 13.43 |
| ATOM | 125 | C | ALA | 171 | -0.931 | -5.613 | 8.588 | 1.00 | 11.04 |
| ATOM | 126 | O | ALA | 171 | -0.658 | -4.507 | 9.058 | 1.00 | 13.43 |
| ATOM | 127 | N | THR | 172 | -0.382 | -6.076 | 7.469 | 1.00 | 12.51 |
| ATOM | 128 | CA | THR | 172 | 0.606 | -5.301 | 6.723 | 1.00 | 12.51 |
| ATOM | 129 | CB | THR | 172 | 1.062 | -6.032 | 5.445 | 1.00 | 14.17 |
| ATOM | 130 | OG1 | THR | 172 | 1.548 | -7.338 | 5.782 | 1.00 | 14.17 |
| ATOM | 131 | CG2 | THR | 172 | 2.175 | -5.255 | 4.756 | 1.00 | 14.17 |
| ATOM | 132 | C | THR | 172 | 0.045 | -3.936 | 6.337 | 1.00 | 12.51 |
| ATOM | 133 | O | THR | 172 | 0.701 | -2.910 | 6.537 | 1.00 | 14.17 |
| ATOM | 134 | N | GLU | 173 | -1.178 | -3.921 | 5.815 | 1.00 | 17.79 |
| ATOM | 135 | CA | GLU | 173 | -1.818 | -2.675 | 5.421 | 1.00 | 17.79 |
| ATOM | 136 | CB | GLU | 173 | -3.130 | -2.946 | 4.682 | 1.00 | 49.44 |
| ATOM | 137 | CG | GLU | 173 | -3.823 | -1.679 | 4.171 | 1.00 | 49.44 |
| ATOM | 138 | CD | GLU | 173 | -2.930 | -0.835 | 3.266 | 1.00 | 49.44 |
| ATOM | 139 | OE1 | GLU | 173 | -2.075 | -1.408 | 2.552 | 1.00 | 49.44 |
| ATOM | 140 | OE2 | GLU | 173 | -3.085 | 0.404 | 3.269 | 1.00 | 49.44 |
| ATOM | 141 | C | GLU | 173 | -2.072 | -1.780 | 6.628 | 1.00 | 17.79 |
| ATOM | 142 | O | GLU | 173 | -1.854 | -0.568 | 6.557 | 1.00 | 49.44 |
| ATOM | 143 | N | ALA | 174 | -2.525 | -2.375 | 7.731 | 1.00 | 13.12 |
| ATOM | 144 | CA | ALA | 174 | -2.798 | -1.631 | 8.957 | 1.00 | 13.12 |
| ATOM | 145 | CB | ALA | 174 | -3.226 | -2.576 | 10.068 | 1.00 | 17.51 |
| ATOM | 146 | C | ALA | 174 | -1.556 | -0.856 | 9.375 | 1.00 | 13.12 |
| ATOM | 147 | O | ALA | 174 | -1.634 | 0.319 | 9.735 | 1.00 | 17.51 |
| ATOM | 148 | N | HIS | 175 | -0.409 | -1.521 | 9.317 | 1.00 | 12.20 |
| ATOM | 149 | CA | HIS | 175 | 0.851 | -0.895 | 9.679 | 1.00 | 12.20 |
| ATOM | 150 | CB | HIS | 175 | 1.944 | -1.949 | 9.886 | 1.00 | 17.52 |
| ATOM | 151 | CG | HIS | 175 | 3.302 | -1.365 | 10.136 | 1.00 | 17.52 |
| ATOM | 152 | CD2 | HIS | 175 | 3.733 | -0.468 | 11.055 | 1.00 | 17.52 |
| ATOM | 153 | ND1 | HIS | 175 | 4.400 | -1.679 | 9.364 | 1.00 | 17.52 |
| ATOM | 154 | CE1 | HIS | 175 | 5.447 | -0.999 | 9.793 | 1.00 | 17.52 |
| ATOM | 155 | NE2 | HIS | 175 | 5.070 | -0.258 | 10.818 | 1.00 | 17.52 |
| ATOM | 156 | C | HIS | 175 | 1.311 | 0.133 | 8.654 | 1.00 | 12.20 |
| ATOM | 157 | O | HIS | 175 | 1.700 | 1.240 | 9.024 | 1.00 | 17.52 |
| ATOM | 158 | N | ARG | 176 | 1.291 | -0.233 | 7.375 | 1.00 | 12.54 |
| ATOM | 159 | CA | ARG | 176 | 1.735 | 0.677 | 6.328 | 1.00 | 12.54 |

FIG. 29A-4

| | | | | | | | | |
|---|---|---|---|---|---|---|---|---|
| ATOM | 160 | CB | ARG | 176 | 1.662 | 0.017 | 4.950 | 1.00 | 50.41 |
| ATOM | 161 | CG | ARG | 176 | 2.683 | -1.088 | 4.730 | 1.00 | 50.41 |
| ATOM | 162 | CD | ARG | 176 | 2.666 | -1.565 | 3.299 | 1.00 | 50.41 |
| ATOM | 163 | NE | ARG | 176 | 3.682 | -2.571 | 2.989 | 1.00 | 50.41 |
| ATOM | 164 | CZ | ARG | 176 | 3.577 | -3.472 | 2.012 | 1.00 | 50.41 |
| ATOM | 165 | NH1 | ARG | 176 | 2.496 | -3.513 | 1.236 | 1.00 | 50.41 |
| ATOM | 166 | NH2 | ARG | 176 | 4.536 | -4.376 | 1.841 | 1.00 | 50.41 |
| ATOM | 167 | C | ARG | 176 | 0.972 | 1.988 | 6.306 | 1.00 | 12.54 |
| ATOM | 168 | O | ARG | 176 | 1.561 | 3.040 | 6.087 | 1.00 | 50.41 |
| ATOM | 169 | N | SER | 177 | -0.326 | 1.935 | 6.581 | 1.00 | 24.74 |
| ATOM | 170 | CA | SER | 177 | -1.147 | 3.145 | 6.584 | 1.00 | 24.74 |
| ATOM | 171 | CB | SER | 177 | -2.622 | 2.792 | 6.414 | 1.00 | 21.56 |
| ATOM | 172 | OG | SER | 177 | -3.069 | 1.913 | 7.436 | 1.00 | 21.56 |
| ATOM | 173 | C | SER | 177 | -0.960 | 4.013 | 7.832 | 1.00 | 24.74 |
| ATOM | 174 | O | SER | 177 | -1.401 | 5.159 | 7.863 | 1.00 | 21.56 |
| ATOM | 175 | N | THR | 178 | -0.347 | 3.453 | 8.870 | 1.00 | 17.96 |
| ATOM | 176 | CA | THR | 178 | -0.104 | 4.181 | 10.115 | 1.00 | 17.96 |
| ATOM | 177 | CB | THR | 178 | -0.736 | 3.440 | 11.323 | 1.00 | 19.76 |
| ATOM | 178 | OG1 | THR | 178 | -0.265 | 2.091 | 11.361 | 1.00 | 19.76 |
| ATOM | 179 | CG2 | THR | 178 | -2.253 | 3.443 | 11.211 | 1.00 | 19.76 |
| ATOM | 180 | C | THR | 178 | 1.376 | 4.395 | 10.382 | 1.00 | 17.96 |
| ATOM | 181 | O | THR | 178 | 1.760 | 4.880 | 11.445 | 1.00 | 19.76 |
| ATOM | 182 | N | ASN | 179 | 2.207 | 4.024 | 9.417 | 1.00 | 25.88 |
| ATOM | 183 | CA | ASN | 179 | 3.654 | 4.180 | 9.546 | 1.00 | 25.88 |
| ATOM | 184 | CB | ASN | 179 | 4.362 | 2.974 | 8.943 | 1.00 | 44.29 |
| ATOM | 185 | CG | ASN | 179 | 5.817 | 2.871 | 9.368 | 1.00 | 44.29 |
| ATOM | 186 | OD1 | ASN | 179 | 6.129 | 2.768 | 10.564 | 1.00 | 44.29 |
| ATOM | 187 | ND2 | ASN | 179 | 6.719 | 2.830 | 8.391 | 1.00 | 44.29 |
| ATOM | 188 | C | ASN | 179 | 4.078 | 5.458 | 8.823 | 1.00 | 25.88 |
| ATOM | 189 | O | ASN | 179 | 4.150 | 5.495 | 7.590 | 1.00 | 44.29 |
| ATOM | 190 | N | ALA | 180 | 4.332 | 6.502 | 9.604 | 1.00 | 45.20 |
| ATOM | 191 | CA | ALA | 180 | 4.740 | 7.818 | 9.126 | 1.00 | 45.20 |
| ATOM | 192 | CB | ALA | 180 | 5.026 | 8.743 | 10.313 | 1.00 | 36.14 |
| ATOM | 193 | C | ALA | 180 | 5.931 | 7.808 | 8.170 | 1.00 | 45.20 |
| ATOM | 194 | O | ALA | 180 | 6.918 | 7.097 | 8.372 | 1.00 | 36.14 |
| ATOM | 195 | N | ALA | 181 | 5.784 | 8.552 | 7.080 | 1.00 | 44.05 |
| ATOM | 196 | CA | ALA | 181 | 6.834 | 8.661 | 6.072 | 1.00 | 44.05 |
| ATOM | 197 | CB | ALA | 181 | 8.170 | 9.116 | 6.722 | 1.00 | 50.21 |
| ATOM | 198 | C | ALA | 181 | 7.069 | 7.427 | 5.196 | 1.00 | 44.05 |
| ATOM | 199 | O | ALA | 181 | 7.663 | 7.550 | 4.118 | 1.00 | 50.21 |
| ATOM | 200 | N | GLY | 182 | 6.567 | 6.268 | 5.622 | 1.00 | 39.06 |
| ATOM | 201 | CA | GLY | 182 | 6.756 | 5.040 | 4.867 | 1.00 | 39.06 |
| ATOM | 202 | C | GLY | 182 | 8.202 | 4.769 | 4.482 | 1.00 | 39.06 |
| ATOM | 203 | O | GLY | 182 | 9.096 | 4.785 | 5.334 | 1.00 | 48.58 |
| ATOM | 204 | N | SER | 183 | 8.438 | 4.564 | 3.189 | 1.00 | 64.55 |
| ATOM | 205 | CA | SER | 183 | 9.781 | 4.270 | 2.693 | 1.00 | 64.55 |
| ATOM | 206 | CB | SER | 183 | 9.690 | 3.402 | 1.430 | 1.00 | 67.68 |
| ATOM | 207 | OG | SER | 183 | 8.822 | 3.978 | 0.467 | 1.00 | 67.68 |
| ATOM | 208 | C | SER | 183 | 10.643 | 5.510 | 2.437 | 1.00 | 64.55 |
| ATOM | 209 | O | SER | 183 | 11.839 | 5.407 | 2.158 | 1.00 | 67.68 |

FIG. 29A-5

| | | | | | | | | |
|---|---|---|---|---|---|---|---|---|
| ATOM | 210 | N | HIS | 184 | 10.035 | 6.683 | 2.579 | 1.00 | 52.73 |
| ATOM | 211 | CA | HIS | 184 | 10.725 | 7.953 | 2.352 | 1.00 | 52.73 |
| ATOM | 212 | CB | HIS | 184 | 9.772 | 8.955 | 1.698 | 1.00 | 44.77 |
| ATOM | 213 | C | HIS | 184 | 11.364 | 8.582 | 3.595 | 1.00 | 52.73 |
| ATOM | 214 | O | HIS | 184 | 11.837 | 9.722 | 3.540 | 1.00 | 44.77 |
| ATOM | 215 | N | TRP | 185 | 11.420 | 7.842 | 4.699 | 1.00 | 54.14 |
| ATOM | 216 | CA | TRP | 185 | 11.977 | 8.389 | 5.940 | 1.00 | 54.14 |
| ATOM | 217 | CB | TRP | 185 | 11.813 | 7.395 | 7.104 | 1.00 | 40.24 |
| ATOM | 218 | CG | TRP | 185 | 12.605 | 6.123 | 6.991 | 1.00 | 40.24 |
| ATOM | 219 | CD2 | TRP | 185 | 13.894 | 5.873 | 7.551 | 1.00 | 40.24 |
| ATOM | 220 | CE2 | TRP | 185 | 14.245 | 4.543 | 7.221 | 1.00 | 40.24 |
| ATOM | 221 | CE3 | TRP | 185 | 14.791 | 6.641 | 8.300 | 1.00 | 40.24 |
| ATOM | 222 | CD1 | TRP | 185 | 12.227 | 4.973 | 6.359 | 1.00 | 40.24 |
| ATOM | 223 | NE1 | TRP | 185 | 13.210 | 4.015 | 6.496 | 1.00 | 40.24 |
| ATOM | 224 | CZ2 | TRP | 185 | 15.461 | 3.968 | 7.619 | 1.00 | 40.24 |
| ATOM | 225 | CZ3 | TRP | 185 | 15.996 | 6.073 | 8.696 | 1.00 | 40.24 |
| ATOM | 226 | CH2 | TRP | 185 | 16.319 | 4.747 | 8.353 | 1.00 | 40.24 |
| ATOM | 227 | C | TRP | 185 | 13.432 | 8.870 | 5.819 | 1.00 | 54.14 |
| ATOM | 228 | O | TRP | 185 | 13.759 | 10.008 | 6.168 | 1.00 | 40.24 |
| ATOM | 229 | N | LYS | 186 | 14.277 | 8.032 | 5.232 | 1.00 | 43.72 |
| ATOM | 230 | CA | LYS | 186 | 15.694 | 8.329 | 5.035 | 1.00 | 43.72 |
| ATOM | 231 | CB | LYS | 186 | 16.353 | 7.168 | 4.282 | 1.00 | 64.14 |
| ATOM | 232 | CG | LYS | 186 | 17.830 | 7.355 | 3.945 | 1.00 | 64.14 |
| ATOM | 233 | CD | LYS | 186 | 18.758 | 7.175 | 5.139 | 1.00 | 64.14 |
| ATOM | 234 | CE | LYS | 186 | 20.195 | 7.060 | 4.652 | 1.00 | 64.14 |
| ATOM | 235 | NZ | LYS | 186 | 20.348 | 5.838 | 3.805 | 1.00 | 64.14 |
| ATOM | 236 | C | LYS | 186 | 15.900 | 9.634 | 4.263 | 1.00 | 43.72 |
| ATOM | 237 | O | LYS | 186 | 16.948 | 10.256 | 4.366 | 1.00 | 64.14 |
| ATOM | 238 | N | GLN | 187 | 14.892 | 10.032 | 3.491 | 1.00 | 58.06 |
| ATOM | 239 | CA | GLN | 187 | 14.958 | 11.244 | 2.682 | 1.00 | 58.06 |
| ATOM | 240 | CB | GLN | 187 | 14.288 | 10.997 | 1.321 | 1.00 | 74.68 |
| ATOM | 241 | CG | GLN | 187 | 14.639 | 9.662 | 0.667 | 1.00 | 74.68 |
| ATOM | 242 | CD | GLN | 187 | 16.133 | 9.397 | 0.607 | 1.00 | 74.68 |
| ATOM | 243 | OE1 | GLN | 187 | 16.926 | 10.312 | 0.381 | 1.00 | 74.68 |
| ATOM | 244 | NE2 | GLN | 187 | 16.528 | 8.156 | 0.855 | 1.00 | 74.68 |
| ATOM | 245 | C | GLN | 187 | 14.322 | 12.466 | 3.342 | 1.00 | 58.06 |
| ATOM | 246 | O | GLN | 187 | 14.897 | 13.551 | 3.358 | 1.00 | 74.68 |
| ATOM | 247 | N | ARG | 188 | 13.117 | 12.280 | 3.866 | 1.00 | 54.11 |
| ATOM | 248 | CA | ARG | 188 | 12.363 | 13.360 | 4.505 | 1.00 | 54.11 |
| ATOM | 249 | CB | ARG | 188 | 10.889 | 13.115 | 4.334 | 1.00 | 53.33 |
| ATOM | 250 | C | ARG | 188 | 12.654 | 13.626 | 5.977 | 1.00 | 54.11 |
| ATOM | 251 | O | ARG | 188 | 11.879 | 14.298 | 6.659 | 1.00 | 53.33 |
| ATOM | 252 | N | ARG | 189 | 13.754 | 13.090 | 6.473 | 1.00 | 39.52 |
| ATOM | 253 | CA | ARG | 189 | 14.089 | 13.271 | 7.875 | 1.00 | 39.52 |
| ATOM | 254 | CB | ARG | 189 | 14.594 | 11.959 | 8.482 | 1.00 | 60.85 |
| ATOM | 255 | CG | ARG | 189 | 15.969 | 11.555 | 7.991 | 1.00 | 60.85 |
| ATOM | 256 | CD | ARG | 189 | 16.442 | 10.298 | 8.693 | 1.00 | 60.85 |
| ATOM | 257 | NE | ARG | 189 | 17.833 | 9.963 | 8.385 | 1.00 | 60.85 |
| ATOM | 258 | CZ | ARG | 189 | 18.627 | 9.261 | 9.190 | 1.00 | 60.85 |
| ATOM | 259 | NH1 | ARG | 189 | 18.178 | 8.805 | 10.356 | 1.00 | 60.85 |

FIG. 29A-6

| | | | | | | | | |
|---|---|---|---|---|---|---|---|---|
| ATOM | 260 | NH2 | ARG | 189 | 19.882 | 9.021 | 8.841 | 1.00 | 60.85 |
| ATOM | 261 | C | ARG | 189 | 15.109 | 14.378 | 8.109 | 1.00 | 39.52 |
| ATOM | 262 | O | ARG | 189 | 16.037 | 14.565 | 7.320 | 1.00 | 60.85 |
| ATOM | 263 | N | LYS | 190 | 14.934 | 15.100 | 9.212 | 1.00 | 44.13 |
| ATOM | 264 | CA | LYS | 190 | 15.834 | 16.183 | 9.586 | 1.00 | 44.13 |
| ATOM | 265 | CB | LYS | 190 | 15.068 | 17.500 | 9.680 | 1.00 | 45.33 |
| ATOM | 266 | C | LYS | 190 | 16.472 | 15.846 | 10.928 | 1.00 | 44.13 |
| ATOM | 267 | O | LYS | 190 | 15.827 | 15.272 | 11.805 | 1.00 | 45.33 |
| ATOM | 268 | N | PHE | 191 | 17.748 | 16.184 | 11.067 | 1.00 | 35.64 |
| ATOM | 269 | CA | PHE | 191 | 18.489 | 15.928 | 12.291 | 1.00 | 35.64 |
| ATOM | 270 | CB | PHE | 191 | 19.993 | 16.008 | 12.025 | 1.00 | 53.94 |
| ATOM | 271 | CG | PHE | 191 | 20.550 | 14.827 | 11.286 | 1.00 | 53.94 |
| ATOM | 272 | CD1 | PHE | 191 | 20.209 | 14.596 | 9.958 | 1.00 | 53.94 |
| ATOM | 273 | CD2 | PHE | 191 | 21.430 | 13.949 | 11.915 | 1.00 | 53.94 |
| ATOM | 274 | CE1 | PHE | 191 | 20.735 | 13.510 | 9.265 | 1.00 | 53.94 |
| ATOM | 275 | CE2 | PHE | 191 | 21.964 | 12.859 | 11.230 | 1.00 | 53.94 |
| ATOM | 276 | CZ | PHE | 191 | 21.615 | 12.639 | 9.900 | 1.00 | 53.94 |
| ATOM | 277 | C | PHE | 191 | 18.135 | 16.928 | 13.384 | 1.00 | 35.64 |
| ATOM | 278 | O | PHE | 191 | 17.997 | 18.127 | 13.120 | 1.00 | 53.94 |
| ATOM | 279 | N | LEU | 192 | 17.978 | 16.439 | 14.610 | 1.00 | 44.53 |
| ATOM | 280 | CA | LEU | 192 | 17.683 | 17.315 | 15.736 | 1.00 | 44.53 |
| ATOM | 281 | CB | LEU | 192 | 17.326 | 16.493 | 16.980 | 1.00 | 22.94 |
| ATOM | 282 | CG | LEU | 192 | 16.931 | 17.259 | 18.246 | 1.00 | 22.94 |
| ATOM | 283 | CD1 | LEU | 192 | 15.568 | 17.906 | 18.064 | 1.00 | 22.94 |
| ATOM | 284 | CD2 | LEU | 192 | 16.909 | 16.308 | 19.427 | 1.00 | 22.94 |
| ATOM | 285 | C | LEU | 192 | 18.974 | 18.101 | 15.980 | 1.00 | 44.53 |
| ATOM | 286 | O | LEU | 192 | 20.049 | 17.507 | 16.129 | 1.00 | 22.94 |
| ATOM | 287 | N | PRO | 193 | 18.895 | 19.444 | 15.977 | 1.00 | 34.26 |
| ATOM | 288 | CD | PRO | 193 | 17.670 | 20.241 | 15.781 | 1.00 | 46.23 |
| ATOM | 289 | CA | PRO | 193 | 20.058 | 20.311 | 16.198 | 1.00 | 34.26 |
| ATOM | 290 | CB | PRO | 193 | 19.417 | 21.670 | 16.465 | 1.00 | 46.23 |
| ATOM | 291 | CG | PRO | 193 | 18.213 | 21.641 | 15.579 | 1.00 | 46.23 |
| ATOM | 292 | C | PRO | 193 | 20.917 | 19.844 | 17.372 | 1.00 | 34.26 |
| ATOM | 293 | O | PRO | 193 | 20.413 | 19.614 | 18.471 | 1.00 | 46.23 |
| ATOM | 294 | N | ASP | 194 | 22.217 | 19.716 | 17.125 | 1.00 | 42.67 |
| ATOM | 295 | CA | ASP | 194 | 23.174 | 19.254 | 18.128 | 1.00 | 42.67 |
| ATOM | 296 | CB | ASP | 194 | 24.583 | 19.226 | 17.536 | 1.00 | 68.50 |
| ATOM | 297 | CG | ASP | 194 | 24.731 | 18.185 | 16.450 | 1.00 | 68.50 |
| ATOM | 298 | OD1 | ASP | 194 | 25.066 | 17.027 | 16.782 | 1.00 | 68.50 |
| ATOM | 299 | OD2 | ASP | 194 | 24.498 | 18.518 | 15.269 | 1.00 | 68.50 |
| ATOM | 300 | C | ASP | 194 | 23.187 | 20.003 | 19.457 | 1.00 | 42.67 |
| ATOM | 301 | O | ASP | 194 | 23.545 | 19.432 | 20.486 | 1.00 | 68.50 |
| ATOM | 302 | N | ASP | 195 | 22.817 | 21.280 | 19.438 | 1.00 | 47.52 |
| ATOM | 303 | CA | ASP | 195 | 22.793 | 22.070 | 20.666 | 1.00 | 47.52 |
| ATOM | 304 | CB | ASP | 195 | 22.586 | 23.559 | 20.351 | 1.00 | 85.02 |
| ATOM | 305 | CG | ASP | 195 | 21.327 | 23.824 | 19.537 | 1.00 | 85.02 |
| ATOM | 306 | OD1 | ASP | 195 | 20.291 | 24.188 | 20.138 | 1.00 | 85.02 |
| ATOM | 307 | OD2 | ASP | 195 | 21.377 | 23.683 | 18.294 | 1.00 | 85.02 |
| ATOM | 308 | C | ASP | 195 | 21.715 | 21.561 | 21.627 | 1.00 | 47.52 |
| ATOM | 309 | O | ASP | 195 | 21.762 | 21.826 | 22.831 | 1.00 | 85.02 |

FIG. 29A-7

| ATOM | 310 | N | ILE | 196 | 20.760 | 20.810 | 21.089 | 1.00 | 44.54 |
|---|---|---|---|---|---|---|---|---|---|
| ATOM | 311 | CA | ILE | 196 | 19.663 | 20.259 | 21.875 | 1.00 | 44.54 |
| ATOM | 312 | CB | ILE | 196 | 18.379 | 20.137 | 21.023 | 1.00 | 39.66 |
| ATOM | 313 | CG2 | ILE | 196 | 17.223 | 19.627 | 21.874 | 1.00 | 39.66 |
| ATOM | 314 | CG1 | ILE | 196 | 18.031 | 21.496 | 20.407 | 1.00 | 39.66 |
| ATOM | 315 | CD1 | ILE | 196 | 16.816 | 21.475 | 19.503 | 1.00 | 39.66 |
| ATOM | 316 | C | ILE | 196 | 20.030 | 18.882 | 22.420 | 1.00 | 44.54 |
| ATOM | 317 | O | ILE | 196 | 20.582 | 18.046 | 21.705 | 1.00 | 39.66 |
| ATOM | 318 | N | GLY | 197 | 19.714 | 18.652 | 23.690 | 1.00 | 42.85 |
| ATOM | 319 | CA | GLY | 197 | 20.006 | 17.372 | 24.307 | 1.00 | 42.85 |
| ATOM | 320 | C | GLY | 197 | 21.371 | 17.285 | 24.956 | 1.00 | 42.85 |
| ATOM | 321 | O | GLY | 197 | 21.815 | 16.198 | 25.318 | 1.00 | 40.22 |
| ATOM | 322 | N | GLN | 198 | 22.029 | 18.425 | 25.137 | 1.00 | 53.07 |
| ATOM | 323 | CA | GLN | 198 | 23.351 | 18.444 | 25.754 | 1.00 | 53.07 |
| ATOM | 324 | CB | GLN | 198 | 24.357 | 19.103 | 24.810 | 1.00 | 44.23 |
| ATOM | 325 | C | GLN | 198 | 23.344 | 19.153 | 27.110 | 1.00 | 53.07 |
| ATOM | 326 | O | GLN | 198 | 24.396 | 19.545 | 27.616 | 1.00 | 44.23 |
| ATOM | 327 | N | SER | 199 | 22.170 | 19.244 | 27.729 | 1.00 | 35.30 |
| ATOM | 328 | CA | SER | 199 | 22.037 | 19.918 | 29.019 | 1.00 | 35.30 |
| ATOM | 329 | CB | SER | 199 | 21.472 | 21.328 | 28.806 | 1.00 | 58.72 |
| ATOM | 330 | OG | SER | 199 | 22.093 | 21.971 | 27.704 | 1.00 | 58.72 |
| ATOM | 331 | C | SER | 199 | 21.168 | 19.169 | 30.036 | 1.00 | 35.30 |
| ATOM | 332 | O | SER | 199 | 20.135 | 19.681 | 30.482 | 1.00 | 58.72 |
| ATOM | 333 | N | PRO | 200 | 21.544 | 17.928 | 30.387 | 1.00 | 34.70 |
| ATOM | 334 | CD | PRO | 200 | 22.656 | 17.108 | 29.872 | 1.00 | 38.71 |
| ATOM | 335 | CA | PRO | 200 | 20.740 | 17.184 | 31.362 | 1.00 | 34.70 |
| ATOM | 336 | CB | PRO | 200 | 21.311 | 15.769 | 31.266 | 1.00 | 38.71 |
| ATOM | 337 | CG | PRO | 200 | 22.737 | 15.992 | 30.878 | 1.00 | 38.71 |
| ATOM | 338 | C | PRO | 200 | 20.923 | 17.784 | 32.759 | 1.00 | 34.70 |
| ATOM | 339 | O | PRO | 200 | 22.006 | 17.692 | 33.341 | 1.00 | 38.71 |
| ATOM | 340 | N | ILE | 201 | 19.876 | 18.413 | 33.286 | 1.00 | 42.94 |
| ATOM | 341 | CA | ILE | 201 | 19.961 | 19.041 | 34.604 | 1.00 | 42.94 |
| ATOM | 342 | CB | ILE | 201 | 20.059 | 20.582 | 34.491 | 1.00 | 51.32 |
| ATOM | 343 | CG2 | ILE | 201 | 21.468 | 20.991 | 34.078 | 1.00 | 51.32 |
| ATOM | 344 | CG1 | ILE | 201 | 19.009 | 21.111 | 33.510 | 1.00 | 51.32 |
| ATOM | 345 | CD1 | ILE | 201 | 19.169 | 22.582 | 33.164 | 1.00 | 51.32 |
| ATOM | 346 | C | ILE | 201 | 18.871 | 18.676 | 35.610 | 1.00 | 42.94 |
| ATOM | 347 | O | ILE | 201 | 19.049 | 18.875 | 36.814 | 1.00 | 51.32 |
| ATOM | 348 | N | VAL | 202 | 17.737 | 18.172 | 35.133 | 1.00 | 50.33 |
| ATOM | 349 | CA | VAL | 202 | 16.661 | 17.787 | 36.043 | 1.00 | 50.33 |
| ATOM | 350 | CB | VAL | 202 | 15.296 | 17.722 | 35.326 | 1.00 | 36.59 |
| ATOM | 351 | CG1 | VAL | 202 | 14.202 | 17.311 | 36.304 | 1.00 | 36.59 |
| ATOM | 352 | CG2 | VAL | 202 | 14.968 | 19.074 | 34.714 | 1.00 | 36.59 |
| ATOM | 353 | C | VAL | 202 | 17.007 | 16.435 | 36.665 | 1.00 | 50.33 |
| ATOM | 354 | O | VAL | 202 | 17.335 | 15.481 | 35.955 | 1.00 | 36.59 |
| ATOM | 355 | N | SER | 203 | 16.960 | 16.375 | 37.991 | 1.00 | 49.46 |
| ATOM | 356 | CA | SER | 203 | 17.289 | 15.166 | 38.736 | 1.00 | 49.46 |
| ATOM | 357 | CB | SER | 203 | 17.298 | 15.467 | 40.241 | 1.00 | 64.20 |
| ATOM | 358 | OG | SER | 203 | 17.673 | 14.330 | 41.003 | 1.00 | 64.20 |
| ATOM | 359 | C | SER | 203 | 16.356 | 13.992 | 38.463 | 1.00 | 49.46 |

FIG. 29A-8

| | | | | | | | | | |
|---|---|---|---|---|---|---|---|---|---|
| ATOM | 360 | O | SER | 203 | 15.147 | 14.166 | 38.310 | 1.00 | 64.20 |
| ATOM | 361 | N | MET | 204 | 16.944 | 12.800 | 38.419 | 1.00 | 41.99 |
| ATOM | 362 | CA | MET | 204 | 16.223 | 11.551 | 38.205 | 1.00 | 41.99 |
| ATOM | 363 | CB | MET | 204 | 16.320 | 11.096 | 36.746 | 1.00 | 48.64 |
| ATOM | 364 | CG | MET | 204 | 15.470 | 11.895 | 35.771 | 1.00 | 48.64 |
| ATOM | 365 | SD | MET | 204 | 13.702 | 11.783 | 36.114 | 1.00 | 48.64 |
| ATOM | 366 | CE | MET | 204 | 13.284 | 10.257 | 35.264 | 1.00 | 48.64 |
| ATOM | 367 | C | MET | 204 | 16.900 | 10.528 | 39.109 | 1.00 | 41.99 |
| ATOM | 368 | O | MET | 204 | 18.127 | 10.417 | 39.121 | 1.00 | 48.64 |
| ATOM | 369 | N | PRO | 205 | 16.108 | 9.754 | 39.869 | 1.00 | 38.42 |
| ATOM | 370 | CD | PRO | 205 | 14.633 | 9.815 | 39.866 | 1.00 | 52.20 |
| ATOM | 371 | CA | PRO | 205 | 16.586 | 8.724 | 40.797 | 1.00 | 38.42 |
| ATOM | 372 | CB | PRO | 205 | 15.334 | 7.888 | 41.041 | 1.00 | 52.20 |
| ATOM | 373 | CG | PRO | 205 | 14.254 | 8.919 | 41.028 | 1.00 | 52.20 |
| ATOM | 374 | C | PRO | 205 | 17.769 | 7.858 | 40.340 | 1.00 | 38.42 |
| ATOM | 375 | O | PRO | 205 | 18.724 | 7.675 | 41.092 | 1.00 | 52.20 |
| ATOM | 376 | N | ASP | 206 | 17.720 | 7.349 | 39.111 | 1.00 | 49.06 |
| ATOM | 377 | CA | ASP | 206 | 18.791 | 6.490 | 38.601 | 1.00 | 49.06 |
| ATOM | 378 | CB | ASP | 206 | 18.282 | 5.627 | 37.437 | 1.00 | 74.42 |
| ATOM | 379 | CG | ASP | 206 | 17.690 | 6.450 | 36.305 | 1.00 | 74.42 |
| ATOM | 380 | OD1 | ASP | 206 | 18.397 | 7.335 | 35.770 | 1.00 | 74.42 |
| ATOM | 381 | OD2 | ASP | 206 | 16.516 | 6.199 | 35.948 | 1.00 | 74.42 |
| ATOM | 382 | C | ASP | 206 | 20.106 | 7.177 | 38.214 | 1.00 | 49.06 |
| ATOM | 383 | O | ASP | 206 | 21.069 | 6.506 | 37.838 | 1.00 | 74.42 |
| ATOM | 384 | N | GLY | 207 | 20.139 | 8.505 | 38.272 | 1.00 | 42.48 |
| ATOM | 385 | CA | GLY | 207 | 21.355 | 9.225 | 37.928 | 1.00 | 42.48 |
| ATOM | 386 | C | GLY | 207 | 21.330 | 9.965 | 36.601 | 1.00 | 42.48 |
| ATOM | 387 | O | GLY | 207 | 21.890 | 11.058 | 36.494 | 1.00 | 42.50 |
| ATOM | 388 | N | ASP | 208 | 20.725 | 9.365 | 35.581 | 1.00 | 46.70 |
| ATOM | 389 | CA | ASP | 208 | 20.636 | 9.999 | 34.266 | 1.00 | 46.70 |
| ATOM | 390 | CB | ASP | 208 | 20.162 | 8.994 | 33.212 | 1.00 | 61.56 |
| ATOM | 391 | CG | ASP | 208 | 21.143 | 7.856 | 33.006 | 1.00 | 61.56 |
| ATOM | 392 | OD1 | ASP | 208 | 20.723 | 6.684 | 33.122 | 1.00 | 61.56 |
| ATOM | 393 | OD2 | ASP | 208 | 22.330 | 8.134 | 32.724 | 1.00 | 61.56 |
| ATOM | 394 | C | ASP | 208 | 19.666 | 11.176 | 34.339 | 1.00 | 46.70 |
| ATOM | 395 | O | ASP | 208 | 18.462 | 10.983 | 34.506 | 1.00 | 61.56 |
| ATOM | 396 | N | LYS | 209 | 20.200 | 12.389 | 34.238 | 1.00 | 41.30 |
| ATOM | 397 | CA | LYS | 209 | 19.389 | 13.602 | 34.308 | 1.00 | 41.30 |
| ATOM | 398 | CB | LYS | 209 | 20.254 | 14.782 | 34.732 | 1.00 | 41.38 |
| ATOM | 399 | C | LYS | 209 | 18.657 | 13.916 | 33.004 | 1.00 | 41.30 |
| ATOM | 400 | O | LYS | 209 | 19.052 | 13.458 | 31.930 | 1.00 | 41.38 |
| ATOM | 401 | N | VAL | 210 | 17.603 | 14.723 | 33.109 | 1.00 | 43.36 |
| ATOM | 402 | CA | VAL | 210 | 16.792 | 15.107 | 31.954 | 1.00 | 43.36 |
| ATOM | 403 | CB | VAL | 210 | 15.275 | 15.014 | 32.282 | 1.00 | 30.23 |
| ATOM | 404 | CG1 | VAL | 210 | 14.440 | 15.358 | 31.055 | 1.00 | 30.23 |
| ATOM | 405 | CG2 | VAL | 210 | 14.923 | 13.624 | 32.782 | 1.00 | 30.23 |
| ATOM | 406 | C | VAL | 210 | 17.088 | 16.522 | 31.442 | 1.00 | 43.36 |
| ATOM | 407 | O | VAL | 210 | 17.395 | 17.430 | 32.221 | 1.00 | 30.23 |
| ATOM | 408 | N | ASP | 211 | 17.004 | 16.685 | 30.125 | 1.00 | 27.49 |
| ATOM | 409 | CA | ASP | 211 | 17.217 | 17.966 | 29.458 | 1.00 | 27.49 |

FIG. 29A-9

| ATOM | 410 | CB | ASP | 211 | 18.073 | 17.765 | 28.198 | 1.00 | 30.75 |
| ATOM | 411 | CG | ASP | 211 | 18.360 | 19.068 | 27.447 | 1.00 | 30.75 |
| ATOM | 412 | OD1 | ASP | 211 | 19.473 | 19.196 | 26.900 | 1.00 | 30.75 |
| ATOM | 413 | OD2 | ASP | 211 | 17.484 | 19.955 | 27.370 | 1.00 | 30.75 |
| ATOM | 414 | C | ASP | 211 | 15.819 | 18.445 | 29.073 | 1.00 | 27.49 |
| ATOM | 415 | O | ASP | 211 | 15.197 | 17.892 | 28.166 | 1.00 | 30.75 |
| ATOM | 416 | N | LEU | 212 | 15.343 | 19.488 | 29.745 | 1.00 | 31.99 |
| ATOM | 417 | CA | LEU | 212 | 14.013 | 20.042 | 29.492 | 1.00 | 31.99 |
| ATOM | 418 | CB | LEU | 212 | 13.778 | 21.274 | 30.369 | 1.00 | 35.19 |
| ATOM | 419 | CG | LEU | 212 | 13.606 | 20.997 | 31.864 | 1.00 | 35.19 |
| ATOM | 420 | CD1 | LEU | 212 | 13.621 | 22.298 | 32.652 | 1.00 | 35.19 |
| ATOM | 421 | CD2 | LEU | 212 | 12.309 | 20.237 | 32.098 | 1.00 | 35.19 |
| ATOM | 422 | C | LEU | 212 | 13.713 | 20.377 | 28.032 | 1.00 | 31.99 |
| ATOM | 423 | O | LEU | 212 | 12.625 | 20.083 | 27.539 | 1.00 | 35.19 |
| ATOM | 424 | N | GLU | 213 | 14.672 | 20.981 | 27.338 | 1.00 | 28.70 |
| ATOM | 425 | CA | GLU | 213 | 14.468 | 21.345 | 25.940 | 1.00 | 28.70 |
| ATOM | 426 | CB | GLU | 213 | 15.623 | 22.209 | 25.428 | 1.00 | 62.21 |
| ATOM | 427 | CG | GLU | 213 | 15.434 | 22.707 | 23.997 | 1.00 | 62.21 |
| ATOM | 428 | CD | GLU | 213 | 16.651 | 23.440 | 23.446 | 1.00 | 62.21 |
| ATOM | 429 | OE1 | GLU | 213 | 17.778 | 23.214 | 23.945 | 1.00 | 62.21 |
| ATOM | 430 | OE2 | GLU | 213 | 16.478 | 24.237 | 22.498 | 1.00 | 62.21 |
| ATOM | 431 | C | GLU | 213 | 14.317 | 20.104 | 25.067 | 1.00 | 28.70 |
| ATOM | 432 | O | GLU | 213 | 13.403 | 20.024 | 24.247 | 1.00 | 62.21 |
| ATOM | 433 | N | ALA | 214 | 15.201 | 19.130 | 25.262 | 1.00 | 28.17 |
| ATOM | 434 | CA | ALA | 214 | 15.162 | 17.890 | 24.494 | 1.00 | 28.17 |
| ATOM | 435 | CB | ALA | 214 | 16.330 | 16.998 | 24.872 | 1.00 | 42.74 |
| ATOM | 436 | C | ALA | 214 | 13.844 | 17.176 | 24.759 | 1.00 | 28.17 |
| ATOM | 437 | O | ALA | 214 | 13.174 | 16.726 | 23.829 | 1.00 | 42.74 |
| ATOM | 438 | N | PHE | 215 | 13.468 | 17.104 | 26.032 | 1.00 | 21.66 |
| ATOM | 439 | CA | PHE | 215 | 12.222 | 16.471 | 26.444 | 1.00 | 21.66 |
| ATOM | 440 | CB | PHE | 215 | 12.033 | 16.628 | 27.958 | 1.00 | 28.76 |
| ATOM | 441 | CG | PHE | 215 | 10.751 | 16.038 | 28.481 | 1.00 | 28.76 |
| ATOM | 442 | CD1 | PHE | 215 | 10.675 | 14.689 | 28.815 | 1.00 | 28.76 |
| ATOM | 443 | CD2 | PHE | 215 | 9.623 | 16.835 | 28.653 | 1.00 | 28.76 |
| ATOM | 444 | CE1 | PHE | 215 | 9.493 | 14.143 | 29.315 | 1.00 | 28.76 |
| ATOM | 445 | CE2 | PHE | 215 | 8.438 | 16.300 | 29.150 | 1.00 | 28.76 |
| ATOM | 446 | CZ | PHE | 215 | 8.373 | 14.951 | 29.482 | 1.00 | 28.76 |
| ATOM | 447 | C | PHE | 215 | 11.068 | 17.132 | 25.696 | 1.00 | 21.66 |
| ATOM | 448 | O | PHE | 215 | 10.215 | 16.451 | 25.122 | 1.00 | 28.76 |
| ATOM | 449 | N | SER | 216 | 11.073 | 18.462 | 25.680 | 1.00 | 28.03 |
| ATOM | 450 | CA | SER | 216 | 10.043 | 19.242 | 25.007 | 1.00 | 28.03 |
| ATOM | 451 | CB | SER | 216 | 10.349 | 20.734 | 25.146 | 1.00 | 33.85 |
| ATOM | 452 | OG | SER | 216 | 9.300 | 21.529 | 24.624 | 1.00 | 33.85 |
| ATOM | 453 | C | SER | 216 | 9.945 | 18.857 | 23.532 | 1.00 | 28.03 |
| ATOM | 454 | O | SER | 216 | 8.852 | 18.613 | 23.019 | 1.00 | 33.85 |
| ATOM | 455 | N | GLU | 217 | 11.092 | 18.761 | 22.868 | 1.00 | 28.84 |
| ATOM | 456 | CA | GLU | 217 | 11.138 | 18.402 | 21.454 | 1.00 | 28.84 |
| ATOM | 457 | CB | GLU | 217 | 12.581 | 18.420 | 20.943 | 1.00 | 47.68 |
| ATOM | 458 | CG | GLU | 217 | 13.174 | 19.815 | 20.811 | 1.00 | 47.68 |
| ATOM | 459 | CD | GLU | 217 | 12.405 | 20.684 | 19.829 | 1.00 | 47.68 |

FIG. 29A-10

| ATOM | 460 | OE1 | GLU | 217 | 11.660 | 21.581 | 20.281 | 1.00 | 47.68 |
|------|-----|-----|-----|-----|--------|--------|--------|------|-------|
| ATOM | 461 | OE2 | GLU | 217 | 12.542 | 20.465 | 18.606 | 1.00 | 47.68 |
| ATOM | 462 | C | GLU | 217 | 10.505 | 17.044 | 21.179 | 1.00 | 28.84 |
| ATOM | 463 | O | GLU | 217 | 9.751 | 16.886 | 20.217 | 1.00 | 47.68 |
| ATOM | 464 | N | PHE | 218 | 10.799 | 16.071 | 22.036 | 1.00 | 21.49 |
| ATOM | 465 | CA | PHE | 218 | 10.259 | 14.725 | 21.883 | 1.00 | 21.49 |
| ATOM | 466 | CB | PHE | 218 | 11.020 | 13.746 | 22.781 | 1.00 | 24.12 |
| ATOM | 467 | CG | PHE | 218 | 12.489 | 13.652 | 22.464 | 1.00 | 24.12 |
| ATOM | 468 | CD1 | PHE | 218 | 13.431 | 13.554 | 23.481 | 1.00 | 24.12 |
| ATOM | 469 | CD2 | PHE | 218 | 12.932 | 13.677 | 21.144 | 1.00 | 24.12 |
| ATOM | 470 | CE1 | PHE | 218 | 14.793 | 13.484 | 23.187 | 1.00 | 24.12 |
| ATOM | 471 | CE2 | PHE | 218 | 14.290 | 13.607 | 20.843 | 1.00 | 24.12 |
| ATOM | 472 | CZ | PHE | 218 | 15.221 | 13.511 | 21.867 | 1.00 | 24.12 |
| ATOM | 473 | C | PHE | 218 | 8.765 | 14.675 | 22.176 | 1.00 | 21.49 |
| ATOM | 474 | O | PHE | 218 | 7.985 | 14.166 | 21.369 | 1.00 | 24.12 |
| ATOM | 475 | N | THR | 219 | 8.358 | 15.227 | 23.312 | 1.00 | 20.07 |
| ATOM | 476 | CA | THR | 219 | 6.949 | 15.231 | 23.685 | 1.00 | 20.07 |
| ATOM | 477 | CB | THR | 219 | 6.741 | 15.766 | 25.118 | 1.00 | 28.98 |
| ATOM | 478 | OG1 | THR | 219 | 7.418 | 17.021 | 25.274 | 1.00 | 28.98 |
| ATOM | 479 | CG2 | THR | 219 | 7.275 | 14.767 | 26.132 | 1.00 | 28.98 |
| ATOM | 480 | C | THR | 219 | 6.080 | 16.011 | 22.696 | 1.00 | 20.07 |
| ATOM | 481 | O | THR | 219 | 4.914 | 15.670 | 22.482 | 1.00 | 28.98 |
| ATOM | 482 | N | LYS | 220 | 6.662 | 17.022 | 22.060 | 1.00 | 25.35 |
| ATOM | 483 | CA | LYS | 220 | 5.943 | 17.840 | 21.088 | 1.00 | 25.35 |
| ATOM | 484 | CB | LYS | 220 | 6.842 | 18.965 | 20.577 | 1.00 | 29.07 |
| ATOM | 485 | C | LYS | 220 | 5.414 | 17.015 | 19.916 | 1.00 | 25.35 |
| ATOM | 486 | O | LYS | 220 | 4.376 | 17.343 | 19.339 | 1.00 | 29.07 |
| ATOM | 487 | N | ILE | 221 | 6.122 | 15.943 | 19.569 | 1.00 | 31.43 |
| ATOM | 488 | CA | ILE | 221 | 5.708 | 15.089 | 18.458 | 1.00 | 31.43 |
| ATOM | 489 | CB | ILE | 221 | 6.842 | 14.915 | 17.413 | 1.00 | 25.19 |
| ATOM | 490 | CG2 | ILE | 221 | 7.240 | 16.264 | 16.838 | 1.00 | 25.19 |
| ATOM | 491 | CG1 | ILE | 221 | 8.050 | 14.215 | 18.043 | 1.00 | 25.19 |
| ATOM | 492 | CD1 | ILE | 221 | 9.113 | 13.799 | 17.044 | 1.00 | 25.19 |
| ATOM | 493 | C | ILE | 221 | 5.240 | 13.700 | 18.892 | 1.00 | 31.43 |
| ATOM | 494 | O | ILE | 221 | 4.930 | 12.857 | 18.046 | 1.00 | 25.19 |
| ATOM | 495 | N | ILE | 222 | 5.129 | 13.474 | 20.198 | 1.00 | 24.41 |
| ATOM | 496 | CA | ILE | 222 | 4.720 | 12.162 | 20.687 | 1.00 | 24.41 |
| ATOM | 497 | CB | ILE | 222 | 5.189 | 11.916 | 22.147 | 1.00 | 27.10 |
| ATOM | 498 | CG2 | ILE | 222 | 4.221 | 12.545 | 23.145 | 1.00 | 27.10 |
| ATOM | 499 | CG1 | ILE | 222 | 5.302 | 10.410 | 22.400 | 1.00 | 27.10 |
| ATOM | 500 | CD1 | ILE | 222 | 6.062 | 10.053 | 23.646 | 1.00 | 27.10 |
| ATOM | 501 | C | ILE | 222 | 3.231 | 11.845 | 20.541 | 1.00 | 24.41 |
| ATOM | 502 | O | ILE | 222 | 2.864 | 10.691 | 20.307 | 1.00 | 27.10 |
| ATOM | 503 | N | THR | 223 | 2.378 | 12.861 | 20.642 | 1.00 | 33.16 |
| ATOM | 504 | CA | THR | 223 | 0.936 | 12.653 | 20.520 | 1.00 | 33.16 |
| ATOM | 505 | CB | THR | 223 | 0.150 | 13.974 | 20.721 | 1.00 | 36.84 |
| ATOM | 506 | OG1 | THR | 223 | 0.352 | 14.442 | 22.063 | 1.00 | 36.84 |
| ATOM | 507 | CG2 | THR | 223 | -1.346 | 13.764 | 20.484 | 1.00 | 36.84 |
| ATOM | 508 | C | THR | 223 | 0.536 | 11.954 | 19.212 | 1.00 | 33.16 |
| ATOM | 509 | O | THR | 223 | -0.156 | 10.932 | 19.242 | 1.00 | 36.84 |

FIG. 29A-11

| ATOM | 510 | N   | PRO | 224 | 0.968  | 12.482 | 18.048 | 1.00 | 18.75 |
|------|-----|-----|-----|-----|--------|--------|--------|------|-------|
| ATOM | 511 | CD  | PRO | 224 | 1.691  | 13.735 | 17.770 | 1.00 | 26.12 |
| ATOM | 512 | CA  | PRO | 224 | 0.590  | 11.805 | 16.802 | 1.00 | 18.75 |
| ATOM | 513 | CB  | PRO | 224 | 1.117  | 12.747 | 15.715 | 1.00 | 26.12 |
| ATOM | 514 | CG  | PRO | 224 | 2.221  | 13.497 | 16.386 | 1.00 | 26.12 |
| ATOM | 515 | C   | PRO | 224 | 1.200  | 10.402 | 16.701 | 1.00 | 18.75 |
| ATOM | 516 | O   | PRO | 224 | 0.606  | 9.502  | 16.101 | 1.00 | 26.12 |
| ATOM | 517 | N   | ALA | 225 | 2.368  | 10.213 | 17.312 | 1.00 | 12.19 |
| ATOM | 518 | CA  | ALA | 225 | 3.040  | 8.916  | 17.300 | 1.00 | 12.19 |
| ATOM | 519 | CB  | ALA | 225 | 4.415  | 9.021  | 17.943 | 1.00 | 20.39 |
| ATOM | 520 | C   | ALA | 225 | 2.187  | 7.881  | 18.030 | 1.00 | 12.19 |
| ATOM | 521 | O   | ALA | 225 | 1.998  | 6.764  | 17.545 | 1.00 | 20.39 |
| ATOM | 522 | N   | ILE | 226 | 1.645  | 8.271  | 19.179 | 1.00 | 14.61 |
| ATOM | 523 | CA  | ILE | 226 | 0.798  | 7.385  | 19.971 | 1.00 | 14.61 |
| ATOM | 524 | CB  | ILE | 226 | 0.450  | 8.025  | 21.332 | 1.00 | 16.10 |
| ATOM | 525 | CG2 | ILE | 226 | -0.508 | 7.132  | 22.108 | 1.00 | 16.10 |
| ATOM | 526 | CG1 | ILE | 226 | 1.729  | 8.293  | 22.132 | 1.00 | 16.10 |
| ATOM | 527 | CD1 | ILE | 226 | 1.509  | 9.113  | 23.387 | 1.00 | 16.10 |
| ATOM | 528 | C   | ILE | 226 | -0.499 | 7.094  | 19.213 | 1.00 | 14.61 |
| ATOM | 529 | O   | ILE | 226 | -0.986 | 5.961  | 19.200 | 1.00 | 16.10 |
| ATOM | 530 | N   | THR | 227 | -1.042 | 8.123  | 18.569 | 1.00 | 15.93 |
| ATOM | 531 | CA  | THR | 227 | -2.278 | 7.997  | 17.800 | 1.00 | 15.93 |
| ATOM | 532 | CB  | THR | 227 | -2.706 | 9.360  | 17.207 | 1.00 | 22.37 |
| ATOM | 533 | OG1 | THR | 227 | -2.890 | 10.301 | 18.273 | 1.00 | 22.37 |
| ATOM | 534 | CG2 | THR | 227 | -4.014 | 9.232  | 16.434 | 1.00 | 22.37 |
| ATOM | 535 | C   | THR | 227 | -2.149 | 6.964  | 16.680 | 1.00 | 15.93 |
| ATOM | 536 | O   | THR | 227 | -3.091 | 6.217  | 16.402 | 1.00 | 22.37 |
| ATOM | 537 | N   | ARG | 228 | -0.982 | 6.916  | 16.045 | 1.00 | 14.49 |
| ATOM | 538 | CA  | ARG | 228 | -0.750 | 5.956  | 14.975 | 1.00 | 14.49 |
| ATOM | 539 | CB  | ARG | 228 | 0.602  | 6.188  | 14.307 | 1.00 | 33.87 |
| ATOM | 540 | CG  | ARG | 228 | 0.701  | 7.482  | 13.540 | 1.00 | 33.87 |
| ATOM | 541 | CD  | ARG | 228 | 2.053  | 7.572  | 12.868 | 1.00 | 33.87 |
| ATOM | 542 | NE  | ARG | 228 | 2.510  | 8.952  | 12.793 | 1.00 | 33.87 |
| ATOM | 543 | CZ  | ARG | 228 | 3.551  | 9.431  | 13.469 | 1.00 | 33.87 |
| ATOM | 544 | NH1 | ARG | 228 | 4.256  | 8.634  | 14.270 | 1.00 | 33.87 |
| ATOM | 545 | NH2 | ARG | 228 | 3.864  | 10.716 | 13.374 | 1.00 | 33.87 |
| ATOM | 546 | C   | ARG | 228 | -0.813 | 4.531  | 15.516 | 1.00 | 14.49 |
| ATOM | 547 | O   | ARG | 228 | -1.309 | 3.632  | 14.839 | 1.00 | 33.87 |
| ATOM | 548 | N   | VAL | 229 | -0.313 | 4.327  | 16.735 | 1.00 | 14.80 |
| ATOM | 549 | CA  | VAL | 229 | -0.333 | 3.002  | 17.352 | 1.00 | 14.80 |
| ATOM | 550 | CB  | VAL | 229 | 0.456  | 2.979  | 18.683 | 1.00 | 13.78 |
| ATOM | 551 | CG1 | VAL | 229 | 0.339  | 1.612  | 19.350 | 1.00 | 13.78 |
| ATOM | 552 | CG2 | VAL | 229 | 1.915  | 3.312  | 18.430 | 1.00 | 13.78 |
| ATOM | 553 | C   | VAL | 229 | -1.788 | 2.602  | 17.591 | 1.00 | 14.80 |
| ATOM | 554 | O   | VAL | 229 | -2.185 | 1.465  | 17.323 | 1.00 | 13.78 |
| ATOM | 555 | N   | VAL | 230 | -2.588 | 3.561  | 18.047 | 1.00 | 9.33  |
| ATOM | 556 | CA  | VAL | 230 | -4.005 | 3.327  | 18.292 | 1.00 | 9.33  |
| ATOM | 557 | CB  | VAL | 230 | -4.679 | 4.564  | 18.909 | 1.00 | 16.07 |
| ATOM | 558 | CG1 | VAL | 230 | -6.168 | 4.319  | 19.076 | 1.00 | 16.07 |
| ATOM | 559 | CG2 | VAL | 230 | -4.038 | 4.896  | 20.253 | 1.00 | 16.07 |

FIG. 29A-12

| ATOM | 560 | C | VAL | 230 | -4.700 | 2.982 | 16.981 | 1.00 | 9.33 |
|---|---|---|---|---|---|---|---|---|---|
| ATOM | 561 | O | VAL | 230 | -5.504 | 2.049 | 16.929 | 1.00 | 16.07 |
| ATOM | 562 | N | ASP | 231 | -4.364 | 3.719 | 15.922 | 1.00 | 12.71 |
| ATOM | 563 | CA | ASP | 231 | -4.951 | 3.496 | 14.603 | 1.00 | 12.71 |
| ATOM | 564 | CB | ASP | 231 | -4.529 | 4.596 | 13.624 | 1.00 | 27.08 |
| ATOM | 565 | CG | ASP | 231 | -5.053 | 5.967 | 14.020 | 1.00 | 27.08 |
| ATOM | 566 | OD1 | ASP | 231 | -6.144 | 6.047 | 14.624 | 1.00 | 27.08 |
| ATOM | 567 | OD2 | ASP | 231 | -4.370 | 6.969 | 13.723 | 1.00 | 27.08 |
| ATOM | 568 | C | ASP | 231 | -4.570 | 2.132 | 14.049 | 1.00 | 12.71 |
| ATOM | 569 | O | ASP | 231 | -5.413 | 1.436 | 13.483 | 1.00 | 27.08 |
| ATOM | 570 | N | PHE | 232 | -3.305 | 1.755 | 14.215 | 1.00 | 14.33 |
| ATOM | 571 | CA | PHE | 232 | -2.823 | 0.461 | 13.748 | 1.00 | 14.33 |
| ATOM | 572 | CB | PHE | 232 | -1.351 | 0.257 | 14.134 | 1.00 | 16.35 |
| ATOM | 573 | CG | PHE | 232 | -0.911 | -1.184 | 14.097 | 1.00 | 16.35 |
| ATOM | 574 | CD1 | PHE | 232 | -0.789 | -1.862 | 12.887 | 1.00 | 16.35 |
| ATOM | 575 | CD2 | PHE | 232 | -0.661 | -1.879 | 15.280 | 1.00 | 16.35 |
| ATOM | 576 | CE1 | PHE | 232 | -0.430 | -3.208 | 12.851 | 1.00 | 16.35 |
| ATOM | 577 | CE2 | PHE | 232 | -0.302 | -3.224 | 15.255 | 1.00 | 16.35 |
| ATOM | 578 | CZ | PHE | 232 | -0.187 | -3.890 | 14.038 | 1.00 | 16.35 |
| ATOM | 579 | C | PHE | 232 | -3.670 | -0.642 | 14.368 | 1.00 | 14.33 |
| ATOM | 580 | O | PHE | 232 | -4.226 | -1.482 | 13.661 | 1.00 | 16.35 |
| ATOM | 581 | N | ALA | 233 | -3.769 | -0.619 | 15.695 | 1.00 | 15.30 |
| ATOM | 582 | CA | ALA | 233 | -4.537 | -1.607 | 16.444 | 1.00 | 15.30 |
| ATOM | 583 | CB | ALA | 233 | -4.413 | -1.335 | 17.938 | 1.00 | 12.88 |
| ATOM | 584 | C | ALA | 233 | -6.005 | -1.609 | 16.030 | 1.00 | 15.30 |
| ATOM | 585 | O | ALA | 233 | -6.627 | -2.663 | 15.902 | 1.00 | 12.88 |
| ATOM | 586 | N | LYS | 234 | -6.542 | -0.419 | 15.795 | 1.00 | 25.69 |
| ATOM | 587 | CA | LYS | 234 | -7.933 | -0.256 | 15.401 | 1.00 | 25.69 |
| ATOM | 588 | CB | LYS | 234 | -8.270 | 1.234 | 15.318 | 1.00 | 45.91 |
| ATOM | 589 | CG | LYS | 234 | -9.574 | 1.595 | 15.979 | 1.00 | 45.91 |
| ATOM | 590 | CD | LYS | 234 | -9.535 | 1.268 | 17.463 | 1.00 | 45.91 |
| ATOM | 591 | CE | LYS | 234 | -10.938 | 1.047 | 18.006 | 1.00 | 45.91 |
| ATOM | 592 | NZ | LYS | 234 | -11.605 | -0.106 | 17.327 | 1.00 | 45.91 |
| ATOM | 593 | C | LYS | 234 | -8.240 | -0.931 | 14.067 | 1.00 | 25.69 |
| ATOM | 594 | O | LYS | 234 | -9.368 | -1.368 | 13.827 | 1.00 | 45.91 |
| ATOM | 595 | N | LYS | 235 | -7.234 | -1.019 | 13.204 | 1.00 | 17.44 |
| ATOM | 596 | CA | LYS | 235 | -7.406 | -1.627 | 11.892 | 1.00 | 17.44 |
| ATOM | 597 | CB | LYS | 235 | -6.459 | -0.975 | 10.884 | 1.00 | 26.26 |
| ATOM | 598 | CG | LYS | 235 | -6.757 | 0.499 | 10.669 | 1.00 | 26.26 |
| ATOM | 599 | CD | LYS | 235 | -5.785 | 1.141 | 9.706 | 1.00 | 26.26 |
| ATOM | 600 | CE | LYS | 235 | -6.154 | 2.593 | 9.460 | 1.00 | 26.26 |
| ATOM | 601 | NZ | LYS | 235 | -5.231 | 3.230 | 8.484 | 1.00 | 26.26 |
| ATOM | 602 | C | LYS | 235 | -7.258 | -3.146 | 11.875 | 1.00 | 17.44 |
| ATOM | 603 | O | LYS | 235 | -7.365 | -3.773 | 10.817 | 1.00 | 26.26 |
| ATOM | 604 | N | LEU | 236 | -7.015 | -3.738 | 13.040 | 1.00 | 21.99 |
| ATOM | 605 | CA | LEU | 236 | -6.880 | -5.187 | 13.144 | 1.00 | 21.99 |
| ATOM | 606 | CB | LEU | 236 | -5.792 | -5.564 | 14.154 | 1.00 | 25.38 |
| ATOM | 607 | CG | LEU | 236 | -4.362 | -5.127 | 13.818 | 1.00 | 25.38 |
| ATOM | 608 | CD1 | LEU | 236 | -3.415 | -5.555 | 14.929 | 1.00 | 25.38 |
| ATOM | 609 | CD2 | LEU | 236 | -3.931 | -5.725 | 12.491 | 1.00 | 25.38 |

FIG. 29A-13

| ATOM | 610 | C   | LEU | 236 | -8.219  | -5.796  | 13.556 | 1.00 | 21.99 |
| ---- | --- | --- | --- | --- | ------- | ------- | ------ | ---- | ----- |
| ATOM | 611 | O   | LEU | 236 | -8.821  | -5.386  | 14.553 | 1.00 | 25.38 |
| ATOM | 612 | N   | PRO | 237 | -8.682  | -6.819  | 12.817 | 1.00 | 34.89 |
| ATOM | 613 | CD  | PRO | 237 | -7.936  | -7.474  | 11.730 | 1.00 | 42.99 |
| ATOM | 614 | CA  | PRO | 237 | -9.953  | -7.513  | 13.071 | 1.00 | 34.89 |
| ATOM | 615 | CB  | PRO | 237 | -9.911  | -8.687  | 12.084 | 1.00 | 42.99 |
| ATOM | 616 | CG  | PRO | 237 | -8.433  | -8.887  | 11.816 | 1.00 | 42.99 |
| ATOM | 617 | C   | PRO | 237 | -10.184 | -7.986  | 14.513 | 1.00 | 34.89 |
| ATOM | 618 | O   | PRO | 237 | -11.142 | -7.563  | 15.159 | 1.00 | 42.99 |
| ATOM | 619 | N   | MET | 238 | -9.301  | -8.843  | 15.021 | 1.00 | 40.45 |
| ATOM | 620 | CA  | MET | 238 | -9.433  | -9.364  | 16.382 | 1.00 | 40.45 |
| ATOM | 621 | CB  | MET | 238 | -8.360  | -10.423 | 16.671 | 1.00 | 59.70 |
| ATOM | 622 | CG  | MET | 238 | -8.689  | -11.839 | 16.195 | 1.00 | 59.70 |
| ATOM | 623 | SD  | MET | 238 | -8.013  | -12.275 | 14.573 | 1.00 | 59.70 |
| ATOM | 624 | CE  | MET | 238 | -6.482  | -13.074 | 15.032 | 1.00 | 59.70 |
| ATOM | 625 | C   | MET | 238 | -9.395  | -8.305  | 17.486 | 1.00 | 40.45 |
| ATOM | 626 | O   | MET | 238 | -9.801  | -8.574  | 18.617 | 1.00 | 59.70 |
| ATOM | 627 | N   | PHE | 239 | -8.928  | -7.103  | 17.160 | 1.00 | 33.70 |
| ATOM | 628 | CA  | PHE | 239 | -8.829  | -6.037  | 18.152 | 1.00 | 33.70 |
| ATOM | 629 | CB  | PHE | 239 | -7.651  | -5.113  | 17.829 | 1.00 | 22.27 |
| ATOM | 630 | CG  | PHE | 239 | -7.386  | -4.079  | 18.885 | 1.00 | 22.27 |
| ATOM | 631 | CD1 | PHE | 239 | -6.602  | -4.385  | 19.990 | 1.00 | 22.27 |
| ATOM | 632 | CD2 | PHE | 239 | -7.926  | -2.802  | 18.778 | 1.00 | 22.27 |
| ATOM | 633 | CE1 | PHE | 239 | -6.358  | -3.436  | 20.974 | 1.00 | 22.27 |
| ATOM | 634 | CE2 | PHE | 239 | -7.688  | -1.846  | 19.757 | 1.00 | 22.27 |
| ATOM | 635 | CZ  | PHE | 239 | -6.901  | -2.163  | 20.857 | 1.00 | 22.27 |
| ATOM | 636 | C   | PHE | 239 | -10.103 | -5.213  | 18.329 | 1.00 | 33.70 |
| ATOM | 637 | O   | PHE | 239 | -10.594 | -5.059  | 19.446 | 1.00 | 22.27 |
| ATOM | 638 | N   | SER | 240 | -10.629 | -4.679  | 17.232 | 1.00 | 23.42 |
| ATOM | 639 | CA  | SER | 240 | -11.837 | -3.857  | 17.278 | 1.00 | 23.42 |
| ATOM | 640 | CB  | SER | 240 | -12.175 | -3.352  | 15.884 | 1.00 | 26.21 |
| ATOM | 641 | C   | SER | 240 | -13.046 | -4.562  | 17.899 | 1.00 | 23.42 |
| ATOM | 642 | O   | SER | 240 | -13.976 | -3.909  | 18.369 | 1.00 | 26.21 |
| ATOM | 643 | N   | GLU | 241 | -13.028 | -5.891  | 17.893 | 1.00 | 26.54 |
| ATOM | 644 | CA  | GLU | 241 | -14.116 | -6.695  | 18.450 | 1.00 | 26.54 |
| ATOM | 645 | CB  | GLU | 241 | -14.007 | -8.139  | 17.957 | 1.00 | 67.32 |
| ATOM | 646 | CG  | GLU | 241 | -14.241 | -8.322  | 16.467 | 1.00 | 67.32 |
| ATOM | 647 | CD  | GLU | 241 | -13.979 | -9.748  | 16.001 | 1.00 | 67.32 |
| ATOM | 648 | OE1 | GLU | 241 | -14.161 | -10.691 | 16.803 | 1.00 | 67.32 |
| ATOM | 649 | OE2 | GLU | 241 | -13.584 | -9.924  | 14.828 | 1.00 | 67.32 |
| ATOM | 650 | C   | GLU | 241 | -14.137 | -6.706  | 19.975 | 1.00 | 26.54 |
| ATOM | 651 | O   | GLU | 241 | -15.182 | -6.924  | 20.589 | 1.00 | 67.32 |
| ATOM | 652 | N   | LEU | 242 | -12.972 | -6.506  | 20.579 | 1.00 | 26.16 |
| ATOM | 653 | CA  | LEU | 242 | -12.835 | -6.514  | 22.030 | 1.00 | 26.16 |
| ATOM | 654 | CB  | LEU | 242 | -11.352 | -6.473  | 22.412 | 1.00 | 19.79 |
| ATOM | 655 | CG  | LEU | 242 | -10.461 | -7.627  | 21.956 | 1.00 | 19.79 |
| ATOM | 656 | CD1 | LEU | 242 | -9.014  | -7.309  | 22.264 | 1.00 | 19.79 |
| ATOM | 657 | CD2 | LEU | 242 | -10.888 | -8.912  | 22.640 | 1.00 | 19.79 |
| ATOM | 658 | C   | LEU | 242 | -13.547 | -5.351  | 22.711 | 1.00 | 26.16 |
| ATOM | 659 | O   | LEU | 242 | -13.738 | -4.290  | 22.115 | 1.00 | 19.79 |

FIG. 29A-14

| ATOM | 660 | N   | PRO | 243 | -13.980 | -5.547 | 23.968 | 1.00 | 17.98 |
|------|-----|-----|-----|-----|---------|--------|--------|------|-------|
| ATOM | 661 | CD  | PRO | 243 | -13.996 | -6.785 | 24.764 | 1.00 | 19.17 |
| ATOM | 662 | CA  | PRO | 243 | -14.657 | -4.454 | 24.671 | 1.00 | 17.98 |
| ATOM | 663 | CB  | PRO | 243 | -15.095 | -5.105 | 25.988 | 1.00 | 19.17 |
| ATOM | 664 | CG  | PRO | 243 | -14.155 | -6.263 | 26.161 | 1.00 | 19.17 |
| ATOM | 665 | C   | PRO | 243 | -13.652 | -3.323 | 24.898 | 1.00 | 17.98 |
| ATOM | 666 | O   | PRO | 243 | -12.458 | -3.572 | 25.081 | 1.00 | 19.17 |
| ATOM | 667 | N   | CYS | 244 | -14.142 | -2.088 | 24.880 | 1.00 | 20.08 |
| ATOM | 668 | CA  | CYS | 244 | -13.310 | -0.900 | 25.059 | 1.00 | 20.08 |
| ATOM | 669 | CB  | CYS | 244 | -14.194 | 0.329  | 25.278 | 1.00 | 61.80 |
| ATOM | 670 | SG  | CYS | 244 | -13.674 | 1.784  | 24.340 | 1.00 | 61.80 |
| ATOM | 671 | C   | CYS | 244 | -12.286 | -1.017 | 26.189 | 1.00 | 20.08 |
| ATOM | 672 | O   | CYS | 244 | -11.141 | -0.590 | 26.040 | 1.00 | 61.80 |
| ATOM | 673 | N   | GLU | 245 | -12.691 | -1.630 | 27.299 | 1.00 | 21.05 |
| ATOM | 674 | CA  | GLU | 245 | -11.814 | -1.811 | 28.454 | 1.00 | 21.05 |
| ATOM | 675 | CB  | GLU | 245 | -12.541 | -2.560 | 29.578 | 1.00 | 40.41 |
| ATOM | 676 | CG  | GLU | 245 | -13.510 | -1.705 | 30.393 | 1.00 | 40.41 |
| ATOM | 677 | CD  | GLU | 245 | -14.953 | -1.773 | 29.910 | 1.00 | 40.41 |
| ATOM | 678 | OE1 | GLU | 245 | -15.854 | -1.761 | 30.775 | 1.00 | 40.41 |
| ATOM | 679 | OE2 | GLU | 245 | -15.197 | -1.824 | 28.683 | 1.00 | 40.41 |
| ATOM | 680 | C   | GLU | 245 | -10.541 | -2.558 | 28.084 | 1.00 | 21.05 |
| ATOM | 681 | O   | GLU | 245 | -9.439  | -2.138 | 28.440 | 1.00 | 40.41 |
| ATOM | 682 | N   | ASP | 246 | -10.698 | -3.654 | 27.351 | 1.00 | 17.22 |
| ATOM | 683 | CA  | ASP | 246 | -9.564  | -4.463 | 26.924 | 1.00 | 17.22 |
| ATOM | 684 | CB  | ASP | 246 | -10.044 | -5.774 | 26.303 | 1.00 | 30.41 |
| ATOM | 685 | CG  | ASP | 246 | -10.634 | -6.727 | 27.327 | 1.00 | 30.41 |
| ATOM | 686 | OD1 | ASP | 246 | -10.755 | -6.349 | 28.512 | 1.00 | 30.41 |
| ATOM | 687 | OD2 | ASP | 246 | -10.975 | -7.864 | 26.946 | 1.00 | 30.41 |
| ATOM | 688 | C   | ASP | 246 | -8.693  | -3.705 | 25.936 | 1.00 | 17.22 |
| ATOM | 689 | O   | ASP | 246 | -7.467  | -3.713 | 26.050 | 1.00 | 30.41 |
| ATOM | 690 | N   | GLN | 247 | -9.332  | -3.045 | 24.973 | 1.00 | 17.12 |
| ATOM | 691 | CA  | GLN | 247 | -8.615  | -2.272 | 23.966 | 1.00 | 17.12 |
| ATOM | 692 | CB  | GLN | 247 | -9.594  | -1.494 | 23.088 | 1.00 | 16.72 |
| ATOM | 693 | CG  | GLN | 247 | -10.504 | -2.365 | 22.242 | 1.00 | 16.72 |
| ATOM | 694 | CD  | GLN | 247 | -11.352 | -1.553 | 21.290 | 1.00 | 16.72 |
| ATOM | 695 | OE1 | GLN | 247 | -10.925 | -0.515 | 20.790 | 1.00 | 16.72 |
| ATOM | 696 | NE2 | GLN | 247 | -12.560 | -2.018 | 21.033 | 1.00 | 16.72 |
| ATOM | 697 | C   | GLN | 247 | -7.650  | -1.303 | 24.637 | 1.00 | 17.12 |
| ATOM | 698 | O   | GLN | 247 | -6.476  | -1.228 | 24.273 | 1.00 | 16.72 |
| ATOM | 699 | N   | ILE | 248 | -8.152  | -0.591 | 25.640 | 1.00 | 19.19 |
| ATOM | 700 | CA  | ILE | 248 | -7.358  | 0.377  | 26.387 | 1.00 | 19.19 |
| ATOM | 701 | CB  | ILE | 248 | -8.238  | 1.137  | 27.410 | 1.00 | 24.32 |
| ATOM | 702 | CG2 | ILE | 248 | -7.385  | 2.055  | 28.282 | 1.00 | 24.32 |
| ATOM | 703 | CG1 | ILE | 248 | -9.312  | 1.942  | 26.668 | 1.00 | 24.32 |
| ATOM | 704 | CD1 | ILE | 248 | -10.327 | 2.618  | 27.573 | 1.00 | 24.32 |
| ATOM | 705 | C   | ILE | 248 | -6.180  | -0.297 | 27.093 | 1.00 | 19.19 |
| ATOM | 706 | O   | ILE | 248 | -5.035  | 0.131  | 26.943 | 1.00 | 24.32 |
| ATOM | 707 | N   | ILE | 249 | -6.457  | -1.367 | 27.830 | 1.00 | 12.09 |
| ATOM | 708 | CA  | ILE | 249 | -5.409  | -2.090 | 28.547 | 1.00 | 12.09 |
| ATOM | 709 | CB  | ILE | 249 | -5.996  | -3.295 | 29.322 | 1.00 | 30.01 |

FIG. 29A-15

| ATOM | 710 | CG2 | ILE | 249 | -4.884 | -4.168 | 29.885 | 1.00 | 30.01 |
|---|---|---|---|---|---|---|---|---|---|
| ATOM | 711 | CG1 | ILE | 249 | -6.899 | -2.794 | 30.451 | 1.00 | 30.01 |
| ATOM | 712 | CD1 | ILE | 249 | -7.598 | -3.893 | 31.215 | 1.00 | 30.01 |
| ATOM | 713 | C | ILE | 249 | -4.299 | -2.561 | 27.602 | 1.00 | 12.09 |
| ATOM | 714 | O | ILE | 249 | -3.115 | -2.339 | 27.866 | 1.00 | 30.01 |
| ATOM | 715 | N | LEU | 250 | -4.691 | -3.168 | 26.486 | 1.00 | 20.87 |
| ATOM | 716 | CA | LEU | 250 | -3.740 | -3.669 | 25.498 | 1.00 | 20.87 |
| ATOM | 717 | CB | LEU | 250 | -4.474 | -4.410 | 24.376 | 1.00 | 15.15 |
| ATOM | 718 | CG | LEU | 250 | -5.252 | -5.669 | 24.761 | 1.00 | 15.15 |
| ATOM | 719 | CD1 | LEU | 250 | -5.907 | -6.256 | 23.533 | 1.00 | 15.15 |
| ATOM | 720 | CD2 | LEU | 250 | -4.325 | -6.686 | 25.400 | 1.00 | 15.15 |
| ATOM | 721 | C | LEU | 250 | -2.900 | -2.548 | 24.902 | 1.00 | 20.87 |
| ATOM | 722 | O | LEU | 250 | -1.680 | -2.667 | 24.792 | 1.00 | 15.15 |
| ATOM | 723 | N | LEU | 251 | -3.559 | -1.455 | 24.532 | 1.00 | 9.31 |
| ATOM | 724 | CA | LEU | 251 | -2.887 | -0.301 | 23.945 | 1.00 | 9.31 |
| ATOM | 725 | CB | LEU | 251 | -3.920 | 0.760 | 23.553 | 1.00 | 19.90 |
| ATOM | 726 | CG | LEU | 251 | -4.075 | 1.127 | 22.073 | 1.00 | 19.90 |
| ATOM | 727 | CD1 | LEU | 251 | -3.281 | 0.190 | 21.180 | 1.00 | 19.90 |
| ATOM | 728 | CD2 | LEU | 251 | -5.550 | 1.113 | 21.699 | 1.00 | 19.90 |
| ATOM | 729 | C | LEU | 251 | -1.851 | 0.307 | 24.887 | 1.00 | 9.31 |
| ATOM | 730 | O | LEU | 251 | -0.699 | 0.521 | 24.507 | 1.00 | 19.90 |
| ATOM | 731 | N | LYS | 252 | -2.253 | 0.545 | 26.127 | 1.00 | 18.83 |
| ATOM | 732 | CA | LYS | 252 | -1.362 | 1.132 | 27.114 | 1.00 | 18.83 |
| ATOM | 733 | CB | LYS | 252 | -2.138 | 1.455 | 28.395 | 1.00 | 42.69 |
| ATOM | 734 | CG | LYS | 252 | -3.395 | 2.274 | 28.130 | 1.00 | 42.69 |
| ATOM | 735 | CD | LYS | 252 | -3.588 | 3.412 | 29.115 | 1.00 | 42.69 |
| ATOM | 736 | CE | LYS | 252 | -3.998 | 2.934 | 30.493 | 1.00 | 42.69 |
| ATOM | 737 | NZ | LYS | 252 | -4.300 | 4.109 | 31.361 | 1.00 | 42.69 |
| ATOM | 738 | C | LYS | 252 | -0.171 | 0.222 | 27.408 | 1.00 | 18.83 |
| ATOM | 739 | O | LYS | 252 | 0.942 | 0.700 | 27.646 | 1.00 | 42.69 |
| ATOM | 740 | N | GLY | 253 | -0.392 | -1.086 | 27.328 | 1.00 | 16.16 |
| ATOM | 741 | CA | GLY | 253 | 0.676 | -2.031 | 27.595 | 1.00 | 16.16 |
| ATOM | 742 | C | GLY | 253 | 1.688 | -2.232 | 26.479 | 1.00 | 16.16 |
| ATOM | 743 | O | GLY | 253 | 2.836 | -2.587 | 26.747 | 1.00 | 34.57 |
| ATOM | 744 | N | CYS | 254 | 1.286 | -1.999 | 25.233 | 1.00 | 21.81 |
| ATOM | 745 | CA | CYS | 254 | 2.194 | -2.203 | 24.108 | 1.00 | 21.81 |
| ATOM | 746 | CB | CYS | 254 | 1.563 | -3.151 | 23.093 | 1.00 | 23.60 |
| ATOM | 747 | SG | CYS | 254 | 0.211 | -2.387 | 22.179 | 1.00 | 23.60 |
| ATOM | 748 | C | CYS | 254 | 2.616 | -0.935 | 23.380 | 1.00 | 21.81 |
| ATOM | 749 | O | CYS | 254 | 3.499 | -0.983 | 22.521 | 1.00 | 23.60 |
| ATOM | 750 | N | CYS | 255 | 2.004 | 0.193 | 23.724 | 1.00 | 14.98 |
| ATOM | 751 | CA | CYS | 255 | 2.309 | 1.461 | 23.066 | 1.00 | 14.98 |
| ATOM | 752 | CB | CYS | 255 | 1.611 | 2.616 | 23.781 | 1.00 | 24.32 |
| ATOM | 753 | SG | CYS | 255 | 1.602 | 4.153 | 22.841 | 1.00 | 24.32 |
| ATOM | 754 | C | CYS | 255 | 3.804 | 1.750 | 22.922 | 1.00 | 14.98 |
| ATOM | 755 | O | CYS | 255 | 4.305 | 1.895 | 21.805 | 1.00 | 24.32 |
| ATOM | 756 | N | MET | 256 | 4.525 | 1.777 | 24.037 | 1.00 | 13.77 |
| ATOM | 757 | CA | MET | 256 | 5.959 | 2.056 | 24.003 | 1.00 | 13.77 |
| ATOM | 758 | CB | MET | 256 | 6.515 | 2.218 | 25.423 | 1.00 | 19.23 |
| ATOM | 759 | CG | MET | 256 | 7.988 | 2.607 | 25.477 | 1.00 | 19.23 |

FIG. 29A-16

| ATOM | 760 | SD  | MET | 256 | 8.344  | 4.132  | 24.571 | 1.00 | 19.23 |
|------|-----|-----|-----|-----|--------|--------|--------|------|-------|
| ATOM | 761 | CE  | MET | 256 | 10.127 | 4.254  | 24.782 | 1.00 | 19.23 |
| ATOM | 762 | C   | MET | 256 | 6.734  | 0.978  | 23.246 | 1.00 | 13.77 |
| ATOM | 763 | O   | MET | 256 | 7.672  | 1.284  | 22.516 | 1.00 | 19.23 |
| ATOM | 764 | N   | GLU | 257 | 6.316  | -0.275 | 23.400 | 1.00 | 12.57 |
| ATOM | 765 | CA  | GLU | 257 | 6.971  | -1.397 | 22.730 | 1.00 | 12.57 |
| ATOM | 766 | CB  | GLU | 257 | 6.342  | -2.716 | 23.182 | 1.00 | 31.54 |
| ATOM | 767 | CG  | GLU | 257 | 6.497  | -2.982 | 24.677 | 1.00 | 31.54 |
| ATOM | 768 | CD  | GLU | 257 | 5.720  | -4.196 | 25.167 | 1.00 | 31.54 |
| ATOM | 769 | OE1 | GLU | 257 | 5.220  | -4.983 | 24.334 | 1.00 | 31.54 |
| ATOM | 770 | OE2 | GLU | 257 | 5.607  | -4.361 | 26.400 | 1.00 | 31.54 |
| ATOM | 771 | C   | GLU | 257 | 6.889  | -1.254 | 21.211 | 1.00 | 12.57 |
| ATOM | 772 | O   | GLU | 257 | 7.881  | -1.452 | 20.505 | 1.00 | 31.54 |
| ATOM | 773 | N   | ILE | 258 | 5.712  | -0.881 | 20.717 | 1.00 | 17.89 |
| ATOM | 774 | CA  | ILE | 258 | 5.508  | -0.692 | 19.288 | 1.00 | 17.89 |
| ATOM | 775 | CB  | ILE | 258 | 4.001  | -0.555 | 18.946 | 1.00 | 15.57 |
| ATOM | 776 | CG2 | ILE | 258 | 3.813  | -0.129 | 17.493 | 1.00 | 15.57 |
| ATOM | 777 | CG1 | ILE | 258 | 3.288  | -1.886 | 19.211 | 1.00 | 15.57 |
| ATOM | 778 | CD1 | ILE | 258 | 1.798  | -1.872 | 18.922 | 1.00 | 15.57 |
| ATOM | 779 | C   | ILE | 258 | 6.289  | 0.535  | 18.811 | 1.00 | 17.89 |
| ATOM | 780 | O   | ILE | 258 | 7.000  | 0.468  | 17.805 | 1.00 | 15.57 |
| ATOM | 781 | N   | MET | 259 | 6.196  | 1.636  | 19.556 | 1.00 | 11.23 |
| ATOM | 782 | CA  | MET | 259 | 6.907  | 2.861  | 19.201 | 1.00 | 11.23 |
| ATOM | 783 | CB  | MET | 259 | 6.568  | 3.995  | 20.175 | 1.00 | 22.19 |
| ATOM | 784 | CG  | MET | 259 | 5.112  | 4.439  | 20.117 | 1.00 | 22.19 |
| ATOM | 785 | SD  | MET | 259 | 4.828  | 6.033  | 20.915 | 1.00 | 22.19 |
| ATOM | 786 | CE  | MET | 259 | 5.038  | 5.606  | 22.621 | 1.00 | 22.19 |
| ATOM | 787 | C   | MET | 259 | 8.415  | 2.637  | 19.131 | 1.00 | 11.23 |
| ATOM | 788 | O   | MET | 259 | 9.060  | 3.008  | 18.145 | 1.00 | 22.19 |
| ATOM | 789 | N   | SER | 260 | 8.974  | 1.994  | 20.153 | 1.00 | 8.59  |
| ATOM | 790 | CA  | SER | 260 | 10.408 | 1.706  | 20.195 | 1.00 | 8.59  |
| ATOM | 791 | CB  | SER | 260 | 10.763 | 0.939  | 21.472 | 1.00 | 23.39 |
| ATOM | 792 | OG  | SER | 260 | 10.430 | 1.685  | 22.623 | 1.00 | 23.39 |
| ATOM | 793 | C   | SER | 260 | 10.793 | 0.864  | 18.977 | 1.00 | 8.59  |
| ATOM | 794 | O   | SER | 260 | 11.824 | 1.100  | 18.350 | 1.00 | 23.39 |
| ATOM | 795 | N   | LEU | 261 | 9.952  | -0.111 | 18.644 | 1.00 | 13.26 |
| ATOM | 796 | CA  | LEU | 261 | 10.194 | -0.992 | 17.507 | 1.00 | 13.26 |
| ATOM | 797 | CB  | LEU | 261 | 9.076  | -2.035 | 17.401 | 1.00 | 14.32 |
| ATOM | 798 | CG  | LEU | 261 | 9.019  | -2.894 | 16.134 | 1.00 | 14.32 |
| ATOM | 799 | CD1 | LEU | 261 | 10.278 | -3.733 | 15.999 | 1.00 | 14.32 |
| ATOM | 800 | CD2 | LEU | 261 | 7.785  | -3.772 | 16.174 | 1.00 | 14.32 |
| ATOM | 801 | C   | LEU | 261 | 10.276 | -0.170 | 16.220 | 1.00 | 13.26 |
| ATOM | 802 | O   | LEU | 261 | 11.213 | -0.313 | 15.432 | 1.00 | 14.32 |
| ATOM | 803 | N   | ARG | 262 | 9.330  | 0.744  | 16.043 | 1.00 | 10.57 |
| ATOM | 804 | CA  | ARG | 262 | 9.278  | 1.598  | 14.861 | 1.00 | 10.57 |
| ATOM | 805 | CB  | ARG | 262 | 8.018  | 2.454  | 14.917 | 1.00 | 16.08 |
| ATOM | 806 | CG  | ARG | 262 | 6.755  | 1.647  | 14.728 | 1.00 | 16.08 |
| ATOM | 807 | CD  | ARG | 262 | 5.540  | 2.525  | 14.614 | 1.00 | 16.08 |
| ATOM | 808 | NE  | ARG | 262 | 4.418  | 1.765  | 14.076 | 1.00 | 16.08 |
| ATOM | 809 | CZ  | ARG | 262 | 3.260  | 2.289  | 13.689 | 1.00 | 16.08 |

FIG. 29A-17

| ATOM | 810 | NH1 | ARG | 262 | 3.050 | 3.596 | 13.780 | 1.00 | 16.08 |
| --- | --- | --- | --- | --- | --- | --- | --- | --- | --- |
| ATOM | 811 | NH2 | ARG | 262 | 2.322 | 1.497 | 13.183 | 1.00 | 16.08 |
| ATOM | 812 | C | ARG | 262 | 10.530 | 2.471 | 14.704 | 1.00 | 10.57 |
| ATOM | 813 | O | ARG | 262 | 11.038 | 2.649 | 13.589 | 1.00 | 16.08 |
| ATOM | 814 | N | ALA | 263 | 11.016 | 3.014 | 15.820 | 1.00 | 13.37 |
| ATOM | 815 | CA | ALA | 263 | 12.221 | 3.842 | 15.831 | 1.00 | 13.37 |
| ATOM | 816 | CB | ALA | 263 | 12.363 | 4.516 | 17.172 | 1.00 | 17.12 |
| ATOM | 817 | C | ALA | 263 | 13.443 | 2.964 | 15.561 | 1.00 | 13.37 |
| ATOM | 818 | O | ALA | 263 | 14.313 | 3.316 | 14.762 | 1.00 | 17.12 |
| ATOM | 819 | N | ALA | 264 | 13.474 | 1.802 | 16.207 | 1.00 | 16.55 |
| ATOM | 820 | CA | ALA | 264 | 14.574 | 0.855 | 16.072 | 1.00 | 16.55 |
| ATOM | 821 | CB | ALA | 264 | 14.375 | -0.327 | 17.019 | 1.00 | 24.62 |
| ATOM | 822 | C | ALA | 264 | 14.770 | 0.364 | 14.642 | 1.00 | 16.55 |
| ATOM | 823 | O | ALA | 264 | 15.904 | 0.244 | 14.169 | 1.00 | 24.62 |
| ATOM | 824 | N | VAL | 265 | 13.670 | 0.073 | 13.955 | 1.00 | 22.25 |
| ATOM | 825 | CA | VAL | 265 | 13.754 | -0.401 | 12.583 | 1.00 | 22.25 |
| ATOM | 826 | CB | VAL | 265 | 12.428 | -1.038 | 12.086 | 1.00 | 25.31 |
| ATOM | 827 | CG1 | VAL | 265 | 12.079 | -2.239 | 12.936 | 1.00 | 25.31 |
| ATOM | 828 | CG2 | VAL | 265 | 11.302 | -0.030 | 12.091 | 1.00 | 25.31 |
| ATOM | 829 | C | VAL | 265 | 14.208 | 0.707 | 11.639 | 1.00 | 22.25 |
| ATOM | 830 | O | VAL | 265 | 14.615 | 0.434 | 10.513 | 1.00 | 25.31 |
| ATOM | 831 | N | ARG | 266 | 14.124 | 1.955 | 12.092 | 1.00 | 26.45 |
| ATOM | 832 | CA | ARG | 266 | 14.567 | 3.086 | 11.283 | 1.00 | 26.45 |
| ATOM | 833 | CB | ARG | 266 | 13.596 | 4.261 | 11.399 | 1.00 | 38.04 |
| ATOM | 834 | CG | ARG | 266 | 12.232 | 4.019 | 10.807 | 1.00 | 38.04 |
| ATOM | 835 | CD | ARG | 266 | 11.503 | 5.339 | 10.651 | 1.00 | 38.04 |
| ATOM | 836 | NE | ARG | 266 | 10.074 | 5.216 | 10.925 | 1.00 | 38.04 |
| ATOM | 837 | CZ | ARG | 266 | 9.504 | 5.551 | 12.079 | 1.00 | 38.04 |
| ATOM | 838 | NH1 | ARG | 266 | 10.237 | 6.038 | 13.075 | 1.00 | 38.04 |
| ATOM | 839 | NH2 | ARG | 266 | 8.196 | 5.411 | 12.240 | 1.00 | 38.04 |
| ATOM | 840 | C | ARG | 266 | 15.957 | 3.531 | 11.729 | 1.00 | 26.45 |
| ATOM | 841 | O | ARG | 266 | 16.296 | 4.717 | 11.660 | 1.00 | 38.04 |
| ATOM | 842 | N | TYR | 267 | 16.733 | 2.590 | 12.251 | 1.00 | 24.87 |
| ATOM | 843 | CA | TYR | 267 | 18.083 | 2.888 | 12.700 | 1.00 | 24.87 |
| ATOM | 844 | CB | TYR | 267 | 18.592 | 1.788 | 13.639 | 1.00 | 25.84 |
| ATOM | 845 | CG | TYR | 267 | 20.073 | 1.865 | 13.931 | 1.00 | 25.84 |
| ATOM | 846 | CD1 | TYR | 267 | 20.579 | 2.789 | 14.844 | 1.00 | 25.84 |
| ATOM | 847 | CE1 | TYR | 267 | 21.940 | 2.865 | 15.103 | 1.00 | 25.84 |
| ATOM | 848 | CD2 | TYR | 267 | 20.971 | 1.017 | 13.284 | 1.00 | 25.84 |
| ATOM | 849 | CE2 | TYR | 267 | 22.331 | 1.085 | 13.536 | 1.00 | 25.84 |
| ATOM | 850 | CZ | TYR | 267 | 22.810 | 2.011 | 14.444 | 1.00 | 25.84 |
| ATOM | 851 | OH | TYR | 267 | 24.162 | 2.078 | 14.683 | 1.00 | 25.84 |
| ATOM | 852 | C | TYR | 267 | 18.999 | 3.009 | 11.488 | 1.00 | 24.87 |
| ATOM | 853 | O | TYR | 267 | 19.019 | 2.130 | 10.625 | 1.00 | 25.84 |
| ATOM | 854 | N | ASP | 268 | 19.751 | 4.102 | 11.423 | 1.00 | 28.13 |
| ATOM | 855 | CA | ASP | 268 | 20.666 | 4.320 | 10.313 | 1.00 | 28.13 |
| ATOM | 856 | CB | ASP | 268 | 20.524 | 5.744 | 9.773 | 1.00 | 51.63 |
| ATOM | 857 | CG | ASP | 268 | 21.339 | 5.973 | 8.517 | 1.00 | 51.63 |
| ATOM | 858 | OD1 | ASP | 268 | 21.060 | 5.305 | 7.498 | 1.00 | 51.63 |
| ATOM | 859 | OD2 | ASP | 268 | 22.262 | 6.814 | 8.547 | 1.00 | 51.63 |

FIG. 29A-18

| ATOM | 860 | C   | ASP | 268 | 22.105 | 4.068 | 10.749 | 1.00 | 28.13 |
|------|-----|-----|-----|-----|--------|-------|--------|------|-------|
| ATOM | 861 | O   | ASP | 268 | 22.683 | 4.854 | 11.500 | 1.00 | 51.63 |
| ATOM | 862 | N   | PRO | 269 | 22.707 | 2.964 | 10.276 | 1.00 | 37.07 |
| ATOM | 863 | CD  | PRO | 269 | 22.103 | 1.938 | 9.410  | 1.00 | 39.18 |
| ATOM | 864 | CA  | PRO | 269 | 24.086 | 2.612 | 10.623 | 1.00 | 37.07 |
| ATOM | 865 | CB  | PRO | 269 | 24.319 | 1.324 | 9.832  | 1.00 | 39.18 |
| ATOM | 866 | CG  | PRO | 269 | 22.950 | 0.735 | 9.706  | 1.00 | 39.18 |
| ATOM | 867 | C   | PRO | 269 | 25.079 | 3.698 | 10.216 | 1.00 | 37.07 |
| ATOM | 868 | O   | PRO | 269 | 26.003 | 4.006 | 10.964 | 1.00 | 39.18 |
| ATOM | 869 | N   | ALA | 270 | 24.855 | 4.295 | 9.047  | 1.00 | 46.88 |
| ATOM | 870 | CA  | ALA | 270 | 25.730 | 5.340 | 8.519  | 1.00 | 46.88 |
| ATOM | 871 | CB  | ALA | 270 | 25.177 | 5.873 | 7.198  | 1.00 | 41.71 |
| ATOM | 872 | C   | ALA | 270 | 25.974 | 6.493 | 9.492  | 1.00 | 46.88 |
| ATOM | 873 | O   | ALA | 270 | 27.121 | 6.844 | 9.763  | 1.00 | 41.71 |
| ATOM | 874 | N   | SER | 271 | 24.899 | 7.081 | 10.009 | 1.00 | 34.54 |
| ATOM | 875 | CA  | SER | 271 | 25.013 | 8.198 | 10.941 | 1.00 | 34.54 |
| ATOM | 876 | CB  | SER | 271 | 23.959 | 9.259 | 10.618 | 1.00 | 42.29 |
| ATOM | 877 | OG  | SER | 271 | 22.686 | 8.668 | 10.422 | 1.00 | 42.29 |
| ATOM | 878 | C   | SER | 271 | 24.910 | 7.793 | 12.408 | 1.00 | 34.54 |
| ATOM | 879 | O   | SER | 271 | 25.169 | 8.607 | 13.297 | 1.00 | 42.29 |
| ATOM | 880 | N   | ASP | 272 | 24.546 | 6.535 | 12.653 | 1.00 | 41.05 |
| ATOM | 881 | CA  | ASP | 272 | 24.388 | 6.005 | 14.007 | 1.00 | 41.05 |
| ATOM | 882 | CB  | ASP | 272 | 25.720 | 6.078 | 14.772 | 1.00 | 47.32 |
| ATOM | 883 | CG  | ASP | 272 | 25.653 | 5.428 | 16.147 | 1.00 | 47.32 |
| ATOM | 884 | OD1 | ASP | 272 | 24.981 | 4.384 | 16.299 | 1.00 | 47.32 |
| ATOM | 885 | OD2 | ASP | 272 | 26.284 | 5.967 | 17.081 | 1.00 | 47.32 |
| ATOM | 886 | C   | ASP | 272 | 23.279 | 6.777 | 14.730 | 1.00 | 41.05 |
| ATOM | 887 | O   | ASP | 272 | 23.444 | 7.233 | 15.866 | 1.00 | 47.32 |
| ATOM | 888 | N   | THR | 273 | 22.139 | 6.905 | 14.058 | 1.00 | 27.60 |
| ATOM | 889 | CA  | THR | 273 | 20.996 | 7.618 | 14.608 | 1.00 | 27.60 |
| ATOM | 890 | CB  | THR | 273 | 20.808 | 8.991 | 13.911 | 1.00 | 30.96 |
| ATOM | 891 | OG1 | THR | 273 | 20.723 | 8.808 | 12.491 | 1.00 | 30.96 |
| ATOM | 892 | CG2 | THR | 273 | 21.967 | 9.924 | 14.228 | 1.00 | 30.96 |
| ATOM | 893 | C   | THR | 273 | 19.701 | 6.829 | 14.442 | 1.00 | 27.60 |
| ATOM | 894 | O   | THR | 273 | 19.633 | 5.883 | 13.650 | 1.00 | 30.96 |
| ATOM | 895 | N   | LEU | 274 | 18.696 | 7.192 | 15.232 | 1.00 | 20.89 |
| ATOM | 896 | CA  | LEU | 274 | 17.374 | 6.574 | 15.161 | 1.00 | 20.89 |
| ATOM | 897 | CB  | LEU | 274 | 16.862 | 6.193 | 16.555 | 1.00 | 22.48 |
| ATOM | 898 | CG  | LEU | 274 | 17.480 | 5.009 | 17.301 | 1.00 | 22.48 |
| ATOM | 899 | CD1 | LEU | 274 | 16.798 | 4.866 | 18.650 | 1.00 | 22.48 |
| ATOM | 900 | CD2 | LEU | 274 | 17.317 | 3.736 | 16.497 | 1.00 | 22.48 |
| ATOM | 901 | C   | LEU | 274 | 16.470 | 7.654 | 14.586 | 1.00 | 20.89 |
| ATOM | 902 | O   | LEU | 274 | 16.753 | 8.842 | 14.744 | 1.00 | 22.48 |
| ATOM | 903 | N   | THR | 275 | 15.393 | 7.258 | 13.922 | 1.00 | 27.89 |
| ATOM | 904 | CA  | THR | 275 | 14.478 | 8.235 | 13.354 | 1.00 | 27.89 |
| ATOM | 905 | CB  | THR | 275 | 14.325 | 8.045 | 11.832 | 1.00 | 37.64 |
| ATOM | 906 | OG1 | THR | 275 | 15.622 | 7.983 | 11.228 | 1.00 | 37.64 |
| ATOM | 907 | CG2 | THR | 275 | 13.570 | 9.215 | 11.222 | 1.00 | 37.64 |
| ATOM | 908 | C   | THR | 275 | 13.120 | 8.135 | 14.032 | 1.00 | 27.89 |
| ATOM | 909 | O   | THR | 275 | 12.493 | 7.081 | 14.019 | 1.00 | 37.64 |

FIG. 29A-19

| | | | | | | | | | |
|---|---|---|---|---|---|---|---|---|---|
| ATOM | 910 | N | LEU | 276 | 12.700 | 9.226 | 14.667 | 1.00 | 28.07 |
| ATOM | 911 | CA | LEU | 276 | 11.418 | 9.275 | 15.358 | 1.00 | 28.07 |
| ATOM | 912 | CB | LEU | 276 | 11.497 | 10.214 | 16.572 | 1.00 | 24.81 |
| ATOM | 913 | CG | LEU | 276 | 12.639 | 10.005 | 17.577 | 1.00 | 24.81 |
| ATOM | 914 | CD1 | LEU | 276 | 12.450 | 10.929 | 18.769 | 1.00 | 24.81 |
| ATOM | 915 | CD2 | LEU | 276 | 12.692 | 8.558 | 18.038 | 1.00 | 24.81 |
| ATOM | 916 | C | LEU | 276 | 10.339 | 9.761 | 14.395 | 1.00 | 28.07 |
| ATOM | 917 | O | LEU | 276 | 10.533 | 10.760 | 13.691 | 1.00 | 24.81 |
| ATOM | 918 | N | SER | 277 | 9.232 | 9.027 | 14.331 | 1.00 | 29.24 |
| ATOM | 919 | CA | SER | 277 | 8.106 | 9.357 | 13.458 | 1.00 | 29.24 |
| ATOM | 920 | CB | SER | 277 | 7.369 | 10.594 | 13.985 | 1.00 | 30.56 |
| ATOM | 921 | OG | SER | 277 | 6.845 | 10.358 | 15.283 | 1.00 | 30.56 |
| ATOM | 922 | C | SER | 277 | 8.533 | 9.569 | 12.005 | 1.00 | 29.24 |
| ATOM | 923 | O | SER | 277 | 7.902 | 10.326 | 11.263 | 1.00 | 30.56 |
| ATOM | 924 | N | GLY | 278 | 9.619 | 8.908 | 11.618 | 1.00 | 34.41 |
| ATOM | 925 | CA | GLY | 278 | 10.135 | 9.024 | 10.263 | 1.00 | 34.41 |
| ATOM | 926 | C | GLY | 278 | 10.472 | 10.442 | 9.830 | 1.00 | 34.41 |
| ATOM | 927 | O | GLY | 278 | 10.516 | 10.725 | 8.631 | 1.00 | 44.04 |
| ATOM | 928 | N | GLU | 279 | 10.733 | 11.326 | 10.791 | 1.00 | 37.82 |
| ATOM | 929 | CA | GLU | 279 | 11.056 | 12.717 | 10.479 | 1.00 | 37.82 |
| ATOM | 930 | CB | GLU | 279 | 9.808 | 13.600 | 10.612 | 1.00 | 70.24 |
| ATOM | 931 | CG | GLU | 279 | 9.202 | 13.631 | 12.014 | 1.00 | 70.24 |
| ATOM | 932 | CD | GLU | 279 | 8.028 | 14.593 | 12.141 | 1.00 | 70.24 |
| ATOM | 933 | OE1 | GLU | 279 | 8.028 | 15.406 | 13.093 | 1.00 | 70.24 |
| ATOM | 934 | OE2 | GLU | 279 | 7.103 | 14.535 | 11.301 | 1.00 | 70.24 |
| ATOM | 935 | C | GLU | 279 | 12.192 | 13.321 | 11.300 | 1.00 | 37.82 |
| ATOM | 936 | O | GLU | 279 | 12.857 | 14.248 | 10.841 | 1.00 | 70.24 |
| ATOM | 937 | N | MET | 280 | 12.424 | 12.811 | 12.505 | 1.00 | 33.77 |
| ATOM | 938 | CA | MET | 280 | 13.482 | 13.360 | 13.344 | 1.00 | 33.77 |
| ATOM | 939 | CB | MET | 280 | 12.903 | 13.848 | 14.674 | 1.00 | 33.89 |
| ATOM | 940 | CG | MET | 280 | 13.898 | 14.595 | 15.545 | 1.00 | 33.89 |
| ATOM | 941 | SD | MET | 280 | 13.350 | 14.740 | 17.256 | 1.00 | 33.89 |
| ATOM | 942 | CE | MET | 280 | 12.100 | 16.017 | 17.121 | 1.00 | 33.89 |
| ATOM | 943 | C | MET | 280 | 14.620 | 12.383 | 13.613 | 1.00 | 33.77 |
| ATOM | 944 | O | MET | 280 | 14.432 | 11.366 | 14.282 | 1.00 | 33.89 |
| ATOM | 945 | N | ALA | 281 | 15.797 | 12.690 | 13.080 | 1.00 | 30.24 |
| ATOM | 946 | CA | ALA | 281 | 16.972 | 11.852 | 13.287 | 1.00 | 30.24 |
| ATOM | 947 | CB | ALA | 281 | 17.937 | 11.998 | 12.120 | 1.00 | 25.10 |
| ATOM | 948 | C | ALA | 281 | 17.631 | 12.309 | 14.587 | 1.00 | 30.24 |
| ATOM | 949 | O | ALA | 281 | 18.008 | 13.477 | 14.718 | 1.00 | 25.10 |
| ATOM | 950 | N | VAL | 282 | 17.743 | 11.401 | 15.551 | 1.00 | 32.12 |
| ATOM | 951 | CA | VAL | 282 | 18.339 | 11.726 | 16.844 | 1.00 | 32.12 |
| ATOM | 952 | CB | VAL | 282 | 17.303 | 11.606 | 17.991 | 1.00 | 37.75 |
| ATOM | 953 | CG1 | VAL | 282 | 16.184 | 12.615 | 17.799 | 1.00 | 37.75 |
| ATOM | 954 | CG2 | VAL | 282 | 16.739 | 10.193 | 18.055 | 1.00 | 37.75 |
| ATOM | 955 | C | VAL | 282 | 19.543 | 10.852 | 17.181 | 1.00 | 32.12 |
| ATOM | 956 | O | VAL | 282 | 19.614 | 9.690 | 16.778 | 1.00 | 37.75 |
| ATOM | 957 | N | LYS | 283 | 20.491 | 11.428 | 17.913 | 1.00 | 26.82 |
| ATOM | 958 | CA | LYS | 283 | 21.700 | 10.722 | 18.328 | 1.00 | 26.82 |
| ATOM | 959 | CB | LYS | 283 | 22.894 | 11.679 | 18.342 | 1.00 | 57.25 |

FIG. 29A-20

| | | | | | | | | |
|---|---|---|---|---|---|---|---|---|
| ATOM | 960 | CG | LYS | 283 | 23.258 | 12.245 | 16.979 | 1.00 | 57.25 |
| ATOM | 961 | CD | LYS | 283 | 24.282 | 13.361 | 17.105 | 1.00 | 57.25 |
| ATOM | 962 | CE | LYS | 283 | 24.752 | 13.836 | 15.741 | 1.00 | 57.25 |
| ATOM | 963 | NZ | LYS | 283 | 25.518 | 12.772 | 15.033 | 1.00 | 57.25 |
| ATOM | 964 | C | LYS | 283 | 21.509 | 10.120 | 19.717 | 1.00 | 26.82 |
| ATOM | 965 | O | LYS | 283 | 20.648 | 10.566 | 20.477 | 1.00 | 57.25 |
| ATOM | 966 | N | ARG | 284 | 22.351 | 9.146 | 20.058 | 1.00 | 26.41 |
| ATOM | 967 | CA | ARG | 284 | 22.297 | 8.457 | 21.351 | 1.00 | 26.41 |
| ATOM | 968 | CB | ARG | 284 | 23.527 | 7.566 | 21.528 | 1.00 | 41.02 |
| ATOM | 969 | CG | ARG | 284 | 23.715 | 6.539 | 20.440 | 1.00 | 41.02 |
| ATOM | 970 | CD | ARG | 284 | 25.016 | 5.794 | 20.616 | 1.00 | 41.02 |
| ATOM | 971 | NE | ARG | 284 | 25.145 | 4.730 | 19.630 | 1.00 | 41.02 |
| ATOM | 972 | CZ | ARG | 284 | 24.759 | 3.475 | 19.831 | 1.00 | 41.02 |
| ATOM | 973 | NH1 | ARG | 284 | 24.221 | 3.117 | 20.990 | 1.00 | 41.02 |
| ATOM | 974 | NH2 | ARG | 284 | 24.886 | 2.584 | 18.859 | 1.00 | 41.02 |
| ATOM | 975 | C | ARG | 284 | 22.200 | 9.399 | 22.543 | 1.00 | 26.41 |
| ATOM | 976 | O | ARG | 284 | 21.296 | 9.278 | 23.370 | 1.00 | 41.02 |
| ATOM | 977 | N | GLU | 285 | 23.152 | 10.321 | 22.634 | 1.00 | 33.23 |
| ATOM | 978 | CA | GLU | 285 | 23.201 | 11.292 | 23.721 | 1.00 | 33.23 |
| ATOM | 979 | CB | GLU | 285 | 24.366 | 12.258 | 23.492 | 1.00 | 69.82 |
| ATOM | 980 | CG | GLU | 285 | 24.485 | 13.359 | 24.533 | 1.00 | 69.82 |
| ATOM | 981 | CD | GLU | 285 | 25.079 | 14.636 | 23.964 | 1.00 | 69.82 |
| ATOM | 982 | OE1 | GLU | 285 | 26.309 | 14.826 | 24.070 | 1.00 | 69.82 |
| ATOM | 983 | OE2 | GLU | 285 | 24.309 | 15.453 | 23.409 | 1.00 | 69.82 |
| ATOM | 984 | C | GLU | 285 | 21.898 | 12.082 | 23.823 | 1.00 | 33.23 |
| ATOM | 985 | O | GLU | 285 | 21.336 | 12.239 | 24.907 | 1.00 | 69.82 |
| ATOM | 986 | N | GLN | 286 | 21.414 | 12.551 | 22.677 | 1.00 | 28.07 |
| ATOM | 987 | CA | GLN | 286 | 20.194 | 13.346 | 22.614 | 1.00 | 28.07 |
| ATOM | 988 | CB | GLN | 286 | 19.948 | 13.824 | 21.181 | 1.00 | 41.05 |
| ATOM | 989 | CG | GLN | 286 | 21.051 | 14.726 | 20.639 | 1.00 | 41.05 |
| ATOM | 990 | CD | GLN | 286 | 20.808 | 15.154 | 19.202 | 1.00 | 41.05 |
| ATOM | 991 | OE1 | GLN | 286 | 20.783 | 14.322 | 18.293 | 1.00 | 41.05 |
| ATOM | 992 | NE2 | GLN | 286 | 20.635 | 16.452 | 18.990 | 1.00 | 41.05 |
| ATOM | 993 | C | GLN | 286 | 18.955 | 12.642 | 23.162 | 1.00 | 28.07 |
| ATOM | 994 | O | GLN | 286 | 18.281 | 13.174 | 24.048 | 1.00 | 41.05 |
| ATOM | 995 | N | LEU | 287 | 18.663 | 11.447 | 22.658 | 1.00 | 30.11 |
| ATOM | 996 | CA | LEU | 287 | 17.492 | 10.705 | 23.116 | 1.00 | 30.11 |
| ATOM | 997 | CB | LEU | 287 | 17.232 | 9.489 | 22.219 | 1.00 | 21.70 |
| ATOM | 998 | CG | LEU | 287 | 15.859 | 8.821 | 22.357 | 1.00 | 21.70 |
| ATOM | 999 | CD1 | LEU | 287 | 14.748 | 9.818 | 22.061 | 1.00 | 21.70 |
| ATOM | 1000 | CD2 | LEU | 287 | 15.763 | 7.628 | 21.421 | 1.00 | 21.70 |
| ATOM | 1001 | C | LEU | 287 | 17.641 | 10.277 | 24.577 | 1.00 | 30.11 |
| ATOM | 1002 | O | LEU | 287 | 16.655 | 10.212 | 25.320 | 1.00 | 21.70 |
| ATOM | 1003 | N | LYS | 288 | 18.878 | 10.015 | 24.992 | 1.00 | 20.72 |
| ATOM | 1004 | CA | LYS | 288 | 19.156 | 9.611 | 26.365 | 1.00 | 20.72 |
| ATOM | 1005 | CB | LYS | 288 | 20.626 | 9.213 | 26.514 | 1.00 | 43.14 |
| ATOM | 1006 | CG | LYS | 288 | 20.991 | 8.721 | 27.903 | 1.00 | 43.14 |
| ATOM | 1007 | CD | LYS | 288 | 22.374 | 8.102 | 27.931 | 1.00 | 43.14 |
| ATOM | 1008 | CE | LYS | 288 | 22.615 | 7.379 | 29.250 | 1.00 | 43.14 |
| ATOM | 1009 | NZ | LYS | 288 | 23.866 | 6.568 | 29.224 | 1.00 | 43.14 |

FIG. 29A-21

| ATOM | 1010 | C | LYS | 288 | 18.819 | 10.742 | 27.331 | 1.00 | 20.72 |
|---|---|---|---|---|---|---|---|---|---|
| ATOM | 1011 | O | LYS | 288 | 18.027 | 10.566 | 28.261 | 1.00 | 43.14 |
| ATOM | 1012 | N | ASN | 289 | 19.380 | 11.917 | 27.067 | 1.00 | 33.64 |
| ATOM | 1013 | CA | ASN | 289 | 19.156 | 13.090 | 27.906 | 1.00 | 33.64 |
| ATOM | 1014 | CB | ASN | 289 | 20.190 | 14.173 | 27.590 | 1.00 | 35.61 |
| ATOM | 1015 | CG | ASN | 289 | 21.607 | 13.730 | 27.898 | 1.00 | 35.61 |
| ATOM | 1016 | OD1 | ASN | 289 | 21.835 | 12.920 | 28.797 | 1.00 | 35.61 |
| ATOM | 1017 | ND2 | ASN | 289 | 22.566 | 14.253 | 27.149 | 1.00 | 35.61 |
| ATOM | 1018 | C | ASN | 289 | 17.747 | 13.654 | 27.757 | 1.00 | 33.64 |
| ATOM | 1019 | O | ASN | 289 | 17.276 | 14.399 | 28.616 | 1.00 | 35.61 |
| ATOM | 1020 | N | GLY | 290 | 17.072 | 13.287 | 26.672 | 1.00 | 22.05 |
| ATOM | 1021 | CA | GLY | 290 | 15.722 | 13.767 | 26.435 | 1.00 | 22.05 |
| ATOM | 1022 | C | GLY | 290 | 14.688 | 13.247 | 27.416 | 1.00 | 22.05 |
| ATOM | 1023 | O | GLY | 290 | 13.550 | 13.710 | 27.420 | 1.00 | 29.95 |
| ATOM | 1024 | N | GLY | 291 | 15.072 | 12.276 | 28.239 | 1.00 | 24.91 |
| ATOM | 1025 | CA | GLY | 291 | 14.142 | 11.732 | 29.211 | 1.00 | 24.91 |
| ATOM | 1026 | C | GLY | 291 | 14.093 | 10.217 | 29.248 | 1.00 | 24.91 |
| ATOM | 1027 | O | GLY | 291 | 13.536 | 9.640 | 30.179 | 1.00 | 29.39 |
| ATOM | 1028 | N | LEU | 292 | 14.676 | 9.567 | 28.246 | 1.00 | 30.21 |
| ATOM | 1029 | CA | LEU | 292 | 14.675 | 8.110 | 28.189 | 1.00 | 30.21 |
| ATOM | 1030 | CB | LEU | 292 | 14.732 | 7.626 | 26.734 | 1.00 | 21.45 |
| ATOM | 1031 | CG | LEU | 292 | 13.439 | 7.795 | 25.928 | 1.00 | 21.45 |
| ATOM | 1032 | CD1 | LEU | 292 | 13.612 | 7.225 | 24.542 | 1.00 | 21.45 |
| ATOM | 1033 | CD2 | LEU | 292 | 12.296 | 7.087 | 26.630 | 1.00 | 21.45 |
| ATOM | 1034 | C | LEU | 292 | 15.785 | 7.461 | 29.013 | 1.00 | 30.21 |
| ATOM | 1035 | O | LEU | 292 | 15.645 | 6.324 | 29.473 | 1.00 | 21.45 |
| ATOM | 1036 | N | GLY | 293 | 16.885 | 8.180 | 29.205 | 1.00 | 16.29 |
| ATOM | 1037 | CA | GLY | 293 | 17.992 | 7.638 | 29.970 | 1.00 | 16.29 |
| ATOM | 1038 | C | GLY | 293 | 18.534 | 6.374 | 29.332 | 1.00 | 16.29 |
| ATOM | 1039 | O | GLY | 293 | 18.763 | 6.334 | 28.122 | 1.00 | 25.88 |
| ATOM | 1040 | N | VAL | 294 | 18.689 | 5.322 | 30.130 | 1.00 | 33.05 |
| ATOM | 1041 | CA | VAL | 294 | 19.211 | 4.050 | 29.635 | 1.00 | 33.05 |
| ATOM | 1042 | CB | VAL | 294 | 19.530 | 3.069 | 30.788 | 1.00 | 30.11 |
| ATOM | 1043 | CG1 | VAL | 294 | 20.718 | 3.577 | 31.582 | 1.00 | 30.11 |
| ATOM | 1044 | CG2 | VAL | 294 | 18.315 | 2.887 | 31.697 | 1.00 | 30.11 |
| ATOM | 1045 | C | VAL | 294 | 18.302 | 3.361 | 28.617 | 1.00 | 33.05 |
| ATOM | 1046 | O | VAL | 294 | 18.768 | 2.545 | 27.817 | 1.00 | 30.11 |
| ATOM | 1047 | N | VAL | 295 | 17.014 | 3.699 | 28.635 | 1.00 | 18.14 |
| ATOM | 1048 | CA | VAL | 295 | 16.056 | 3.118 | 27.698 | 1.00 | 18.14 |
| ATOM | 1049 | CB | VAL | 295 | 14.638 | 3.698 | 27.902 | 1.00 | 28.34 |
| ATOM | 1050 | CG1 | VAL | 295 | 13.668 | 3.099 | 26.893 | 1.00 | 28.34 |
| ATOM | 1051 | CG2 | VAL | 295 | 14.159 | 3.431 | 29.317 | 1.00 | 28.34 |
| ATOM | 1052 | C | VAL | 295 | 16.521 | 3.415 | 26.275 | 1.00 | 18.14 |
| ATOM | 1053 | O | VAL | 295 | 16.395 | 2.577 | 25.383 | 1.00 | 28.34 |
| ATOM | 1054 | N | SER | 296 | 17.091 | 4.601 | 26.085 | 1.00 | 20.84 |
| ATOM | 1055 | CA | SER | 296 | 17.596 | 5.028 | 24.785 | 1.00 | 20.84 |
| ATOM | 1056 | CB | SER | 296 | 18.160 | 6.446 | 24.884 | 1.00 | 25.61 |
| ATOM | 1057 | OG | SER | 296 | 18.615 | 6.911 | 23.627 | 1.00 | 25.61 |
| ATOM | 1058 | C | SER | 296 | 18.687 | 4.074 | 24.307 | 1.00 | 20.84 |
| ATOM | 1059 | O | SER | 296 | 18.723 | 3.691 | 23.133 | 1.00 | 25.61 |

FIG. 29A-22

| ATOM | 1060 | N   | ASP | 297 | 19.571 | 3.691  | 25.224 | 1.00 | 28.08 |
|------|------|-----|-----|-----|--------|--------|--------|------|-------|
| ATOM | 1061 | CA  | ASP | 297 | 20.660 | 2.777  | 24.904 | 1.00 | 28.08 |
| ATOM | 1062 | CB  | ASP | 297 | 21.555 | 2.552  | 26.129 | 1.00 | 51.15 |
| ATOM | 1063 | CG  | ASP | 297 | 22.207 | 3.835  | 26.629 | 1.00 | 51.15 |
| ATOM | 1064 | OD1 | ASP | 297 | 22.508 | 4.725  | 25.804 | 1.00 | 51.15 |
| ATOM | 1065 | OD2 | ASP | 297 | 22.425 | 3.948  | 27.855 | 1.00 | 51.15 |
| ATOM | 1066 | C   | ASP | 297 | 20.079 | 1.450  | 24.434 | 1.00 | 28.08 |
| ATOM | 1067 | O   | ASP | 297 | 20.549 | 0.869  | 23.456 | 1.00 | 51.15 |
| ATOM | 1068 | N   | ALA | 298 | 19.024 | 1.006  | 25.111 | 1.00 | 26.12 |
| ATOM | 1069 | CA  | ALA | 298 | 18.357 | -0.245 | 24.778 | 1.00 | 26.12 |
| ATOM | 1070 | CB  | ALA | 298 | 17.253 | -0.530 | 25.787 | 1.00 | 18.80 |
| ATOM | 1071 | C   | ALA | 298 | 17.790 | -0.223 | 23.356 | 1.00 | 26.12 |
| ATOM | 1072 | O   | ALA | 298 | 18.014 | -1.154 | 22.575 | 1.00 | 18.80 |
| ATOM | 1073 | N   | ILE | 299 | 17.078 | 0.848  | 23.013 | 1.00 | 17.42 |
| ATOM | 1074 | CA  | ILE | 299 | 16.483 | 0.979  | 21.686 | 1.00 | 17.42 |
| ATOM | 1075 | CB  | ILE | 299 | 15.559 | 2.211  | 21.597 | 1.00 | 16.69 |
| ATOM | 1076 | CG2 | ILE | 299 | 14.845 | 2.238  | 20.253 | 1.00 | 16.69 |
| ATOM | 1077 | CG1 | ILE | 299 | 14.515 | 2.149  | 22.712 | 1.00 | 16.69 |
| ATOM | 1078 | CD1 | ILE | 299 | 13.713 | 3.406  | 22.872 | 1.00 | 16.69 |
| ATOM | 1079 | C   | ILE | 299 | 17.563 | 1.042  | 20.609 | 1.00 | 17.42 |
| ATOM | 1080 | O   | ILE | 299 | 17.416 | 0.443  | 19.542 | 1.00 | 16.69 |
| ATOM | 1081 | N   | PHE | 300 | 18.652 | 1.752  | 20.889 | 1.00 | 14.46 |
| ATOM | 1082 | CA  | PHE | 300 | 19.751 | 1.851  | 19.935 | 1.00 | 14.46 |
| ATOM | 1083 | CB  | PHE | 300 | 20.804 | 2.854  | 20.409 | 1.00 | 24.01 |
| ATOM | 1084 | CG  | PHE | 300 | 20.656 | 4.221  | 19.801 | 1.00 | 24.01 |
| ATOM | 1085 | CD1 | PHE | 300 | 19.904 | 5.204  | 20.435 | 1.00 | 24.01 |
| ATOM | 1086 | CD2 | PHE | 300 | 21.271 | 4.526  | 18.591 | 1.00 | 24.01 |
| ATOM | 1087 | CE1 | PHE | 300 | 19.766 | 6.472  | 19.873 | 1.00 | 24.01 |
| ATOM | 1088 | CE2 | PHE | 300 | 21.140 | 5.791  | 18.020 | 1.00 | 24.01 |
| ATOM | 1089 | CZ  | PHE | 300 | 20.385 | 6.765  | 18.663 | 1.00 | 24.01 |
| ATOM | 1090 | C   | PHE | 300 | 20.383 | 0.480  | 19.726 | 1.00 | 14.46 |
| ATOM | 1091 | O   | PHE | 300 | 20.696 | 0.102  | 18.596 | 1.00 | 24.01 |
| ATOM | 1092 | N   | GLU | 301 | 20.547 | -0.270 | 20.813 | 1.00 | 21.61 |
| ATOM | 1093 | CA  | GLU | 301 | 21.123 | -1.609 | 20.744 | 1.00 | 21.61 |
| ATOM | 1094 | CB  | GLU | 301 | 21.289 | -2.192 | 22.143 | 1.00 | 23.89 |
| ATOM | 1095 | C   | GLU | 301 | 20.211 | -2.498 | 19.904 | 1.00 | 21.61 |
| ATOM | 1096 | O   | GLU | 301 | 20.681 | -3.251 | 19.043 | 1.00 | 23.89 |
| ATOM | 1097 | N   | LEU | 302 | 18.906 | -2.390 | 20.140 | 1.00 | 14.43 |
| ATOM | 1098 | CA  | LEU | 302 | 17.922 | -3.168 | 19.399 | 1.00 | 14.43 |
| ATOM | 1099 | CB  | LEU | 302 | 16.512 | -2.872 | 19.912 | 1.00 | 23.43 |
| ATOM | 1100 | CG  | LEU | 302 | 15.350 | -3.669 | 19.312 | 1.00 | 23.43 |
| ATOM | 1101 | CD1 | LEU | 302 | 15.459 | -5.140 | 19.688 | 1.00 | 23.43 |
| ATOM | 1102 | CD2 | LEU | 302 | 14.035 | -3.094 | 19.804 | 1.00 | 23.43 |
| ATOM | 1103 | C   | LEU | 302 | 18.027 | -2.812 | 17.917 | 1.00 | 14.43 |
| ATOM | 1104 | O   | LEU | 302 | 18.089 | -3.697 | 17.066 | 1.00 | 23.43 |
| ATOM | 1105 | N   | GLY | 303 | 18.098 | -1.515 | 17.625 | 1.00 | 15.17 |
| ATOM | 1106 | CA  | GLY | 303 | 18.208 | -1.056 | 16.251 | 1.00 | 15.17 |
| ATOM | 1107 | C   | GLY | 303 | 19.411 | -1.640 | 15.530 | 1.00 | 15.17 |
| ATOM | 1108 | O   | GLY | 303 | 19.290 | -2.137 | 14.406 | 1.00 | 27.67 |
| ATOM | 1109 | N   | LYS | 304 | 20.570 | -1.594 | 16.182 | 1.00 | 19.04 |

FIG. 29A-23

| ATOM | 1110 | CA | LYS | 304 | 21.802 | -2.127 | 15.605 | 1.00 | 19.04 |
|------|------|------|-----|-----|--------|--------|--------|------|-------|
| ATOM | 1111 | CB | LYS | 304 | 22.979 | -1.975 | 16.577 | 1.00 | 56.94 |
| ATOM | 1112 | CG | LYS | 304 | 23.496 | -0.556 | 16.741 | 1.00 | 56.94 |
| ATOM | 1113 | CD | LYS | 304 | 24.811 | -0.524 | 17.516 | 1.00 | 56.94 |
| ATOM | 1114 | CE | LYS | 304 | 24.634 | -0.965 | 18.968 | 1.00 | 56.94 |
| ATOM | 1115 | NZ | LYS | 304 | 23.838 | 0.008 | 19.778 | 1.00 | 56.94 |
| ATOM | 1116 | C | LYS | 304 | 21.653 | -3.596 | 15.229 | 1.00 | 19.04 |
| ATOM | 1117 | O | LYS | 304 | 21.974 | -3.993 | 14.107 | 1.00 | 56.94 |
| ATOM | 1118 | N | SER | 305 | 21.146 | -4.394 | 16.164 | 1.00 | 24.46 |
| ATOM | 1119 | CA | SER | 305 | 20.965 | -5.822 | 15.932 | 1.00 | 24.46 |
| ATOM | 1120 | CB | SER | 305 | 20.610 | -6.533 | 17.240 | 1.00 | 37.46 |
| ATOM | 1121 | OG | SER | 305 | 19.444 | -5.984 | 17.827 | 1.00 | 37.46 |
| ATOM | 1122 | C | SER | 305 | 19.926 | -6.128 | 14.853 | 1.00 | 24.46 |
| ATOM | 1123 | O | SER | 305 | 20.146 | -6.996 | 14.006 | 1.00 | 37.46 |
| ATOM | 1124 | N | LEU | 306 | 18.819 | -5.390 | 14.858 | 1.00 | 25.47 |
| ATOM | 1125 | CA | LEU | 306 | 17.753 | -5.592 | 13.881 | 1.00 | 25.47 |
| ATOM | 1126 | CB | LEU | 306 | 16.525 | -4.746 | 14.224 | 1.00 | 15.99 |
| ATOM | 1127 | CG | LEU | 306 | 15.700 | -5.190 | 15.432 | 1.00 | 15.99 |
| ATOM | 1128 | CD1 | LEU | 306 | 14.504 | -4.271 | 15.600 | 1.00 | 15.99 |
| ATOM | 1129 | CD2 | LEU | 306 | 15.244 | -6.624 | 15.247 | 1.00 | 15.99 |
| ATOM | 1130 | C | LEU | 306 | 18.174 | -5.330 | 12.439 | 1.00 | 25.47 |
| ATOM | 1131 | O | LEU | 306 | 17.596 | -5.902 | 11.513 | 1.00 | 15.99 |
| ATOM | 1132 | N | SER | 307 | 19.182 | -4.482 | 12.247 | 1.00 | 24.28 |
| ATOM | 1133 | CA | SER | 307 | 19.670 | -4.160 | 10.907 | 1.00 | 24.28 |
| ATOM | 1134 | CB | SER | 307 | 20.910 | -3.263 | 10.989 | 1.00 | 40.92 |
| ATOM | 1135 | OG | SER | 307 | 20.617 | -2.028 | 11.622 | 1.00 | 40.92 |
| ATOM | 1136 | C | SER | 307 | 19.995 | -5.422 | 10.107 | 1.00 | 24.28 |
| ATOM | 1137 | O | SER | 307 | 19.625 | -5.535 | 8.936 | 1.00 | 40.92 |
| ATOM | 1138 | N | ALA | 308 | 20.644 | -6.383 | 10.761 | 1.00 | 30.97 |
| ATOM | 1139 | CA | ALA | 308 | 21.027 | -7.640 | 10.124 | 1.00 | 30.97 |
| ATOM | 1140 | CB | ALA | 308 | 22.004 | -8.399 | 11.013 | 1.00 | 37.84 |
| ATOM | 1141 | C | ALA | 308 | 19.830 | -8.528 | 9.779 | 1.00 | 30.97 |
| ATOM | 1142 | O | ALA | 308 | 19.897 | -9.336 | 8.853 | 1.00 | 37.84 |
| ATOM | 1143 | N | PHE | 309 | 18.737 | -8.372 | 10.520 | 1.00 | 22.78 |
| ATOM | 1144 | CA | PHE | 309 | 17.533 | -9.166 | 10.292 | 1.00 | 22.78 |
| ATOM | 1145 | CB | PHE | 309 | 16.571 | -9.037 | 11.477 | 1.00 | 30.14 |
| ATOM | 1146 | CG | PHE | 309 | 17.032 | -9.751 | 12.716 | 1.00 | 30.14 |
| ATOM | 1147 | CD1 | PHE | 309 | 16.299 | -10.809 | 13.236 | 1.00 | 30.14 |
| ATOM | 1148 | CD2 | PHE | 309 | 18.204 | -9.372 | 13.359 | 1.00 | 30.14 |
| ATOM | 1149 | CE1 | PHE | 309 | 16.725 | -11.481 | 14.378 | 1.00 | 30.14 |
| ATOM | 1150 | CE2 | PHE | 309 | 18.640 | -10.038 | 14.503 | 1.00 | 30.14 |
| ATOM | 1151 | CZ | PHE | 309 | 17.896 | -11.094 | 15.013 | 1.00 | 30.14 |
| ATOM | 1152 | C | PHE | 309 | 16.818 | -8.813 | 8.990 | 1.00 | 22.78 |
| ATOM | 1153 | O | PHE | 309 | 16.068 | -9.631 | 8.451 | 1.00 | 30.14 |
| ATOM | 1154 | N | ASN | 310 | 17.051 | -7.598 | 8.496 | 1.00 | 35.30 |
| ATOM | 1155 | CA | ASN | 310 | 16.441 | -7.109 | 7.255 | 1.00 | 35.30 |
| ATOM | 1156 | CB | ASN | 310 | 17.109 | -7.760 | 6.037 | 1.00 | 28.28 |
| ATOM | 1157 | C | ASN | 310 | 14.929 | -7.339 | 7.229 | 1.00 | 35.30 |
| ATOM | 1158 | O | ASN | 310 | 14.395 | -7.970 | 6.312 | 1.00 | 28.28 |
| ATOM | 1159 | N | LEU | 311 | 14.249 | -6.831 | 8.251 | 1.00 | 27.52 |

FIG. 29A-24

| ATOM | 1160 | CA | LEU | 311 | 12.803 | -6.979 | 8.369 | 1.00 | 27.52 |
| ATOM | 1161 | CB | LEU | 311 | 12.351 | -6.630 | 9.788 | 1.00 | 22.62 |
| ATOM | 1162 | CG | LEU | 311 | 12.950 | -7.396 | 10.968 | 1.00 | 22.62 |
| ATOM | 1163 | CD1 | LEU | 311 | 12.360 | -6.864 | 12.268 | 1.00 | 22.62 |
| ATOM | 1164 | CD2 | LEU | 311 | 12.672 | -8.881 | 10.821 | 1.00 | 22.62 |
| ATOM | 1165 | C | LEU | 311 | 12.060 | -6.085 | 7.382 | 1.00 | 27.52 |
| ATOM | 1166 | O | LEU | 311 | 12.519 | -4.986 | 7.067 | 1.00 | 22.62 |
| ATOM | 1167 | N | ASP | 312 | 10.918 | -6.563 | 6.892 | 1.00 | 16.74 |
| ATOM | 1168 | CA | ASP | 312 | 10.095 | -5.789 | 5.968 | 1.00 | 16.74 |
| ATOM | 1169 | CB | ASP | 312 | 9.803 | -6.578 | 4.673 | 1.00 | 16.35 |
| ATOM | 1170 | CG | ASP | 312 | 8.924 | -7.814 | 4.888 | 1.00 | 16.35 |
| ATOM | 1171 | OD1 | ASP | 312 | 8.591 | -8.168 | 6.037 | 1.00 | 16.35 |
| ATOM | 1172 | OD2 | ASP | 312 | 8.559 | -8.446 | 3.876 | 1.00 | 16.35 |
| ATOM | 1173 | C | ASP | 312 | 8.808 | -5.354 | 6.678 | 1.00 | 16.74 |
| ATOM | 1174 | O | ASP | 312 | 8.535 | -5.798 | 7.797 | 1.00 | 16.35 |
| ATOM | 1175 | N | ASP | 313 | 8.007 | -4.520 | 6.019 | 1.00 | 5.43 |
| ATOM | 1176 | CA | ASP | 313 | 6.758 | -4.016 | 6.592 | 1.00 | 5.43 |
| ATOM | 1177 | CB | ASP | 313 | 5.974 | -3.201 | 5.559 | 1.00 | 31.80 |
| ATOM | 1178 | CG | ASP | 313 | 6.670 | -1.906 | 5.183 | 1.00 | 31.80 |
| ATOM | 1179 | OD1 | ASP | 313 | 7.392 | -1.340 | 6.033 | 1.00 | 31.80 |
| ATOM | 1180 | OD2 | ASP | 313 | 6.493 | -1.452 | 4.032 | 1.00 | 31.80 |
| ATOM | 1181 | C | ASP | 313 | 5.849 | -5.081 | 7.189 | 1.00 | 5.43 |
| ATOM | 1182 | O | ASP | 313 | 5.216 | -4.849 | 8.221 | 1.00 | 31.80 |
| ATOM | 1183 | N | THR | 314 | 5.777 | -6.238 | 6.543 | 1.00 | 12.98 |
| ATOM | 1184 | CA | THR | 314 | 4.934 | -7.327 | 7.022 | 1.00 | 12.98 |
| ATOM | 1185 | CB | THR | 314 | 4.825 | -8.441 | 5.968 | 1.00 | 18.90 |
| ATOM | 1186 | OG1 | THR | 314 | 4.249 | -7.904 | 4.769 | 1.00 | 18.90 |
| ATOM | 1187 | CG2 | THR | 314 | 3.960 | -9.578 | 6.477 | 1.00 | 18.90 |
| ATOM | 1188 | C | THR | 314 | 5.426 | -7.910 | 8.349 | 1.00 | 12.98 |
| ATOM | 1189 | O | THR | 314 | 4.636 | -8.124 | 9.268 | 1.00 | 18.90 |
| ATOM | 1190 | N | GLU | 315 | 6.731 | -8.135 | 8.457 | 1.00 | 9.13 |
| ATOM | 1191 | CA | GLU | 315 | 7.316 | -8.685 | 9.675 | 1.00 | 9.13 |
| ATOM | 1192 | CB | GLU | 315 | 8.771 | -9.078 | 9.427 | 1.00 | 11.49 |
| ATOM | 1193 | CG | GLU | 315 | 8.870 | -10.323 | 8.562 | 1.00 | 11.49 |
| ATOM | 1194 | CD | GLU | 315 | 10.233 | -10.544 | 7.945 | 1.00 | 11.49 |
| ATOM | 1195 | OE1 | GLU | 315 | 10.964 | -9.561 | 7.705 | 1.00 | 11.49 |
| ATOM | 1196 | OE2 | GLU | 315 | 10.558 | -11.715 | 7.669 | 1.00 | 11.49 |
| ATOM | 1197 | C | GLU | 315 | 7.180 | -7.720 | 10.847 | 1.00 | 9.13 |
| ATOM | 1198 | O | GLU | 315 | 6.863 | -8.131 | 11.967 | 1.00 | 11.49 |
| ATOM | 1199 | N | VAL | 316 | 7.376 | -6.433 | 10.575 | 1.00 | 9.46 |
| ATOM | 1200 | CA | VAL | 316 | 7.240 | -5.406 | 11.602 | 1.00 | 9.46 |
| ATOM | 1201 | CB | VAL | 316 | 7.655 | -4.015 | 11.063 | 1.00 | 7.95 |
| ATOM | 1202 | CG1 | VAL | 316 | 7.434 | -2.941 | 12.124 | 1.00 | 7.95 |
| ATOM | 1203 | CG2 | VAL | 316 | 9.112 | -4.037 | 10.625 | 1.00 | 7.95 |
| ATOM | 1204 | C | VAL | 316 | 5.777 | -5.365 | 12.051 | 1.00 | 9.46 |
| ATOM | 1205 | O | VAL | 316 | 5.484 | -5.300 | 13.247 | 1.00 | 7.95 |
| ATOM | 1206 | N | ALA | 317 | 4.866 | -5.438 | 11.083 | 1.00 | 5.52 |
| ATOM | 1207 | CA | ALA | 317 | 3.434 | -5.417 | 11.355 | 1.00 | 5.52 |
| ATOM | 1208 | CB | ALA | 317 | 2.656 | -5.415 | 10.054 | 1.00 | 10.98 |
| ATOM | 1209 | C | ALA | 317 | 3.002 | -6.595 | 12.225 | 1.00 | 5.52 |

FIG. 29A-25

| ATOM | 1210 | O | ALA | 317 | 2.317 | -6.412 | 13.230 | 1.00 | 10.98 |
|---|---|---|---|---|---|---|---|---|---|
| ATOM | 1211 | N | LEU | 318 | 3.411 | -7.799 | 11.838 | 1.00 | 8.62 |
| ATOM | 1212 | CA | LEU | 318 | 3.067 | -9.003 | 12.584 | 1.00 | 8.62 |
| ATOM | 1213 | CB | LEU | 318 | 3.523 | -10.249 | 11.825 | 1.00 | 10.49 |
| ATOM | 1214 | CG | LEU | 318 | 2.770 | -10.494 | 10.514 | 1.00 | 10.49 |
| ATOM | 1215 | CD1 | LEU | 318 | 3.376 | -11.664 | 9.769 | 1.00 | 10.49 |
| ATOM | 1216 | CD2 | LEU | 318 | 1.297 | -10.741 | 10.799 | 1.00 | 10.49 |
| ATOM | 1217 | C | LEU | 318 | 3.674 | -8.971 | 13.978 | 1.00 | 8.62 |
| ATOM | 1218 | O | LEU | 318 | 3.047 | -9.407 | 14.945 | 1.00 | 10.49 |
| ATOM | 1219 | N | LEU | 319 | 4.885 | -8.435 | 14.082 | 1.00 | 9.43 |
| ATOM | 1220 | CA | LEU | 319 | 5.560 | -8.325 | 15.366 | 1.00 | 9.43 |
| ATOM | 1221 | CB | LEU | 319 | 6.975 | -7.773 | 15.173 | 1.00 | 24.05 |
| ATOM | 1222 | CG | LEU | 319 | 7.901 | -7.680 | 16.389 | 1.00 | 24.05 |
| ATOM | 1223 | CD1 | LEU | 319 | 7.889 | -8.977 | 17.182 | 1.00 | 24.05 |
| ATOM | 1224 | CD2 | LEU | 319 | 9.310 | -7.356 | 15.922 | 1.00 | 24.05 |
| ATOM | 1225 | C | LEU | 319 | 4.731 | -7.404 | 16.259 | 1.00 | 9.43 |
| ATOM | 1226 | O | LEU | 319 | 4.456 | -7.731 | 17.416 | 1.00 | 24.05 |
| ATOM | 1227 | N | GLN | 320 | 4.287 | -6.282 | 15.699 | 1.00 | 8.67 |
| ATOM | 1228 | CA | GLN | 320 | 3.467 | -5.325 | 16.437 | 1.00 | 8.67 |
| ATOM | 1229 | CB | GLN | 320 | 3.151 | -4.102 | 15.573 | 1.00 | 10.94 |
| ATOM | 1230 | CG | GLN | 320 | 4.361 | -3.256 | 15.218 | 1.00 | 10.94 |
| ATOM | 1231 | CD | GLN | 320 | 4.025 | -2.045 | 14.359 | 1.00 | 10.94 |
| ATOM | 1232 | OE1 | GLN | 320 | 4.889 | -1.217 | 14.082 | 1.00 | 10.94 |
| ATOM | 1233 | NE2 | GLN | 320 | 2.773 | -1.940 | 13.924 | 1.00 | 10.94 |
| ATOM | 1234 | C | GLN | 320 | 2.169 | -5.984 | 16.895 | 1.00 | 8.67 |
| ATOM | 1235 | O | GLN | 320 | 1.708 | -5.751 | 18.013 | 1.00 | 10.94 |
| ATOM | 1236 | N | ALA | 321 | 1.586 | -6.806 | 16.028 | 1.00 | 9.21 |
| ATOM | 1237 | CA | ALA | 321 | 0.349 | -7.513 | 16.342 | 1.00 | 9.21 |
| ATOM | 1238 | CB | ALA | 321 | -0.136 | -8.283 | 15.129 | 1.00 | 12.83 |
| ATOM | 1239 | C | ALA | 321 | 0.558 | -8.460 | 17.523 | 1.00 | 9.21 |
| ATOM | 1240 | O | ALA | 321 | -0.315 | -8.591 | 18.382 | 1.00 | 12.83 |
| ATOM | 1241 | N | VAL | 322 | 1.718 | -9.111 | 17.566 | 1.00 | 9.10 |
| ATOM | 1242 | CA | VAL | 322 | 2.043 | -10.030 | 18.651 | 1.00 | 9.10 |
| ATOM | 1243 | CB | VAL | 322 | 3.340 | -10.827 | 18.352 | 1.00 | 15.92 |
| ATOM | 1244 | CG1 | VAL | 322 | 3.783 | -11.614 | 19.575 | 1.00 | 15.92 |
| ATOM | 1245 | CG2 | VAL | 322 | 3.106 | -11.780 | 17.194 | 1.00 | 15.92 |
| ATOM | 1246 | C | VAL | 322 | 2.192 | -9.256 | 19.960 | 1.00 | 9.10 |
| ATOM | 1247 | O | VAL | 322 | 1.707 | -9.691 | 21.003 | 1.00 | 15.92 |
| ATOM | 1248 | N | LEU | 323 | 2.856 | -8.106 | 19.893 | 1.00 | 11.07 |
| ATOM | 1249 | CA | LEU | 323 | 3.062 | -7.257 | 21.064 | 1.00 | 11.07 |
| ATOM | 1250 | CB | LEU | 323 | 3.959 | -6.070 | 20.705 | 1.00 | 16.31 |
| ATOM | 1251 | CG | LEU | 323 | 5.377 | -6.393 | 20.229 | 1.00 | 16.31 |
| ATOM | 1252 | CD1 | LEU | 323 | 6.039 | -5.149 | 19.669 | 1.00 | 16.31 |
| ATOM | 1253 | CD2 | LEU | 323 | 6.187 | -6.966 | 21.375 | 1.00 | 16.31 |
| ATOM | 1254 | C | LEU | 323 | 1.729 | -6.742 | 21.595 | 1.00 | 11.07 |
| ATOM | 1255 | O | LEU | 323 | 1.523 | -6.650 | 22.803 | 1.00 | 16.31 |
| ATOM | 1256 | N | LEU | 324 | 0.827 | -6.413 | 20.677 | 1.00 | 13.48 |
| ATOM | 1257 | CA | LEU | 324 | -0.494 | -5.900 | 21.015 | 1.00 | 13.48 |
| ATOM | 1258 | CB | LEU | 324 | -1.185 | -5.383 | 19.752 | 1.00 | 15.92 |
| ATOM | 1259 | CG | LEU | 324 | -2.607 | -4.837 | 19.889 | 1.00 | 15.92 |

FIG. 29A-26

| ATOM | 1260 | CD1 | LEU | 324 | -2.602 | -3.547 | 20.692 | 1.00 | 15.92 |
|---|---|---|---|---|---|---|---|---|---|
| ATOM | 1261 | CD2 | LEU | 324 | -3.182 | -4.598 | 18.511 | 1.00 | 15.92 |
| ATOM | 1262 | C | LEU | 324 | -1.393 | -6.924 | 21.707 | 1.00 | 13.48 |
| ATOM | 1263 | O | LEU | 324 | -1.896 | -6.678 | 22.802 | 1.00 | 15.92 |
| ATOM | 1264 | N | MET | 325 | -1.593 | -8.074 | 21.072 | 1.00 | 11.47 |
| ATOM | 1265 | CA | MET | 325 | -2.458 | -9.111 | 21.631 | 1.00 | 11.47 |
| ATOM | 1266 | CB | MET | 325 | -2.959 | -10.043 | 20.520 | 1.00 | 22.90 |
| ATOM | 1267 | CG | MET | 325 | -3.689 | -9.347 | 19.375 | 1.00 | 22.90 |
| ATOM | 1268 | SD | MET | 325 | -5.052 | -8.287 | 19.908 | 1.00 | 22.90 |
| ATOM | 1269 | CE | MET | 325 | -6.284 | -9.475 | 20.353 | 1.00 | 22.90 |
| ATOM | 1270 | C | MET | 325 | -1.814 | -9.932 | 22.752 | 1.00 | 11.47 |
| ATOM | 1271 | O | MET | 325 | -1.899 | -11.160 | 22.758 | 1.00 | 22.90 |
| ATOM | 1272 | N | SER | 326 | -1.193 | -9.256 | 23.711 | 1.00 | 30.07 |
| ATOM | 1273 | CA | SER | 326 | -0.543 | -9.936 | 24.826 | 1.00 | 30.07 |
| ATOM | 1274 | CB | SER | 326 | 0.723 | -9.175 | 25.239 | 1.00 | 32.79 |
| ATOM | 1275 | OG | SER | 326 | 1.283 | -9.699 | 26.433 | 1.00 | 32.79 |
| ATOM | 1276 | C | SER | 326 | -1.492 | -10.061 | 26.014 | 1.00 | 30.07 |
| ATOM | 1277 | O | SER | 326 | -2.343 | -9.198 | 26.235 | 1.00 | 32.79 |
| ATOM | 1278 | N | THR | 327 | -1.347 | -11.143 | 26.773 | 1.00 | 29.08 |
| ATOM | 1279 | CA | THR | 327 | -2.179 | -11.368 | 27.948 | 1.00 | 29.08 |
| ATOM | 1280 | CB | THR | 327 | -2.705 | -12.817 | 27.998 | 1.00 | 36.96 |
| ATOM | 1281 | OG1 | THR | 327 | -1.612 | -13.734 | 27.856 | 1.00 | 36.96 |
| ATOM | 1282 | CG2 | THR | 327 | -3.716 | -13.055 | 26.890 | 1.00 | 36.96 |
| ATOM | 1283 | C | THR | 327 | -1.426 | -11.049 | 29.239 | 1.00 | 29.08 |
| ATOM | 1284 | O | THR | 327 | -1.930 | -11.295 | 30.333 | 1.00 | 36.96 |
| ATOM | 1285 | N | ASP | 328 | -0.214 | -10.513 | 29.111 | 1.00 | 38.93 |
| ATOM | 1286 | CA | ASP | 328 | 0.596 | -10.152 | 30.273 | 1.00 | 38.93 |
| ATOM | 1287 | CB | ASP | 328 | 2.082 | -10.089 | 29.899 | 1.00 | 85.70 |
| ATOM | 1288 | CG | ASP | 328 | 2.660 | -11.451 | 29.556 | 1.00 | 85.70 |
| ATOM | 1289 | OD1 | ASP | 328 | 3.388 | -11.554 | 28.542 | 1.00 | 85.70 |
| ATOM | 1290 | OD2 | ASP | 328 | 2.393 | -12.418 | 30.303 | 1.00 | 85.70 |
| ATOM | 1291 | C | ASP | 328 | 0.148 | -8.810 | 30.845 | 1.00 | 38.93 |
| ATOM | 1292 | O | ASP | 328 | 0.962 | -7.911 | 31.061 | 1.00 | 85.70 |
| ATOM | 1293 | N | ARG | 329 | -1.154 | -8.673 | 31.070 | 1.00 | 28.95 |
| ATOM | 1294 | CA | ARG | 329 | -1.716 | -7.445 | 31.608 | 1.00 | 28.95 |
| ATOM | 1295 | CB | ARG | 329 | -2.390 | -6.612 | 30.509 | 1.00 | 38.88 |
| ATOM | 1296 | CG | ARG | 329 | -1.449 | -5.887 | 29.554 | 1.00 | 38.88 |
| ATOM | 1297 | CD | ARG | 329 | -1.107 | -6.739 | 28.347 | 1.00 | 38.88 |
| ATOM | 1298 | NE | ARG | 329 | -0.322 | -6.005 | 27.356 | 1.00 | 38.88 |
| ATOM | 1299 | CZ | ARG | 329 | 1.006 | -5.936 | 27.351 | 1.00 | 38.88 |
| ATOM | 1300 | NH1 | ARG | 329 | 1.713 | -6.552 | 28.290 | 1.00 | 38.88 |
| ATOM | 1301 | NH2 | ARG | 329 | 1.631 | -5.270 | 26.391 | 1.00 | 38.88 |
| ATOM | 1302 | C | ARG | 329 | -2.745 | -7.790 | 32.672 | 1.00 | 28.95 |
| ATOM | 1303 | O | ARG | 329 | -3.279 | -8.898 | 32.696 | 1.00 | 38.88 |
| ATOM | 1304 | N | SER | 330 | -3.029 | -6.829 | 33.542 | 1.00 | 42.07 |
| ATOM | 1305 | CA | SER | 330 | -3.999 | -7.025 | 34.607 | 1.00 | 42.07 |
| ATOM | 1306 | CB | SER | 330 | -3.488 | -6.399 | 35.899 | 1.00 | 37.35 |
| ATOM | 1307 | C | SER | 330 | -5.340 | -6.413 | 34.220 | 1.00 | 42.07 |
| ATOM | 1308 | O | SER | 330 | -5.386 | -5.382 | 33.550 | 1.00 | 37.35 |
| ATOM | 1309 | N | GLY | 331 | -6.424 | -7.085 | 34.598 | 1.00 | 26.57 |

FIG. 29A-27

| ATOM | 1310 | CA | GLY | 331 | -7.754 | -6.572 | 34.318 | 1.00 | 26.57 |
| --- | --- | --- | --- | --- | --- | --- | --- | --- | --- |
| ATOM | 1311 | C | GLY | 331 | -8.404 | -6.915 | 32.991 | 1.00 | 26.57 |
| ATOM | 1312 | O | GLY | 331 | -9.462 | -6.371 | 32.671 | 1.00 | 30.06 |
| ATOM | 1313 | N | LEU | 332 | -7.797 | -7.807 | 32.214 | 1.00 | 31.47 |
| ATOM | 1314 | CA | LEU | 332 | -8.374 | -8.189 | 30.928 | 1.00 | 31.47 |
| ATOM | 1315 | CB | LEU | 332 | -7.351 | -8.933 | 30.065 | 1.00 | 23.83 |
| ATOM | 1316 | CG | LEU | 332 | -6.261 | -8.076 | 29.425 | 1.00 | 23.83 |
| ATOM | 1317 | CD1 | LEU | 332 | -5.296 | -8.960 | 28.652 | 1.00 | 23.83 |
| ATOM | 1318 | CD2 | LEU | 332 | -6.897 | -7.041 | 28.509 | 1.00 | 23.83 |
| ATOM | 1319 | C | LEU | 332 | -9.630 | -9.039 | 31.091 | 1.00 | 31.47 |
| ATOM | 1320 | O | LEU | 332 | -9.665 | -9.969 | 31.895 | 1.00 | 23.83 |
| ATOM | 1321 | N | LEU | 333 | -10.659 | -8.702 | 30.321 | 1.00 | 27.66 |
| ATOM | 1322 | CA | LEU | 333 | -11.927 | -9.422 | 30.351 | 1.00 | 27.66 |
| ATOM | 1323 | CB | LEU | 333 | -13.072 | -8.500 | 29.918 | 1.00 | 49.79 |
| ATOM | 1324 | CG | LEU | 333 | -13.416 | -7.312 | 30.820 | 1.00 | 49.79 |
| ATOM | 1325 | CD1 | LEU | 333 | -14.328 | -6.339 | 30.083 | 1.00 | 49.79 |
| ATOM | 1326 | CD2 | LEU | 333 | -14.072 | -7.803 | 32.104 | 1.00 | 49.79 |
| ATOM | 1327 | C | LEU | 333 | -11.904 | -10.663 | 29.456 | 1.00 | 27.66 |
| ATOM | 1328 | O | LEU | 333 | -12.117 | -11.780 | 29.919 | 1.00 | 49.79 |
| ATOM | 1329 | N | CYS | 334 | -11.616 | -10.464 | 28.174 | 1.00 | 29.56 |
| ATOM | 1330 | CA | CYS | 334 | -11.583 | -11.566 | 27.220 | 1.00 | 29.56 |
| ATOM | 1331 | CB | CYS | 334 | -12.134 | -11.106 | 25.865 | 1.00 | 47.01 |
| ATOM | 1332 | SG | CYS | 334 | -13.888 | -10.657 | 25.883 | 1.00 | 47.01 |
| ATOM | 1333 | C | CYS | 334 | -10.187 | -12.161 | 27.050 | 1.00 | 29.56 |
| ATOM | 1334 | O | CYS | 334 | -9.652 | -12.202 | 25.942 | 1.00 | 47.01 |
| ATOM | 1335 | N | VAL | 335 | -9.617 | -12.655 | 28.147 | 1.00 | 30.69 |
| ATOM | 1336 | CA | VAL | 335 | -8.280 | -13.250 | 28.132 | 1.00 | 30.69 |
| ATOM | 1337 | CB | VAL | 335 | -7.913 | -13.844 | 29.514 | 1.00 | 32.18 |
| ATOM | 1338 | CG1 | VAL | 335 | -6.517 | -14.456 | 29.480 | 1.00 | 32.18 |
| ATOM | 1339 | CG2 | VAL | 335 | -7.988 | -12.768 | 30.584 | 1.00 | 32.18 |
| ATOM | 1340 | C | VAL | 335 | -8.120 | -14.340 | 27.068 | 1.00 | 30.69 |
| ATOM | 1341 | O | VAL | 335 | -7.149 | -14.337 | 26.309 | 1.00 | 32.18 |
| ATOM | 1342 | N | ASP | 336 | -9.079 | -15.260 | 27.012 | 1.00 | 30.13 |
| ATOM | 1343 | CA | ASP | 336 | -9.040 | -16.360 | 26.052 | 1.00 | 30.13 |
| ATOM | 1344 | CB | ASP | 336 | -10.218 | -17.311 | 26.284 | 1.00 | 63.22 |
| ATOM | 1345 | CG | ASP | 336 | -10.178 | -18.528 | 25.370 | 1.00 | 63.22 |
| ATOM | 1346 | OD1 | ASP | 336 | -11.119 | -18.700 | 24.565 | 1.00 | 63.22 |
| ATOM | 1347 | OD2 | ASP | 336 | -9.205 | -19.311 | 25.452 | 1.00 | 63.22 |
| ATOM | 1348 | C | ASP | 336 | -9.012 | -15.903 | 24.594 | 1.00 | 30.13 |
| ATOM | 1349 | O | ASP | 336 | -8.156 | -16.339 | 23.823 | 1.00 | 63.22 |
| ATOM | 1350 | N | LYS | 337 | -9.944 | -15.027 | 24.223 | 1.00 | 26.63 |
| ATOM | 1351 | CA | LYS | 337 | -10.024 | -14.515 | 22.856 | 1.00 | 26.63 |
| ATOM | 1352 | CB | LYS | 337 | -11.172 | -13.516 | 22.729 | 1.00 | 21.38 |
| ATOM | 1353 | C | LYS | 337 | -8.706 | -13.865 | 22.438 | 1.00 | 26.63 |
| ATOM | 1354 | O | LYS | 337 | -8.204 | -14.110 | 21.338 | 1.00 | 21.38 |
| ATOM | 1355 | N | ILE | 338 | -8.141 | -13.060 | 23.334 | 1.00 | 24.65 |
| ATOM | 1356 | CA | ILE | 338 | -6.879 | -12.376 | 23.078 | 1.00 | 24.65 |
| ATOM | 1357 | CB | ILE | 338 | -6.543 | -11.380 | 24.215 | 1.00 | 20.45 |
| ATOM | 1358 | CG2 | ILE | 338 | -5.198 | -10.719 | 23.966 | 1.00 | 20.45 |
| ATOM | 1359 | CG1 | ILE | 338 | -7.632 | -10.308 | 24.308 | 1.00 | 20.45 |

FIG. 29A-28

| | | | | | | | | | |
|---|---|---|---|---|---|---|---|---|---|
| ATOM | 1360 | CD1 | ILE | 338 | -7.479 | -9.374 | 25.486 | 1.00 | 20.45 |
| ATOM | 1361 | C | ILE | 338 | -5.744 | -13.388 | 22.911 | 1.00 | 24.65 |
| ATOM | 1362 | O | ILE | 338 | -4.948 | -13.288 | 21.974 | 1.00 | 20.45 |
| ATOM | 1363 | N | GLU | 339 | -5.700 | -14.383 | 23.795 | 1.00 | 35.34 |
| ATOM | 1364 | CA | GLU | 339 | -4.673 | -15.422 | 23.745 | 1.00 | 35.34 |
| ATOM | 1365 | CB | GLU | 339 | -4.836 | -16.388 | 24.916 | 1.00 | 29.51 |
| ATOM | 1366 | C | GLU | 339 | -4.744 | -16.180 | 22.421 | 1.00 | 35.34 |
| ATOM | 1367 | O | GLU | 339 | -3.720 | -16.421 | 21.777 | 1.00 | 29.51 |
| ATOM | 1368 | N | LYS | 340 | -5.959 | -16.536 | 22.009 | 1.00 | 24.19 |
| ATOM | 1369 | CA | LYS | 340 | -6.168 | -17.256 | 20.755 | 1.00 | 24.19 |
| ATOM | 1370 | CB | LYS | 340 | -7.627 | -17.671 | 20.624 | 1.00 | 23.97 |
| ATOM | 1371 | C | LYS | 340 | -5.754 | -16.377 | 19.576 | 1.00 | 24.19 |
| ATOM | 1372 | O | LYS | 340 | -5.197 | -16.860 | 18.586 | 1.00 | 23.97 |
| ATOM | 1373 | N | SER | 341 | -6.000 | -15.079 | 19.708 | 1.00 | 16.85 |
| ATOM | 1374 | CA | SER | 341 | -5.651 | -14.115 | 18.676 | 1.00 | 16.85 |
| ATOM | 1375 | CB | SER | 341 | -6.223 | -12.744 | 19.033 | 1.00 | 26.59 |
| ATOM | 1376 | OG | SER | 341 | -5.852 | -11.765 | 18.080 | 1.00 | 26.59 |
| ATOM | 1377 | C | SER | 341 | -4.137 | -14.026 | 18.500 | 1.00 | 16.85 |
| ATOM | 1378 | O | SER | 341 | -3.638 | -14.042 | 17.374 | 1.00 | 26.59 |
| ATOM | 1379 | N | GLN | 342 | -3.406 | -13.932 | 19.608 | 1.00 | 17.35 |
| ATOM | 1380 | CA | GLN | 342 | -1.952 | -13.845 | 19.537 | 1.00 | 17.35 |
| ATOM | 1381 | CB | GLN | 342 | -1.337 | -13.597 | 20.913 | 1.00 | 30.07 |
| ATOM | 1382 | CG | GLN | 342 | 0.140 | -13.245 | 20.832 | 1.00 | 30.07 |
| ATOM | 1383 | CD | GLN | 342 | 0.811 | -13.196 | 22.182 | 1.00 | 30.07 |
| ATOM | 1384 | OE1 | GLN | 342 | 0.884 | -14.201 | 22.884 | 1.00 | 30.07 |
| ATOM | 1385 | NE2 | GLN | 342 | 1.318 | -12.030 | 22.548 | 1.00 | 30.07 |
| ATOM | 1386 | C | GLN | 342 | -1.368 | -15.118 | 18.944 | 1.00 | 17.35 |
| ATOM | 1387 | O | GLN | 342 | -0.405 | -15.066 | 18.178 | 1.00 | 30.07 |
| ATOM | 1388 | N | GLU | 343 | -1.949 | -16.260 | 19.303 | 1.00 | 18.35 |
| ATOM | 1389 | CA | GLU | 343 | -1.489 | -17.546 | 18.791 | 1.00 | 18.35 |
| ATOM | 1390 | CB | GLU | 343 | -2.308 | -18.676 | 19.394 | 1.00 | 16.98 |
| ATOM | 1391 | C | GLU | 343 | -1.603 | -17.560 | 17.267 | 1.00 | 18.35 |
| ATOM | 1392 | O | GLU | 343 | -0.699 | -18.026 | 16.568 | 1.00 | 16.98 |
| ATOM | 1393 | N | ALA | 344 | -2.706 | -17.017 | 16.761 | 1.00 | 14.83 |
| ATOM | 1394 | CA | ALA | 344 | -2.946 | -16.948 | 15.324 | 1.00 | 14.83 |
| ATOM | 1395 | CB | ALA | 344 | -4.327 | -16.376 | 15.049 | 1.00 | 19.42 |
| ATOM | 1396 | C | ALA | 344 | -1.872 | -16.102 | 14.640 | 1.00 | 14.83 |
| ATOM | 1397 | O | ALA | 344 | -1.311 | -16.507 | 13.619 | 1.00 | 19.42 |
| ATOM | 1398 | N | TYR | 345 | -1.586 | -14.934 | 15.211 | 1.00 | 13.10 |
| ATOM | 1399 | CA | TYR | 345 | -0.569 | -14.041 | 14.665 | 1.00 | 13.10 |
| ATOM | 1400 | CB | TYR | 345 | -0.573 | -12.697 | 15.393 | 1.00 | 2.00 |
| ATOM | 1401 | CG | TYR | 345 | -1.670 | -11.767 | 14.938 | 1.00 | 2.00 |
| ATOM | 1402 | CD1 | TYR | 345 | -2.707 | -11.409 | 15.794 | 1.00 | 2.00 |
| ATOM | 1403 | CE1 | TYR | 345 | -3.722 | -10.562 | 15.377 | 1.00 | 2.00 |
| ATOM | 1404 | CD2 | TYR | 345 | -1.674 | -11.248 | 13.647 | 1.00 | 2.00 |
| ATOM | 1405 | CE2 | TYR | 345 | -2.683 | -10.398 | 13.219 | 1.00 | 2.00 |
| ATOM | 1406 | CZ | TYR | 345 | -3.706 | -10.061 | 14.087 | 1.00 | 2.00 |
| ATOM | 1407 | OH | TYR | 345 | -4.722 | -9.233 | 13.669 | 1.00 | 2.00 |
| ATOM | 1408 | C | TYR | 345 | 0.818 | -14.666 | 14.732 | 1.00 | 13.10 |
| ATOM | 1409 | O | TYR | 345 | 1.614 | -14.504 | 13.811 | 1.00 | 2.00 |

FIG. 29A-29

| ATOM | 1410 | N | LEU | 346 | 1.101 | -15.387 | 15.813 | 1.00 | 12.59 |
| ATOM | 1411 | CA | LEU | 346 | 2.396 | -16.041 | 15.976 | 1.00 | 12.59 |
| ATOM | 1412 | CB | LEU | 346 | 2.498 | -16.715 | 17.347 | 1.00 | 22.61 |
| ATOM | 1413 | CG | LEU | 346 | 2.899 | -15.799 | 18.504 | 1.00 | 22.61 |
| ATOM | 1414 | CD1 | LEU | 346 | 2.717 | -16.511 | 19.830 | 1.00 | 22.61 |
| ATOM | 1415 | CD2 | LEU | 346 | 4.341 | -15.357 | 18.324 | 1.00 | 22.61 |
| ATOM | 1416 | C | LEU | 346 | 2.629 | -17.057 | 14.865 | 1.00 | 12.59 |
| ATOM | 1417 | O | LEU | 346 | 3.706 | -17.099 | 14.272 | 1.00 | 22.61 |
| ATOM | 1418 | N | LEU | 347 | 1.612 | -17.862 | 14.574 | 1.00 | 18.42 |
| ATOM | 1419 | CA | LEU | 347 | 1.706 | -18.863 | 13.517 | 1.00 | 18.42 |
| ATOM | 1420 | CB | LEU | 347 | 0.471 | -19.762 | 13.512 | 1.00 | 23.56 |
| ATOM | 1421 | CG | LEU | 347 | 0.509 | -20.965 | 14.456 | 1.00 | 23.56 |
| ATOM | 1422 | CD1 | LEU | 347 | -0.819 | -21.702 | 14.398 | 1.00 | 23.56 |
| ATOM | 1423 | CD2 | LEU | 347 | 1.659 | -21.890 | 14.068 | 1.00 | 23.56 |
| ATOM | 1424 | C | LEU | 347 | 1.870 | -18.201 | 12.154 | 1.00 | 18.42 |
| ATOM | 1425 | O | LEU | 347 | 2.672 | -18.651 | 11.330 | 1.00 | 23.56 |
| ATOM | 1426 | N | ALA | 348 | 1.099 | -17.144 | 11.917 | 1.00 | 12.49 |
| ATOM | 1427 | CA | ALA | 348 | 1.157 | -16.403 | 10.663 | 1.00 | 12.49 |
| ATOM | 1428 | CB | ALA | 348 | 0.098 | -15.302 | 10.654 | 1.00 | 14.77 |
| ATOM | 1429 | C | ALA | 348 | 2.545 | -15.798 | 10.504 | 1.00 | 12.49 |
| ATOM | 1430 | O | ALA | 348 | 3.154 | -15.874 | 9.436 | 1.00 | 14.77 |
| ATOM | 1431 | N | PHE | 349 | 3.048 | -15.246 | 11.602 | 1.00 | 15.52 |
| ATOM | 1432 | CA | PHE | 349 | 4.357 | -14.613 | 11.664 | 1.00 | 15.52 |
| ATOM | 1433 | CB | PHE | 349 | 4.566 | -14.049 | 13.076 | 1.00 | 14.41 |
| ATOM | 1434 | CG | PHE | 349 | 5.714 | -13.085 | 13.203 | 1.00 | 14.41 |
| ATOM | 1435 | CD1 | PHE | 349 | 6.473 | -12.712 | 12.099 | 1.00 | 14.41 |
| ATOM | 1436 | CD2 | PHE | 349 | 6.027 | -12.540 | 14.443 | 1.00 | 14.41 |
| ATOM | 1437 | CE1 | PHE | 349 | 7.523 | -11.813 | 12.230 | 1.00 | 14.41 |
| ATOM | 1438 | CE2 | PHE | 349 | 7.075 | -11.640 | 14.584 | 1.00 | 14.41 |
| ATOM | 1439 | CZ | PHE | 349 | 7.825 | -11.275 | 13.475 | 1.00 | 14.41 |
| ATOM | 1440 | C | PHE | 349 | 5.444 | -15.633 | 11.324 | 1.00 | 15.52 |
| ATOM | 1441 | O | PHE | 349 | 6.252 | -15.413 | 10.422 | 1.00 | 14.41 |
| ATOM | 1442 | N | GLU | 350 | 5.439 | -16.760 | 12.026 | 1.00 | 13.20 |
| ATOM | 1443 | CA | GLU | 350 | 6.424 | -17.811 | 11.801 | 1.00 | 13.20 |
| ATOM | 1444 | CB | GLU | 350 | 6.152 | -18.995 | 12.734 | 1.00 | 33.43 |
| ATOM | 1445 | CG | GLU | 350 | 7.068 | -20.193 | 12.519 | 1.00 | 33.43 |
| ATOM | 1446 | CD | GLU | 350 | 6.786 | -21.331 | 13.482 | 1.00 | 33.43 |
| ATOM | 1447 | OE1 | GLU | 350 | 7.746 | -22.035 | 13.857 | 1.00 | 33.43 |
| ATOM | 1448 | OE2 | GLU | 350 | 5.611 | -21.525 | 13.865 | 1.00 | 33.43 |
| ATOM | 1449 | C | GLU | 350 | 6.409 | -18.283 | 10.352 | 1.00 | 13.20 |
| ATOM | 1450 | O | GLU | 350 | 7.449 | -18.355 | 9.694 | 1.00 | 33.43 |
| ATOM | 1451 | N | HIS | 351 | 5.217 | -18.573 | 9.850 | 1.00 | 19.10 |
| ATOM | 1452 | CA | HIS | 351 | 5.062 | -19.051 | 8.485 | 1.00 | 19.10 |
| ATOM | 1453 | CB | HIS | 351 | 3.632 | -19.536 | 8.256 | 1.00 | 18.97 |
| ATOM | 1454 | CG | HIS | 351 | 3.249 | -20.700 | 9.117 | 1.00 | 18.97 |
| ATOM | 1455 | CD2 | HIS | 351 | 3.987 | -21.474 | 9.948 | 1.00 | 18.97 |
| ATOM | 1456 | ND1 | HIS | 351 | 1.960 | -21.180 | 9.194 | 1.00 | 18.97 |
| ATOM | 1457 | CE1 | HIS | 351 | 1.918 | -22.195 | 10.039 | 1.00 | 18.97 |
| ATOM | 1458 | NE2 | HIS | 351 | 3.134 | -22.394 | 10.509 | 1.00 | 18.97 |
| ATOM | 1459 | C | HIS | 351 | 5.477 | -18.011 | 7.449 | 1.00 | 19.10 |

FIG. 29A-30

| ATOM | 1460 | O | HIS | 351 | 5.955 | -18.366 | 6.371 | 1.00 | 18.97 |
| ATOM | 1461 | N | TYR | 352 | 5.304 | -16.732 | 7.767 | 1.00 | 9.38 |
| ATOM | 1462 | CA | TYR | 352 | 5.711 | -15.683 | 6.843 | 1.00 | 9.38 |
| ATOM | 1463 | CB | TYR | 352 | 5.168 | -14.317 | 7.257 | 1.00 | 16.06 |
| ATOM | 1464 | CG | TYR | 352 | 5.539 | -13.238 | 6.268 | 1.00 | 16.06 |
| ATOM | 1465 | CD1 | TYR | 352 | 4.939 | -13.190 | 5.008 | 1.00 | 16.06 |
| ATOM | 1466 | CE1 | TYR | 352 | 5.321 | -12.242 | 4.060 | 1.00 | 16.06 |
| ATOM | 1467 | CD2 | TYR | 352 | 6.531 | -12.303 | 6.562 | 1.00 | 16.06 |
| ATOM | 1468 | CE2 | TYR | 352 | 6.923 | -11.349 | 5.620 | 1.00 | 16.06 |
| ATOM | 1469 | CZ | TYR | 352 | 6.313 | -11.326 | 4.371 | 1.00 | 16.06 |
| ATOM | 1470 | OH | TYR | 352 | 6.710 | -10.401 | 3.431 | 1.00 | 16.06 |
| ATOM | 1471 | C | TYR | 352 | 7.234 | -15.639 | 6.812 | 1.00 | 9.38 |
| ATOM | 1472 | O | TYR | 352 | 7.838 | -15.475 | 5.751 | 1.00 | 16.06 |
| ATOM | 1473 | N | VAL | 353 | 7.851 | -15.789 | 7.980 | 1.00 | 15.38 |
| ATOM | 1474 | CA | VAL | 353 | 9.305 | -15.790 | 8.087 | 1.00 | 15.38 |
| ATOM | 1475 | CB | VAL | 353 | 9.761 | -15.945 | 9.558 | 1.00 | 18.40 |
| ATOM | 1476 | CG1 | VAL | 353 | 11.262 | -16.163 | 9.633 | 1.00 | 18.40 |
| ATOM | 1477 | CG2 | VAL | 353 | 9.384 | -14.703 | 10.349 | 1.00 | 18.40 |
| ATOM | 1478 | C | VAL | 353 | 9.853 | -16.938 | 7.237 | 1.00 | 15.38 |
| ATOM | 1479 | O | VAL | 353 | 10.850 | -16.773 | 6.525 | 1.00 | 18.40 |
| ATOM | 1480 | N | ASN | 354 | 9.183 | -18.086 | 7.298 | 1.00 | 14.74 |
| ATOM | 1481 | CA | ASN | 354 | 9.578 | -19.259 | 6.521 | 1.00 | 14.74 |
| ATOM | 1482 | CB | ASN | 354 | 8.640 | -20.435 | 6.799 | 1.00 | 19.97 |
| ATOM | 1483 | CG | ASN | 354 | 8.832 | -21.020 | 8.180 | 1.00 | 19.97 |
| ATOM | 1484 | OD1 | ASN | 354 | 9.879 | -20.848 | 8.799 | 1.00 | 19.97 |
| ATOM | 1485 | ND2 | ASN | 354 | 7.826 | -21.734 | 8.664 | 1.00 | 19.97 |
| ATOM | 1486 | C | ASN | 354 | 9.550 | -18.939 | 5.034 | 1.00 | 14.74 |
| ATOM | 1487 | O | ASN | 354 | 10.452 | -19.319 | 4.290 | 1.00 | 19.97 |
| ATOM | 1488 | N | HIS | 355 | 8.507 | -18.230 | 4.613 | 1.00 | 13.03 |
| ATOM | 1489 | CA | HIS | 355 | 8.329 | -17.837 | 3.220 | 1.00 | 13.03 |
| ATOM | 1490 | CB | HIS | 355 | 6.960 | -17.164 | 3.042 | 1.00 | 24.39 |
| ATOM | 1491 | CG | HIS | 355 | 6.753 | -16.541 | 1.695 | 1.00 | 24.39 |
| ATOM | 1492 | CD2 | HIS | 355 | 7.195 | -15.370 | 1.176 | 1.00 | 24.39 |
| ATOM | 1493 | ND1 | HIS | 355 | 6.009 | -17.138 | 0.701 | 1.00 | 24.39 |
| ATOM | 1494 | CE1 | HIS | 355 | 6.005 | -16.368 | -0.372 | 1.00 | 24.39 |
| ATOM | 1495 | NE2 | HIS | 355 | 6.720 | -15.289 | -0.107 | 1.00 | 24.39 |
| ATOM | 1496 | C | HIS | 355 | 9.434 | -16.894 | 2.758 | 1.00 | 13.03 |
| ATOM | 1497 | O | HIS | 355 | 9.834 | -16.920 | 1.595 | 1.00 | 24.39 |
| ATOM | 1498 | N | ARG | 356 | 9.878 | -16.027 | 3.660 | 1.00 | 19.55 |
| ATOM | 1499 | CA | ARG | 356 | 10.920 | -15.054 | 3.358 | 1.00 | 19.55 |
| ATOM | 1500 | CB | ARG | 356 | 10.970 | -14.001 | 4.460 | 1.00 | 22.01 |
| ATOM | 1501 | CG | ARG | 356 | 9.772 | -13.081 | 4.454 | 1.00 | 22.01 |
| ATOM | 1502 | CD | ARG | 356 | 10.097 | -11.784 | 3.750 | 1.00 | 22.01 |
| ATOM | 1503 | NE | ARG | 356 | 10.932 | -10.934 | 4.592 | 1.00 | 22.01 |
| ATOM | 1504 | CZ | ARG | 356 | 11.822 | -10.059 | 4.137 | 1.00 | 22.01 |
| ATOM | 1505 | NH1 | ARG | 356 | 12.010 | -9.907 | 2.833 | 1.00 | 22.01 |
| ATOM | 1506 | NH2 | ARG | 356 | 12.519 | -9.325 | 4.992 | 1.00 | 22.01 |
| ATOM | 1507 | C | ARG | 356 | 12.297 | -15.675 | 3.158 | 1.00 | 19.55 |
| ATOM | 1508 | O | ARG | 356 | 13.127 | -15.126 | 2.434 | 1.00 | 22.01 |
| ATOM | 1509 | N | LYS | 357 | 12.547 | -16.788 | 3.841 | 1.00 | 23.18 |

FIG. 29A-31

| ATOM | 1510 | CA | LYS | 357 | 13.815 | -17.504 | 3.739 | 1.00 | 23.18 |
| --- | --- | --- | --- | --- | --- | --- | --- | --- | --- |
| ATOM | 1511 | CB | LYS | 357 | 13.879 | -18.273 | 2.415 | 1.00 | 42.91 |
| ATOM | 1512 | CG | LYS | 357 | 12.750 | -19.277 | 2.274 | 1.00 | 42.91 |
| ATOM | 1513 | CD | LYS | 357 | 12.773 | -20.021 | 0.960 | 1.00 | 42.91 |
| ATOM | 1514 | CE | LYS | 357 | 11.619 | -21.011 | 0.913 | 1.00 | 42.91 |
| ATOM | 1515 | NZ | LYS | 357 | 11.629 | -21.845 | -0.316 | 1.00 | 42.91 |
| ATOM | 1516 | C | LYS | 357 | 15.047 | -16.619 | 3.918 | 1.00 | 23.18 |
| ATOM | 1517 | O | LYS | 357 | 15.816 | -16.396 | 2.982 | 1.00 | 42.91 |
| ATOM | 1518 | N | HIS | 358 | 15.228 | -16.122 | 5.137 | 1.00 | 32.39 |
| ATOM | 1519 | CA | HIS | 358 | 16.367 | -15.272 | 5.460 | 1.00 | 32.39 |
| ATOM | 1520 | CB | HIS | 358 | 16.181 | -14.626 | 6.835 | 1.00 | 26.77 |
| ATOM | 1521 | CG | HIS | 358 | 15.232 | -13.468 | 6.841 | 1.00 | 26.77 |
| ATOM | 1522 | CD2 | HIS | 358 | 15.452 | -12.138 | 6.709 | 1.00 | 26.77 |
| ATOM | 1523 | ND1 | HIS | 358 | 13.875 | -13.615 | 7.028 | 1.00 | 26.77 |
| ATOM | 1524 | CE1 | HIS | 358 | 13.300 | -12.426 | 7.012 | 1.00 | 26.77 |
| ATOM | 1525 | NE2 | HIS | 358 | 14.234 | -11.513 | 6.821 | 1.00 | 26.77 |
| ATOM | 1526 | C | HIS | 358 | 17.633 | -16.115 | 5.480 | 1.00 | 32.39 |
| ATOM | 1527 | O | HIS | 358 | 17.618 | -17.248 | 5.961 | 1.00 | 26.77 |
| ATOM | 1528 | N | ASN | 359 | 18.728 | -15.561 | 4.972 | 1.00 | 41.97 |
| ATOM | 1529 | CA | ASN | 359 | 20.000 | -16.273 | 4.959 | 1.00 | 41.97 |
| ATOM | 1530 | CB | ASN | 359 | 20.909 | -15.716 | 3.863 | 1.00 | 46.84 |
| ATOM | 1531 | C | ASN | 359 | 20.663 | -16.134 | 6.331 | 1.00 | 41.97 |
| ATOM | 1532 | O | ASN | 359 | 21.821 | -15.731 | 6.436 | 1.00 | 46.84 |
| ATOM | 1533 | N | ILE | 360 | 19.908 | -16.450 | 7.379 | 1.00 | 35.72 |
| ATOM | 1534 | CA | ILE | 360 | 20.394 | -16.359 | 8.753 | 1.00 | 35.72 |
| ATOM | 1535 | CB | ILE | 360 | 19.819 | -15.113 | 9.480 | 1.00 | 36.14 |
| ATOM | 1536 | CG2 | ILE | 360 | 20.327 | -15.050 | 10.918 | 1.00 | 36.14 |
| ATOM | 1537 | CG1 | ILE | 360 | 20.204 | -13.833 | 8.734 | 1.00 | 36.14 |
| ATOM | 1538 | CD1 | ILE | 360 | 19.526 | -12.591 | 9.265 | 1.00 | 36.14 |
| ATOM | 1539 | C | ILE | 360 | 19.935 | -17.611 | 9.493 | 1.00 | 35.72 |
| ATOM | 1540 | O | ILE | 360 | 18.748 | -17.953 | 9.479 | 1.00 | 36.14 |
| ATOM | 1541 | N | PRO | 361 | 20.877 | -18.338 | 10.109 | 1.00 | 31.56 |
| ATOM | 1542 | CD | PRO | 361 | 22.334 | -18.114 | 10.100 | 1.00 | 33.50 |
| ATOM | 1543 | CA | PRO | 361 | 20.532 | -19.556 | 10.847 | 1.00 | 31.56 |
| ATOM | 1544 | CB | PRO | 361 | 21.901 | -20.163 | 11.161 | 1.00 | 33.50 |
| ATOM | 1545 | CG | PRO | 361 | 22.801 | -18.967 | 11.249 | 1.00 | 33.50 |
| ATOM | 1546 | C | PRO | 361 | 19.743 | -19.256 | 12.121 | 1.00 | 31.56 |
| ATOM | 1547 | O | PRO | 361 | 20.080 | -18.338 | 12.867 | 1.00 | 33.50 |
| ATOM | 1548 | N | HIS | 362 | 18.688 | -20.034 | 12.355 | 1.00 | 18.84 |
| ATOM | 1549 | CA | HIS | 362 | 17.840 | -19.887 | 13.541 | 1.00 | 18.84 |
| ATOM | 1550 | CB | HIS | 362 | 18.656 | -20.151 | 14.812 | 1.00 | 31.38 |
| ATOM | 1551 | CG | HIS | 362 | 19.540 | -21.357 | 14.731 | 1.00 | 31.38 |
| ATOM | 1552 | CD2 | HIS | 362 | 19.250 | -22.667 | 14.537 | 1.00 | 31.38 |
| ATOM | 1553 | ND1 | HIS | 362 | 20.910 | -21.286 | 14.860 | 1.00 | 31.38 |
| ATOM | 1554 | CE1 | HIS | 362 | 21.427 | -22.497 | 14.754 | 1.00 | 31.38 |
| ATOM | 1555 | NE2 | HIS | 362 | 20.439 | -23.353 | 14.558 | 1.00 | 31.38 |
| ATOM | 1556 | C | HIS | 362 | 17.189 | -18.506 | 13.628 | 1.00 | 18.84 |
| ATOM | 1557 | O | HIS | 362 | 16.980 | -17.979 | 14.723 | 1.00 | 31.38 |
| ATOM | 1558 | N | PHE | 363 | 16.825 | -17.950 | 12.476 | 1.00 | 18.69 |
| ATOM | 1559 | CA | PHE | 363 | 16.209 | -16.630 | 12.408 | 1.00 | 18.69 |

FIG. 29A-32

| ATOM | 1560 | CB | PHE | 363 | 15.825 | -16.302 | 10.962 | 1.00 | 19.25 |
| ATOM | 1561 | CG | PHE | 363 | 15.339 | -14.894 | 10.765 | 1.00 | 19.25 |
| ATOM | 1562 | CD1 | PHE | 363 | 16.239 | -13.862 | 10.530 | 1.00 | 19.25 |
| ATOM | 1563 | CD2 | PHE | 363 | 13.981 | -14.598 | 10.819 | 1.00 | 19.25 |
| ATOM | 1564 | CE1 | PHE | 363 | 15.794 | -12.556 | 10.351 | 1.00 | 19.25 |
| ATOM | 1565 | CE2 | PHE | 363 | 13.527 | -13.296 | 10.642 | 1.00 | 19.25 |
| ATOM | 1566 | CZ | PHE | 363 | 14.435 | -12.273 | 10.407 | 1.00 | 19.25 |
| ATOM | 1567 | C | PHE | 363 | 14.995 | -16.461 | 13.323 | 1.00 | 18.69 |
| ATOM | 1568 | O | PHE | 363 | 14.955 | -15.540 | 14.138 | 1.00 | 19.25 |
| ATOM | 1569 | N | TRP | 364 | 14.016 | -17.351 | 13.191 | 1.00 | 16.46 |
| ATOM | 1570 | CA | TRP | 364 | 12.797 | -17.280 | 13.995 | 1.00 | 16.46 |
| ATOM | 1571 | CB | TRP | 364 | 11.882 | -18.482 | 13.706 | 1.00 | 17.81 |
| ATOM | 1572 | CG | TRP | 364 | 10.588 | -18.488 | 14.481 | 1.00 | 17.81 |
| ATOM | 1573 | CD2 | TRP | 364 | 9.586 | -17.458 | 14.504 | 1.00 | 17.81 |
| ATOM | 1574 | CE2 | TRP | 364 | 8.547 | -17.905 | 15.350 | 1.00 | 17.81 |
| ATOM | 1575 | CE3 | TRP | 364 | 9.467 | -16.202 | 13.894 | 1.00 | 17.81 |
| ATOM | 1576 | CD1 | TRP | 364 | 10.126 | -19.486 | 15.290 | 1.00 | 17.81 |
| ATOM | 1577 | NE1 | TRP | 364 | 8.902 | -19.144 | 15.814 | 1.00 | 17.81 |
| ATOM | 1578 | CZ2 | TRP | 364 | 7.403 | -17.142 | 15.602 | 1.00 | 17.81 |
| ATOM | 1579 | CZ3 | TRP | 364 | 8.329 | -15.444 | 14.145 | 1.00 | 17.81 |
| ATOM | 1580 | CH2 | TRP | 364 | 7.312 | -15.919 | 14.992 | 1.00 | 17.81 |
| ATOM | 1581 | C | TRP | 364 | 13.046 | -17.114 | 15.500 | 1.00 | 16.46 |
| ATOM | 1582 | O | TRP | 364 | 12.595 | -16.133 | 16.087 | 1.00 | 17.81 |
| ATOM | 1583 | N | PRO | 365 | 13.779 | -18.051 | 16.137 | 1.00 | 18.31 |
| ATOM | 1584 | CD | PRO | 365 | 14.342 | -19.314 | 15.625 | 1.00 | 25.61 |
| ATOM | 1585 | CA | PRO | 365 | 14.038 | -17.920 | 17.577 | 1.00 | 18.31 |
| ATOM | 1586 | CB | PRO | 365 | 14.939 | -19.118 | 17.874 | 1.00 | 25.61 |
| ATOM | 1587 | CG | PRO | 365 | 14.500 | -20.130 | 16.882 | 1.00 | 25.61 |
| ATOM | 1588 | C | PRO | 365 | 14.732 | -16.606 | 17.933 | 1.00 | 18.31 |
| ATOM | 1589 | O | PRO | 365 | 14.387 | -15.963 | 18.926 | 1.00 | 25.61 |
| ATOM | 1590 | N | LYS | 366 | 15.699 | -16.207 | 17.112 | 1.00 | 25.16 |
| ATOM | 1591 | CA | LYS | 366 | 16.439 | -14.968 | 17.338 | 1.00 | 25.16 |
| ATOM | 1592 | CB | LYS | 366 | 17.537 | -14.805 | 16.289 | 1.00 | 40.51 |
| ATOM | 1593 | CG | LYS | 366 | 18.679 | -15.792 | 16.417 | 1.00 | 40.51 |
| ATOM | 1594 | CD | LYS | 366 | 19.664 | -15.607 | 15.278 | 1.00 | 40.51 |
| ATOM | 1595 | CE | LYS | 366 | 20.884 | -16.492 | 15.440 | 1.00 | 40.51 |
| ATOM | 1596 | NZ | LYS | 366 | 21.800 | -16.360 | 14.275 | 1.00 | 40.51 |
| ATOM | 1597 | C | LYS | 366 | 15.521 | -13.747 | 17.317 | 1.00 | 25.16 |
| ATOM | 1598 | O | LYS | 366 | 15.593 | -12.893 | 18.202 | 1.00 | 40.51 |
| ATOM | 1599 | N | LEU | 367 | 14.661 | -13.666 | 16.307 | 1.00 | 25.30 |
| ATOM | 1600 | CA | LEU | 367 | 13.729 | -12.551 | 16.184 | 1.00 | 25.30 |
| ATOM | 1601 | CB | LEU | 367 | 12.989 | -12.620 | 14.845 | 1.00 | 27.80 |
| ATOM | 1602 | CG | LEU | 367 | 11.964 | -11.519 | 14.561 | 1.00 | 27.80 |
| ATOM | 1603 | CD1 | LEU | 367 | 12.621 | -10.147 | 14.679 | 1.00 | 27.80 |
| ATOM | 1604 | CD2 | LEU | 367 | 11.367 | -11.724 | 13.175 | 1.00 | 27.80 |
| ATOM | 1605 | C | LEU | 367 | 12.730 | -12.596 | 17.332 | 1.00 | 25.30 |
| ATOM | 1606 | O | LEU | 367 | 12.337 | -11.563 | 17.877 | 1.00 | 27.80 |
| ATOM | 1607 | N | LEU | 368 | 12.345 | -13.807 | 17.712 | 1.00 | 26.12 |
| ATOM | 1608 | CA | LEU | 368 | 11.396 | -14.019 | 18.793 | 1.00 | 26.12 |
| ATOM | 1609 | CB | LEU | 368 | 11.105 | -15.515 | 18.919 | 1.00 | 33.27 |

FIG. 29A-33

| ATOM | 1610 | CG | LEU | 368 | 9.696 | -15.976 | 19.289 | 1.00 | 33.27 |
| --- | --- | --- | --- | --- | --- | --- | --- | --- | --- |
| ATOM | 1611 | CD1 | LEU | 368 | 8.640 | -15.182 | 18.529 | 1.00 | 33.27 |
| ATOM | 1612 | CD2 | LEU | 368 | 9.582 | -17.460 | 18.976 | 1.00 | 33.27 |
| ATOM | 1613 | C | LEU | 368 | 11.973 | -13.466 | 20.096 | 1.00 | 26.12 |
| ATOM | 1614 | O | LEU | 368 | 11.249 | -12.920 | 20.930 | 1.00 | 33.27 |
| ATOM | 1615 | N | MET | 369 | 13.289 | -13.571 | 20.244 | 1.00 | 24.39 |
| ATOM | 1616 | CA | MET | 369 | 13.971 | -13.076 | 21.432 | 1.00 | 24.39 |
| ATOM | 1617 | CB | MET | 369 | 15.382 | -13.656 | 21.511 | 1.00 | 47.44 |
| ATOM | 1618 | CG | MET | 369 | 15.407 | -15.096 | 22.009 | 1.00 | 47.44 |
| ATOM | 1619 | SD | MET | 369 | 16.850 | -16.029 | 21.464 | 1.00 | 47.44 |
| ATOM | 1620 | CE | MET | 369 | 18.186 | -15.114 | 22.246 | 1.00 | 47.44 |
| ATOM | 1621 | C | MET | 369 | 13.996 | -11.552 | 21.491 | 1.00 | 24.39 |
| ATOM | 1622 | O | MET | 369 | 14.212 | -10.971 | 22.557 | 1.00 | 47.44 |
| ATOM | 1623 | N | LYS | 370 | 13.749 | -10.904 | 20.354 | 1.00 | 27.31 |
| ATOM | 1624 | CA | LYS | 370 | 13.713 | -9.445 | 20.297 | 1.00 | 27.31 |
| ATOM | 1625 | CB | LYS | 370 | 13.739 | -8.951 | 18.847 | 1.00 | 28.20 |
| ATOM | 1626 | CG | LYS | 370 | 15.004 | -9.312 | 18.090 | 1.00 | 28.20 |
| ATOM | 1627 | CD | LYS | 370 | 16.231 | -8.810 | 18.824 | 1.00 | 28.20 |
| ATOM | 1628 | CE | LYS | 370 | 17.512 | -9.244 | 18.142 | 1.00 | 28.20 |
| ATOM | 1629 | NZ | LYS | 370 | 18.696 | -8.851 | 18.952 | 1.00 | 28.20 |
| ATOM | 1630 | C | LYS | 370 | 12.453 | -8.945 | 21.002 | 1.00 | 27.31 |
| ATOM | 1631 | O | LYS | 370 | 12.424 | -7.835 | 21.535 | 1.00 | 28.20 |
| ATOM | 1632 | N | VAL | 371 | 11.413 | -9.776 | 21.009 | 1.00 | 26.41 |
| ATOM | 1633 | CA | VAL | 371 | 10.157 | -9.432 | 21.668 | 1.00 | 26.41 |
| ATOM | 1634 | CB | VAL | 371 | 9.109 | -10.561 | 21.512 | 1.00 | 25.61 |
| ATOM | 1635 | CG1 | VAL | 371 | 7.825 | -10.205 | 22.245 | 1.00 | 25.61 |
| ATOM | 1636 | CG2 | VAL | 371 | 8.819 | -10.805 | 20.044 | 1.00 | 25.61 |
| ATOM | 1637 | C | VAL | 371 | 10.450 | -9.205 | 23.151 | 1.00 | 26.41 |
| ATOM | 1638 | O | VAL | 371 | 9.962 | -8.248 | 23.752 | 1.00 | 25.61 |
| ATOM | 1639 | N | THR | 372 | 11.294 | -10.065 | 23.713 | 1.00 | 26.28 |
| ATOM | 1640 | CA | THR | 372 | 11.683 | -9.972 | 25.116 | 1.00 | 26.28 |
| ATOM | 1641 | CB | THR | 372 | 12.656 | -11.109 | 25.500 | 1.00 | 28.14 |
| ATOM | 1642 | OG1 | THR | 372 | 12.025 | -12.377 | 25.275 | 1.00 | 28.14 |
| ATOM | 1643 | CG2 | THR | 372 | 13.055 | -11.001 | 26.965 | 1.00 | 28.14 |
| ATOM | 1644 | C | THR | 372 | 12.358 | -8.624 | 25.372 | 1.00 | 26.28 |
| ATOM | 1645 | O | THR | 372 | 12.047 | -7.937 | 26.350 | 1.00 | 28.14 |
| ATOM | 1646 | N | ASP | 373 | 13.269 | -8.247 | 24.478 | 1.00 | 15.09 |
| ATOM | 1647 | CA | ASP | 373 | 13.977 | -6.979 | 24.588 | 1.00 | 15.09 |
| ATOM | 1648 | CB | ASP | 373 | 14.976 | -6.822 | 23.435 | 1.00 | 37.94 |
| ATOM | 1649 | CG | ASP | 373 | 16.065 | -7.893 | 23.445 | 1.00 | 37.94 |
| ATOM | 1650 | OD1 | ASP | 373 | 16.248 | -8.571 | 24.483 | 1.00 | 37.94 |
| ATOM | 1651 | OD2 | ASP | 373 | 16.750 | -8.052 | 22.410 | 1.00 | 37.94 |
| ATOM | 1652 | C | ASP | 373 | 12.969 | -5.833 | 24.577 | 1.00 | 15.09 |
| ATOM | 1653 | O | ASP | 373 | 13.040 | -4.928 | 25.407 | 1.00 | 37.94 |
| ATOM | 1654 | N | LEU | 374 | 12.008 | -5.901 | 23.659 | 1.00 | 17.04 |
| ATOM | 1655 | CA | LEU | 374 | 10.974 | -4.880 | 23.549 | 1.00 | 17.04 |
| ATOM | 1656 | CB | LEU | 374 | 10.071 | -5.155 | 22.344 | 1.00 | 20.58 |
| ATOM | 1657 | CG | LEU | 374 | 10.624 | -4.720 | 20.985 | 1.00 | 20.58 |
| ATOM | 1658 | CD1 | LEU | 374 | 9.826 | -5.352 | 19.862 | 1.00 | 20.58 |
| ATOM | 1659 | CD2 | LEU | 374 | 10.599 | -3.202 | 20.882 | 1.00 | 20.58 |

FIG. 29A-34

| ATOM | 1660 | C | LEU | 374 | 10.145 | -4.786 | 24.825 | 1.00 | 17.04 |
| --- | --- | --- | --- | --- | --- | --- | --- | --- | --- |
| ATOM | 1661 | O | LEU | 374 | 9.783 | -3.688 | 25.256 | 1.00 | 20.58 |
| ATOM | 1662 | N | ARG | 375 | 9.850 | -5.935 | 25.430 | 1.00 | 20.46 |
| ATOM | 1663 | CA | ARG | 375 | 9.080 | -5.977 | 26.673 | 1.00 | 20.46 |
| ATOM | 1664 | CB | ARG | 375 | 8.873 | -7.422 | 27.140 | 1.00 | 55.89 |
| ATOM | 1665 | CG | ARG | 375 | 8.180 | -8.354 | 26.152 | 1.00 | 55.89 |
| ATOM | 1666 | CD | ARG | 375 | 6.692 | -8.084 | 26.027 | 1.00 | 55.89 |
| ATOM | 1667 | NE | ARG | 375 | 5.943 | -9.338 | 25.968 | 1.00 | 55.89 |
| ATOM | 1668 | CZ | ARG | 375 | 5.054 | -9.654 | 25.028 | 1.00 | 55.89 |
| ATOM | 1669 | NH1 | ARG | 375 | 4.782 | -8.808 | 24.040 | 1.00 | 55.89 |
| ATOM | 1670 | NH2 | ARG | 375 | 4.438 | -10.829 | 25.073 | 1.00 | 55.89 |
| ATOM | 1671 | C | ARG | 375 | 9.874 | -5.221 | 27.735 | 1.00 | 20.46 |
| ATOM | 1672 | O | ARG | 375 | 9.328 | -4.391 | 28.463 | 1.00 | 55.89 |
| ATOM | 1673 | N | MET | 376 | 11.174 | -5.502 | 27.794 | 1.00 | 20.10 |
| ATOM | 1674 | CA | MET | 376 | 12.076 | -4.863 | 28.744 | 1.00 | 20.10 |
| ATOM | 1675 | CB | MET | 376 | 13.493 | -5.417 | 28.580 | 1.00 | 63.73 |
| ATOM | 1676 | CG | MET | 376 | 13.956 | -6.310 | 29.722 | 1.00 | 63.73 |
| ATOM | 1677 | SD | MET | 376 | 14.494 | -5.373 | 31.182 | 1.00 | 63.73 |
| ATOM | 1678 | CE | MET | 376 | 12.934 | -5.151 | 32.087 | 1.00 | 63.73 |
| ATOM | 1679 | C | MET | 376 | 12.081 | -3.347 | 28.566 | 1.00 | 20.10 |
| ATOM | 1680 | O | MET | 376 | 11.973 | -2.602 | 29.539 | 1.00 | 63.73 |
| ATOM | 1681 | N | ILE | 377 | 12.194 | -2.896 | 27.321 | 1.00 | 30.02 |
| ATOM | 1682 | CA | ILE | 377 | 12.198 | -1.469 | 27.014 | 1.00 | 30.02 |
| ATOM | 1683 | CB | ILE | 377 | 12.329 | -1.228 | 25.488 | 1.00 | 19.31 |
| ATOM | 1684 | CG2 | ILE | 377 | 12.088 | 0.242 | 25.152 | 1.00 | 19.31 |
| ATOM | 1685 | CG1 | ILE | 377 | 13.711 | -1.685 | 25.011 | 1.00 | 19.31 |
| ATOM | 1686 | CD1 | ILE | 377 | 13.906 | -1.634 | 23.507 | 1.00 | 19.31 |
| ATOM | 1687 | C | ILE | 377 | 10.915 | -0.821 | 27.542 | 1.00 | 30.02 |
| ATOM | 1688 | O | ILE | 377 | 10.962 | 0.216 | 28.211 | 1.00 | 19.31 |
| ATOM | 1689 | N | GLY | 378 | 9.779 | -1.455 | 27.266 | 1.00 | 21.85 |
| ATOM | 1690 | CA | GLY | 378 | 8.505 | -0.936 | 27.729 | 1.00 | 21.85 |
| ATOM | 1691 | C | GLY | 378 | 8.459 | -0.821 | 29.243 | 1.00 | 21.85 |
| ATOM | 1692 | O | GLY | 378 | 7.990 | 0.185 | 29.779 | 1.00 | 34.01 |
| ATOM | 1693 | N | ALA | 379 | 8.967 | -1.842 | 29.928 | 1.00 | 31.30 |
| ATOM | 1694 | CA | ALA | 379 | 8.996 | -1.870 | 31.388 | 1.00 | 31.30 |
| ATOM | 1695 | CB | ALA | 379 | 9.471 | -3.231 | 31.880 | 1.00 | 30.06 |
| ATOM | 1696 | C | ALA | 379 | 9.895 | -0.763 | 31.938 | 1.00 | 31.30 |
| ATOM | 1697 | O | ALA | 379 | 9.482 | 0.002 | 32.810 | 1.00 | 30.06 |
| ATOM | 1698 | N | CYS | 380 | 11.117 | -0.677 | 31.418 | 1.00 | 28.61 |
| ATOM | 1699 | CA | CYS | 380 | 12.067 | 0.349 | 31.841 | 1.00 | 28.61 |
| ATOM | 1700 | CB | CYS | 380 | 13.360 | 0.268 | 31.025 | 1.00 | 60.26 |
| ATOM | 1701 | SG | CYS | 380 | 14.499 | -1.067 | 31.470 | 1.00 | 60.26 |
| ATOM | 1702 | C | CYS | 380 | 11.449 | 1.730 | 31.658 | 1.00 | 28.61 |
| ATOM | 1703 | O | CYS | 380 | 11.516 | 2.573 | 32.554 | 1.00 | 60.26 |
| ATOM | 1704 | N | HIS | 381 | 10.840 | 1.957 | 30.498 | 1.00 | 30.42 |
| ATOM | 1705 | CA | HIS | 381 | 10.212 | 3.243 | 30.216 | 1.00 | 30.42 |
| ATOM | 1706 | CB | HIS | 381 | 9.696 | 3.306 | 28.779 | 1.00 | 16.49 |
| ATOM | 1707 | CG | HIS | 381 | 8.942 | 4.562 | 28.472 | 1.00 | 16.49 |
| ATOM | 1708 | CD2 | HIS | 381 | 9.370 | 5.805 | 28.151 | 1.00 | 16.49 |
| ATOM | 1709 | ND1 | HIS | 381 | 7.566 | 4.633 | 28.524 | 1.00 | 16.49 |

FIG. 29A-35

| ATOM | 1710 | CE1 | HIS | 381 | 7.180 | 5.866 | 28.251 | 1.00 | 16.49 |
|------|------|-----|-----|-----|-------|-------|--------|------|-------|
| ATOM | 1711 | NE2 | HIS | 381 | 8.255 | 6.596 | 28.021 | 1.00 | 16.49 |
| ATOM | 1712 | C | HIS | 381 | 9.073 | 3.539 | 31.182 | 1.00 | 30.42 |
| ATOM | 1713 | O | HIS | 381 | 8.856 | 4.690 | 31.552 | 1.00 | 16.49 |
| ATOM | 1714 | N | ALA | 382 | 8.330 | 2.506 | 31.564 | 1.00 | 22.89 |
| ATOM | 1715 | CA | ALA | 382 | 7.218 | 2.666 | 32.493 | 1.00 | 22.89 |
| ATOM | 1716 | CB | ALA | 382 | 6.520 | 1.336 | 32.708 | 1.00 | 34.50 |
| ATOM | 1717 | C | ALA | 382 | 7.738 | 3.213 | 33.819 | 1.00 | 22.89 |
| ATOM | 1718 | O | ALA | 382 | 7.219 | 4.200 | 34.343 | 1.00 | 34.50 |
| ATOM | 1719 | N | SER | 383 | 8.789 | 2.586 | 34.336 | 1.00 | 26.39 |
| ATOM | 1720 | CA | SER | 383 | 9.400 | 3.006 | 35.591 | 1.00 | 26.39 |
| ATOM | 1721 | CB | SER | 383 | 10.510 | 2.030 | 35.985 | 1.00 | 52.94 |
| ATOM | 1722 | OG | SER | 383 | 10.015 | 0.702 | 36.046 | 1.00 | 52.94 |
| ATOM | 1723 | C | SER | 383 | 9.966 | 4.418 | 35.470 | 1.00 | 26.39 |
| ATOM | 1724 | O | SER | 383 | 9.772 | 5.253 | 36.357 | 1.00 | 52.94 |
| ATOM | 1725 | N | ARG | 384 | 10.662 | 4.683 | 34.368 | 1.00 | 30.36 |
| ATOM | 1726 | CA | ARG | 384 | 11.249 | 5.995 | 34.134 | 1.00 | 30.36 |
| ATOM | 1727 | CB | ARG | 384 | 12.116 | 5.977 | 32.874 | 1.00 | 37.39 |
| ATOM | 1728 | CG | ARG | 384 | 12.601 | 7.344 | 32.431 | 1.00 | 37.39 |
| ATOM | 1729 | CD | ARG | 384 | 14.070 | 7.321 | 32.060 | 1.00 | 37.39 |
| ATOM | 1730 | NE | ARG | 384 | 14.935 | 7.597 | 33.204 | 1.00 | 37.39 |
| ATOM | 1731 | CZ | ARG | 384 | 15.750 | 8.646 | 33.291 | 1.00 | 37.39 |
| ATOM | 1732 | NH1 | ARG | 384 | 15.824 | 9.529 | 32.303 | 1.00 | 37.39 |
| ATOM | 1733 | NH2 | ARG | 384 | 16.488 | 8.819 | 34.376 | 1.00 | 37.39 |
| ATOM | 1734 | C | ARG | 384 | 10.169 | 7.067 | 34.030 | 1.00 | 30.36 |
| ATOM | 1735 | O | ARG | 384 | 10.301 | 8.144 | 34.616 | 1.00 | 37.39 |
| ATOM | 1736 | N | PHE | 385 | 9.078 | 6.749 | 33.338 | 1.00 | 24.47 |
| ATOM | 1737 | CA | PHE | 385 | 7.980 | 7.693 | 33.171 | 1.00 | 24.47 |
| ATOM | 1738 | CB | PHE | 385 | 6.859 | 7.092 | 32.319 | 1.00 | 28.70 |
| ATOM | 1739 | CG | PHE | 385 | 5.710 | 8.036 | 32.075 | 1.00 | 28.70 |
| ATOM | 1740 | CD1 | PHE | 385 | 5.795 | 9.017 | 31.092 | 1.00 | 28.70 |
| ATOM | 1741 | CD2 | PHE | 385 | 4.549 | 7.954 | 32.836 | 1.00 | 28.70 |
| ATOM | 1742 | CE1 | PHE | 385 | 4.740 | 9.903 | 30.874 | 1.00 | 28.70 |
| ATOM | 1743 | CE2 | PHE | 385 | 3.491 | 8.835 | 32.624 | 1.00 | 28.70 |
| ATOM | 1744 | CZ | PHE | 385 | 3.587 | 9.812 | 31.641 | 1.00 | 28.70 |
| ATOM | 1745 | C | PHE | 385 | 7.436 | 8.097 | 34.533 | 1.00 | 24.47 |
| ATOM | 1746 | O | PHE | 385 | 7.250 | 9.285 | 34.805 | 1.00 | 28.70 |
| ATOM | 1747 | N | LEU | 386 | 7.208 | 7.107 | 35.391 | 1.00 | 31.13 |
| ATOM | 1748 | CA | LEU | 386 | 6.690 | 7.352 | 36.734 | 1.00 | 31.13 |
| ATOM | 1749 | CB | LEU | 386 | 6.596 | 6.044 | 37.513 | 1.00 | 39.10 |
| ATOM | 1750 | C | LEU | 386 | 7.577 | 8.348 | 37.474 | 1.00 | 31.13 |
| ATOM | 1751 | O | LEU | 386 | 7.085 | 9.201 | 38.217 | 1.00 | 39.10 |
| ATOM | 1752 | N | HIS | 387 | 8.884 | 8.254 | 37.243 | 1.00 | 36.46 |
| ATOM | 1753 | CA | HIS | 387 | 9.837 | 9.152 | 37.881 | 1.00 | 36.46 |
| ATOM | 1754 | CB | HIS | 387 | 11.258 | 8.589 | 37.794 | 1.00 | 62.78 |
| ATOM | 1755 | CG | HIS | 387 | 11.459 | 7.338 | 38.590 | 1.00 | 62.78 |
| ATOM | 1756 | CD2 | HIS | 387 | 10.601 | 6.614 | 39.346 | 1.00 | 62.78 |
| ATOM | 1757 | ND1 | HIS | 387 | 12.675 | 6.689 | 38.663 | 1.00 | 62.78 |
| ATOM | 1758 | CE1 | HIS | 387 | 12.554 | 5.620 | 39.431 | 1.00 | 62.78 |
| ATOM | 1759 | NE2 | HIS | 387 | 11.309 | 5.550 | 39.856 | 1.00 | 62.78 |

FIG. 29A-36

| ATOM | 1760 | C   | HIS | 387 | 9.778  | 10.544 | 37.266 | 1.00 | 36.46 |
|------|------|-----|-----|-----|--------|--------|--------|------|-------|
| ATOM | 1761 | O   | HIS | 387 | 9.885  | 11.543 | 37.979 | 1.00 | 62.78 |
| ATOM | 1762 | N   | MET | 388 | 9.587  | 10.612 | 35.950 | 1.00 | 33.41 |
| ATOM | 1763 | CA  | MET | 388 | 9.505  | 11.894 | 35.258 | 1.00 | 33.41 |
| ATOM | 1764 | CB  | MET | 388 | 9.269  | 11.703 | 33.755 | 1.00 | 42.63 |
| ATOM | 1765 | CG  | MET | 388 | 10.456 | 11.144 | 32.982 | 1.00 | 42.63 |
| ATOM | 1766 | SD  | MET | 388 | 10.253 | 11.325 | 31.192 | 1.00 | 42.63 |
| ATOM | 1767 | CE  | MET | 388 | 9.501  | 9.772  | 30.748 | 1.00 | 42.63 |
| ATOM | 1768 | C   | MET | 388 | 8.385  | 12.746 | 35.849 | 1.00 | 33.41 |
| ATOM | 1769 | O   | MET | 388 | 8.573  | 13.934 | 36.103 | 1.00 | 42.63 |
| ATOM | 1770 | N   | LYS | 389 | 7.235  | 12.126 | 36.092 | 1.00 | 39.26 |
| ATOM | 1771 | CA  | LYS | 389 | 6.082  | 12.825 | 36.659 | 1.00 | 39.26 |
| ATOM | 1772 | CB  | LYS | 389 | 4.867  | 11.900 | 36.719 | 1.00 | 52.87 |
| ATOM | 1773 | CG  | LYS | 389 | 4.237  | 11.594 | 35.379 | 1.00 | 52.87 |
| ATOM | 1774 | CD  | LYS | 389 | 3.048  | 10.667 | 35.553 | 1.00 | 52.87 |
| ATOM | 1775 | CE  | LYS | 389 | 3.482  | 9.327  | 36.125 | 1.00 | 52.87 |
| ATOM | 1776 | NZ  | LYS | 389 | 2.335  | 8.407  | 36.326 | 1.00 | 52.87 |
| ATOM | 1777 | C   | LYS | 389 | 6.363  | 13.360 | 38.056 | 1.00 | 39.26 |
| ATOM | 1778 | O   | LYS | 389 | 5.837  | 14.404 | 38.452 | 1.00 | 52.87 |
| ATOM | 1779 | N   | VAL | 390 | 7.156  | 12.614 | 38.818 | 1.00 | 44.18 |
| ATOM | 1780 | CA  | VAL | 390 | 7.508  | 13.016 | 40.172 | 1.00 | 44.18 |
| ATOM | 1781 | CB  | VAL | 390 | 8.299  | 11.898 | 40.905 | 1.00 | 50.50 |
| ATOM | 1782 | CG1 | VAL | 390 | 8.718  | 12.362 | 42.293 | 1.00 | 50.50 |
| ATOM | 1783 | CG2 | VAL | 390 | 7.455  | 10.640 | 41.012 | 1.00 | 50.50 |
| ATOM | 1784 | C   | VAL | 390 | 8.352  | 14.288 | 40.145 | 1.00 | 44.18 |
| ATOM | 1785 | O   | VAL | 390 | 8.144  | 15.198 | 40.948 | 1.00 | 50.50 |
| ATOM | 1786 | N   | GLU | 391 | 9.261  | 14.368 | 39.179 | 1.00 | 38.64 |
| ATOM | 1787 | CA  | GLU | 391 | 10.161 | 15.509 | 39.056 | 1.00 | 38.64 |
| ATOM | 1788 | CB  | GLU | 391 | 11.483 | 15.060 | 38.424 | 1.00 | 64.18 |
| ATOM | 1789 | CG  | GLU | 391 | 12.065 | 13.766 | 39.009 | 1.00 | 64.18 |
| ATOM | 1790 | CD  | GLU | 391 | 12.662 | 13.922 | 40.405 | 1.00 | 64.18 |
| ATOM | 1791 | OE1 | GLU | 391 | 12.190 | 14.773 | 41.192 | 1.00 | 64.18 |
| ATOM | 1792 | OE2 | GLU | 391 | 13.611 | 13.173 | 40.721 | 1.00 | 64.18 |
| ATOM | 1793 | C   | GLU | 391 | 9.623  | 16.737 | 38.314 | 1.00 | 38.64 |
| ATOM | 1794 | O   | GLU | 391 | 9.656  | 17.850 | 38.849 | 1.00 | 64.18 |
| ATOM | 1795 | N   | CYS | 392 | 9.125  | 16.539 | 37.096 | 1.00 | 37.24 |
| ATOM | 1796 | CA  | CYS | 392 | 8.611  | 17.635 | 36.271 | 1.00 | 37.24 |
| ATOM | 1797 | CB  | CYS | 392 | 8.879  | 17.345 | 34.784 | 1.00 | 30.64 |
| ATOM | 1798 | SG  | CYS | 392 | 10.634 | 17.137 | 34.283 | 1.00 | 30.64 |
| ATOM | 1799 | C   | CYS | 392 | 7.110  | 17.882 | 36.496 | 1.00 | 37.24 |
| ATOM | 1800 | O   | CYS | 392 | 6.403  | 17.011 | 37.006 | 1.00 | 30.64 |
| ATOM | 1801 | N   | PRO | 393 | 6.625  | 19.107 | 36.199 | 1.00 | 40.56 |
| ATOM | 1802 | CD  | PRO | 393 | 7.444  | 20.297 | 35.904 | 1.00 | 33.41 |
| ATOM | 1803 | CA  | PRO | 393 | 5.209  | 19.473 | 36.358 | 1.00 | 40.56 |
| ATOM | 1804 | CB  | PRO | 393 | 5.253  | 21.001 | 36.404 | 1.00 | 33.41 |
| ATOM | 1805 | CG  | PRO | 393 | 6.409  | 21.332 | 35.527 | 1.00 | 33.41 |
| ATOM | 1806 | C   | PRO | 393 | 4.330  | 18.975 | 35.207 | 1.00 | 40.56 |
| ATOM | 1807 | O   | PRO | 393 | 4.776  | 18.907 | 34.057 | 1.00 | 33.41 |
| ATOM | 1808 | N   | THR | 394 | 3.067  | 18.691 | 35.516 | 1.00 | 41.91 |
| ATOM | 1809 | CA  | THR | 394 | 2.101  | 18.186 | 34.540 | 1.00 | 41.91 |

FIG. 29A-37

| ATOM | 1810 | CB  | THR | 394 | 0.691  | 18.075 | 35.156 | 1.00 | 62.04 |
|------|------|-----|-----|-----|--------|--------|--------|------|-------|
| ATOM | 1811 | OG1 | THR | 394 | 0.706  | 18.582 | 36.497 | 1.00 | 62.04 |
| ATOM | 1812 | CG2 | THR | 394 | 0.232  | 16.626 | 35.168 | 1.00 | 62.04 |
| ATOM | 1813 | C   | THR | 394 | 1.995  | 18.984 | 33.242 | 1.00 | 41.91 |
| ATOM | 1814 | O   | THR | 394 | 1.758  | 18.411 | 32.181 | 1.00 | 62.04 |
| ATOM | 1815 | N   | GLU | 395 | 2.191  | 20.297 | 33.327 | 1.00 | 43.92 |
| ATOM | 1816 | CA  | GLU | 395 | 2.104  | 21.176 | 32.160 | 1.00 | 43.92 |
| ATOM | 1817 | CB  | GLU | 395 | 2.313  | 22.626 | 32.585 | 1.00 | 34.22 |
| ATOM | 1818 | C   | GLU | 395 | 3.071  | 20.814 | 31.031 | 1.00 | 43.92 |
| ATOM | 1819 | O   | GLU | 395 | 2.887  | 21.243 | 29.891 | 1.00 | 34.22 |
| ATOM | 1820 | N   | LEU | 396 | 4.104  | 20.041 | 31.350 | 1.00 | 34.92 |
| ATOM | 1821 | CA  | LEU | 396 | 5.096  | 19.634 | 30.359 | 1.00 | 34.92 |
| ATOM | 1822 | CB  | LEU | 396 | 6.473  | 19.495 | 31.017 | 1.00 | 35.81 |
| ATOM | 1823 | CG  | LEU | 396 | 7.074  | 20.747 | 31.662 | 1.00 | 35.81 |
| ATOM | 1824 | CD1 | LEU | 396 | 8.427  | 20.410 | 32.263 | 1.00 | 35.81 |
| ATOM | 1825 | CD2 | LEU | 396 | 7.209  | 21.857 | 30.629 | 1.00 | 35.81 |
| ATOM | 1826 | C   | LEU | 396 | 4.731  | 18.324 | 29.661 | 1.00 | 34.92 |
| ATOM | 1827 | O   | LEU | 396 | 5.343  | 17.954 | 28.659 | 1.00 | 35.81 |
| ATOM | 1828 | N   | PHE | 397 | 3.734  | 17.627 | 30.197 | 1.00 | 35.28 |
| ATOM | 1829 | CA  | PHE | 397 | 3.302  | 16.352 | 29.640 | 1.00 | 35.28 |
| ATOM | 1830 | CB  | PHE | 397 | 3.059  | 15.341 | 30.764 | 1.00 | 27.13 |
| ATOM | 1831 | CG  | PHE | 397 | 4.285  | 15.004 | 31.561 | 1.00 | 27.13 |
| ATOM | 1832 | CD1 | PHE | 397 | 4.700  | 15.824 | 32.604 | 1.00 | 27.13 |
| ATOM | 1833 | CD2 | PHE | 397 | 5.021  | 13.860 | 31.273 | 1.00 | 27.13 |
| ATOM | 1834 | CE1 | PHE | 397 | 5.831  | 15.510 | 33.349 | 1.00 | 27.13 |
| ATOM | 1835 | CE2 | PHE | 397 | 6.155  | 13.537 | 32.013 | 1.00 | 27.13 |
| ATOM | 1836 | CZ  | PHE | 397 | 6.561  | 14.364 | 33.052 | 1.00 | 27.13 |
| ATOM | 1837 | C   | PHE | 397 | 2.027  | 16.474 | 28.812 | 1.00 | 35.28 |
| ATOM | 1838 | O   | PHE | 397 | 0.977  | 16.861 | 29.331 | 1.00 | 27.13 |
| ATOM | 1839 | N   | PRO | 398 | 2.102  | 16.164 | 27.505 | 1.00 | 26.41 |
| ATOM | 1840 | CD  | PRO | 398 | 3.305  | 15.850 | 26.713 | 1.00 | 19.32 |
| ATOM | 1841 | CA  | PRO | 398 | 0.917  | 16.247 | 26.647 | 1.00 | 26.41 |
| ATOM | 1842 | CB  | PRO | 398 | 1.439  | 15.752 | 25.300 | 1.00 | 19.32 |
| ATOM | 1843 | CG  | PRO | 398 | 2.867  | 16.193 | 25.312 | 1.00 | 19.32 |
| ATOM | 1844 | C   | PRO | 398 | -0.157 | 15.313 | 27.206 | 1.00 | 26.41 |
| ATOM | 1845 | O   | PRO | 398 | 0.160  | 14.232 | 27.710 | 1.00 | 19.32 |
| ATOM | 1846 | N   | PRO | 399 | -1.439 | 15.702 | 27.104 | 1.00 | 25.12 |
| ATOM | 1847 | CD  | PRO | 399 | -1.935 | 16.929 | 26.454 | 1.00 | 24.32 |
| ATOM | 1848 | CA  | PRO | 399 | -2.554 | 14.894 | 27.612 | 1.00 | 25.12 |
| ATOM | 1849 | CB  | PRO | 399 | -3.777 | 15.594 | 27.022 | 1.00 | 24.32 |
| ATOM | 1850 | CG  | PRO | 399 | -3.349 | 17.026 | 26.974 | 1.00 | 24.32 |
| ATOM | 1851 | C   | PRO | 399 | -2.502 | 13.416 | 27.222 | 1.00 | 25.12 |
| ATOM | 1852 | O   | PRO | 399 | -2.599 | 12.540 | 28.085 | 1.00 | 24.32 |
| ATOM | 1853 | N   | LEU | 400 | -2.322 | 13.139 | 25.933 | 1.00 | 23.10 |
| ATOM | 1854 | CA  | LEU | 400 | -2.265 | 11.759 | 25.454 | 1.00 | 23.10 |
| ATOM | 1855 | CB  | LEU | 400 | -2.230 | 11.720 | 23.923 | 1.00 | 22.35 |
| ATOM | 1856 | CG  | LEU | 400 | -2.485 | 10.354 | 23.276 | 1.00 | 22.35 |
| ATOM | 1857 | CD1 | LEU | 400 | -3.792 | 9.765  | 23.792 | 1.00 | 22.35 |
| ATOM | 1858 | CD2 | LEU | 400 | -2.523 | 10.494 | 21.763 | 1.00 | 22.35 |
| ATOM | 1859 | C   | LEU | 400 | -1.066 | 11.012 | 26.032 | 1.00 | 23.10 |

FIG. 29A-38

| | | | | | | | | |
|---|---|---|---|---|---|---|---|---|
| ATOM | 1860 | O | LEU | 400 | -1.160 | 9.825 | 26.345 | 1.00 | 22.35 |
| ATOM | 1861 | N | PHE | 401 | 0.044 | 11.723 | 26.202 | 1.00 | 13.85 |
| ATOM | 1862 | CA | PHE | 401 | 1.269 | 11.150 | 26.755 | 1.00 | 13.85 |
| ATOM | 1863 | CB | PHE | 401 | 2.374 | 12.213 | 26.753 | 1.00 | 26.97 |
| ATOM | 1864 | CG | PHE | 401 | 3.729 | 11.702 | 27.164 | 1.00 | 26.97 |
| ATOM | 1865 | CD1 | PHE | 401 | 4.189 | 10.461 | 26.732 | 1.00 | 26.97 |
| ATOM | 1866 | CD2 | PHE | 401 | 4.561 | 12.481 | 27.963 | 1.00 | 26.97 |
| ATOM | 1867 | CE1 | PHE | 401 | 5.459 | 10.005 | 27.091 | 1.00 | 26.97 |
| ATOM | 1868 | CE2 | PHE | 401 | 5.830 | 12.035 | 28.327 | 1.00 | 26.97 |
| ATOM | 1869 | CZ | PHE | 401 | 6.280 | 10.795 | 27.889 | 1.00 | 26.97 |
| ATOM | 1870 | C | PHE | 401 | 0.993 | 10.659 | 28.179 | 1.00 | 13.85 |
| ATOM | 1871 | O | PHE | 401 | 1.393 | 9.558 | 28.555 | 1.00 | 26.97 |
| ATOM | 1872 | N | LEU | 402 | 0.274 | 11.473 | 28.947 | 1.00 | 25.21 |
| ATOM | 1873 | CA | LEU | 402 | -0.080 | 11.145 | 30.325 | 1.00 | 25.21 |
| ATOM | 1874 | CB | LEU | 402 | -0.640 | 12.380 | 31.035 | 1.00 | 29.34 |
| ATOM | 1875 | CG | LEU | 402 | 0.334 | 13.411 | 31.600 | 1.00 | 29.34 |
| ATOM | 1876 | CD1 | LEU | 402 | -0.430 | 14.658 | 32.018 | 1.00 | 29.34 |
| ATOM | 1877 | CD2 | LEU | 402 | 1.090 | 12.814 | 32.775 | 1.00 | 29.34 |
| ATOM | 1878 | C | LEU | 402 | -1.109 | 10.025 | 30.425 | 1.00 | 25.21 |
| ATOM | 1879 | O | LEU | 402 | -1.034 | 9.189 | 31.320 | 1.00 | 29.34 |
| ATOM | 1880 | N | GLU | 403 | -2.090 | 10.043 | 29.529 | 1.00 | 23.54 |
| ATOM | 1881 | CA | GLU | 403 | -3.159 | 9.046 | 29.521 | 1.00 | 23.54 |
| ATOM | 1882 | CB | GLU | 403 | -4.274 | 9.482 | 28.562 | 1.00 | 63.22 |
| ATOM | 1883 | CG | GLU | 403 | -5.469 | 8.531 | 28.506 | 1.00 | 63.22 |
| ATOM | 1884 | CD | GLU | 403 | -6.530 | 8.952 | 27.498 | 1.00 | 63.22 |
| ATOM | 1885 | OE1 | GLU | 403 | -6.237 | 9.786 | 26.613 | 1.00 | 63.22 |
| ATOM | 1886 | OE2 | GLU | 403 | -7.666 | 8.436 | 27.589 | 1.00 | 63.22 |
| ATOM | 1887 | C | GLU | 403 | -2.708 | 7.629 | 29.170 | 1.00 | 23.54 |
| ATOM | 1888 | O | GLU | 403 | -3.210 | 6.656 | 29.735 | 1.00 | 63.22 |
| ATOM | 1889 | N | VAL | 404 | -1.787 | 7.515 | 28.221 | 1.00 | 33.24 |
| ATOM | 1890 | CA | VAL | 404 | -1.297 | 6.213 | 27.782 | 1.00 | 33.24 |
| ATOM | 1891 | CB | VAL | 404 | -0.621 | 6.314 | 26.390 | 1.00 | 30.71 |
| ATOM | 1892 | CG1 | VAL | 404 | -0.097 | 4.957 | 25.947 | 1.00 | 30.71 |
| ATOM | 1893 | CG2 | VAL | 404 | -1.611 | 6.841 | 25.371 | 1.00 | 30.71 |
| ATOM | 1894 | C | VAL | 404 | -0.338 | 5.528 | 28.752 | 1.00 | 33.24 |
| ATOM | 1895 | O | VAL | 404 | -0.386 | 4.305 | 28.914 | 1.00 | 30.71 |
| ATOM | 1896 | N | PHE | 405 | 0.526 | 6.309 | 29.392 | 1.00 | 33.66 |
| ATOM | 1897 | CA | PHE | 405 | 1.516 | 5.752 | 30.308 | 1.00 | 33.66 |
| ATOM | 1898 | CB | PHE | 405 | 2.901 | 6.326 | 29.984 | 1.00 | 34.35 |
| ATOM | 1899 | CG | PHE | 405 | 3.343 | 6.076 | 28.568 | 1.00 | 34.35 |
| ATOM | 1900 | CD1 | PHE | 405 | 3.519 | 7.134 | 27.683 | 1.00 | 34.35 |
| ATOM | 1901 | CD2 | PHE | 405 | 3.569 | 4.782 | 28.114 | 1.00 | 34.35 |
| ATOM | 1902 | CE1 | PHE | 405 | 3.911 | 6.906 | 26.365 | 1.00 | 34.35 |
| ATOM | 1903 | CE2 | PHE | 405 | 3.960 | 4.545 | 26.798 | 1.00 | 34.35 |
| ATOM | 1904 | CZ | PHE | 405 | 4.131 | 5.610 | 25.922 | 1.00 | 34.35 |
| ATOM | 1905 | C | PHE | 405 | 1.189 | 5.931 | 31.790 | 1.00 | 33.66 |
| ATOM | 1906 | O | PHE | 405 | 2.036 | 5.539 | 32.623 | 1.00 | 34.35 |
| ATOM | 1907 | OXT | PHE | 405 | 0.090 | 6.434 | 32.107 | 1.00 | 34.35 |
| ATOM | 1908 | C1 | TRI | 1 | 8.375 | 7.063 | 18.475 | 1.00 | 34.21 |
| ATOM | 1909 | C2 | TRI | 1 | 10.048 | 8.688 | 23.016 | 1.00 | 33.36 |

FIG. 29A-39

| | | | | | | | | |
|---|---|---|---|---|---|---|---|---|
| ATOM | 1910 | C3 | TRI | 1 | 8.104 | 8.391 | 18.941 | 1.00 | 34.21 |
| ATOM | 1911 | C4 | TRI | 1 | 10.496 | 9.696 | 23.813 | 1.00 | 33.36 |
| ATOM | 1912 | C5 | TRI | 1 | 8.916 | 8.943 | 19.927 | 1.00 | 34.21 |
| ATOM | 1913 | C6 | TRI | 1 | 10.152 | 9.772 | 25.121 | 1.00 | 33.36 |
| ATOM | 1914 | C7 | TRI | 1 | 9.862 | 8.178 | 20.609 | 1.00 | 34.21 |
| ATOM | 1915 | C8 | TRI | 1 | 9.246 | 8.821 | 25.653 | 1.00 | 33.36 |
| ATOM | 1916 | C9 | TRI | 1 | 10.117 | 6.865 | 20.147 | 1.00 | 34.21 |
| ATOM | 1917 | C10 | TRI | 1 | 8.805 | 7.754 | 24.847 | 1.00 | 33.36 |
| ATOM | 1918 | C11 | TRI | 1 | 9.375 | 6.339 | 19.026 | 1.00 | 34.21 |
| ATOM | 1919 | C12 | TRI | 1 | 9.125 | 7.756 | 23.490 | 1.00 | 33.36 |
| ATOM | 1920 | C13 | TRI | 1 | 7.540 | 6.470 | 17.383 | 1.00 | 35.85 |
| ATOM | 1921 | C15 | TRI | 1 | 8.158 | 6.555 | 15.938 | 1.00 | 35.85 |
| ATOM | 1922 | I1 | TRI | 1 | 8.713 | 10.990 | 20.395 | 1.00 | 34.21 |
| ATOM | 1923 | I2 | TRI | 1 | 10.951 | 11.289 | 26.315 | 1.00 | 33.36 |
| ATOM | 1924 | I3 | TRI | 1 | 11.592 | 5.685 | 21.118 | 1.00 | 34.21 |
| ATOM | 1925 | O3 | TRI | 1 | 9.407 | 6.654 | 15.852 | 1.00 | 35.85 |
| ATOM | 1926 | O2 | TRI | 1 | 10.570 | 8.649 | 21.717 | 1.00 | 33.36 |
| ATOM | 1927 | O1 | TRI | 1 | 8.798 | 8.969 | 26.979 | 1.00 | 33.36 |
| ATOM | 1928 | O4 | TRI | 1 | 7.352 | 6.522 | 14.973 | 1.00 | 35.85 |
| ATOM | 1929 | O1 | HOH | 501 | 9.189 | 2.098 | 11.091 | 1.00 | 33.36 |
| ATOM | 1930 | O1 | HOH | 503 | 5.152 | 5.261 | 12.137 | 1.00 | 33.36 |
| ATOM | 1931 | O1 | HOH | 504 | 3.970 | 5.057 | 16.390 | 1.00 | 33.36 |
| ATOM | 1932 | O1 | HOH | 534 | 8.296 | -0.941 | 8.998 | 1.00 | 33.36 |
| ATOM | 1933 | O1 | HOH | 538 | 4.845 | 14.369 | 13.635 | 1.00 | 33.36 |
| ATOM | 1934 | O1 | HOH | 540 | 5.789 | 12.049 | 10.352 | 1.00 | 33.36 |
| ATOM | 1936 | O1 | HOH | 555 | 5.721 | 2.525 | 28.939 | 1.00 | 33.36 |
| ATOM | 1937 | O1 | HOH | 556 | 3.732 | 1.273 | 26.724 | 1.00 | 33.36 |
| ATOM | 1935 | O1 | HOH | 600 | 8.767 | 4.847 | 8.517 | 1.00 | 33.36 |
| ATOM | 1938 | AS1 | CAD | 701 | 1.863 | 1.579 | 0.837 | 1.00 | 37.00 |
| ATOM | 1939 | C2 | CAD | 701 | 1.760 | -0.100 | 0.335 | 1.00 | 33.36 |
| ATOM | 1940 | C3 | CAD | 701 | 3.511 | 1.872 | 1.858 | 1.00 | 28.02 |
| ATOM | 1941 | O4 | CAD | 701 | 1.785 | 2.506 | -0.433 | 1.00 | 28.02 |
| ATOM | 1942 | O5 | CAD | 701 | 0.592 | 2.019 | 1.654 | 1.00 | 28.02 |
| ATOM | 1943 | AS | AS | 801 | 11.254 | 16.718 | 33.126 | 1.00 | 37.00 AS |
| ATOM | 1944 | AS | AS | 802 | 16.338 | -1.161 | 29.914 | 1.00 | 37.00 AS |
| ATOM | 1945 | AS | AS | 803 | -14.931 | -11.763 | 25.324 | 1.00 | 37.00 AS |

END

FIG. 30

REMARK rTR_ipbr2 full length numbering
REMARK
REMARK Rfactor 0.214 Rfree 0.224
REMARK Resolution 15. 2.2 all reflections
REMARK
REMARK Three cacodylate-modified cysteines (CYA)
REMARK Cya334, Cya380, Cya392
REMARK cacodylate modeled as single arsenic atom
REMARK
REMARK side chain of certain residues modeled as ALA due to poor density;
REMARK however, residue name reflects true residue for clarity
REMARK
REMARK clone obtained from Murray et. al.
REMARK deposited sequence confirmed,
REMARK differing from that reported by Thompson et. al.
REMARK in the following codons:
REMARK 281 Thr - Ala
REMARK 285 Lys - Glu
REMARK identical to that reported by Mitsuhashi et. al.
REMARK gb:RNTRAVI X07409
JRNL    AUTH   M.B. MURRAY, N.D.ZILZ, N.L.MCCREARY,M.J.MACDONALD
JRNL    AUTH 2 H.C.TOWLE
JRNL       TITL   ISOLATION AND CHARACTERIZATION OF RAT CDNA CLONES FOR TWO
JRNL       TITL 2 DISTINCT THYROID HORMONE RECPTORS
JRNL    REF   JBC           V. 263 25 1988
JRNL    AUTH   C.C.THOMPSON, C.WEINBERGER, R.LEBO, R.M.EVANS
JRNL       TITL   IDENTIFICATION OF A NOVEL THYROID HORMONE RECEPTOR EXPRESSED
JRNL       TITL 2 IN THE MAMMALIAN CENTRAL NERVOUS SYSTEM
JRNL    REF   SCIENCE        V. 237   1987
JRNL    AUTH   T.MITSUHASHI,G.TENNYSON,V.NIKODEM
JRNL       TITL   NUCLEOTIDE SEQUENCE OF NOVEL CDNAS GENERATED BY ALTERNATIVE
JRNL       TITL 2 SPLICING OF A RAT THYROID HORMONE RECEPTOR GENE TRANSCRIPT
JRNL    REF   NUC. ACIDS. RES.    V. 16 12 1988
REMARK

| ATOM | 1  | CB  | ARG | 157 | 68.481 | 10.663 | 6.906  | 1.00 | 57.50 |
| ATOM | 2  | CG  | ARG | 157 | 69.793 | 10.213 | 7.512  | 1.00 | 59.93 |
| ATOM | 3  | CD  | ARG | 157 | 70.510 | 11.365 | 8.189  | 1.00 | 70.24 |
| ATOM | 4  | NE  | ARG | 157 | 71.661 | 10.906 | 8.961  | 1.00 | 77.62 |
| ATOM | 5  | CZ  | ARG | 157 | 71.599 | 10.492 | 10.224 | 1.00 | 78.75 |
| ATOM | 6  | NH1 | ARG | 157 | 70.440 | 10.480 | 10.870 | 1.00 | 74.33 |
| ATOM | 7  | NH2 | ARG | 157 | 72.697 | 10.075 | 10.839 | 1.00 | 83.44 |
| ATOM | 8  | C   | ARG | 157 | 66.314 | 10.014 | 5.809  | 1.00 | 46.84 |
| ATOM | 9  | O   | ARG | 157 | 66.109 | 10.397 | 4.659  | 1.00 | 54.49 |
| ATOM | 10 | N   | ARG | 157 | 68.442 | 9.069  | 5.013  | 1.00 | 56.54 |
| ATOM | 11 | CA  | ARG | 157 | 67.704 | 9.537  | 6.222  | 1.00 | 52.92 |

FIG. 30A-1

| ATOM | 12 | N | PRO | 158 | 65.335 | 9.953 | 6.727 | 1.00 | 39.44 |
|---|---|---|---|---|---|---|---|---|---|
| ATOM | 13 | CD | PRO | 158 | 65.503 | 9.448 | 8.099 | 1.00 | 41.72 |
| ATOM | 14 | CA | PRO | 158 | 63.946 | 10.368 | 6.487 | 1.00 | 34.98 |
| ATOM | 15 | CB | PRO | 158 | 63.282 | 10.172 | 7.854 | 1.00 | 34.92 |
| ATOM | 16 | CG | PRO | 158 | 64.096 | 9.096 | 8.487 | 1.00 | 45.83 |
| ATOM | 17 | C | PRO | 158 | 63.765 | 11.804 | 5.992 | 1.00 | 34.13 |
| ATOM | 18 | O | PRO | 158 | 64.223 | 12.757 | 6.621 | 1.00 | 31.07 |
| ATOM | 19 | N | GLU | 159 | 63.110 | 11.932 | 4.841 | 1.00 | 31.36 |
| ATOM | 20 | CA | GLU | 159 | 62.814 | 13.220 | 4.228 | 1.00 | 27.34 |
| ATOM | 21 | CB | GLU | 159 | 62.569 | 13.041 | 2.726 | 1.00 | 24.27 |
| ATOM | 22 | CG | GLU | 159 | 63.814 | 12.866 | 1.887 | 1.00 | 24.85 |
| ATOM | 23 | CD | GLU | 159 | 64.409 | 14.188 | 1.454 | 1.00 | 28.12 |
| ATOM | 24 | OE1 | GLU | 159 | 63.642 | 15.144 | 1.224 | 1.00 | 29.26 |
| ATOM | 25 | OE2 | GLU | 159 | 65.646 | 14.269 | 1.326 | 1.00 | 29.52 |
| ATOM | 26 | C | GLU | 159 | 61.528 | 13.707 | 4.870 | 1.00 | 24.30 |
| ATOM | 27 | O | GLU | 159 | 60.855 | 12.934 | 5.566 | 1.00 | 29.01 |
| ATOM | 28 | N | PRO | 160 | 61.192 | 14.989 | 4.718 | 1.00 | 24.62 |
| ATOM | 29 | CD | PRO | 160 | 61.979 | 16.126 | 4.188 | 1.00 | 18.72 |
| ATOM | 30 | CA | PRO | 160 | 59.947 | 15.451 | 5.330 | 1.00 | 21.62 |
| ATOM | 31 | CB | PRO | 160 | 59.945 | 16.955 | 5.048 | 1.00 | 12.71 |
| ATOM | 32 | CG | PRO | 160 | 61.394 | 17.297 | 4.930 | 1.00 | 15.12 |
| ATOM | 33 | C | PRO | 160 | 58.743 | 14.752 | 4.671 | 1.00 | 24.61 |
| ATOM | 34 | O | PRO | 160 | 58.789 | 14.384 | 3.490 | 1.00 | 22.63 |
| ATOM | 35 | N | THR | 161 | 57.705 | 14.504 | 5.450 | 1.00 | 25.86 |
| ATOM | 36 | CA | THR | 161 | 56.515 | 13.864 | 4.921 | 1.00 | 23.77 |
| ATOM | 37 | CB | THR | 161 | 55.689 | 13.201 | 6.048 | 1.00 | 21.75 |
| ATOM | 38 | OG1 | THR | 161 | 55.178 | 14.210 | 6.926 | 1.00 | 20.78 |
| ATOM | 39 | CG2 | THR | 161 | 56.549 | 12.227 | 6.847 | 1.00 | 18.44 |
| ATOM | 40 | C | THR | 161 | 55.680 | 14.967 | 4.269 | 1.00 | 28.67 |
| ATOM | 41 | O | THR | 161 | 55.917 | 16.151 | 4.510 | 1.00 | 29.90 |
| ATOM | 42 | N | PRO | 162 | 54.685 | 14.597 | 3.448 | 1.00 | 27.79 |
| ATOM | 43 | CD | PRO | 162 | 54.313 | 13.237 | 3.019 | 1.00 | 23.25 |
| ATOM | 44 | CA | PRO | 162 | 53.843 | 15.603 | 2.795 | 1.00 | 26.19 |
| ATOM | 45 | CB | PRO | 162 | 52.699 | 14.766 | 2.227 | 1.00 | 19.89 |
| ATOM | 46 | CG | PRO | 162 | 53.394 | 13.492 | 1.848 | 1.00 | 20.63 |
| ATOM | 47 | C | PRO | 162 | 53.334 | 16.661 | 3.775 | 1.00 | 24.81 |
| ATOM | 48 | O | PRO | 162 | 53.477 | 17.863 | 3.526 | 1.00 | 21.10 |
| ATOM | 49 | N | GLU | 163 | 52.812 | 16.198 | 4.911 | 1.00 | 26.34 |
| ATOM | 50 | CA | GLU | 163 | 52.266 | 17.065 | 5.959 | 1.00 | 30.38 |
| ATOM | 51 | CB | GLU | 163 | 51.640 | 16.231 | 7.086 | 1.00 | 29.46 |
| ATOM | 52 | CG | GLU | 163 | 50.482 | 15.321 | 6.666 | 1.00 | 48.37 |
| ATOM | 53 | CD | GLU | 163 | 50.918 | 14.132 | 5.816 | 1.00 | 53.12 |
| ATOM | 54 | OE1 | GLU | 163 | 51.890 | 13.441 | 6.194 | 1.00 | 52.22 |
| ATOM | 55 | OE2 | GLU | 163 | 50.282 | 13.886 | 4.766 | 1.00 | 59.14 |
| ATOM | 56 | C | GLU | 163 | 53.353 | 17.949 | 6.552 | 1.00 | 26.74 |
| ATOM | 57 | O | GLU | 163 | 53.109 | 19.107 | 6.898 | 1.00 | 27.03 |
| ATOM | 58 | N | GLU | 164 | 54.553 | 17.389 | 6.677 | 1.00 | 26.74 |
| ATOM | 59 | CA | GLU | 164 | 55.679 | 18.124 | 7.221 | 1.00 | 23.65 |
| ATOM | 60 | CB | GLU | 164 | 56.805 | 17.174 | 7.609 | 1.00 | 18.85 |
| ATOM | 61 | CG | GLU | 164 | 56.441 | 16.306 | 8.804 | 1.00 | 26.81 |

FIG. 30A-2

| ATOM | 62 | CD | GLU | 164 | 57.536 | 15.334 | 9.188 | 1.00 | 31.06 |
|---|---|---|---|---|---|---|---|---|---|
| ATOM | 63 | OE1 | GLU | 164 | 58.404 | 15.050 | 8.340 | 1.00 | 29.21 |
| ATOM | 64 | OE2 | GLU | 164 | 57.524 | 14.848 | 10.340 | 1.00 | 31.39 |
| ATOM | 65 | C | GLU | 164 | 56.165 | 19.204 | 6.276 | 1.00 | 26.54 |
| ATOM | 66 | O | GLU | 164 | 56.609 | 20.258 | 6.724 | 1.00 | 32.48 |
| ATOM | 67 | N | TRP | 165 | 56.075 | 18.957 | 4.971 | 1.00 | 23.41 |
| ATOM | 68 | CA | TRP | 165 | 56.488 | 19.962 | 3.998 | 1.00 | 20.81 |
| ATOM | 69 | CB | TRP | 165 | 56.462 | 19.405 | 2.573 | 1.00 | 18.15 |
| ATOM | 70 | CG | TRP | 165 | 57.762 | 18.747 | 2.164 | 1.00 | 15.80 |
| ATOM | 71 | CD2 | TRP | 165 | 59.058 | 19.377 | 2.064 | 1.00 | 15.35 |
| ATOM | 72 | CE2 | TRP | 165 | 59.959 | 18.392 | 1.628 | 1.00 | 12.14 |
| ATOM | 73 | CE3 | TRP | 165 | 59.527 | 20.676 | 2.287 | 1.00 | 17.56 |
| ATOM | 74 | CD1 | TRP | 165 | 57.939 | 17.449 | 1.804 | 1.00 | 12.78 |
| ATOM | 75 | NE1 | TRP | 165 | 59.253 | 17.230 | 1.484 | 1.00 | 16.10 |
| ATOM | 76 | CZ2 | TRP | 165 | 61.318 | 18.657 | 1.419 | 1.00 | 16.26 |
| ATOM | 77 | CZ3 | TRP | 165 | 60.879 | 20.944 | 2.079 | 1.00 | 19.52 |
| ATOM | 78 | CH2 | TRP | 165 | 61.760 | 19.933 | 1.642 | 1.00 | 16.48 |
| ATOM | 79 | C | TRP | 165 | 55.547 | 21.151 | 4.109 | 1.00 | 19.66 |
| ATOM | 80 | O | TRP | 165 | 55.975 | 22.295 | 3.960 | 1.00 | 23.61 |
| ATOM | 81 | N | ASP | 166 | 54.269 | 20.882 | 4.376 | 1.00 | 22.66 |
| ATOM | 82 | CA | ASP | 166 | 53.269 | 21.943 | 4.537 | 1.00 | 23.35 |
| ATOM | 83 | CB | ASP | 166 | 51.863 | 21.359 | 4.716 | 1.00 | 22.61 |
| ATOM | 84 | CG | ASP | 166 | 51.347 | 20.681 | 3.458 | 1.00 | 31.41 |
| ATOM | 85 | OD1 | ASP | 166 | 51.816 | 21.028 | 2.360 | 1.00 | 26.38 |
| ATOM | 86 | OD2 | ASP | 166 | 50.464 | 19.803 | 3.570 | 1.00 | 32.25 |
| ATOM | 87 | C | ASP | 166 | 53.631 | 22.760 | 5.773 | 1.00 | 26.47 |
| ATOM | 88 | O | ASP | 166 | 53.694 | 23.991 | 5.718 | 1.00 | 30.25 |
| ATOM | 89 | N | LEU | 167 | 53.887 | 22.054 | 6.872 | 1.00 | 24.12 |
| ATOM | 90 | CA | LEU | 167 | 54.268 | 22.663 | 8.139 | 1.00 | 26.44 |
| ATOM | 91 | CB | LEU | 167 | 54.596 | 21.557 | 9.148 | 1.00 | 32.57 |
| ATOM | 92 | CG | LEU | 167 | 54.659 | 21.919 | 10.629 | 1.00 | 36.97 |
| ATOM | 93 | CD1 | LEU | 167 | 53.289 | 22.402 | 11.080 | 1.00 | 43.83 |
| ATOM | 94 | CD2 | LEU | 167 | 55.096 | 20.712 | 11.448 | 1.00 | 34.75 |
| ATOM | 95 | C | LEU | 167 | 55.501 | 23.533 | 7.904 | 1.00 | 23.19 |
| ATOM | 96 | O | LEU | 167 | 55.570 | 24.670 | 8.368 | 1.00 | 28.18 |
| ATOM | 97 | N | ILE | 168 | 56.450 | 22.988 | 7.147 | 1.00 | 19.25 |
| ATOM | 98 | CA | ILE | 168 | 57.703 | 23.651 | 6.801 | 1.00 | 17.71 |
| ATOM | 99 | CB | ILE | 168 | 58.632 | 22.693 | 6.006 | 1.00 | 14.43 |
| ATOM | 100 | CG2 | ILE | 168 | 59.740 | 23.451 | 5.304 | 1.00 | 16.71 |
| ATOM | 101 | CG1 | ILE | 168 | 59.219 | 21.644 | 6.948 | 1.00 | 21.24 |
| ATOM | 102 | CD1 | ILE | 168 | 60.063 | 20.588 | 6.264 | 1.00 | 18.18 |
| ATOM | 103 | C | ILE | 168 | 57.475 | 24.931 | 6.002 | 1.00 | 28.73 |
| ATOM | 104 | O | ILE | 168 | 58.064 | 25.977 | 6.307 | 1.00 | 29.36 |
| ATOM | 105 | N | HIS | 169 | 56.601 | 24.866 | 5.005 | 1.00 | 24.43 |
| ATOM | 106 | CA | HIS | 169 | 56.319 | 26.027 | 4.169 | 1.00 | 23.64 |
| ATOM | 107 | CB | HIS | 169 | 55.459 | 25.631 | 2.971 | 1.00 | 23.55 |
| ATOM | 108 | CG | HIS | 169 | 56.140 | 24.683 | 2.034 | 1.00 | 23.82 |
| ATOM | 109 | CD2 | HIS | 169 | 57.455 | 24.429 | 1.824 | 1.00 | 19.23 |
| ATOM | 110 | ND1 | HIS | 169 | 55.450 | 23.833 | 1.199 | 1.00 | 22.92 |
| ATOM | 111 | CE1 | HIS | 169 | 56.302 | 23.089 | 0.522 | 1.00 | 19.56 |

FIG. 30A-3

| | | | | | | | | |
|---|---|---|---|---|---|---|---|---|
| ATOM | 112 | NE2 | HIS | 169 | 57.527 | 23.431 | 0.883 | 1.00 | 26.00 |
| ATOM | 113 | C | HIS | 169 | 55.653 | 27.135 | 4.962 | 1.00 | 19.37 |
| ATOM | 114 | O | HIS | 169 | 56.069 | 28.288 | 4.880 | 1.00 | 25.64 |
| ATOM | 115 | N | VAL | 170 | 54.638 | 26.782 | 5.745 | 1.00 | 19.88 |
| ATOM | 116 | CA | VAL | 170 | 53.925 | 27.758 | 6.555 | 1.00 | 20.28 |
| ATOM | 117 | CB | VAL | 170 | 52.755 | 27.100 | 7.330 | 1.00 | 26.06 |
| ATOM | 118 | CG1 | VAL | 170 | 52.093 | 28.109 | 8.259 | 1.00 | 20.15 |
| ATOM | 119 | CG2 | VAL | 170 | 51.725 | 26.541 | 6.352 | 1.00 | 18.69 |
| ATOM | 120 | C | VAL | 170 | 54.886 | 28.442 | 7.532 | 1.00 | 23.11 |
| ATOM | 121 | O | VAL | 170 | 54.907 | 29.672 | 7.625 | 1.00 | 28.86 |
| ATOM | 122 | N | ALA | 171 | 55.716 | 27.644 | 8.203 | 1.00 | 20.48 |
| ATOM | 123 | CA | ALA | 171 | 56.686 | 28.146 | 9.173 | 1.00 | 19.84 |
| ATOM | 124 | CB | ALA | 171 | 57.365 | 26.985 | 9.902 | 1.00 | 18.07 |
| ATOM | 125 | C | ALA | 171 | 57.728 | 29.049 | 8.512 | 1.00 | 20.62 |
| ATOM | 126 | O | ALA | 171 | 58.033 | 30.127 | 9.037 | 1.00 | 24.67 |
| ATOM | 127 | N | THR | 172 | 58.251 | 28.632 | 7.359 | 1.00 | 20.65 |
| ATOM | 128 | CA | THR | 172 | 59.247 | 29.428 | 6.640 | 1.00 | 18.91 |
| ATOM | 129 | CB | THR | 172 | 59.755 | 28.709 | 5.380 | 1.00 | 20.06 |
| ATOM | 130 | OG1 | THR | 172 | 60.267 | 27.417 | 5.734 | 1.00 | 20.30 |
| ATOM | 131 | CG2 | THR | 172 | 60.877 | 29.516 | 4.726 | 1.00 | 18.38 |
| ATOM | 132 | C | THR | 172 | 58.675 | 30.786 | 6.235 | 1.00 | 24.43 |
| ATOM | 133 | O | THR | 172 | 59.346 | 31.815 | 6.360 | 1.00 | 23.54 |
| ATOM | 134 | N | GLU | 173 | 57.430 | 30.792 | 5.766 | 1.00 | 24.33 |
| ATOM | 135 | CA | GLU | 173 | 56.783 | 32.031 | 5.361 | 1.00 | 25.98 |
| ATOM | 136 | CB | GLU | 173 | 55.460 | 31.734 | 4.651 | 1.00 | 28.39 |
| ATOM | 137 | CG | GLU | 173 | 54.679 | 32.974 | 4.207 | 1.00 | 40.39 |
| ATOM | 138 | CD | GLU | 173 | 55.487 | 33.951 | 3.347 | 1.00 | 48.33 |
| ATOM | 139 | OE1 | GLU | 173 | 55.261 | 35.172 | 3.478 | 1.00 | 51.86 |
| ATOM | 140 | OE2 | GLU | 173 | 56.334 | 33.513 | 2.533 | 1.00 | 46.92 |
| ATOM | 141 | C | GLU | 173 | 56.564 | 32.953 | 6.562 | 1.00 | 25.57 |
| ATOM | 142 | O | GLU | 173 | 56.877 | 34.141 | 6.498 | 1.00 | 27.76 |
| ATOM | 143 | N | ALA | 174 | 56.071 | 32.383 | 7.664 | 1.00 | 25.31 |
| ATOM | 144 | CA | ALA | 174 | 55.823 | 33.128 | 8.900 | 1.00 | 22.66 |
| ATOM | 145 | CB | ALA | 174 | 55.340 | 32.183 | 10.000 | 1.00 | 18.21 |
| ATOM | 146 | C | ALA | 174 | 57.097 | 33.847 | 9.338 | 1.00 | 23.47 |
| ATOM | 147 | O | ALA | 174 | 57.056 | 35.003 | 9.755 | 1.00 | 23.76 |
| ATOM | 148 | N | HIS | 175 | 58.233 | 33.168 | 9.226 | 1.00 | 22.22 |
| ATOM | 149 | CA | HIS | 175 | 59.503 | 33.769 | 9.592 | 1.00 | 20.21 |
| ATOM | 150 | CB | HIS | 175 | 60.586 | 32.700 | 9.738 | 1.00 | 13.82 |
| ATOM | 151 | CG | HIS | 175 | 61.950 | 33.261 | 9.984 | 1.00 | 20.53 |
| ATOM | 152 | CD2 | HIS | 175 | 62.378 | 34.221 | 10.843 | 1.00 | 10.04 |
| ATOM | 153 | ND1 | HIS | 175 | 63.054 | 32.890 | 9.249 | 1.00 | 22.39 |
| ATOM | 154 | CE1 | HIS | 175 | 64.103 | 33.596 | 9.640 | 1.00 | 13.46 |
| ATOM | 155 | NE2 | HIS | 175 | 63.715 | 34.410 | 10.605 | 1.00 | 20.86 |
| ATOM | 156 | C | HIS | 175 | 59.949 | 34.822 | 8.571 | 1.00 | 25.39 |
| ATOM | 157 | O | HIS | 175 | 60.370 | 35.920 | 8.949 | 1.00 | 26.31 |
| ATOM | 158 | N | ARG | 176 | 59.868 | 34.494 | 7.284 | 1.00 | 23.17 |
| ATOM | 159 | CA | ARG | 176 | 60.292 | 35.423 | 6.239 | 1.00 | 24.26 |
| ATOM | 160 | CB | ARG | 176 | 60.168 | 34.767 | 4.872 | 1.00 | 30.31 |
| ATOM | 161 | CG | ARG | 176 | 61.286 | 33.793 | 4.576 | 1.00 | 39.36 |

FIG. 30A-4

| ATOM | 162 | CD | ARG | 176 | 61.049 | 33.139 | 3.243 | 1.00 | 49.23 |
|---|---|---|---|---|---|---|---|---|---|
| ATOM | 163 | NE | ARG | 176 | 62.188 | 32.346 | 2.808 | 1.00 | 60.62 |
| ATOM | 164 | CZ | ARG | 176 | 62.230 | 31.688 | 1.653 | 1.00 | 67.96 |
| ATOM | 165 | NH1 | ARG | 176 | 61.192 | 31.731 | 0.823 | 1.00 | 68.84 |
| ATOM | 166 | NH2 | ARG | 176 | 63.313 | 30.999 | 1.321 | 1.00 | 67.97 |
| ATOM | 167 | C | ARG | 176 | 59.548 | 36.749 | 6.267 | 1.00 | 23.09 |
| ATOM | 168 | O | ARG | 176 | 60.163 | 37.807 | 6.173 | 1.00 | 30.71 |
| ATOM | 169 | N | SER | 177 | 58.240 | 36.686 | 6.488 | 1.00 | 22.69 |
| ATOM | 170 | CA | SER | 177 | 57.416 | 37.885 | 6.536 | 1.00 | 26.50 |
| ATOM | 171 | CB | SER | 177 | 55.946 | 37.520 | 6.341 | 1.00 | 19.42 |
| ATOM | 172 | OG | SER | 177 | 55.507 | 36.611 | 7.331 | 1.00 | 27.68 |
| ATOM | 173 | C | SER | 177 | 57.574 | 38.695 | 7.821 | 1.00 | 28.70 |
| ATOM | 174 | O | SER | 177 | 56.986 | 39.772 | 7.948 | 1.00 | 34.31 |
| ATOM | 175 | N | THR | 178 | 58.327 | 38.165 | 8.786 | 1.00 | 27.42 |
| ATOM | 176 | CA | THR | 178 | 58.540 | 38.850 | 10.060 | 1.00 | 21.88 |
| ATOM | 177 | CB | THR | 178 | 57.842 | 38.107 | 11.228 | 1.00 | 23.73 |
| ATOM | 178 | OG1 | THR | 178 | 58.354 | 36.776 | 11.337 | 1.00 | 24.26 |
| ATOM | 179 | CG2 | THR | 178 | 56.344 | 38.037 | 10.994 | 1.00 | 16.77 |
| ATOM | 180 | C | THR | 178 | 60.027 | 39.018 | 10.375 | 1.00 | 23.86 |
| ATOM | 181 | O | THR | 178 | 60.399 | 39.439 | 11.474 | 1.00 | 24.64 |
| ATOM | 182 | N | ASN | 179 | 60.873 | 38.690 | 9.402 | 1.00 | 23.79 |
| ATOM | 183 | CA | ASN | 179 | 62.315 | 38.813 | 9.563 | 1.00 | 26.01 |
| ATOM | 184 | CB | ASN | 179 | 63.018 | 37.607 | 8.947 | 1.00 | 23.77 |
| ATOM | 185 | CG | ASN | 179 | 64.451 | 37.495 | 9.386 | 1.00 | 30.79 |
| ATOM | 186 | OD1 | ASN | 179 | 64.737 | 37.376 | 10.575 | 1.00 | 36.19 |
| ATOM | 187 | ND2 | ASN | 179 | 65.364 | 37.516 | 8.432 | 1.00 | 35.34 |
| ATOM | 188 | C | ASN | 179 | 62.767 | 40.101 | 8.875 | 1.00 | 32.11 |
| ATOM | 189 | O | ASN | 179 | 62.947 | 40.136 | 7.652 | 1.00 | 36.36 |
| ATOM | 190 | N | ALA | 180 | 62.945 | 41.153 | 9.670 | 1.00 | 34.40 |
| ATOM | 191 | CA | ALA | 180 | 63.333 | 42.473 | 9.179 | 1.00 | 28.75 |
| ATOM | 192 | CB | ALA | 180 | 63.653 | 43.390 | 10.346 | 1.00 | 29.96 |
| ATOM | 193 | C | ALA | 180 | 64.481 | 42.481 | 8.182 | 1.00 | 37.02 |
| ATOM | 194 | O | ALA | 180 | 65.518 | 41.866 | 8.414 | 1.00 | 41.85 |
| ATOM | 195 | N | GLN | 181 | 64.266 | 43.163 | 7.057 | 1.00 | 37.15 |
| ATOM | 196 | CA | GLN | 181 | 65.261 | 43.306 | 5.995 | 1.00 | 39.33 |
| ATOM | 197 | CB | GLN | 181 | 66.572 | 43.877 | 6.552 | 1.00 | 37.42 |
| ATOM | 198 | CG | GLN | 181 | 66.420 | 45.190 | 7.309 | 1.00 | 44.86 |
| ATOM | 199 | CD | GLN | 181 | 65.779 | 46.285 | 6.479 | 1.00 | 53.60 |
| ATOM | 200 | OE1 | GLN | 181 | 64.712 | 46.793 | 6.821 | 1.00 | 58.51 |
| ATOM | 201 | NE2 | GLN | 181 | 66.422 | 46.650 | 5.378 | 1.00 | 63.36 |
| ATOM | 202 | C | GLN | 181 | 65.549 | 42.053 | 5.164 | 1.00 | 44.18 |
| ATOM | 203 | O | GLN | 181 | 66.367 | 42.102 | 4.239 | 1.00 | 46.35 |
| ATOM | 204 | N | GLY | 182 | 64.873 | 40.949 | 5.474 | 1.00 | 43.76 |
| ATOM | 205 | CA | GLY | 182 | 65.074 | 39.713 | 4.732 | 1.00 | 46.26 |
| ATOM | 206 | C | GLY | 182 | 66.531 | 39.363 | 4.477 | 1.00 | 49.98 |
| ATOM | 207 | O | GLY | 182 | 67.309 | 39.175 | 5.419 | 1.00 | 56.26 |
| ATOM | 208 | N | SER | 183 | 66.907 | 39.274 | 3.205 | 1.00 | 50.96 |
| ATOM | 209 | CA | SER | 183 | 68.281 | 38.947 | 2.830 | 1.00 | 55.69 |
| ATOM | 210 | CB | SER | 183 | 68.284 | 38.024 | 1.608 | 1.00 | 56.52 |
| ATOM | 211 | OG | SER | 183 | 67.398 | 38.497 | 0.609 | 1.00 | 60.82 |

FIG. 30A-5

| ATOM | 212 | C   | SER | 183 | 69.121 | 40.197 | 2.558  | 1.00 | 59.84 |
|------|-----|-----|-----|-----|--------|--------|--------|------|-------|
| ATOM | 213 | O   | SER | 183 | 70.352 | 40.138 | 2.540  | 1.00 | 66.02 |
| ATOM | 214 | N   | HIS | 184 | 68.453 | 41.338 | 2.413  | 1.00 | 60.68 |
| ATOM | 215 | CA  | HIS | 184 | 69.131 | 42.600 | 2.139  | 1.00 | 60.01 |
| ATOM | 216 | CB  | HIS | 184 | 68.150 | 43.596 | 1.517  | 1.00 | 53.49 |
| ATOM | 217 | C   | HIS | 184 | 69.798 | 43.209 | 3.380  | 1.00 | 59.43 |
| ATOM | 218 | O   | HIS | 184 | 70.373 | 44.300 | 3.303  | 1.00 | 59.56 |
| ATOM | 219 | N   | TRP | 185 | 69.753 | 42.500 | 4.508  | 1.00 | 57.54 |
| ATOM | 220 | CA  | TRP | 185 | 70.343 | 42.995 | 5.754  | 1.00 | 54.25 |
| ATOM | 221 | CB  | TRP | 185 | 70.147 | 41.988 | 6.899  | 1.00 | 47.54 |
| ATOM | 222 | CG  | TRP | 185 | 70.905 | 40.692 | 6.752  | 1.00 | 41.08 |
| ATOM | 223 | CD2 | TRP | 185 | 72.233 | 40.404 | 7.230  | 1.00 | 39.59 |
| ATOM | 224 | CE2 | TRP | 185 | 72.522 | 39.070 | 6.874  | 1.00 | 30.27 |
| ATOM | 225 | CE3 | TRP | 185 | 73.202 | 41.146 | 7.919  | 1.00 | 35.23 |
| ATOM | 226 | CD1 | TRP | 185 | 70.462 | 39.553 | 6.149  | 1.00 | 39.73 |
| ATOM | 227 | NE1 | TRP | 185 | 71.427 | 38.577 | 6.219  | 1.00 | 40.01 |
| ATOM | 228 | CZ2 | TRP | 185 | 73.740 | 38.457 | 7.188  | 1.00 | 31.35 |
| ATOM | 229 | CZ3 | TRP | 185 | 74.416 | 40.535 | 8.230  | 1.00 | 32.76 |
| ATOM | 230 | CH2 | TRP | 185 | 74.673 | 39.203 | 7.861  | 1.00 | 31.71 |
| ATOM | 231 | C   | TRP | 185 | 71.818 | 43.382 | 5.655  | 1.00 | 54.21 |
| ATOM | 232 | O   | TRP | 185 | 72.229 | 44.403 | 6.200  | 1.00 | 52.82 |
| ATOM | 233 | N   | LYS | 186 | 72.605 | 42.584 | 4.938  | 1.00 | 54.57 |
| ATOM | 234 | CA  | LYS | 186 | 74.034 | 42.848 | 4.788  | 1.00 | 55.46 |
| ATOM | 235 | CB  | LYS | 186 | 74.712 | 41.682 | 4.080  | 1.00 | 53.31 |
| ATOM | 236 | C   | LYS | 186 | 74.338 | 44.160 | 4.061  | 1.00 | 58.96 |
| ATOM | 237 | O   | LYS | 186 | 75.417 | 44.731 | 4.226  | 1.00 | 62.57 |
| ATOM | 238 | N   | GLN | 187 | 73.382 | 44.640 | 3.268  | 1.00 | 60.12 |
| ATOM | 239 | CA  | GLN | 187 | 73.563 | 45.873 | 2.512  | 1.00 | 60.15 |
| ATOM | 240 | CB  | GLN | 187 | 73.157 | 45.653 | 1.050  | 1.00 | 57.00 |
| ATOM | 241 | C   | GLN | 187 | 72.809 | 47.064 | 3.101  | 1.00 | 60.91 |
| ATOM | 242 | O   | GLN | 187 | 73.149 | 48.213 | 2.822  | 1.00 | 66.50 |
| ATOM | 243 | N   | ARG | 188 | 71.795 | 46.790 | 3.919  | 1.00 | 59.55 |
| ATOM | 244 | CA  | ARG | 188 | 70.983 | 47.847 | 4.525  | 1.00 | 59.26 |
| ATOM | 245 | CB  | ARG | 188 | 69.504 | 47.462 | 4.466  | 1.00 | 55.21 |
| ATOM | 246 | C   | ARG | 188 | 71.372 | 48.243 | 5.959  | 1.00 | 58.97 |
| ATOM | 247 | O   | ARG | 188 | 70.914 | 49.269 | 6.469  | 1.00 | 58.54 |
| ATOM | 248 | N   | ARG | 189 | 72.202 | 47.432 | 6.607  | 1.00 | 55.46 |
| ATOM | 249 | CA  | ARG | 189 | 72.630 | 47.704 | 7.979  | 1.00 | 52.98 |
| ATOM | 250 | CB  | ARG | 189 | 73.211 | 46.437 | 8.619  | 1.00 | 47.73 |
| ATOM | 251 | CG  | ARG | 189 | 74.509 | 45.985 | 7.989  | 1.00 | 47.88 |
| ATOM | 252 | CD  | ARG | 189 | 75.080 | 44.763 | 8.654  | 1.00 | 46.96 |
| ATOM | 253 | NE  | ARG | 189 | 76.377 | 44.441 | 8.068  | 1.00 | 57.93 |
| ATOM | 254 | CZ  | ARG | 189 | 77.450 | 44.090 | 8.768  | 1.00 | 64.81 |
| ATOM | 255 | NH1 | ARG | 189 | 77.385 | 44.005 | 10.087 | 1.00 | 67.27 |
| ATOM | 256 | NH2 | ARG | 189 | 78.600 | 43.860 | 8.148  | 1.00 | 67.84 |
| ATOM | 257 | C   | ARG | 189 | 73.650 | 48.838 | 8.091  | 1.00 | 53.48 |
| ATOM | 258 | O   | ARG | 189 | 74.513 | 49.004 | 7.227  | 1.00 | 57.14 |
| ATOM | 259 | N   | LYS | 190 | 73.533 | 49.617 | 9.161  | 1.00 | 51.31 |
| ATOM | 260 | CA  | LYS | 190 | 74.444 | 50.722 | 9.435  | 1.00 | 48.83 |
| ATOM | 261 | CB  | LYS | 190 | 73.682 | 52.036 | 9.516  | 1.00 | 45.36 |

FIG. 30A-6

| ATOM | 262 | C | LYS | 190 | 75.101 | 50.411 | 10.773 | 1.00 | 46.88 |
|---|---|---|---|---|---|---|---|---|---|
| ATOM | 263 | O | LYS | 190 | 74.454 | 49.872 | 11.675 | 1.00 | 48.81 |
| ATOM | 264 | N | PHE | 191 | 76.385 | 50.724 | 10.894 | 1.00 | 46.98 |
| ATOM | 265 | CA | PHE | 191 | 77.123 | 50.462 | 12.125 | 1.00 | 44.38 |
| ATOM | 266 | CB | PHE | 191 | 78.630 | 50.520 | 11.873 | 1.00 | 44.25 |
| ATOM | 267 | CG | PHE | 191 | 79.170 | 49.336 | 11.123 | 1.00 | 49.51 |
| ATOM | 268 | CD1 | PHE | 191 | 78.828 | 49.124 | 9.791 | 1.00 | 52.20 |
| ATOM | 269 | CD2 | PHE | 191 | 80.029 | 48.437 | 11.748 | 1.00 | 47.25 |
| ATOM | 270 | CE1 | PHE | 191 | 79.335 | 48.031 | 9.090 | 1.00 | 55.86 |
| ATOM | 271 | CE2 | PHE | 191 | 80.542 | 47.343 | 11.059 | 1.00 | 49.73 |
| ATOM | 272 | CZ | PHE | 191 | 80.195 | 47.139 | 9.727 | 1.00 | 51.55 |
| ATOM | 273 | C | PHE | 191 | 76.764 | 51.443 | 13.233 | 1.00 | 46.44 |
| ATOM | 274 | O | PHE | 191 | 76.647 | 52.645 | 12.996 | 1.00 | 51.28 |
| ATOM | 275 | N | LEU | 192 | 76.567 | 50.924 | 14.439 | 1.00 | 47.66 |
| ATOM | 276 | CA | LEU | 192 | 76.256 | 51.776 | 15.577 | 1.00 | 46.44 |
| ATOM | 277 | CB | LEU | 192 | 75.930 | 50.924 | 16.808 | 1.00 | 38.06 |
| ATOM | 278 | CG | LEU | 192 | 75.527 | 51.672 | 18.082 | 1.00 | 33.55 |
| ATOM | 279 | CD1 | LEU | 192 | 74.180 | 52.339 | 17.871 | 1.00 | 28.17 |
| ATOM | 280 | CD2 | LEU | 192 | 75.476 | 50.717 | 19.268 | 1.00 | 26.95 |
| ATOM | 281 | C | LEU | 192 | 77.524 | 52.595 | 15.824 | 1.00 | 45.82 |
| ATOM | 282 | O | LEU | 192 | 78.604 | 52.024 | 16.008 | 1.00 | 41.65 |
| ATOM | 283 | N | PRO | 193 | 77.422 | 53.936 | 15.782 | 1.00 | 48.88 |
| ATOM | 284 | CD | PRO | 193 | 76.176 | 54.701 | 15.577 | 1.00 | 47.51 |
| ATOM | 285 | CA | PRO | 193 | 78.560 | 54.836 | 15.999 | 1.00 | 47.34 |
| ATOM | 286 | CB | PRO | 193 | 77.879 | 56.162 | 16.319 | 1.00 | 46.04 |
| ATOM | 287 | CG | PRO | 193 | 76.675 | 56.126 | 15.438 | 1.00 | 46.24 |
| ATOM | 288 | C | PRO | 193 | 79.475 | 54.377 | 17.137 | 1.00 | 49.60 |
| ATOM | 289 | O | PRO | 193 | 79.000 | 54.033 | 18.218 | 1.00 | 54.05 |
| ATOM | 290 | N | ASP | 194 | 80.783 | 54.383 | 16.891 | 1.00 | 50.63 |
| ATOM | 291 | CA | ASP | 194 | 81.769 | 53.951 | 17.885 | 1.00 | 54.57 |
| ATOM | 292 | CB | ASP | 194 | 83.164 | 53.965 | 17.272 | 1.00 | 59.28 |
| ATOM | 293 | CG | ASP | 194 | 83.309 | 52.952 | 16.170 | 1.00 | 66.39 |
| ATOM | 294 | OD1 | ASP | 194 | 83.057 | 53.311 | 14.998 | 1.00 | 72.95 |
| ATOM | 295 | OD2 | ASP | 194 | 83.640 | 51.787 | 16.486 | 1.00 | 69.00 |
| ATOM | 296 | C | ASP | 194 | 81.769 | 54.726 | 19.198 | 1.00 | 54.41 |
| ATOM | 297 | O | ASP | 194 | 82.229 | 54.221 | 20.222 | 1.00 | 55.27 |
| ATOM | 298 | N | ASP | 195 | 81.268 | 55.956 | 19.168 | 1.00 | 57.20 |
| ATOM | 299 | CA | ASP | 195 | 81.206 | 56.775 | 20.371 | 1.00 | 59.68 |
| ATOM | 300 | CB | ASP | 195 | 81.017 | 58.261 | 20.006 | 1.00 | 62.99 |
| ATOM | 301 | CG | ASP | 195 | 79.747 | 58.526 | 19.187 | 1.00 | 71.67 |
| ATOM | 302 | OD1 | ASP | 195 | 78.734 | 58.956 | 19.796 | 1.00 | 70.17 |
| ATOM | 303 | OD2 | ASP | 195 | 79.782 | 58.311 | 17.951 | 1.00 | 75.23 |
| ATOM | 304 | C | ASP | 195 | 80.092 | 56.289 | 21.306 | 1.00 | 58.39 |
| ATOM | 305 | O | ASP | 195 | 80.032 | 56.676 | 22.474 | 1.00 | 59.81 |
| ATOM | 306 | N | ILE | 196 | 79.245 | 55.399 | 20.794 | 1.00 | 54.47 |
| ATOM | 307 | CA | ILE | 196 | 78.141 | 54.840 | 21.568 | 1.00 | 49.00 |
| ATOM | 308 | CB | ILE | 196 | 76.839 | 54.780 | 20.731 | 1.00 | 46.64 |
| ATOM | 309 | CG2 | ILE | 196 | 75.701 | 54.195 | 21.560 | 1.00 | 42.11 |
| ATOM | 310 | CG1 | ILE | 196 | 76.467 | 56.184 | 20.241 | 1.00 | 44.23 |
| ATOM | 311 | CD1 | ILE | 196 | 75.214 | 56.238 | 19.373 | 1.00 | 48.45 |

FIG. 30A-7

| ATOM | 312 | C | ILE | 196 | 78.497 | 53.436 | 22.068 | 1.00 | 46.22 |
|---|---|---|---|---|---|---|---|---|---|
| ATOM | 313 | O | ILE | 196 | 78.912 | 52.570 | 21.298 | 1.00 | 42.07 |
| ATOM | 314 | N | GLY | 197 | 78.357 | 53.228 | 23.370 | 1.00 | 45.62 |
| ATOM | 315 | CA | GLY | 197 | 78.658 | 51.930 | 23.941 | 1.00 | 51.49 |
| ATOM | 316 | C | GLY | 197 | 80.005 | 51.832 | 24.625 | 1.00 | 54.64 |
| ATOM | 317 | O | GLY | 197 | 80.377 | 50.759 | 25.092 | 1.00 | 49.98 |
| ATOM | 318 | N | GLN | 198 | 80.726 | 52.946 | 24.725 | 1.00 | 60.08 |
| ATOM | 319 | CA | GLN | 198 | 82.039 | 52.939 | 25.366 | 1.00 | 61.01 |
| ATOM | 320 | CB | GLN | 198 | 83.082 | 53.568 | 24.441 | 1.00 | 55.55 |
| ATOM | 321 | C | GLN | 198 | 82.044 | 53.633 | 26.733 | 1.00 | 59.57 |
| ATOM | 322 | O | GLN | 198 | 83.103 | 54.016 | 27.232 | 1.00 | 61.30 |
| ATOM | 323 | N | SER | 199 | 80.875 | 53.738 | 27.362 | 1.00 | 57.27 |
| ATOM | 324 | CA | SER | 199 | 80.758 | 54.397 | 28.665 | 1.00 | 50.61 |
| ATOM | 325 | CB | SER | 199 | 80.276 | 55.842 | 28.478 | 1.00 | 53.70 |
| ATOM | 326 | OG | SER | 199 | 81.010 | 56.508 | 27.463 | 1.00 | 61.92 |
| ATOM | 327 | C | SER | 199 | 79.848 | 53.684 | 29.675 | 1.00 | 46.41 |
| ATOM | 328 | O | SER | 199 | 78.798 | 54.210 | 30.060 | 1.00 | 41.16 |
| ATOM | 329 | N | PRO | 200 | 80.222 | 52.466 | 30.096 | 1.00 | 42.08 |
| ATOM | 330 | CD | PRO | 200 | 81.349 | 51.648 | 29.605 | 1.00 | 38.31 |
| ATOM | 331 | CA | PRO | 200 | 79.409 | 51.722 | 31.065 | 1.00 | 44.04 |
| ATOM | 332 | CB | PRO | 200 | 79.941 | 50.297 | 30.925 | 1.00 | 36.06 |
| ATOM | 333 | CG | PRO | 200 | 81.377 | 50.504 | 30.583 | 1.00 | 37.43 |
| ATOM | 334 | C | PRO | 200 | 79.615 | 52.270 | 32.485 | 1.00 | 50.91 |
| ATOM | 335 | O | PRO | 200 | 80.629 | 51.980 | 33.123 | 1.00 | 55.65 |
| ATOM | 336 | N | ILE | 201 | 78.663 | 53.060 | 32.975 | 1.00 | 55.81 |
| ATOM | 337 | CA | ILE | 201 | 78.781 | 53.651 | 34.311 | 1.00 | 57.24 |
| ATOM | 338 | CB | ILE | 201 | 78.861 | 55.192 | 34.250 | 1.00 | 58.40 |
| ATOM | 339 | CG2 | ILE | 201 | 80.218 | 55.622 | 33.709 | 1.00 | 60.49 |
| ATOM | 340 | CG1 | ILE | 201 | 77.716 | 55.751 | 33.404 | 1.00 | 62.42 |
| ATOM | 341 | CD1 | ILE | 201 | 77.819 | 57.234 | 33.137 | 1.00 | 61.68 |
| ATOM | 342 | C | ILE | 201 | 77.728 | 53.241 | 35.332 | 1.00 | 56.52 |
| ATOM | 343 | O | ILE | 201 | 77.961 | 53.352 | 36.537 | 1.00 | 60.89 |
| ATOM | 344 | N | VAL | 202 | 76.564 | 52.794 | 34.871 | 1.00 | 52.76 |
| ATOM | 345 | CA | VAL | 202 | 75.522 | 52.366 | 35.802 | 1.00 | 47.37 |
| ATOM | 346 | CB | VAL | 202 | 74.117 | 52.377 | 35.153 | 1.00 | 38.14 |
| ATOM | 347 | CG1 | VAL | 202 | 73.092 | 51.804 | 36.117 | 1.00 | 30.35 |
| ATOM | 348 | CG2 | VAL | 202 | 73.730 | 53.798 | 34.763 | 1.00 | 26.69 |
| ATOM | 349 | C | VAL | 202 | 75.885 | 50.958 | 36.285 | 1.00 | 53.65 |
| ATOM | 350 | O | VAL | 202 | 75.914 | 50.010 | 35.500 | 1.00 | 55.10 |
| ATOM | 351 | N | SER | 203 | 76.226 | 50.839 | 37.561 | 1.00 | 59.85 |
| ATOM | 352 | CA | SER | 203 | 76.614 | 49.556 | 38.132 | 1.00 | 64.58 |
| ATOM | 353 | CB | SER | 203 | 77.209 | 49.749 | 39.532 | 1.00 | 68.95 |
| ATOM | 354 | OG | SER | 203 | 78.396 | 50.523 | 39.483 | 1.00 | 74.02 |
| ATOM | 355 | C | SER | 203 | 75.493 | 48.528 | 38.197 | 1.00 | 61.69 |
| ATOM | 356 | O | SER | 203 | 74.351 | 48.846 | 38.535 | 1.00 | 63.63 |
| ATOM | 357 | N | MET | 204 | 75.848 | 47.295 | 37.859 | 1.00 | 57.37 |
| ATOM | 358 | CA | MET | 204 | 74.932 | 46.162 | 37.885 | 1.00 | 57.54 |
| ATOM | 359 | CB | MET | 204 | 74.847 | 45.505 | 36.501 | 1.00 | 56.59 |
| ATOM | 360 | CG | MET | 204 | 74.012 | 46.270 | 35.489 | 1.00 | 44.08 |
| ATOM | 361 | SD | MET | 204 | 72.255 | 46.228 | 35.884 | 1.00 | 46.62 |

FIG. 30A-8

| ATOM | 362 | CE | MET | 204 | 71.775 | 44.758 | 35.013 | 1.00 | 48.37 |
|---|---|---|---|---|---|---|---|---|---|
| ATOM | 363 | C | MET | 204 | 75.522 | 45.178 | 38.888 | 1.00 | 55.86 |
| ATOM | 364 | O | MET | 204 | 76.746 | 45.089 | 39.027 | 1.00 | 58.94 |
| ATOM | 365 | N | PRO | 205 | 74.671 | 44.432 | 39.607 | 1.00 | 55.36 |
| ATOM | 366 | CD | PRO | 205 | 73.203 | 44.570 | 39.625 | 1.00 | 57.73 |
| ATOM | 367 | CA | PRO | 205 | 75.119 | 43.453 | 40.604 | 1.00 | 56.82 |
| ATOM | 368 | CB | PRO | 205 | 73.814 | 43.042 | 41.295 | 1.00 | 59.79 |
| ATOM | 369 | CG | PRO | 205 | 72.769 | 43.281 | 40.255 | 1.00 | 57.85 |
| ATOM | 370 | C | PRO | 205 | 75.902 | 42.239 | 40.083 | 1.00 | 57.25 |
| ATOM | 371 | O | PRO | 205 | 75.683 | 41.118 | 40.541 | 1.00 | 66.28 |
| ATOM | 372 | N | ASP | 206 | 76.822 | 42.462 | 39.147 | 1.00 | 58.75 |
| ATOM | 373 | CA | ASP | 206 | 77.639 | 41.389 | 38.586 | 1.00 | 61.09 |
| ATOM | 374 | CB | ASP | 206 | 76.802 | 40.462 | 37.685 | 1.00 | 66.07 |
| ATOM | 375 | CG | ASP | 206 | 76.158 | 41.190 | 36.521 | 1.00 | 70.97 |
| ATOM | 376 | OD1 | ASP | 206 | 74.989 | 41.613 | 36.662 | 1.00 | 76.97 |
| ATOM | 377 | OD2 | ASP | 206 | 76.813 | 41.322 | 35.465 | 1.00 | 61.12 |
| ATOM | 378 | C | ASP | 206 | 78.865 | 41.910 | 37.832 | 1.00 | 61.96 |
| ATOM | 379 | O | ASP | 206 | 79.406 | 41.230 | 36.957 | 1.00 | 65.14 |
| ATOM | 380 | N | GLY | 207 | 79.282 | 43.130 | 38.158 | 1.00 | 63.00 |
| ATOM | 381 | CA | GLY | 207 | 80.455 | 43.709 | 37.522 | 1.00 | 64.43 |
| ATOM | 382 | C | GLY | 207 | 80.224 | 44.467 | 36.229 | 1.00 | 64.81 |
| ATOM | 383 | O | GLY | 207 | 80.649 | 45.619 | 36.110 | 1.00 | 68.76 |
| ATOM | 384 | N | ASP | 208 | 79.584 | 43.827 | 35.253 | 1.00 | 63.53 |
| ATOM | 385 | CA | ASP | 208 | 79.316 | 44.459 | 33.962 | 1.00 | 58.96 |
| ATOM | 386 | CB | ASP | 208 | 78.746 | 43.434 | 32.974 | 1.00 | 62.84 |
| ATOM | 387 | CG | ASP | 208 | 79.743 | 42.336 | 32.633 | 1.00 | 64.73 |
| ATOM | 388 | OD1 | ASP | 208 | 79.575 | 41.200 | 33.121 | 1.00 | 66.65 |
| ATOM | 389 | OD2 | ASP | 208 | 80.701 | 42.610 | 31.878 | 1.00 | 68.91 |
| ATOM | 390 | C | ASP | 208 | 78.368 | 45.646 | 34.110 | 1.00 | 56.65 |
| ATOM | 391 | O | ASP | 208 | 77.182 | 45.473 | 34.392 | 1.00 | 55.79 |
| ATOM | 392 | N | LYS | 209 | 78.911 | 46.852 | 33.953 | 1.00 | 54.66 |
| ATOM | 393 | CA | LYS | 209 | 78.132 | 48.081 | 34.082 | 1.00 | 53.92 |
| ATOM | 394 | CB | LYS | 209 | 79.034 | 49.236 | 34.515 | 1.00 | 49.71 |
| ATOM | 395 | C | LYS | 209 | 77.395 | 48.420 | 32.785 | 1.00 | 48.30 |
| ATOM | 396 | O | LYS | 209 | 77.767 | 47.945 | 31.711 | 1.00 | 45.62 |
| ATOM | 397 | N | VAL | 210 | 76.367 | 49.258 | 32.894 | 1.00 | 43.87 |
| ATOM | 398 | CA | VAL | 210 | 75.539 | 49.662 | 31.757 | 1.00 | 41.25 |
| ATOM | 399 | CB | VAL | 210 | 74.020 | 49.624 | 32.125 | 1.00 | 32.99 |
| ATOM | 400 | CG1 | VAL | 210 | 73.153 | 50.029 | 30.937 | 1.00 | 31.44 |
| ATOM | 401 | CG2 | VAL | 210 | 73.626 | 48.239 | 32.604 | 1.00 | 27.57 |
| ATOM | 402 | C | VAL | 210 | 75.868 | 51.061 | 31.234 | 1.00 | 43.30 |
| ATOM | 403 | O | VAL | 210 | 76.261 | 51.951 | 31.994 | 1.00 | 44.65 |
| ATOM | 404 | N | ASP | 211 | 75.688 | 51.235 | 29.931 | 1.00 | 43.23 |
| ATOM | 405 | CA | ASP | 211 | 75.906 | 52.498 | 29.240 | 1.00 | 40.62 |
| ATOM | 406 | CB | ASP | 211 | 76.686 | 52.232 | 27.943 | 1.00 | 43.49 |
| ATOM | 407 | CG | ASP | 211 | 77.014 | 53.499 | 27.161 | 1.00 | 40.77 |
| ATOM | 408 | OD1 | ASP | 211 | 76.180 | 54.427 | 27.092 | 1.00 | 42.13 |
| ATOM | 409 | OD2 | ASP | 211 | 78.111 | 53.549 | 26.574 | 1.00 | 37.49 |
| ATOM | 410 | C | ASP | 211 | 74.491 | 53.001 | 28.921 | 1.00 | 44.56 |
| ATOM | 411 | O | ASP | 211 | 73.849 | 52.500 | 27.998 | 1.00 | 46.44 |

FIG. 30A-9

| | | | | | | | | |
|---|---|---|---|---|---|---|---|---|
| ATOM | 412 | N | LEU | 212 | 74.006 | 53.982 | 29.684 | 1.00 | 43.76 |
| ATOM | 413 | CA | LEU | 212 | 72.662 | 54.538 | 29.494 | 1.00 | 41.47 |
| ATOM | 414 | CB | LEU | 212 | 72.473 | 55.785 | 30.359 | 1.00 | 40.45 |
| ATOM | 415 | CG | LEU | 212 | 72.360 | 55.585 | 31.867 | 1.00 | 44.47 |
| ATOM | 416 | CD1 | LEU | 212 | 72.127 | 56.923 | 32.551 | 1.00 | 40.49 |
| ATOM | 417 | CD2 | LEU | 212 | 71.217 | 54.634 | 32.153 | 1.00 | 45.94 |
| ATOM | 418 | C | LEU | 212 | 72.325 | 54.886 | 28.049 | 1.00 | 40.77 |
| ATOM | 419 | O | LEU | 212 | 71.254 | 54.540 | 27.548 | 1.00 | 42.25 |
| ATOM | 420 | N | GLU | 213 | 73.241 | 55.588 | 27.394 | 1.00 | 42.53 |
| ATOM | 421 | CA | GLU | 213 | 73.068 | 56.008 | 26.009 | 1.00 | 43.60 |
| ATOM | 422 | CB | GLU | 213 | 74.267 | 56.860 | 25.598 | 1.00 | 43.84 |
| ATOM | 423 | CG | GLU | 213 | 74.246 | 57.334 | 24.167 | 1.00 | 51.70 |
| ATOM | 424 | CD | GLU | 213 | 75.598 | 57.848 | 23.722 | 1.00 | 59.23 |
| ATOM | 425 | OE1 | GLU | 213 | 75.655 | 58.939 | 23.121 | 1.00 | 60.14 |
| ATOM | 426 | OE2 | GLU | 213 | 76.611 | 57.158 | 23.980 | 1.00 | 64.78 |
| ATOM | 427 | C | GLU | 213 | 72.913 | 54.810 | 25.066 | 1.00 | 42.63 |
| ATOM | 428 | O | GLU | 213 | 72.008 | 54.779 | 24.226 | 1.00 | 37.04 |
| ATOM | 429 | N | ALA | 214 | 73.775 | 53.814 | 25.245 | 1.00 | 39.28 |
| ATOM | 430 | CA | ALA | 214 | 73.753 | 52.605 | 24.424 | 1.00 | 39.52 |
| ATOM | 431 | CB | ALA | 214 | 74.952 | 51.726 | 24.740 | 1.00 | 35.16 |
| ATOM | 432 | C | ALA | 214 | 72.460 | 51.852 | 24.694 | 1.00 | 37.14 |
| ATOM | 433 | O | ALA | 214 | 71.795 | 51.390 | 23.767 | 1.00 | 42.29 |
| ATOM | 434 | N | PHE | 215 | 72.098 | 51.773 | 25.970 | 1.00 | 31.60 |
| ATOM | 435 | CA | PHE | 215 | 70.883 | 51.102 | 26.404 | 1.00 | 31.67 |
| ATOM | 436 | CB | PHE | 215 | 70.728 | 51.217 | 27.922 | 1.00 | 24.80 |
| ATOM | 437 | CG | PHE | 215 | 69.512 | 50.522 | 28.458 | 1.00 | 21.78 |
| ATOM | 438 | CD1 | PHE | 215 | 69.553 | 49.171 | 28.771 | 1.00 | 24.64 |
| ATOM | 439 | CD2 | PHE | 215 | 68.328 | 51.223 | 28.658 | 1.00 | 21.53 |
| ATOM | 440 | CE1 | PHE | 215 | 68.429 | 48.528 | 29.277 | 1.00 | 27.63 |
| ATOM | 441 | CE2 | PHE | 215 | 67.200 | 50.591 | 29.163 | 1.00 | 21.60 |
| ATOM | 442 | CZ | PHE | 215 | 67.249 | 49.242 | 29.472 | 1.00 | 21.35 |
| ATOM | 443 | C | PHE | 215 | 69.675 | 51.706 | 25.694 | 1.00 | 35.75 |
| ATOM | 444 | O | PHE | 215 | 68.838 | 50.975 | 25.161 | 1.00 | 34.84 |
| ATOM | 445 | N | SER | 216 | 69.604 | 53.035 | 25.665 | 1.00 | 39.09 |
| ATOM | 446 | CA | SER | 216 | 68.506 | 53.739 | 25.001 | 1.00 | 40.61 |
| ATOM | 447 | CB | SER | 216 | 68.668 | 55.249 | 25.165 | 1.00 | 43.86 |
| ATOM | 448 | OG | SER | 216 | 68.616 | 55.603 | 26.537 | 1.00 | 68.66 |
| ATOM | 449 | C | SER | 216 | 68.444 | 53.380 | 23.518 | 1.00 | 40.76 |
| ATOM | 450 | O | SER | 216 | 67.362 | 53.161 | 22.969 | 1.00 | 35.50 |
| ATOM | 451 | N | GLU | 217 | 69.611 | 53.332 | 22.878 | 1.00 | 38.37 |
| ATOM | 452 | CA | GLU | 217 | 69.709 | 52.989 | 21.462 | 1.00 | 37.80 |
| ATOM | 453 | CB | GLU | 217 | 71.164 | 53.049 | 20.997 | 1.00 | 39.67 |
| ATOM | 454 | CG | GLU | 217 | 71.701 | 54.461 | 20.880 | 1.00 | 46.65 |
| ATOM | 455 | CD | GLU | 217 | 70.881 | 55.315 | 19.925 | 1.00 | 53.25 |
| ATOM | 456 | OE1 | GLU | 217 | 70.920 | 55.056 | 18.702 | 1.00 | 57.12 |
| ATOM | 457 | OE2 | GLU | 217 | 70.189 | 56.240 | 20.400 | 1.00 | 54.13 |
| ATOM | 458 | C | GLU | 217 | 69.135 | 51.598 | 21.209 | 1.00 | 38.48 |
| ATOM | 459 | O | GLU | 217 | 68.416 | 51.378 | 20.228 | 1.00 | 43.00 |
| ATOM | 460 | N | PHE | 218 | 69.426 | 50.677 | 22.120 | 1.00 | 35.49 |
| ATOM | 461 | CA | PHE | 218 | 68.934 | 49.313 | 22.018 | 1.00 | 31.76 |

FIG. 30A-10

| ATOM | 462 | CB  | PHE | 218 | 69.743 | 48.392 | 22.925 | 1.00 | 29.10 |
| --- | --- | --- | --- | --- | --- | --- | --- | --- | --- |
| ATOM | 463 | CG  | PHE | 218 | 71.169 | 48.260 | 22.510 | 1.00 | 26.25 |
| ATOM | 464 | CD1 | PHE | 218 | 72.176 | 48.177 | 23.459 | 1.00 | 24.59 |
| ATOM | 465 | CD2 | PHE | 218 | 71.510 | 48.233 | 21.163 | 1.00 | 23.53 |
| ATOM | 466 | CE1 | PHE | 218 | 73.504 | 48.072 | 23.073 | 1.00 | 27.68 |
| ATOM | 467 | CE2 | PHE | 218 | 72.832 | 48.128 | 20.765 | 1.00 | 25.37 |
| ATOM | 468 | CZ  | PHE | 218 | 73.834 | 48.047 | 21.721 | 1.00 | 28.43 |
| ATOM | 469 | C   | PHE | 218 | 67.445 | 49.202 | 22.321 | 1.00 | 31.30 |
| ATOM | 470 | O   | PHE | 218 | 66.726 | 48.496 | 21.621 | 1.00 | 35.18 |
| ATOM | 471 | N   | THR | 219 | 66.967 | 49.915 | 23.333 | 1.00 | 30.54 |
| ATOM | 472 | CA  | THR | 219 | 65.552 | 49.853 | 23.675 | 1.00 | 33.53 |
| ATOM | 473 | CB  | THR | 219 | 65.269 | 50.467 | 25.057 | 1.00 | 36.07 |
| ATOM | 474 | OG1 | THR | 219 | 65.903 | 51.746 | 25.157 | 1.00 | 42.99 |
| ATOM | 475 | CG2 | THR | 219 | 65.797 | 49.562 | 26.145 | 1.00 | 34.32 |
| ATOM | 476 | C   | THR | 219 | 64.680 | 50.514 | 22.609 | 1.00 | 34.53 |
| ATOM | 477 | O   | THR | 219 | 63.507 | 50.162 | 22.450 | 1.00 | 36.57 |
| ATOM | 478 | N   | LYS | 220 | 65.267 | 51.457 | 21.873 | 1.00 | 38.13 |
| ATOM | 479 | CA  | LYS | 220 | 64.563 | 52.158 | 20.806 | 1.00 | 41.42 |
| ATOM | 480 | CB  | LYS | 220 | 65.452 | 53.257 | 20.208 | 1.00 | 41.62 |
| ATOM | 481 | C   | LYS | 220 | 64.140 | 51.182 | 19.716 | 1.00 | 41.80 |
| ATOM | 482 | O   | LYS | 220 | 63.032 | 51.274 | 19.192 | 1.00 | 43.29 |
| ATOM | 483 | N   | ILE | 221 | 65.018 | 50.234 | 19.393 | 1.00 | 36.93 |
| ATOM | 484 | CA  | ILE | 221 | 64.726 | 49.250 | 18.355 | 1.00 | 37.33 |
| ATOM | 485 | CB  | ILE | 221 | 65.965 | 48.932 | 17.482 | 1.00 | 33.71 |
| ATOM | 486 | CG2 | ILE | 221 | 66.491 | 50.202 | 16.826 | 1.00 | 41.26 |
| ATOM | 487 | CG1 | ILE | 221 | 67.042 | 48.235 | 18.309 | 1.00 | 30.36 |
| ATOM | 488 | CD1 | ILE | 221 | 68.178 | 47.687 | 17.472 | 1.00 | 26.28 |
| ATOM | 489 | C   | ILE | 221 | 64.141 | 47.922 | 18.845 | 1.00 | 40.49 |
| ATOM | 490 | O   | ILE | 221 | 63.593 | 47.159 | 18.048 | 1.00 | 43.43 |
| ATOM | 491 | N   | ILE | 222 | 64.219 | 47.651 | 20.144 | 1.00 | 39.43 |
| ATOM | 492 | CA  | ILE | 222 | 63.703 | 46.394 | 20.667 | 1.00 | 35.49 |
| ATOM | 493 | CB  | ILE | 222 | 64.169 | 46.133 | 22.130 | 1.00 | 34.06 |
| ATOM | 494 | CG2 | ILE | 222 | 63.287 | 46.881 | 23.130 | 1.00 | 26.15 |
| ATOM | 495 | CG1 | ILE | 222 | 64.155 | 44.627 | 22.405 | 1.00 | 34.08 |
| ATOM | 496 | CD1 | ILE | 222 | 64.760 | 44.220 | 23.719 | 1.00 | 33.67 |
| ATOM | 497 | C   | ILE | 222 | 62.186 | 46.230 | 20.539 | 1.00 | 37.60 |
| ATOM | 498 | O   | ILE | 222 | 61.703 | 45.127 | 20.279 | 1.00 | 42.14 |
| ATOM | 499 | N   | THR | 223 | 61.438 | 47.324 | 20.665 | 1.00 | 34.60 |
| ATOM | 500 | CA  | THR | 223 | 59.979 | 47.257 | 20.562 | 1.00 | 35.96 |
| ATOM | 501 | CB  | THR | 223 | 59.323 | 48.645 | 20.799 | 1.00 | 41.70 |
| ATOM | 502 | OG1 | THR | 223 | 59.681 | 49.119 | 22.106 | 1.00 | 44.59 |
| ATOM | 503 | CG2 | THR | 223 | 57.796 | 48.548 | 20.706 | 1.00 | 42.58 |
| ATOM | 504 | C   | THR | 223 | 59.478 | 46.614 | 19.252 | 1.00 | 34.77 |
| ATOM | 505 | O   | THR | 223 | 58.671 | 45.680 | 19.289 | 1.00 | 30.60 |
| ATOM | 506 | N   | PRO | 224 | 59.942 | 47.103 | 18.084 | 1.00 | 31.99 |
| ATOM | 507 | CD  | PRO | 224 | 60.784 | 48.288 | 17.839 | 1.00 | 30.37 |
| ATOM | 508 | CA  | PRO | 224 | 59.496 | 46.517 | 16.815 | 1.00 | 29.25 |
| ATOM | 509 | CB  | PRO | 224 | 60.225 | 47.366 | 15.769 | 1.00 | 29.27 |
| ATOM | 510 | CG  | PRO | 224 | 60.393 | 48.677 | 16.441 | 1.00 | 36.31 |
| ATOM | 511 | C   | PRO | 224 | 59.913 | 45.050 | 16.723 | 1.00 | 29.20 |

FIG. 30A-11

| ATOM | 512 | O | PRO | 224 | 59.146 | 44.209 | 16.251 | 1.00 | 33.73 |
|---|---|---|---|---|---|---|---|---|---|
| ATOM | 513 | N | ALA | 225 | 61.124 | 44.754 | 17.192 | 1.00 | 19.86 |
| ATOM | 514 | CA | ALA | 225 | 61.663 | 43.395 | 17.175 | 1.00 | 19.61 |
| ATOM | 515 | CB | ALA | 225 | 63.086 | 43.388 | 17.730 | 1.00 | 19.08 |
| ATOM | 516 | C | ALA | 225 | 60.777 | 42.428 | 17.960 | 1.00 | 20.48 |
| ATOM | 517 | O | ALA | 225 | 60.474 | 41.331 | 17.489 | 1.00 | 24.33 |
| ATOM | 518 | N | ILE | 226 | 60.330 | 42.847 | 19.141 | 1.00 | 23.72 |
| ATOM | 519 | CA | ILE | 226 | 59.471 | 42.001 | 19.972 | 1.00 | 21.94 |
| ATOM | 520 | CB | ILE | 226 | 59.152 | 42.667 | 21.333 | 1.00 | 21.01 |
| ATOM | 521 | CG2 | ILE | 226 | 58.118 | 41.846 | 22.095 | 1.00 | 15.14 |
| ATOM | 522 | CG1 | ILE | 226 | 60.425 | 42.841 | 22.163 | 1.00 | 20.45 |
| ATOM | 523 | CD1 | ILE | 226 | 60.216 | 43.741 | 23.358 | 1.00 | 17.65 |
| ATOM | 524 | C | ILE | 226 | 58.165 | 41.758 | 19.228 | 1.00 | 24.04 |
| ATOM | 525 | O | ILE | 226 | 57.640 | 40.642 | 19.220 | 1.00 | 26.92 |
| ATOM | 526 | N | THR | 227 | 57.653 | 42.811 | 18.596 | 1.00 | 25.22 |
| ATOM | 527 | CA | THR | 227 | 56.410 | 42.730 | 17.836 | 1.00 | 27.92 |
| ATOM | 528 | CB | THR | 227 | 55.984 | 44.132 | 17.333 | 1.00 | 34.33 |
| ATOM | 529 | OG1 | THR | 227 | 55.823 | 45.007 | 18.458 | 1.00 | 33.62 |
| ATOM | 530 | CG2 | THR | 227 | 54.669 | 44.061 | 16.563 | 1.00 | 39.18 |
| ATOM | 531 | C | THR | 227 | 56.524 | 41.733 | 16.671 | 1.00 | 23.61 |
| ATOM | 532 | O | THR | 227 | 55.587 | 40.977 | 16.413 | 1.00 | 24.41 |
| ATOM | 533 | N | ARG | 228 | 57.670 | 41.704 | 15.995 | 1.00 | 15.49 |
| ATOM | 534 | CA | ARG | 228 | 57.872 | 40.773 | 14.885 | 1.00 | 17.92 |
| ATOM | 535 | CB | ARG | 228 | 59.174 | 41.075 | 14.137 | 1.00 | 19.84 |
| ATOM | 536 | CG | ARG | 228 | 59.203 | 42.437 | 13.452 | 1.00 | 20.62 |
| ATOM | 537 | CD | ARG | 228 | 60.351 | 42.523 | 12.453 | 1.00 | 24.29 |
| ATOM | 538 | NE | ARG | 228 | 61.641 | 42.168 | 13.047 | 1.00 | 27.04 |
| ATOM | 539 | CZ | ARG | 228 | 62.452 | 43.039 | 13.642 | 1.00 | 37.92 |
| ATOM | 540 | NH1 | ARG | 228 | 62.113 | 44.327 | 13.725 | 1.00 | 42.82 |
| ATOM | 541 | NH2 | ARG | 228 | 63.618 | 42.634 | 14.136 | 1.00 | 34.80 |
| ATOM | 542 | C | ARG | 228 | 57.870 | 39.323 | 15.387 | 1.00 | 22.51 |
| ATOM | 543 | O | ARG | 228 | 57.402 | 38.421 | 14.686 | 1.00 | 28.49 |
| ATOM | 544 | N | VAL | 229 | 58.362 | 39.104 | 16.607 | 1.00 | 21.46 |
| ATOM | 545 | CA | VAL | 229 | 58.372 | 37.762 | 17.187 | 1.00 | 20.12 |
| ATOM | 546 | CB | VAL | 229 | 59.149 | 37.707 | 18.524 | 1.00 | 17.21 |
| ATOM | 547 | CG1 | VAL | 229 | 59.023 | 36.322 | 19.152 | 1.00 | 13.73 |
| ATOM | 548 | CG2 | VAL | 229 | 60.611 | 38.019 | 18.287 | 1.00 | 15.80 |
| ATOM | 549 | C | VAL | 229 | 56.926 | 37.348 | 17.421 | 1.00 | 19.19 |
| ATOM | 550 | O | VAL | 229 | 56.528 | 36.224 | 17.089 | 1.00 | 19.86 |
| ATOM | 551 | N | VAL | 230 | 56.134 | 38.275 | 17.953 | 1.00 | 21.49 |
| ATOM | 552 | CA | VAL | 230 | 54.721 | 38.023 | 18.217 | 1.00 | 17.69 |
| ATOM | 553 | CB | VAL | 230 | 54.041 | 39.239 | 18.881 | 1.00 | 21.30 |
| ATOM | 554 | CG1 | VAL | 230 | 52.568 | 38.952 | 19.090 | 1.00 | 17.26 |
| ATOM | 555 | CG2 | VAL | 230 | 54.706 | 39.572 | 20.218 | 1.00 | 17.13 |
| ATOM | 556 | C | VAL | 230 | 54.003 | 37.707 | 16.902 | 1.00 | 26.39 |
| ATOM | 557 | O | VAL | 230 | 53.180 | 36.790 | 16.843 | 1.00 | 29.63 |
| ATOM | 558 | N | ASP | 231 | 54.333 | 38.451 | 15.848 | 1.00 | 25.52 |
| ATOM | 559 | CA | ASP | 231 | 53.724 | 38.242 | 14.537 | 1.00 | 26.78 |
| ATOM | 560 | CB | ASP | 231 | 54.132 | 39.353 | 13.571 | 1.00 | 23.70 |
| ATOM | 561 | CG | ASP | 231 | 53.649 | 40.728 | 14.012 | 1.00 | 31.60 |

FIG. 30A-12

| ATOM | 562 | OD1 | ASP | 231 | 52.656 | 40.820 | 14.771 | 1.00 | 31.79 |
|------|-----|-----|-----|-----|--------|--------|--------|------|-------|
| ATOM | 563 | OD2 | ASP | 231 | 54.271 | 41.727 | 13.593 | 1.00 | 35.74 |
| ATOM | 564 | C   | ASP | 231 | 54.108 | 36.879 | 13.970 | 1.00 | 27.69 |
| ATOM | 565 | O   | ASP | 231 | 53.279 | 36.196 | 13.366 | 1.00 | 25.15 |
| ATOM | 566 | N   | PHE | 232 | 55.364 | 36.490 | 14.170 | 1.00 | 22.29 |
| ATOM | 567 | CA  | PHE | 232 | 55.858 | 35.200 | 13.703 | 1.00 | 23.78 |
| ATOM | 568 | CB  | PHE | 232 | 57.328 | 35.008 | 14.097 | 1.00 | 24.76 |
| ATOM | 569 | CG  | PHE | 232 | 57.794 | 33.581 | 14.017 | 1.00 | 25.63 |
| ATOM | 570 | CD1 | PHE | 232 | 58.000 | 32.967 | 12.785 | 1.00 | 24.50 |
| ATOM | 571 | CD2 | PHE | 232 | 57.980 | 32.830 | 15.181 | 1.00 | 19.35 |
| ATOM | 572 | CE1 | PHE | 232 | 58.381 | 31.630 | 12.705 | 1.00 | 22.27 |
| ATOM | 573 | CE2 | PHE | 232 | 58.359 | 31.496 | 15.114 | 1.00 | 20.63 |
| ATOM | 574 | CZ  | PHE | 232 | 58.561 | 30.893 | 13.873 | 1.00 | 26.10 |
| ATOM | 575 | C   | PHE | 232 | 55.018 | 34.093 | 14.328 | 1.00 | 23.51 |
| ATOM | 576 | O   | PHE | 232 | 54.541 | 33.189 | 13.637 | 1.00 | 22.39 |
| ATOM | 577 | N   | ALA | 233 | 54.837 | 34.182 | 15.644 | 1.00 | 24.55 |
| ATOM | 578 | CA  | ALA | 233 | 54.070 | 33.192 | 16.387 | 1.00 | 23.10 |
| ATOM | 579 | CB  | ALA | 233 | 54.145 | 33.490 | 17.869 | 1.00 | 17.99 |
| ATOM | 580 | C   | ALA | 233 | 52.616 | 33.137 | 15.929 | 1.00 | 27.99 |
| ATOM | 581 | O   | ALA | 233 | 52.063 | 32.051 | 15.744 | 1.00 | 25.71 |
| ATOM | 582 | N   | LYS | 234 | 51.997 | 34.305 | 15.760 | 1.00 | 30.19 |
| ATOM | 583 | CA  | LYS | 234 | 50.601 | 34.380 | 15.325 | 1.00 | 31.58 |
| ATOM | 584 | CB  | LYS | 234 | 50.136 | 35.838 | 15.229 | 1.00 | 30.40 |
| ATOM | 585 | CG  | LYS | 234 | 50.100 | 36.593 | 16.555 | 1.00 | 37.97 |
| ATOM | 586 | CD  | LYS | 234 | 49.151 | 35.947 | 17.569 | 1.00 | 53.64 |
| ATOM | 587 | CE  | LYS | 234 | 47.694 | 35.958 | 17.101 | 1.00 | 59.60 |
| ATOM | 588 | NZ  | LYS | 234 | 46.773 | 35.268 | 18.060 | 1.00 | 54.22 |
| ATOM | 589 | C   | LYS | 234 | 50.388 | 33.686 | 13.978 | 1.00 | 30.35 |
| ATOM | 590 | O   | LYS | 234 | 49.318 | 33.142 | 13.716 | 1.00 | 32.50 |
| ATOM | 591 | N   | LYS | 235 | 51.425 | 33.687 | 13.144 | 1.00 | 23.98 |
| ATOM | 592 | CA  | LYS | 235 | 51.351 | 33.071 | 11.828 | 1.00 | 22.75 |
| ATOM | 593 | CB  | LYS | 235 | 52.353 | 33.737 | 10.896 | 1.00 | 23.12 |
| ATOM | 594 | CG  | LYS | 235 | 51.997 | 35.181 | 10.631 | 1.00 | 20.88 |
| ATOM | 595 | CD  | LYS | 235 | 52.982 | 35.836 | 9.688  | 1.00 | 26.50 |
| ATOM | 596 | CE  | LYS | 235 | 52.512 | 37.227 | 9.310  | 1.00 | 31.33 |
| ATOM | 597 | NZ  | LYS | 235 | 53.439 | 37.862 | 8.341  | 1.00 | 36.51 |
| ATOM | 598 | C   | LYS | 235 | 51.508 | 31.554 | 11.791 | 1.00 | 28.37 |
| ATOM | 599 | O   | LYS | 235 | 51.491 | 30.948 | 10.721 | 1.00 | 29.62 |
| ATOM | 600 | N   | LEU | 236 | 51.700 | 30.943 | 12.954 | 1.00 | 33.22 |
| ATOM | 601 | CA  | LEU | 236 | 51.828 | 29.494 | 13.036 | 1.00 | 32.24 |
| ATOM | 602 | CB  | LEU | 236 | 52.911 | 29.101 | 14.043 | 1.00 | 26.25 |
| ATOM | 603 | CG  | LEU | 236 | 54.327 | 29.582 | 13.730 | 1.00 | 23.40 |
| ATOM | 604 | CD1 | LEU | 236 | 55.289 | 29.113 | 14.806 | 1.00 | 20.52 |
| ATOM | 605 | CD2 | LEU | 236 | 54.750 | 29.054 | 12.374 | 1.00 | 20.29 |
| ATOM | 606 | C   | LEU | 236 | 50.470 | 28.984 | 13.502 | 1.00 | 37.08 |
| ATOM | 607 | O   | LEU | 236 | 50.013 | 29.342 | 14.588 | 1.00 | 34.23 |
| ATOM | 608 | N   | PRO | 237 | 49.811 | 28.134 | 12.695 | 1.00 | 44.89 |
| ATOM | 609 | CD  | PRO | 237 | 50.351 | 27.597 | 11.432 | 1.00 | 42.95 |
| ATOM | 610 | CA  | PRO | 237 | 48.491 | 27.556 | 12.990 | 1.00 | 48.88 |
| ATOM | 611 | CB  | PRO | 237 | 48.396 | 26.406 | 11.987 | 1.00 | 51.40 |

FIG. 30A-13

| | | | | | | | | |
|---|---|---|---|---|---|---|---|---|
| ATOM | 612 | CG | PRO | 237 | 49.142 | 26.931 | 10.813 | 1.00 | 53.54 |
| ATOM | 613 | C | PRO | 237 | 48.278 | 27.072 | 14.430 | 1.00 | 49.12 |
| ATOM | 614 | O | PRO | 237 | 47.387 | 27.551 | 15.133 | 1.00 | 48.18 |
| ATOM | 615 | N | MET | 238 | 49.104 | 26.126 | 14.860 | 1.00 | 45.79 |
| ATOM | 616 | CA | MET | 238 | 49.029 | 25.558 | 16.200 | 1.00 | 52.79 |
| ATOM | 617 | CB | MET | 238 | 50.133 | 24.505 | 16.378 | 1.00 | 49.72 |
| ATOM | 618 | CG | MET | 238 | 49.861 | 23.195 | 15.637 | 1.00 | 58.16 |
| ATOM | 619 | SD | MET | 238 | 51.342 | 22.205 | 15.284 | 1.00 | 60.11 |
| ATOM | 620 | CE | MET | 238 | 50.993 | 21.626 | 13.625 | 1.00 | 53.03 |
| ATOM | 621 | C | MET | 238 | 49.103 | 26.593 | 17.324 | 1.00 | 53.36 |
| ATOM | 622 | O | MET | 238 | 48.583 | 26.365 | 18.420 | 1.00 | 58.87 |
| ATOM | 623 | N | PHE | 239 | 49.713 | 27.742 | 17.043 | 1.00 | 48.09 |
| ATOM | 624 | CA | PHE | 239 | 49.861 | 28.793 | 18.045 | 1.00 | 41.38 |
| ATOM | 625 | CB | PHE | 239 | 51.011 | 29.736 | 17.677 | 1.00 | 32.92 |
| ATOM | 626 | CG | PHE | 239 | 51.307 | 30.763 | 18.734 | 1.00 | 31.32 |
| ATOM | 627 | CD1 | PHE | 239 | 52.162 | 30.462 | 19.790 | 1.00 | 28.28 |
| ATOM | 628 | CD2 | PHE | 239 | 50.715 | 32.024 | 18.689 | 1.00 | 24.80 |
| ATOM | 629 | CE1 | PHE | 239 | 52.425 | 31.402 | 20.790 | 1.00 | 29.45 |
| ATOM | 630 | CE2 | PHE | 239 | 50.970 | 32.973 | 19.682 | 1.00 | 32.29 |
| ATOM | 631 | CZ | PHE | 239 | 51.828 | 32.659 | 20.737 | 1.00 | 26.00 |
| ATOM | 632 | C | PHE | 239 | 48.590 | 29.592 | 18.344 | 1.00 | 37.40 |
| ATOM | 633 | O | PHE | 239 | 48.194 | 29.696 | 19.501 | 1.00 | 33.32 |
| ATOM | 634 | N | SER | 240 | 47.958 | 30.166 | 17.321 | 1.00 | 36.32 |
| ATOM | 635 | CA | SER | 240 | 46.745 | 30.959 | 17.529 | 1.00 | 39.00 |
| ATOM | 636 | CB | SER | 240 | 46.385 | 31.724 | 16.258 | 1.00 | 47.52 |
| ATOM | 637 | OG | SER | 240 | 47.390 | 32.671 | 15.947 | 1.00 | 52.67 |
| ATOM | 638 | C | SER | 240 | 45.539 | 30.158 | 18.032 | 1.00 | 36.82 |
| ATOM | 639 | O | SER | 240 | 44.548 | 30.743 | 18.485 | 1.00 | 43.02 |
| ATOM | 640 | N | GLU | 241 | 45.617 | 28.833 | 17.931 | 1.00 | 38.98 |
| ATOM | 641 | CA | GLU | 241 | 44.554 | 27.954 | 18.408 | 1.00 | 40.35 |
| ATOM | 642 | CB | GLU | 241 | 44.788 | 26.521 | 17.926 | 1.00 | 49.38 |
| ATOM | 643 | CG | GLU | 241 | 44.541 | 26.287 | 16.452 | 1.00 | 65.25 |
| ATOM | 644 | CD | GLU | 241 | 44.873 | 24.856 | 16.002 | 1.00 | 70.72 |
| ATOM | 645 | OE1 | GLU | 241 | 44.806 | 23.923 | 16.845 | 1.00 | 73.36 |
| ATOM | 646 | OE2 | GLU | 241 | 45.211 | 24.679 | 14.805 | 1.00 | 68.60 |
| ATOM | 647 | C | GLU | 241 | 44.550 | 27.968 | 19.934 | 1.00 | 37.83 |
| ATOM | 648 | O | GLU | 241 | 43.504 | 27.857 | 20.570 | 1.00 | 40.77 |
| ATOM | 649 | N | LEU | 242 | 45.747 | 28.103 | 20.498 | 1.00 | 34.71 |
| ATOM | 650 | CA | LEU | 242 | 45.974 | 28.132 | 21.944 | 1.00 | 31.77 |
| ATOM | 651 | CB | LEU | 242 | 47.478 | 28.240 | 22.215 | 1.00 | 24.87 |
| ATOM | 652 | CG | LEU | 242 | 48.345 | 27.006 | 22.455 | 1.00 | 30.51 |
| ATOM | 653 | CD1 | LEU | 242 | 47.814 | 25.763 | 21.772 | 1.00 | 31.72 |
| ATOM | 654 | CD2 | LEU | 242 | 49.743 | 27.328 | 21.996 | 1.00 | 24.25 |
| ATOM | 655 | C | LEU | 242 | 45.274 | 29.287 | 22.657 | 1.00 | 29.41 |
| ATOM | 656 | O | LEU | 242 | 45.029 | 30.339 | 22.071 | 1.00 | 28.12 |
| ATOM | 657 | N | PRO | 243 | 44.913 | 29.089 | 23.938 | 1.00 | 32.37 |
| ATOM | 658 | CD | PRO | 243 | 44.976 | 27.849 | 24.728 | 1.00 | 27.94 |
| ATOM | 659 | CA | PRO | 243 | 44.253 | 30.165 | 24.685 | 1.00 | 33.92 |
| ATOM | 660 | CB | PRO | 243 | 44.041 | 29.537 | 26.065 | 1.00 | 29.41 |
| ATOM | 661 | CG | PRO | 243 | 43.929 | 28.072 | 25.775 | 1.00 | 30.77 |

FIG. 30A-14

| | | | | | | | | |
|---|---|---|---|---|---|---|---|---|
| ATOM | 662 | C | PRO | 243 | 45.246 | 31.334 | 24.775 | 1.00 35.86 |
| ATOM | 663 | O | PRO | 243 | 46.461 | 31.110 | 24.809 | 1.00 38.79 |
| ATOM | 664 | N | CYS | 244 | 44.751 | 32.570 | 24.834 | 1.00 39.67 |
| ATOM | 665 | CA | CYS | 244 | 45.621 | 33.749 | 24.931 | 1.00 45.78 |
| ATOM | 666 | CB | CYS | 244 | 44.788 | 35.028 | 25.102 | 1.00 71.13 |
| ATOM | 667 | SG | CYS | 244 | 44.068 | 35.680 | 23.580 | 1.00100.76 |
| ATOM | 669 | C | CYS | 244 | 46.660 | 33.665 | 26.051 | 1.00 40.08 |
| ATOM | 670 | O | CYS | 244 | 47.797 | 34.096 | 25.879 | 1.00 35.68 |
| ATOM | 671 | N | GLU | 245 | 46.265 | 33.088 | 27.184 | 1.00 34.25 |
| ATOM | 672 | CA | GLU | 245 | 47.156 | 32.939 | 28.337 | 1.00 34.60 |
| ATOM | 673 | CB | GLU | 245 | 46.426 | 32.296 | 29.524 | 1.00 42.20 |
| ATOM | 674 | CG | GLU | 245 | 45.356 | 33.171 | 30.160 | 1.00 41.92 |
| ATOM | 675 | CD | GLU | 245 | 43.947 | 32.808 | 29.730 | 1.00 39.68 |
| ATOM | 676 | OE1 | GLU | 245 | 43.080 | 32.693 | 30.618 | 1.00 38.31 |
| ATOM | 677 | OE2 | GLU | 245 | 43.697 | 32.644 | 28.516 | 1.00 48.13 |
| ATOM | 678 | C | GLU | 245 | 48.376 | 32.109 | 27.984 | 1.00 29.54 |
| ATOM | 679 | O | GLU | 245 | 49.497 | 32.437 | 28.381 | 1.00 33.54 |
| ATOM | 680 | N | ASP | 246 | 48.146 | 31.034 | 27.236 | 1.00 26.40 |
| ATOM | 681 | CA | ASP | 246 | 49.219 | 30.154 | 26.794 | 1.00 26.99 |
| ATOM | 682 | CB | ASP | 246 | 48.650 | 28.887 | 26.153 | 1.00 29.86 |
| ATOM | 683 | CG | ASP | 246 | 48.184 | 27.876 | 27.175 | 1.00 34.10 |
| ATOM | 684 | OD1 | ASP | 246 | 48.149 | 28.199 | 28.381 | 1.00 31.83 |
| ATOM | 685 | OD2 | ASP | 246 | 47.863 | 26.742 | 26.772 | 1.00 35.79 |
| ATOM | 686 | C | ASP | 246 | 50.103 | 30.875 | 25.790 | 1.00 28.07 |
| ATOM | 687 | O | ASP | 246 | 51.331 | 30.789 | 25.863 | 1.00 27.35 |
| ATOM | 688 | N | GLN | 247 | 49.472 | 31.577 | 24.851 | 1.00 25.53 |
| ATOM | 689 | CA | GLN | 247 | 50.198 | 32.327 | 23.829 | 1.00 26.08 |
| ATOM | 690 | CB | GLN | 247 | 49.228 | 33.089 | 22.924 | 1.00 23.38 |
| ATOM | 691 | CG | GLN | 247 | 48.303 | 32.213 | 22.091 | 1.00 23.76 |
| ATOM | 692 | CD | GLN | 247 | 47.429 | 33.029 | 21.151 | 1.00 26.89 |
| ATOM | 693 | OE1 | GLN | 247 | 47.853 | 34.054 | 20.628 | 1.00 33.51 |
| ATOM | 694 | NE2 | GLN | 247 | 46.198 | 32.593 | 20.957 | 1.00 27.44 |
| ATOM | 695 | C | GLN | 247 | 51.133 | 33.313 | 24.511 | 1.00 22.74 |
| ATOM | 696 | O | GLN | 247 | 52.326 | 33.373 | 24.205 | 1.00 27.63 |
| ATOM | 697 | N | ILE | 248 | 50.588 | 34.047 | 25.473 | 1.00 25.03 |
| ATOM | 698 | CA | ILE | 248 | 51.353 | 35.035 | 26.220 | 1.00 25.94 |
| ATOM | 699 | CB | ILE | 248 | 50.436 | 35.781 | 27.226 | 1.00 24.84 |
| ATOM | 700 | CG2 | ILE | 248 | 51.251 | 36.633 | 28.179 | 1.00 21.87 |
| ATOM | 701 | CG1 | ILE | 248 | 49.430 | 36.652 | 26.459 | 1.00 27.98 |
| ATOM | 702 | CD1 | ILE | 248 | 48.359 | 37.298 | 27.328 | 1.00 29.90 |
| ATOM | 703 | C | ILE | 248 | 52.535 | 34.382 | 26.939 | 1.00 27.53 |
| ATOM | 704 | O | ILE | 248 | 53.671 | 34.847 | 26.833 | 1.00 29.35 |
| ATOM | 705 | N | ILE | 249 | 52.279 | 33.274 | 27.622 | 1.00 24.38 |
| ATOM | 706 | CA | ILE | 249 | 53.334 | 32.582 | 28.354 | 1.00 26.26 |
| ATOM | 707 | CB | ILE | 249 | 52.759 | 31.395 | 29.166 | 1.00 29.81 |
| ATOM | 708 | CG2 | ILE | 249 | 53.874 | 30.521 | 29.726 | 1.00 29.16 |
| ATOM | 709 | CG1 | ILE | 249 | 51.883 | 31.923 | 30.300 | 1.00 27.15 |
| ATOM | 710 | CD1 | ILE | 249 | 51.173 | 30.838 | 31.076 | 1.00 32.35 |
| ATOM | 711 | C | ILE | 249 | 54.448 | 32.103 | 27.422 | 1.00 27.78 |
| ATOM | 712 | O | ILE | 249 | 55.634 | 32.297 | 27.708 | 1.00 29.37 |

FIG. 30A-15

| ATOM | 713 | N | LEU | 250 | 54.061 | 31.516 | 26.289 | 1.00 | 29.25 |
| --- | --- | --- | --- | --- | --- | --- | --- | --- | --- |
| ATOM | 714 | CA | LEU | 250 | 55.021 | 31.005 | 25.319 | 1.00 | 24.49 |
| ATOM | 715 | CB | LEU | 250 | 54.303 | 30.224 | 24.214 | 1.00 | 23.75 |
| ATOM | 716 | CG | LEU | 250 | 53.541 | 28.962 | 24.629 | 1.00 | 23.18 |
| ATOM | 717 | CD1 | LEU | 250 | 52.886 | 28.353 | 23.416 | 1.00 | 19.94 |
| ATOM | 718 | CD2 | LEU | 250 | 54.475 | 27.960 | 25.278 | 1.00 | 20.76 |
| ATOM | 719 | C | LEU | 250 | 55.878 | 32.116 | 24.714 | 1.00 | 22.20 |
| ATOM | 720 | O | LEU | 250 | 57.082 | 31.940 | 24.528 | 1.00 | 23.49 |
| ATOM | 721 | N | LEU | 251 | 55.256 | 33.249 | 24.399 | 1.00 | 24.21 |
| ATOM | 722 | CA | LEU | 251 | 55.980 | 34.384 | 23.831 | 1.00 | 27.98 |
| ATOM | 723 | CB | LEU | 251 | 55.010 | 35.488 | 23.408 | 1.00 | 25.91 |
| ATOM | 724 | CG | LEU | 251 | 54.287 | 35.245 | 22.085 | 1.00 | 29.46 |
| ATOM | 725 | CD1 | LEU | 251 | 53.121 | 36.217 | 21.939 | 1.00 | 35.03 |
| ATOM | 726 | CD2 | LEU | 251 | 55.268 | 35.364 | 20.924 | 1.00 | 23.65 |
| ATOM | 727 | C | LEU | 251 | 56.998 | 34.931 | 24.828 | 1.00 | 26.85 |
| ATOM | 728 | O | LEU | 251 | 58.165 | 35.143 | 24.484 | 1.00 | 23.12 |
| ATOM | 729 | N | LYS | 252 | 56.556 | 35.145 | 26.063 | 1.00 | 25.33 |
| ATOM | 730 | CA | LYS | 252 | 57.427 | 35.644 | 27.119 | 1.00 | 31.33 |
| ATOM | 731 | CB | LYS | 252 | 56.659 | 35.723 | 28.437 | 1.00 | 37.06 |
| ATOM | 732 | CG | LYS | 252 | 55.593 | 36.805 | 28.511 | 1.00 | 41.75 |
| ATOM | 733 | CD | LYS | 252 | 54.779 | 36.619 | 29.783 | 1.00 | 52.64 |
| ATOM | 734 | CE | LYS | 252 | 53.822 | 37.767 | 30.057 | 1.00 | 62.60 |
| ATOM | 735 | NZ | LYS | 252 | 54.503 | 39.005 | 30.520 | 1.00 | 71.68 |
| ATOM | 736 | C | LYS | 252 | 58.622 | 34.705 | 27.293 | 1.00 | 29.08 |
| ATOM | 737 | O | LYS | 252 | 59.758 | 35.150 | 27.460 | 1.00 | 35.24 |
| ATOM | 738 | N | GLY | 253 | 58.355 | 33.403 | 27.211 | 1.00 | 24.98 |
| ATOM | 739 | CA | GLY | 253 | 59.407 | 32.416 | 27.369 | 1.00 | 22.80 |
| ATOM | 740 | C | GLY | 253 | 60.413 | 32.282 | 26.235 | 1.00 | 26.90 |
| ATOM | 741 | O | GLY | 253 | 61.572 | 31.948 | 26.489 | 1.00 | 31.90 |
| ATOM | 742 | N | CYS | 254 | 60.013 | 32.574 | 24.997 | 1.00 | 25.42 |
| ATOM | 743 | CA | CYS | 254 | 60.932 | 32.427 | 23.863 | 1.00 | 20.71 |
| ATOM | 744 | CB | CYS | 254 | 60.314 | 31.509 | 22.811 | 1.00 | 24.98 |
| ATOM | 745 | SG | CYS | 254 | 58.976 | 32.310 | 21.909 | 1.00 | 24.24 |
| ATOM | 746 | C | CYS | 254 | 61.353 | 33.716 | 23.164 | 1.00 | 22.79 |
| ATOM | 747 | O | CYS | 254 | 62.217 | 33.683 | 22.282 | 1.00 | 23.23 |
| ATOM | 748 | N | CYS | 255 | 60.757 | 34.842 | 23.539 | 1.00 | 21.47 |
| ATOM | 749 | CA | CYS | 255 | 61.061 | 36.114 | 22.884 | 1.00 | 22.50 |
| ATOM | 750 | CB | CYS | 255 | 60.318 | 37.262 | 23.567 | 1.00 | 21.72 |
| ATOM | 751 | SG | CYS | 255 | 60.353 | 38.768 | 22.597 | 1.00 | 24.73 |
| ATOM | 752 | C | CYS | 255 | 62.547 | 36.457 | 22.738 | 1.00 | 23.81 |
| ATOM | 753 | O | CYS | 255 | 63.015 | 36.746 | 21.632 | 1.00 | 23.48 |
| ATOM | 754 | N | MET | 256 | 63.294 | 36.402 | 23.838 | 1.00 | 22.13 |
| ATOM | 755 | CA | MET | 256 | 64.719 | 36.713 | 23.792 | 1.00 | 22.91 |
| ATOM | 756 | CB | MET | 256 | 65.286 | 36.810 | 25.213 | 1.00 | 23.78 |
| ATOM | 757 | CG | MET | 256 | 66.781 | 37.094 | 25.272 | 1.00 | 17.41 |
| ATOM | 758 | SD | MET | 256 | 67.196 | 38.632 | 24.415 | 1.00 | 23.65 |
| ATOM | 759 | CE | MET | 256 | 69.010 | 38.715 | 24.624 | 1.00 | 18.57 |
| ATOM | 760 | C | MET | 256 | 65.487 | 35.671 | 22.980 | 1.00 | 21.41 |
| ATOM | 761 | O | MET | 256 | 66.432 | 36.005 | 22.260 | 1.00 | 22.01 |
| ATOM | 762 | N | GLU | 257 | 65.058 | 34.415 | 23.068 | 1.00 | 23.18 |

FIG. 30A-16

| ATOM | 763 | CA | GLU | 257 | 65.705 | 33.323 | 22.345 | 1.00 | 22.90 |
|---|---|---|---|---|---|---|---|---|---|
| ATOM | 764 | CB | GLU | 257 | 65.085 | 31.989 | 22.753 | 1.00 | 24.00 |
| ATOM | 765 | CG | GLU | 257 | 65.522 | 31.521 | 24.125 | 1.00 | 33.44 |
| ATOM | 766 | CD | GLU | 257 | 64.564 | 30.527 | 24.735 | 1.00 | 38.03 |
| ATOM | 767 | OE1 | GLU | 257 | 63.977 | 29.705 | 24.000 | 1.00 | 45.59 |
| ATOM | 768 | OE2 | GLU | 257 | 64.385 | 30.577 | 25.965 | 1.00 | 45.75 |
| ATOM | 769 | C | GLU | 257 | 65.595 | 33.526 | 20.840 | 1.00 | 21.68 |
| ATOM | 770 | O | GLU | 257 | 66.586 | 33.421 | 20.107 | 1.00 | 20.02 |
| ATOM | 771 | N | ILE | 258 | 64.383 | 33.852 | 20.391 | 1.00 | 17.07 |
| ATOM | 772 | CA | ILE | 258 | 64.135 | 34.090 | 18.973 | 1.00 | 17.01 |
| ATOM | 773 | CB | ILE | 258 | 62.613 | 34.207 | 18.684 | 1.00 | 17.33 |
| ATOM | 774 | CG2 | ILE | 258 | 62.369 | 34.758 | 17.276 | 1.00 | 15.91 |
| ATOM | 775 | CG1 | ILE | 258 | 61.952 | 32.831 | 18.885 | 1.00 | 16.69 |
| ATOM | 776 | CD1 | ILE | 258 | 60.450 | 32.783 | 18.632 | 1.00 | 16.31 |
| ATOM | 777 | C | ILE | 258 | 64.911 | 35.324 | 18.501 | 1.00 | 17.65 |
| ATOM | 778 | O | ILE | 258 | 65.605 | 35.263 | 17.484 | 1.00 | 22.58 |
| ATOM | 779 | N | MET | 259 | 64.865 | 36.410 | 19.274 | 1.00 | 20.17 |
| ATOM | 780 | CA | MET | 259 | 65.584 | 37.628 | 18.909 | 1.00 | 15.03 |
| ATOM | 781 | CB | MET | 259 | 65.234 | 38.771 | 19.856 | 1.00 | 20.12 |
| ATOM | 782 | CG | MET | 259 | 63.791 | 39.191 | 19.775 | 1.00 | 17.19 |
| ATOM | 783 | SD | MET | 259 | 63.523 | 40.795 | 20.524 | 1.00 | 28.92 |
| ATOM | 784 | CE | MET | 259 | 63.718 | 40.406 | 22.261 | 1.00 | 19.58 |
| ATOM | 785 | C | MET | 259 | 67.090 | 37.402 | 18.884 | 1.00 | 18.84 |
| ATOM | 786 | O | MET | 259 | 67.783 | 37.912 | 17.996 | 1.00 | 29.07 |
| ATOM | 787 | N | SER | 260 | 67.590 | 36.618 | 19.837 | 1.00 | 21.45 |
| ATOM | 788 | CA | SER | 260 | 69.019 | 36.319 | 19.906 | 1.00 | 18.71 |
| ATOM | 789 | CB | SER | 260 | 69.367 | 35.595 | 21.207 | 1.00 | 18.35 |
| ATOM | 790 | OG | SER | 260 | 69.128 | 36.421 | 22.329 | 1.00 | 25.42 |
| ATOM | 791 | C | SER | 260 | 69.430 | 35.469 | 18.709 | 1.00 | 17.83 |
| ATOM | 792 | O | SER | 260 | 70.497 | 35.673 | 18.131 | 1.00 | 22.97 |
| ATOM | 793 | N | LEU | 261 | 68.572 | 34.522 | 18.331 | 1.00 | 21.66 |
| ATOM | 794 | CA | LEU | 261 | 68.837 | 33.663 | 17.179 | 1.00 | 20.98 |
| ATOM | 795 | CB | LEU | 261 | 67.739 | 32.608 | 17.053 | 1.00 | 22.66 |
| ATOM | 796 | CG | LEU | 261 | 67.719 | 31.759 | 15.781 | 1.00 | 22.12 |
| ATOM | 797 | CD1 | LEU | 261 | 68.998 | 30.938 | 15.665 | 1.00 | 18.51 |
| ATOM | 798 | CD2 | LEU | 261 | 66.498 | 30.851 | 15.800 | 1.00 | 19.60 |
| ATOM | 799 | C | LEU | 261 | 68.873 | 34.527 | 15.920 | 1.00 | 22.95 |
| ATOM | 800 | O | LEU | 261 | 69.779 | 34.402 | 15.091 | 1.00 | 22.62 |
| ATOM | 801 | N | ARG | 262 | 67.892 | 35.418 | 15.798 | 1.00 | 22.12 |
| ATOM | 802 | CA | ARG | 262 | 67.816 | 36.301 | 14.643 | 1.00 | 25.32 |
| ATOM | 803 | CB | ARG | 262 | 66.525 | 37.115 | 14.677 | 1.00 | 21.95 |
| ATOM | 804 | CG | ARG | 262 | 65.304 | 36.268 | 14.362 | 1.00 | 21.48 |
| ATOM | 805 | CD | ARG | 262 | 64.026 | 37.077 | 14.345 | 1.00 | 19.12 |
| ATOM | 806 | NE | ARG | 262 | 62.990 | 36.377 | 13.599 | 1.00 | 22.18 |
| ATOM | 807 | CZ | ARG | 262 | 61.780 | 36.862 | 13.333 | 1.00 | 22.88 |
| ATOM | 808 | NH1 | ARG | 262 | 61.429 | 38.075 | 13.752 | 1.00 | 20.81 |
| ATOM | 809 | NH2 | ARG | 262 | 60.912 | 36.129 | 12.648 | 1.00 | 20.26 |
| ATOM | 810 | C | ARG | 262 | 69.044 | 37.196 | 14.531 | 1.00 | 25.05 |
| ATOM | 811 | O | ARG | 262 | 69.485 | 37.513 | 13.427 | 1.00 | 22.98 |
| ATOM | 812 | N | ALA | 263 | 69.608 | 37.579 | 15.676 | 1.00 | 26.36 |

FIG. 30A-17

| ATOM | 813 | CA | ALA | 263 | 70.818 | 38.400 | 15.705 | 1.00 | 27.02 |
|---|---|---|---|---|---|---|---|---|---|
| ATOM | 814 | CB | ALA | 263 | 70.997 | 39.045 | 17.087 | 1.00 | 25.80 |
| ATOM | 815 | C | ALA | 263 | 72.026 | 37.514 | 15.368 | 1.00 | 25.21 |
| ATOM | 816 | O | ALA | 263 | 72.825 | 37.844 | 14.492 | 1.00 | 31.14 |
| ATOM | 817 | N | ALA | 264 | 72.109 | 36.358 | 16.027 | 1.00 | 25.62 |
| ATOM | 818 | CA | ALA | 264 | 73.203 | 35.408 | 15.828 | 1.00 | 23.85 |
| ATOM | 819 | CB | ALA | 264 | 73.062 | 34.237 | 16.794 | 1.00 | 17.15 |
| ATOM | 820 | C | ALA | 264 | 73.345 | 34.901 | 14.391 | 1.00 | 26.03 |
| ATOM | 821 | O | ALA | 264 | 74.460 | 34.773 | 13.886 | 1.00 | 25.66 |
| ATOM | 822 | N | VAL | 265 | 72.234 | 34.615 | 13.723 | 1.00 | 25.22 |
| ATOM | 823 | CA | VAL | 265 | 72.327 | 34.128 | 12.350 | 1.00 | 28.38 |
| ATOM | 824 | CB | VAL | 265 | 71.028 | 33.457 | 11.857 | 1.00 | 24.59 |
| ATOM | 825 | CG1 | VAL | 265 | 70.707 | 32.264 | 12.719 | 1.00 | 25.53 |
| ATOM | 826 | CG2 | VAL | 265 | 69.881 | 34.440 | 11.853 | 1.00 | 20.86 |
| ATOM | 827 | C | VAL | 265 | 72.747 | 35.235 | 11.393 | 1.00 | 31.46 |
| ATOM | 828 | O | VAL | 265 | 73.024 | 34.973 | 10.222 | 1.00 | 34.75 |
| ATOM | 829 | N | ARG | 266 | 72.795 | 36.464 | 11.896 | 1.00 | 30.10 |
| ATOM | 830 | CA | ARG | 266 | 73.211 | 37.602 | 11.089 | 1.00 | 30.69 |
| ATOM | 831 | CB | ARG | 266 | 72.170 | 38.713 | 11.148 | 1.00 | 25.13 |
| ATOM | 832 | CG | ARG | 266 | 70.976 | 38.406 | 10.299 | 1.00 | 25.43 |
| ATOM | 833 | CD | ARG | 266 | 69.999 | 39.537 | 10.277 | 1.00 | 29.56 |
| ATOM | 834 | NE | ARG | 266 | 69.032 | 39.340 | 9.205 | 1.00 | 31.59 |
| ATOM | 835 | CZ | ARG | 266 | 67.814 | 39.861 | 9.197 | 1.00 | 31.18 |
| ATOM | 836 | NH1 | ARG | 266 | 67.408 | 40.611 | 10.215 | 1.00 | 31.01 |
| ATOM | 837 | NH2 | ARG | 266 | 67.012 | 39.648 | 8.163 | 1.00 | 28.21 |
| ATOM | 838 | C | ARG | 266 | 74.568 | 38.111 | 11.544 | 1.00 | 34.28 |
| ATOM | 839 | O | ARG | 266 | 74.877 | 39.300 | 11.423 | 1.00 | 41.19 |
| ATOM | 840 | N | TYR | 267 | 75.362 | 37.207 | 12.108 | 1.00 | 30.80 |
| ATOM | 841 | CA | TYR | 267 | 76.694 | 37.544 | 12.573 | 1.00 | 33.84 |
| ATOM | 842 | CB | TYR | 267 | 77.202 | 36.461 | 13.534 | 1.00 | 32.56 |
| ATOM | 843 | CG | TYR | 267 | 78.674 | 36.570 | 13.867 | 1.00 | 34.23 |
| ATOM | 844 | CD1 | TYR | 267 | 79.131 | 37.465 | 14.835 | 1.00 | 32.60 |
| ATOM | 845 | CE1 | TYR | 267 | 80.491 | 37.593 | 15.106 | 1.00 | 34.90 |
| ATOM | 846 | CD2 | TYR | 267 | 79.615 | 35.801 | 13.184 | 1.00 | 32.84 |
| ATOM | 847 | CE2 | TYR | 267 | 80.972 | 35.920 | 13.446 | 1.00 | 34.70 |
| ATOM | 848 | CZ | TYR | 267 | 81.404 | 36.816 | 14.405 | 1.00 | 36.21 |
| ATOM | 849 | OH | TYR | 267 | 82.749 | 36.940 | 14.651 | 1.00 | 39.48 |
| ATOM | 850 | C | TYR | 267 | 77.615 | 37.649 | 11.360 | 1.00 | 37.82 |
| ATOM | 851 | O | TYR | 267 | 77.648 | 36.749 | 10.517 | 1.00 | 39.45 |
| ATOM | 852 | N | ASP | 268 | 78.319 | 38.769 | 11.239 | 1.00 | 44.62 |
| ATOM | 853 | CA | ASP | 268 | 79.248 | 38.963 | 10.133 | 1.00 | 45.56 |
| ATOM | 854 | CB | ASP | 268 | 79.096 | 40.366 | 9.533 | 1.00 | 46.62 |
| ATOM | 855 | CG | ASP | 268 | 80.068 | 40.624 | 8.391 | 1.00 | 50.96 |
| ATOM | 856 | OD1 | ASP | 268 | 80.204 | 39.755 | 7.502 | 1.00 | 55.65 |
| ATOM | 857 | OD2 | ASP | 268 | 80.700 | 41.699 | 8.384 | 1.00 | 52.09 |
| ATOM | 858 | C | ASP | 268 | 80.675 | 38.751 | 10.630 | 1.00 | 44.44 |
| ATOM | 859 | O | ASP | 268 | 81.242 | 39.614 | 11.304 | 1.00 | 45.68 |
| ATOM | 860 | N | PRO | 269 | 81.281 | 37.600 | 10.296 | 1.00 | 45.94 |
| ATOM | 861 | CD | PRO | 269 | 80.739 | 36.503 | 9.476 | 1.00 | 43.72 |
| ATOM | 862 | CA | PRO | 269 | 82.651 | 37.309 | 10.730 | 1.00 | 46.63 |

FIG. 30A-18

| | | | | | | | | |
|---|---|---|---|---|---|---|---|---|
| ATOM | 863 | CB | PRO | 269 | 82.884 | 35.889 | 10.208 | 1.00 | 43.88 |
| ATOM | 864 | CG | PRO | 269 | 81.983 | 35.797 | 9.018 | 1.00 | 44.66 |
| ATOM | 865 | C | PRO | 269 | 83.682 | 38.298 | 10.190 | 1.00 | 50.80 |
| ATOM | 866 | O | PRO | 269 | 84.681 | 38.578 | 10.854 | 1.00 | 48.56 |
| ATOM | 867 | N | ALA | 270 | 83.407 | 38.858 | 9.012 | 1.00 | 55.09 |
| ATOM | 868 | CA | ALA | 270 | 84.306 | 39.820 | 8.374 | 1.00 | 55.68 |
| ATOM | 869 | CB | ALA | 270 | 83.799 | 40.168 | 6.974 | 1.00 | 53.64 |
| ATOM | 870 | C | ALA | 270 | 84.528 | 41.096 | 9.196 | 1.00 | 56.18 |
| ATOM | 871 | O | ALA | 270 | 85.577 | 41.729 | 9.082 | 1.00 | 61.07 |
| ATOM | 872 | N | SER | 271 | 83.543 | 41.479 | 10.006 | 1.00 | 51.38 |
| ATOM | 873 | CA | SER | 271 | 83.661 | 42.678 | 10.836 | 1.00 | 45.90 |
| ATOM | 874 | CB | SER | 271 | 82.710 | 43.774 | 10.346 | 1.00 | 44.49 |
| ATOM | 875 | OG | SER | 271 | 81.360 | 43.358 | 10.404 | 1.00 | 45.26 |
| ATOM | 876 | C | SER | 271 | 83.409 | 42.395 | 12.317 | 1.00 | 46.61 |
| ATOM | 877 | O | SER | 271 | 83.431 | 43.309 | 13.143 | 1.00 | 48.31 |
| ATOM | 878 | N | ASP | 272 | 83.172 | 41.126 | 12.642 | 1.00 | 46.73 |
| ATOM | 879 | CA | ASP | 272 | 82.920 | 40.689 | 14.013 | 1.00 | 42.49 |
| ATOM | 880 | CB | ASP | 272 | 84.200 | 40.807 | 14.849 | 1.00 | 42.12 |
| ATOM | 881 | CG | ASP | 272 | 84.103 | 40.072 | 16.169 | 1.00 | 50.30 |
| ATOM | 882 | OD1 | ASP | 272 | 83.417 | 39.028 | 16.218 | 1.00 | 45.10 |
| ATOM | 883 | OD2 | ASP | 272 | 84.708 | 40.537 | 17.160 | 1.00 | 57.61 |
| ATOM | 884 | C | ASP | 272 | 81.769 | 41.465 | 14.658 | 1.00 | 40.95 |
| ATOM | 885 | O | ASP | 272 | 81.885 | 41.975 | 15.779 | 1.00 | 42.93 |
| ATOM | 886 | N | THR | 273 | 80.651 | 41.531 | 13.945 | 1.00 | 38.57 |
| ATOM | 887 | CA | THR | 273 | 79.473 | 42.239 | 14.425 | 1.00 | 40.99 |
| ATOM | 888 | CB | THR | 273 | 79.262 | 43.574 | 13.656 | 1.00 | 40.76 |
| ATOM | 889 | OG1 | THR | 273 | 79.240 | 43.318 | 12.248 | 1.00 | 42.61 |
| ATOM | 890 | CG2 | THR | 273 | 80.373 | 44.574 | 13.965 | 1.00 | 39.67 |
| ATOM | 891 | C | THR | 273 | 78.210 | 41.397 | 14.251 | 1.00 | 39.94 |
| ATOM | 892 | O | THR | 273 | 78.202 | 40.419 | 13.494 | 1.00 | 36.66 |
| ATOM | 893 | N | LEU | 274 | 77.168 | 41.757 | 14.993 | 1.00 | 36.08 |
| ATOM | 894 | CA | LEU | 274 | 75.867 | 41.096 | 14.907 | 1.00 | 34.28 |
| ATOM | 895 | CB | LEU | 274 | 75.343 | 40.699 | 16.292 | 1.00 | 30.96 |
| ATOM | 896 | CG | LEU | 274 | 75.952 | 39.536 | 17.068 | 1.00 | 30.19 |
| ATOM | 897 | CD1 | LEU | 274 | 75.310 | 39.472 | 18.444 | 1.00 | 26.29 |
| ATOM | 898 | CD2 | LEU | 274 | 75.744 | 38.237 | 16.309 | 1.00 | 27.43 |
| ATOM | 899 | C | LEU | 274 | 74.943 | 42.163 | 14.347 | 1.00 | 36.49 |
| ATOM | 900 | O | LEU | 274 | 75.152 | 43.354 | 14.596 | 1.00 | 40.27 |
| ATOM | 901 | N | THR | 275 | 73.923 | 41.758 | 13.606 | 1.00 | 36.42 |
| ATOM | 902 | CA | THR | 275 | 72.994 | 42.731 | 13.062 | 1.00 | 35.07 |
| ATOM | 903 | CB | THR | 275 | 72.773 | 42.522 | 11.556 | 1.00 | 36.04 |
| ATOM | 904 | OG1 | THR | 275 | 74.028 | 42.625 | 10.875 | 1.00 | 41.52 |
| ATOM | 905 | CG2 | THR | 275 | 71.852 | 43.583 | 11.008 | 1.00 | 36.47 |
| ATOM | 906 | C | THR | 275 | 71.673 | 42.655 | 13.814 | 1.00 | 34.32 |
| ATOM | 907 | O | THR | 275 | 71.055 | 41.590 | 13.907 | 1.00 | 34.96 |
| ATOM | 908 | N | LEU | 276 | 71.292 | 43.767 | 14.432 | 1.00 | 31.79 |
| ATOM | 909 | CA | LEU | 276 | 70.044 | 43.840 | 15.173 | 1.00 | 29.47 |
| ATOM | 910 | CB | LEU | 276 | 70.181 | 44.766 | 16.389 | 1.00 | 25.29 |
| ATOM | 911 | CG | LEU | 276 | 71.328 | 44.501 | 17.383 | 1.00 | 29.01 |
| ATOM | 912 | CD1 | LEU | 276 | 71.179 | 45.410 | 18.594 | 1.00 | 20.92 |

FIG. 30A-19

| | | | | | | | | |
|---|---|---|---|---|---|---|---|---|
| ATOM | 913 | CD2 | LEU | 276 | 71.358 | 43.042 | 17.834 | 1.00 | 22.79 |
| ATOM | 914 | C | LEU | 276 | 68.966 | 44.350 | 14.228 | 1.00 | 31.69 |
| ATOM | 915 | O | LEU | 276 | 69.175 | 45.335 | 13.510 | 1.00 | 33.87 |
| ATOM | 916 | N | SER | 277 | 67.862 | 43.608 | 14.162 | 1.00 | 33.07 |
| ATOM | 917 | CA | SER | 277 | 66.721 | 43.935 | 13.315 | 1.00 | 30.61 |
| ATOM | 918 | CB | SER | 277 | 65.949 | 45.111 | 13.909 | 1.00 | 22.87 |
| ATOM | 919 | OG | SER | 277 | 65.587 | 44.822 | 15.250 | 1.00 | 23.35 |
| ATOM | 920 | C | SER | 277 | 67.103 | 44.200 | 11.860 | 1.00 | 31.85 |
| ATOM | 921 | O | SER | 277 | 66.433 | 44.958 | 11.158 | 1.00 | 32.13 |
| ATOM | 922 | N | GLY | 278 | 68.188 | 43.566 | 11.421 | 1.00 | 32.29 |
| ATOM | 923 | CA | GLY | 278 | 68.664 | 43.716 | 10.058 | 1.00 | 37.59 |
| ATOM | 924 | C | GLY | 278 | 69.063 | 45.122 | 9.639 | 1.00 | 43.26 |
| ATOM | 925 | O | GLY | 278 | 69.313 | 45.358 | 8.455 | 1.00 | 42.60 |
| ATOM | 926 | N | GLU | 279 | 69.177 | 46.038 | 10.599 | 1.00 | 43.42 |
| ATOM | 927 | CA | GLU | 279 | 69.532 | 47.420 | 10.291 | 1.00 | 44.55 |
| ATOM | 928 | CB | GLU | 279 | 68.292 | 48.310 | 10.394 | 1.00 | 44.66 |
| ATOM | 929 | CG | GLU | 279 | 67.671 | 48.344 | 11.783 | 1.00 | 54.19 |
| ATOM | 930 | CD | GLU | 279 | 66.400 | 49.171 | 11.845 | 1.00 | 64.96 |
| ATOM | 931 | OE1 | GLU | 279 | 65.627 | 49.174 | 10.859 | 1.00 | 71.43 |
| ATOM | 932 | OE2 | GLU | 279 | 66.167 | 49.814 | 12.891 | 1.00 | 66.65 |
| ATOM | 933 | C | GLU | 279 | 70.654 | 48.019 | 11.133 | 1.00 | 45.52 |
| ATOM | 934 | O | GLU | 279 | 71.207 | 49.057 | 10.772 | 1.00 | 51.83 |
| ATOM | 935 | N | MET | 280 | 71.007 | 47.373 | 12.242 | 1.00 | 44.66 |
| ATOM | 936 | CA | MET | 280 | 72.060 | 47.904 | 13.105 | 1.00 | 34.22 |
| ATOM | 937 | CB | MET | 280 | 71.470 | 48.382 | 14.433 | 1.00 | 32.38 |
| ATOM | 938 | CG | MET | 280 | 72.479 | 49.058 | 15.345 | 1.00 | 37.87 |
| ATOM | 939 | SD | MET | 280 | 71.912 | 49.201 | 17.052 | 1.00 | 41.78 |
| ATOM | 940 | CE | MET | 280 | 70.650 | 50.495 | 16.911 | 1.00 | 37.01 |
| ATOM | 941 | C | MET | 280 | 73.183 | 46.920 | 13.386 | 1.00 | 35.70 |
| ATOM | 942 | O | MET | 280 | 72.976 | 45.900 | 14.044 | 1.00 | 36.99 |
| ATOM | 943 | N | ALA | 281 | 74.366 | 47.221 | 12.867 | 1.00 | 34.80 |
| ATOM | 944 | CA | ALA | 281 | 75.535 | 46.377 | 13.091 | 1.00 | 35.11 |
| ATOM | 945 | CB | ALA | 281 | 76.529 | 46.527 | 11.955 | 1.00 | 31.27 |
| ATOM | 946 | C | ALA | 281 | 76.155 | 46.837 | 14.406 | 1.00 | 35.96 |
| ATOM | 947 | O | ALA | 281 | 76.478 | 48.015 | 14.570 | 1.00 | 39.10 |
| ATOM | 948 | N | VAL | 282 | 76.285 | 45.916 | 15.353 | 1.00 | 36.46 |
| ATOM | 949 | CA | VAL | 282 | 76.839 | 46.246 | 16.655 | 1.00 | 36.05 |
| ATOM | 950 | CB | VAL | 282 | 75.783 | 46.090 | 17.783 | 1.00 | 35.60 |
| ATOM | 951 | CG1 | VAL | 282 | 74.633 | 47.069 | 17.568 | 1.00 | 38.73 |
| ATOM | 952 | CG2 | VAL | 282 | 75.262 | 44.660 | 17.844 | 1.00 | 33.27 |
| ATOM | 953 | C | VAL | 282 | 78.062 | 45.408 | 16.996 | 1.00 | 37.70 |
| ATOM | 954 | O | VAL | 282 | 78.137 | 44.223 | 16.660 | 1.00 | 37.45 |
| ATOM | 955 | N | ALA | 283 | 79.032 | 46.047 | 17.637 | 1.00 | 39.21 |
| ATOM | 956 | CA | ALA | 283 | 80.254 | 45.375 | 18.048 | 1.00 | 43.73 |
| ATOM | 957 | CB | ALA | 283 | 81.433 | 46.352 | 18.047 | 1.00 | 42.04 |
| ATOM | 958 | C | ALA | 283 | 80.060 | 44.752 | 19.435 | 1.00 | 43.28 |
| ATOM | 959 | O | ALA | 283 | 79.179 | 45.157 | 20.203 | 1.00 | 45.77 |
| ATOM | 960 | N | ARG | 284 | 80.903 | 43.774 | 19.744 | 1.00 | 41.96 |
| ATOM | 961 | CA | ARG | 284 | 80.866 | 43.044 | 21.004 | 1.00 | 44.87 |
| ATOM | 962 | CB | ARG | 284 | 82.084 | 42.125 | 21.087 | 1.00 | 46.34 |

FIG. 30A-20

| ATOM | 963 | CG | ARG | 284 | 81.930 | 40.947 | 22.017 | 1.00 | 51.85 |
|---|---|---|---|---|---|---|---|---|---|
| ATOM | 964 | CD | ARG | 284 | 83.107 | 40.010 | 21.844 | 1.00 | 60.73 |
| ATOM | 965 | NE | ARG | 284 | 83.262 | 39.571 | 20.455 | 1.00 | 54.30 |
| ATOM | 966 | CZ | ARG | 284 | 83.221 | 38.300 | 20.074 | 1.00 | 53.66 |
| ATOM | 967 | NH1 | ARG | 284 | 83.032 | 37.343 | 20.973 | 1.00 | 49.99 |
| ATOM | 968 | NH2 | ARG | 284 | 83.379 | 37.984 | 18.797 | 1.00 | 47.31 |
| ATOM | 969 | C | ARG | 284 | 80.803 | 43.945 | 22.237 | 1.00 | 44.85 |
| ATOM | 970 | O | ARG | 284 | 79.896 | 43.806 | 23.062 | 1.00 | 48.26 |
| ATOM | 971 | N | GLU | 285 | 81.750 | 44.873 | 22.349 | 1.00 | 41.60 |
| ATOM | 972 | CA | GLU | 285 | 81.802 | 45.787 | 23.484 | 1.00 | 41.17 |
| ATOM | 973 | CB | GLU | 285 | 83.043 | 46.675 | 23.392 | 1.00 | 39.97 |
| ATOM | 974 | C | GLU | 285 | 80.538 | 46.640 | 23.603 | 1.00 | 40.08 |
| ATOM | 975 | O | GLU | 285 | 80.023 | 46.849 | 24.703 | 1.00 | 41.16 |
| ATOM | 976 | N | GLN | 286 | 80.017 | 47.088 | 22.463 | 1.00 | 38.49 |
| ATOM | 977 | CA | GLN | 286 | 78.818 | 47.926 | 22.425 | 1.00 | 36.25 |
| ATOM | 978 | CB | GLN | 286 | 78.549 | 48.401 | 20.997 | 1.00 | 39.50 |
| ATOM | 979 | CG | GLN | 286 | 79.619 | 49.311 | 20.424 | 1.00 | 43.62 |
| ATOM | 980 | CD | GLN | 286 | 79.324 | 49.710 | 18.987 | 1.00 | 49.48 |
| ATOM | 981 | OE1 | GLN | 286 | 79.253 | 48.856 | 18.097 | 1.00 | 48.41 |
| ATOM | 982 | NE2 | GLN | 286 | 79.125 | 51.000 | 18.755 | 1.00 | 47.15 |
| ATOM | 983 | C | GLN | 286 | 77.563 | 47.255 | 22.988 | 1.00 | 35.40 |
| ATOM | 984 | O | GLN | 286 | 76.903 | 47.806 | 23.871 | 1.00 | 31.24 |
| ATOM | 985 | N | LEU | 287 | 77.234 | 46.071 | 22.480 | 1.00 | 32.96 |
| ATOM | 986 | CA | LEU | 287 | 76.055 | 45.349 | 22.950 | 1.00 | 33.40 |
| ATOM | 987 | CB | LEU | 287 | 75.767 | 44.138 | 22.054 | 1.00 | 28.67 |
| ATOM | 988 | CG | LEU | 287 | 74.466 | 43.375 | 22.342 | 1.00 | 26.66 |
| ATOM | 989 | CD1 | LEU | 287 | 73.263 | 44.305 | 22.244 | 1.00 | 19.41 |
| ATOM | 990 | CD2 | LEU | 287 | 74.325 | 42.221 | 21.368 | 1.00 | 24.84 |
| ATOM | 991 | C | LEU | 287 | 76.234 | 44.914 | 24.406 | 1.00 | 34.81 |
| ATOM | 992 | O | LEU | 287 | 75.265 | 44.857 | 25.175 | 1.00 | 33.92 |
| ATOM | 993 | N | LYS | 288 | 77.476 | 44.621 | 24.781 | 1.00 | 35.38 |
| ATOM | 994 | CA | LYS | 288 | 77.814 | 44.204 | 26.140 | 1.00 | 36.12 |
| ATOM | 995 | CB | LYS | 288 | 79.296 | 43.839 | 26.210 | 1.00 | 37.13 |
| ATOM | 996 | CG | LYS | 288 | 79.762 | 43.280 | 27.533 | 1.00 | 44.61 |
| ATOM | 997 | CD | LYS | 288 | 81.256 | 43.018 | 27.494 | 1.00 | 54.07 |
| ATOM | 998 | CE | LYS | 288 | 81.757 | 42.435 | 28.801 | 1.00 | 60.87 |
| ATOM | 999 | NZ | LYS | 288 | 81.291 | 41.041 | 29.039 | 1.00 | 61.53 |
| ATOM | 1000 | C | LYS | 288 | 77.510 | 45.345 | 27.109 | 1.00 | 36.90 |
| ATOM | 1001 | O | LYS | 288 | 76.684 | 45.206 | 28.013 | 1.00 | 40.68 |
| ATOM | 1002 | N | ASN | 289 | 78.129 | 46.495 | 26.863 | 1.00 | 35.94 |
| ATOM | 1003 | CA | ASN | 289 | 77.947 | 47.680 | 27.695 | 1.00 | 36.12 |
| ATOM | 1004 | CB | ASN | 289 | 78.982 | 48.738 | 27.332 | 1.00 | 31.78 |
| ATOM | 1005 | CG | ASN | 289 | 80.388 | 48.263 | 27.569 | 1.00 | 40.31 |
| ATOM | 1006 | OD1 | ASN | 289 | 80.627 | 47.422 | 28.440 | 1.00 | 43.12 |
| ATOM | 1007 | ND2 | ASN | 289 | 81.326 | 48.758 | 26.775 | 1.00 | 35.36 |
| ATOM | 1008 | C | ASN | 289 | 76.553 | 48.277 | 27.590 | 1.00 | 36.98 |
| ATOM | 1009 | O | ASN | 289 | 76.099 | 48.959 | 28.509 | 1.00 | 34.29 |
| ATOM | 1010 | N | GLY | 290 | 75.883 | 48.032 | 26.466 | 1.00 | 32.65 |
| ATOM | 1011 | CA | GLY | 290 | 74.541 | 48.550 | 26.256 | 1.00 | 28.61 |
| ATOM | 1012 | C | GLY | 290 | 73.497 | 48.001 | 27.210 | 1.00 | 26.54 |

FIG. 30A-21

| ATOM | 1013 | O | GLY | 290 | 72.362 | 48.480 | 27.234 | 1.00 | 31.06 |
|---|---|---|---|---|---|---|---|---|---|
| ATOM | 1014 | N | GLY | 291 | 73.861 | 46.978 | 27.977 | 1.00 | 28.89 |
| ATOM | 1015 | CA | GLY | 291 | 72.929 | 46.413 | 28.937 | 1.00 | 25.24 |
| ATOM | 1016 | C | GLY | 291 | 72.872 | 44.900 | 28.997 | 1.00 | 28.12 |
| ATOM | 1017 | O | GLY | 291 | 72.335 | 44.345 | 29.955 | 1.00 | 31.16 |
| ATOM | 1018 | N | LEU | 292 | 73.406 | 44.223 | 27.985 | 1.00 | 29.51 |
| ATOM | 1019 | CA | LEU | 292 | 73.361 | 42.766 | 27.969 | 1.00 | 32.79 |
| ATOM | 1020 | CB | LEU | 292 | 73.304 | 42.240 | 26.531 | 1.00 | 28.00 |
| ATOM | 1021 | CG | LEU | 292 | 71.948 | 42.355 | 25.827 | 1.00 | 23.68 |
| ATOM | 1022 | CD1 | LEU | 292 | 72.004 | 41.626 | 24.509 | 1.00 | 26.12 |
| ATOM | 1023 | CD2 | LEU | 292 | 70.851 | 41.764 | 26.694 | 1.00 | 23.36 |
| ATOM | 1024 | C | LEU | 292 | 74.484 | 42.085 | 28.742 | 1.00 | 32.33 |
| ATOM | 1025 | O | LEU | 292 | 74.312 | 40.967 | 29.232 | 1.00 | 32.22 |
| ATOM | 1026 | N | GLY | 293 | 75.627 | 42.750 | 28.846 | 1.00 | 30.31 |
| ATOM | 1027 | CA | GLY | 293 | 76.751 | 42.176 | 29.561 | 1.00 | 28.82 |
| ATOM | 1028 | C | GLY | 293 | 77.238 | 40.894 | 28.913 | 1.00 | 29.87 |
| ATOM | 1029 | O | GLY | 293 | 77.432 | 40.843 | 27.698 | 1.00 | 35.43 |
| ATOM | 1030 | N | VAL | 294 | 77.392 | 39.848 | 29.714 | 1.00 | 31.88 |
| ATOM | 1031 | CA | VAL | 294 | 77.866 | 38.561 | 29.217 | 1.00 | 35.77 |
| ATOM | 1032 | CB | VAL | 294 | 78.232 | 37.590 | 30.363 | 1.00 | 34.29 |
| ATOM | 1033 | CG1 | VAL | 294 | 79.462 | 38.092 | 31.095 | 1.00 | 37.54 |
| ATOM | 1034 | CG2 | VAL | 294 | 77.065 | 37.425 | 31.322 | 1.00 | 25.62 |
| ATOM | 1035 | C | VAL | 294 | 76.882 | 37.879 | 28.274 | 1.00 | 35.89 |
| ATOM | 1036 | O | VAL | 294 | 77.263 | 36.960 | 27.541 | 1.00 | 37.99 |
| ATOM | 1037 | N | VAL | 295 | 75.619 | 38.304 | 28.305 | 1.00 | 34.41 |
| ATOM | 1038 | CA | VAL | 295 | 74.616 | 37.728 | 27.413 | 1.00 | 32.98 |
| ATOM | 1039 | CB | VAL | 295 | 73.208 | 38.298 | 27.677 | 1.00 | 31.25 |
| ATOM | 1040 | CG1 | VAL | 295 | 72.208 | 37.706 | 26.694 | 1.00 | 23.54 |
| ATOM | 1041 | CG2 | VAL | 295 | 72.783 | 37.993 | 29.101 | 1.00 | 23.07 |
| ATOM | 1042 | C | VAL | 295 | 75.057 | 38.062 | 25.993 | 1.00 | 33.92 |
| ATOM | 1043 | O | VAL | 295 | 74.932 | 37.238 | 25.090 | 1.00 | 36.95 |
| ATOM | 1044 | N | SER | 296 | 75.625 | 39.253 | 25.820 | 1.00 | 31.27 |
| ATOM | 1045 | CA | SER | 296 | 76.118 | 39.695 | 24.521 | 1.00 | 33.38 |
| ATOM | 1046 | CB | SER | 296 | 76.667 | 41.115 | 24.620 | 1.00 | 24.78 |
| ATOM | 1047 | OG | SER | 296 | 77.368 | 41.478 | 23.449 | 1.00 | 25.43 |
| ATOM | 1048 | C | SER | 296 | 77.216 | 38.748 | 24.045 | 1.00 | 35.86 |
| ATOM | 1049 | O | SER | 296 | 77.220 | 38.324 | 22.886 | 1.00 | 39.60 |
| ATOM | 1050 | N | ASP | 297 | 78.135 | 38.402 | 24.943 | 1.00 | 37.41 |
| ATOM | 1051 | CA | ASP | 297 | 79.227 | 37.490 | 24.602 | 1.00 | 35.39 |
| ATOM | 1052 | CB | ASP | 297 | 80.147 | 37.269 | 25.808 | 1.00 | 43.07 |
| ATOM | 1053 | CG | ASP | 297 | 80.839 | 38.540 | 26.266 | 1.00 | 45.07 |
| ATOM | 1054 | OD1 | ASP | 297 | 81.175 | 39.398 | 25.419 | 1.00 | 48.02 |
| ATOM | 1055 | OD2 | ASP | 297 | 81.064 | 38.670 | 27.485 | 1.00 | 50.13 |
| ATOM | 1056 | C | ASP | 297 | 78.662 | 36.145 | 24.161 | 1.00 | 30.87 |
| ATOM | 1057 | O | ASP | 297 | 79.155 | 35.534 | 23.213 | 1.00 | 33.92 |
| ATOM | 1058 | N | ALA | 298 | 77.625 | 35.698 | 24.861 | 1.00 | 28.96 |
| ATOM | 1059 | CA | ALA | 298 | 76.971 | 34.428 | 24.574 | 1.00 | 30.60 |
| ATOM | 1060 | CB | ALA | 298 | 75.889 | 34.157 | 25.610 | 1.00 | 27.56 |
| ATOM | 1061 | C | ALA | 298 | 76.377 | 34.408 | 23.163 | 1.00 | 33.04 |
| ATOM | 1062 | O | ALA | 298 | 76.538 | 33.426 | 22.426 | 1.00 | 32.48 |

FIG. 30A-22

| ATOM | 1063 | N | ILE | 299 | 75.706 | 35.493 | 22.786 | 1.00 | 30.92 |
|---|---|---|---|---|---|---|---|---|---|
| ATOM | 1064 | CA | ILE | 299 | 75.091 | 35.588 | 21.468 | 1.00 | 24.71 |
| ATOM | 1065 | CB | ILE | 299 | 74.138 | 36.789 | 21.368 | 1.00 | 22.98 |
| ATOM | 1066 | CG2 | ILE | 299 | 73.430 | 36.786 | 20.018 | 1.00 | 21.90 |
| ATOM | 1067 | CG1 | ILE | 299 | 73.091 | 36.707 | 22.477 | 1.00 | 20.91 |
| ATOM | 1068 | CD1 | ILE | 299 | 72.266 | 37.951 | 22.634 | 1.00 | 19.86 |
| ATOM | 1069 | C | ILE | 299 | 76.168 | 35.680 | 20.395 | 1.00 | 26.77 |
| ATOM | 1070 | O | ILE | 299 | 76.036 | 35.069 | 19.335 | 1.00 | 30.21 |
| ATOM | 1071 | N | PHE | 300 | 77.238 | 36.428 | 20.673 | 1.00 | 29.08 |
| ATOM | 1072 | CA | PHE | 300 | 78.345 | 36.562 | 19.726 | 1.00 | 28.06 |
| ATOM | 1073 | CB | PHE | 300 | 79.386 | 37.565 | 20.235 | 1.00 | 29.06 |
| ATOM | 1074 | CG | PHE | 300 | 79.289 | 38.920 | 19.590 | 1.00 | 28.14 |
| ATOM | 1075 | CD1 | PHE | 300 | 78.449 | 39.896 | 20.113 | 1.00 | 27.20 |
| ATOM | 1076 | CD2 | PHE | 300 | 80.017 | 39.209 | 18.437 | 1.00 | 29.11 |
| ATOM | 1077 | CE1 | PHE | 300 | 78.332 | 41.139 | 19.499 | 1.00 | 28.18 |
| ATOM | 1078 | CE2 | PHE | 300 | 79.908 | 40.450 | 17.815 | 1.00 | 29.07 |
| ATOM | 1079 | CZ | PHE | 300 | 79.064 | 41.416 | 18.348 | 1.00 | 22.61 |
| ATOM | 1080 | C | PHE | 300 | 78.991 | 35.201 | 19.485 | 1.00 | 29.00 |
| ATOM | 1081 | O | PHE | 300 | 79.278 | 34.833 | 18.344 | 1.00 | 30.35 |
| ATOM | 1082 | N | GLU | 301 | 79.183 | 34.442 | 20.560 | 1.00 | 31.81 |
| ATOM | 1083 | CA | GLU | 301 | 79.767 | 33.111 | 20.470 | 1.00 | 34.96 |
| ATOM | 1084 | CB | GLU | 301 | 79.962 | 32.528 | 21.865 | 1.00 | 30.78 |
| ATOM | 1085 | C | GLU | 301 | 78.850 | 32.210 | 19.634 | 1.00 | 35.49 |
| ATOM | 1086 | O | GLU | 301 | 79.322 | 31.438 | 18.793 | 1.00 | 35.76 |
| ATOM | 1087 | N | LEU | 302 | 77.543 | 32.313 | 19.869 | 1.00 | 32.14 |
| ATOM | 1088 | CA | LEU | 302 | 76.559 | 31.522 | 19.132 | 1.00 | 25.56 |
| ATOM | 1089 | CB | LEU | 302 | 75.147 | 31.760 | 19.682 | 1.00 | 23.33 |
| ATOM | 1090 | CG | LEU | 302 | 73.992 | 31.006 | 19.010 | 1.00 | 28.73 |
| ATOM | 1091 | CD1 | LEU | 302 | 74.093 | 29.509 | 19.270 | 1.00 | 23.93 |
| ATOM | 1092 | CD2 | LEU | 302 | 72.667 | 31.551 | 19.514 | 1.00 | 21.32 |
| ATOM | 1093 | C | LEU | 302 | 76.617 | 31.885 | 17.650 | 1.00 | 23.10 |
| ATOM | 1094 | O | LEU | 302 | 76.664 | 31.001 | 16.796 | 1.00 | 26.79 |
| ATOM | 1095 | N | GLY | 303 | 76.672 | 33.181 | 17.353 | 1.00 | 22.79 |
| ATOM | 1096 | CA | GLY | 303 | 76.745 | 33.631 | 15.974 | 1.00 | 21.60 |
| ATOM | 1097 | C | GLY | 303 | 77.978 | 33.104 | 15.256 | 1.00 | 30.42 |
| ATOM | 1098 | O | GLY | 303 | 77.889 | 32.619 | 14.125 | 1.00 | 29.18 |
| ATOM | 1099 | N | ALA | 304 | 79.132 | 33.182 | 15.912 | 1.00 | 31.15 |
| ATOM | 1100 | CA | ALA | 304 | 80.375 | 32.703 | 15.313 | 1.00 | 35.44 |
| ATOM | 1101 | CB | ALA | 304 | 81.562 | 32.995 | 16.235 | 1.00 | 29.16 |
| ATOM | 1102 | C | ALA | 304 | 80.300 | 31.208 | 14.978 | 1.00 | 35.15 |
| ATOM | 1103 | O | ALA | 304 | 80.705 | 30.785 | 13.891 | 1.00 | 37.13 |
| ATOM | 1104 | N | SER | 305 | 79.753 | 30.414 | 15.892 | 1.00 | 33.91 |
| ATOM | 1105 | CA | SER | 305 | 79.638 | 28.979 | 15.663 | 1.00 | 36.39 |
| ATOM | 1106 | CB | SER | 305 | 79.395 | 28.237 | 16.980 | 1.00 | 32.71 |
| ATOM | 1107 | OG | SER | 305 | 78.265 | 28.749 | 17.663 | 1.00 | 48.66 |
| ATOM | 1108 | C | SER | 305 | 78.558 | 28.619 | 14.641 | 1.00 | 37.61 |
| ATOM | 1109 | O | SER | 305 | 78.747 | 27.697 | 13.845 | 1.00 | 39.92 |
| ATOM | 1110 | N | LEU | 306 | 77.443 | 29.349 | 14.651 | 1.00 | 38.21 |
| ATOM | 1111 | CA | LEU | 306 | 76.350 | 29.092 | 13.714 | 1.00 | 35.65 |
| ATOM | 1112 | CB | LEU | 306 | 75.094 | 29.894 | 14.077 | 1.00 | 25.49 |

FIG. 30A-23

| ATOM | 1113 | CG | LEU | 306 | 74.209 | 29.374 | 15.212 | 1.00 | 26.18 |
| --- | --- | --- | --- | --- | --- | --- | --- | --- | --- |
| ATOM | 1114 | CD1 | LEU | 306 | 72.988 | 30.262 | 15.361 | 1.00 | 23.40 |
| ATOM | 1115 | CD2 | LEU | 306 | 73.777 | 27.952 | 14.921 | 1.00 | 23.57 |
| ATOM | 1116 | C | LEU | 306 | 76.723 | 29.356 | 12.258 | 1.00 | 38.05 |
| ATOM | 1117 | O | LEU | 306 | 76.092 | 28.809 | 11.353 | 1.00 | 37.22 |
| ATOM | 1118 | N | SER | 307 | 77.743 | 30.185 | 12.030 | 1.00 | 40.41 |
| ATOM | 1119 | CA | SER | 307 | 78.199 | 30.511 | 10.677 | 1.00 | 40.85 |
| ATOM | 1120 | CB | SER | 307 | 79.415 | 31.442 | 10.736 | 1.00 | 37.32 |
| ATOM | 1121 | OG | SER | 307 | 79.086 | 32.678 | 11.344 | 1.00 | 56.20 |
| ATOM | 1122 | C | SER | 307 | 78.550 | 29.270 | 9.852 | 1.00 | 39.87 |
| ATOM | 1123 | O | SER | 307 | 78.221 | 29.191 | 8.670 | 1.00 | 44.27 |
| ATOM | 1124 | N | ALA | 308 | 79.207 | 28.305 | 10.487 | 1.00 | 39.29 |
| ATOM | 1125 | CA | ALA | 308 | 79.609 | 27.066 | 9.826 | 1.00 | 33.10 |
| ATOM | 1126 | CB | ALA | 308 | 80.607 | 26.310 | 10.696 | 1.00 | 33.37 |
| ATOM | 1127 | C | ALA | 308 | 78.403 | 26.177 | 9.502 | 1.00 | 34.07 |
| ATOM | 1128 | O | ALA | 308 | 78.467 | 25.340 | 8.600 | 1.00 | 40.61 |
| ATOM | 1129 | N | PHE | 309 | 77.305 | 26.368 | 10.230 | 1.00 | 31.85 |
| ATOM | 1130 | CA | PHE | 309 | 76.095 | 25.581 | 10.015 | 1.00 | 35.24 |
| ATOM | 1131 | CB | PHE | 309 | 75.149 | 25.698 | 11.219 | 1.00 | 33.69 |
| ATOM | 1132 | CG | PHE | 309 | 75.618 | 24.954 | 12.437 | 1.00 | 36.16 |
| ATOM | 1133 | CD1 | PHE | 309 | 76.785 | 25.327 | 13.090 | 1.00 | 43.79 |
| ATOM | 1134 | CD2 | PHE | 309 | 74.903 | 23.867 | 12.922 | 1.00 | 38.03 |
| ATOM | 1135 | CE1 | PHE | 309 | 77.237 | 24.627 | 14.210 | 1.00 | 41.12 |
| ATOM | 1136 | CE2 | PHE | 309 | 75.346 | 23.161 | 14.040 | 1.00 | 41.08 |
| ATOM | 1137 | CZ | PHE | 309 | 76.514 | 23.543 | 14.683 | 1.00 | 38.37 |
| ATOM | 1138 | C | PHE | 309 | 75.361 | 25.934 | 8.720 | 1.00 | 36.31 |
| ATOM | 1139 | O | PHE | 309 | 74.633 | 25.095 | 8.173 | 1.00 | 37.84 |
| ATOM | 1140 | N | ASN | 310 | 75.567 | 27.155 | 8.225 | 1.00 | 35.22 |
| ATOM | 1141 | CA | ASN | 310 | 74.933 | 27.625 | 6.988 | 1.00 | 43.66 |
| ATOM | 1142 | CB | ASN | 310 | 75.536 | 26.930 | 5.760 | 1.00 | 54.13 |
| ATOM | 1143 | CG | ASN | 310 | 76.980 | 27.339 | 5.501 | 1.00 | 68.29 |
| ATOM | 1144 | OD1 | ASN | 310 | 77.297 | 28.527 | 5.412 | 1.00 | 74.62 |
| ATOM | 1145 | ND2 | ASN | 310 | 77.859 | 26.348 | 5.352 | 1.00 | 68.85 |
| ATOM | 1146 | C | ASN | 310 | 73.430 | 27.385 | 7.013 | 1.00 | 38.37 |
| ATOM | 1147 | O | ASN | 310 | 72.882 | 26.735 | 6.123 | 1.00 | 36.70 |
| ATOM | 1148 | N | LEU | 311 | 72.780 | 27.865 | 8.062 | 1.00 | 35.22 |
| ATOM | 1149 | CA | LEU | 311 | 71.345 | 27.690 | 8.206 | 1.00 | 34.32 |
| ATOM | 1150 | CB | LEU | 311 | 70.895 | 28.054 | 9.630 | 1.00 | 30.19 |
| ATOM | 1151 | CG | LEU | 311 | 71.458 | 27.306 | 10.845 | 1.00 | 26.76 |
| ATOM | 1152 | CD1 | LEU | 311 | 70.792 | 27.847 | 12.104 | 1.00 | 21.37 |
| ATOM | 1153 | CD2 | LEU | 311 | 71.217 | 25.813 | 10.722 | 1.00 | 22.95 |
| ATOM | 1154 | C | LEU | 311 | 70.601 | 28.561 | 7.206 | 1.00 | 34.64 |
| ATOM | 1155 | O | LEU | 311 | 71.087 | 29.625 | 6.820 | 1.00 | 37.70 |
| ATOM | 1156 | N | ASP | 312 | 69.444 | 28.091 | 6.752 | 1.00 | 29.40 |
| ATOM | 1157 | CA | ASP | 312 | 68.634 | 28.867 | 5.823 | 1.00 | 28.65 |
| ATOM | 1158 | CB | ASP | 312 | 68.302 | 28.061 | 4.545 | 1.00 | 24.79 |
| ATOM | 1159 | CG | ASP | 312 | 67.459 | 26.804 | 4.804 | 1.00 | 21.47 |
| ATOM | 1160 | OD1 | ASP | 312 | 66.994 | 26.549 | 5.932 | 1.00 | 27.92 |
| ATOM | 1161 | OD2 | ASP | 312 | 67.250 | 26.057 | 3.832 | 1.00 | 27.53 |
| ATOM | 1162 | C | ASP | 312 | 67.380 | 29.346 | 6.557 | 1.00 | 25.92 |

FIG. 30A-24

| ATOM | 1163 | O   | ASP | 312 | 67.167 | 28.985 | 7.717  | 1.00 | 26.98 |
| ATOM | 1164 | N   | ASP | 313 | 66.540 | 30.122 | 5.878  | 1.00 | 21.78 |
| ATOM | 1165 | CA  | ASP | 313 | 65.315 | 30.653 | 6.471  | 1.00 | 22.89 |
| ATOM | 1166 | CB  | ASP | 313 | 64.517 | 31.458 | 5.439  | 1.00 | 29.19 |
| ATOM | 1167 | CG  | ASP | 313 | 65.216 | 32.739 | 5.025  | 1.00 | 36.82 |
| ATOM | 1168 | OD1 | ASP | 313 | 65.985 | 33.285 | 5.845  | 1.00 | 41.51 |
| ATOM | 1169 | OD2 | ASP | 313 | 64.997 | 33.203 | 3.883  | 1.00 | 44.19 |
| ATOM | 1170 | C   | ASP | 313 | 64.421 | 29.587 | 7.085  | 1.00 | 25.09 |
| ATOM | 1171 | O   | ASP | 313 | 63.778 | 29.829 | 8.110  | 1.00 | 27.60 |
| ATOM | 1172 | N   | THR | 314 | 64.363 | 28.420 | 6.449  | 1.00 | 20.90 |
| ATOM | 1173 | CA  | THR | 314 | 63.538 | 27.322 | 6.942  | 1.00 | 22.71 |
| ATOM | 1174 | CB  | THR | 314 | 63.408 | 26.208 | 5.884  | 1.00 | 22.07 |
| ATOM | 1175 | OG1 | THR | 314 | 62.825 | 26.746 | 4.693  | 1.00 | 23.15 |
| ATOM | 1176 | CG2 | THR | 314 | 62.542 | 25.079 | 6.401  | 1.00 | 18.17 |
| ATOM | 1177 | C   | THR | 314 | 64.080 | 26.734 | 8.249  | 1.00 | 19.95 |
| ATOM | 1178 | O   | THR | 314 | 63.326 | 26.477 | 9.182  | 1.00 | 22.40 |
| ATOM | 1179 | N   | GLU | 315 | 65.391 | 26.536 | 8.318  | 1.00 | 20.01 |
| ATOM | 1180 | CA  | GLU | 315 | 65.997 | 25.987 | 9.523  | 1.00 | 19.40 |
| ATOM | 1181 | CB  | GLU | 315 | 67.454 | 25.626 | 9.254  | 1.00 | 11.72 |
| ATOM | 1182 | CG  | GLU | 315 | 67.544 | 24.440 | 8.322  | 1.00 | 13.43 |
| ATOM | 1183 | CD  | GLU | 315 | 68.925 | 24.157 | 7.791  | 1.00 | 18.51 |
| ATOM | 1184 | OE1 | GLU | 315 | 69.666 | 25.107 | 7.451  | 1.00 | 23.24 |
| ATOM | 1185 | OE2 | GLU | 315 | 69.254 | 22.962 | 7.673  | 1.00 | 24.23 |
| ATOM | 1186 | C   | GLU | 315 | 65.833 | 26.960 | 10.681 | 1.00 | 20.12 |
| ATOM | 1187 | O   | GLU | 315 | 65.425 | 26.570 | 11.777 | 1.00 | 20.53 |
| ATOM | 1188 | N   | VAL | 316 | 66.055 | 28.240 | 10.406 | 1.00 | 21.79 |
| ATOM | 1189 | CA  | VAL | 316 | 65.898 | 29.270 | 11.425 | 1.00 | 18.14 |
| ATOM | 1190 | CB  | VAL | 316 | 66.346 | 30.659 | 10.898 | 1.00 | 18.97 |
| ATOM | 1191 | CG1 | VAL | 316 | 66.040 | 31.741 | 11.929 | 1.00 | 19.08 |
| ATOM | 1192 | CG2 | VAL | 316 | 67.840 | 30.641 | 10.537 | 1.00 | 17.97 |
| ATOM | 1193 | C   | VAL | 316 | 64.430 | 29.332 | 11.880 | 1.00 | 22.54 |
| ATOM | 1194 | O   | VAL | 316 | 64.146 | 29.433 | 13.072 | 1.00 | 26.47 |
| ATOM | 1195 | N   | ALA | 317 | 63.505 | 29.242 | 10.924 | 1.00 | 19.66 |
| ATOM | 1196 | CA  | ALA | 317 | 62.076 | 29.286 | 11.216 | 1.00 | 16.99 |
| ATOM | 1197 | CB  | ALA | 317 | 61.279 | 29.329 | 9.926  | 1.00 | 17.79 |
| ATOM | 1198 | C   | ALA | 317 | 61.619 | 28.105 | 12.063 | 1.00 | 14.12 |
| ATOM | 1199 | O   | ALA | 317 | 60.808 | 28.263 | 12.970 | 1.00 | 17.04 |
| ATOM | 1200 | N   | LEU | 318 | 62.104 | 26.911 | 11.740 | 1.00 | 20.37 |
| ATOM | 1201 | CA  | LEU | 318 | 61.725 | 25.714 | 12.485 | 1.00 | 21.12 |
| ATOM | 1202 | CB  | LEU | 318 | 62.131 | 24.448 | 11.718 | 1.00 | 21.80 |
| ATOM | 1203 | CG  | LEU | 318 | 61.364 | 24.265 | 10.398 | 1.00 | 18.11 |
| ATOM | 1204 | CD1 | LEU | 318 | 61.946 | 23.125 | 9.594  | 1.00 | 16.79 |
| ATOM | 1205 | CD2 | LEU | 318 | 59.891 | 24.024 | 10.676 | 1.00 | 12.66 |
| ATOM | 1206 | C   | LEU | 318 | 62.335 | 25.752 | 13.880 | 1.00 | 22.03 |
| ATOM | 1207 | O   | LEU | 318 | 61.688 | 25.373 | 14.858 | 1.00 | 21.35 |
| ATOM | 1208 | N   | LEU | 319 | 63.564 | 26.257 | 13.964 | 1.00 | 20.03 |
| ATOM | 1209 | CA  | LEU | 319 | 64.260 | 26.395 | 15.236 | 1.00 | 20.24 |
| ATOM | 1210 | CB  | LEU | 319 | 65.657 | 26.960 | 15.001 | 1.00 | 19.07 |
| ATOM | 1211 | CG  | LEU | 319 | 66.594 | 27.108 | 16.196 | 1.00 | 27.61 |
| ATOM | 1212 | CD1 | LEU | 319 | 66.518 | 25.883 | 17.083 | 1.00 | 29.73 |

FIG. 30A-25

| ATOM | 1213 | CD2 | LEU | 319 | 68.012 | 27.326 | 15.699 | 1.00 | 20.98 |
|------|------|-----|-----|-----|--------|--------|--------|------|-------|
| ATOM | 1214 | C   | LEU | 319 | 63.422 | 27.334 | 16.118 | 1.00 | 21.16 |
| ATOM | 1215 | O   | LEU | 319 | 63.144 | 27.032 | 17.279 | 1.00 | 26.65 |
| ATOM | 1216 | N   | GLN | 320 | 62.958 | 28.439 | 15.539 | 1.00 | 20.77 |
| ATOM | 1217 | CA  | GLN | 320 | 62.119 | 29.390 | 16.265 | 1.00 | 17.87 |
| ATOM | 1218 | CB  | GLN | 320 | 61.781 | 30.594 | 15.388 | 1.00 | 18.74 |
| ATOM | 1219 | CG  | GLN | 320 | 62.957 | 31.496 | 15.111 | 1.00 | 21.07 |
| ATOM | 1220 | CD  | GLN | 320 | 62.637 | 32.617 | 14.150 | 1.00 | 22.88 |
| ATOM | 1221 | OE1 | GLN | 320 | 61.571 | 32.653 | 13.528 | 1.00 | 26.07 |
| ATOM | 1222 | NE2 | GLN | 320 | 63.574 | 33.537 | 14.006 | 1.00 | 20.11 |
| ATOM | 1223 | C   | GLN | 320 | 60.829 | 28.728 | 16.730 | 1.00 | 19.08 |
| ATOM | 1224 | O   | GLN | 320 | 60.368 | 28.976 | 17.844 | 1.00 | 23.39 |
| ATOM | 1225 | N   | ALA | 321 | 60.251 | 27.886 | 15.876 | 1.00 | 22.71 |
| ATOM | 1226 | CA  | ALA | 321 | 59.010 | 27.187 | 16.201 | 1.00 | 18.86 |
| ATOM | 1227 | CB  | ALA | 321 | 58.495 | 26.422 | 14.993 | 1.00 | 17.22 |
| ATOM | 1228 | C   | ALA | 321 | 59.220 | 26.235 | 17.376 | 1.00 | 19.85 |
| ATOM | 1229 | O   | ALA | 321 | 58.362 | 26.119 | 18.250 | 1.00 | 19.60 |
| ATOM | 1230 | N   | VAL | 322 | 60.368 | 25.561 | 17.396 | 1.00 | 20.25 |
| ATOM | 1231 | CA  | VAL | 322 | 60.693 | 24.628 | 18.469 | 1.00 | 21.32 |
| ATOM | 1232 | CB  | VAL | 322 | 61.956 | 23.800 | 18.116 | 1.00 | 20.46 |
| ATOM | 1233 | CG1 | VAL | 322 | 62.418 | 22.971 | 19.304 | 1.00 | 20.39 |
| ATOM | 1234 | CG2 | VAL | 322 | 61.662 | 22.890 | 16.930 | 1.00 | 16.83 |
| ATOM | 1235 | C   | VAL | 322 | 60.880 | 25.393 | 19.785 | 1.00 | 20.67 |
| ATOM | 1236 | O   | VAL | 322 | 60.444 | 24.941 | 20.850 | 1.00 | 21.28 |
| ATOM | 1237 | N   | LEU | 323 | 61.492 | 26.574 | 19.701 | 1.00 | 21.14 |
| ATOM | 1238 | CA  | LEU | 323 | 61.722 | 27.417 | 20.869 | 1.00 | 22.94 |
| ATOM | 1239 | CB  | LEU | 323 | 62.610 | 28.608 | 20.511 | 1.00 | 16.12 |
| ATOM | 1240 | CG  | LEU | 323 | 64.051 | 28.291 | 20.115 | 1.00 | 22.28 |
| ATOM | 1241 | CD1 | LEU | 323 | 64.719 | 29.532 | 19.528 | 1.00 | 14.87 |
| ATOM | 1242 | CD2 | LEU | 323 | 64.816 | 27.750 | 21.320 | 1.00 | 21.55 |
| ATOM | 1243 | C   | LEU | 323 | 60.398 | 27.932 | 21.410 | 1.00 | 22.55 |
| ATOM | 1244 | O   | LEU | 323 | 60.185 | 27.986 | 22.615 | 1.00 | 25.21 |
| ATOM | 1245 | N   | LEU | 324 | 59.507 | 28.300 | 20.502 | 1.00 | 24.15 |
| ATOM | 1246 | CA  | LEU | 324 | 58.200 | 28.827 | 20.855 | 1.00 | 19.88 |
| ATOM | 1247 | CB  | LEU | 324 | 57.499 | 29.384 | 19.608 | 1.00 | 15.20 |
| ATOM | 1248 | CG  | LEU | 324 | 56.067 | 29.908 | 19.767 | 1.00 | 17.21 |
| ATOM | 1249 | CD1 | LEU | 324 | 56.021 | 31.161 | 20.637 | 1.00 | 15.99 |
| ATOM | 1250 | CD2 | LEU | 324 | 55.496 | 30.208 | 18.395 | 1.00 | 20.03 |
| ATOM | 1251 | C   | LEU | 324 | 57.311 | 27.795 | 21.536 | 1.00 | 19.83 |
| ATOM | 1252 | O   | LEU | 324 | 56.767 | 28.064 | 22.609 | 1.00 | 24.47 |
| ATOM | 1253 | N   | MET | 325 | 57.197 | 26.603 | 20.956 | 1.00 | 25.02 |
| ATOM | 1254 | CA  | MET | 325 | 56.339 | 25.563 | 21.522 | 1.00 | 26.72 |
| ATOM | 1255 | CB  | MET | 325 | 55.823 | 24.644 | 20.410 | 1.00 | 30.03 |
| ATOM | 1256 | CG  | MET | 325 | 55.129 | 25.358 | 19.241 | 1.00 | 25.09 |
| ATOM | 1257 | SD  | MET | 325 | 53.714 | 26.409 | 19.672 | 1.00 | 27.29 |
| ATOM | 1258 | CE  | MET | 325 | 52.503 | 25.220 | 20.084 | 1.00 | 20.67 |
| ATOM | 1259 | C   | MET | 325 | 56.995 | 24.736 | 22.635 | 1.00 | 28.94 |
| ATOM | 1260 | O   | MET | 325 | 56.881 | 23.510 | 22.672 | 1.00 | 32.94 |
| ATOM | 1261 | N   | SER | 326 | 57.642 | 25.418 | 23.569 | 1.00 | 29.36 |
| ATOM | 1262 | CA  | SER | 326 | 58.311 | 24.759 | 24.680 | 1.00 | 31.62 |

FIG. 30A-26

| ATOM | 1263 | CB | SER | 326 | 59.554 | 25.559 | 25.064 | 1.00 | 38.13 |
| ATOM | 1264 | OG | SER | 326 | 60.277 | 24.949 | 26.119 | 1.00 | 48.99 |
| ATOM | 1265 | C | SER | 326 | 57.361 | 24.653 | 25.871 | 1.00 | 33.69 |
| ATOM | 1266 | O | SER | 326 | 56.620 | 25.594 | 26.166 | 1.00 | 33.66 |
| ATOM | 1267 | N | THR | 327 | 57.356 | 23.499 | 26.536 | 1.00 | 38.27 |
| ATOM | 1268 | CA | THR | 327 | 56.497 | 23.306 | 27.701 | 1.00 | 38.98 |
| ATOM | 1269 | CB | THR | 327 | 55.875 | 21.896 | 27.730 | 1.00 | 33.30 |
| ATOM | 1270 | OG1 | THR | 327 | 56.908 | 20.911 | 27.627 | 1.00 | 44.01 |
| ATOM | 1271 | CG2 | THR | 327 | 54.888 | 21.722 | 26.587 | 1.00 | 38.09 |
| ATOM | 1272 | C | THR | 327 | 57.239 | 23.570 | 29.018 | 1.00 | 42.88 |
| ATOM | 1273 | O | THR | 327 | 56.702 | 23.325 | 30.099 | 1.00 | 43.36 |
| ATOM | 1274 | N | ASP | 328 | 58.462 | 24.091 | 28.924 | 1.00 | 45.92 |
| ATOM | 1275 | CA | ASP | 328 | 59.268 | 24.410 | 30.104 | 1.00 | 49.59 |
| ATOM | 1276 | CB | ASP | 328 | 60.760 | 24.411 | 29.760 | 1.00 | 59.87 |
| ATOM | 1277 | CG | ASP | 328 | 61.273 | 23.040 | 29.387 | 1.00 | 75.73 |
| ATOM | 1278 | OD1 | ASP | 328 | 62.008 | 22.939 | 28.382 | 1.00 | 85.81 |
| ATOM | 1279 | OD2 | ASP | 328 | 60.946 | 22.063 | 30.098 | 1.00 | 85.56 |
| ATOM | 1280 | C | ASP | 328 | 58.873 | 25.767 | 30.673 | 1.00 | 48.50 |
| ATOM | 1281 | O | ASP | 328 | 59.725 | 26.609 | 30.961 | 1.00 | 57.50 |
| ATOM | 1282 | N | ARG | 329 | 57.569 | 25.980 | 30.805 | 1.00 | 49.62 |
| ATOM | 1283 | CA | ARG | 329 | 57.032 | 27.222 | 31.340 | 1.00 | 50.52 |
| ATOM | 1284 | CB | ARG | 329 | 56.400 | 28.080 | 30.230 | 1.00 | 53.57 |
| ATOM | 1285 | CG | ARG | 329 | 57.376 | 28.828 | 29.324 | 1.00 | 51.09 |
| ATOM | 1286 | CD | ARG | 329 | 57.897 | 27.951 | 28.204 | 1.00 | 49.73 |
| ATOM | 1287 | NE | ARG | 329 | 58.692 | 28.699 | 27.233 | 1.00 | 47.44 |
| ATOM | 1288 | CZ | ARG | 329 | 60.005 | 28.569 | 27.080 | 1.00 | 54.28 |
| ATOM | 1289 | NH1 | ARG | 329 | 60.688 | 27.722 | 27.839 | 1.00 | 58.35 |
| ATOM | 1290 | NH2 | ARG | 329 | 60.631 | 29.256 | 26.136 | 1.00 | 51.92 |
| ATOM | 1291 | C | ARG | 329 | 55.970 | 26.870 | 32.375 | 1.00 | 51.90 |
| ATOM | 1292 | O | ARG | 329 | 55.378 | 25.790 | 32.324 | 1.00 | 50.77 |
| ATOM | 1293 | N | SER | 330 | 55.728 | 27.784 | 33.303 | 1.00 | 50.56 |
| ATOM | 1294 | CA | SER | 330 | 54.744 | 27.564 | 34.349 | 1.00 | 50.67 |
| ATOM | 1295 | CB | SER | 330 | 55.271 | 28.108 | 35.678 | 1.00 | 46.64 |
| ATOM | 1296 | C | SER | 330 | 53.404 | 28.213 | 34.004 | 1.00 | 47.63 |
| ATOM | 1297 | O | SER | 330 | 53.371 | 29.309 | 33.440 | 1.00 | 48.02 |
| ATOM | 1298 | N | GLY | 331 | 52.314 | 27.496 | 34.277 | 1.00 | 44.44 |
| ATOM | 1299 | CA | GLY | 331 | 50.977 | 28.023 | 34.044 | 1.00 | 38.77 |
| ATOM | 1300 | C | GLY | 331 | 50.236 | 27.710 | 32.756 | 1.00 | 41.74 |
| ATOM | 1301 | O | GLY | 331 | 49.147 | 28.246 | 32.537 | 1.00 | 49.57 |
| ATOM | 1302 | N | LEU | 332 | 50.783 | 26.841 | 31.912 | 1.00 | 39.75 |
| ATOM | 1303 | CA | LEU | 332 | 50.123 | 26.502 | 30.651 | 1.00 | 37.55 |
| ATOM | 1304 | CB | LEU | 332 | 51.107 | 25.829 | 29.694 | 1.00 | 32.36 |
| ATOM | 1305 | CG | LEU | 332 | 52.268 | 26.659 | 29.153 | 1.00 | 34.40 |
| ATOM | 1306 | CD1 | LEU | 332 | 53.207 | 25.749 | 28.379 | 1.00 | 30.22 |
| ATOM | 1307 | CD2 | LEU | 332 | 51.742 | 27.786 | 28.277 | 1.00 | 23.33 |
| ATOM | 1308 | C | LEU | 332 | 48.921 | 25.589 | 30.834 | 1.00 | 36.73 |
| ATOM | 1309 | O | LEU | 332 | 48.987 | 24.608 | 31.577 | 1.00 | 39.29 |
| ATOM | 1310 | N | LEU | 333 | 47.822 | 25.925 | 30.168 | 1.00 | 36.07 |
| ATOM | 1311 | CA | LEU | 333 | 46.615 | 25.107 | 30.215 | 1.00 | 39.58 |
| ATOM | 1312 | CB | LEU | 333 | 45.384 | 25.906 | 29.754 | 1.00 | 41.08 |

FIG. 30A-27

| ATOM | 1313 | CG | LEU | 333 | 44.601 | 26.883 | 30.644 | 1.00 | 47.59 |
|---|---|---|---|---|---|---|---|---|---|
| ATOM | 1314 | CD1 | LEU | 333 | 44.268 | 26.213 | 31.961 | 1.00 | 45.65 |
| ATOM | 1315 | CD2 | LEU | 333 | 45.366 | 28.171 | 30.874 | 1.00 | 47.42 |
| ATOM | 1316 | C | LEU | 333 | 46.791 | 23.911 | 29.278 | 1.00 | 40.00 |
| ATOM | 1317 | O | LEU | 333 | 46.690 | 22.754 | 29.689 | 1.00 | 44.77 |
| ATOM | 1318 | N | CYA | 334 | 47.102 | 24.213 | 28.022 | 1.00 | 37.70 |
| ATOM | 1319 | CA | CYA | 334 | 47.265 | 23.209 | 26.968 | 1.00 | 36.04 |
| ATOM | 1320 | CB | CYA | 334 | 46.815 | 23.808 | 25.635 | 1.00 | 40.64 |
| ATOM | 1321 | SG | CYA | 334 | 45.280 | 24.738 | 25.758 | 1.00 | 44.31 |
| ATOM | 1322 | AS | CYA | 334 | 43.972 | 22.946 | 25.380 | 1.00 | 76.30 |
| ATOM | 1323 | C | CYA | 334 | 48.668 | 22.617 | 26.815 | 1.00 | 34.91 |
| ATOM | 1324 | O | CYA | 334 | 49.237 | 22.615 | 25.722 | 1.00 | 37.63 |
| ATOM | 1325 | N | VAL | 335 | 49.189 | 22.056 | 27.903 | 1.00 | 35.43 |
| ATOM | 1326 | CA | VAL | 335 | 50.518 | 21.452 | 27.909 | 1.00 | 34.27 |
| ATOM | 1327 | CB | VAL | 335 | 50.861 | 20.868 | 29.298 | 1.00 | 34.21 |
| ATOM | 1328 | CG1 | VAL | 335 | 52.261 | 20.258 | 29.292 | 1.00 | 33.66 |
| ATOM | 1329 | CG2 | VAL | 335 | 50.755 | 21.945 | 30.362 | 1.00 | 31.77 |
| ATOM | 1330 | C | VAL | 335 | 50.662 | 20.349 | 26.865 | 1.00 | 37.14 |
| ATOM | 1331 | O | VAL | 335 | 51.639 | 20.320 | 26.114 | 1.00 | 37.59 |
| ATOM | 1332 | N | ASP | 336 | 49.683 | 19.451 | 26.813 | 1.00 | 39.99 |
| ATOM | 1333 | CA | ASP | 336 | 49.705 | 18.339 | 25.866 | 1.00 | 41.64 |
| ATOM | 1334 | CB | ASP | 336 | 48.532 | 17.392 | 26.146 | 1.00 | 54.27 |
| ATOM | 1335 | CG | ASP | 336 | 48.596 | 16.118 | 25.322 | 1.00 | 67.42 |
| ATOM | 1336 | OD1 | ASP | 336 | 47.915 | 16.049 | 24.274 | 1.00 | 70.98 |
| ATOM | 1337 | OD2 | ASP | 336 | 49.337 | 15.191 | 25.717 | 1.00 | 76.88 |
| ATOM | 1338 | C | ASP | 336 | 49.702 | 18.762 | 24.393 | 1.00 | 38.31 |
| ATOM | 1339 | O | ASP | 336 | 50.469 | 18.229 | 23.586 | 1.00 | 37.46 |
| ATOM | 1340 | N | LYS | 337 | 48.853 | 19.729 | 24.052 | 1.00 | 30.23 |
| ATOM | 1341 | CA | LYS | 337 | 48.740 | 20.211 | 22.676 | 1.00 | 29.21 |
| ATOM | 1342 | CB | LYS | 337 | 47.561 | 21.189 | 22.559 | 1.00 | 30.53 |
| ATOM | 1343 | CG | LYS | 337 | 47.012 | 21.360 | 21.162 | 1.00 | 51.63 |
| ATOM | 1344 | CD | LYS | 337 | 45.636 | 21.997 | 21.186 | 1.00 | 59.57 |
| ATOM | 1345 | CE | LYS | 337 | 45.066 | 22.115 | 19.774 | 1.00 | 66.05 |
| ATOM | 1346 | NZ | LYS | 337 | 43.673 | 22.693 | 19.776 | 1.00 | 67.20 |
| ATOM | 1347 | C | LYS | 337 | 50.054 | 20.873 | 22.249 | 1.00 | 28.33 |
| ATOM | 1348 | O | LYS | 337 | 50.581 | 20.594 | 21.170 | 1.00 | 26.08 |
| ATOM | 1349 | N | ILE | 338 | 50.609 | 21.696 | 23.141 | 1.00 | 26.74 |
| ATOM | 1350 | CA | ILE | 338 | 51.873 | 22.390 | 22.902 | 1.00 | 25.42 |
| ATOM | 1351 | CB | ILE | 338 | 52.177 | 23.379 | 24.052 | 1.00 | 23.57 |
| ATOM | 1352 | CG2 | ILE | 338 | 53.559 | 23.991 | 23.874 | 1.00 | 22.59 |
| ATOM | 1353 | CG1 | ILE | 338 | 51.105 | 24.471 | 24.096 | 1.00 | 23.57 |
| ATOM | 1354 | CD1 | ILE | 338 | 51.157 | 25.362 | 25.333 | 1.00 | 24.30 |
| ATOM | 1355 | C | ILE | 338 | 53.018 | 21.382 | 22.768 | 1.00 | 29.20 |
| ATOM | 1356 | O | ILE | 338 | 53.905 | 21.537 | 21.916 | 1.00 | 31.59 |
| ATOM | 1357 | N | GLU | 339 | 52.977 | 20.340 | 23.595 | 1.00 | 34.82 |
| ATOM | 1358 | CA | GLU | 339 | 53.980 | 19.277 | 23.597 | 1.00 | 34.23 |
| ATOM | 1359 | CB | GLU | 339 | 53.639 | 18.256 | 24.681 | 1.00 | 40.38 |
| ATOM | 1360 | CG | GLU | 339 | 54.785 | 17.354 | 25.072 | 1.00 | 54.98 |
| ATOM | 1361 | CD | GLU | 339 | 55.644 | 17.964 | 26.178 | 1.00 | 71.26 |
| ATOM | 1362 | OE1 | GLU | 339 | 56.766 | 18.444 | 25.858 | 1.00 | 77.82 |

FIG. 30A-28

| ATOM | 1363 | OE2 | GLU | 339 | 55.170 | 17.985 | 27.349 | 1.00 | 65.14 |
|---|---|---|---|---|---|---|---|---|---|
| ATOM | 1364 | C | GLU | 339 | 53.972 | 18.582 | 22.231 | 1.00 | 34.42 |
| ATOM | 1365 | O | GLU | 339 | 55.018 | 18.431 | 21.590 | 1.00 | 29.41 |
| ATOM | 1366 | N | LYS | 340 | 52.778 | 18.189 | 21.786 | 1.00 | 34.13 |
| ATOM | 1367 | CA | LYS | 340 | 52.592 | 17.513 | 20.502 | 1.00 | 32.05 |
| ATOM | 1368 | CB | LYS | 340 | 51.121 | 17.105 | 20.325 | 1.00 | 34.59 |
| ATOM | 1369 | C | LYS | 340 | 53.064 | 18.390 | 19.337 | 1.00 | 32.56 |
| ATOM | 1370 | O | LYS | 340 | 53.762 | 17.913 | 18.441 | 1.00 | 32.93 |
| ATOM | 1371 | N | SER | 341 | 52.725 | 19.677 | 19.374 | 1.00 | 31.42 |
| ATOM | 1372 | CA | SER | 341 | 53.134 | 20.621 | 18.334 | 1.00 | 27.79 |
| ATOM | 1373 | CB | SER | 341 | 52.559 | 22.009 | 18.601 | 1.00 | 27.85 |
| ATOM | 1374 | OG | SER | 341 | 51.149 | 21.966 | 18.579 | 1.00 | 47.20 |
| ATOM | 1375 | C | SER | 341 | 54.647 | 20.713 | 18.240 | 1.00 | 26.01 |
| ATOM | 1376 | O | SER | 341 | 55.205 | 20.706 | 17.139 | 1.00 | 27.10 |
| ATOM | 1377 | N | GLN | 342 | 55.318 | 20.794 | 19.389 | 1.00 | 24.25 |
| ATOM | 1378 | CA | GLN | 342 | 56.771 | 20.875 | 19.392 | 1.00 | 27.16 |
| ATOM | 1379 | CB | GLN | 342 | 57.309 | 21.089 | 20.799 | 1.00 | 25.60 |
| ATOM | 1380 | CG | GLN | 342 | 58.768 | 21.466 | 20.777 | 1.00 | 27.99 |
| ATOM | 1381 | CD | GLN | 342 | 59.407 | 21.429 | 22.133 | 1.00 | 29.58 |
| ATOM | 1382 | OE1 | GLN | 342 | 60.123 | 22.356 | 22.513 | 1.00 | 31.18 |
| ATOM | 1383 | NE2 | GLN | 342 | 59.184 | 20.345 | 22.868 | 1.00 | 29.17 |
| ATOM | 1384 | C | GLN | 342 | 57.377 | 19.609 | 18.786 | 1.00 | 28.45 |
| ATOM | 1385 | O | GLN | 342 | 58.378 | 19.675 | 18.062 | 1.00 | 29.79 |
| ATOM | 1386 | N | GLU | 343 | 56.777 | 18.458 | 19.078 | 1.00 | 26.58 |
| ATOM | 1387 | CA | GLU | 343 | 57.251 | 17.190 | 18.525 | 1.00 | 30.07 |
| ATOM | 1388 | CB | GLU | 343 | 56.462 | 16.016 | 19.114 | 1.00 | 40.79 |
| ATOM | 1389 | CG | GLU | 343 | 56.812 | 15.700 | 20.568 | 1.00 | 61.22 |
| ATOM | 1390 | CD | GLU | 343 | 55.951 | 14.594 | 21.166 | 1.00 | 71.76 |
| ATOM | 1391 | OE1 | GLU | 343 | 55.472 | 13.719 | 20.405 | 1.00 | 76.73 |
| ATOM | 1392 | OE2 | GLU | 343 | 55.758 | 14.601 | 22.403 | 1.00 | 74.09 |
| ATOM | 1393 | C | GLU | 343 | 57.097 | 17.225 | 17.001 | 1.00 | 25.87 |
| ATOM | 1394 | O | GLU | 343 | 58.008 | 16.842 | 16.260 | 1.00 | 27.26 |
| ATOM | 1395 | N | ALA | 344 | 55.947 | 17.727 | 16.550 | 1.00 | 23.70 |
| ATOM | 1396 | CA | ALA | 344 | 55.647 | 17.853 | 15.124 | 1.00 | 22.16 |
| ATOM | 1397 | CB | ALA | 344 | 54.275 | 18.489 | 14.927 | 1.00 | 21.18 |
| ATOM | 1398 | C | ALA | 344 | 56.729 | 18.694 | 14.454 | 1.00 | 21.24 |
| ATOM | 1399 | O | ALA | 344 | 57.303 | 18.284 | 13.438 | 1.00 | 26.47 |
| ATOM | 1400 | N | TYR | 345 | 57.048 | 19.840 | 15.055 | 1.00 | 22.48 |
| ATOM | 1401 | CA | TYR | 345 | 58.073 | 20.738 | 14.531 | 1.00 | 21.41 |
| ATOM | 1402 | CB | TYR | 345 | 58.085 | 22.059 | 15.304 | 1.00 | 20.10 |
| ATOM | 1403 | CG | TYR | 345 | 57.023 | 23.015 | 14.830 | 1.00 | 15.87 |
| ATOM | 1404 | CD1 | TYR | 345 | 56.004 | 23.434 | 15.682 | 1.00 | 10.54 |
| ATOM | 1405 | CE1 | TYR | 345 | 54.983 | 24.259 | 15.225 | 1.00 | 17.09 |
| ATOM | 1406 | CD2 | TYR | 345 | 57.003 | 23.448 | 13.505 | 1.00 | 16.86 |
| ATOM | 1407 | CE2 | TYR | 345 | 55.991 | 24.269 | 13.036 | 1.00 | 16.84 |
| ATOM | 1408 | CZ | TYR | 345 | 54.984 | 24.668 | 13.896 | 1.00 | 17.97 |
| ATOM | 1409 | OH | TYR | 345 | 53.963 | 25.455 | 13.406 | 1.00 | 27.11 |
| ATOM | 1410 | C | TYR | 345 | 59.465 | 20.120 | 14.548 | 1.00 | 24.43 |
| ATOM | 1411 | O | TYR | 345 | 60.238 | 20.291 | 13.597 | 1.00 | 24.69 |
| ATOM | 1412 | N | LEU | 346 | 59.777 | 19.401 | 15.621 | 1.00 | 26.75 |

FIG. 30A-29

| ATOM | 1413 | CA | LEU | 346 | 61.074 | 18.746 | 15.767 | 1.00 | 25.06 |
|---|---|---|---|---|---|---|---|---|---|
| ATOM | 1414 | CB | LEU | 346 | 61.207 | 18.108 | 17.150 | 1.00 | 24.59 |
| ATOM | 1415 | CG | LEU | 346 | 61.637 | 19.076 | 18.252 | 1.00 | 26.46 |
| ATOM | 1416 | CD1 | LEU | 346 | 61.387 | 18.468 | 19.610 | 1.00 | 26.46 |
| ATOM | 1417 | CD2 | LEU | 346 | 63.101 | 19.437 | 18.076 | 1.00 | 21.78 |
| ATOM | 1418 | C | LEU | 346 | 61.322 | 17.713 | 14.683 | 1.00 | 23.24 |
| ATOM | 1419 | O | LEU | 346 | 62.416 | 17.645 | 14.127 | 1.00 | 27.54 |
| ATOM | 1420 | N | LEU | 347 | 60.314 | 16.900 | 14.395 | 1.00 | 25.75 |
| ATOM | 1421 | CA | LEU | 347 | 60.437 | 15.881 | 13.356 | 1.00 | 25.41 |
| ATOM | 1422 | CB | LEU | 347 | 59.208 | 14.970 | 13.330 | 1.00 | 23.78 |
| ATOM | 1423 | CG | LEU | 347 | 59.302 | 13.713 | 14.190 | 1.00 | 31.85 |
| ATOM | 1424 | CD1 | LEU | 347 | 58.004 | 12.928 | 14.089 | 1.00 | 39.88 |
| ATOM | 1425 | CD2 | LEU | 347 | 60.483 | 12.864 | 13.738 | 1.00 | 27.65 |
| ATOM | 1426 | C | LEU | 347 | 60.611 | 16.535 | 11.998 | 1.00 | 23.22 |
| ATOM | 1427 | O | LEU | 347 | 61.468 | 16.133 | 11.211 | 1.00 | 28.58 |
| ATOM | 1428 | N | ALA | 348 | 59.784 | 17.542 | 11.731 | 1.00 | 26.40 |
| ATOM | 1429 | CA | ALA | 348 | 59.840 | 18.273 | 10.474 | 1.00 | 23.85 |
| ATOM | 1430 | CB | ALA | 348 | 58.732 | 19.324 | 10.433 | 1.00 | 25.27 |
| ATOM | 1431 | C | ALA | 348 | 61.210 | 18.924 | 10.337 | 1.00 | 23.69 |
| ATOM | 1432 | O | ALA | 348 | 61.847 | 18.835 | 9.288 | 1.00 | 29.11 |
| ATOM | 1433 | N | PHE | 349 | 61.678 | 19.506 | 11.438 | 1.00 | 24.71 |
| ATOM | 1434 | CA | PHE | 349 | 62.973 | 20.181 | 11.493 | 1.00 | 20.48 |
| ATOM | 1435 | CB | PHE | 349 | 63.164 | 20.772 | 12.900 | 1.00 | 17.84 |
| ATOM | 1436 | CG | PHE | 349 | 64.334 | 21.721 | 13.031 | 1.00 | 14.90 |
| ATOM | 1437 | CD1 | PHE | 349 | 65.109 | 22.069 | 11.933 | 1.00 | 17.58 |
| ATOM | 1438 | CD2 | PHE | 349 | 64.651 | 22.269 | 14.271 | 1.00 | 24.77 |
| ATOM | 1439 | CE1 | PHE | 349 | 66.185 | 22.944 | 12.063 | 1.00 | 20.26 |
| ATOM | 1440 | CE2 | PHE | 349 | 65.727 | 23.147 | 14.413 | 1.00 | 23.83 |
| ATOM | 1441 | CZ | PHE | 349 | 66.494 | 23.486 | 13.299 | 1.00 | 20.36 |
| ATOM | 1442 | C | PHE | 349 | 64.084 | 19.181 | 11.159 | 1.00 | 23.43 |
| ATOM | 1443 | O | PHE | 349 | 64.916 | 19.427 | 10.278 | 1.00 | 24.35 |
| ATOM | 1444 | N | GLU | 350 | 64.057 | 18.028 | 11.820 | 1.00 | 25.79 |
| ATOM | 1445 | CA | GLU | 350 | 65.060 | 16.991 | 11.606 | 1.00 | 26.75 |
| ATOM | 1446 | CB | GLU | 350 | 64.813 | 15.822 | 12.567 | 1.00 | 29.56 |
| ATOM | 1447 | CG | GLU | 350 | 65.774 | 14.661 | 12.391 | 1.00 | 39.94 |
| ATOM | 1448 | CD | GLU | 350 | 65.574 | 13.549 | 13.407 | 1.00 | 45.06 |
| ATOM | 1449 | OE1 | GLU | 350 | 64.413 | 13.192 | 13.715 | 1.00 | 49.26 |
| ATOM | 1450 | OE2 | GLU | 350 | 66.593 | 13.017 | 13.887 | 1.00 | 56.67 |
| ATOM | 1451 | C | GLU | 350 | 65.051 | 16.494 | 10.162 | 1.00 | 26.95 |
| ATOM | 1452 | O | GLU | 350 | 66.096 | 16.398 | 9.513 | 1.00 | 28.77 |
| ATOM | 1453 | N | HIS | 351 | 63.858 | 16.219 | 9.652 | 1.00 | 22.56 |
| ATOM | 1454 | CA | HIS | 351 | 63.699 | 15.728 | 8.294 | 1.00 | 22.20 |
| ATOM | 1455 | CB | HIS | 351 | 62.263 | 15.265 | 8.083 | 1.00 | 22.47 |
| ATOM | 1456 | CG | HIS | 351 | 61.881 | 14.106 | 8.947 | 1.00 | 23.61 |
| ATOM | 1457 | CD2 | HIS | 351 | 62.633 | 13.300 | 9.739 | 1.00 | 27.65 |
| ATOM | 1458 | ND1 | HIS | 351 | 60.585 | 13.653 | 9.069 | 1.00 | 26.13 |
| ATOM | 1459 | CE1 | HIS | 351 | 60.548 | 12.629 | 9.898 | 1.00 | 22.87 |
| ATOM | 1460 | NE2 | HIS | 351 | 61.779 | 12.393 | 10.319 | 1.00 | 27.53 |
| ATOM | 1461 | C | HIS | 351 | 64.135 | 16.764 | 7.259 | 1.00 | 21.76 |
| ATOM | 1462 | O | HIS | 351 | 64.708 | 16.419 | 6.226 | 1.00 | 27.02 |

FIG. 30A-30

| ATOM | 1463 | N | TYR | 352 | 63.909 | 18.041 | 7.555 | 1.00 | 18.26 |
|---|---|---|---|---|---|---|---|---|---|
| ATOM | 1464 | CA | TYR | 352 | 64.327 | 19.101 | 6.649 | 1.00 | 16.94 |
| ATOM | 1465 | CB | TYR | 352 | 63.749 | 20.455 | 7.066 | 1.00 | 19.07 |
| ATOM | 1466 | CG | TYR | 352 | 64.107 | 21.534 | 6.081 | 1.00 | 21.11 |
| ATOM | 1467 | CD1 | TYR | 352 | 63.518 | 21.564 | 4.819 | 1.00 | 21.33 |
| ATOM | 1468 | CE1 | TYR | 352 | 63.921 | 22.482 | 3.859 | 1.00 | 21.06 |
| ATOM | 1469 | CD2 | TYR | 352 | 65.105 | 22.462 | 6.367 | 1.00 | 22.07 |
| ATOM | 1470 | CE2 | TYR | 352 | 65.515 | 23.388 | 5.412 | 1.00 | 25.40 |
| ATOM | 1471 | CZ | TYR | 352 | 64.921 | 23.384 | 4.161 | 1.00 | 21.90 |
| ATOM | 1472 | OH | TYR | 352 | 65.334 | 24.268 | 3.197 | 1.00 | 23.57 |
| ATOM | 1473 | C | TYR | 352 | 65.853 | 19.156 | 6.657 | 1.00 | 18.49 |
| ATOM | 1474 | O | TYR | 352 | 66.487 | 19.323 | 5.609 | 1.00 | 24.99 |
| ATOM | 1475 | N | VAL | 353 | 66.451 | 19.008 | 7.836 | 1.00 | 24.64 |
| ATOM | 1476 | CA | VAL | 353 | 67.904 | 19.011 | 7.955 | 1.00 | 22.20 |
| ATOM | 1477 | CB | VAL | 353 | 68.350 | 18.925 | 9.440 | 1.00 | 23.72 |
| ATOM | 1478 | CG1 | VAL | 353 | 69.838 | 18.597 | 9.546 | 1.00 | 21.24 |
| ATOM | 1479 | CG2 | VAL | 353 | 68.063 | 20.245 | 10.142 | 1.00 | 20.07 |
| ATOM | 1480 | C | VAL | 353 | 68.452 | 17.829 | 7.146 | 1.00 | 25.07 |
| ATOM | 1481 | O | VAL | 353 | 69.467 | 17.955 | 6.457 | 1.00 | 24.75 |
| ATOM | 1482 | N | ASN | 354 | 67.768 | 16.690 | 7.221 | 1.00 | 24.59 |
| ATOM | 1483 | CA | ASN | 354 | 68.171 | 15.502 | 6.474 | 1.00 | 25.64 |
| ATOM | 1484 | CB | ASN | 354 | 67.223 | 14.331 | 6.751 | 1.00 | 26.05 |
| ATOM | 1485 | CG | ASN | 354 | 67.368 | 13.763 | 8.151 | 1.00 | 30.27 |
| ATOM | 1486 | OD1 | ASN | 354 | 66.443 | 13.139 | 8.672 | 1.00 | 33.71 |
| ATOM | 1487 | ND2 | ASN | 354 | 68.529 | 13.959 | 8.765 | 1.00 | 34.78 |
| ATOM | 1488 | C | ASN | 354 | 68.143 | 15.813 | 4.981 | 1.00 | 30.50 |
| ATOM | 1489 | O | ASN | 354 | 69.042 | 15.423 | 4.233 | 1.00 | 33.73 |
| ATOM | 1490 | N | HIS | 355 | 67.098 | 16.519 | 4.555 | 1.00 | 30.54 |
| ATOM | 1491 | CA | HIS | 355 | 66.926 | 16.901 | 3.157 | 1.00 | 26.02 |
| ATOM | 1492 | CB | HIS | 355 | 65.535 | 17.521 | 2.953 | 1.00 | 29.93 |
| ATOM | 1493 | CG | HIS | 355 | 65.367 | 18.217 | 1.638 | 1.00 | 37.91 |
| ATOM | 1494 | CD2 | HIS | 355 | 65.654 | 19.486 | 1.264 | 1.00 | 31.26 |
| ATOM | 1495 | ND1 | HIS | 355 | 64.861 | 17.593 | 0.518 | 1.00 | 32.67 |
| ATOM | 1496 | CE1 | HIS | 355 | 64.843 | 18.447 | -0.488 | 1.00 | 33.22 |
| ATOM | 1497 | NE2 | HIS | 355 | 65.322 | 19.601 | -0.061 | 1.00 | 32.69 |
| ATOM | 1498 | C | HIS | 355 | 68.009 | 17.851 | 2.652 | 1.00 | 24.29 |
| ATOM | 1499 | O | HIS | 355 | 68.381 | 17.798 | 1.484 | 1.00 | 26.82 |
| ATOM | 1500 | N | ARG | 356 | 68.484 | 18.735 | 3.526 | 1.00 | 29.72 |
| ATOM | 1501 | CA | ARG | 356 | 69.516 | 19.711 | 3.167 | 1.00 | 26.65 |
| ATOM | 1502 | CB | ARG | 356 | 69.593 | 20.804 | 4.225 | 1.00 | 22.74 |
| ATOM | 1503 | CG | ARG | 356 | 68.409 | 21.735 | 4.222 | 1.00 | 21.64 |
| ATOM | 1504 | CD | ARG | 356 | 68.757 | 23.024 | 3.524 | 1.00 | 28.04 |
| ATOM | 1505 | NE | ARG | 356 | 69.550 | 23.900 | 4.380 | 1.00 | 33.79 |
| ATOM | 1506 | CZ | ARG | 356 | 70.508 | 24.716 | 3.952 | 1.00 | 29.26 |
| ATOM | 1507 | NH1 | ARG | 356 | 70.814 | 24.776 | 2.667 | 1.00 | 29.08 |
| ATOM | 1508 | NH2 | ARG | 356 | 71.136 | 25.493 | 4.816 | 1.00 | 33.61 |
| ATOM | 1509 | C | ARG | 356 | 70.904 | 19.115 | 2.950 | 1.00 | 27.58 |
| ATOM | 1510 | O | ARG | 356 | 71.757 | 19.740 | 2.312 | 1.00 | 31.44 |
| ATOM | 1511 | N | LYS | 357 | 71.140 | 17.937 | 3.519 | 1.00 | 30.56 |
| ATOM | 1512 | CA | LYS | 357 | 72.422 | 17.244 | 3.390 | 1.00 | 34.56 |

FIG. 30A-31

| ATOM | 1513 | CB | LYS | 357 | 72.500 | 16.518 | 2.043 | 1.00 | 39.66 |
|---|---|---|---|---|---|---|---|---|---|
| ATOM | 1514 | CG | LYS | 357 | 71.476 | 15.402 | 1.871 | 1.00 | 42.16 |
| ATOM | 1515 | CD | LYS | 357 | 71.674 | 14.676 | 0.550 | 1.00 | 54.23 |
| ATOM | 1516 | CE | LYS | 357 | 70.691 | 13.523 | 0.371 | 1.00 | 61.97 |
| ATOM | 1517 | NZ | LYS | 357 | 69.288 | 13.974 | 0.162 | 1.00 | 65.88 |
| ATOM | 1518 | C | LYS | 357 | 73.665 | 18.119 | 3.606 | 1.00 | 36.73 |
| ATOM | 1519 | O | LYS | 357 | 74.522 | 18.248 | 2.728 | 1.00 | 40.70 |
| ATOM | 1520 | N | HIS | 358 | 73.738 | 18.732 | 4.786 | 1.00 | 33.69 |
| ATOM | 1521 | CA | HIS | 358 | 74.863 | 19.581 | 5.163 | 1.00 | 33.59 |
| ATOM | 1522 | CB | HIS | 358 | 74.660 | 20.155 | 6.571 | 1.00 | 32.07 |
| ATOM | 1523 | CG | HIS | 358 | 73.593 | 21.200 | 6.666 | 1.00 | 29.74 |
| ATOM | 1524 | CD2 | HIS | 358 | 72.245 | 21.098 | 6.736 | 1.00 | 23.35 |
| ATOM | 1525 | ND1 | HIS | 358 | 73.876 | 22.547 | 6.731 | 1.00 | 28.13 |
| ATOM | 1526 | CE1 | HIS | 358 | 72.752 | 23.231 | 6.834 | 1.00 | 26.94 |
| ATOM | 1527 | NE2 | HIS | 358 | 71.747 | 22.373 | 6.838 | 1.00 | 23.32 |
| ATOM | 1528 | C | HIS | 358 | 76.121 | 18.720 | 5.180 | 1.00 | 37.98 |
| ATOM | 1529 | O | HIS | 358 | 76.087 | 17.581 | 5.654 | 1.00 | 41.07 |
| ATOM | 1530 | N | ASN | 359 | 77.231 | 19.261 | 4.690 | 1.00 | 44.20 |
| ATOM | 1531 | CA | ASN | 359 | 78.492 | 18.523 | 4.676 | 1.00 | 49.72 |
| ATOM | 1532 | CB | ASN | 359 | 79.406 | 19.053 | 3.572 | 1.00 | 46.66 |
| ATOM | 1533 | C | ASN | 359 | 79.174 | 18.648 | 6.039 | 1.00 | 51.77 |
| ATOM | 1534 | O | ASN | 359 | 80.356 | 18.985 | 6.122 | 1.00 | 57.32 |
| ATOM | 1535 | N | ILE | 360 | 78.414 | 18.383 | 7.101 | 1.00 | 51.04 |
| ATOM | 1536 | CA | ILE | 360 | 78.906 | 18.471 | 8.477 | 1.00 | 48.24 |
| ATOM | 1537 | CB | ILE | 360 | 78.340 | 19.721 | 9.207 | 1.00 | 47.20 |
| ATOM | 1538 | CG2 | ILE | 360 | 78.781 | 19.741 | 10.673 | 1.00 | 43.50 |
| ATOM | 1539 | CG1 | ILE | 360 | 78.777 | 21.005 | 8.491 | 1.00 | 45.94 |
| ATOM | 1540 | CD1 | ILE | 360 | 78.157 | 22.262 | 9.050 | 1.00 | 43.00 |
| ATOM | 1541 | C | ILE | 360 | 78.462 | 17.222 | 9.239 | 1.00 | 47.23 |
| ATOM | 1542 | O | ILE | 360 | 77.272 | 16.901 | 9.278 | 1.00 | 45.13 |
| ATOM | 1543 | N | PRO | 361 | 79.416 | 16.490 | 9.838 | 1.00 | 48.61 |
| ATOM | 1544 | CD | PRO | 361 | 80.869 | 16.705 | 9.729 | 1.00 | 50.93 |
| ATOM | 1545 | CA | PRO | 361 | 79.129 | 15.270 | 10.599 | 1.00 | 45.46 |
| ATOM | 1546 | CB | PRO | 361 | 80.524 | 14.725 | 10.927 | 1.00 | 49.01 |
| ATOM | 1547 | CG | PRO | 361 | 81.402 | 15.307 | 9.862 | 1.00 | 54.41 |
| ATOM | 1548 | C | PRO | 361 | 78.330 | 15.514 | 11.879 | 1.00 | 36.54 |
| ATOM | 1549 | O | PRO | 361 | 78.666 | 16.394 | 12.672 | 1.00 | 39.83 |
| ATOM | 1550 | N | HIS | 362 | 77.282 | 14.716 | 12.075 | 1.00 | 31.35 |
| ATOM | 1551 | CA | HIS | 362 | 76.430 | 14.798 | 13.264 | 1.00 | 33.34 |
| ATOM | 1552 | CB | HIS | 362 | 77.246 | 14.495 | 14.524 | 1.00 | 33.77 |
| ATOM | 1553 | CG | HIS | 362 | 78.129 | 13.292 | 14.397 | 1.00 | 34.40 |
| ATOM | 1554 | CD2 | HIS | 362 | 77.837 | 11.999 | 14.130 | 1.00 | 32.60 |
| ATOM | 1555 | ND1 | HIS | 362 | 79.501 | 13.362 | 14.506 | 1.00 | 36.14 |
| ATOM | 1556 | CE1 | HIS | 362 | 80.017 | 12.160 | 14.311 | 1.00 | 36.26 |
| ATOM | 1557 | NE2 | HIS | 362 | 79.029 | 11.316 | 14.080 | 1.00 | 35.73 |
| ATOM | 1558 | C | HIS | 362 | 75.778 | 16.164 | 13.389 | 1.00 | 33.55 |
| ATOM | 1559 | O | HIS | 362 | 75.539 | 16.652 | 14.495 | 1.00 | 31.93 |
| ATOM | 1560 | N | PHE | 363 | 75.449 | 16.748 | 12.240 | 1.00 | 35.83 |
| ATOM | 1561 | CA | PHE | 363 | 74.834 | 18.067 | 12.166 | 1.00 | 30.93 |
| ATOM | 1562 | CB | PHE | 363 | 74.464 | 18.394 | 10.712 | 1.00 | 28.82 |

FIG. 30A-32

| ATOM | 1563 | CG | PHE | 363 | 73.959 | 19.797 | 10.514 | 1.00 | 26.59 |
|---|---|---|---|---|---|---|---|---|---|
| ATOM | 1564 | CD1 | PHE | 363 | 74.846 | 20.843 | 10.301 | 1.00 | 26.96 |
| ATOM | 1565 | CD2 | PHE | 363 | 72.596 | 20.076 | 10.575 | 1.00 | 27.51 |
| ATOM | 1566 | CE1 | PHE | 363 | 74.384 | 22.151 | 10.155 | 1.00 | 31.83 |
| ATOM | 1567 | CE2 | PHE | 363 | 72.124 | 21.378 | 10.433 | 1.00 | 26.65 |
| ATOM | 1568 | CZ | PHE | 363 | 73.019 | 22.417 | 10.223 | 1.00 | 24.42 |
| ATOM | 1569 | C | PHE | 363 | 73.613 | 18.235 | 13.063 | 1.00 | 28.73 |
| ATOM | 1570 | O | PHE | 363 | 73.550 | 19.174 | 13.848 | 1.00 | 25.33 |
| ATOM | 1571 | N | TRP | 364 | 72.663 | 17.310 | 12.969 | 1.00 | 22.89 |
| ATOM | 1572 | CA | TRP | 364 | 71.443 | 17.405 | 13.760 | 1.00 | 24.19 |
| ATOM | 1573 | CB | TRP | 364 | 70.481 | 16.254 | 13.439 | 1.00 | 26.31 |
| ATOM | 1574 | CG | TRP | 364 | 69.198 | 16.275 | 14.228 | 1.00 | 20.24 |
| ATOM | 1575 | CD2 | TRP | 364 | 68.213 | 17.325 | 14.262 | 1.00 | 24.50 |
| ATOM | 1576 | CE2 | TRP | 364 | 67.175 | 16.894 | 15.120 | 1.00 | 25.84 |
| ATOM | 1577 | CE3 | TRP | 364 | 68.106 | 18.583 | 13.652 | 1.00 | 25.83 |
| ATOM | 1578 | CD1 | TRP | 364 | 68.731 | 15.289 | 15.040 | 1.00 | 23.61 |
| ATOM | 1579 | NE1 | TRP | 364 | 67.515 | 15.648 | 15.579 | 1.00 | 32.26 |
| ATOM | 1580 | CZ2 | TRP | 364 | 66.048 | 17.674 | 15.386 | 1.00 | 21.95 |
| ATOM | 1581 | CZ3 | TRP | 364 | 66.979 | 19.360 | 13.919 | 1.00 | 20.73 |
| ATOM | 1582 | CH2 | TRP | 364 | 65.967 | 18.899 | 14.779 | 1.00 | 22.37 |
| ATOM | 1583 | C | TRP | 364 | 71.663 | 17.551 | 15.267 | 1.00 | 28.84 |
| ATOM | 1584 | O | TRP | 364 | 71.246 | 18.554 | 15.839 | 1.00 | 31.25 |
| ATOM | 1585 | N | PRO | 365 | 72.305 | 16.568 | 15.932 | 1.00 | 29.69 |
| ATOM | 1586 | CD | PRO | 365 | 72.790 | 15.245 | 15.497 | 1.00 | 30.89 |
| ATOM | 1587 | CA | PRO | 365 | 72.499 | 16.748 | 17.373 | 1.00 | 25.62 |
| ATOM | 1588 | CB | PRO | 365 | 73.195 | 15.451 | 17.810 | 1.00 | 25.50 |
| ATOM | 1589 | CG | PRO | 365 | 73.804 | 14.915 | 16.560 | 1.00 | 34.15 |
| ATOM | 1590 | C | PRO | 365 | 73.320 | 18.002 | 17.698 | 1.00 | 24.07 |
| ATOM | 1591 | O | PRO | 365 | 73.079 | 18.654 | 18.711 | 1.00 | 23.58 |
| ATOM | 1592 | N | LYS | 366 | 74.250 | 18.365 | 16.820 | 1.00 | 24.09 |
| ATOM | 1593 | CA | LYS | 366 | 75.063 | 19.562 | 17.027 | 1.00 | 29.44 |
| ATOM | 1594 | CB | LYS | 366 | 76.131 | 19.681 | 15.945 | 1.00 | 27.18 |
| ATOM | 1595 | CG | LYS | 366 | 77.341 | 18.802 | 16.149 | 1.00 | 23.71 |
| ATOM | 1596 | CD | LYS | 366 | 78.304 | 19.019 | 15.001 | 1.00 | 27.50 |
| ATOM | 1597 | CE | LYS | 366 | 79.624 | 18.329 | 15.231 | 1.00 | 35.88 |
| ATOM | 1598 | NZ | LYS | 366 | 80.550 | 18.591 | 14.097 | 1.00 | 41.92 |
| ATOM | 1599 | C | LYS | 366 | 74.195 | 20.820 | 17.012 | 1.00 | 32.76 |
| ATOM | 1600 | O | LYS | 366 | 74.326 | 21.694 | 17.873 | 1.00 | 36.13 |
| ATOM | 1601 | N | LEU | 367 | 73.307 | 20.907 | 16.028 | 1.00 | 33.70 |
| ATOM | 1602 | CA | LEU | 367 | 72.409 | 22.041 | 15.905 | 1.00 | 30.60 |
| ATOM | 1603 | CB | LEU | 367 | 71.636 | 21.955 | 14.587 | 1.00 | 24.26 |
| ATOM | 1604 | CG | LEU | 367 | 70.675 | 23.103 | 14.274 | 1.00 | 32.42 |
| ATOM | 1605 | CD1 | LEU | 367 | 71.394 | 24.440 | 14.404 | 1.00 | 24.78 |
| ATOM | 1606 | CD2 | LEU | 367 | 70.098 | 22.924 | 12.878 | 1.00 | 28.84 |
| ATOM | 1607 | C | LEU | 367 | 71.450 | 22.015 | 17.087 | 1.00 | 31.90 |
| ATOM | 1608 | O | LEU | 367 | 71.113 | 23.052 | 17.655 | 1.00 | 39.20 |
| ATOM | 1609 | N | LEU | 368 | 71.051 | 20.812 | 17.485 | 1.00 | 33.86 |
| ATOM | 1610 | CA | LEU | 368 | 70.144 | 20.617 | 18.608 | 1.00 | 32.97 |
| ATOM | 1611 | CB | LEU | 368 | 69.866 | 19.123 | 18.759 | 1.00 | 34.22 |
| ATOM | 1612 | CG | LEU | 368 | 68.458 | 18.633 | 19.084 | 1.00 | 38.15 |

FIG. 30A-33

| ATOM | 1613 | CD1 | LEU | 368 | 67.400 | 19.449 | 18.345 | 1.00 | 27.75 |
|---|---|---|---|---|---|---|---|---|---|
| ATOM | 1614 | CD2 | LEU | 368 | 68.374 | 17.154 | 18.733 | 1.00 | 31.51 |
| ATOM | 1615 | C | LEU | 368 | 70.793 | 21.181 | 19.875 | 1.00 | 35.29 |
| ATOM | 1616 | O | LEU | 368 | 70.128 | 21.806 | 20.703 | 1.00 | 36.16 |
| ATOM | 1617 | N | MET | 369 | 72.106 | 21.001 | 19.994 | 1.00 | 41.13 |
| ATOM | 1618 | CA | MET | 369 | 72.857 | 21.504 | 21.139 | 1.00 | 40.92 |
| ATOM | 1619 | CB | MET | 369 | 74.283 | 20.955 | 21.115 | 1.00 | 43.32 |
| ATOM | 1620 | CG | MET | 369 | 74.383 | 19.497 | 21.545 | 1.00 | 50.01 |
| ATOM | 1621 | SD | MET | 369 | 75.997 | 18.770 | 21.190 | 1.00 | 56.63 |
| ATOM | 1622 | CE | MET | 369 | 77.032 | 19.596 | 22.409 | 1.00 | 62.26 |
| ATOM | 1623 | C | MET | 369 | 72.872 | 23.032 | 21.186 | 1.00 | 43.46 |
| ATOM | 1624 | O | MET | 369 | 73.137 | 23.619 | 22.233 | 1.00 | 47.51 |
| ATOM | 1625 | N | LYS | 370 | 72.594 | 23.673 | 20.053 | 1.00 | 41.60 |
| ATOM | 1626 | CA | LYS | 370 | 72.561 | 25.131 | 19.988 | 1.00 | 34.48 |
| ATOM | 1627 | CB | LYS | 370 | 72.689 | 25.623 | 18.546 | 1.00 | 31.53 |
| ATOM | 1628 | CG | LYS | 370 | 74.012 | 25.278 | 17.896 | 1.00 | 30.76 |
| ATOM | 1629 | CD | LYS | 370 | 75.168 | 25.774 | 18.731 | 1.00 | 32.16 |
| ATOM | 1630 | CE | LYS | 370 | 76.488 | 25.388 | 18.116 | 1.00 | 31.08 |
| ATOM | 1631 | NZ | LYS | 370 | 77.604 | 25.822 | 18.993 | 1.00 | 51.52 |
| ATOM | 1632 | C | LYS | 370 | 71.269 | 25.652 | 20.606 | 1.00 | 36.35 |
| ATOM | 1633 | O | LYS | 370 | 71.197 | 26.806 | 21.032 | 1.00 | 39.02 |
| ATOM | 1634 | N | VAL | 371 | 70.248 | 24.804 | 20.652 | 1.00 | 34.33 |
| ATOM | 1635 | CA | VAL | 371 | 68.975 | 25.186 | 21.249 | 1.00 | 36.27 |
| ATOM | 1636 | CB | VAL | 371 | 67.885 | 24.097 | 21.046 | 1.00 | 36.15 |
| ATOM | 1637 | CG1 | VAL | 371 | 66.600 | 24.487 | 21.758 | 1.00 | 32.69 |
| ATOM | 1638 | CG2 | VAL | 371 | 67.612 | 23.892 | 19.567 | 1.00 | 33.75 |
| ATOM | 1639 | C | VAL | 371 | 69.196 | 25.423 | 22.745 | 1.00 | 41.55 |
| ATOM | 1640 | O | VAL | 371 | 68.638 | 26.367 | 23.316 | 1.00 | 40.82 |
| ATOM | 1641 | N | THR | 372 | 70.018 | 24.581 | 23.378 | 1.00 | 40.42 |
| ATOM | 1642 | CA | THR | 372 | 70.300 | 24.733 | 24.804 | 1.00 | 41.69 |
| ATOM | 1643 | CB | THR | 372 | 71.037 | 23.499 | 25.397 | 1.00 | 42.36 |
| ATOM | 1644 | OG1 | THR | 372 | 72.125 | 23.133 | 24.548 | 1.00 | 53.57 |
| ATOM | 1645 | CG2 | THR | 372 | 70.090 | 22.313 | 25.523 | 1.00 | 43.54 |
| ATOM | 1646 | C | THR | 372 | 71.090 | 26.021 | 25.048 | 1.00 | 38.75 |
| ATOM | 1647 | O | THR | 372 | 70.858 | 26.714 | 26.042 | 1.00 | 37.51 |
| ATOM | 1648 | N | ASP | 373 | 71.987 | 26.360 | 24.122 | 1.00 | 36.73 |
| ATOM | 1649 | CA | ASP | 373 | 72.768 | 27.594 | 24.223 | 1.00 | 30.96 |
| ATOM | 1650 | CB | ASP | 373 | 73.741 | 27.732 | 23.047 | 1.00 | 31.26 |
| ATOM | 1651 | CG | ASP | 373 | 74.865 | 26.707 | 23.085 | 1.00 | 35.85 |
| ATOM | 1652 | OD1 | ASP | 373 | 75.523 | 26.508 | 22.042 | 1.00 | 36.73 |
| ATOM | 1653 | OD2 | ASP | 373 | 75.102 | 26.103 | 24.153 | 1.00 | 39.92 |
| ATOM | 1654 | C | ASP | 373 | 71.797 | 28.769 | 24.230 | 1.00 | 31.30 |
| ATOM | 1655 | O | ASP | 373 | 71.926 | 29.689 | 25.039 | 1.00 | 35.37 |
| ATOM | 1656 | N | LEU | 374 | 70.804 | 28.711 | 23.348 | 1.00 | 27.72 |
| ATOM | 1657 | CA | LEU | 374 | 69.783 | 29.751 | 23.257 | 1.00 | 28.18 |
| ATOM | 1658 | CB | LEU | 374 | 68.881 | 29.521 | 22.042 | 1.00 | 28.41 |
| ATOM | 1659 | CG | LEU | 374 | 69.391 | 30.055 | 20.703 | 1.00 | 29.87 |
| ATOM | 1660 | CD1 | LEU | 374 | 68.533 | 29.520 | 19.563 | 1.00 | 25.44 |
| ATOM | 1661 | CD2 | LEU | 374 | 69.385 | 31.581 | 20.728 | 1.00 | 23.74 |
| ATOM | 1662 | C | LEU | 374 | 68.946 | 29.786 | 24.527 | 1.00 | 28.61 |

FIG. 30A-34

| ATOM | 1663 | O | LEU | 374 | 68.516 | 30.859 | 24.968 | 1.00 | 29.51 |
|------|------|-----|-----|-----|--------|--------|--------|------|-------|
| ATOM | 1664 | N | ARG | 375 | 68.690 | 28.615 | 25.105 | 1.00 | 32.32 |
| ATOM | 1665 | CA | ARG | 375 | 67.925 | 28.532 | 26.345 | 1.00 | 33.19 |
| ATOM | 1666 | CB | ARG | 375 | 67.758 | 27.074 | 26.776 | 1.00 | 41.70 |
| ATOM | 1667 | CG | ARG | 375 | 66.360 | 26.524 | 26.609 | 1.00 | 51.03 |
| ATOM | 1668 | CD | ARG | 375 | 65.979 | 26.416 | 25.153 | 1.00 | 60.16 |
| ATOM | 1669 | NE | ARG | 375 | 64.648 | 25.840 | 24.987 | 1.00 | 74.28 |
| ATOM | 1670 | CZ | ARG | 375 | 64.324 | 24.587 | 25.296 | 1.00 | 79.34 |
| ATOM | 1671 | NH1 | ARG | 375 | 65.233 | 23.756 | 25.796 | 1.00 | 80.84 |
| ATOM | 1672 | NH2 | ARG | 375 | 63.084 | 24.157 | 25.092 | 1.00 | 77.44 |
| ATOM | 1673 | C | ARG | 375 | 68.692 | 29.296 | 27.423 | 1.00 | 32.02 |
| ATOM | 1674 | O | ARG | 375 | 68.132 | 30.150 | 28.108 | 1.00 | 30.42 |
| ATOM | 1675 | N | MET | 376 | 69.993 | 29.020 | 27.521 | 1.00 | 32.30 |
| ATOM | 1676 | CA | MET | 376 | 70.860 | 29.668 | 28.499 | 1.00 | 36.82 |
| ATOM | 1677 | CB | MET | 376 | 72.278 | 29.097 | 28.433 | 1.00 | 45.36 |
| ATOM | 1678 | CG | MET | 376 | 72.375 | 27.645 | 28.866 | 1.00 | 66.71 |
| ATOM | 1679 | SD | MET | 376 | 74.078 | 27.057 | 28.966 | 1.00 | 89.64 |
| ATOM | 1680 | CE | MET | 376 | 74.256 | 26.229 | 27.400 | 1.00 | 85.51 |
| ATOM | 1681 | C | MET | 376 | 70.880 | 31.182 | 28.310 | 1.00 | 37.49 |
| ATOM | 1682 | O | MET | 376 | 70.780 | 31.928 | 29.281 | 1.00 | 39.99 |
| ATOM | 1683 | N | ILE | 377 | 71.008 | 31.630 | 27.060 | 1.00 | 33.14 |
| ATOM | 1684 | CA | ILE | 377 | 71.009 | 33.057 | 26.740 | 1.00 | 25.98 |
| ATOM | 1685 | CB | ILE | 377 | 71.181 | 33.291 | 25.211 | 1.00 | 22.79 |
| ATOM | 1686 | CG2 | ILE | 377 | 70.838 | 34.727 | 24.834 | 1.00 | 25.29 |
| ATOM | 1687 | CG1 | ILE | 377 | 72.606 | 32.947 | 24.785 | 1.00 | 21.42 |
| ATOM | 1688 | CD1 | ILE | 377 | 72.816 | 32.971 | 23.282 | 1.00 | 19.37 |
| ATOM | 1689 | C | ILE | 377 | 69.690 | 33.664 | 27.228 | 1.00 | 27.11 |
| ATOM | 1690 | O | ILE | 377 | 69.676 | 34.727 | 27.856 | 1.00 | 28.09 |
| ATOM | 1691 | N | GLY | 378 | 68.584 | 32.969 | 26.975 | 1.00 | 29.34 |
| ATOM | 1692 | CA | GLY | 378 | 67.292 | 33.457 | 27.418 | 1.00 | 30.41 |
| ATOM | 1693 | C | GLY | 378 | 67.233 | 33.532 | 28.934 | 1.00 | 36.85 |
| ATOM | 1694 | O | GLY | 378 | 66.672 | 34.481 | 29.489 | 1.00 | 36.44 |
| ATOM | 1695 | N | ALA | 379 | 67.837 | 32.547 | 29.603 | 1.00 | 37.98 |
| ATOM | 1696 | CA | ALA | 379 | 67.869 | 32.483 | 31.066 | 1.00 | 36.44 |
| ATOM | 1697 | CB | ALA | 379 | 68.415 | 31.133 | 31.528 | 1.00 | 35.63 |
| ATOM | 1698 | C | ALA | 379 | 68.712 | 33.613 | 31.642 | 1.00 | 34.14 |
| ATOM | 1699 | O | ALA | 379 | 68.259 | 34.343 | 32.523 | 1.00 | 35.15 |
| ATOM | 1700 | N | CYA | 380 | 69.941 | 33.747 | 31.144 | 1.00 | 36.66 |
| ATOM | 1701 | CA | CYA | 380 | 70.860 | 34.795 | 31.587 | 1.00 | 37.27 |
| ATOM | 1702 | CB | CYA | 380 | 72.172 | 34.728 | 30.810 | 1.00 | 36.85 |
| ATOM | 1703 | SG | CYA | 380 | 73.201 | 33.338 | 31.250 | 1.00 | 52.80 |
| ATOM | 1704 | AS | CYA | 380 | 74.942 | 33.593 | 29.823 | 1.00 | 65.79 |
| ATOM | 1705 | C | CYA | 380 | 70.230 | 36.165 | 31.398 | 1.00 | 38.70 |
| ATOM | 1706 | O | CYA | 380 | 70.337 | 37.033 | 32.270 | 1.00 | 45.73 |
| ATOM | 1707 | N | HIS | 381 | 69.555 | 36.354 | 30.265 | 1.00 | 37.32 |
| ATOM | 1708 | CA | HIS | 381 | 68.906 | 37.623 | 29.994 | 1.00 | 32.11 |
| ATOM | 1709 | CB | HIS | 381 | 68.377 | 37.687 | 28.565 | 1.00 | 25.76 |
| ATOM | 1710 | CG | HIS | 381 | 67.596 | 38.932 | 28.285 | 1.00 | 20.30 |
| ATOM | 1711 | CD2 | HIS | 381 | 67.998 | 40.200 | 28.044 | 1.00 | 16.31 |
| ATOM | 1712 | ND1 | HIS | 381 | 66.218 | 38.971 | 28.336 | 1.00 | 22.06 |

FIG. 30A-35

| ATOM | 1713 | CE1 | HIS | 381 | 65.807 | 40.210 | 28.146 | 1.00 | 21.20 |
|---|---|---|---|---|---|---|---|---|---|
| ATOM | 1714 | NE2 | HIS | 381 | 66.869 | 40.976 | 27.968 | 1.00 | 22.58 |
| ATOM | 1715 | C | HIS | 381 | 67.773 | 37.893 | 30.980 | 1.00 | 32.68 |
| ATOM | 1716 | O | HIS | 381 | 67.602 | 39.024 | 31.431 | 1.00 | 33.38 |
| ATOM | 1717 | N | ALA | 382 | 66.982 | 36.873 | 31.296 | 1.00 | 31.27 |
| ATOM | 1718 | CA | ALA | 382 | 65.884 | 37.045 | 32.243 | 1.00 | 29.39 |
| ATOM | 1719 | CB | ALA | 382 | 65.121 | 35.742 | 32.409 | 1.00 | 25.18 |
| ATOM | 1720 | C | ALA | 382 | 66.420 | 37.531 | 33.596 | 1.00 | 34.32 |
| ATOM | 1721 | O | ALA | 382 | 65.902 | 38.501 | 34.160 | 1.00 | 37.79 |
| ATOM | 1722 | N | SER | 383 | 67.483 | 36.893 | 34.085 | 1.00 | 36.88 |
| ATOM | 1723 | CA | SER | 383 | 68.100 | 37.268 | 35.361 | 1.00 | 39.74 |
| ATOM | 1724 | CB | SER | 383 | 69.233 | 36.297 | 35.719 | 1.00 | 42.58 |
| ATOM | 1725 | OG | SER | 383 | 68.734 | 35.010 | 36.049 | 1.00 | 61.85 |
| ATOM | 1726 | C | SER | 383 | 68.638 | 38.697 | 35.311 | 1.00 | 36.49 |
| ATOM | 1727 | O | SER | 383 | 68.443 | 39.480 | 36.243 | 1.00 | 43.81 |
| ATOM | 1728 | N | ARG | 384 | 69.305 | 39.036 | 34.213 | 1.00 | 33.66 |
| ATOM | 1729 | CA | ARG | 384 | 69.866 | 40.367 | 34.043 | 1.00 | 35.39 |
| ATOM | 1730 | CB | ARG | 384 | 70.800 | 40.404 | 32.835 | 1.00 | 29.29 |
| ATOM | 1731 | CG | ARG | 384 | 71.590 | 41.679 | 32.731 | 1.00 | 29.20 |
| ATOM | 1732 | CD | ARG | 384 | 72.881 | 41.435 | 31.995 | 1.00 | 37.73 |
| ATOM | 1733 | NE | ARG | 384 | 73.657 | 42.663 | 31.850 | 1.00 | 48.97 |
| ATOM | 1734 | CZ | ARG | 384 | 74.346 | 43.245 | 32.826 | 1.00 | 45.41 |
| ATOM | 1735 | NH1 | ARG | 384 | 74.371 | 42.715 | 34.038 | 1.00 | 44.51 |
| ATOM | 1736 | NH2 | ARG | 384 | 75.008 | 44.368 | 32.584 | 1.00 | 41.43 |
| ATOM | 1737 | C | ARG | 384 | 68.777 | 41.431 | 33.916 | 1.00 | 39.45 |
| ATOM | 1738 | O | ARG | 384 | 68.913 | 42.537 | 34.444 | 1.00 | 44.47 |
| ATOM | 1739 | N | PHE | 385 | 67.673 | 41.077 | 33.270 | 1.00 | 36.42 |
| ATOM | 1740 | CA | PHE | 385 | 66.568 | 42.007 | 33.099 | 1.00 | 34.68 |
| ATOM | 1741 | CB | PHE | 385 | 65.444 | 41.393 | 32.262 | 1.00 | 30.21 |
| ATOM | 1742 | CG | PHE | 385 | 64.263 | 42.304 | 32.081 | 1.00 | 29.48 |
| ATOM | 1743 | CD1 | PHE | 385 | 64.289 | 43.313 | 31.127 | 1.00 | 29.70 |
| ATOM | 1744 | CD2 | PHE | 385 | 63.130 | 42.161 | 32.873 | 1.00 | 28.04 |
| ATOM | 1745 | CE1 | PHE | 385 | 63.203 | 44.169 | 30.966 | 1.00 | 33.50 |
| ATOM | 1746 | CE2 | PHE | 385 | 62.040 | 43.012 | 32.718 | 1.00 | 31.35 |
| ATOM | 1747 | CZ | PHE | 385 | 62.077 | 44.017 | 31.763 | 1.00 | 32.08 |
| ATOM | 1748 | C | PHE | 385 | 66.040 | 42.412 | 34.468 | 1.00 | 35.76 |
| ATOM | 1749 | O | PHE | 385 | 65.761 | 43.590 | 34.693 | 1.00 | 40.58 |
| ATOM | 1750 | N | LEU | 386 | 65.906 | 41.441 | 35.373 | 1.00 | 37.55 |
| ATOM | 1751 | CA | LEU | 386 | 65.429 | 41.706 | 36.735 | 1.00 | 41.01 |
| ATOM | 1752 | CB | LEU | 386 | 65.394 | 40.413 | 37.563 | 1.00 | 42.30 |
| ATOM | 1753 | CG | LEU | 386 | 64.240 | 39.434 | 37.317 | 1.00 | 43.34 |
| ATOM | 1754 | CD1 | LEU | 386 | 64.559 | 38.066 | 37.912 | 1.00 | 43.50 |
| ATOM | 1755 | CD2 | LEU | 386 | 62.946 | 39.992 | 37.899 | 1.00 | 44.01 |
| ATOM | 1756 | C | LEU | 386 | 66.342 | 42.735 | 37.405 | 1.00 | 40.08 |
| ATOM | 1757 | O | LEU | 386 | 65.875 | 43.632 | 38.112 | 1.00 | 42.08 |
| ATOM | 1758 | N | HIS | 387 | 67.643 | 42.613 | 37.153 | 1.00 | 34.86 |
| ATOM | 1759 | CA | HIS | 387 | 68.631 | 43.537 | 37.700 | 1.00 | 39.09 |
| ATOM | 1760 | CB | HIS | 387 | 70.046 | 43.034 | 37.421 | 1.00 | 39.99 |
| ATOM | 1761 | CG | HIS | 387 | 70.402 | 41.791 | 38.172 | 1.00 | 56.37 |
| ATOM | 1762 | CD2 | HIS | 387 | 71.384 | 40.881 | 37.974 | 1.00 | 60.11 |

FIG. 30A-36

| ATOM | 1763 | ND1 | HIS | 387 | 69.711 | 41.370 | 39.290 | 1.00 | 60.40 |
|---|---|---|---|---|---|---|---|---|---|
| ATOM | 1764 | CE1 | HIS | 387 | 70.252 | 40.255 | 39.746 | 1.00 | 61.89 |
| ATOM | 1765 | NE2 | HIS | 387 | 71.269 | 39.937 | 38.966 | 1.00 | 63.96 |
| ATOM | 1766 | C | HIS | 387 | 68.446 | 44.928 | 37.101 | 1.00 | 41.00 |
| ATOM | 1767 | O | HIS | 387 | 68.492 | 45.927 | 37.817 | 1.00 | 46.99 |
| ATOM | 1768 | N | MET | 388 | 68.213 | 44.982 | 35.792 | 1.00 | 39.15 |
| ATOM | 1769 | CA | MET | 388 | 68.011 | 46.243 | 35.088 | 1.00 | 35.32 |
| ATOM | 1770 | CB | MET | 388 | 67.676 | 45.992 | 33.612 | 1.00 | 35.12 |
| ATOM | 1771 | CG | MET | 388 | 68.810 | 45.442 | 32.753 | 1.00 | 37.24 |
| ATOM | 1772 | SD | MET | 388 | 68.259 | 45.150 | 31.051 | 1.00 | 41.75 |
| ATOM | 1773 | CE | MET | 388 | 69.274 | 43.748 | 30.573 | 1.00 | 35.23 |
| ATOM | 1774 | C | MET | 388 | 66.880 | 47.048 | 35.733 | 1.00 | 36.52 |
| ATOM | 1775 | O | MET | 388 | 66.994 | 48.265 | 35.888 | 1.00 | 43.39 |
| ATOM | 1776 | N | LYS | 389 | 65.792 | 46.371 | 36.103 | 1.00 | 38.05 |
| ATOM | 1777 | CA | LYS | 389 | 64.637 | 47.025 | 36.729 | 1.00 | 42.88 |
| ATOM | 1778 | CB | LYS | 389 | 63.481 | 46.035 | 36.866 | 1.00 | 47.83 |
| ATOM | 1779 | CG | LYS | 389 | 62.835 | 45.627 | 35.560 | 1.00 | 52.36 |
| ATOM | 1780 | CD | LYS | 389 | 62.040 | 44.340 | 35.731 | 1.00 | 61.84 |
| ATOM | 1781 | CE | LYS | 389 | 60.978 | 44.451 | 36.814 | 1.00 | 69.04 |
| ATOM | 1782 | NZ | LYS | 389 | 60.254 | 43.162 | 36.987 | 1.00 | 70.00 |
| ATOM | 1783 | C | LYS | 389 | 64.983 | 47.587 | 38.107 | 1.00 | 43.99 |
| ATOM | 1784 | O | LYS | 389 | 64.455 | 48.621 | 38.525 | 1.00 | 44.22 |
| ATOM | 1785 | N | VAL | 390 | 65.851 | 46.878 | 38.816 | 1.00 | 45.50 |
| ATOM | 1786 | CA | VAL | 390 | 66.290 | 47.286 | 40.142 | 1.00 | 47.76 |
| ATOM | 1787 | CB | VAL | 390 | 67.152 | 46.186 | 40.804 | 1.00 | 46.30 |
| ATOM | 1788 | CG1 | VAL | 390 | 67.796 | 46.706 | 42.079 | 1.00 | 49.20 |
| ATOM | 1789 | CG2 | VAL | 390 | 66.305 | 44.962 | 41.097 | 1.00 | 42.69 |
| ATOM | 1790 | C | VAL | 390 | 67.109 | 48.571 | 40.070 | 1.00 | 47.25 |
| ATOM | 1791 | O | VAL | 390 | 66.811 | 49.540 | 40.760 | 1.00 | 48.67 |
| ATOM | 1792 | N | GLU | 391 | 68.115 | 48.580 | 39.199 | 1.00 | 44.11 |
| ATOM | 1793 | CA | GLU | 391 | 69.009 | 49.721 | 39.047 | 1.00 | 45.79 |
| ATOM | 1794 | CB | GLU | 391 | 70.266 | 49.311 | 38.273 | 1.00 | 45.78 |
| ATOM | 1795 | CG | GLU | 391 | 70.998 | 48.091 | 38.830 | 1.00 | 57.29 |
| ATOM | 1796 | CD | GLU | 391 | 71.479 | 48.268 | 40.261 | 1.00 | 61.20 |
| ATOM | 1797 | OE1 | GLU | 391 | 71.845 | 49.400 | 40.646 | 1.00 | 57.29 |
| ATOM | 1798 | OE2 | GLU | 391 | 71.496 | 47.263 | 41.001 | 1.00 | 63.69 |
| ATOM | 1799 | C | GLU | 391 | 68.410 | 50.959 | 38.391 | 1.00 | 49.16 |
| ATOM | 1800 | O | GLU | 391 | 68.463 | 52.055 | 38.956 | 1.00 | 58.82 |
| ATOM | 1801 | N | CYA | 392 | 67.802 | 50.782 | 37.224 | 1.00 | 49.75 |
| ATOM | 1802 | CA | CYA | 392 | 67.255 | 51.908 | 36.475 | 1.00 | 45.56 |
| ATOM | 1803 | CB | CYA | 392 | 67.667 | 51.768 | 35.016 | 1.00 | 44.82 |
| ATOM | 1804 | SG | CYA | 392 | 69.443 | 51.771 | 34.913 | 1.00 | 50.78 |
| ATOM | 1805 | AS | CYA | 392 | 69.929 | 50.778 | 33.022 | 1.00 | 53.29 |
| ATOM | 1806 | C | CYA | 392 | 65.771 | 52.200 | 36.601 | 1.00 | 44.35 |
| ATOM | 1807 | O | CYA | 392 | 64.988 | 51.324 | 36.962 | 1.00 | 44.10 |
| ATOM | 1808 | N | PRO | 393 | 65.378 | 53.469 | 36.365 | 1.00 | 45.52 |
| ATOM | 1809 | CD | PRO | 393 | 66.275 | 54.603 | 36.075 | 1.00 | 37.38 |
| ATOM | 1810 | CA | PRO | 393 | 63.982 | 53.916 | 36.444 | 1.00 | 45.41 |
| ATOM | 1811 | CB | PRO | 393 | 64.105 | 55.438 | 36.376 | 1.00 | 43.33 |
| ATOM | 1812 | CG | PRO | 393 | 65.329 | 55.644 | 35.542 | 1.00 | 39.89 |

FIG. 30A-37

| ATOM | 1813 | C | PRO | 393 | 63.108 | 53.376 | 35.318 | 1.00 | 44.89 |
|---|---|---|---|---|---|---|---|---|---|
| ATOM | 1814 | O | PRO | 393 | 63.556 | 53.239 | 34.175 | 1.00 | 45.60 |
| ATOM | 1815 | N | THR | 394 | 61.843 | 53.135 | 35.647 | 1.00 | 47.52 |
| ATOM | 1816 | CA | THR | 394 | 60.853 | 52.603 | 34.713 | 1.00 | 53.06 |
| ATOM | 1817 | CB | THR | 394 | 59.459 | 52.583 | 35.371 | 1.00 | 61.06 |
| ATOM | 1818 | OG1 | THR | 394 | 59.609 | 52.470 | 36.794 | 1.00 | 72.44 |
| ATOM | 1819 | CG2 | THR | 394 | 58.640 | 51.401 | 34.860 | 1.00 | 61.05 |
| ATOM | 1820 | C | THR | 394 | 60.767 | 53.373 | 33.392 | 1.00 | 49.98 |
| ATOM | 1821 | O | THR | 394 | 60.507 | 52.786 | 32.339 | 1.00 | 51.06 |
| ATOM | 1822 | N | GLU | 395 | 61.024 | 54.676 | 33.452 | 1.00 | 48.55 |
| ATOM | 1823 | CA | GLU | 395 | 60.970 | 55.548 | 32.282 | 1.00 | 44.21 |
| ATOM | 1824 | CB | GLU | 395 | 61.258 | 56.987 | 32.697 | 1.00 | 41.66 |
| ATOM | 1825 | C | GLU | 395 | 61.899 | 55.134 | 31.134 | 1.00 | 43.46 |
| ATOM | 1826 | O | GLU | 395 | 61.684 | 55.527 | 29.988 | 1.00 | 44.17 |
| ATOM | 1827 | N | LEU | 396 | 62.934 | 54.359 | 31.449 | 1.00 | 41.05 |
| ATOM | 1828 | CA | LEU | 396 | 63.898 | 53.899 | 30.448 | 1.00 | 39.55 |
| ATOM | 1829 | CB | LEU | 396 | 65.270 | 53.708 | 31.106 | 1.00 | 35.03 |
| ATOM | 1830 | CG | LEU | 396 | 66.296 | 54.834 | 30.945 | 1.00 | 40.06 |
| ATOM | 1831 | CD1 | LEU | 396 | 65.638 | 56.200 | 31.055 | 1.00 | 39.06 |
| ATOM | 1832 | CD2 | LEU | 396 | 67.398 | 54.669 | 31.978 | 1.00 | 32.78 |
| ATOM | 1833 | C | LEU | 396 | 63.468 | 52.602 | 29.757 | 1.00 | 38.50 |
| ATOM | 1834 | O | LEU | 396 | 64.106 | 52.150 | 28.804 | 1.00 | 34.72 |
| ATOM | 1835 | N | PHE | 397 | 62.364 | 52.028 | 30.225 | 1.00 | 38.76 |
| ATOM | 1836 | CA | PHE | 397 | 61.860 | 50.774 | 29.683 | 1.00 | 36.57 |
| ATOM | 1837 | CB | PHE | 397 | 61.610 | 49.775 | 30.819 | 1.00 | 33.96 |
| ATOM | 1838 | CG | PHE | 397 | 62.842 | 49.421 | 31.607 | 1.00 | 36.95 |
| ATOM | 1839 | CD1 | PHE | 397 | 63.331 | 50.280 | 32.587 | 1.00 | 34.61 |
| ATOM | 1840 | CD2 | PHE | 397 | 63.523 | 48.234 | 31.362 | 1.00 | 37.14 |
| ATOM | 1841 | CE1 | PHE | 397 | 64.481 | 49.964 | 33.310 | 1.00 | 31.57 |
| ATOM | 1842 | CE2 | PHE | 397 | 64.675 | 47.908 | 32.082 | 1.00 | 37.85 |
| ATOM | 1843 | CZ | PHE | 397 | 65.153 | 48.776 | 33.056 | 1.00 | 33.08 |
| ATOM | 1844 | C | PHE | 397 | 60.584 | 50.921 | 28.858 | 1.00 | 35.65 |
| ATOM | 1845 | O | PHE | 397 | 59.519 | 51.249 | 29.399 | 1.00 | 35.75 |
| ATOM | 1846 | N | PRO | 398 | 60.672 | 50.685 | 27.536 | 1.00 | 35.78 |
| ATOM | 1847 | CD | PRO | 398 | 61.891 | 50.367 | 26.767 | 1.00 | 32.81 |
| ATOM | 1848 | CA | PRO | 398 | 59.503 | 50.786 | 26.658 | 1.00 | 33.94 |
| ATOM | 1849 | CB | PRO | 398 | 60.041 | 50.297 | 25.315 | 1.00 | 33.91 |
| ATOM | 1850 | CG | PRO | 398 | 61.488 | 50.707 | 25.356 | 1.00 | 33.09 |
| ATOM | 1851 | C | PRO | 398 | 58.434 | 49.840 | 27.210 | 1.00 | 34.98 |
| ATOM | 1852 | O | PRO | 398 | 58.753 | 48.729 | 27.654 | 1.00 | 35.76 |
| ATOM | 1853 | N | PRO | 399 | 57.163 | 50.267 | 27.219 | 1.00 | 37.67 |
| ATOM | 1854 | CD | PRO | 399 | 56.661 | 51.578 | 26.776 | 1.00 | 38.02 |
| ATOM | 1855 | CA | PRO | 399 | 56.070 | 49.433 | 27.733 | 1.00 | 36.86 |
| ATOM | 1856 | CB | PRO | 399 | 54.803 | 50.183 | 27.291 | 1.00 | 34.14 |
| ATOM | 1857 | CG | PRO | 399 | 55.282 | 51.240 | 26.310 | 1.00 | 37.00 |
| ATOM | 1858 | C | PRO | 399 | 56.085 | 47.970 | 27.273 | 1.00 | 37.06 |
| ATOM | 1859 | O | PRO | 399 | 55.967 | 47.063 | 28.099 | 1.00 | 37.07 |
| ATOM | 1860 | N | LEU | 400 | 56.299 | 47.738 | 25.980 | 1.00 | 35.13 |
| ATOM | 1861 | CA | LEU | 400 | 56.327 | 46.374 | 25.445 | 1.00 | 35.86 |
| ATOM | 1862 | CB | LEU | 400 | 56.314 | 46.385 | 23.914 | 1.00 | 31.49 |

FIG. 30A-38

| ATOM | 1863 | CG | LEU | 400 | 56.181 | 45.017 | 23.227 | 1.00 | 30.73 |
|---|---|---|---|---|---|---|---|---|---|
| ATOM | 1864 | CD1 | LEU | 400 | 54.901 | 44.330 | 23.674 | 1.00 | 21.35 |
| ATOM | 1865 | CD2 | LEU | 400 | 56.197 | 45.183 | 21.720 | 1.00 | 25.42 |
| ATOM | 1866 | C | LEU | 400 | 57.542 | 45.597 | 25.958 | 1.00 | 36.51 |
| ATOM | 1867 | O | LEU | 400 | 57.458 | 44.392 | 26.219 | 1.00 | 37.47 |
| ATOM | 1868 | N | PHE | 401 | 58.671 | 46.290 | 26.095 | 1.00 | 32.26 |
| ATOM | 1869 | CA | PHE | 401 | 59.899 | 45.682 | 26.596 | 1.00 | 35.15 |
| ATOM | 1870 | CB | PHE | 401 | 61.014 | 46.739 | 26.648 | 1.00 | 35.99 |
| ATOM | 1871 | CG | PHE | 401 | 62.346 | 46.213 | 27.117 | 1.00 | 39.41 |
| ATOM | 1872 | CD1 | PHE | 401 | 62.845 | 45.003 | 26.639 | 1.00 | 35.94 |
| ATOM | 1873 | CD2 | PHE | 401 | 63.119 | 46.944 | 28.019 | 1.00 | 40.55 |
| ATOM | 1874 | CE1 | PHE | 401 | 64.088 | 44.531 | 27.055 | 1.00 | 30.16 |
| ATOM | 1875 | CE2 | PHE | 401 | 64.367 | 46.478 | 28.439 | 1.00 | 35.53 |
| ATOM | 1876 | CZ | PHE | 401 | 64.849 | 45.271 | 27.952 | 1.00 | 36.39 |
| ATOM | 1877 | C | PHE | 401 | 59.607 | 45.129 | 27.996 | 1.00 | 36.42 |
| ATOM | 1878 | O | PHE | 401 | 59.957 | 43.995 | 28.317 | 1.00 | 36.71 |
| ATOM | 1879 | N | LEU | 402 | 58.920 | 45.925 | 28.805 | 1.00 | 36.59 |
| ATOM | 1880 | CA | LEU | 402 | 58.561 | 45.528 | 30.158 | 1.00 | 37.68 |
| ATOM | 1881 | CB | LEU | 402 | 57.986 | 46.720 | 30.917 | 1.00 | 40.71 |
| ATOM | 1882 | CG | LEU | 402 | 58.963 | 47.751 | 31.463 | 1.00 | 43.13 |
| ATOM | 1883 | CD1 | LEU | 402 | 58.180 | 48.926 | 32.031 | 1.00 | 39.88 |
| ATOM | 1884 | CD2 | LEU | 402 | 59.847 | 47.103 | 32.527 | 1.00 | 38.39 |
| ATOM | 1885 | C | LEU | 402 | 57.521 | 44.420 | 30.164 | 1.00 | 38.02 |
| ATOM | 1886 | O | LEU | 402 | 57.582 | 43.507 | 30.984 | 1.00 | 37.39 |
| ATOM | 1887 | N | GLU | 403 | 56.558 | 44.522 | 29.251 | 1.00 | 39.74 |
| ATOM | 1888 | CA | GLU | 403 | 55.469 | 43.559 | 29.166 | 1.00 | 42.79 |
| ATOM | 1889 | CB | GLU | 403 | 54.445 | 44.022 | 28.129 | 1.00 | 46.21 |
| ATOM | 1890 | CG | GLU | 403 | 53.092 | 43.330 | 28.232 | 1.00 | 56.88 |
| ATOM | 1891 | CD | GLU | 403 | 52.090 | 43.833 | 27.202 | 1.00 | 65.21 |
| ATOM | 1892 | OE1 | GLU | 403 | 52.230 | 44.983 | 26.728 | 1.00 | 70.60 |
| ATOM | 1893 | OE2 | GLU | 403 | 51.154 | 43.073 | 26.870 | 1.00 | 70.53 |
| ATOM | 1894 | C | GLU | 403 | 55.890 | 42.121 | 28.886 | 1.00 | 40.14 |
| ATOM | 1895 | O | GLU | 403 | 55.368 | 41.200 | 29.506 | 1.00 | 40.57 |
| ATOM | 1896 | N | VAL | 404 | 56.835 | 41.932 | 27.966 | 1.00 | 39.43 |
| ATOM | 1897 | CA | VAL | 404 | 57.292 | 40.586 | 27.610 | 1.00 | 40.96 |
| ATOM | 1898 | CB | VAL | 404 | 57.851 | 40.516 | 26.159 | 1.00 | 35.50 |
| ATOM | 1899 | CG1 | VAL | 404 | 56.807 | 40.995 | 25.177 | 1.00 | 43.46 |
| ATOM | 1900 | CG2 | VAL | 404 | 59.132 | 41.321 | 26.030 | 1.00 | 25.74 |
| ATOM | 1901 | C | VAL | 404 | 58.317 | 39.946 | 28.536 | 1.00 | 41.94 |
| ATOM | 1902 | O | VAL | 404 | 58.468 | 38.722 | 28.533 | 1.00 | 43.82 |
| ATOM | 1903 | N | PHE | 405 | 59.026 | 40.759 | 29.310 | 1.00 | 39.84 |
| ATOM | 1904 | CA | PHE | 405 | 60.051 | 40.223 | 30.189 | 1.00 | 42.73 |
| ATOM | 1905 | CB | PHE | 405 | 61.401 | 40.897 | 29.913 | 1.00 | 36.85 |
| ATOM | 1906 | CG | PHE | 405 | 61.963 | 40.596 | 28.551 | 1.00 | 33.23 |
| ATOM | 1907 | CD1 | PHE | 405 | 62.283 | 41.625 | 27.672 | 1.00 | 33.90 |
| ATOM | 1908 | CD2 | PHE | 405 | 62.157 | 39.281 | 28.138 | 1.00 | 31.62 |
| ATOM | 1909 | CE1 | PHE | 405 | 62.786 | 41.351 | 26.399 | 1.00 | 39.16 |
| ATOM | 1910 | CE2 | PHE | 405 | 62.657 | 38.997 | 26.872 | 1.00 | 33.33 |
| ATOM | 1911 | CZ | PHE | 405 | 62.972 | 40.033 | 25.999 | 1.00 | 31.99 |
| ATOM | 1912 | C | PHE | 405 | 59.723 | 40.273 | 31.676 | 1.00 | 43.97 |

FIG. 30A-39

| ATOM | 1913 | O | PHE | 405 | 60.636 | 39.943 | 32.460 | 1.00 | 46.56 |
|---|---|---|---|---|---|---|---|---|---|
| ATOM | 1 | O1 | HOH | 501 | 67.928 | 36.755 | 11.188 | 1.00 | 33.04 |
| ATOM | 2 | O1 | HOH | 502 | 69.618 | 40.719 | 13.009 | 1.00 | 23.00 |
| ATOM | 3 | O1 | HOH | 503 | 64.885 | 40.168 | 12.340 | 1.00 | 23.00 |
| ATOM | 4 | O1 | HOH | 504 | 63.079 | 40.108 | 15.841 | 1.00 | 23.00 |
| ATOM | 5 | O1 | HOH | 505 | 63.404 | 46.536 | 15.354 | 1.00 | 36.41 |
| ATOM | 6 | O1 | HOH | 506 | 61.299 | 15.617 | -0.595 | 1.00 | 23.00 |
| ATOM | 7 | O1 | HOH | 507 | 67.359 | 15.375 | 0.551 | 1.00 | 23.00 |
| ATOM | 8 | O1 | HOH | 508 | 67.230 | 12.002 | -0.634 | 1.00 | 23.00 |
| ATOM | 9 | O1 | HOH | 509 | 66.906 | 12.467 | 3.855 | 1.00 | 23.00 |
| ATOM | 10 | O1 | HOH | 510 | 61.785 | 9.946 | 3.983 | 1.00 | 23.00 |
| ATOM | 11 | O1 | HOH | 511 | 57.670 | 11.385 | 9.909 | 1.00 | 23.00 |
| ATOM | 12 | O1 | HOH | 512 | 55.791 | 11.570 | 10.291 | 1.00 | 23.00 |
| ATOM | 13 | O1 | HOH | 513 | 54.637 | 14.058 | 9.201 | 1.00 | 23.00 |
| ATOM | 14 | O1 | HOH | 514 | 55.882 | 16.054 | 12.204 | 1.00 | 26.53 |
| ATOM | 15 | O1 | HOH | 515 | 53.685 | 15.842 | 18.209 | 1.00 | 23.00 |
| ATOM | 16 | O1 | HOH | 516 | 49.559 | 24.773 | 19.020 | 1.00 | 23.00 |
| ATOM | 17 | O1 | HOH | 517 | 51.258 | 25.512 | 13.384 | 1.00 | 37.74 |
| ATOM | 18 | O1 | HOH | 518 | 53.551 | 25.749 | 10.593 | 1.00 | 42.31 |
| ATOM | 19 | O1 | HOH | 519 | 50.338 | 23.299 | 7.662 | 1.00 | 41.19 |
| ATOM | 20 | O1 | HOH | 520 | 50.830 | 20.272 | 8.323 | 1.00 | 28.46 |
| ATOM | 21 | O1 | HOH | 521 | 48.630 | 20.291 | 6.429 | 1.00 | 23.00 |
| ATOM | 22 | O1 | HOH | 522 | 49.233 | 17.389 | 2.867 | 1.00 | 23.00 |
| ATOM | 23 | O1 | HOH | 523 | 52.076 | 22.770 | 1.260 | 1.00 | 23.00 |
| ATOM | 24 | O1 | HOH | 524 | 51.671 | 23.621 | -1.020 | 1.00 | 23.00 |
| ATOM | 25 | O1 | HOH | 525 | 58.294 | 31.509 | 2.147 | 1.00 | 31.83 |
| ATOM | 26 | O1 | HOH | 526 | 57.497 | 36.071 | 2.268 | 1.00 | 23.00 |
| ATOM | 27 | O1 | HOH | 527 | 65.373 | 36.025 | 6.809 | 1.00 | 23.00 |
| ATOM | 28 | O1 | HOH | 528 | 67.871 | 36.399 | 6.419 | 1.00 | 66.52 |
| ATOM | 29 | O1 | HOH | 529 | 67.189 | 33.811 | 9.409 | 1.00 | 23.00 |
| ATOM | 30 | O1 | HOH | 530 | 62.458 | 48.056 | 13.590 | 1.00 | 23.00 |
| ATOM | 31 | O1 | HOH | 531 | 63.943 | 46.824 | 10.638 | 1.00 | 39.26 |
| ATOM | 32 | O1 | HOH | 532 | 57.465 | 45.867 | 13.186 | 1.00 | 23.00 |
| ATOM | 33 | O1 | HOH | 533 | 55.223 | 40.774 | 10.959 | 1.00 | 23.00 |
| ATOM | 34 | O1 | HOH | 534 | 53.737 | 44.032 | 19.560 | 1.00 | 23.00 |
| ATOM | 35 | O1 | HOH | 535 | 55.982 | 49.757 | 24.168 | 1.00 | 23.00 |
| ATOM | 36 | O1 | HOH | 536 | 58.575 | 52.330 | 31.881 | 1.00 | 23.00 |
| ATOM | 37 | O1 | HOH | 537 | 62.563 | 49.327 | 37.804 | 1.00 | 23.00 |
| ATOM | 38 | O1 | HOH | 538 | 61.736 | 40.280 | 35.059 | 1.00 | 60.53 |
| ATOM | 39 | O1 | HOH | 539 | 63.271 | 38.155 | 34.156 | 1.00 | 52.21 |
| ATOM | 40 | O1 | HOH | 540 | 61.872 | 35.187 | 29.990 | 1.00 | 23.00 |
| ATOM | 41 | O1 | HOH | 541 | 63.701 | 36.808 | 28.720 | 1.00 | 23.00 |
| ATOM | 42 | O1 | HOH | 542 | 62.255 | 35.864 | 26.425 | 1.00 | 26.69 |
| ATOM | 43 | O1 | HOH | 543 | 63.567 | 33.453 | 25.308 | 1.00 | 44.90 |
| ATOM | 44 | O1 | HOH | 544 | 65.456 | 30.135 | 27.713 | 1.00 | 23.00 |
| ATOM | 45 | O1 | HOH | 545 | 61.997 | 26.566 | 24.157 | 1.00 | 23.00 |
| ATOM | 46 | O1 | HOH | 546 | 61.422 | 22.231 | 24.358 | 1.00 | 23.00 |
| ATOM | 47 | O1 | HOH | 547 | 59.636 | 21.462 | 25.378 | 1.00 | 23.00 |
| ATOM | 48 | O1 | HOH | 548 | 64.860 | 21.210 | 22.578 | 1.00 | 23.00 |
| ATOM | 49 | O1 | HOH | 549 | 63.316 | 14.964 | 15.508 | 1.00 | 52.55 |

FIG. 30A-40

| ATOM | 50 | O1 | HOH | 550 | 62.770 | 10.707 | 15.710 | 1.00 | 48.78 |
|---|---|---|---|---|---|---|---|---|---|
| ATOM | 51 | O1 | HOH | 551 | 61.579 | 9.665 | 12.081 | 1.00 | 23.00 |
| ATOM | 52 | O1 | HOH | 552 | 65.916 | 11.929 | 11.639 | 1.00 | 23.00 |
| ATOM | 53 | O1 | HOH | 553 | 68.086 | 12.882 | 11.226 | 1.00 | 23.00 |
| ATOM | 54 | O1 | HOH | 554 | 69.504 | 11.968 | 14.083 | 1.00 | 23.00 |
| ATOM | 55 | O1 | HOH | 555 | 72.311 | 15.121 | 10.552 | 1.00 | 23.00 |
| ATOM | 56 | O1 | HOH | 556 | 74.716 | 15.172 | 10.253 | 1.00 | 23.00 |
| ATOM | 57 | O1 | HOH | 557 | 73.109 | 17.916 | 7.451 | 1.00 | 23.00 |
| ATOM | 58 | O1 | HOH | 558 | 71.316 | 15.446 | 7.652 | 1.00 | 23.00 |
| ATOM | 59 | O1 | HOH | 559 | 74.717 | 14.555 | 5.957 | 1.00 | 23.00 |
| ATOM | 60 | O1 | HOH | 560 | 73.523 | 22.311 | 2.467 | 1.00 | 23.00 |
| ATOM | 61 | O1 | HOH | 561 | 76.491 | 23.094 | 5.700 | 1.00 | 51.34 |
| ATOM | 62 | O1 | HOH | 562 | 73.961 | 29.841 | 10.035 | 1.00 | 33.87 |
| ATOM | 63 | O1 | HOH | 563 | 76.164 | 33.031 | 11.370 | 1.00 | 23.00 |
| ATOM | 64 | O1 | HOH | 564 | 77.193 | 34.039 | 9.712 | 1.00 | 37.14 |
| ATOM | 65 | O1 | HOH | 565 | 76.525 | 41.395 | 10.460 | 1.00 | 23.00 |
| ATOM | 66 | O1 | HOH | 566 | 79.358 | 49.535 | 15.048 | 1.00 | 53.78 |
| ATOM | 67 | O1 | HOH | 567 | 78.046 | 53.530 | 9.188 | 1.00 | 23.00 |
| ATOM | 68 | O1 | HOH | 568 | 68.058 | 52.158 | 15.548 | 1.00 | 23.00 |
| ATOM | 69 | O1 | HOH | 569 | 68.598 | 53.164 | 18.083 | 1.00 | 45.72 |
| ATOM | 70 | O1 | HOH | 570 | 73.482 | 58.914 | 21.552 | 1.00 | 58.99 |
| ATOM | 71 | O1 | HOH | 571 | 65.648 | 53.551 | 26.240 | 1.00 | 23.00 |
| ATOM | 72 | O1 | HOH | 572 | 75.776 | 46.207 | 30.367 | 1.00 | 33.32 |
| ATOM | 73 | O1 | HOH | 573 | 78.686 | 46.470 | 31.087 | 1.00 | 23.00 |
| ATOM | 74 | O1 | HOH | 574 | 77.580 | 41.209 | 31.884 | 1.00 | 23.00 |
| ATOM | 75 | O1 | HOH | 575 | 76.879 | 31.531 | 24.067 | 1.00 | 23.00 |
| ATOM | 76 | O1 | HOH | 576 | 77.927 | 29.163 | 20.647 | 1.00 | 23.00 |
| ATOM | 77 | O1 | HOH | 577 | 80.180 | 24.963 | 17.233 | 1.00 | 53.36 |
| ATOM | 78 | O1 | HOH | 578 | 80.631 | 25.802 | 15.508 | 1.00 | 23.00 |
| ATOM | 79 | O1 | HOH | 579 | 82.104 | 22.566 | 14.156 | 1.00 | 23.00 |
| ATOM | 80 | O1 | HOH | 580 | 76.954 | 22.077 | 18.425 | 1.00 | 46.50 |
| ATOM | 81 | O1 | HOH | 581 | 86.619 | 37.903 | 16.945 | 1.00 | 47.66 |
| ATOM | 82 | O1 | HOH | 582 | 83.586 | 42.305 | 18.576 | 1.00 | 23.00 |
| ATOM | 83 | O1 | HOH | 583 | 83.481 | 45.262 | 19.526 | 1.00 | 23.00 |
| ATOM | 84 | O1 | HOH | 584 | 66.787 | 32.864 | 33.796 | 1.00 | 23.00 |
| ATOM | 85 | O1 | HOH | 585 | 59.447 | 33.572 | 30.734 | 1.00 | 23.00 |
| ATOM | 86 | O1 | HOH | 586 | 57.013 | 32.278 | 31.125 | 1.00 | 23.00 |
| ATOM | 87 | O1 | HOH | 587 | 58.084 | 29.428 | 24.648 | 1.00 | 24.06 |
| ATOM | 88 | O1 | HOH | 588 | 52.774 | 25.054 | 32.650 | 1.00 | 57.81 |
| ATOM | 89 | O1 | HOH | 589 | 53.800 | 24.465 | 34.834 | 1.00 | 23.00 |
| ATOM | 90 | O1 | HOH | 590 | 47.195 | 30.205 | 30.414 | 1.00 | 23.00 |
| ATOM | 91 | O1 | HOH | 591 | 48.978 | 35.051 | 30.228 | 1.00 | 23.00 |
| ATOM | 92 | O1 | HOH | 592 | 49.280 | 39.962 | 31.041 | 1.00 | 23.00 |
| ATOM | 93 | O1 | HOH | 593 | 42.329 | 32.230 | 20.993 | 1.00 | 23.00 |
| ATOM | 94 | O1 | HOH | 594 | 44.199 | 32.910 | 19.088 | 1.00 | 23.00 |
| ATOM | 95 | O1 | HOH | 595 | 41.542 | 27.336 | 19.178 | 1.00 | 23.00 |
| ATOM | 96 | O1 | HOH | 596 | 48.971 | 31.296 | 14.022 | 1.00 | 23.00 |
| ATOM | 97 | O1 | HOH | 597 | 50.180 | 31.092 | 7.307 | 1.00 | 23.00 |
| ATOM | 98 | O1 | HOH | 598 | 64.465 | 28.209 | 3.208 | 1.00 | 45.35 |
| ATOM | 99 | O1 | HOH | 599 | 67.740 | 26.910 | 1.986 | 1.00 | 23.00 |

FIG. 30A-41

| ATOM | 100 | O1 | HOH | 600 | 67.958 | 31.203 | 3.532 | 1.00 | 23.00 |
|------|-----|----|----|-----|--------|--------|-------|------|-------|
| ATOM | 101 | O1 | HOH | 601 | 68.885 | 22.721 | 0.234 | 1.00 | 39.53 |
| ATOM | 102 | O1 | HOH | 602 | 46.735 | 20.335 | 25.877 | 1.00 | 44.92 |
| ATOM | 103 | O1 | HOH | 603 | 47.359 | 19.644 | 28.494 | 1.00 | 41.57 |
| ATOM | 2300 | C | ACY | 701 | 52.555 | 39.909 | 24.622 | 1.00 | 48.75 |
| ATOM | 2301 | O | ACY | 701 | 52.351 | 40.361 | 25.771 | 1.00 | 48.92 |
| ATOM | 2302 | OXT | ACY | 701 | 53.503 | 39.156 | 24.279 | 1.00 | 50.69 |
| ATOM | 2303 | CH3 | ACY | 701 | 51.543 | 40.314 | 23.527 | 1.00 | 41.32 |
| ATOM | 2304 | C1 | IBR | 1 | 67.309 | 42.207 | 18.510 | 1.00 | 32.20 |
| ATOM | 2305 | C2 | IBR | 1 | 68.795 | 43.194 | 23.237 | 1.00 | 29.59 |
| ATOM | 2306 | C3 | IBR | 1 | 67.192 | 43.467 | 19.068 | 1.00 | 25.49 |
| ATOM | 2307 | C4 | IBR | 1 | 69.096 | 44.270 | 24.011 | 1.00 | 25.67 |
| ATOM | 2308 | C5 | IBR | 1 | 67.884 | 43.772 | 20.218 | 1.00 | 35.08 |
| ATOM | 2309 | C6 | IBR | 1 | 68.489 | 44.345 | 25.356 | 1.00 | 30.87 |
| ATOM | 2310 | C7 | IBR | 1 | 68.673 | 42.828 | 20.790 | 1.00 | 30.76 |
| ATOM | 2311 | C8 | IBR | 1 | 67.681 | 43.327 | 25.704 | 1.00 | 29.18 |
| ATOM | 2312 | C9 | IBR | 1 | 68.811 | 41.580 | 20.269 | 1.00 | 32.19 |
| ATOM | 2313 | C10 | IBR | 1 | 67.383 | 42.244 | 24.921 | 1.00 | 26.78 |
| ATOM | 2314 | C11 | IBR | 1 | 68.122 | 41.241 | 19.099 | 1.00 | 25.50 |
| ATOM | 2315 | C12 | IBR | 1 | 67.979 | 42.171 | 23.609 | 1.00 | 24.47 |
| ATOM | 2316 | C13 | IBR | 1 | 66.529 | 41.932 | 17.285 | 1.00 | 17.69 |
| ATOM | 2317 | C14 | IBR | 1 | 68.730 | 45.450 | 26.287 | 1.00 | 30.43 |
| ATOM | 2318 | C15 | IBR | 1 | 67.011 | 40.785 | 16.271 | 1.00 | 21.37 |
| ATOM | 2319 | C16 | IBR | 1 | 67.939 | 46.867 | 25.912 | 1.00 | 23.75 |
| ATOM | 2320 | C17 | IBR | 1 | 65.946 | 40.598 | 15.151 | 1.00 | 23.91 |
| ATOM | 2321 | C18 | IBR | 1 | 70.126 | 46.087 | 26.069 | 1.00 | 26.02 |
| ATOM | 2322 | BR1 | IBR | 1 | 67.708 | 45.504 | 20.878 | 1.00 | 34.64 |
| ATOM | 2323 | BR2 | IBR | 1 | 69.927 | 40.301 | 21.039 | 1.00 | 32.01 |
| ATOM | 2324 | N1 | IBR | 1 | 68.284 | 40.938 | 15.821 | 1.00 | 18.75 |
| ATOM | 2325 | O1 | IBR | 1 | 67.068 | 43.397 | 26.981 | 1.00 | 26.31 |
| ATOM | 2326 | O2 | IBR | 1 | 69.393 | 43.153 | 21.933 | 1.00 | 30.15 |
| ATOM | 2327 | O3 | IBR | 1 | 66.368 | 40.592 | 14.004 | 1.00 | 23.29 |
| ATOM | 2328 | O4 | IBR | 1 | 64.786 | 40.511 | 15.515 | 1.00 | 23.47 |

END  
END

FIG. 31

REMARK rTR_t3 full length numbering
REMARK
REMARK Rfactor 0.221 Rfree 0.240
REMARK Resolution 5. 2.0 all reflections
REMARK conformation of MET 388 confirmed by SA_omit map
REMARK
REMARK Three cacodylate-modified cysteines (CYA)
REMARK Cya334, Cya380, Cya392
REMARK cacodylate modeled as single arsenic atom
REMARK
REMARK side chain of certain residues modeled as ALA due to poor density;
REMARK however, residue name reflects true residue for clarity
REMARK
REMARK clone obtained from Murray et. al.
REMARK deposited sequence confirmed,
REMARK differing from that reported by Thompson et. al.
REMARK in the following codons:
REMARK 281 Thr - Ala
REMARK 285 Lys - Glu
REMARK identical to that reported by Mitsuhashi et. al.
REMARK gb:RNTRAVI X07409
JRNL     AUTH   M.B. MURRAY, N.D.ZILZ, N.L.MCCREARY,M.J.MACDONALD
JRNL     AUTH 2 H.C.TOWLE
JRNL     TITL   ISOLATION AND CHARACTERIZATION OF RAT CDNA CLONES FOR TWO
JRNL     TITL 2 DISTINCT THYROID HORMONE RECPTORS
JRNL     REF    JBC              V. 263 25   1988
JRNL     AUTH   C.C.THOMPSON, C.WEINBERGER, R.LEBO, R.M.EVANS
JRNL     TITL   IDENTIFICATION OF A NOVEL THYROID HORMONE RECEPTOR EXPRESSED
JRNL     TITL 2 IN THE MAMMALIAN CENTRAL NERVOUS SYSTEM
JRNL     REF    SCIENCE          V. 237      1987
JRNL     AUTH   T.MITSUHASHI,G.TENNYSON,V.NIKODEM
JRNL     TITL   NUCLEOTIDE SEQUENCE OF NOVEL CDNAS GENERATED BY ALTERNATIVE
JRNL     TITL 2 SPLICING OF A RAT THYROID HORMONE RECEPTOR GENE TRANSCRIPT
JRNL     REF    NUC. ACIDS. RES.  V. 16 12   1988
REMARK
ATOM   1    CB    ARG  157   68.406   10.620    7.027   1.00   41.66
ATOM   2    CG    ARG  157   69.926   10.540    6.997   1.00   44.48
ATOM   3    CD    ARG  157   70.552   11.261    8.173   1.00   47.02
ATOM   4    NE    ARG  157   70.112   10.680    9.435   1.00   49.73
ATOM   5    CZ    ARG  157   70.917   10.392   10.450   1.00   51.21
ATOM   6    NH1   ARG  157   72.223   10.629   10.361   1.00   51.79
ATOM   7    NH2   ARG  157   70.405    9.871   11.556   1.00   51.92
ATOM   8    C     ARG  157   66.308    9.993    5.774   1.00   36.48
ATOM   9    O     ARG  157   66.047   10.318    4.622   1.00   38.84
ATOM  10    N     ARG  157   68.479    9.473    4.839   1.00   41.22
ATOM  11    CA    ARG  157   67.734    9.580    6.135   1.00   39.98

FIG. 31A-1

| | | | | | | | | |
|---|---|---|---|---|---|---|---|---|
| ATOM | 12 | N | PRO | 158 | 65.366 | 9.953 | 6.728 | 1.00 | 33.85 |
| ATOM | 13 | CD | PRO | 158 | 65.494 | 9.553 | 8.139 | 1.00 | 34.72 |
| ATOM | 14 | CA | PRO | 158 | 63.981 | 10.336 | 6.407 | 1.00 | 31.89 |
| ATOM | 15 | CB | PRO | 158 | 63.219 | 10.015 | 7.694 | 1.00 | 31.87 |
| ATOM | 16 | CG | PRO | 158 | 64.260 | 10.158 | 8.759 | 1.00 | 33.55 |
| ATOM | 17 | C | PRO | 158 | 63.758 | 11.783 | 5.947 | 1.00 | 29.77 |
| ATOM | 18 | O | PRO | 158 | 64.221 | 12.739 | 6.575 | 1.00 | 27.93 |
| ATOM | 19 | N | GLU | 159 | 63.071 | 11.918 | 4.819 | 1.00 | 26.20 |
| ATOM | 20 | CA | GLU | 159 | 62.759 | 13.217 | 4.239 | 1.00 | 24.07 |
| ATOM | 21 | CB | GLU | 159 | 62.565 | 13.080 | 2.721 | 1.00 | 22.90 |
| ATOM | 22 | CG | GLU | 159 | 63.847 | 12.933 | 1.916 | 1.00 | 22.04 |
| ATOM | 23 | CD | GLU | 159 | 64.386 | 14.260 | 1.427 | 1.00 | 22.07 |
| ATOM | 24 | OE1 | GLU | 159 | 63.577 | 15.175 | 1.203 | 1.00 | 24.63 |
| ATOM | 25 | OE2 | GLU | 159 | 65.612 | 14.389 | 1.240 | 1.00 | 23.54 |
| ATOM | 26 | C | GLU | 159 | 61.463 | 13.717 | 4.855 | 1.00 | 21.56 |
| ATOM | 27 | O | GLU | 159 | 60.747 | 12.958 | 5.516 | 1.00 | 21.03 |
| ATOM | 28 | N | PRO | 160 | 61.176 | 15.022 | 4.713 | 1.00 | 19.69 |
| ATOM | 29 | CD | PRO | 160 | 61.997 | 16.139 | 4.207 | 1.00 | 16.57 |
| ATOM | 30 | CA | PRO | 160 | 59.923 | 15.500 | 5.292 | 1.00 | 18.12 |
| ATOM | 31 | CB | PRO | 160 | 59.935 | 16.990 | 4.955 | 1.00 | 15.65 |
| ATOM | 32 | CG | PRO | 160 | 61.390 | 17.328 | 4.905 | 1.00 | 14.83 |
| ATOM | 33 | C | PRO | 160 | 58.741 | 14.782 | 4.626 | 1.00 | 19.79 |
| ATOM | 34 | O | PRO | 160 | 58.793 | 14.431 | 3.445 | 1.00 | 20.20 |
| ATOM | 35 | N | THR | 161 | 57.713 | 14.497 | 5.412 | 1.00 | 20.15 |
| ATOM | 36 | CA | THR | 161 | 56.525 | 13.846 | 4.901 | 1.00 | 20.73 |
| ATOM | 37 | CB | THR | 161 | 55.672 | 13.274 | 6.060 | 1.00 | 20.77 |
| ATOM | 38 | OG1 | THR | 161 | 55.195 | 14.348 | 6.881 | 1.00 | 21.74 |
| ATOM | 39 | CG2 | THR | 161 | 56.489 | 12.324 | 6.917 | 1.00 | 19.52 |
| ATOM | 40 | C | THR | 161 | 55.724 | 14.954 | 4.219 | 1.00 | 21.64 |
| ATOM | 41 | O | THR | 161 | 56.010 | 16.139 | 4.421 | 1.00 | 23.13 |
| ATOM | 42 | N | PRO | 162 | 54.701 | 14.596 | 3.425 | 1.00 | 21.21 |
| ATOM | 43 | CD | PRO | 162 | 54.309 | 13.235 | 3.012 | 1.00 | 19.57 |
| ATOM | 44 | CA | PRO | 162 | 53.884 | 15.602 | 2.751 | 1.00 | 21.01 |
| ATOM | 45 | CB | PRO | 162 | 52.722 | 14.776 | 2.223 | 1.00 | 19.74 |
| ATOM | 46 | CG | PRO | 162 | 53.387 | 13.490 | 1.861 | 1.00 | 20.34 |
| ATOM | 47 | C | PRO | 162 | 53.391 | 16.643 | 3.753 | 1.00 | 22.52 |
| ATOM | 48 | O | PRO | 162 | 53.508 | 17.851 | 3.526 | 1.00 | 21.68 |
| ATOM | 49 | N | GLU | 163 | 52.880 | 16.151 | 4.878 | 1.00 | 23.01 |
| ATOM | 50 | CA | GLU | 163 | 52.349 | 16.996 | 5.941 | 1.00 | 25.97 |
| ATOM | 51 | CB | GLU | 163 | 51.672 | 16.148 | 7.022 | 1.00 | 29.50 |
| ATOM | 52 | CG | GLU | 163 | 50.476 | 15.312 | 6.543 | 1.00 | 37.07 |
| ATOM | 53 | CD | GLU | 163 | 50.865 | 14.159 | 5.614 | 1.00 | 41.36 |
| ATOM | 54 | OE1 | GLU | 163 | 51.937 | 13.544 | 5.828 | 1.00 | 40.11 |
| ATOM | 55 | OE2 | GLU | 163 | 50.094 | 13.874 | 4.660 | 1.00 | 46.16 |
| ATOM | 56 | C | GLU | 163 | 53.415 | 17.879 | 6.581 | 1.00 | 24.92 |
| ATOM | 57 | O | GLU | 163 | 53.110 | 18.971 | 7.061 | 1.00 | 25.82 |
| ATOM | 58 | N | GLU | 164 | 54.661 | 17.412 | 6.600 | 1.00 | 22.87 |
| ATOM | 59 | CA | GLU | 164 | 55.724 | 18.209 | 7.187 | 1.00 | 21.46 |
| ATOM | 60 | CB | GLU | 164 | 56.880 | 17.340 | 7.664 | 1.00 | 21.23 |
| ATOM | 61 | CG | GLU | 164 | 56.509 | 16.508 | 8.886 | 1.00 | 20.30 |

FIG. 31A-2

| ATOM | 62 | CD | GLU | 164 | 57.557 | 15.483 | 9.243 | 1.00 | 20.07 |
|---|---|---|---|---|---|---|---|---|---|
| ATOM | 63 | OE1 | GLU | 164 | 58.409 | 15.186 | 8.385 | 1.00 | 19.80 |
| ATOM | 64 | OE2 | GLU | 164 | 57.532 | 14.977 | 10.385 | 1.00 | 21.00 |
| ATOM | 65 | C | GLU | 164 | 56.195 | 19.289 | 6.235 | 1.00 | 22.45 |
| ATOM | 66 | O | GLU | 164 | 56.607 | 20.354 | 6.684 | 1.00 | 23.36 |
| ATOM | 67 | N | TRP | 165 | 56.140 | 19.024 | 4.928 | 1.00 | 21.06 |
| ATOM | 68 | CA | TRP | 165 | 56.518 | 20.031 | 3.936 | 1.00 | 19.57 |
| ATOM | 69 | CB | TRP | 165 | 56.486 | 19.466 | 2.518 | 1.00 | 16.06 |
| ATOM | 70 | CG | TRP | 165 | 57.775 | 18.839 | 2.120 | 1.00 | 14.01 |
| ATOM | 71 | CD2 | TRP | 165 | 59.055 | 19.480 | 2.037 | 1.00 | 13.26 |
| ATOM | 72 | CE2 | TRP | 165 | 59.976 | 18.515 | 1.588 | 1.00 | 12.91 |
| ATOM | 73 | CE3 | TRP | 165 | 59.507 | 20.779 | 2.300 | 1.00 | 14.44 |
| ATOM | 74 | CD1 | TRP | 165 | 57.972 | 17.544 | 1.738 | 1.00 | 12.89 |
| ATOM | 75 | NE1 | TRP | 165 | 59.290 | 17.343 | 1.413 | 1.00 | 12.80 |
| ATOM | 76 | CZ2 | TRP | 165 | 61.328 | 18.805 | 1.388 | 1.00 | 15.06 |
| ATOM | 77 | CZ3 | TRP | 165 | 60.850 | 21.069 | 2.103 | 1.00 | 14.72 |
| ATOM | 78 | CH2 | TRP | 165 | 61.747 | 20.084 | 1.649 | 1.00 | 16.82 |
| ATOM | 79 | C | TRP | 165 | 55.553 | 21.210 | 4.056 | 1.00 | 18.93 |
| ATOM | 80 | O | TRP | 165 | 55.960 | 22.359 | 3.926 | 1.00 | 21.12 |
| ATOM | 81 | N | ASP | 166 | 54.279 | 20.922 | 4.307 | 1.00 | 19.33 |
| ATOM | 82 | CA | ASP | 166 | 53.262 | 21.963 | 4.483 | 1.00 | 20.35 |
| ATOM | 83 | CB | ASP | 166 | 51.864 | 21.353 | 4.672 | 1.00 | 20.22 |
| ATOM | 84 | CG | ASP | 166 | 51.302 | 20.748 | 3.386 | 1.00 | 23.36 |
| ATOM | 85 | OD1 | ASP | 166 | 51.746 | 21.153 | 2.296 | 1.00 | 23.42 |
| ATOM | 86 | OD2 | ASP | 166 | 50.414 | 19.878 | 3.462 | 1.00 | 21.02 |
| ATOM | 87 | C | ASP | 166 | 53.623 | 22.785 | 5.712 | 1.00 | 21.02 |
| ATOM | 88 | O | ASP | 166 | 53.627 | 24.013 | 5.654 | 1.00 | 22.56 |
| ATOM | 89 | N | LEU | 167 | 53.926 | 22.096 | 6.813 | 1.00 | 20.50 |
| ATOM | 90 | CA | LEU | 167 | 54.312 | 22.726 | 8.071 | 1.00 | 21.37 |
| ATOM | 91 | CB | LEU | 167 | 54.661 | 21.657 | 9.109 | 1.00 | 23.49 |
| ATOM | 92 | CG | LEU | 167 | 54.223 | 21.846 | 10.565 | 1.00 | 27.19 |
| ATOM | 93 | CD1 | LEU | 167 | 55.312 | 21.291 | 11.453 | 1.00 | 27.70 |
| ATOM | 94 | CD2 | LEU | 167 | 53.940 | 23.314 | 10.906 | 1.00 | 27.71 |
| ATOM | 95 | C | LEU | 167 | 55.541 | 23.602 | 7.839 | 1.00 | 20.72 |
| ATOM | 96 | O | LEU | 167 | 55.601 | 24.748 | 8.294 | 1.00 | 22.98 |
| ATOM | 97 | N | ILE | 168 | 56.505 | 23.051 | 7.114 | 1.00 | 18.54 |
| ATOM | 98 | CA | ILE | 168 | 57.747 | 23.725 | 6.778 | 1.00 | 18.60 |
| ATOM | 99 | CB | ILE | 168 | 58.671 | 22.771 | 5.995 | 1.00 | 17.54 |
| ATOM | 100 | CG2 | ILE | 168 | 59.695 | 23.533 | 5.163 | 1.00 | 17.65 |
| ATOM | 101 | CG1 | ILE | 168 | 59.330 | 21.794 | 6.972 | 1.00 | 20.27 |
| ATOM | 102 | CD1 | ILE | 168 | 60.048 | 20.631 | 6.322 | 1.00 | 17.96 |
| ATOM | 103 | C | ILE | 168 | 57.486 | 25.002 | 5.979 | 1.00 | 21.96 |
| ATOM | 104 | O | ILE | 168 | 58.045 | 26.064 | 6.291 | 1.00 | 23.06 |
| ATOM | 105 | N | HIS | 169 | 56.591 | 24.925 | 4.996 | 1.00 | 22.04 |
| ATOM | 106 | CA | HIS | 169 | 56.285 | 26.092 | 4.164 | 1.00 | 21.21 |
| ATOM | 107 | CB | HIS | 169 | 55.413 | 25.702 | 2.969 | 1.00 | 20.12 |
| ATOM | 108 | CG | HIS | 169 | 56.101 | 24.799 | 2.001 | 1.00 | 19.18 |
| ATOM | 109 | CD2 | HIS | 169 | 57.398 | 24.733 | 1.619 | 1.00 | 18.62 |
| ATOM | 110 | ND1 | HIS | 169 | 55.457 | 23.764 | 1.357 | 1.00 | 17.90 |
| ATOM | 111 | CE1 | HIS | 169 | 56.327 | 23.096 | 0.625 | 1.00 | 18.43 |

FIG. 31A-3

| ATOM | 112 | NE2 | HIS | 169 | 57.513 | 23.660 | 0.772 | 1.00 | 20.10 |
|---|---|---|---|---|---|---|---|---|---|
| ATOM | 113 | C | HIS | 169 | 55.615 | 27.198 | 4.959 | 1.00 | 20.61 |
| ATOM | 114 | O | HIS | 169 | 55.979 | 28.370 | 4.836 | 1.00 | 20.08 |
| ATOM | 115 | N | VAL | 170 | 54.632 | 26.821 | 5.769 | 1.00 | 20.01 |
| ATOM | 116 | CA | VAL | 170 | 53.922 | 27.785 | 6.580 | 1.00 | 20.52 |
| ATOM | 117 | CB | VAL | 170 | 52.816 | 27.120 | 7.384 | 1.00 | 21.33 |
| ATOM | 118 | CG1 | VAL | 170 | 52.224 | 28.113 | 8.366 | 1.00 | 22.32 |
| ATOM | 119 | CG2 | VAL | 170 | 51.740 | 26.608 | 6.438 | 1.00 | 23.27 |
| ATOM | 120 | C | VAL | 170 | 54.891 | 28.477 | 7.521 | 1.00 | 20.58 |
| ATOM | 121 | O | VAL | 170 | 54.926 | 29.704 | 7.554 | 1.00 | 22.32 |
| ATOM | 122 | N | ALA | 171 | 55.712 | 27.696 | 8.230 | 1.00 | 18.83 |
| ATOM | 123 | CA | ALA | 171 | 56.692 | 28.234 | 9.182 | 1.00 | 18.34 |
| ATOM | 124 | CB | ALA | 171 | 57.375 | 27.102 | 9.946 | 1.00 | 17.05 |
| ATOM | 125 | C | ALA | 171 | 57.733 | 29.151 | 8.533 | 1.00 | 17.84 |
| ATOM | 126 | O | ALA | 171 | 58.084 | 30.200 | 9.091 | 1.00 | 18.67 |
| ATOM | 127 | N | THR | 172 | 58.231 | 28.756 | 7.367 | 1.00 | 17.81 |
| ATOM | 128 | CA | THR | 172 | 59.215 | 29.551 | 6.639 | 1.00 | 18.88 |
| ATOM | 129 | CB | THR | 172 | 59.726 | 28.794 | 5.380 | 1.00 | 20.47 |
| ATOM | 130 | OG1 | THR | 172 | 60.280 | 27.531 | 5.776 | 1.00 | 21.38 |
| ATOM | 131 | CG2 | THR | 172 | 60.806 | 29.599 | 4.648 | 1.00 | 20.22 |
| ATOM | 132 | C | THR | 172 | 58.655 | 30.932 | 6.251 | 1.00 | 19.42 |
| ATOM | 133 | O | THR | 172 | 59.320 | 31.957 | 6.435 | 1.00 | 17.98 |
| ATOM | 134 | N | GLU | 173 | 57.425 | 30.970 | 5.756 | 1.00 | 19.97 |
| ATOM | 135 | CA | GLU | 173 | 56.811 | 32.236 | 5.374 | 1.00 | 22.51 |
| ATOM | 136 | CB | GLU | 173 | 55.520 | 31.981 | 4.577 | 1.00 | 27.26 |
| ATOM | 137 | CG | GLU | 173 | 54.823 | 33.244 | 4.005 | 1.00 | 34.96 |
| ATOM | 138 | CD | GLU | 173 | 55.690 | 34.040 | 3.020 | 1.00 | 39.54 |
| ATOM | 139 | OE1 | GLU | 173 | 56.610 | 33.454 | 2.395 | 1.00 | 41.82 |
| ATOM | 140 | OE2 | GLU | 173 | 55.443 | 35.259 | 2.872 | 1.00 | 41.06 |
| ATOM | 141 | C | GLU | 173 | 56.538 | 33.099 | 6.622 | 1.00 | 21.60 |
| ATOM | 142 | O | GLU | 173 | 56.726 | 34.313 | 6.595 | 1.00 | 21.73 |
| ATOM | 143 | N | ALA | 174 | 56.123 | 32.461 | 7.716 | 1.00 | 19.69 |
| ATOM | 144 | CA | ALA | 174 | 55.844 | 33.155 | 8.968 | 1.00 | 18.07 |
| ATOM | 145 | CB | ALA | 174 | 55.423 | 32.169 | 10.037 | 1.00 | 16.90 |
| ATOM | 146 | C | ALA | 174 | 57.101 | 33.883 | 9.400 | 1.00 | 17.65 |
| ATOM | 147 | O | ALA | 174 | 57.052 | 35.031 | 9.829 | 1.00 | 19.80 |
| ATOM | 148 | N | HIS | 175 | 58.240 | 33.222 | 9.259 | 1.00 | 16.39 |
| ATOM | 149 | CA | HIS | 175 | 59.498 | 33.831 | 9.629 | 1.00 | 16.41 |
| ATOM | 150 | CB | HIS | 175 | 60.574 | 32.758 | 9.804 | 1.00 | 12.71 |
| ATOM | 151 | CG | HIS | 175 | 61.938 | 33.318 | 10.043 | 1.00 | 11.09 |
| ATOM | 152 | CD2 | HIS | 175 | 62.373 | 34.252 | 10.920 | 1.00 | 8.26 |
| ATOM | 153 | ND1 | HIS | 175 | 63.030 | 32.977 | 9.273 | 1.00 | 13.39 |
| ATOM | 154 | CE1 | HIS | 175 | 64.076 | 33.683 | 9.658 | 1.00 | 13.77 |
| ATOM | 155 | NE2 | HIS | 175 | 63.702 | 34.464 | 10.658 | 1.00 | 12.70 |
| ATOM | 156 | C | HIS | 175 | 59.959 | 34.903 | 8.624 | 1.00 | 19.55 |
| ATOM | 157 | O | HIS | 175 | 60.293 | 36.027 | 9.016 | 1.00 | 18.38 |
| ATOM | 158 | N | ARG | 176 | 59.987 | 34.555 | 7.339 | 1.00 | 20.77 |
| ATOM | 159 | CA | ARG | 176 | 60.424 | 35.494 | 6.307 | 1.00 | 21.30 |
| ATOM | 160 | CB | ARG | 176 | 60.315 | 34.876 | 4.917 | 1.00 | 24.87 |
| ATOM | 161 | CG | ARG | 176 | 61.361 | 33.827 | 4.609 | 1.00 | 30.22 |

FIG. 31A-4

| | | | | | | | | | |
|---|---|---|---|---|---|---|---|---|---|
| ATOM | 162 | CD | ARG | 176 | 61.429 | 33.603 | 3.116 | 1.00 | 36.29 |
| ATOM | 163 | NE | ARG | 176 | 62.256 | 32.457 | 2.758 | 1.00 | 44.72 |
| ATOM | 164 | CZ | ARG | 176 | 62.031 | 31.680 | 1.700 | 1.00 | 49.80 |
| ATOM | 165 | NH1 | ARG | 176 | 61.000 | 31.935 | 0.894 | 1.00 | 50.83 |
| ATOM | 166 | NH2 | ARG | 176 | 62.812 | 30.627 | 1.466 | 1.00 | 50.14 |
| ATOM | 167 | C | ARG | 176 | 59.658 | 36.807 | 6.337 | 1.00 | 20.67 |
| ATOM | 168 | O | ARG | 176 | 60.256 | 37.877 | 6.238 | 1.00 | 20.53 |
| ATOM | 169 | N | SER | 177 | 58.344 | 36.730 | 6.508 | 1.00 | 20.67 |
| ATOM | 170 | CA | SER | 177 | 57.526 | 37.934 | 6.551 | 1.00 | 21.86 |
| ATOM | 171 | CB | SER | 177 | 56.061 | 37.588 | 6.298 | 1.00 | 19.59 |
| ATOM | 172 | OG | SER | 177 | 55.541 | 36.774 | 7.329 | 1.00 | 21.85 |
| ATOM | 173 | C | SER | 177 | 57.659 | 38.733 | 7.857 | 1.00 | 23.27 |
| ATOM | 174 | O | SER | 177 | 57.073 | 39.807 | 7.989 | 1.00 | 24.40 |
| ATOM | 175 | N | THR | 178 | 58.383 | 38.202 | 8.837 | 1.00 | 22.16 |
| ATOM | 176 | CA | THR | 178 | 58.542 | 38.913 | 10.095 | 1.00 | 20.62 |
| ATOM | 177 | CB | THR | 178 | 57.853 | 38.162 | 11.265 | 1.00 | 19.93 |
| ATOM | 178 | OG1 | THR | 178 | 58.386 | 36.838 | 11.381 | 1.00 | 18.72 |
| ATOM | 179 | CG2 | THR | 178 | 56.359 | 38.057 | 11.033 | 1.00 | 16.95 |
| ATOM | 180 | C | THR | 178 | 60.015 | 39.137 | 10.394 | 1.00 | 21.57 |
| ATOM | 181 | O | THR | 178 | 60.368 | 39.649 | 11.449 | 1.00 | 23.91 |
| ATOM | 182 | N | ASN | 179 | 60.870 | 38.769 | 9.445 | 1.00 | 22.22 |
| ATOM | 183 | CA | ASN | 179 | 62.316 | 38.912 | 9.585 | 1.00 | 24.22 |
| ATOM | 184 | CB | ASN | 179 | 63.013 | 37.690 | 8.970 | 1.00 | 22.49 |
| ATOM | 185 | CG | ASN | 179 | 64.480 | 37.596 | 9.344 | 1.00 | 23.53 |
| ATOM | 186 | OD1 | ASN | 179 | 64.866 | 37.912 | 10.464 | 1.00 | 22.32 |
| ATOM | 187 | ND2 | ASN | 179 | 65.296 | 37.100 | 8.425 | 1.00 | 23.84 |
| ATOM | 188 | C | ASN | 179 | 62.744 | 40.210 | 8.881 | 1.00 | 26.52 |
| ATOM | 189 | O | ASN | 179 | 62.923 | 40.253 | 7.657 | 1.00 | 26.65 |
| ATOM | 190 | N | ALA | 180 | 62.898 | 41.267 | 9.671 | 1.00 | 27.47 |
| ATOM | 191 | CA | ALA | 180 | 63.255 | 42.582 | 9.166 | 1.00 | 30.30 |
| ATOM | 192 | CB | ALA | 180 | 63.552 | 43.508 | 10.321 | 1.00 | 27.21 |
| ATOM | 193 | C | ALA | 180 | 64.404 | 42.593 | 8.166 | 1.00 | 33.14 |
| ATOM | 194 | O | ALA | 180 | 65.440 | 41.972 | 8.397 | 1.00 | 33.71 |
| ATOM | 195 | N | GLN | 181 | 64.209 | 43.295 | 7.049 | 0.50 | 35.09 | ALTA |
| ATOM | 196 | CA | GLN | 181 | 65.212 | 43.423 | 5.980 | 0.50 | 37.44 | ALTA |
| ATOM | 197 | CB | GLN | 181 | 66.544 | 43.974 | 6.511 | 0.50 | 38.60 | ALTA |
| ATOM | 198 | CG | GLN | 181 | 66.728 | 45.462 | 6.299 | 0.50 | 40.53 | ALTA |
| ATOM | 199 | CD | GLN | 181 | 65.805 | 46.291 | 7.162 | 0.50 | 42.72 | ALTA |
| ATOM | 200 | OE1 | GLN | 181 | 64.639 | 46.512 | 6.828 | 0.50 | 42.05 | ALTA |
| ATOM | 201 | NE2 | GLN | 181 | 66.324 | 46.756 | 8.284 | 0.50 | 44.59 | ALTA |
| ATOM | 202 | C | GLN | 181 | 65.481 | 42.180 | 5.138 | 0.50 | 38.43 | ALTA |
| ATOM | 203 | O | GLN | 181 | 66.175 | 42.262 | 4.118 | 0.50 | 38.92 | ALTA |
| ATOM | 204 | N | GLY | 182 | 64.958 | 41.034 | 5.562 | 1.00 | 38.74 | |
| ATOM | 205 | CA | GLY | 182 | 65.166 | 39.808 | 4.805 | 1.00 | 40.07 | |
| ATOM | 206 | C | GLY | 182 | 66.634 | 39.554 | 4.486 | 1.00 | 42.06 | |
| ATOM | 207 | O | GLY | 182 | 67.504 | 39.684 | 5.346 | 1.00 | 43.28 | |
| ATOM | 208 | N | SER | 183 | 66.926 | 39.272 | 3.224 | 1.00 | 43.72 | |
| ATOM | 209 | CA | SER | 183 | 68.299 | 39.001 | 2.812 | 1.00 | 45.88 | |
| ATOM | 210 | CB | SER | 183 | 68.304 | 38.069 | 1.593 | 1.00 | 47.26 | |
| ATOM | 211 | OG | SER | 183 | 67.519 | 38.605 | 0.531 | 1.00 | 47.23 | |

FIG. 31A-5

| ATOM | 212 | C | SER | 183 | 69.095 | 40.268 | 2.497 | 1.00 | 46.24 | |
|---|---|---|---|---|---|---|---|---|---|---|
| ATOM | 213 | O | SER | 183 | 70.290 | 40.194 | 2.185 | 1.00 | 48.13 | |
| ATOM | 214 | N | HIS | 184 | 68.445 | 41.426 | 2.579 | 1.00 | 45.79 | |
| ATOM | 215 | CA | HIS | 184 | 69.111 | 42.690 | 2.276 | 1.00 | 45.00 | |
| ATOM | 216 | CB | HIS | 184 | 68.127 | 43.636 | 1.594 | 1.00 | 43.54 | |
| ATOM | 217 | C | HIS | 184 | 69.732 | 43.351 | 3.516 | 1.00 | 44.67 | |
| ATOM | 218 | O | HIS | 184 | 70.316 | 44.440 | 3.428 | 1.00 | 45.02 | |
| ATOM | 219 | N | TRP | 185 | 69.659 | 42.663 | 4.653 | 1.00 | 43.24 | |
| ATOM | 220 | CA | TRP | 185 | 70.190 | 43.172 | 5.919 | 1.00 | 40.98 | |
| ATOM | 221 | CB | TRP | 185 | 70.078 | 42.106 | 7.020 | 1.00 | 37.96 | |
| ATOM | 222 | CG | TRP | 185 | 70.889 | 40.874 | 6.775 | 1.00 | 34.14 | |
| ATOM | 223 | CD2 | TRP | 185 | 72.197 | 40.593 | 7.291 | 1.00 | 33.38 | |
| ATOM | 224 | CE2 | TRP | 185 | 72.572 | 39.321 | 6.807 | 1.00 | 31.68 | |
| ATOM | 225 | CE3 | TRP | 185 | 73.092 | 41.296 | 8.107 | 1.00 | 31.65 | |
| ATOM | 226 | CD1 | TRP | 185 | 70.530 | 39.790 | 6.028 | 1.00 | 34.27 | |
| ATOM | 227 | NE1 | TRP | 185 | 71.536 | 38.852 | 6.043 | 1.00 | 33.51 | |
| ATOM | 228 | CZ2 | TRP | 185 | 73.795 | 38.733 | 7.121 | 1.00 | 31.67 | |
| ATOM | 229 | CZ3 | TRP | 185 | 74.308 | 40.713 | 8.419 | 1.00 | 31.29 | |
| ATOM | 230 | CH2 | TRP | 185 | 74.651 | 39.444 | 7.923 | 1.00 | 31.06 | |
| ATOM | 231 | C | TRP | 185 | 71.618 | 43.720 | 5.856 | 1.00 | 41.52 | |
| ATOM | 232 | O | TRP | 185 | 71.893 | 44.817 | 6.335 | 1.00 | 40.52 | |
| ATOM | 233 | N | LYS | 186 | 72.520 | 42.976 | 5.234 | 1.00 | 42.94 | |
| ATOM | 234 | CA | LYS | 186 | 73.896 | 43.417 | 5.143 | 1.00 | 45.25 | |
| ATOM | 235 | CB | LYS | 186 | 74.764 | 42.328 | 4.508 | 1.00 | 45.96 | |
| ATOM | 236 | CG | LYS | 186 | 76.255 | 42.600 | 4.590 | 1.00 | 48.07 | |
| ATOM | 237 | CD | LYS | 186 | 77.053 | 41.307 | 4.504 | 1.00 | 51.20 | |
| ATOM | 238 | CE | LYS | 186 | 78.554 | 41.574 | 4.457 | 1.00 | 52.69 | |
| ATOM | 239 | NZ | LYS | 186 | 78.975 | 42.277 | 3.201 | 1.00 | 55.56 | |
| ATOM | 240 | C | LYS | 186 | 74.025 | 44.730 | 4.377 | 1.00 | 47.38 | |
| ATOM | 241 | O | LYS | 186 | 74.914 | 45.535 | 4.663 | 1.00 | 47.65 | |
| ATOM | 242 | N | GLN | 187 | 73.134 | 44.959 | 3.418 | 0.50 | 48.02 | ALTA |
| ATOM | 243 | CA | GLN | 187 | 73.193 | 46.183 | 2.623 | 0.50 | 48.69 | ALTA |
| ATOM | 244 | CB | GLN | 187 | 72.547 | 45.973 | 1.246 | 0.50 | 48.66 | ALTA |
| ATOM | 245 | CG | GLN | 187 | 73.104 | 44.771 | 0.453 | 0.50 | 49.05 | ALTA |
| ATOM | 246 | CD | GLN | 187 | 74.624 | 44.766 | 0.339 | 0.50 | 49.17 | ALTA |
| ATOM | 247 | OE1 | GLN | 187 | 75.225 | 45.691 | -0.209 | 0.50 | 49.71 | ALTA |
| ATOM | 248 | NE2 | GLN | 187 | 75.250 | 43.710 | 0.847 | 0.50 | 48.57 | ALTA |
| ATOM | 249 | C | GLN | 187 | 72.551 | 47.373 | 3.343 | 0.50 | 49.06 | ALTA |
| ATOM | 250 | O | GLN | 187 | 73.094 | 48.475 | 3.329 | 0.50 | 49.53 | ALTA |
| ATOM | 251 | N | ARG | 188 | 71.405 | 47.152 | 3.980 | 1.00 | 49.18 | |
| ATOM | 252 | CA | ARG | 188 | 70.723 | 48.221 | 4.695 | 1.00 | 49.90 | |
| ATOM | 253 | CB | ARG | 188 | 69.209 | 47.988 | 4.653 | 1.00 | 53.68 | |
| ATOM | 254 | CG | ARG | 188 | 68.617 | 47.798 | 3.251 | 1.00 | 57.22 | |
| ATOM | 255 | CD | ARG | 188 | 67.099 | 47.962 | 3.302 | 1.00 | 60.67 | |
| ATOM | 256 | NE | ARG | 188 | 66.430 | 47.441 | 2.110 | 1.00 | 64.43 | |
| ATOM | 257 | CZ | ARG | 188 | 65.931 | 46.208 | 2.009 | 1.00 | 66.13 | |
| ATOM | 258 | NH1 | ARG | 188 | 66.027 | 45.362 | 3.031 | 1.00 | 66.69 | |
| ATOM | 259 | NH2 | ARG | 188 | 65.318 | 45.823 | 0.893 | 1.00 | 66.10 | |
| ATOM | 260 | C | ARG | 188 | 71.150 | 48.510 | 6.133 | 1.00 | 48.42 | |
| ATOM | 261 | O | ARG | 188 | 70.544 | 49.368 | 6.784 | 1.00 | 48.86 | |

FIG. 31A-6

| ATOM | 262 | N   | ARG | 189 | 72.153 | 47.804 | 6.647  | 1.00 | 46.00 |
|------|-----|-----|-----|-----|--------|--------|--------|------|-------|
| ATOM | 263 | CA  | ARG | 189 | 72.581 | 48.030 | 8.028  | 1.00 | 44.24 |
| ATOM | 264 | CB  | ARG | 189 | 73.039 | 46.726 | 8.690  | 1.00 | 43.40 |
| ATOM | 265 | CG  | ARG | 189 | 74.367 | 46.204 | 8.203  | 1.00 | 43.05 |
| ATOM | 266 | CD  | ARG | 189 | 74.808 | 45.021 | 9.019  | 1.00 | 43.62 |
| ATOM | 267 | NE  | ARG | 189 | 76.185 | 44.660 | 8.717  | 1.00 | 45.95 |
| ATOM | 268 | CZ  | ARG | 189 | 76.981 | 43.976 | 9.536  | 1.00 | 48.56 |
| ATOM | 269 | NH1 | ARG | 189 | 76.548 | 43.560 | 10.724 | 1.00 | 46.34 |
| ATOM | 270 | NH2 | ARG | 189 | 78.233 | 43.735 | 9.174  | 1.00 | 50.12 |
| ATOM | 271 | C   | ARG | 189 | 73.642 | 49.116 | 8.238  | 1.00 | 43.20 |
| ATOM | 272 | O   | ARG | 189 | 74.629 | 49.210 | 7.500  | 1.00 | 43.07 |
| ATOM | 273 | N   | LYS | 190 | 73.427 | 49.925 | 9.268  | 1.00 | 41.56 |
| ATOM | 274 | CA  | LYS | 190 | 74.335 | 51.003 | 9.628  | 1.00 | 39.96 |
| ATOM | 275 | CB  | LYS | 190 | 73.563 | 52.323 | 9.757  | 1.00 | 38.85 |
| ATOM | 276 | C   | LYS | 190 | 74.983 | 50.631 | 10.956 | 1.00 | 38.91 |
| ATOM | 277 | O   | LYS | 190 | 74.345 | 50.015 | 11.806 | 1.00 | 38.17 |
| ATOM | 278 | N   | PHE | 191 | 76.261 | 50.959 | 11.104 | 1.00 | 38.49 |
| ATOM | 279 | CA  | PHE | 191 | 76.998 | 50.673 | 12.326 | 1.00 | 38.42 |
| ATOM | 280 | CB  | PHE | 191 | 78.500 | 50.762 | 12.073 | 1.00 | 38.37 |
| ATOM | 281 | CG  | PHE | 191 | 79.056 | 49.608 | 11.308 | 1.00 | 39.05 |
| ATOM | 282 | CD1 | PHE | 191 | 78.712 | 49.408 | 9.976  | 1.00 | 40.02 |
| ATOM | 283 | CD2 | PHE | 191 | 79.942 | 48.727 | 11.917 | 1.00 | 39.19 |
| ATOM | 284 | CE1 | PHE | 191 | 79.245 | 48.344 | 9.256  | 1.00 | 40.57 |
| ATOM | 285 | CE2 | PHE | 191 | 80.482 | 47.661 | 11.213 | 1.00 | 40.32 |
| ATOM | 286 | CZ  | PHE | 191 | 80.133 | 47.466 | 9.875  | 1.00 | 41.84 |
| ATOM | 287 | C   | PHE | 191 | 76.650 | 51.673 | 13.416 | 1.00 | 37.96 |
| ATOM | 288 | O   | PHE | 191 | 76.568 | 52.872 | 13.151 | 1.00 | 38.95 |
| ATOM | 289 | N   | LEU | 192 | 76.433 | 51.184 | 14.634 | 1.00 | 37.05 |
| ATOM | 290 | CA  | LEU | 192 | 76.138 | 52.063 | 15.759 | 1.00 | 35.99 |
| ATOM | 291 | CB  | LEU | 192 | 75.833 | 51.247 | 17.014 | 1.00 | 33.04 |
| ATOM | 292 | CG  | LEU | 192 | 75.503 | 52.074 | 18.260 | 1.00 | 31.38 |
| ATOM | 293 | CD1 | LEU | 192 | 74.116 | 52.651 | 18.102 | 1.00 | 29.02 |
| ATOM | 294 | CD2 | LEU | 192 | 75.592 | 51.229 | 19.536 | 1.00 | 30.32 |
| ATOM | 295 | C   | LEU | 192 | 77.436 | 52.831 | 15.976 | 1.00 | 36.99 |
| ATOM | 296 | O   | LEU | 192 | 78.500 | 52.218 | 16.112 | 1.00 | 37.66 |
| ATOM | 297 | N   | PRO | 193 | 77.377 | 54.177 | 15.988 | 1.00 | 38.15 |
| ATOM | 298 | CD  | PRO | 193 | 76.156 | 54.996 | 15.902 | 1.00 | 37.90 |
| ATOM | 299 | CA  | PRO | 193 | 78.561 | 55.025 | 16.187 | 1.00 | 38.68 |
| ATOM | 300 | CB  | PRO | 193 | 77.950 | 56.365 | 16.568 | 1.00 | 37.20 |
| ATOM | 301 | CG  | PRO | 193 | 76.711 | 56.397 | 15.758 | 1.00 | 37.08 |
| ATOM | 302 | C   | PRO | 193 | 79.475 | 54.503 | 17.294 | 1.00 | 41.12 |
| ATOM | 303 | O   | PRO | 193 | 79.005 | 54.129 | 18.367 | 1.00 | 42.26 |
| ATOM | 304 | N   | ASP | 194 | 80.782 | 54.509 | 17.052 | 1.00 | 43.62 |
| ATOM | 305 | CA  | ASP | 194 | 81.731 | 54.012 | 18.050 | 1.00 | 46.71 |
| ATOM | 306 | CB  | ASP | 194 | 83.131 | 53.938 | 17.470 | 1.00 | 49.32 |
| ATOM | 307 | CG  | ASP | 194 | 83.237 | 52.904 | 16.397 | 1.00 | 52.34 |
| ATOM | 308 | OD1 | ASP | 194 | 83.539 | 51.726 | 16.719 | 1.00 | 53.18 |
| ATOM | 309 | OD2 | ASP | 194 | 82.981 | 53.268 | 15.227 | 1.00 | 55.10 |
| ATOM | 310 | C   | ASP | 194 | 81.769 | 54.743 | 19.386 | 1.00 | 47.12 |
| ATOM | 311 | O   | ASP | 194 | 82.158 | 54.163 | 20.403 | 1.00 | 48.16 |

FIG. 31A-7

| ATOM | 312 | N   | ASP | 195 | 81.389 | 56.015 | 19.386 | 1.00 | 47.54 |
|------|-----|-----|-----|-----|--------|--------|--------|------|-------|
| ATOM | 313 | CA  | ASP | 195 | 81.382 | 56.791 | 20.620 | 1.00 | 48.68 |
| ATOM | 314 | CB  | ASP | 195 | 81.180 | 58.285 | 20.322 | 1.00 | 50.76 |
| ATOM | 315 | CG  | ASP | 195 | 79.871 | 58.572 | 19.602 | 1.00 | 54.24 |
| ATOM | 316 | OD1 | ASP | 195 | 78.929 | 59.082 | 20.253 | 1.00 | 56.17 |
| ATOM | 317 | OD2 | ASP | 195 | 79.786 | 58.292 | 18.385 | 1.00 | 56.08 |
| ATOM | 318 | C   | ASP | 195 | 80.304 | 56.274 | 21.580 | 1.00 | 47.63 |
| ATOM | 319 | O   | ASP | 195 | 80.294 | 56.621 | 22.772 | 1.00 | 49.07 |
| ATOM | 320 | N   | ILE | 196 | 79.400 | 55.444 | 21.065 | 1.00 | 44.87 |
| ATOM | 321 | CA  | ILE | 196 | 78.330 | 54.890 | 21.888 | 1.00 | 42.53 |
| ATOM | 322 | CB  | ILE | 196 | 76.983 | 54.813 | 21.121 | 1.00 | 42.19 |
| ATOM | 323 | CG2 | ILE | 196 | 75.870 | 54.357 | 22.060 | 1.00 | 40.29 |
| ATOM | 324 | CG1 | ILE | 196 | 76.635 | 56.191 | 20.535 | 1.00 | 41.32 |
| ATOM | 325 | CD1 | ILE | 196 | 75.344 | 56.219 | 19.732 | 1.00 | 41.32 |
| ATOM | 326 | C   | ILE | 196 | 78.725 | 53.509 | 22.391 | 1.00 | 40.89 |
| ATOM | 327 | O   | ILE | 196 | 79.358 | 52.722 | 21.679 | 1.00 | 40.08 |
| ATOM | 328 | N   | GLY | 197 | 78.384 | 53.240 | 23.642 | 1.00 | 40.16 |
| ATOM | 329 | CA  | GLY | 197 | 78.705 | 51.957 | 24.228 | 1.00 | 40.21 |
| ATOM | 330 | C   | GLY | 197 | 80.066 | 51.907 | 24.879 | 1.00 | 40.18 |
| ATOM | 331 | O   | GLY | 197 | 80.512 | 50.839 | 25.267 | 1.00 | 40.55 |
| ATOM | 332 | N   | GLN | 198 | 80.718 | 53.057 | 25.029 | 1.00 | 41.25 |
| ATOM | 333 | CA  | GLN | 198 | 82.038 | 53.111 | 25.664 | 1.00 | 40.94 |
| ATOM | 334 | CB  | GLN | 198 | 83.041 | 53.823 | 24.738 | 1.00 | 39.51 |
| ATOM | 335 | C   | GLN | 198 | 81.995 | 53.796 | 27.046 | 1.00 | 40.93 |
| ATOM | 336 | O   | GLN | 198 | 83.036 | 54.197 | 27.571 | 1.00 | 41.83 |
| ATOM | 337 | N   | SER | 199 | 80.806 | 53.859 | 27.654 | 1.00 | 39.68 |
| ATOM | 338 | CA  | SER | 199 | 80.615 | 54.510 | 28.961 | 1.00 | 37.74 |
| ATOM | 339 | CB  | SER | 199 | 79.995 | 55.905 | 28.768 | 1.00 | 38.50 |
| ATOM | 340 | OG  | SER | 199 | 80.687 | 56.672 | 27.792 | 1.00 | 40.71 |
| ATOM | 341 | C   | SER | 199 | 79.743 | 53.726 | 29.958 | 1.00 | 36.31 |
| ATOM | 342 | O   | SER | 199 | 78.719 | 54.228 | 30.436 | 1.00 | 35.69 |
| ATOM | 343 | N   | PRO | 200 | 80.123 | 52.484 | 30.280 | 1.00 | 35.05 |
| ATOM | 344 | CD  | PRO | 200 | 81.246 | 51.684 | 29.760 | 1.00 | 33.97 |
| ATOM | 345 | CA  | PRO | 200 | 79.313 | 51.715 | 31.228 | 1.00 | 35.89 |
| ATOM | 346 | CB  | PRO | 200 | 79.872 | 50.304 | 31.075 | 1.00 | 33.94 |
| ATOM | 347 | CG  | PRO | 200 | 81.297 | 50.532 | 30.708 | 1.00 | 33.31 |
| ATOM | 348 | C   | PRO | 200 | 79.477 | 52.241 | 32.656 | 1.00 | 37.75 |
| ATOM | 349 | O   | PRO | 200 | 80.484 | 51.959 | 33.299 | 1.00 | 38.78 |
| ATOM | 350 | N   | ILE | 201 | 78.493 | 52.988 | 33.158 | 1.00 | 39.61 |
| ATOM | 351 | CA  | ILE | 201 | 78.590 | 53.551 | 34.511 | 1.00 | 40.56 |
| ATOM | 352 | CB  | ILE | 201 | 78.715 | 55.093 | 34.484 | 1.00 | 40.20 |
| ATOM | 353 | CG2 | ILE | 201 | 80.125 | 55.501 | 34.082 | 1.00 | 41.06 |
| ATOM | 354 | CG1 | ILE | 201 | 77.690 | 55.694 | 33.532 | 1.00 | 40.98 |
| ATOM | 355 | CD1 | ILE | 201 | 77.969 | 57.147 | 33.205 | 1.00 | 44.31 |
| ATOM | 356 | C   | ILE | 201 | 77.535 | 53.160 | 35.546 | 1.00 | 41.40 |
| ATOM | 357 | O   | ILE | 201 | 77.768 | 53.313 | 36.751 | 1.00 | 42.09 |
| ATOM | 358 | N   | VAL | 202 | 76.365 | 52.701 | 35.104 | 1.00 | 41.42 |
| ATOM | 359 | CA  | VAL | 202 | 75.325 | 52.293 | 36.053 | 1.00 | 40.70 |
| ATOM | 360 | CB  | VAL | 202 | 73.913 | 52.292 | 35.422 | 1.00 | 38.44 |
| ATOM | 361 | CG1 | VAL | 202 | 72.881 | 51.826 | 36.435 | 1.00 | 35.91 |

FIG. 31A-8

| ATOM | 362 | CG2 | VAL | 202 | 73.560 | 53.692 | 34.934 | 1.00 | 36.42 |
|---|---|---|---|---|---|---|---|---|---|
| ATOM | 363 | C | VAL | 202 | 75.687 | 50.917 | 36.622 | 1.00 | 41.64 |
| ATOM | 364 | O | VAL | 202 | 76.094 | 50.008 | 35.894 | 1.00 | 42.05 |
| ATOM | 365 | N | SER | 203 | 75.596 | 50.800 | 37.938 | 1.00 | 43.06 |
| ATOM | 366 | CA | SER | 203 | 75.947 | 49.576 | 38.639 | 1.00 | 44.57 |
| ATOM | 367 | CB | SER | 203 | 75.916 | 49.842 | 40.154 | 1.00 | 46.82 |
| ATOM | 368 | OG | SER | 203 | 76.457 | 48.772 | 40.916 | 1.00 | 50.18 |
| ATOM | 369 | C | SER | 203 | 75.052 | 48.388 | 38.294 | 1.00 | 44.08 |
| ATOM | 370 | O | SER | 203 | 73.849 | 48.534 | 38.093 | 1.00 | 44.28 |
| ATOM | 371 | N | MET | 204 | 75.656 | 47.210 | 38.231 | 1.00 | 43.11 |
| ATOM | 372 | CA | MET | 204 | 74.930 | 45.980 | 37.963 | 1.00 | 43.12 |
| ATOM | 373 | CB | MET | 204 | 75.048 | 45.557 | 36.494 | 1.00 | 41.07 |
| ATOM | 374 | CG | MET | 204 | 74.126 | 46.320 | 35.554 | 1.00 | 36.96 |
| ATOM | 375 | SD | MET | 204 | 72.375 | 46.134 | 35.990 | 1.00 | 38.66 |
| ATOM | 376 | CE | MET | 204 | 71.970 | 44.592 | 35.098 | 1.00 | 37.26 |
| ATOM | 377 | C | MET | 204 | 75.561 | 44.943 | 38.866 | 1.00 | 43.68 |
| ATOM | 378 | O | MET | 204 | 76.784 | 44.817 | 38.912 | 1.00 | 44.32 |
| ATOM | 379 | N | PRO | 205 | 74.735 | 44.204 | 39.619 | 1.00 | 44.22 |
| ATOM | 380 | CD | PRO | 205 | 73.261 | 44.310 | 39.610 | 1.00 | 44.44 |
| ATOM | 381 | CA | PRO | 205 | 75.187 | 43.164 | 40.546 | 1.00 | 44.32 |
| ATOM | 382 | CB | PRO | 205 | 73.944 | 42.299 | 40.701 | 1.00 | 45.18 |
| ATOM | 383 | CG | PRO | 205 | 72.832 | 43.335 | 40.691 | 1.00 | 44.29 |
| ATOM | 384 | C | PRO | 205 | 76.417 | 42.354 | 40.122 | 1.00 | 44.31 |
| ATOM | 385 | O | PRO | 205 | 77.393 | 42.293 | 40.864 | 1.00 | 43.97 |
| ATOM | 386 | N | ASP | 206 | 76.404 | 41.802 | 38.912 | 1.00 | 44.30 |
| ATOM | 387 | CA | ASP | 206 | 77.524 | 40.984 | 38.433 | 1.00 | 44.77 |
| ATOM | 388 | CB | ASP | 206 | 77.073 | 40.106 | 37.270 | 1.00 | 47.12 |
| ATOM | 389 | CG | ASP | 206 | 76.503 | 40.912 | 36.120 | 1.00 | 49.73 |
| ATOM | 390 | OD1 | ASP | 206 | 76.992 | 42.039 | 35.863 | 1.00 | 49.65 |
| ATOM | 391 | OD2 | ASP | 206 | 75.553 | 40.416 | 35.478 | 1.00 | 51.96 |
| ATOM | 392 | C | ASP | 206 | 78.805 | 41.718 | 38.037 | 1.00 | 44.10 |
| ATOM | 393 | O | ASP | 206 | 79.754 | 41.099 | 37.549 | 1.00 | 43.60 |
| ATOM | 394 | N | GLY | 207 | 78.804 | 43.039 | 38.145 | 1.00 | 44.19 |
| ATOM | 395 | CA | GLY | 207 | 80.001 | 43.785 | 37.803 | 1.00 | 43.51 |
| ATOM | 396 | C | GLY | 207 | 80.041 | 44.425 | 36.433 | 1.00 | 43.29 |
| ATOM | 397 | O | GLY | 207 | 80.745 | 45.421 | 36.257 | 1.00 | 44.47 |
| ATOM | 398 | N | ASP | 208 | 79.363 | 43.845 | 35.446 | 1.00 | 42.45 |
| ATOM | 399 | CA | ASP | 208 | 79.347 | 44.436 | 34.106 | 1.00 | 41.51 |
| ATOM | 400 | CB | ASP | 208 | 78.915 | 43.402 | 33.070 | 1.00 | 42.91 |
| ATOM | 401 | CG | ASP | 208 | 80.001 | 42.379 | 32.785 | 1.00 | 43.57 |
| ATOM | 402 | OD1 | ASP | 208 | 79.675 | 41.218 | 32.468 | 1.00 | 44.55 |
| ATOM | 403 | OD2 | ASP | 208 | 81.191 | 42.742 | 32.868 | 1.00 | 47.14 |
| ATOM | 404 | C | ASP | 208 | 78.378 | 45.606 | 34.143 | 1.00 | 40.78 |
| ATOM | 405 | O | ASP | 208 | 77.176 | 45.403 | 34.277 | 1.00 | 42.50 |
| ATOM | 406 | N | LYS | 209 | 78.902 | 46.827 | 34.058 | 1.00 | 39.10 |
| ATOM | 407 | CA | LYS | 209 | 78.071 | 48.033 | 34.150 | 1.00 | 37.23 |
| ATOM | 408 | CB | LYS | 209 | 78.910 | 49.211 | 34.681 | 1.00 | 37.29 |
| ATOM | 409 | C | LYS | 209 | 77.326 | 48.423 | 32.871 | 1.00 | 34.47 |
| ATOM | 410 | O | LYS | 209 | 77.707 | 48.013 | 31.776 | 1.00 | 33.85 |
| ATOM | 411 | N | VAL | 210 | 76.275 | 49.228 | 33.028 | 1.00 | 33.30 |

FIG. 31A-9

| ATOM | 412 | CA | VAL | 210 | 75.448 | 49.684 | 31.907 | 1.00 | 31.78 |
|------|-----|-----|-----|-----|--------|--------|--------|------|-------|
| ATOM | 413 | CB | VAL | 210 | 73.929 | 49.618 | 32.235 | 1.00 | 29.51 |
| ATOM | 414 | CG1 | VAL | 210 | 73.102 | 50.012 | 31.010 | 1.00 | 29.24 |
| ATOM | 415 | CG2 | VAL | 210 | 73.541 | 48.237 | 32.698 | 1.00 | 29.84 |
| ATOM | 416 | C | VAL | 210 | 75.731 | 51.115 | 31.451 | 1.00 | 32.68 |
| ATOM | 417 | O | VAL | 210 | 75.845 | 52.033 | 32.264 | 1.00 | 32.69 |
| ATOM | 418 | N | ASP | 211 | 75.769 | 51.290 | 30.134 | 1.00 | 33.00 |
| ATOM | 419 | CA | ASP | 211 | 75.978 | 52.574 | 29.476 | 1.00 | 31.85 |
| ATOM | 420 | CB | ASP | 211 | 76.826 | 52.353 | 28.221 | 1.00 | 32.38 |
| ATOM | 421 | CG | ASP | 211 | 77.019 | 53.612 | 27.386 | 1.00 | 31.88 |
| ATOM | 422 | OD1 | ASP | 211 | 78.123 | 53.768 | 26.843 | 1.00 | 32.78 |
| ATOM | 423 | OD2 | ASP | 211 | 76.079 | 54.412 | 27.208 | 1.00 | 32.32 |
| ATOM | 424 | C | ASP | 211 | 74.562 | 53.023 | 29.101 | 1.00 | 33.39 |
| ATOM | 425 | O | ASP | 211 | 73.925 | 52.444 | 28.206 | 1.00 | 31.94 |
| ATOM | 426 | N | LEU | 212 | 74.078 | 54.063 | 29.770 | 1.00 | 32.50 |
| ATOM | 427 | CA | LEU | 212 | 72.731 | 54.568 | 29.532 | 1.00 | 32.29 |
| ATOM | 428 | CB | LEU | 212 | 72.440 | 55.736 | 30.470 | 1.00 | 32.41 |
| ATOM | 429 | CG | LEU | 212 | 72.311 | 55.336 | 31.936 | 1.00 | 32.11 |
| ATOM | 430 | CD1 | LEU | 212 | 72.447 | 56.555 | 32.830 | 1.00 | 32.35 |
| ATOM | 431 | CD2 | LEU | 212 | 70.979 | 54.650 | 32.148 | 1.00 | 30.87 |
| ATOM | 432 | C | LEU | 212 | 72.419 | 54.962 | 28.092 | 1.00 | 32.29 |
| ATOM | 433 | O | LEU | 212 | 71.326 | 54.695 | 27.609 | 1.00 | 32.13 |
| ATOM | 434 | N | GLU | 213 | 73.370 | 55.589 | 27.407 | 1.00 | 32.21 |
| ATOM | 435 | CA | GLU | 213 | 73.144 | 56.007 | 26.028 | 1.00 | 33.12 |
| ATOM | 436 | CB | GLU | 213 | 74.305 | 56.864 | 25.530 | 1.00 | 36.72 |
| ATOM | 437 | CG | GLU | 213 | 74.067 | 57.468 | 24.146 | 1.00 | 40.61 |
| ATOM | 438 | CD | GLU | 213 | 75.316 | 58.101 | 23.545 | 1.00 | 44.21 |
| ATOM | 439 | OE1 | GLU | 213 | 76.434 | 57.851 | 24.059 | 1.00 | 46.23 |
| ATOM | 440 | OE2 | GLU | 213 | 75.178 | 58.836 | 22.543 | 1.00 | 45.81 |
| ATOM | 441 | C | GLU | 213 | 72.966 | 54.801 | 25.111 | 1.00 | 31.91 |
| ATOM | 442 | O | GLU | 213 | 72.064 | 54.775 | 24.273 | 1.00 | 31.31 |
| ATOM | 443 | N | ALA | 214 | 73.827 | 53.803 | 25.285 | 1.00 | 30.66 |
| ATOM | 444 | CA | ALA | 214 | 73.769 | 52.585 | 24.482 | 1.00 | 30.43 |
| ATOM | 445 | CB | ALA | 214 | 74.971 | 51.690 | 24.783 | 1.00 | 29.77 |
| ATOM | 446 | C | ALA | 214 | 72.464 | 51.854 | 24.778 | 1.00 | 29.34 |
| ATOM | 447 | O | ALA | 214 | 71.772 | 51.421 | 23.862 | 1.00 | 28.33 |
| ATOM | 448 | N | PHE | 215 | 72.116 | 51.762 | 26.058 | 1.00 | 28.45 |
| ATOM | 449 | CA | PHE | 215 | 70.882 | 51.116 | 26.492 | 1.00 | 29.05 |
| ATOM | 450 | CB | PHE | 215 | 70.732 | 51.240 | 28.005 | 1.00 | 25.98 |
| ATOM | 451 | CG | PHE | 215 | 69.443 | 50.689 | 28.535 | 1.00 | 25.53 |
| ATOM | 452 | CD1 | PHE | 215 | 69.330 | 49.344 | 28.854 | 1.00 | 26.16 |
| ATOM | 453 | CD2 | PHE | 215 | 68.349 | 51.519 | 28.737 | 1.00 | 25.04 |
| ATOM | 454 | CE1 | PHE | 215 | 68.144 | 48.831 | 29.370 | 1.00 | 25.73 |
| ATOM | 455 | CE2 | PHE | 215 | 67.160 | 51.018 | 29.252 | 1.00 | 25.84 |
| ATOM | 456 | CZ | PHE | 215 | 67.058 | 49.669 | 29.570 | 1.00 | 25.25 |
| ATOM | 457 | C | PHE | 215 | 69.694 | 51.780 | 25.801 | 1.00 | 30.92 |
| ATOM | 458 | O | PHE | 215 | 68.773 | 51.107 | 25.316 | 1.00 | 30.38 |
| ATOM | 459 | N | SER | 216 | 69.714 | 53.108 | 25.776 | 1.00 | 31.41 |
| ATOM | 460 | CA | SER | 216 | 68.667 | 53.887 | 25.136 | 1.00 | 31.23 |
| ATOM | 461 | CB | SER | 216 | 68.976 | 55.375 | 25.256 | 1.00 | 32.50 |

FIG. 31A-10

| ATOM | 462 | OG  | SER | 216 | 67.972 | 56.153 | 24.628 | 1.00 | 35.83 |
|------|-----|-----|-----|-----|--------|--------|--------|------|-------|
| ATOM | 463 | C   | SER | 216 | 68.600 | 53.504 | 23.663 | 1.00 | 31.67 |
| ATOM | 464 | O   | SER | 216 | 67.527 | 53.235 | 23.129 | 1.00 | 31.34 |
| ATOM | 465 | N   | GLU | 217 | 69.756 | 53.475 | 23.014 | 1.00 | 31.72 |
| ATOM | 466 | CA  | GLU | 217 | 69.823 | 53.121 | 21.609 | 1.00 | 33.06 |
| ATOM | 467 | CB  | GLU | 217 | 71.269 | 53.153 | 21.110 | 1.00 | 34.93 |
| ATOM | 468 | CG  | GLU | 217 | 71.824 | 54.557 | 20.921 | 1.00 | 38.98 |
| ATOM | 469 | CD  | GLU | 217 | 70.986 | 55.399 | 19.963 | 1.00 | 41.92 |
| ATOM | 470 | OE1 | GLU | 217 | 70.177 | 56.221 | 20.444 | 1.00 | 44.02 |
| ATOM | 471 | OE2 | GLU | 217 | 71.139 | 55.246 | 18.731 | 1.00 | 44.46 |
| ATOM | 472 | C   | GLU | 217 | 69.199 | 51.759 | 21.330 | 1.00 | 31.78 |
| ATOM | 473 | O   | GLU | 217 | 68.447 | 51.607 | 20.369 | 1.00 | 32.51 |
| ATOM | 474 | N   | PHE | 218 | 69.477 | 50.779 | 22.181 | 1.00 | 29.80 |
| ATOM | 475 | CA  | PHE | 218 | 68.924 | 49.447 | 21.979 | 1.00 | 27.65 |
| ATOM | 476 | CB  | PHE | 218 | 69.668 | 48.416 | 22.827 | 1.00 | 26.79 |
| ATOM | 477 | CG  | PHE | 218 | 71.114 | 48.292 | 22.467 | 1.00 | 24.76 |
| ATOM | 478 | CD1 | PHE | 218 | 72.083 | 48.191 | 23.446 | 1.00 | 24.37 |
| ATOM | 479 | CD2 | PHE | 218 | 71.510 | 48.354 | 21.134 | 1.00 | 24.30 |
| ATOM | 480 | CE1 | PHE | 218 | 73.424 | 48.167 | 23.106 | 1.00 | 23.85 |
| ATOM | 481 | CE2 | PHE | 218 | 72.843 | 48.329 | 20.785 | 1.00 | 23.07 |
| ATOM | 482 | CZ  | PHE | 218 | 73.804 | 48.236 | 21.772 | 1.00 | 24.45 |
| ATOM | 483 | C   | PHE | 218 | 67.441 | 49.403 | 22.255 | 1.00 | 26.94 |
| ATOM | 484 | O   | PHE | 218 | 66.658 | 48.985 | 21.409 | 1.00 | 27.98 |
| ATOM | 485 | N   | THR | 219 | 67.032 | 49.906 | 23.405 | 1.00 | 26.97 |
| ATOM | 486 | CA  | THR | 219 | 65.619 | 49.876 | 23.740 | 1.00 | 27.25 |
| ATOM | 487 | CB  | THR | 219 | 65.379 | 50.304 | 25.195 | 1.00 | 27.35 |
| ATOM | 488 | OG1 | THR | 219 | 65.924 | 51.612 | 25.410 | 1.00 | 26.48 |
| ATOM | 489 | CG2 | THR | 219 | 66.034 | 49.303 | 26.139 | 1.00 | 24.51 |
| ATOM | 490 | C   | THR | 219 | 64.747 | 50.689 | 22.782 | 1.00 | 27.21 |
| ATOM | 491 | O   | THR | 219 | 63.588 | 50.348 | 22.557 | 1.00 | 28.58 |
| ATOM | 492 | N   | LYS | 220 | 65.318 | 51.726 | 22.184 | 1.00 | 26.75 |
| ATOM | 493 | CA  | LYS | 220 | 64.576 | 52.569 | 21.254 | 1.00 | 27.81 |
| ATOM | 494 | CB  | LYS | 220 | 65.439 | 53.753 | 20.782 | 1.00 | 27.46 |
| ATOM | 495 | C   | LYS | 220 | 64.058 | 51.772 | 20.056 | 1.00 | 28.62 |
| ATOM | 496 | O   | LYS | 220 | 63.014 | 52.101 | 19.500 | 1.00 | 28.63 |
| ATOM | 497 | N   | ILE | 221 | 64.774 | 50.721 | 19.662 | 1.00 | 28.92 |
| ATOM | 498 | CA  | ILE | 221 | 64.331 | 49.907 | 18.527 | 1.00 | 28.19 |
| ATOM | 499 | CB  | ILE | 221 | 65.450 | 49.732 | 17.465 | 1.00 | 27.17 |
| ATOM | 500 | CG2 | ILE | 221 | 65.866 | 51.095 | 16.911 | 1.00 | 26.61 |
| ATOM | 501 | CG1 | ILE | 221 | 66.645 | 48.977 | 18.061 | 1.00 | 26.80 |
| ATOM | 502 | CD1 | ILE | 221 | 67.621 | 48.417 | 17.029 | 1.00 | 24.91 |
| ATOM | 503 | C   | ILE | 221 | 63.840 | 48.512 | 18.937 | 1.00 | 28.82 |
| ATOM | 504 | O   | ILE | 221 | 63.552 | 47.678 | 18.076 | 1.00 | 28.59 |
| ATOM | 505 | N   | ILE | 222 | 63.690 | 48.263 | 20.236 | 1.00 | 27.09 |
| ATOM | 506 | CA  | ILE | 222 | 63.279 | 46.934 | 20.665 | 1.00 | 27.22 |
| ATOM | 507 | CB  | ILE | 222 | 63.777 | 46.591 | 22.101 | 1.00 | 26.58 |
| ATOM | 508 | CG2 | ILE | 222 | 62.815 | 47.151 | 23.171 | 1.00 | 23.83 |
| ATOM | 509 | CG1 | ILE | 222 | 63.949 | 45.065 | 22.230 | 1.00 | 24.15 |
| ATOM | 510 | CD1 | ILE | 222 | 64.727 | 44.610 | 23.458 | 1.00 | 21.43 |
| ATOM | 511 | C   | ILE | 222 | 61.797 | 46.614 | 20.519 | 1.00 | 28.33 |

FIG. 31A-11

| ATOM | 512 | O | ILE | 222 | 61.445 | 45.459 | 20.260 | 1.00 | 29.81 |
|---|---|---|---|---|---|---|---|---|---|
| ATOM | 513 | N | THR | 223 | 60.929 | 47.618 | 20.622 | 1.00 | 27.63 |
| ATOM | 514 | CA | THR | 223 | 59.494 | 47.366 | 20.505 | 1.00 | 26.83 |
| ATOM | 515 | CB | THR | 223 | 58.667 | 48.631 | 20.797 | 1.00 | 29.85 |
| ATOM | 516 | OG1 | THR | 223 | 58.839 | 48.983 | 22.180 | 1.00 | 30.67 |
| ATOM | 517 | CG2 | THR | 223 | 57.183 | 48.390 | 20.525 | 1.00 | 26.50 |
| ATOM | 518 | C | THR | 223 | 59.103 | 46.698 | 19.183 | 1.00 | 25.28 |
| ATOM | 519 | O | THR | 223 | 58.390 | 45.691 | 19.196 | 1.00 | 24.87 |
| ATOM | 520 | N | PRO | 224 | 59.535 | 47.256 | 18.031 | 1.00 | 23.96 |
| ATOM | 521 | CD | PRO | 224 | 60.138 | 48.580 | 17.792 | 1.00 | 22.28 |
| ATOM | 522 | CA | PRO | 224 | 59.181 | 46.612 | 16.759 | 1.00 | 23.13 |
| ATOM | 523 | CB | PRO | 224 | 59.747 | 47.570 | 15.699 | 1.00 | 22.96 |
| ATOM | 524 | CG | PRO | 224 | 60.762 | 48.406 | 16.443 | 1.00 | 24.53 |
| ATOM | 525 | C | PRO | 224 | 59.790 | 45.204 | 16.634 | 1.00 | 22.56 |
| ATOM | 526 | O | PRO | 224 | 59.198 | 44.332 | 15.994 | 1.00 | 22.77 |
| ATOM | 527 | N | ALA | 225 | 60.960 | 44.989 | 17.240 | 1.00 | 19.17 |
| ATOM | 528 | CA | ALA | 225 | 61.622 | 43.684 | 17.213 | 1.00 | 18.54 |
| ATOM | 529 | CB | ALA | 225 | 63.009 | 43.773 | 17.806 | 1.00 | 16.79 |
| ATOM | 530 | C | ALA | 225 | 60.802 | 42.643 | 17.969 | 1.00 | 19.08 |
| ATOM | 531 | O | ALA | 225 | 60.681 | 41.502 | 17.523 | 1.00 | 21.30 |
| ATOM | 532 | N | ILE | 226 | 60.253 | 43.033 | 19.117 | 1.00 | 18.30 |
| ATOM | 533 | CA | ILE | 226 | 59.420 | 42.147 | 19.929 | 1.00 | 18.65 |
| ATOM | 534 | CB | ILE | 226 | 59.092 | 42.779 | 21.288 | 1.00 | 17.30 |
| ATOM | 535 | CG2 | ILE | 226 | 58.057 | 41.952 | 22.020 | 1.00 | 17.76 |
| ATOM | 536 | CG1 | ILE | 226 | 60.361 | 42.915 | 22.123 | 1.00 | 17.07 |
| ATOM | 537 | CD1 | ILE | 226 | 60.175 | 43.775 | 23.351 | 1.00 | 14.65 |
| ATOM | 538 | C | ILE | 226 | 58.109 | 41.858 | 19.199 | 1.00 | 19.56 |
| ATOM | 539 | O | ILE | 226 | 57.638 | 40.719 | 19.163 | 1.00 | 19.51 |
| ATOM | 540 | N | THR | 227 | 57.521 | 42.903 | 18.627 | 1.00 | 20.26 |
| ATOM | 541 | CA | THR | 227 | 56.278 | 42.782 | 17.881 | 1.00 | 21.19 |
| ATOM | 542 | CB | THR | 227 | 55.856 | 44.150 | 17.326 | 1.00 | 22.41 |
| ATOM | 543 | OG1 | THR | 227 | 55.670 | 45.053 | 18.420 | 1.00 | 25.09 |
| ATOM | 544 | CG2 | THR | 227 | 54.558 | 44.041 | 16.560 | 1.00 | 24.29 |
| ATOM | 545 | C | THR | 227 | 56.411 | 41.758 | 16.742 | 1.00 | 20.16 |
| ATOM | 546 | O | THR | 227 | 55.487 | 40.978 | 16.496 | 1.00 | 21.18 |
| ATOM | 547 | N | ARG | 228 | 57.558 | 41.744 | 16.069 | 1.00 | 18.42 |
| ATOM | 548 | CA | ARG | 228 | 57.783 | 40.786 | 14.991 | 1.00 | 18.29 |
| ATOM | 549 | CB | ARG | 228 | 59.032 | 41.136 | 14.191 | 1.00 | 19.95 |
| ATOM | 550 | CG | ARG | 228 | 58.810 | 42.349 | 13.286 | 1.00 | 23.31 |
| ATOM | 551 | CD | ARG | 228 | 60.001 | 42.646 | 12.405 | 1.00 | 25.64 |
| ATOM | 552 | NE | ARG | 228 | 61.139 | 43.138 | 13.171 | 1.00 | 27.01 |
| ATOM | 553 | CZ | ARG | 228 | 62.209 | 42.413 | 13.468 | 1.00 | 28.20 |
| ATOM | 554 | NH1 | ARG | 228 | 62.280 | 41.155 | 13.067 | 1.00 | 28.99 |
| ATOM | 555 | NH2 | ARG | 228 | 63.219 | 42.951 | 14.141 | 1.00 | 27.25 |
| ATOM | 556 | C | ARG | 228 | 57.834 | 39.352 | 15.502 | 1.00 | 18.40 |
| ATOM | 557 | O | ARG | 228 | 57.433 | 38.431 | 14.788 | 1.00 | 17.50 |
| ATOM | 558 | N | VAL | 229 | 58.278 | 39.162 | 16.747 | 1.00 | 17.42 |
| ATOM | 559 | CA | VAL | 229 | 58.316 | 37.822 | 17.334 | 1.00 | 16.40 |
| ATOM | 560 | CB | VAL | 229 | 59.116 | 37.779 | 18.674 | 1.00 | 15.88 |
| ATOM | 561 | CG1 | VAL | 229 | 58.955 | 36.422 | 19.334 | 1.00 | 16.19 |

FIG. 31A-12

| ATOM | 562 | CG2 | VAL | 229 | 60.591 | 38.010 | 18.421 | 1.00 | 14.44 |
|---|---|---|---|---|---|---|---|---|---|
| ATOM | 563 | C | VAL | 229 | 56.852 | 37.408 | 17.552 | 1.00 | 16.75 |
| ATOM | 564 | O | VAL | 229 | 56.456 | 36.282 | 17.219 | 1.00 | 16.06 |
| ATOM | 565 | N | VAL | 230 | 56.039 | 38.343 | 18.046 | 1.00 | 16.09 |
| ATOM | 566 | CA | VAL | 230 | 54.612 | 38.097 | 18.266 | 1.00 | 16.97 |
| ATOM | 567 | CB | VAL | 230 | 53.896 | 39.327 | 18.897 | 1.00 | 18.60 |
| ATOM | 568 | CG1 | VAL | 230 | 52.401 | 39.084 | 18.972 | 1.00 | 17.19 |
| ATOM | 569 | CG2 | VAL | 230 | 54.445 | 39.629 | 20.299 | 1.00 | 17.82 |
| ATOM | 570 | C | VAL | 230 | 53.938 | 37.780 | 16.916 | 1.00 | 18.46 |
| ATOM | 571 | O | VAL | 230 | 53.115 | 36.863 | 16.828 | 1.00 | 18.46 |
| ATOM | 572 | N | ASP | 231 | 54.289 | 38.539 | 15.874 | 1.00 | 19.21 |
| ATOM | 573 | CA | ASP | 231 | 53.730 | 38.339 | 14.531 | 1.00 | 19.93 |
| ATOM | 574 | CB | ASP | 231 | 54.231 | 39.415 | 13.555 | 1.00 | 20.98 |
| ATOM | 575 | CG | ASP | 231 | 53.754 | 40.817 | 13.915 | 1.00 | 24.11 |
| ATOM | 576 | OD1 | ASP | 231 | 52.704 | 40.953 | 14.586 | 1.00 | 24.23 |
| ATOM | 577 | OD2 | ASP | 231 | 54.443 | 41.784 | 13.522 | 1.00 | 25.90 |
| ATOM | 578 | C | ASP | 231 | 54.097 | 36.962 | 13.982 | 1.00 | 19.27 |
| ATOM | 579 | O | ASP | 231 | 53.266 | 36.279 | 13.380 | 1.00 | 17.80 |
| ATOM | 580 | N | PHE | 232 | 55.357 | 36.582 | 14.163 | 1.00 | 18.91 |
| ATOM | 581 | CA | PHE | 232 | 55.841 | 35.288 | 13.712 | 1.00 | 19.65 |
| ATOM | 582 | CB | PHE | 232 | 57.308 | 35.078 | 14.104 | 1.00 | 18.14 |
| ATOM | 583 | CG | PHE | 232 | 57.752 | 33.639 | 14.027 | 1.00 | 19.70 |
| ATOM | 584 | CD1 | PHE | 232 | 57.895 | 33.005 | 12.799 | 1.00 | 19.18 |
| ATOM | 585 | CD2 | PHE | 232 | 57.987 | 32.904 | 15.188 | 1.00 | 17.61 |
| ATOM | 586 | CE1 | PHE | 232 | 58.259 | 31.660 | 12.723 | 1.00 | 19.86 |
| ATOM | 587 | CE2 | PHE | 232 | 58.350 | 31.560 | 15.126 | 1.00 | 18.98 |
| ATOM | 588 | CZ | PHE | 232 | 58.487 | 30.935 | 13.892 | 1.00 | 19.46 |
| ATOM | 589 | C | PHE | 232 | 54.996 | 34.179 | 14.320 | 1.00 | 21.02 |
| ATOM | 590 | O | PHE | 232 | 54.458 | 33.339 | 13.598 | 1.00 | 20.88 |
| ATOM | 591 | N | ALA | 233 | 54.863 | 34.202 | 15.645 | 1.00 | 21.64 |
| ATOM | 592 | CA | ALA | 233 | 54.106 | 33.187 | 16.378 | 1.00 | 21.43 |
| ATOM | 593 | CB | ALA | 233 | 54.223 | 33.443 | 17.868 | 1.00 | 18.72 |
| ATOM | 594 | C | ALA | 233 | 52.643 | 33.134 | 15.955 | 1.00 | 23.15 |
| ATOM | 595 | O | ALA | 233 | 52.043 | 32.062 | 15.857 | 1.00 | 21.76 |
| ATOM | 596 | N | LYS | 234 | 52.083 | 34.307 | 15.689 | 1.00 | 25.54 |
| ATOM | 597 | CA | LYS | 234 | 50.695 | 34.446 | 15.273 | 1.00 | 27.57 |
| ATOM | 598 | CB | LYS | 234 | 50.360 | 35.935 | 15.146 | 1.00 | 30.65 |
| ATOM | 599 | CG | LYS | 234 | 49.110 | 36.349 | 15.867 | 1.00 | 36.27 |
| ATOM | 600 | CD | LYS | 234 | 49.192 | 35.988 | 17.334 | 1.00 | 41.19 |
| ATOM | 601 | CE | LYS | 234 | 47.800 | 35.677 | 17.890 | 1.00 | 43.69 |
| ATOM | 602 | NZ | LYS | 234 | 47.119 | 34.565 | 17.147 | 1.00 | 44.98 |
| ATOM | 603 | C | LYS | 234 | 50.443 | 33.739 | 13.933 | 1.00 | 27.70 |
| ATOM | 604 | O | LYS | 234 | 49.355 | 33.200 | 13.693 | 1.00 | 28.42 |
| ATOM | 605 | N | LYS | 235 | 51.458 | 33.732 | 13.074 | 1.00 | 26.06 |
| ATOM | 606 | CA | LYS | 235 | 51.364 | 33.113 | 11.758 | 1.00 | 26.47 |
| ATOM | 607 | CB | LYS | 235 | 52.350 | 33.791 | 10.819 | 1.00 | 25.23 |
| ATOM | 608 | CG | LYS | 235 | 52.051 | 35.269 | 10.644 | 1.00 | 26.92 |
| ATOM | 609 | CD | LYS | 235 | 53.017 | 35.959 | 9.697 | 1.00 | 28.41 |
| ATOM | 610 | CE | LYS | 235 | 52.500 | 37.350 | 9.318 | 1.00 | 29.31 |
| ATOM | 611 | NZ | LYS | 235 | 53.400 | 38.026 | 8.347 | 1.00 | 30.37 |

FIG. 31A-13

| ATOM | 612 | C | LYS | 235 | 51.540 | 31.588 | 11.722 | 1.00 | 27.93 |
| --- | --- | --- | --- | --- | --- | --- | --- | --- | --- |
| ATOM | 613 | O | LYS | 235 | 51.540 | 30.984 | 10.649 | 1.00 | 29.04 |
| ATOM | 614 | N | LEU | 236 | 51.718 | 30.973 | 12.887 | 1.00 | 28.83 |
| ATOM | 615 | CA | LEU | 236 | 51.866 | 29.524 | 12.986 | 1.00 | 29.05 |
| ATOM | 616 | CB | LEU | 236 | 52.928 | 29.150 | 14.026 | 1.00 | 27.43 |
| ATOM | 617 | CG | LEU | 236 | 54.352 | 29.660 | 13.774 | 1.00 | 25.84 |
| ATOM | 618 | CD1 | LEU | 236 | 55.311 | 29.118 | 14.847 | 1.00 | 23.99 |
| ATOM | 619 | CD2 | LEU | 236 | 54.801 | 29.236 | 12.389 | 1.00 | 23.86 |
| ATOM | 620 | C | LEU | 236 | 50.513 | 28.948 | 13.392 | 1.00 | 31.19 |
| ATOM | 621 | O | LEU | 236 | 49.870 | 29.435 | 14.328 | 1.00 | 31.48 |
| ATOM | 622 | N | PRO | 237 | 50.078 | 27.875 | 12.717 | 1.00 | 34.60 |
| ATOM | 623 | CD | PRO | 237 | 50.829 | 27.156 | 11.668 | 1.00 | 35.04 |
| ATOM | 624 | CA | PRO | 237 | 48.789 | 27.223 | 13.002 | 1.00 | 36.52 |
| ATOM | 625 | CB | PRO | 237 | 48.751 | 26.081 | 11.981 | 1.00 | 37.48 |
| ATOM | 626 | CG | PRO | 237 | 50.229 | 25.776 | 11.718 | 1.00 | 36.60 |
| ATOM | 627 | C | PRO | 237 | 48.582 | 26.720 | 14.447 | 1.00 | 37.82 |
| ATOM | 628 | O | PRO | 237 | 47.629 | 27.102 | 15.125 | 1.00 | 37.08 |
| ATOM | 629 | N | MET | 238 | 49.495 | 25.893 | 14.935 | 1.00 | 40.42 |
| ATOM | 630 | CA | MET | 238 | 49.366 | 25.350 | 16.285 | 1.00 | 43.00 |
| ATOM | 631 | CB | MET | 238 | 50.453 | 24.298 | 16.549 | 1.00 | 45.20 |
| ATOM | 632 | CG | MET | 238 | 50.043 | 22.837 | 16.296 | 1.00 | 47.16 |
| ATOM | 633 | SD | MET | 238 | 50.598 | 22.117 | 14.725 | 1.00 | 52.25 |
| ATOM | 634 | CE | MET | 238 | 52.305 | 21.809 | 15.033 | 1.00 | 47.29 |
| ATOM | 635 | C | MET | 238 | 49.389 | 26.389 | 17.414 | 1.00 | 43.25 |
| ATOM | 636 | O | MET | 238 | 49.061 | 26.056 | 18.558 | 1.00 | 44.74 |
| ATOM | 637 | N | PHE | 239 | 49.720 | 27.642 | 17.088 | 1.00 | 41.55 |
| ATOM | 638 | CA | PHE | 239 | 49.825 | 28.716 | 18.091 | 1.00 | 37.31 |
| ATOM | 639 | CB | PHE | 239 | 51.031 | 29.615 | 17.765 | 1.00 | 32.40 |
| ATOM | 640 | CG | PHE | 239 | 51.293 | 30.673 | 18.795 | 1.00 | 27.12 |
| ATOM | 641 | CD1 | PHE | 239 | 52.099 | 30.398 | 19.893 | 1.00 | 24.57 |
| ATOM | 642 | CD2 | PHE | 239 | 50.705 | 31.933 | 18.686 | 1.00 | 24.70 |
| ATOM | 643 | CE1 | PHE | 239 | 52.319 | 31.356 | 20.876 | 1.00 | 25.09 |
| ATOM | 644 | CE2 | PHE | 239 | 50.915 | 32.901 | 19.659 | 1.00 | 25.90 |
| ATOM | 645 | CZ | PHE | 239 | 51.726 | 32.612 | 20.761 | 1.00 | 24.52 |
| ATOM | 646 | C | PHE | 239 | 48.574 | 29.582 | 18.352 | 1.00 | 36.84 |
| ATOM | 647 | O | PHE | 239 | 48.136 | 29.728 | 19.497 | 1.00 | 34.67 |
| ATOM | 648 | N | SER | 240 | 48.027 | 30.180 | 17.299 | 1.00 | 36.92 |
| ATOM | 649 | CA | SER | 240 | 46.857 | 31.038 | 17.433 | 1.00 | 37.16 |
| ATOM | 650 | CB | SER | 240 | 46.534 | 31.706 | 16.094 | 1.00 | 38.34 |
| ATOM | 651 | C | SER | 240 | 45.627 | 30.304 | 17.981 | 1.00 | 37.30 |
| ATOM | 652 | O | SER | 240 | 44.680 | 30.941 | 18.433 | 1.00 | 36.95 |
| ATOM | 653 | N | GLU | 241 | 45.639 | 28.974 | 17.917 | 1.00 | 37.73 |
| ATOM | 654 | CA | GLU | 241 | 44.531 | 28.155 | 18.418 | 1.00 | 38.44 |
| ATOM | 655 | CB | GLU | 241 | 44.644 | 26.705 | 17.912 | 1.00 | 42.18 |
| ATOM | 656 | CG | GLU | 241 | 44.290 | 26.471 | 16.436 | 1.00 | 48.01 |
| ATOM | 657 | CD | GLU | 241 | 44.559 | 25.028 | 15.973 | 1.00 | 50.12 |
| ATOM | 658 | OE1 | GLU | 241 | 44.375 | 24.088 | 16.779 | 1.00 | 51.14 |
| ATOM | 659 | OE2 | GLU | 241 | 44.957 | 24.838 | 14.799 | 1.00 | 50.68 |
| ATOM | 660 | C | GLU | 241 | 44.571 | 28.122 | 19.937 | 1.00 | 35.85 |
| ATOM | 661 | O | GLU | 241 | 43.561 | 27.868 | 20.598 | 1.00 | 36.01 |

FIG. 31A-14

| ATOM | 662 | N   | LEU | 242 | 45.762 | 28.329 | 20.480 | 1.00 | 33.28 |
|------|-----|-----|-----|-----|--------|--------|--------|------|-------|
| ATOM | 663 | CA  | LEU | 242 | 45.959 | 28.296 | 21.920 | 1.00 | 31.31 |
| ATOM | 664 | CB  | LEU | 242 | 47.452 | 28.382 | 22.244 | 1.00 | 29.28 |
| ATOM | 665 | CG  | LEU | 242 | 48.318 | 27.202 | 21.797 | 1.00 | 29.95 |
| ATOM | 666 | CD1 | LEU | 242 | 49.771 | 27.538 | 22.025 | 1.00 | 29.19 |
| ATOM | 667 | CD2 | LEU | 242 | 47.935 | 25.931 | 22.564 | 1.00 | 29.57 |
| ATOM | 668 | C   | LEU | 242 | 45.223 | 29.390 | 22.676 | 1.00 | 30.10 |
| ATOM | 669 | O   | LEU | 242 | 44.874 | 30.434 | 22.116 | 1.00 | 28.69 |
| ATOM | 670 | N   | PRO | 243 | 44.867 | 29.115 | 23.937 | 1.00 | 30.09 |
| ATOM | 671 | CD  | PRO | 243 | 44.783 | 27.843 | 24.674 | 1.00 | 28.53 |
| ATOM | 672 | CA  | PRO | 243 | 44.183 | 30.200 | 24.640 | 1.00 | 31.01 |
| ATOM | 673 | CB  | PRO | 243 | 43.829 | 29.577 | 26.005 | 1.00 | 30.34 |
| ATOM | 674 | CG  | PRO | 243 | 44.640 | 28.300 | 26.093 | 1.00 | 29.25 |
| ATOM | 675 | C   | PRO | 243 | 45.195 | 31.356 | 24.774 | 1.00 | 31.71 |
| ATOM | 676 | O   | PRO | 243 | 46.412 | 31.128 | 24.840 | 1.00 | 30.69 |
| ATOM | 677 | N   | CYS | 244 | 44.694 | 32.585 | 24.804 | 1.00 | 32.36 |
| ATOM | 678 | CA  | CYS | 244 | 45.539 | 33.763 | 24.920 | 1.00 | 33.57 |
| ATOM | 679 | CB  | CYS | 244 | 44.675 | 35.028 | 25.050 | 1.00 | 37.62 |
| ATOM | 680 | SG  | CYS | 244 | 45.262 | 36.418 | 24.022 | 1.00 | 51.95 |
| ATOM | 681 | C   | CYS | 244 | 46.536 | 33.660 | 26.081 | 1.00 | 31.12 |
| ATOM | 682 | O   | CYS | 244 | 47.677 | 34.087 | 25.942 | 1.00 | 30.37 |
| ATOM | 683 | N   | GLU | 245 | 46.124 | 33.045 | 27.194 | 1.00 | 30.00 |
| ATOM | 684 | CA  | GLU | 245 | 46.993 | 32.877 | 28.366 | 1.00 | 29.62 |
| ATOM | 685 | CB  | GLU | 245 | 46.270 | 32.159 | 29.514 | 1.00 | 33.10 |
| ATOM | 686 | CG  | GLU | 245 | 45.325 | 33.018 | 30.333 | 1.00 | 36.43 |
| ATOM | 687 | CD  | GLU | 245 | 43.882 | 32.940 | 29.860 | 1.00 | 37.87 |
| ATOM | 688 | OE1 | GLU | 245 | 42.989 | 33.006 | 30.730 | 1.00 | 37.36 |
| ATOM | 689 | OE2 | GLU | 245 | 43.639 | 32.813 | 28.634 | 1.00 | 39.63 |
| ATOM | 690 | C   | GLU | 245 | 48.239 | 32.077 | 28.030 | 1.00 | 28.34 |
| ATOM | 691 | O   | GLU | 245 | 49.322 | 32.343 | 28.557 | 1.00 | 27.88 |
| ATOM | 692 | N   | ASP | 246 | 48.063 | 31.043 | 27.213 | 1.00 | 26.10 |
| ATOM | 693 | CA  | ASP | 246 | 49.182 | 30.212 | 26.798 | 1.00 | 25.23 |
| ATOM | 694 | CB  | ASP | 246 | 48.685 | 28.923 | 26.135 | 1.00 | 26.98 |
| ATOM | 695 | CG  | ASP | 246 | 48.146 | 27.912 | 27.137 | 1.00 | 29.13 |
| ATOM | 696 | OD1 | ASP | 246 | 48.158 | 28.193 | 28.354 | 1.00 | 26.52 |
| ATOM | 697 | OD2 | ASP | 246 | 47.712 | 26.824 | 26.696 | 1.00 | 31.38 |
| ATOM | 698 | C   | ASP | 246 | 50.065 | 30.983 | 25.826 | 1.00 | 23.57 |
| ATOM | 699 | O   | ASP | 246 | 51.288 | 30.993 | 25.955 | 1.00 | 22.61 |
| ATOM | 700 | N   | GLN | 247 | 49.431 | 31.630 | 24.852 | 1.00 | 23.23 |
| ATOM | 701 | CA  | GLN | 247 | 50.144 | 32.408 | 23.855 | 1.00 | 22.20 |
| ATOM | 702 | CB  | GLN | 247 | 49.159 | 33.178 | 22.991 | 1.00 | 22.06 |
| ATOM | 703 | CG  | GLN | 247 | 48.329 | 32.307 | 22.066 | 1.00 | 22.74 |
| ATOM | 704 | CD  | GLN | 247 | 47.435 | 33.141 | 21.169 | 1.00 | 24.91 |
| ATOM | 705 | OE1 | GLN | 247 | 47.860 | 34.160 | 20.625 | 1.00 | 26.30 |
| ATOM | 706 | NE2 | GLN | 247 | 46.186 | 32.732 | 21.035 | 1.00 | 25.65 |
| ATOM | 707 | C   | GLN | 247 | 51.098 | 33.374 | 24.528 | 1.00 | 22.10 |
| ATOM | 708 | O   | GLN | 247 | 52.280 | 33.454 | 24.182 | 1.00 | 23.07 |
| ATOM | 709 | N   | ILE | 248 | 50.587 | 34.076 | 25.527 | 1.00 | 23.27 |
| ATOM | 710 | CA  | ILE | 248 | 51.379 | 35.042 | 26.276 | 1.00 | 23.21 |
| ATOM | 711 | CB  | ILE | 248 | 50.473 | 35.824 | 27.273 | 1.00 | 24.59 |

FIG. 31A-15

| ATOM | 712 | CG2 | ILE | 248 | 51.304 | 36.682 | 28.242 | 1.00 | 24.09 |
|---|---|---|---|---|---|---|---|---|---|
| ATOM | 713 | CG1 | ILE | 248 | 49.499 | 36.707 | 26.487 | 1.00 | 23.47 |
| ATOM | 714 | CD1 | ILE | 248 | 48.413 | 37.323 | 27.341 | 1.00 | 23.84 |
| ATOM | 715 | C | ILE | 248 | 52.568 | 34.387 | 26.986 | 1.00 | 22.27 |
| ATOM | 716 | O | ILE | 248 | 53.705 | 34.833 | 26.829 | 1.00 | 22.06 |
| ATOM | 717 | N | ILE | 249 | 52.321 | 33.313 | 27.729 | 1.00 | 21.40 |
| ATOM | 718 | CA | ILE | 249 | 53.398 | 32.630 | 28.440 | 1.00 | 21.40 |
| ATOM | 719 | CB | ILE | 249 | 52.850 | 31.438 | 29.279 | 1.00 | 23.53 |
| ATOM | 720 | CG2 | ILE | 249 | 53.972 | 30.489 | 29.711 | 1.00 | 21.44 |
| ATOM | 721 | CG1 | ILE | 249 | 52.098 | 31.963 | 30.500 | 1.00 | 22.76 |
| ATOM | 722 | CD1 | ILE | 249 | 51.252 | 30.911 | 31.175 | 1.00 | 25.03 |
| ATOM | 723 | C | ILE | 249 | 54.481 | 32.148 | 27.470 | 1.00 | 22.24 |
| ATOM | 724 | O | ILE | 249 | 55.677 | 32.321 | 27.733 | 1.00 | 22.90 |
| ATOM | 725 | N | LEU | 250 | 54.072 | 31.582 | 26.334 | 1.00 | 22.65 |
| ATOM | 726 | CA | LEU | 250 | 55.028 | 31.079 | 25.345 | 1.00 | 21.40 |
| ATOM | 727 | CB | LEU | 250 | 54.319 | 30.290 | 24.239 | 1.00 | 20.06 |
| ATOM | 728 | CG | LEU | 250 | 53.566 | 29.038 | 24.677 | 1.00 | 20.22 |
| ATOM | 729 | CD1 | LEU | 250 | 52.952 | 28.406 | 23.453 | 1.00 | 19.19 |
| ATOM | 730 | CD2 | LEU | 250 | 54.494 | 28.050 | 25.386 | 1.00 | 18.52 |
| ATOM | 731 | C | LEU | 250 | 55.850 | 32.209 | 24.736 | 1.00 | 20.82 |
| ATOM | 732 | O | LEU | 250 | 57.069 | 32.094 | 24.603 | 1.00 | 20.27 |
| ATOM | 733 | N | LEU | 251 | 55.179 | 33.302 | 24.384 | 1.00 | 22.14 |
| ATOM | 734 | CA | LEU | 251 | 55.842 | 34.467 | 23.805 | 1.00 | 22.90 |
| ATOM | 735 | CB | LEU | 251 | 54.806 | 35.543 | 23.471 | 1.00 | 22.76 |
| ATOM | 736 | CG | LEU | 251 | 54.513 | 35.899 | 22.012 | 1.00 | 23.35 |
| ATOM | 737 | CD1 | LEU | 251 | 55.347 | 35.103 | 21.047 | 1.00 | 22.38 |
| ATOM | 738 | CD2 | LEU | 251 | 53.040 | 35.708 | 21.747 | 1.00 | 22.86 |
| ATOM | 739 | C | LEU | 251 | 56.891 | 35.030 | 24.776 | 1.00 | 23.67 |
| ATOM | 740 | O | LEU | 251 | 58.051 | 35.234 | 24.402 | 1.00 | 22.58 |
| ATOM | 741 | N | LYS | 252 | 56.491 | 35.236 | 26.029 | 1.00 | 24.64 |
| ATOM | 742 | CA | LYS | 252 | 57.395 | 35.754 | 27.057 | 1.00 | 26.22 |
| ATOM | 743 | CB | LYS | 252 | 56.617 | 36.037 | 28.350 | 1.00 | 27.79 |
| ATOM | 744 | CG | LYS | 252 | 55.351 | 36.838 | 28.093 | 1.00 | 32.69 |
| ATOM | 745 | CD | LYS | 252 | 55.185 | 38.023 | 29.003 | 1.00 | 35.85 |
| ATOM | 746 | CE | LYS | 252 | 54.773 | 37.626 | 30.397 | 1.00 | 39.34 |
| ATOM | 747 | NZ | LYS | 252 | 54.477 | 38.870 | 31.168 | 1.00 | 44.60 |
| ATOM | 748 | C | LYS | 252 | 58.566 | 34.793 | 27.312 | 1.00 | 25.26 |
| ATOM | 749 | O | LYS | 252 | 59.701 | 35.222 | 27.555 | 1.00 | 26.67 |
| ATOM | 750 | N | GLY | 253 | 58.306 | 33.497 | 27.195 | 1.00 | 23.97 |
| ATOM | 751 | CA | GLY | 253 | 59.356 | 32.521 | 27.404 | 1.00 | 22.00 |
| ATOM | 752 | C | GLY | 253 | 60.397 | 32.429 | 26.292 | 1.00 | 23.10 |
| ATOM | 753 | O | GLY | 253 | 61.568 | 32.165 | 26.585 | 1.00 | 25.12 |
| ATOM | 754 | N | CYS | 254 | 60.014 | 32.702 | 25.041 | 1.00 | 22.27 |
| ATOM | 755 | CA | CYS | 254 | 60.944 | 32.584 | 23.908 | 1.00 | 20.91 |
| ATOM | 756 | CB | CYS | 254 | 60.353 | 31.648 | 22.845 | 1.00 | 21.46 |
| ATOM | 757 | SG | CYS | 254 | 58.992 | 32.385 | 21.893 | 1.00 | 22.92 |
| ATOM | 758 | C | CYS | 254 | 61.354 | 33.869 | 23.201 | 1.00 | 19.77 |
| ATOM | 759 | O | CYS | 254 | 62.215 | 33.834 | 22.316 | 1.00 | 19.88 |
| ATOM | 760 | N | CYS | 255 | 60.731 | 34.984 | 23.561 | 1.00 | 19.56 |
| ATOM | 761 | CA | CYS | 255 | 61.018 | 36.264 | 22.917 | 1.00 | 21.16 |

FIG. 31A-16

| ATOM | 762 | CB  | CYS | 255 | 60.292 | 37.407 | 23.634 | 1.00 | 21.21 |
|------|-----|-----|-----|-----|--------|--------|--------|------|-------|
| ATOM | 763 | SG  | CYS | 255 | 60.404 | 38.957 | 22.735 | 1.00 | 22.22 |
| ATOM | 764 | C   | CYS | 255 | 62.504 | 36.590 | 22.775 | 1.00 | 21.36 |
| ATOM | 765 | O   | CYS | 255 | 62.986 | 36.847 | 21.667 | 1.00 | 20.58 |
| ATOM | 766 | N   | MET | 256 | 63.232 | 36.574 | 23.887 | 1.00 | 20.52 |
| ATOM | 767 | CA  | MET | 256 | 64.657 | 36.874 | 23.835 | 1.00 | 20.07 |
| ATOM | 768 | CB  | MET | 256 | 65.255 | 36.967 | 25.253 | 1.00 | 20.39 |
| ATOM | 769 | CG  | MET | 256 | 66.744 | 37.360 | 25.267 | 1.00 | 19.20 |
| ATOM | 770 | SD  | MET | 256 | 67.066 | 38.952 | 24.447 | 1.00 | 20.26 |
| ATOM | 771 | CE  | MET | 256 | 68.856 | 38.971 | 24.375 | 1.00 | 18.47 |
| ATOM | 772 | C   | MET | 256 | 65.408 | 35.830 | 23.005 | 1.00 | 18.75 |
| ATOM | 773 | O   | MET | 256 | 66.305 | 36.164 | 22.225 | 1.00 | 18.15 |
| ATOM | 774 | N   | GLU | 257 | 65.035 | 34.568 | 23.170 | 1.00 | 19.00 |
| ATOM | 775 | CA  | GLU | 257 | 65.685 | 33.480 | 22.443 | 1.00 | 19.71 |
| ATOM | 776 | CB  | GLU | 257 | 65.104 | 32.145 | 22.882 | 1.00 | 21.15 |
| ATOM | 777 | CG  | GLU | 257 | 65.451 | 31.821 | 24.319 | 1.00 | 26.39 |
| ATOM | 778 | CD  | GLU | 257 | 64.513 | 30.820 | 24.929 | 1.00 | 30.75 |
| ATOM | 779 | OE1 | GLU | 257 | 63.875 | 30.069 | 24.162 | 1.00 | 32.36 |
| ATOM | 780 | OE2 | GLU | 257 | 64.415 | 30.783 | 26.172 | 1.00 | 33.70 |
| ATOM | 781 | C   | GLU | 257 | 65.545 | 33.648 | 20.940 | 1.00 | 18.54 |
| ATOM | 782 | O   | GLU | 257 | 66.521 | 33.506 | 20.197 | 1.00 | 17.58 |
| ATOM | 783 | N   | ILE | 258 | 64.336 | 33.977 | 20.497 | 1.00 | 17.78 |
| ATOM | 784 | CA  | ILE | 258 | 64.101 | 34.176 | 19.081 | 1.00 | 17.60 |
| ATOM | 785 | CB  | ILE | 258 | 62.590 | 34.267 | 18.765 | 1.00 | 16.35 |
| ATOM | 786 | CG2 | ILE | 258 | 62.376 | 34.777 | 17.326 | 1.00 | 16.20 |
| ATOM | 787 | CG1 | ILE | 258 | 61.935 | 32.884 | 18.980 | 1.00 | 17.24 |
| ATOM | 788 | CD1 | ILE | 258 | 60.437 | 32.787 | 18.593 | 1.00 | 14.08 |
| ATOM | 789 | C   | ILE | 258 | 64.872 | 35.408 | 18.595 | 1.00 | 19.11 |
| ATOM | 790 | O   | ILE | 258 | 65.609 | 35.326 | 17.601 | 1.00 | 19.02 |
| ATOM | 791 | N   | MET | 259 | 64.785 | 36.517 | 19.341 | 1.00 | 19.71 |
| ATOM | 792 | CA  | MET | 259 | 65.486 | 37.744 | 18.956 | 1.00 | 18.43 |
| ATOM | 793 | CB  | MET | 259 | 65.162 | 38.890 | 19.910 | 1.00 | 19.99 |
| ATOM | 794 | CG  | MET | 259 | 63.700 | 39.278 | 19.962 | 1.00 | 21.15 |
| ATOM | 795 | SD  | MET | 259 | 63.452 | 40.921 | 20.700 | 1.00 | 24.33 |
| ATOM | 796 | CE  | MET | 259 | 63.769 | 40.595 | 22.415 | 1.00 | 22.50 |
| ATOM | 797 | C   | MET | 259 | 66.993 | 37.540 | 18.888 | 1.00 | 18.64 |
| ATOM | 798 | O   | MET | 259 | 67.638 | 37.993 | 17.941 | 1.00 | 19.96 |
| ATOM | 799 | N   | SER | 260 | 67.556 | 36.858 | 19.884 | 1.00 | 17.37 |
| ATOM | 800 | CA  | SER | 260 | 68.993 | 36.592 | 19.915 | 1.00 | 16.76 |
| ATOM | 801 | CB  | SER | 260 | 69.387 | 35.840 | 21.195 | 1.00 | 17.25 |
| ATOM | 802 | OG  | SER | 260 | 69.078 | 36.589 | 22.346 | 1.00 | 22.89 |
| ATOM | 803 | C   | SER | 260 | 69.387 | 35.750 | 18.717 | 1.00 | 15.13 |
| ATOM | 804 | O   | SER | 260 | 70.460 | 35.941 | 18.137 | 1.00 | 16.62 |
| ATOM | 805 | N   | LEU | 261 | 68.539 | 34.781 | 18.385 | 1.00 | 15.15 |
| ATOM | 806 | CA  | LEU | 261 | 68.802 | 33.900 | 17.262 | 1.00 | 15.31 |
| ATOM | 807 | CB  | LEU | 261 | 67.708 | 32.834 | 17.153 | 1.00 | 15.43 |
| ATOM | 808 | CG  | LEU | 261 | 67.652 | 32.014 | 15.858 | 1.00 | 15.82 |
| ATOM | 809 | CD1 | LEU | 261 | 68.963 | 31.251 | 15.621 | 1.00 | 16.35 |
| ATOM | 810 | CD2 | LEU | 261 | 66.470 | 31.060 | 15.937 | 1.00 | 13.72 |
| ATOM | 811 | C   | LEU | 261 | 68.839 | 34.741 | 16.001 | 1.00 | 16.31 |

FIG. 31A-17

| ATOM | 812 | O | LEU | 261 | 69.766 | 34.619 | 15.194 | 1.00 | 16.68 |
|---|---|---|---|---|---|---|---|---|---|
| ATOM | 813 | N | ARG | 262 | 67.848 | 35.620 | 15.853 | 1.00 | 16.47 |
| ATOM | 814 | CA | ARG | 262 | 67.778 | 36.493 | 14.680 | 1.00 | 16.66 |
| ATOM | 815 | CB | ARG | 262 | 66.475 | 37.279 | 14.693 | 1.00 | 16.00 |
| ATOM | 816 | CG | ARG | 262 | 65.291 | 36.404 | 14.354 | 1.00 | 15.62 |
| ATOM | 817 | CD | ARG | 262 | 63.995 | 37.167 | 14.378 | 1.00 | 17.31 |
| ATOM | 818 | NE | ARG | 262 | 62.967 | 36.454 | 13.628 | 1.00 | 20.09 |
| ATOM | 819 | CZ | ARG | 262 | 61.755 | 36.932 | 13.361 | 1.00 | 21.06 |
| ATOM | 820 | NH1 | ARG | 262 | 61.390 | 38.136 | 13.787 | 1.00 | 19.02 |
| ATOM | 821 | NH2 | ARG | 262 | 60.909 | 36.207 | 12.640 | 1.00 | 22.63 |
| ATOM | 822 | C | ARG | 262 | 69.003 | 37.396 | 14.527 | 1.00 | 16.80 |
| ATOM | 823 | O | ARG | 262 | 69.440 | 37.664 | 13.412 | 1.00 | 16.82 |
| ATOM | 824 | N | ALA | 263 | 69.578 | 37.832 | 15.650 | 1.00 | 17.77 |
| ATOM | 825 | CA | ALA | 263 | 70.795 | 38.647 | 15.637 | 1.00 | 18.41 |
| ATOM | 826 | CB | ALA | 263 | 70.996 | 39.337 | 17.004 | 1.00 | 18.26 |
| ATOM | 827 | C | ALA | 263 | 71.998 | 37.740 | 15.327 | 1.00 | 19.15 |
| ATOM | 828 | O | ALA | 263 | 72.837 | 38.063 | 14.475 | 1.00 | 19.40 |
| ATOM | 829 | N | ALA | 264 | 72.056 | 36.587 | 15.996 | 1.00 | 19.84 |
| ATOM | 830 | CA | ALA | 264 | 73.155 | 35.633 | 15.818 | 1.00 | 20.35 |
| ATOM | 831 | CB | ALA | 264 | 73.045 | 34.483 | 16.832 | 1.00 | 18.09 |
| ATOM | 832 | C | ALA | 264 | 73.289 | 35.079 | 14.398 | 1.00 | 20.66 |
| ATOM | 833 | O | ALA | 264 | 74.406 | 34.870 | 13.922 | 1.00 | 21.04 |
| ATOM | 834 | N | VAL | 265 | 72.173 | 34.822 | 13.723 | 1.00 | 21.14 |
| ATOM | 835 | CA | VAL | 265 | 72.249 | 34.299 | 12.358 | 1.00 | 22.96 |
| ATOM | 836 | CB | VAL | 265 | 70.910 | 33.660 | 11.879 | 1.00 | 21.04 |
| ATOM | 837 | CG1 | VAL | 265 | 70.458 | 32.600 | 12.866 | 1.00 | 19.48 |
| ATOM | 838 | CG2 | VAL | 265 | 69.838 | 34.708 | 11.698 | 1.00 | 18.96 |
| ATOM | 839 | C | VAL | 265 | 72.718 | 35.387 | 11.382 | 1.00 | 24.66 |
| ATOM | 840 | O | VAL | 265 | 73.026 | 35.103 | 10.224 | 1.00 | 26.03 |
| ATOM | 841 | N | ARG | 266 | 72.777 | 36.628 | 11.858 | 1.00 | 25.11 |
| ATOM | 842 | CA | ARG | 266 | 73.233 | 37.729 | 11.031 | 1.00 | 25.60 |
| ATOM | 843 | CB | ARG | 266 | 72.187 | 38.819 | 10.964 | 1.00 | 24.09 |
| ATOM | 844 | CG | ARG | 266 | 71.035 | 38.427 | 10.088 | 1.00 | 23.37 |
| ATOM | 845 | CD | ARG | 266 | 69.998 | 39.492 | 10.098 | 1.00 | 24.80 |
| ATOM | 846 | NE | ARG | 266 | 68.961 | 39.253 | 9.109 | 1.00 | 24.01 |
| ATOM | 847 | CZ | ARG | 266 | 67.833 | 39.940 | 9.069 | 1.00 | 23.26 |
| ATOM | 848 | NH1 | ARG | 266 | 67.613 | 40.880 | 9.970 | 1.00 | 24.16 |
| ATOM | 849 | NH2 | ARG | 266 | 66.960 | 39.733 | 8.099 | 1.00 | 23.31 |
| ATOM | 850 | C | ARG | 266 | 74.543 | 38.273 | 11.543 | 1.00 | 28.07 |
| ATOM | 851 | O | ARG | 266 | 74.786 | 39.479 | 11.517 | 1.00 | 29.67 |
| ATOM | 852 | N | TYR | 267 | 75.367 | 37.366 | 12.053 | 1.00 | 28.90 |
| ATOM | 853 | CA | TYR | 267 | 76.679 | 37.714 | 12.558 | 1.00 | 30.23 |
| ATOM | 854 | CB | TYR | 267 | 77.223 | 36.584 | 13.434 | 1.00 | 29.98 |
| ATOM | 855 | CG | TYR | 267 | 78.699 | 36.702 | 13.727 | 1.00 | 31.75 |
| ATOM | 856 | CD1 | TYR | 267 | 79.179 | 37.577 | 14.712 | 1.00 | 31.21 |
| ATOM | 857 | CE1 | TYR | 267 | 80.544 | 37.705 | 14.950 | 1.00 | 31.29 |
| ATOM | 858 | CD2 | TYR | 267 | 79.625 | 35.958 | 12.994 | 1.00 | 31.84 |
| ATOM | 859 | CE2 | TYR | 267 | 80.986 | 36.078 | 13.222 | 1.00 | 32.15 |
| ATOM | 860 | CZ | TYR | 267 | 81.442 | 36.949 | 14.197 | 1.00 | 32.60 |
| ATOM | 861 | OH | TYR | 267 | 82.801 | 37.052 | 14.389 | 1.00 | 34.13 |

FIG. 31A-18

| ATOM | 862 | C   | TYR | 267 | 77.570 | 37.900 | 11.343 | 1.00 | 31.17 |
|------|-----|-----|-----|-----|--------|--------|--------|------|-------|
| ATOM | 863 | O   | TYR | 267 | 77.543 | 37.086 | 10.426 | 1.00 | 30.91 |
| ATOM | 864 | N   | ASP | 268 | 78.361 | 38.966 | 11.336 | 1.00 | 33.09 |
| ATOM | 865 | CA  | ASP | 268 | 79.252 | 39.233 | 10.216 | 1.00 | 35.57 |
| ATOM | 866 | CB  | ASP | 268 | 79.085 | 40.679 | 9.747  | 1.00 | 39.39 |
| ATOM | 867 | CG  | ASP | 268 | 79.796 | 40.954 | 8.432  | 1.00 | 42.22 |
| ATOM | 868 | OD1 | ASP | 268 | 79.426 | 40.331 | 7.412  | 1.00 | 46.07 |
| ATOM | 869 | OD2 | ASP | 268 | 80.718 | 41.798 | 8.415  | 1.00 | 44.30 |
| ATOM | 870 | C   | ASP | 268 | 80.700 | 38.967 | 10.620 | 1.00 | 35.72 |
| ATOM | 871 | O   | ASP | 268 | 81.287 | 39.737 | 11.384 | 1.00 | 34.49 |
| ATOM | 872 | N   | PRO | 269 | 81.295 | 37.872 | 10.108 | 1.00 | 37.00 |
| ATOM | 873 | CD  | PRO | 269 | 80.712 | 36.887 | 9.182  | 1.00 | 36.77 |
| ATOM | 874 | CA  | PRO | 269 | 82.679 | 37.514 | 10.427 | 1.00 | 38.52 |
| ATOM | 875 | CB  | PRO | 269 | 82.905 | 36.239 | 9.611  | 1.00 | 37.06 |
| ATOM | 876 | CG  | PRO | 269 | 81.549 | 35.669 | 9.453  | 1.00 | 36.19 |
| ATOM | 877 | C   | PRO | 269 | 83.656 | 38.613 | 10.019 | 1.00 | 40.96 |
| ATOM | 878 | O   | PRO | 269 | 84.586 | 38.929 | 10.760 | 1.00 | 42.23 |
| ATOM | 879 | N   | ALA | 270 | 83.418 | 39.209 | 8.854  | 1.00 | 41.92 |
| ATOM | 880 | CA  | ALA | 270 | 84.277 | 40.272 | 8.342  | 1.00 | 42.08 |
| ATOM | 881 | CB  | ALA | 270 | 83.709 | 40.838 | 7.029  | 1.00 | 42.64 |
| ATOM | 882 | C   | ALA | 270 | 84.495 | 41.394 | 9.355  | 1.00 | 41.70 |
| ATOM | 883 | O   | ALA | 270 | 85.632 | 41.709 | 9.684  | 1.00 | 42.25 |
| ATOM | 884 | N   | SER | 271 | 83.408 | 41.970 | 9.865  | 1.00 | 41.87 |
| ATOM | 885 | CA  | SER | 271 | 83.495 | 43.073 | 10.830 | 1.00 | 40.75 |
| ATOM | 886 | CB  | SER | 271 | 82.454 | 44.143 | 10.500 | 1.00 | 40.60 |
| ATOM | 887 | OG  | SER | 271 | 81.150 | 43.590 | 10.464 | 1.00 | 40.31 |
| ATOM | 888 | C   | SER | 271 | 83.344 | 42.658 | 12.290 | 1.00 | 39.99 |
| ATOM | 889 | O   | SER | 271 | 83.484 | 43.487 | 13.194 | 1.00 | 38.77 |
| ATOM | 890 | N   | ASP | 272 | 83.042 | 41.381 | 12.508 | 1.00 | 38.94 |
| ATOM | 891 | CA  | ASP | 272 | 82.859 | 40.844 | 13.845 | 1.00 | 37.78 |
| ATOM | 892 | CB  | ASP | 272 | 84.182 | 40.904 | 14.625 | 1.00 | 38.86 |
| ATOM | 893 | CG  | ASP | 272 | 84.094 | 40.255 | 16.000 | 1.00 | 41.09 |
| ATOM | 894 | OD1 | ASP | 272 | 83.342 | 39.275 | 16.173 | 1.00 | 41.64 |
| ATOM | 895 | OD2 | ASP | 272 | 84.781 | 40.734 | 16.924 | 1.00 | 43.84 |
| ATOM | 896 | C   | ASP | 272 | 81.744 | 41.634 | 14.536 | 1.00 | 36.92 |
| ATOM | 897 | O   | ASP | 272 | 81.907 | 42.156 | 15.648 | 1.00 | 37.56 |
| ATOM | 898 | N   | THR | 273 | 80.603 | 41.723 | 13.865 | 1.00 | 33.65 |
| ATOM | 899 | CA  | THR | 273 | 79.469 | 42.443 | 14.425 | 1.00 | 31.57 |
| ATOM | 900 | CB  | THR | 273 | 79.246 | 43.790 | 13.695 | 1.00 | 31.69 |
| ATOM | 901 | OG1 | THR | 273 | 79.087 | 43.557 | 12.289 | 1.00 | 30.71 |
| ATOM | 902 | CG2 | THR | 273 | 80.426 | 44.730 | 13.922 | 1.00 | 31.53 |
| ATOM | 903 | C   | THR | 273 | 78.184 | 41.631 | 14.310 | 1.00 | 30.15 |
| ATOM | 904 | O   | THR | 273 | 78.104 | 40.697 | 13.504 | 1.00 | 30.10 |
| ATOM | 905 | N   | LEU | 274 | 77.213 | 41.942 | 15.164 | 1.00 | 27.09 |
| ATOM | 906 | CA  | LEU | 274 | 75.907 | 41.303 | 15.103 | 1.00 | 25.94 |
| ATOM | 907 | CB  | LEU | 274 | 75.396 | 40.936 | 16.496 | 1.00 | 24.47 |
| ATOM | 908 | CG  | LEU | 274 | 76.020 | 39.731 | 17.206 | 1.00 | 23.33 |
| ATOM | 909 | CD1 | LEU | 274 | 75.436 | 39.631 | 18.602 | 1.00 | 21.14 |
| ATOM | 910 | CD2 | LEU | 274 | 75.792 | 38.444 | 16.427 | 1.00 | 20.04 |
| ATOM | 911 | C   | LEU | 274 | 75.010 | 42.377 | 14.500 | 1.00 | 26.57 |

FIG. 31A-19

| ATOM | 912 | O   | LEU | 274 | 75.339 | 43.557 | 14.568 | 1.00 | 27.03 |
|------|-----|-----|-----|-----|--------|--------|--------|------|-------|
| ATOM | 913 | N   | THR | 275 | 73.914 | 41.987 | 13.865 | 1.00 | 26.60 |
| ATOM | 914 | CA  | THR | 275 | 73.009 | 42.966 | 13.285 | 1.00 | 26.48 |
| ATOM | 915 | CB  | THR | 275 | 72.786 | 42.717 | 11.781 | 1.00 | 26.52 |
| ATOM | 916 | OG1 | THR | 275 | 74.044 | 42.719 | 11.097 | 1.00 | 28.67 |
| ATOM | 917 | CG2 | THR | 275 | 71.919 | 43.799 | 11.198 | 1.00 | 27.35 |
| ATOM | 918 | C   | THR | 275 | 71.674 | 42.898 | 14.014 | 1.00 | 26.57 |
| ATOM | 919 | O   | THR | 275 | 71.069 | 41.825 | 14.121 | 1.00 | 28.50 |
| ATOM | 920 | N   | LEU | 276 | 71.236 | 44.026 | 14.564 | 1.00 | 25.18 |
| ATOM | 921 | CA  | LEU | 276 | 69.970 | 44.069 | 15.276 | 1.00 | 24.61 |
| ATOM | 922 | CB  | LEU | 276 | 70.057 | 44.987 | 16.506 | 1.00 | 23.61 |
| ATOM | 923 | CG  | LEU | 276 | 71.199 | 44.730 | 17.503 | 1.00 | 24.36 |
| ATOM | 924 | CD1 | LEU | 276 | 71.039 | 45.654 | 18.709 | 1.00 | 19.91 |
| ATOM | 925 | CD2 | LEU | 276 | 71.225 | 43.253 | 17.947 | 1.00 | 22.20 |
| ATOM | 926 | C   | LEU | 276 | 68.894 | 44.560 | 14.322 | 1.00 | 25.63 |
| ATOM | 927 | O   | LEU | 276 | 69.100 | 45.556 | 13.623 | 1.00 | 25.35 |
| ATOM | 928 | N   | SER | 277 | 67.787 | 43.814 | 14.249 | 1.00 | 25.94 |
| ATOM | 929 | CA  | SER | 277 | 66.634 | 44.141 | 13.403 | 1.00 | 24.61 |
| ATOM | 930 | CB  | SER | 277 | 65.874 | 45.335 | 13.987 | 1.00 | 21.96 |
| ATOM | 931 | OG  | SER | 277 | 65.368 | 45.029 | 15.273 | 1.00 | 19.68 |
| ATOM | 932 | C   | SER | 277 | 67.005 | 44.406 | 11.946 | 1.00 | 25.20 |
| ATOM | 933 | O   | SER | 277 | 66.350 | 45.199 | 11.267 | 1.00 | 25.21 |
| ATOM | 934 | N   | GLY | 278 | 68.067 | 43.747 | 11.489 | 1.00 | 27.08 |
| ATOM | 935 | CA  | GLY | 278 | 68.556 | 43.899 | 10.127 | 1.00 | 29.27 |
| ATOM | 936 | C   | GLY | 278 | 69.022 | 45.297 | 9.753  | 1.00 | 31.57 |
| ATOM | 937 | O   | GLY | 278 | 69.303 | 45.564 | 8.591  | 1.00 | 31.42 |
| ATOM | 938 | N   | GLU | 279 | 69.159 | 46.177 | 10.740 | 1.00 | 33.41 |
| ATOM | 939 | CA  | GLU | 279 | 69.558 | 47.560 | 10.484 | 1.00 | 34.84 |
| ATOM | 940 | CB  | GLU | 279 | 68.345 | 48.485 | 10.650 | 1.00 | 36.16 |
| ATOM | 941 | CG  | GLU | 279 | 67.843 | 48.606 | 12.090 | 1.00 | 38.08 |
| ATOM | 942 | CD  | GLU | 279 | 66.566 | 49.419 | 12.206 | 1.00 | 41.07 |
| ATOM | 943 | OE1 | GLU | 279 | 66.475 | 50.279 | 13.108 | 1.00 | 41.98 |
| ATOM | 944 | OE2 | GLU | 279 | 65.643 | 49.197 | 11.399 | 1.00 | 43.80 |
| ATOM | 945 | C   | GLU | 279 | 70.706 | 48.116 | 11.326 | 1.00 | 34.38 |
| ATOM | 946 | O   | GLU | 279 | 71.366 | 49.057 | 10.901 | 1.00 | 35.60 |
| ATOM | 947 | N   | MET | 280 | 70.944 | 47.565 | 12.511 | 1.00 | 33.43 |
| ATOM | 948 | CA  | MET | 280 | 72.014 | 48.085 | 13.358 | 1.00 | 32.27 |
| ATOM | 949 | CB  | MET | 280 | 71.443 | 48.544 | 14.702 | 1.00 | 31.81 |
| ATOM | 950 | CG  | MET | 280 | 72.471 | 49.181 | 15.637 | 1.00 | 29.76 |
| ATOM | 951 | SD  | MET | 280 | 71.813 | 49.482 | 17.289 | 1.00 | 29.63 |
| ATOM | 952 | CE  | MET | 280 | 70.592 | 50.735 | 16.989 | 1.00 | 24.91 |
| ATOM | 953 | C   | MET | 280 | 73.161 | 47.119 | 13.603 | 1.00 | 32.51 |
| ATOM | 954 | O   | MET | 280 | 72.995 | 46.117 | 14.303 | 1.00 | 32.78 |
| ATOM | 955 | N   | ALA | 281 | 74.321 | 47.408 | 13.021 | 1.00 | 31.74 |
| ATOM | 956 | CA  | ALA | 281 | 75.491 | 46.564 | 13.231 | 1.00 | 32.25 |
| ATOM | 957 | CB  | ALA | 281 | 76.494 | 46.740 | 12.108 | 1.00 | 30.91 |
| ATOM | 958 | C   | ALA | 281 | 76.091 | 47.006 | 14.563 | 1.00 | 33.09 |
| ATOM | 959 | O   | ALA | 281 | 76.261 | 48.202 | 14.805 | 1.00 | 34.06 |
| ATOM | 960 | N   | VAL | 282 | 76.358 | 46.053 | 15.447 | 1.00 | 33.78 |
| ATOM | 961 | CA  | VAL | 282 | 76.913 | 46.366 | 16.755 | 1.00 | 33.45 |

FIG. 31A-20

| | | | | | | | | |
|---|---|---|---|---|---|---|---|---|
| ATOM | 962 | CB | VAL | 282 | 75.858 | 46.208 | 17.885 | 1.00 | 34.92 |
| ATOM | 963 | CG1 | VAL | 282 | 74.775 | 47.269 | 17.744 | 1.00 | 34.90 |
| ATOM | 964 | CG2 | VAL | 282 | 75.246 | 44.806 | 17.860 | 1.00 | 34.39 |
| ATOM | 965 | C | VAL | 282 | 78.119 | 45.514 | 17.087 | 1.00 | 33.93 |
| ATOM | 966 | O | VAL | 282 | 78.202 | 44.347 | 16.702 | 1.00 | 35.11 |
| ATOM | 967 | N | LYS | 283 | 79.071 | 46.123 | 17.777 | 1.00 | 33.49 |
| ATOM | 968 | CA | LYS | 283 | 80.285 | 45.446 | 18.187 | 1.00 | 34.83 |
| ATOM | 969 | CB | LYS | 283 | 81.446 | 46.445 | 18.183 | 1.00 | 35.96 |
| ATOM | 970 | CG | LYS | 283 | 81.726 | 47.013 | 16.797 | 1.00 | 39.20 |
| ATOM | 971 | CD | LYS | 283 | 82.621 | 48.245 | 16.844 | 1.00 | 43.38 |
| ATOM | 972 | CE | LYS | 283 | 83.142 | 48.611 | 15.455 | 1.00 | 44.17 |
| ATOM | 973 | NZ | LYS | 283 | 84.077 | 47.563 | 14.922 | 1.00 | 47.27 |
| ATOM | 974 | C | LYS | 283 | 80.068 | 44.832 | 19.572 | 1.00 | 33.94 |
| ATOM | 975 | O | LYS | 283 | 79.134 | 45.215 | 20.290 | 1.00 | 33.85 |
| ATOM | 976 | N | ARG | 284 | 80.939 | 43.895 | 19.941 | 1.00 | 33.63 |
| ATOM | 977 | CA | ARG | 284 | 80.873 | 43.184 | 21.217 | 1.00 | 34.00 |
| ATOM | 978 | CB | ARG | 284 | 82.094 | 42.285 | 21.381 | 1.00 | 34.04 |
| ATOM | 979 | CG | ARG | 284 | 82.332 | 41.369 | 20.219 | 1.00 | 36.31 |
| ATOM | 980 | CD | ARG | 284 | 83.638 | 40.643 | 20.354 | 1.00 | 37.03 |
| ATOM | 981 | NE | ARG | 284 | 83.724 | 39.576 | 19.369 | 1.00 | 39.27 |
| ATOM | 982 | CZ | ARG | 284 | 83.323 | 38.326 | 19.583 | 1.00 | 40.07 |
| ATOM | 983 | NH1 | ARG | 284 | 82.804 | 37.973 | 20.759 | 1.00 | 39.78 |
| ATOM | 984 | NH2 | ARG | 284 | 83.434 | 37.428 | 18.613 | 1.00 | 40.16 |
| ATOM | 985 | C | ARG | 284 | 80.787 | 44.101 | 22.419 | 1.00 | 35.16 |
| ATOM | 986 | O | ARG | 284 | 79.884 | 43.977 | 23.249 | 1.00 | 35.87 |
| ATOM | 987 | N | GLU | 285 | 81.763 | 44.993 | 22.530 | 1.00 | 35.75 |
| ATOM | 988 | CA | GLU | 285 | 81.827 | 45.939 | 23.632 | 1.00 | 36.86 |
| ATOM | 989 | CB | GLU | 285 | 83.071 | 46.818 | 23.464 | 1.00 | 40.47 |
| ATOM | 990 | CG | GLU | 285 | 83.202 | 47.973 | 24.444 | 1.00 | 49.23 |
| ATOM | 991 | CD | GLU | 285 | 83.587 | 49.284 | 23.747 | 1.00 | 54.22 |
| ATOM | 992 | OE1 | GLU | 285 | 84.784 | 49.657 | 23.760 | 1.00 | 55.37 |
| ATOM | 993 | OE2 | GLU | 285 | 82.686 | 49.942 | 23.176 | 1.00 | 56.95 |
| ATOM | 994 | C | GLU | 285 | 80.552 | 46.785 | 23.684 | 1.00 | 34.45 |
| ATOM | 995 | O | GLU | 285 | 79.990 | 47.007 | 24.754 | 1.00 | 34.47 |
| ATOM | 996 | N | GLN | 286 | 80.046 | 47.166 | 22.515 | 1.00 | 32.27 |
| ATOM | 997 | CA | GLN | 286 | 78.853 | 47.991 | 22.438 | 1.00 | 30.35 |
| ATOM | 998 | CB | GLN | 286 | 78.615 | 48.472 | 21.006 | 1.00 | 33.34 |
| ATOM | 999 | CG | GLN | 286 | 79.632 | 49.497 | 20.500 | 1.00 | 35.09 |
| ATOM | 1000 | CD | GLN | 286 | 79.293 | 50.023 | 19.108 | 1.00 | 38.42 |
| ATOM | 1001 | OE1 | GLN | 286 | 79.161 | 49.248 | 18.158 | 1.00 | 39.03 |
| ATOM | 1002 | NE2 | GLN | 286 | 79.156 | 51.339 | 18.982 | 1.00 | 37.82 |
| ATOM | 1003 | C | GLN | 286 | 77.605 | 47.308 | 22.970 | 1.00 | 29.57 |
| ATOM | 1004 | O | GLN | 286 | 76.870 | 47.891 | 23.770 | 1.00 | 26.96 |
| ATOM | 1005 | N | LEU | 287 | 77.352 | 46.080 | 22.524 | 1.00 | 29.50 |
| ATOM | 1006 | CA | LEU | 287 | 76.164 | 45.350 | 22.979 | 1.00 | 28.93 |
| ATOM | 1007 | CB | LEU | 287 | 75.831 | 44.182 | 22.029 | 1.00 | 27.14 |
| ATOM | 1008 | CG | LEU | 287 | 74.474 | 43.484 | 22.227 | 1.00 | 24.66 |
| ATOM | 1009 | CD1 | LEU | 287 | 73.316 | 44.475 | 22.184 | 1.00 | 22.70 |
| ATOM | 1010 | CD2 | LEU | 287 | 74.297 | 42.413 | 21.163 | 1.00 | 25.17 |
| ATOM | 1011 | C | LEU | 287 | 76.303 | 44.874 | 24.433 | 1.00 | 28.10 |

FIG. 31A-21

| | | | | | | | |
|---|---|---|---|---|---|---|---|
| ATOM | 1012 | O | LEU | 287 | 75.301 | 44.748 | 25.155 | 1.00 | 28.58 |
| ATOM | 1013 | N | LYS | 288 | 77.541 | 44.652 | 24.868 | 1.00 | 27.97 |
| ATOM | 1014 | CA | LYS | 288 | 77.808 | 44.218 | 26.230 | 1.00 | 28.55 |
| ATOM | 1015 | CB | LYS | 288 | 79.270 | 43.800 | 26.376 | 1.00 | 28.93 |
| ATOM | 1016 | CG | LYS | 288 | 79.603 | 43.254 | 27.750 | 1.00 | 32.46 |
| ATOM | 1017 | CD | LYS | 288 | 81.015 | 42.725 | 27.826 | 1.00 | 33.48 |
| ATOM | 1018 | CE | LYS | 288 | 81.205 | 41.878 | 29.071 | 1.00 | 35.76 |
| ATOM | 1019 | NZ | LYS | 288 | 82.525 | 41.186 | 29.029 | 1.00 | 40.52 |
| ATOM | 1020 | C | LYS | 288 | 77.497 | 45.341 | 27.220 | 1.00 | 29.15 |
| ATOM | 1021 | O | LYS | 288 | 76.782 | 45.132 | 28.207 | 1.00 | 31.28 |
| ATOM | 1022 | N | ASN | 289 | 77.996 | 46.539 | 26.933 | 1.00 | 28.58 |
| ATOM | 1023 | CA | ASN | 289 | 77.794 | 47.692 | 27.811 | 1.00 | 28.40 |
| ATOM | 1024 | CB | ASN | 289 | 78.815 | 48.775 | 27.485 | 1.00 | 28.28 |
| ATOM | 1025 | CG | ASN | 289 | 80.224 | 48.329 | 27.770 | 1.00 | 31.30 |
| ATOM | 1026 | OD1 | ASN | 289 | 80.445 | 47.442 | 28.601 | 1.00 | 33.02 |
| ATOM | 1027 | ND2 | ASN | 289 | 81.190 | 48.928 | 27.087 | 1.00 | 30.49 |
| ATOM | 1028 | C | ASN | 289 | 76.395 | 48.278 | 27.792 | 1.00 | 28.33 |
| ATOM | 1029 | O | ASN | 289 | 76.005 | 48.977 | 28.724 | 1.00 | 28.36 |
| ATOM | 1030 | N | GLY | 290 | 75.638 | 47.977 | 26.740 | 1.00 | 26.71 |
| ATOM | 1031 | CA | GLY | 290 | 74.286 | 48.487 | 26.606 | 1.00 | 23.27 |
| ATOM | 1032 | C | GLY | 290 | 73.233 | 47.852 | 27.484 | 1.00 | 22.93 |
| ATOM | 1033 | O | GLY | 290 | 72.063 | 48.219 | 27.399 | 1.00 | 23.84 |
| ATOM | 1034 | N | GLY | 291 | 73.620 | 46.905 | 28.330 | 1.00 | 21.30 |
| ATOM | 1035 | CA | GLY | 291 | 72.637 | 46.290 | 29.199 | 1.00 | 20.38 |
| ATOM | 1036 | C | GLY | 291 | 72.653 | 44.778 | 29.200 | 1.00 | 20.05 |
| ATOM | 1037 | O | GLY | 291 | 72.190 | 44.165 | 30.147 | 1.00 | 21.91 |
| ATOM | 1038 | N | LEU | 292 | 73.211 | 44.173 | 28.160 | 1.00 | 21.36 |
| ATOM | 1039 | CA | LEU | 292 | 73.248 | 42.717 | 28.062 | 1.00 | 21.51 |
| ATOM | 1040 | CB | LEU | 292 | 73.319 | 42.280 | 26.593 | 1.00 | 18.52 |
| ATOM | 1041 | CG | LEU | 292 | 72.019 | 42.506 | 25.815 | 1.00 | 17.07 |
| ATOM | 1042 | CD1 | LEU | 292 | 72.103 | 41.818 | 24.479 | 1.00 | 18.09 |
| ATOM | 1043 | CD2 | LEU | 292 | 70.844 | 41.947 | 26.599 | 1.00 | 16.35 |
| ATOM | 1044 | C | LEU | 292 | 74.347 | 42.046 | 28.872 | 1.00 | 22.17 |
| ATOM | 1045 | O | LEU | 292 | 74.176 | 40.923 | 29.352 | 1.00 | 21.91 |
| ATOM | 1046 | N | GLY | 293 | 75.479 | 42.724 | 29.011 | 1.00 | 23.76 |
| ATOM | 1047 | CA | GLY | 293 | 76.588 | 42.169 | 29.760 | 1.00 | 23.92 |
| ATOM | 1048 | C | GLY | 293 | 77.134 | 40.926 | 29.091 | 1.00 | 25.09 |
| ATOM | 1049 | O | GLY | 293 | 77.362 | 40.919 | 27.883 | 1.00 | 26.51 |
| ATOM | 1050 | N | VAL | 294 | 77.332 | 39.866 | 29.867 | 1.00 | 26.08 |
| ATOM | 1051 | CA | VAL | 294 | 77.854 | 38.618 | 29.329 | 1.00 | 26.34 |
| ATOM | 1052 | CB | VAL | 294 | 78.263 | 37.636 | 30.443 | 1.00 | 26.97 |
| ATOM | 1053 | CG1 | VAL | 294 | 79.440 | 38.199 | 31.209 | 1.00 | 28.20 |
| ATOM | 1054 | CG2 | VAL | 294 | 77.099 | 37.371 | 31.384 | 1.00 | 25.56 |
| ATOM | 1055 | C | VAL | 294 | 76.891 | 37.937 | 28.360 | 1.00 | 26.41 |
| ATOM | 1056 | O | VAL | 294 | 77.315 | 37.097 | 27.568 | 1.00 | 27.65 |
| ATOM | 1057 | N | VAL | 295 | 75.608 | 38.304 | 28.408 | 1.00 | 26.09 |
| ATOM | 1058 | CA | VAL | 295 | 74.606 | 37.740 | 27.499 | 1.00 | 26.65 |
| ATOM | 1059 | CB | VAL | 295 | 73.186 | 38.312 | 27.777 | 1.00 | 28.39 |
| ATOM | 1060 | CG1 | VAL | 295 | 72.164 | 37.740 | 26.782 | 1.00 | 26.69 |
| ATOM | 1061 | CG2 | VAL | 295 | 72.763 | 38.005 | 29.206 | 1.00 | 26.23 |

FIG. 31A-22

| ATOM | 1062 | C   | VAL | 295 | 75.035 | 38.089 | 26.069 | 1.00 | 25.83 |
|------|------|-----|-----|-----|--------|--------|--------|------|-------|
| ATOM | 1063 | O   | VAL | 295 | 74.903 | 37.286 | 25.151 | 1.00 | 27.12 |
| ATOM | 1064 | N   | SER | 296 | 75.609 | 39.275 | 25.908 | 1.00 | 24.95 |
| ATOM | 1065 | CA  | SER | 296 | 76.097 | 39.725 | 24.619 | 1.00 | 26.17 |
| ATOM | 1066 | CB  | SER | 296 | 76.665 | 41.132 | 24.742 | 1.00 | 25.82 |
| ATOM | 1067 | OG  | SER | 296 | 77.253 | 41.554 | 23.525 | 1.00 | 26.64 |
| ATOM | 1068 | C   | SER | 296 | 77.196 | 38.783 | 24.142 | 1.00 | 28.63 |
| ATOM | 1069 | O   | SER | 296 | 77.241 | 38.420 | 22.963 | 1.00 | 29.19 |
| ATOM | 1070 | N   | ASP | 297 | 78.118 | 38.443 | 25.046 | 1.00 | 29.69 |
| ATOM | 1071 | CA  | ASP | 297 | 79.211 | 37.531 | 24.731 | 1.00 | 28.96 |
| ATOM | 1072 | CB  | ASP | 297 | 80.058 | 37.234 | 25.973 | 1.00 | 31.82 |
| ATOM | 1073 | CG  | ASP | 297 | 80.768 | 38.454 | 26.506 | 1.00 | 35.23 |
| ATOM | 1074 | OD1 | ASP | 297 | 80.958 | 39.429 | 25.743 | 1.00 | 35.71 |
| ATOM | 1075 | OD2 | ASP | 297 | 81.140 | 38.430 | 27.698 | 1.00 | 37.68 |
| ATOM | 1076 | C   | ASP | 297 | 78.605 | 36.227 | 24.247 | 1.00 | 27.63 |
| ATOM | 1077 | O   | ASP | 297 | 79.048 | 35.666 | 23.248 | 1.00 | 29.88 |
| ATOM | 1078 | N   | ALA | 298 | 77.581 | 35.762 | 24.952 | 1.00 | 25.15 |
| ATOM | 1079 | CA  | ALA | 298 | 76.909 | 34.527 | 24.592 | 1.00 | 24.49 |
| ATOM | 1080 | CB  | ALA | 298 | 75.811 | 34.224 | 25.594 | 1.00 | 21.91 |
| ATOM | 1081 | C   | ALA | 298 | 76.343 | 34.569 | 23.158 | 1.00 | 24.93 |
| ATOM | 1082 | O   | ALA | 298 | 76.589 | 33.654 | 22.357 | 1.00 | 24.83 |
| ATOM | 1083 | N   | ILE | 299 | 75.632 | 35.647 | 22.814 | 1.00 | 24.70 |
| ATOM | 1084 | CA  | ILE | 299 | 75.041 | 35.756 | 21.480 | 1.00 | 22.49 |
| ATOM | 1085 | CB  | ILE | 299 | 74.057 | 36.950 | 21.351 | 1.00 | 21.96 |
| ATOM | 1086 | CG2 | ILE | 299 | 73.338 | 36.876 | 20.005 | 1.00 | 19.17 |
| ATOM | 1087 | CG1 | ILE | 299 | 72.994 | 36.876 | 22.459 | 1.00 | 21.16 |
| ATOM | 1088 | CD1 | ILE | 299 | 72.363 | 38.228 | 22.853 | 1.00 | 22.04 |
| ATOM | 1089 | C   | ILE | 299 | 76.127 | 35.829 | 20.428 | 1.00 | 22.33 |
| ATOM | 1090 | O   | ILE | 299 | 75.995 | 35.234 | 19.367 | 1.00 | 24.80 |
| ATOM | 1091 | N   | PHE | 300 | 77.209 | 36.538 | 20.724 | 1.00 | 21.92 |
| ATOM | 1092 | CA  | PHE | 300 | 78.322 | 36.641 | 19.785 | 1.00 | 23.08 |
| ATOM | 1093 | CB  | PHE | 300 | 79.385 | 37.636 | 20.278 | 1.00 | 24.08 |
| ATOM | 1094 | CG  | PHE | 300 | 79.249 | 39.017 | 19.686 | 1.00 | 24.18 |
| ATOM | 1095 | CD1 | PHE | 300 | 78.494 | 39.991 | 20.325 | 1.00 | 22.64 |
| ATOM | 1096 | CD2 | PHE | 300 | 79.857 | 39.331 | 18.471 | 1.00 | 23.76 |
| ATOM | 1097 | CE1 | PHE | 300 | 78.347 | 41.253 | 19.770 | 1.00 | 22.38 |
| ATOM | 1098 | CE2 | PHE | 300 | 79.715 | 40.596 | 17.904 | 1.00 | 23.21 |
| ATOM | 1099 | CZ  | PHE | 300 | 78.957 | 41.558 | 18.554 | 1.00 | 22.46 |
| ATOM | 1100 | C   | PHE | 300 | 78.948 | 35.274 | 19.561 | 1.00 | 23.06 |
| ATOM | 1101 | O   | PHE | 300 | 79.264 | 34.913 | 18.426 | 1.00 | 23.97 |
| ATOM | 1102 | N   | GLU | 301 | 79.113 | 34.506 | 20.636 | 1.00 | 23.75 |
| ATOM | 1103 | CA  | GLU | 301 | 79.694 | 33.169 | 20.525 | 1.00 | 24.16 |
| ATOM | 1104 | CB  | GLU | 301 | 79.884 | 32.545 | 21.902 | 1.00 | 23.03 |
| ATOM | 1105 | C   | GLU | 301 | 78.776 | 32.302 | 19.672 | 1.00 | 23.62 |
| ATOM | 1106 | O   | GLU | 301 | 79.240 | 31.591 | 18.777 | 1.00 | 25.11 |
| ATOM | 1107 | N   | LEU | 302 | 77.472 | 32.394 | 19.926 | 1.00 | 23.12 |
| ATOM | 1108 | CA  | LEU | 302 | 76.495 | 31.624 | 19.166 | 1.00 | 23.56 |
| ATOM | 1109 | CB  | LEU | 302 | 75.082 | 31.865 | 19.701 | 1.00 | 21.75 |
| ATOM | 1110 | CG  | LEU | 302 | 73.953 | 31.120 | 18.979 | 1.00 | 22.61 |
| ATOM | 1111 | CD1 | LEU | 302 | 74.084 | 29.612 | 19.193 | 1.00 | 22.31 |

FIG. 31A-23

| ATOM | 1112 | CD2 | LEU | 302 | 72.611 | 31.604 | 19.485 | 1.00 | 19.27 |
|---|---|---|---|---|---|---|---|---|---|
| ATOM | 1113 | C | LEU | 302 | 76.588 | 32.011 | 17.687 | 1.00 | 24.41 |
| ATOM | 1114 | O | LEU | 302 | 76.670 | 31.140 | 16.814 | 1.00 | 24.63 |
| ATOM | 1115 | N | GLY | 303 | 76.651 | 33.316 | 17.425 | 1.00 | 25.69 |
| ATOM | 1116 | CA | GLY | 303 | 76.746 | 33.816 | 16.062 | 1.00 | 25.87 |
| ATOM | 1117 | C | GLY | 303 | 77.975 | 33.288 | 15.338 | 1.00 | 28.63 |
| ATOM | 1118 | O | GLY | 303 | 77.893 | 32.895 | 14.170 | 1.00 | 28.30 |
| ATOM | 1119 | N | LYS | 304 | 79.116 | 33.279 | 16.023 | 1.00 | 29.53 |
| ATOM | 1120 | CA | LYS | 304 | 80.360 | 32.791 | 15.437 | 1.00 | 31.18 |
| ATOM | 1121 | CB | LYS | 304 | 81.529 | 32.931 | 16.418 | 1.00 | 34.79 |
| ATOM | 1122 | CG | LYS | 304 | 82.157 | 34.307 | 16.506 | 1.00 | 40.28 |
| ATOM | 1123 | CD | LYS | 304 | 83.441 | 34.262 | 17.332 | 1.00 | 44.37 |
| ATOM | 1124 | CE | LYS | 304 | 83.174 | 33.814 | 18.775 | 1.00 | 47.63 |
| ATOM | 1125 | NZ | LYS | 304 | 82.459 | 34.847 | 19.592 | 1.00 | 48.83 |
| ATOM | 1126 | C | LYS | 304 | 80.245 | 31.328 | 15.042 | 1.00 | 30.87 |
| ATOM | 1127 | O | LYS | 304 | 80.632 | 30.944 | 13.932 | 1.00 | 29.53 |
| ATOM | 1128 | N | SER | 305 | 79.720 | 30.518 | 15.961 | 1.00 | 30.46 |
| ATOM | 1129 | CA | SER | 305 | 79.566 | 29.086 | 15.731 | 1.00 | 31.09 |
| ATOM | 1130 | CB | SER | 305 | 79.243 | 28.370 | 17.041 | 1.00 | 29.83 |
| ATOM | 1131 | OG | SER | 305 | 77.990 | 28.783 | 17.550 | 1.00 | 34.66 |
| ATOM | 1132 | C | SER | 305 | 78.532 | 28.732 | 14.653 | 1.00 | 31.06 |
| ATOM | 1133 | O | SER | 305 | 78.745 | 27.799 | 13.872 | 1.00 | 31.84 |
| ATOM | 1134 | N | LEU | 306 | 77.436 | 29.491 | 14.594 | 1.00 | 29.43 |
| ATOM | 1135 | CA | LEU | 306 | 76.378 | 29.258 | 13.611 | 1.00 | 28.39 |
| ATOM | 1136 | CB | LEU | 306 | 75.121 | 30.055 | 13.962 | 1.00 | 26.05 |
| ATOM | 1137 | CG | LEU | 306 | 74.306 | 29.573 | 15.157 | 1.00 | 26.33 |
| ATOM | 1138 | CD1 | LEU | 306 | 73.061 | 30.430 | 15.285 | 1.00 | 26.22 |
| ATOM | 1139 | CD2 | LEU | 306 | 73.924 | 28.110 | 14.985 | 1.00 | 25.86 |
| ATOM | 1140 | C | LEU | 306 | 76.754 | 29.529 | 12.157 | 1.00 | 28.66 |
| ATOM | 1141 | O | LEU | 306 | 76.116 | 29.001 | 11.253 | 1.00 | 28.58 |
| ATOM | 1142 | N | SER | 307 | 77.786 | 30.338 | 11.931 | 1.00 | 29.72 |
| ATOM | 1143 | CA | SER | 307 | 78.224 | 30.667 | 10.577 | 1.00 | 31.19 |
| ATOM | 1144 | CB | SER | 307 | 79.466 | 31.556 | 10.617 | 1.00 | 30.15 |
| ATOM | 1145 | OG | SER | 307 | 79.226 | 32.710 | 11.396 | 1.00 | 35.19 |
| ATOM | 1146 | C | SER | 307 | 78.531 | 29.412 | 9.777 | 1.00 | 32.75 |
| ATOM | 1147 | O | SER | 307 | 78.110 | 29.283 | 8.621 | 1.00 | 33.09 |
| ATOM | 1148 | N | ALA | 308 | 79.248 | 28.482 | 10.407 | 1.00 | 33.36 |
| ATOM | 1149 | CA | ALA | 308 | 79.626 | 27.223 | 9.769 | 1.00 | 34.50 |
| ATOM | 1150 | CB | ALA | 308 | 80.636 | 26.473 | 10.637 | 1.00 | 33.55 |
| ATOM | 1151 | C | ALA | 308 | 78.417 | 26.328 | 9.466 | 1.00 | 35.00 |
| ATOM | 1152 | O | ALA | 308 | 78.469 | 25.501 | 8.550 | 1.00 | 37.10 |
| ATOM | 1153 | N | PHE | 309 | 77.335 | 26.496 | 10.226 | 1.00 | 32.76 |
| ATOM | 1154 | CA | PHE | 309 | 76.134 | 25.698 | 10.028 | 1.00 | 31.73 |
| ATOM | 1155 | CB | PHE | 309 | 75.214 | 25.818 | 11.232 | 1.00 | 30.04 |
| ATOM | 1156 | CG | PHE | 309 | 75.705 | 25.091 | 12.438 | 1.00 | 31.19 |
| ATOM | 1157 | CD1 | PHE | 309 | 74.973 | 24.048 | 12.975 | 1.00 | 31.61 |
| ATOM | 1158 | CD2 | PHE | 309 | 76.884 | 25.459 | 13.054 | 1.00 | 31.92 |
| ATOM | 1159 | CE1 | PHE | 309 | 75.400 | 23.391 | 14.110 | 1.00 | 31.22 |
| ATOM | 1160 | CE2 | PHE | 309 | 77.320 | 24.807 | 14.194 | 1.00 | 31.01 |
| ATOM | 1161 | CZ | PHE | 309 | 76.577 | 23.771 | 14.720 | 1.00 | 30.47 |

FIG. 31A-24

| ATOM | 1162 | C   | PHE | 309 | 75.364 | 26.050 | 8.753  | 1.00 | 31.53 |
|------|------|-----|-----|-----|--------|--------|--------|------|-------|
| ATOM | 1163 | O   | PHE | 309 | 74.516 | 25.269 | 8.310  | 1.00 | 31.28 |
| ATOM | 1164 | N   | ASN | 310 | 75.661 | 27.220 | 8.181  | 1.00 | 31.12 |
| ATOM | 1165 | CA  | ASN | 310 | 75.020 | 27.711 | 6.957  | 1.00 | 30.34 |
| ATOM | 1166 | CB  | ASN | 310 | 75.636 | 27.036 | 5.719  | 1.00 | 31.63 |
| ATOM | 1167 | C   | ASN | 310 | 73.511 | 27.492 | 7.003  | 1.00 | 29.40 |
| ATOM | 1168 | O   | ASN | 310 | 72.939 | 26.791 | 6.156  | 1.00 | 29.15 |
| ATOM | 1169 | N   | LEU | 311 | 72.875 | 28.055 | 8.026  | 1.00 | 27.60 |
| ATOM | 1170 | CA  | LEU | 311 | 71.435 | 27.907 | 8.205  | 1.00 | 28.23 |
| ATOM | 1171 | CB  | LEU | 311 | 71.021 | 28.313 | 9.621  | 1.00 | 27.41 |
| ATOM | 1172 | CG  | LEU | 311 | 71.603 | 27.558 | 10.822 | 1.00 | 26.80 |
| ATOM | 1173 | CD1 | LEU | 311 | 70.949 | 28.078 | 12.112 | 1.00 | 25.05 |
| ATOM | 1174 | CD2 | LEU | 311 | 71.360 | 26.062 | 10.662 | 1.00 | 24.72 |
| ATOM | 1175 | C   | LEU | 311 | 70.628 | 28.719 | 7.192  | 1.00 | 29.01 |
| ATOM | 1176 | O   | LEU | 311 | 71.040 | 29.808 | 6.782  | 1.00 | 30.66 |
| ATOM | 1177 | N   | ASP | 312 | 69.503 | 28.168 | 6.748  | 1.00 | 26.30 |
| ATOM | 1178 | CA  | ASP | 312 | 68.675 | 28.894 | 5.817  | 1.00 | 25.13 |
| ATOM | 1179 | CB  | ASP | 312 | 68.391 | 28.067 | 4.539  | 1.00 | 23.90 |
| ATOM | 1180 | CG  | ASP | 312 | 67.438 | 26.890 | 4.754  | 1.00 | 21.34 |
| ATOM | 1181 | OD1 | ASP | 312 | 66.959 | 26.631 | 5.868  | 1.00 | 22.47 |
| ATOM | 1182 | OD2 | ASP | 312 | 67.154 | 26.206 | 3.758  | 1.00 | 22.18 |
| ATOM | 1183 | C   | ASP | 312 | 67.419 | 29.379 | 6.542  | 1.00 | 24.49 |
| ATOM | 1184 | O   | ASP | 312 | 67.221 | 29.056 | 7.725  | 1.00 | 24.01 |
| ATOM | 1185 | N   | ASP | 313 | 66.587 | 30.153 | 5.845  | 1.00 | 23.40 |
| ATOM | 1186 | CA  | ASP | 313 | 65.363 | 30.697 | 6.421  | 1.00 | 22.63 |
| ATOM | 1187 | CB  | ASP | 313 | 64.557 | 31.486 | 5.385  | 1.00 | 24.99 |
| ATOM | 1188 | CG  | ASP | 313 | 65.224 | 32.799 | 4.994  | 1.00 | 28.02 |
| ATOM | 1189 | OD1 | ASP | 313 | 66.036 | 33.334 | 5.778  | 1.00 | 30.34 |
| ATOM | 1190 | OD2 | ASP | 313 | 64.936 | 33.306 | 3.897  | 1.00 | 30.41 |
| ATOM | 1191 | C   | ASP | 313 | 64.480 | 29.650 | 7.053  | 1.00 | 21.47 |
| ATOM | 1192 | O   | ASP | 313 | 63.853 | 29.917 | 8.082  | 1.00 | 21.76 |
| ATOM | 1193 | N   | THR | 314 | 64.407 | 28.474 | 6.435  | 1.00 | 19.16 |
| ATOM | 1194 | CA  | THR | 314 | 63.580 | 27.386 | 6.966  | 1.00 | 18.79 |
| ATOM | 1195 | CB  | THR | 314 | 63.398 | 26.240 | 5.913  | 1.00 | 19.68 |
| ATOM | 1196 | OG1 | THR | 314 | 62.743 | 26.758 | 4.747  | 1.00 | 20.56 |
| ATOM | 1197 | CG2 | THR | 314 | 62.558 | 25.112 | 6.482  | 1.00 | 18.84 |
| ATOM | 1198 | C   | THR | 314 | 64.133 | 26.818 | 8.293  | 1.00 | 15.38 |
| ATOM | 1199 | O   | THR | 314 | 63.383 | 26.538 | 9.223  | 1.00 | 14.08 |
| ATOM | 1200 | N   | GLU | 315 | 65.445 | 26.656 | 8.376  | 1.00 | 15.16 |
| ATOM | 1201 | CA  | GLU | 315 | 66.051 | 26.126 | 9.593  | 1.00 | 16.78 |
| ATOM | 1202 | CB  | GLU | 315 | 67.513 | 25.785 | 9.340  | 1.00 | 14.29 |
| ATOM | 1203 | CG  | GLU | 315 | 67.611 | 24.483 | 8.579  | 1.00 | 15.13 |
| ATOM | 1204 | CD  | GLU | 315 | 68.910 | 24.291 | 7.872  | 1.00 | 15.90 |
| ATOM | 1205 | OE1 | GLU | 315 | 69.625 | 25.285 | 7.639  | 1.00 | 19.80 |
| ATOM | 1206 | OE2 | GLU | 315 | 69.211 | 23.129 | 7.527  | 1.00 | 19.34 |
| ATOM | 1207 | C   | GLU | 315 | 65.872 | 27.119 | 10.736 | 1.00 | 17.27 |
| ATOM | 1208 | O   | GLU | 315 | 65.457 | 26.742 | 11.836 | 1.00 | 17.46 |
| ATOM | 1209 | N   | VAL | 316 | 66.081 | 28.399 | 10.440 | 1.00 | 17.12 |
| ATOM | 1210 | CA  | VAL | 316 | 65.897 | 29.441 | 11.446 | 1.00 | 16.92 |
| ATOM | 1211 | CB  | VAL | 316 | 66.336 | 30.828 | 10.918 | 1.00 | 15.89 |

FIG. 31A-25

| ATOM | 1212 | CG1 | VAL | 316 | 66.062 | 31.921 | 11.962 | 1.00 | 14.60 |
|---|---|---|---|---|---|---|---|---|---|
| ATOM | 1213 | CG2 | VAL | 316 | 67.811 | 30.785 | 10.579 | 1.00 | 15.95 |
| ATOM | 1214 | C | VAL | 316 | 64.430 | 29.472 | 11.869 | 1.00 | 17.32 |
| ATOM | 1215 | O | VAL | 316 | 64.131 | 29.582 | 13.055 | 1.00 | 18.11 |
| ATOM | 1216 | N | ALA | 317 | 63.515 | 29.324 | 10.905 | 1.00 | 17.42 |
| ATOM | 1217 | CA | ALA | 317 | 62.076 | 29.342 | 11.195 | 1.00 | 16.21 |
| ATOM | 1218 | CB | ALA | 317 | 61.262 | 29.321 | 9.910 | 1.00 | 14.63 |
| ATOM | 1219 | C | ALA | 317 | 61.656 | 28.181 | 12.079 | 1.00 | 16.84 |
| ATOM | 1220 | O | ALA | 317 | 60.904 | 28.359 | 13.036 | 1.00 | 16.08 |
| ATOM | 1221 | N | LEU | 318 | 62.146 | 26.990 | 11.759 | 1.00 | 17.27 |
| ATOM | 1222 | CA | LEU | 318 | 61.783 | 25.804 | 12.526 | 1.00 | 17.88 |
| ATOM | 1223 | CB | LEU | 318 | 62.141 | 24.525 | 11.748 | 1.00 | 17.58 |
| ATOM | 1224 | CG | LEU | 318 | 61.331 | 24.333 | 10.439 | 1.00 | 16.87 |
| ATOM | 1225 | CD1 | LEU | 318 | 61.837 | 23.155 | 9.658 | 1.00 | 15.79 |
| ATOM | 1226 | CD2 | LEU | 318 | 59.860 | 24.149 | 10.728 | 1.00 | 14.08 |
| ATOM | 1227 | C | LEU | 318 | 62.394 | 25.852 | 13.932 | 1.00 | 18.20 |
| ATOM | 1228 | O | LEU | 318 | 61.733 | 25.495 | 14.910 | 1.00 | 18.71 |
| ATOM | 1229 | N | LEU | 319 | 63.614 | 26.380 | 14.034 | 1.00 | 17.73 |
| ATOM | 1230 | CA | LEU | 319 | 64.288 | 26.531 | 15.321 | 1.00 | 16.57 |
| ATOM | 1231 | CB | LEU | 319 | 65.689 | 27.105 | 15.107 | 1.00 | 18.81 |
| ATOM | 1232 | CG | LEU | 319 | 66.733 | 27.223 | 16.224 | 1.00 | 21.77 |
| ATOM | 1233 | CD1 | LEU | 319 | 66.767 | 25.994 | 17.117 | 1.00 | 23.03 |
| ATOM | 1234 | CD2 | LEU | 319 | 68.076 | 27.421 | 15.554 | 1.00 | 20.86 |
| ATOM | 1235 | C | LEU | 319 | 63.433 | 27.471 | 16.160 | 1.00 | 16.07 |
| ATOM | 1236 | O | LEU | 319 | 63.134 | 27.183 | 17.319 | 1.00 | 16.40 |
| ATOM | 1237 | N | GLN | 320 | 62.948 | 28.546 | 15.545 | 1.00 | 13.91 |
| ATOM | 1238 | CA | GLN | 320 | 62.101 | 29.490 | 16.253 | 1.00 | 13.86 |
| ATOM | 1239 | CB | GLN | 320 | 61.782 | 30.697 | 15.373 | 1.00 | 13.26 |
| ATOM | 1240 | CG | GLN | 320 | 62.994 | 31.553 | 15.080 | 1.00 | 12.17 |
| ATOM | 1241 | CD | GLN | 320 | 62.691 | 32.802 | 14.253 | 1.00 | 13.98 |
| ATOM | 1242 | OE1 | GLN | 320 | 63.597 | 33.568 | 13.950 | 1.00 | 15.61 |
| ATOM | 1243 | NE2 | GLN | 320 | 61.436 | 32.993 | 13.862 | 1.00 | 13.85 |
| ATOM | 1244 | C | GLN | 320 | 60.813 | 28.832 | 16.746 | 1.00 | 14.52 |
| ATOM | 1245 | O | GLN | 320 | 60.367 | 29.087 | 17.864 | 1.00 | 15.12 |
| ATOM | 1246 | N | ALA | 321 | 60.211 | 27.982 | 15.924 | 1.00 | 14.21 |
| ATOM | 1247 | CA | ALA | 321 | 58.976 | 27.298 | 16.309 | 1.00 | 15.04 |
| ATOM | 1248 | CB | ALA | 321 | 58.408 | 26.519 | 15.115 | 1.00 | 13.84 |
| ATOM | 1249 | C | ALA | 321 | 59.217 | 26.349 | 17.487 | 1.00 | 15.98 |
| ATOM | 1250 | O | ALA | 321 | 58.358 | 26.197 | 18.355 | 1.00 | 15.12 |
| ATOM | 1251 | N | VAL | 322 | 60.373 | 25.687 | 17.488 | 1.00 | 16.63 |
| ATOM | 1252 | CA | VAL | 322 | 60.720 | 24.757 | 18.557 | 1.00 | 18.74 |
| ATOM | 1253 | CB | VAL | 322 | 62.012 | 23.943 | 18.231 | 1.00 | 19.42 |
| ATOM | 1254 | CG1 | VAL | 322 | 62.493 | 23.154 | 19.455 | 1.00 | 19.45 |
| ATOM | 1255 | CG2 | VAL | 322 | 61.745 | 22.986 | 17.083 | 1.00 | 19.05 |
| ATOM | 1256 | C | VAL | 322 | 60.910 | 25.556 | 19.833 | 1.00 | 18.42 |
| ATOM | 1257 | O | VAL | 322 | 60.421 | 25.164 | 20.886 | 1.00 | 19.46 |
| ATOM | 1258 | N | LEU | 323 | 61.607 | 26.685 | 19.735 | 1.00 | 18.65 |
| ATOM | 1259 | CA | LEU | 323 | 61.836 | 27.543 | 20.894 | 1.00 | 18.49 |
| ATOM | 1260 | CB | LEU | 323 | 62.710 | 28.740 | 20.508 | 1.00 | 18.36 |
| ATOM | 1261 | CG | LEU | 323 | 64.179 | 28.449 | 20.186 | 1.00 | 18.13 |

FIG. 31A-26

| ATOM | 1262 | CD1 | LEU | 323 | 64.829 | 29.669 | 19.585 | 1.00 | 17.37 |
|---|---|---|---|---|---|---|---|---|---|
| ATOM | 1263 | CD2 | LEU | 323 | 64.923 | 27.999 | 21.447 | 1.00 | 17.27 |
| ATOM | 1264 | C | LEU | 323 | 60.499 | 28.029 | 21.454 | 1.00 | 18.38 |
| ATOM | 1265 | O | LEU | 323 | 60.275 | 28.008 | 22.663 | 1.00 | 18.81 |
| ATOM | 1266 | N | LEU | 324 | 59.595 | 28.406 | 20.557 | 1.00 | 18.67 |
| ATOM | 1267 | CA | LEU | 324 | 58.275 | 28.897 | 20.924 | 1.00 | 19.02 |
| ATOM | 1268 | CB | LEU | 324 | 57.564 | 29.467 | 19.685 | 1.00 | 17.78 |
| ATOM | 1269 | CG | LEU | 324 | 56.095 | 29.891 | 19.838 | 1.00 | 17.59 |
| ATOM | 1270 | CD1 | LEU | 324 | 55.983 | 31.123 | 20.709 | 1.00 | 18.15 |
| ATOM | 1271 | CD2 | LEU | 324 | 55.489 | 30.180 | 18.476 | -1.00 | 16.43 |
| ATOM | 1272 | C | LEU | 324 | 57.354 | 27.884 | 21.610 | 1.00 | 19.62 |
| ATOM | 1273 | O | LEU | 324 | 56.735 | 28.185 | 22.633 | 1.00 | 19.40 |
| ATOM | 1274 | N | MET | 325 | 57.224 | 26.701 | 21.029 | 1.00 | 21.14 |
| ATOM | 1275 | CA | MET | 325 | 56.330 | 25.680 | 21.585 | 1.00 | 24.06 |
| ATOM | 1276 | CB | MET | 325 | 55.857 | 24.738 | 20.473 | 1.00 | 24.68 |
| ATOM | 1277 | CG | MET | 325 | 55.169 | 25.444 | 19.303 | 1.00 | 24.49 |
| ATOM | 1278 | SD | MET | 325 | 53.759 | 26.457 | 19.820 | 1.00 | 26.18 |
| ATOM | 1279 | CE | MET | 325 | 52.609 | 25.252 | 20.373 | 1.00 | 24.03 |
| ATOM | 1280 | C | MET | 325 | 56.996 | 24.887 | 22.705 | 1.00 | 26.15 |
| ATOM | 1281 | O | MET | 325 | 57.021 | 23.664 | 22.693 | 1.00 | 25.68 |
| ATOM | 1282 | N | SER | 326 | 57.555 | 25.593 | 23.671 | 1.00 | 29.34 |
| ATOM | 1283 | CA | SER | 326 | 58.232 | 24.938 | 24.774 | 1.00 | 32.40 |
| ATOM | 1284 | CB | SER | 326 | 59.512 | 25.701 | 25.112 | 1.00 | 32.12 |
| ATOM | 1285 | OG | SER | 326 | 60.127 | 25.173 | 26.272 | 1.00 | 36.86 |
| ATOM | 1286 | C | SER | 326 | 57.317 | 24.831 | 25.996 | 1.00 | 34.04 |
| ATOM | 1287 | O | SER | 326 | 56.532 | 25.741 | 26.280 | 1.00 | 33.24 |
| ATOM | 1288 | N | THR | 327 | 57.366 | 23.687 | 26.674 | 1.00 | 35.62 |
| ATOM | 1289 | CA | THR | 327 | 56.560 | 23.486 | 27.867 | 1.00 | 36.88 |
| ATOM | 1290 | CB | THR | 327 | 55.938 | 22.085 | 27.907 | 1.00 | 36.58 |
| ATOM | 1291 | OG1 | THR | 327 | 56.953 | 21.094 | 27.714 | 1.00 | 38.58 |
| ATOM | 1292 | CG2 | THR | 327 | 54.883 | 21.938 | 26.826 | 1.00 | 37.73 |
| ATOM | 1293 | C | THR | 327 | 57.378 | 23.733 | 29.135 | 1.00 | 38.77 |
| ATOM | 1294 | O | THR | 327 | 56.921 | 23.438 | 30.240 | 1.00 | 39.53 |
| ATOM | 1295 | N | ASP | 328 | 58.593 | 24.260 | 28.972 | 1.00 | 41.25 |
| ATOM | 1296 | CA | ASP | 328 | 59.473 | 24.573 | 30.099 | 1.00 | 43.20 |
| ATOM | 1297 | CB | ASP | 328 | 60.940 | 24.698 | 29.655 | 1.00 | 46.47 |
| ATOM | 1298 | CG | ASP | 328 | 61.618 | 23.346 | 29.439 | 1.00 | 51.94 |
| ATOM | 1299 | OD1 | ASP | 328 | 62.547 | 23.278 | 28.601 | 1.00 | 55.43 |
| ATOM | 1300 | OD2 | ASP | 328 | 61.251 | 22.354 | 30.111 | 1.00 | 54.77 |
| ATOM | 1301 | C | ASP | 328 | 59.001 | 25.905 | 30.653 | 1.00 | 43.79 |
| ATOM | 1302 | O | ASP | 328 | 59.755 | 26.877 | 30.709 | 1.00 | 45.91 |
| ATOM | 1303 | N | ARG | 329 | 57.724 | 25.967 | 30.995 | 1.00 | 43.55 |
| ATOM | 1304 | CA | ARG | 329 | 57.143 | 27.178 | 31.542 | 1.00 | 43.04 |
| ATOM | 1305 | CB | ARG | 329 | 56.398 | 27.997 | 30.482 | 1.00 | 43.87 |
| ATOM | 1306 | CG | ARG | 329 | 57.258 | 28.740 | 29.504 | 1.00 | 40.87 |
| ATOM | 1307 | CD | ARG | 329 | 57.545 | 27.886 | 28.314 | 1.00 | 39.52 |
| ATOM | 1308 | NE | ARG | 329 | 58.301 | 28.643 | 27.341 | 1.00 | 38.90 |
| ATOM | 1309 | CZ | ARG | 329 | 59.624 | 28.708 | 27.313 | 1.00 | 40.59 |
| ATOM | 1310 | NH1 | ARG | 329 | 60.359 | 28.052 | 28.196 | 1.00 | 42.41 |
| ATOM | 1311 | NH2 | ARG | 329 | 60.210 | 29.466 | 26.413 | 1.00 | 41.87 |

FIG. 31A-27

| | | | | | | | |
|---|---|---|---|---|---|---|---|
| ATOM | 1312 C | ARG | 329 | 56.152 | 26.817 | 32.609 | 1.00 | 43.00 |
| ATOM | 1313 O | ARG | 329 | 55.600 | 25.716 | 32.628 | 1.00 | 43.66 |
| ATOM | 1314 N | SER | 330 | 55.886 | 27.797 | 33.456 | 1.00 | 41.58 |
| ATOM | 1315 CA | SER | 330 | 54.953 | 27.641 | 34.538 | 1.00 | 40.11 |
| ATOM | 1316 CB | SER | 330 | 55.491 | 28.362 | 35.777 | 1.00 | 40.38 |
| ATOM | 1317 C | SER | 330 | 53.602 | 28.223 | 34.103 | 1.00 | 38.99 |
| ATOM | 1318 O | SER | 330 | 53.553 | 29.172 | 33.320 | 1.00 | 39.22 |
| ATOM | 1319 N | GLY | 331 | 52.517 | 27.581 | 34.529 | 1.00 | 37.52 |
| ATOM | 1320 CA | GLY | 331 | 51.176 | 28.063 | 34.232 | 1.00 | 35.64 |
| ATOM | 1321 C | GLY | 331 | 50.493 | 27.782 | 32.906 | 1.00 | 35.14 |
| ATOM | 1322 O | GLY | 331 | 49.439 | 28.363 | 32.640 | 1.00 | 34.48 |
| ATOM | 1323 N | LEU | 332 | 51.059 | 26.925 | 32.066 | 1.00 | 34.54 |
| ATOM | 1324 CA | LEU | 332 | 50.424 | 26.637 | 30.780 | 1.00 | 34.59 |
| ATOM | 1325 CB | LEU | 332 | 51.394 | 25.942 | 29.828 | 1.00 | 33.09 |
| ATOM | 1326 CG | LEU | 332 | 52.532 | 26.765 | 29.236 | 1.00 | 32.72 |
| ATOM | 1327 CD1 | LEU | 332 | 53.473 | 25.834 | 28.497 | 1.00 | 30.29 |
| ATOM | 1328 CD2 | LEU | 332 | 51.987 | 27.844 | 28.313 | 1.00 | 29.20 |
| ATOM | 1329 C | LEU | 332 | 49.191 | 25.763 | 30.969 | 1.00 | 35.14 |
| ATOM | 1330 O | LEU | 332 | 49.178 | 24.874 | 31.811 | 1.00 | 35.96 |
| ATOM | 1331 N | LEU | 333 | 48.153 | 26.076 | 30.204 | 1.00 | 35.65 |
| ATOM | 1332 CA | LEU | 333 | 46.898 | 25.345 | 30.215 | 1.00 | 37.97 |
| ATOM | 1333 CB | LEU | 333 | 45.743 | 26.271 | 29.796 | 1.00 | 40.71 |
| ATOM | 1334 CG | LEU | 333 | 45.389 | 27.483 | 30.670 | 1.00 | 43.46 |
| ATOM | 1335 CD1 | LEU | 333 | 44.713 | 28.620 | 29.882 | 1.00 | 42.72 |
| ATOM | 1336 CD2 | LEU | 333 | 44.487 | 27.021 | 31.806 | 1.00 | 45.25 |
| ATOM | 1337 C | LEU | 333 | 46.952 | 24.115 | 29.300 | 1.00 | 37.78 |
| ATOM | 1338 O | LEU | 333 | 46.695 | 22.991 | 29.720 | 1.00 | 37.65 |
| ATOM | 1339 N | CYA | 334 | 47.361 | 24.323 | 28.060 | 1.00 | 38.65 |
| ATOM | 1340 CA | CYA | 334 | 47.413 | 23.249 | 27.073 | 1.00 | 40.91 |
| ATOM | 1341 CB | CYA | 334 | 46.936 | 23.788 | 25.721 | 1.00 | 47.35 |
| ATOM | 1342 SG | CYA | 334 | 45.406 | 24.693 | 25.867 | 1.00 | 52.24 |
| ATOM | 1343 AS | CYA | 334 | 44.066 | 22.890 | 25.562 | 1.00 | 70.72 |
| ATOM | 1344 C | CYA | 334 | 48.778 | 22.588 | 26.901 | 1.00 | 39.85 |
| ATOM | 1345 O | CYA | 334 | 49.287 | 22.473 | 25.775 | 1.00 | 39.54 |
| ATOM | 1346 N | VAL | 335 | 49.329 | 22.078 | 27.997 | 1.00 | 37.67 |
| ATOM | 1347 CA | VAL | 335 | 50.641 | 21.432 | 27.967 | 1.00 | 36.07 |
| ATOM | 1348 CB | VAL | 335 | 51.019 | 20.905 | 29.384 | 1.00 | 33.70 |
| ATOM | 1349 CG1 | VAL | 335 | 52.434 | 20.332 | 29.401 | 1.00 | 33.70 |
| ATOM | 1350 CG2 | VAL | 335 | 50.913 | 22.028 | 30.387 | 1.00 | 31.84 |
| ATOM | 1351 C | VAL | 335 | 50.734 | 20.334 | 26.885 | 1.00 | 36.09 |
| ATOM | 1352 O | VAL | 335 | 51.662 | 20.335 | 26.064 | 1.00 | 34.41 |
| ATOM | 1353 N | ASP | 336 | 49.747 | 19.444 | 26.833 | 1.00 | 35.95 |
| ATOM | 1354 CA | ASP | 336 | 49.748 | 18.372 | 25.844 | 1.00 | 36.34 |
| ATOM | 1355 CB | ASP | 336 | 48.591 | 17.394 | 26.091 | 1.00 | 41.36 |
| ATOM | 1356 CG | ASP | 336 | 48.613 | 16.206 | 25.129 | 1.00 | 46.23 |
| ATOM | 1357 OD1 | ASP | 336 | 47.615 | 16.021 | 24.392 | 1.00 | 49.55 |
| ATOM | 1358 OD2 | ASP | 336 | 49.639 | 15.470 | 25.097 | 1.00 | 48.07 |
| ATOM | 1359 C | ASP | 336 | 49.727 | 18.846 | 24.390 | 1.00 | 33.05 |
| ATOM | 1360 O | ASP | 336 | 50.527 | 18.377 | 23.573 | 1.00 | 32.33 |
| ATOM | 1361 N | LYS | 337 | 48.794 | 19.743 | 24.076 | 1.00 | 29.57 |

FIG. 31A-28

| ATOM | 1362 | CA | LYS | 337 | 48.661 | 20.286 | 22.723 | 1.00 | 27.76 |
|---|---|---|---|---|---|---|---|---|---|
| ATOM | 1363 | CB | LYS | 337 | 47.520 | 21.313 | 22.689 | 1.00 | 27.09 |
| ATOM | 1364 | C | LYS | 337 | 49.988 | 20.941 | 22.286 | 1.00 | 27.64 |
| ATOM | 1365 | O | LYS | 337 | 50.472 | 20.713 | 21.173 | 1.00 | 26.09 |
| ATOM | 1366 | N | ILE | 338 | 50.597 | 21.688 | 23.208 | 1.00 | 25.90 |
| ATOM | 1367 | CA | ILE | 338 | 51.852 | 22.394 | 22.971 | 1.00 | 24.21 |
| ATOM | 1368 | CB | ILE | 338 | 52.128 | 23.391 | 24.122 | 1.00 | 23.30 |
| ATOM | 1369 | CG2 | ILE | 338 | 53.500 | 24.048 | 23.958 | 1.00 | 21.75 |
| ATOM | 1370 | CG1 | ILE | 338 | 51.014 | 24.448 | 24.155 | 1.00 | 21.19 |
| ATOM | 1371 | CD1 | ILE | 338 | 51.055 | 25.393 | 25.361 | 1.00 | 21.39 |
| ATOM | 1372 | C | ILE | 338 | 53.041 | 21.451 | 22.782 | 1.00 | 25.55 |
| ATOM | 1373 | O | ILE | 338 | 53.861 | 21.640 | 21.875 | 1.00 | 24.74 |
| ATOM | 1374 | N | GLU | 339 | 53.124 | 20.421 | 23.622 | 1.00 | 27.43 |
| ATOM | 1375 | CA | GLU | 339 | 54.220 | 19.448 | 23.536 | 1.00 | 27.60 |
| ATOM | 1376 | CB | GLU | 339 | 54.201 | 18.512 | 24.755 | 1.00 | 27.21 |
| ATOM | 1377 | C | GLU | 339 | 54.112 | 18.650 | 22.236 | 1.00 | 26.85 |
| ATOM | 1378 | O | GLU | 339 | 55.119 | 18.385 | 21.581 | 1.00 | 26.71 |
| ATOM | 1379 | N | LYS | 340 | 52.888 | 18.276 | 21.872 | 1.00 | 27.04 |
| ATOM | 1380 | CA | LYS | 340 | 52.663 | 17.515 | 20.654 | 1.00 | 28.19 |
| ATOM | 1381 | CB | LYS | 340 | 51.210 | 17.008 | 20.609 | 1.00 | 28.67 |
| ATOM | 1382 | C | LYS | 340 | 53.002 | 18.402 | 19.439 | 1.00 | 27.96 |
| ATOM | 1383 | O | LYS | 340 | 53.558 | 17.934 | 18.436 | 1.00 | 27.48 |
| ATOM | 1384 | N | SER | 341 | 52.746 | 19.700 | 19.567 | 1.00 | 28.32 |
| ATOM | 1385 | CA | SER | 341 | 53.058 | 20.662 | 18.514 | 1.00 | 28.02 |
| ATOM | 1386 | CB | SER | 341 | 52.457 | 22.022 | 18.867 | 1.00 | 31.25 |
| ATOM | 1387 | OG | SER | 341 | 52.880 | 23.029 | 17.965 | 1.00 | 37.69 |
| ATOM | 1388 | C | SER | 341 | 54.578 | 20.773 | 18.350 | 1.00 | 26.01 |
| ATOM | 1389 | O | SER | 341 | 55.096 | 20.717 | 17.234 | 1.00 | 25.06 |
| ATOM | 1390 | N | GLN | 342 | 55.297 | 20.899 | 19.462 | 1.00 | 25.71 |
| ATOM | 1391 | CA | GLN | 342 | 56.750 | 20.993 | 19.398 | 1.00 | 26.39 |
| ATOM | 1392 | CB | GLN | 342 | 57.356 | 21.254 | 20.777 | 1.00 | 24.17 |
| ATOM | 1393 | CG | GLN | 342 | 58.834 | 21.590 | 20.703 | 1.00 | 25.09 |
| ATOM | 1394 | CD | GLN | 342 | 59.476 | 21.677 | 22.057 | 1.00 | 26.93 |
| ATOM | 1395 | OE1 | GLN | 342 | 59.479 | 20.704 | 22.810 | 1.00 | 27.77 |
| ATOM | 1396 | NE2 | GLN | 342 | 60.022 | 22.839 | 22.386 | 1.00 | 24.61 |
| ATOM | 1397 | C | GLN | 342 | 57.354 | 19.715 | 18.806 | 1.00 | 25.69 |
| ATOM | 1398 | O | GLN | 342 | 58.356 | 19.771 | 18.075 | 1.00 | 24.99 |
| ATOM | 1399 | N | GLU | 343 | 56.753 | 18.569 | 19.127 | 1.00 | 25.00 |
| ATOM | 1400 | CA | GLU | 343 | 57.222 | 17.280 | 18.610 | 1.00 | 25.34 |
| ATOM | 1401 | CB | GLU | 343 | 56.411 | 16.118 | 19.245 | 1.00 | 25.90 |
| ATOM | 1402 | C | GLU | 343 | 57.089 | 17.276 | 17.076 | 1.00 | 24.32 |
| ATOM | 1403 | O | GLU | 343 | 58.021 | 16.891 | 16.365 | 1.00 | 23.99 |
| ATOM | 1404 | N | ALA | 344 | 55.961 | 17.789 | 16.587 | 1.00 | 23.56 |
| ATOM | 1405 | CA | ALA | 344 | 55.701 | 17.875 | 15.153 | 1.00 | 22.85 |
| ATOM | 1406 | CB | ALA | 344 | 54.320 | 18.451 | 14.917 | 1.00 | 22.64 |
| ATOM | 1407 | C | ALA | 344 | 56.768 | 18.743 | 14.489 | 1.00 | 22.77 |
| ATOM | 1408 | O | ALA | 344 | 57.355 | 18.360 | 13.477 | 1.00 | 22.08 |
| ATOM | 1409 | N | TYR | 345 | 57.057 | 19.893 | 15.092 | 1.00 | 21.89 |
| ATOM | 1410 | CA | TYR | 345 | 58.075 | 20.792 | 14.550 | 1.00 | 21.18 |
| ATOM | 1411 | CB | TYR | 345 | 58.108 | 22.119 | 15.313 | 1.00 | 20.27 |

FIG. 31A-29

| ATOM | 1412 | CG  | TYR | 345 | 57.048 | 23.078 | 14.856 | 1.00 | 17.45 |
|------|------|-----|-----|-----|--------|--------|--------|------|-------|
| ATOM | 1413 | CD1 | TYR | 345 | 56.001 | 23.431 | 15.698 | 1.00 | 17.99 |
| ATOM | 1414 | CE1 | TYR | 345 | 54.992 | 24.253 | 15.270 | 1.00 | 19.97 |
| ATOM | 1415 | CD2 | TYR | 345 | 57.063 | 23.589 | 13.562 | 1.00 | 19.11 |
| ATOM | 1416 | CE2 | TYR | 345 | 56.055 | 24.424 | 13.116 | 1.00 | 19.14 |
| ATOM | 1417 | CZ  | TYR | 345 | 55.017 | 24.749 | 13.972 | 1.00 | 20.78 |
| ATOM | 1418 | OH  | TYR | 345 | 53.983 | 25.539 | 13.530 | 1.00 | 20.70 |
| ATOM | 1419 | C   | TYR | 345 | 59.454 | 20.167 | 14.583 | 1.00 | 20.96 |
| ATOM | 1420 | O   | TYR | 345 | 60.221 | 20.314 | 13.632 | 1.00 | 22.29 |
| ATOM | 1421 | N   | LEU | 346 | 59.778 | 19.480 | 15.677 | 1.00 | 20.82 |
| ATOM | 1422 | CA  | LEU | 346 | 61.079 | 18.838 | 15.817 | 1.00 | 20.18 |
| ATOM | 1423 | CB  | LEU | 346 | 61.216 | 18.203 | 17.205 | 1.00 | 21.04 |
| ATOM | 1424 | CG  | LEU | 346 | 61.606 | 19.158 | 18.335 | 1.00 | 21.25 |
| ATOM | 1425 | CD1 | LEU | 346 | 61.226 | 18.595 | 19.685 | 1.00 | 20.95 |
| ATOM | 1426 | CD2 | LEU | 346 | 63.099 | 19.438 | 18.267 | 1.00 | 19.90 |
| ATOM | 1427 | C   | LEU | 346 | 61.317 | 17.806 | 14.716 | 1.00 | 20.19 |
| ATOM | 1428 | O   | LEU | 346 | 62.407 | 17.755 | 14.142 | 1.00 | 20.69 |
| ATOM | 1429 | N   | LEU | 347 | 60.290 | 17.016 | 14.390 | 1.00 | 22.00 |
| ATOM | 1430 | CA  | LEU | 347 | 60.406 | 15.994 | 13.344 | 1.00 | 21.81 |
| ATOM | 1431 | CB  | LEU | 347 | 59.199 | 15.051 | 13.366 | 1.00 | 24.03 |
| ATOM | 1432 | CG  | LEU | 347 | 59.301 | 13.805 | 14.250 | 1.00 | 26.28 |
| ATOM | 1433 | CD1 | LEU | 347 | 57.964 | 13.072 | 14.277 | 1.00 | 27.79 |
| ATOM | 1434 | CD2 | LEU | 347 | 60.409 | 12.889 | 13.728 | 1.00 | 24.78 |
| ATOM | 1435 | C   | LEU | 347 | 60.544 | 16.623 | 11.966 | 1.00 | 20.50 |
| ATOM | 1436 | O   | LEU | 347 | 61.351 | 16.179 | 11.143 | 1.00 | 21.39 |
| ATOM | 1437 | N   | ALA | 348 | 59.767 | 17.674 | 11.727 | 1.00 | 20.84 |
| ATOM | 1438 | CA  | ALA | 348 | 59.788 | 18.381 | 10.456 | 1.00 | 18.12 |
| ATOM | 1439 | CB  | ALA | 348 | 58.729 | 19.480 | 10.457 | 1.00 | 18.49 |
| ATOM | 1440 | C   | ALA | 348 | 61.168 | 18.963 | 10.269 | 1.00 | 17.53 |
| ATOM | 1441 | O   | ALA | 348 | 61.785 | 18.781 | 9.228  | 1.00 | 18.78 |
| ATOM | 1442 | N   | PHE | 349 | 61.677 | 19.569 | 11.338 | 1.00 | 19.55 |
| ATOM | 1443 | CA  | PHE | 349 | 63.001 | 20.196 | 11.389 | 1.00 | 19.84 |
| ATOM | 1444 | CB  | PHE | 349 | 63.188 | 20.823 | 12.786 | 1.00 | 18.68 |
| ATOM | 1445 | CG  | PHE | 349 | 64.380 | 21.758 | 12.917 | 1.00 | 19.12 |
| ATOM | 1446 | CD1 | PHE | 349 | 65.234 | 22.008 | 11.851 | 1.00 | 19.95 |
| ATOM | 1447 | CD2 | PHE | 349 | 64.618 | 22.420 | 14.126 | 1.00 | 20.06 |
| ATOM | 1448 | CE1 | PHE | 349 | 66.294 | 22.905 | 11.971 | 1.00 | 18.99 |
| ATOM | 1449 | CE2 | PHE | 349 | 65.674 | 23.317 | 14.261 | 1.00 | 16.79 |
| ATOM | 1450 | CZ  | PHE | 349 | 66.516 | 23.562 | 13.184 | 1.00 | 18.91 |
| ATOM | 1451 | C   | PHE | 349 | 64.108 | 19.170 | 11.103 | 1.00 | 20.44 |
| ATOM | 1452 | O   | PHE | 349 | 64.980 | 19.401 | 10.260 | 1.00 | 19.83 |
| ATOM | 1453 | N   | GLU | 350 | 64.064 | 18.032 | 11.794 | 1.00 | 23.59 |
| ATOM | 1454 | CA  | GLU | 350 | 65.077 | 16.995 | 11.610 | 1.00 | 23.46 |
| ATOM | 1455 | CB  | GLU | 350 | 64.830 | 15.845 | 12.584 | 1.00 | 25.26 |
| ATOM | 1456 | CG  | GLU | 350 | 65.694 | 14.644 | 12.288 | 1.00 | 31.98 |
| ATOM | 1457 | CD  | GLU | 350 | 65.526 | 13.482 | 13.257 | 1.00 | 35.49 |
| ATOM | 1458 | OE1 | GLU | 350 | 66.560 | 12.853 | 13.555 | 1.00 | 40.26 |
| ATOM | 1459 | OE2 | GLU | 350 | 64.380 | 13.173 | 13.689 | 1.00 | 36.23 |
| ATOM | 1460 | C   | GLU | 350 | 65.083 | 16.489 | 10.165 | 1.00 | 21.12 |
| ATOM | 1461 | O   | GLU | 350 | 66.133 | 16.384 | 9.526  | 1.00 | 19.81 |

FIG. 31A-30

| ATOM | 1462 | N   | HIS | 351 | 63.888 | 16.234 | 9.651  | 1.00 | 21.98 |
|------|------|-----|-----|-----|--------|--------|--------|------|-------|
| ATOM | 1463 | CA  | HIS | 351 | 63.694 | 15.751 | 8.292  | 1.00 | 21.31 |
| ATOM | 1464 | CB  | HIS | 351 | 62.238 | 15.321 | 8.107  | 1.00 | 21.76 |
| ATOM | 1465 | CG  | HIS | 351 | 61.839 | 14.160 | 8.967  | 1.00 | 22.08 |
| ATOM | 1466 | CD2 | HIS | 351 | 62.578 | 13.317 | 9.728  | 1.00 | 22.65 |
| ATOM | 1467 | ND1 | HIS | 351 | 60.532 | 13.751 | 9.115  | 1.00 | 22.37 |
| ATOM | 1468 | CE1 | HIS | 351 | 60.478 | 12.716 | 9.930  | 1.00 | 21.44 |
| ATOM | 1469 | NE2 | HIS | 351 | 61.705 | 12.429 | 10.314 | 1.00 | 20.85 |
| ATOM | 1470 | C   | HIS | 351 | 64.117 | 16.815 | 7.275  | 1.00 | 21.18 |
| ATOM | 1471 | O   | HIS | 351 | 64.683 | 16.489 | 6.231  | 1.00 | 22.65 |
| ATOM | 1472 | N   | TYR | 352 | 63.915 | 18.088 | 7.602  | 1.00 | 19.79 |
| ATOM | 1473 | CA  | TYR | 352 | 64.327 | 19.146 | 6.697  | 1.00 | 18.72 |
| ATOM | 1474 | CB  | TYR | 352 | 63.768 | 20.502 | 7.122  | 1.00 | 19.55 |
| ATOM | 1475 | CG  | TYR | 352 | 64.140 | 21.580 | 6.137  | 1.00 | 19.27 |
| ATOM | 1476 | CD1 | TYR | 352 | 63.556 | 21.623 | 4.867  | 1.00 | 19.29 |
| ATOM | 1477 | CE1 | TYR | 352 | 63.961 | 22.555 | 3.927  | 1.00 | 17.55 |
| ATOM | 1478 | CD2 | TYR | 352 | 65.132 | 22.507 | 6.438  | 1.00 | 18.91 |
| ATOM | 1479 | CE2 | TYR | 352 | 65.545 | 23.443 | 5.503  | 1.00 | 17.30 |
| ATOM | 1480 | CZ  | TYR | 352 | 64.954 | 23.459 | 4.256  | 1.00 | 18.41 |
| ATOM | 1481 | OH  | TYR | 352 | 65.355 | 24.384 | 3.334  | 1.00 | 19.40 |
| ATOM | 1482 | C   | TYR | 352 | 65.849 | 19.182 | 6.687  | 1.00 | 19.31 |
| ATOM | 1483 | O   | TYR | 352 | 66.479 | 19.333 | 5.639  | 1.00 | 20.25 |
| ATOM | 1484 | N   | VAL | 353 | 66.446 | 19.017 | 7.858  | 1.00 | 21.25 |
| ATOM | 1485 | CA  | VAL | 353 | 67.899 | 18.993 | 7.960  | 1.00 | 22.03 |
| ATOM | 1486 | CB  | VAL | 353 | 68.348 | 18.880 | 9.450  | 1.00 | 22.60 |
| ATOM | 1487 | CG1 | VAL | 353 | 69.843 | 18.635 | 9.550  | 1.00 | 20.34 |
| ATOM | 1488 | CG2 | VAL | 353 | 67.997 | 20.167 | 10.183 | 1.00 | 22.61 |
| ATOM | 1489 | C   | VAL | 353 | 68.442 | 17.827 | 7.108  | 1.00 | 22.74 |
| ATOM | 1490 | O   | VAL | 353 | 69.448 | 17.985 | 6.398  | 1.00 | 23.44 |
| ATOM | 1491 | N   | ASN | 354 | 67.773 | 16.674 | 7.165  | 1.00 | 22.30 |
| ATOM | 1492 | CA  | ASN | 354 | 68.185 | 15.508 | 6.373  | 1.00 | 23.56 |
| ATOM | 1493 | CB  | ASN | 354 | 67.241 | 14.320 | 6.603  | 1.00 | 22.26 |
| ATOM | 1494 | CG  | ASN | 354 | 67.374 | 13.715 | 7.981  | 1.00 | 23.06 |
| ATOM | 1495 | OD1 | ASN | 354 | 68.406 | 13.843 | 8.628  | 1.00 | 25.79 |
| ATOM | 1496 | ND2 | ASN | 354 | 66.327 | 13.044 | 8.435  | 1.00 | 21.07 |
| ATOM | 1497 | C   | ASN | 354 | 68.134 | 15.877 | 4.888  | 1.00 | 25.10 |
| ATOM | 1498 | O   | ASN | 354 | 69.024 | 15.534 | 4.111  | 1.00 | 26.70 |
| ATOM | 1499 | N   | HIS | 355 | 67.067 | 16.568 | 4.503  | 1.00 | 24.50 |
| ATOM | 1500 | CA  | HIS | 355 | 66.881 | 16.986 | 3.123  | 1.00 | 24.46 |
| ATOM | 1501 | CB  | HIS | 355 | 65.557 | 17.750 | 2.969  | 1.00 | 26.07 |
| ATOM | 1502 | CG  | HIS | 355 | 65.365 | 18.337 | 1.604  | 1.00 | 28.28 |
| ATOM | 1503 | CD2 | HIS | 355 | 65.918 | 19.422 | 1.018  | 1.00 | 28.10 |
| ATOM | 1504 | ND1 | HIS | 355 | 64.600 | 17.724 | 0.632  | 1.00 | 26.32 |
| ATOM | 1505 | CE1 | HIS | 355 | 64.706 | 18.407 | -0.499 | 1.00 | 27.71 |
| ATOM | 1506 | NE2 | HIS | 355 | 65.502 | 19.435 | -0.288 | 1.00 | 27.79 |
| ATOM | 1507 | C   | HIS | 355 | 68.022 | 17.857 | 2.624  | 1.00 | 24.07 |
| ATOM | 1508 | O   | HIS | 355 | 68.460 | 17.729 | 1.484  | 1.00 | 23.54 |
| ATOM | 1509 | N   | ARG | 356 | 68.463 | 18.774 | 3.471  | 1.00 | 25.31 |
| ATOM | 1510 | CA  | ARG | 356 | 69.523 | 19.714 | 3.130  | 1.00 | 25.69 |
| ATOM | 1511 | CB  | ARG | 356 | 69.561 | 20.820 | 4.168  | 1.00 | 24.06 |

FIG. 31A-31

| ATOM | 1512 | CG | ARG | 356 | 68.337 | 21.682 | 4.094 | 1.00 | 23.23 |
| --- | --- | --- | --- | --- | --- | --- | --- | --- | --- |
| ATOM | 1513 | CD | ARG | 356 | 68.670 | 22.973 | 3.424 | 1.00 | 25.91 |
| ATOM | 1514 | NE | ARG | 356 | 69.447 | 23.814 | 4.322 | 1.00 | 24.87 |
| ATOM | 1515 | CZ | ARG | 356 | 70.325 | 24.726 | 3.928 | 1.00 | 25.05 |
| ATOM | 1516 | NH1 | ARG | 356 | 70.546 | 24.920 | 2.640 | 1.00 | 24.97 |
| ATOM | 1517 | NH2 | ARG | 356 | 70.978 | 25.453 | 4.831 | 1.00 | 25.62 |
| ATOM | 1518 | C | ARG | 356 | 70.900 | 19.109 | 2.949 | 1.00 | 27.73 |
| ATOM | 1519 | O | ARG | 356 | 71.724 | 19.645 | 2.208 | 1.00 | 28.38 |
| ATOM | 1520 | N | LYS | 357 | 71.179 | 18.048 | 3.693 | 1.00 | 29.45 |
| ATOM | 1521 | CA | LYS | 357 | 72.457 | 17.355 | 3.588 | 1.00 | 31.35 |
| ATOM | 1522 | CB | LYS | 357 | 72.503 | 16.566 | 2.270 | 1.00 | 32.80 |
| ATOM | 1523 | CG | LYS | 357 | 71.290 | 15.650 | 2.103 | 1.00 | 35.78 |
| ATOM | 1524 | CD | LYS | 357 | 71.264 | 14.927 | 0.778 | 1.00 | 39.43 |
| ATOM | 1525 | CE | LYS | 357 | 70.121 | 13.918 | 0.739 | 1.00 | 42.93 |
| ATOM | 1526 | NZ | LYS | 357 | 70.162 | 13.074 | -0.498 | 1.00 | 45.97 |
| ATOM | 1527 | C | LYS | 357 | 73.692 | 18.247 | 3.743 | 1.00 | 31.34 |
| ATOM | 1528 | O | LYS | 357 | 74.489 | 18.390 | 2.818 | 1.00 | 32.65 |
| ATOM | 1529 | N | HIS | 358 | 73.837 | 18.861 | 4.913 | 1.00 | 30.72 |
| ATOM | 1530 | CA | HIS | 358 | 74.995 | 19.706 | 5.186 | 1.00 | 31.49 |
| ATOM | 1531 | CB | HIS | 358 | 74.895 | 20.322 | 6.579 | 1.00 | 29.13 |
| ATOM | 1532 | CG | HIS | 358 | 73.882 | 21.415 | 6.688 | 1.00 | 25.30 |
| ATOM | 1533 | CD2 | HIS | 358 | 74.026 | 22.760 | 6.646 | 1.00 | 24.90 |
| ATOM | 1534 | ND1 | HIS | 358 | 72.543 | 21.175 | 6.892 | 1.00 | 24.54 |
| ATOM | 1535 | CE1 | HIS | 358 | 71.901 | 22.324 | 6.975 | 1.00 | 23.68 |
| ATOM | 1536 | NE2 | HIS | 358 | 72.777 | 23.302 | 6.830 | 1.00 | 25.28 |
| ATOM | 1537 | C | HIS | 358 | 76.235 | 18.831 | 5.161 | 1.00 | 33.38 |
| ATOM | 1538 | O | HIS | 358 | 76.166 | 17.647 | 5.495 | 1.00 | 35.46 |
| ATOM | 1539 | N | ASN | 359 | 77.366 | 19.399 | 4.768 | 1.00 | 35.34 |
| ATOM | 1540 | CA | ASN | 359 | 78.606 | 18.636 | 4.746 | 1.00 | 38.17 |
| ATOM | 1541 | CB | ASN | 359 | 79.544 | 19.150 | 3.646 | 1.00 | 37.84 |
| ATOM | 1542 | C | ASN | 359 | 79.236 | 18.825 | 6.120 | 1.00 | 39.85 |
| ATOM | 1543 | O | ASN | 359 | 80.317 | 19.406 | 6.240 | 1.00 | 42.72 |
| ATOM | 1544 | N | ILE | 360 | 78.510 | 18.411 | 7.159 | 1.00 | 39.01 |
| ATOM | 1545 | CA | ILE | 360 | 78.968 | 18.526 | 8.549 | 1.00 | 36.72 |
| ATOM | 1546 | CB | ILE | 360 | 78.351 | 19.752 | 9.264 | 1.00 | 37.69 |
| ATOM | 1547 | CG2 | ILE | 360 | 78.802 | 19.793 | 10.722 | 1.00 | 37.56 |
| ATOM | 1548 | CG1 | ILE | 360 | 78.735 | 21.049 | 8.549 | 1.00 | 37.68 |
| ATOM | 1549 | CD1 | ILE | 360 | 77.970 | 22.253 | 9.041 | 1.00 | 38.40 |
| ATOM | 1550 | C | ILE | 360 | 78.524 | 17.278 | 9.303 | 1.00 | 35.15 |
| ATOM | 1551 | O | ILE | 360 | 77.343 | 16.931 | 9.314 | 1.00 | 33.75 |
| ATOM | 1552 | N | PRO | 361 | 79.475 | 16.564 | 9.912 | 1.00 | 34.64 |
| ATOM | 1553 | CD | PRO | 361 | 80.930 | 16.785 | 9.873 | 1.00 | 35.59 |
| ATOM | 1554 | CA | PRO | 361 | 79.138 | 15.349 | 10.660 | 1.00 | 33.92 |
| ATOM | 1555 | CB | PRO | 361 | 80.513 | 14.768 | 11.014 | 1.00 | 35.27 |
| ATOM | 1556 | CG | PRO | 361 | 81.412 | 15.972 | 11.048 | 1.00 | 35.97 |
| ATOM | 1557 | C | PRO | 361 | 78.292 | 15.618 | 11.909 | 1.00 | 30.95 |
| ATOM | 1558 | O | PRO | 361 | 78.555 | 16.554 | 12.653 | 1.00 | 31.50 |
| ATOM | 1559 | N | HIS | 362 | 77.269 | 14.793 | 12.112 | 1.00 | 28.75 |
| ATOM | 1560 | CA | HIS | 362 | 76.378 | 14.900 | 13.263 | 1.00 | 30.25 |
| ATOM | 1561 | CB | HIS | 362 | 77.152 | 14.612 | 14.548 | 1.00 | 31.20 |

FIG. 31A-32

| | | | | | | | |
|---|---|---|---|---|---|---|---|
| ATOM | 1562 | CG | HIS | 362 | 78.075 | 13.441 | 14.440 | 1.00 | 33.72 |
| ATOM | 1563 | CD2 | HIS | 362 | 77.826 | 12.122 | 14.275 | 1.00 | 34.55 |
| ATOM | 1564 | ND1 | HIS | 362 | 79.449 | 13.569 | 14.469 | 1.00 | 35.55 |
| ATOM | 1565 | CE1 | HIS | 362 | 80.006 | 12.377 | 14.322 | 1.00 | 35.28 |
| ATOM | 1566 | NE2 | HIS | 362 | 79.040 | 11.484 | 14.204 | 1.00 | 37.61 |
| ATOM | 1567 | C | HIS | 362 | 75.742 | 16.275 | 13.368 | 1.00 | 29.44 |
| ATOM | 1568 | O | HIS | 362 | 75.521 | 16.769 | 14.472 | 1.00 | 29.93 |
| ATOM | 1569 | N | PHE | 363 | 75.397 | 16.856 | 12.222 | 1.00 | 29.22 |
| ATOM | 1570 | CA | PHE | 363 | 74.803 | 18.188 | 12.160 | 1.00 | 27.72 |
| ATOM | 1571 | CB | PHE | 363 | 74.446 | 18.538 | 10.709 | 1.00 | 26.85 |
| ATOM | 1572 | CG | PHE | 363 | 73.901 | 19.931 | 10.532 | 1.00 | 27.48 |
| ATOM | 1573 | CD1 | PHE | 363 | 74.758 | 21.017 | 10.391 | 1.00 | 27.76 |
| ATOM | 1574 | CD2 | PHE | 363 | 72.523 | 20.157 | 10.513 | 1.00 | 27.45 |
| ATOM | 1575 | CE1 | PHE | 363 | 74.244 | 22.313 | 10.234 | 1.00 | 28.56 |
| ATOM | 1576 | CE2 | PHE | 363 | 72.001 | 21.446 | 10.357 | 1.00 | 25.15 |
| ATOM | 1577 | CZ | PHE | 363 | 72.860 | 22.521 | 10.219 | 1.00 | 24.41 |
| ATOM | 1578 | C | PHE | 363 | 73.597 | 18.385 | 13.075 | 1.00 | 27.45 |
| ATOM | 1579 | O | PHE | 363 | 73.577 | 19.324 | 13.880 | 1.00 | 27.73 |
| ATOM | 1580 | N | TRP | 364 | 72.616 | 17.489 | 12.983 | 1.00 | 25.89 |
| ATOM | 1581 | CA | TRP | 364 | 71.401 | 17.592 | 13.800 | 1.00 | 25.85 |
| ATOM | 1582 | CB | TRP | 364 | 70.444 | 16.426 | 13.506 | 1.00 | 24.27 |
| ATOM | 1583 | CG | TRP | 364 | 69.168 | 16.391 | 14.328 | 1.00 | 23.75 |
| ATOM | 1584 | CD2 | TRP | 364 | 68.152 | 17.407 | 14.397 | 1.00 | 24.87 |
| ATOM | 1585 | CE2 | TRP | 364 | 67.140 | 16.922 | 15.261 | 1.00 | 24.81 |
| ATOM | 1586 | CE3 | TRP | 364 | 67.989 | 18.674 | 13.820 | 1.00 | 25.47 |
| ATOM | 1587 | CD1 | TRP | 364 | 68.745 | 15.370 | 15.122 | 1.00 | 22.98 |
| ATOM | 1588 | NE1 | TRP | 364 | 67.530 | 15.679 | 15.684 | 1.00 | 25.99 |
| ATOM | 1589 | CZ2 | TRP | 364 | 65.987 | 17.661 | 15.560 | 1.00 | 25.14 |
| ATOM | 1590 | CZ3 | TRP | 364 | 66.844 | 19.405 | 14.116 | 1.00 | 25.29 |
| ATOM | 1591 | CH2 | TRP | 364 | 65.857 | 18.894 | 14.982 | 1.00 | 24.53 |
| ATOM | 1592 | C | TRP | 364 | 71.659 | 17.747 | 15.308 | 1.00 | 26.94 |
| ATOM | 1593 | O | TRP | 364 | 71.202 | 18.721 | 15.904 | 1.00 | 27.16 |
| ATOM | 1594 | N | PRO | 365 | 72.382 | 16.796 | 15.944 | 1.00 | 27.60 |
| ATOM | 1595 | CD | PRO | 365 | 72.912 | 15.522 | 15.411 | 1.00 | 27.55 |
| ATOM | 1596 | CA | PRO | 365 | 72.655 | 16.915 | 17.387 | 1.00 | 25.90 |
| ATOM | 1597 | CB | PRO | 365 | 73.565 | 15.717 | 17.668 | 1.00 | 26.00 |
| ATOM | 1598 | CG | PRO | 365 | 73.136 | 14.705 | 16.658 | 1.00 | 28.32 |
| ATOM | 1599 | C | PRO | 365 | 73.374 | 18.225 | 17.714 | 1.00 | 23.89 |
| ATOM | 1600 | O | PRO | 365 | 73.088 | 18.861 | 18.725 | 1.00 | 23.81 |
| ATOM | 1601 | N | LYS | 366 | 74.297 | 18.626 | 16.845 | 1.00 | 24.24 |
| ATOM | 1602 | CA | LYS | 366 | 75.058 | 19.862 | 17.027 | 1.00 | 26.24 |
| ATOM | 1603 | CB | LYS | 366 | 76.144 | 19.982 | 15.963 | 1.00 | 27.44 |
| ATOM | 1604 | CG | LYS | 366 | 77.310 | 19.022 | 16.138 | 1.00 | 28.76 |
| ATOM | 1605 | CD | LYS | 366 | 78.254 | 19.171 | 14.975 | 1.00 | 30.53 |
| ATOM | 1606 | CE | LYS | 366 | 79.527 | 18.387 | 15.167 | 1.00 | 34.25 |
| ATOM | 1607 | NZ | LYS | 366 | 80.388 | 18.463 | 13.947 | 1.00 | 37.89 |
| ATOM | 1608 | C | LYS | 366 | 74.181 | 21.107 | 16.993 | 1.00 | 26.73 |
| ATOM | 1609 | O | LYS | 366 | 74.385 | 22.042 | 17.762 | 1.00 | 27.36 |
| ATOM | 1610 | N | LEU | 367 | 73.216 | 21.124 | 16.086 | 1.00 | 27.98 |
| ATOM | 1611 | CA | LEU | 367 | 72.308 | 22.256 | 15.967 | 1.00 | 27.87 |

FIG. 31A-33

| | | | | | | | |
|---|---|---|---|---|---|---|---|
| ATOM | 1612 | CB | LEU | 367 | 71.559 | 22.192 | 14.632 | 1.00 | 27.29 |
| ATOM | 1613 | CG | LEU | 367 | 70.613 | 23.356 | 14.318 | 1.00 | 27.25 |
| ATOM | 1614 | CD1 | LEU | 367 | 71.334 | 24.707 | 14.510 | 1.00 | 22.90 |
| ATOM | 1615 | CD2 | LEU | 367 | 70.081 | 23.189 | 12.896 | 1.00 | 24.54 |
| ATOM | 1616 | C | LEU | 367 | 71.327 | 22.223 | 17.134 | 1.00 | 29.38 |
| ATOM | 1617 | O | LEU | 367 | 70.993 | 23.249 | 17.716 | 1.00 | 31.09 |
| ATOM | 1618 | N | LEU | 368 | 70.889 | 21.026 | 17.491 | 1.00 | 30.38 |
| ATOM | 1619 | CA | LEU | 368 | 69.962 | 20.843 | 18.594 | 1.00 | 31.14 |
| ATOM | 1620 | CB | LEU | 368 | 69.659 | 19.353 | 18.731 | 1.00 | 32.20 |
| ATOM | 1621 | CG | LEU | 368 | 68.247 | 18.852 | 19.014 | 1.00 | 33.52 |
| ATOM | 1622 | CD1 | LEU | 368 | 67.184 | 19.651 | 18.267 | 1.00 | 31.14 |
| ATOM | 1623 | CD2 | LEU | 368 | 68.210 | 17.379 | 18.632 | 1.00 | 33.99 |
| ATOM | 1624 | C | LEU | 368 | 70.601 | 21.395 | 19.876 | 1.00 | 32.36 |
| ATOM | 1625 | O | LEU | 368 | 69.917 | 21.963 | 20.730 | 1.00 | 32.58 |
| ATOM | 1626 | N | MET | 369 | 71.922 | 21.272 | 19.985 | 1.00 | 33.30 |
| ATOM | 1627 | CA | MET | 369 | 72.641 | 21.771 | 21.149 | 1.00 | 34.04 |
| ATOM | 1628 | CB | MET | 369 | 74.051 | 21.190 | 21.209 | 1.00 | 35.31 |
| ATOM | 1629 | CG | MET | 369 | 74.108 | 19.858 | 21.935 | 1.00 | 36.83 |
| ATOM | 1630 | SD | MET | 369 | 75.312 | 18.728 | 21.235 | 1.00 | 43.07 |
| ATOM | 1631 | CE | MET | 369 | 76.862 | 19.636 | 21.472 | 1.00 | 41.31 |
| ATOM | 1632 | C | MET | 369 | 72.675 | 23.297 | 21.212 | 1.00 | 34.30 |
| ATOM | 1633 | O | MET | 369 | 72.961 | 23.876 | 22.269 | 1.00 | 35.82 |
| ATOM | 1634 | N | LYS | 370 | 72.368 | 23.949 | 20.091 | 1.00 | 32.14 |
| ATOM | 1635 | CA | LYS | 370 | 72.325 | 25.405 | 20.044 | 1.00 | 29.17 |
| ATOM | 1636 | CB | LYS | 370 | 72.394 | 25.904 | 18.608 | 1.00 | 28.18 |
| ATOM | 1637 | CG | LYS | 370 | 73.662 | 25.518 | 17.900 | 1.00 | 27.72 |
| ATOM | 1638 | CD | LYS | 370 | 74.866 | 25.969 | 18.679 | 1.00 | 28.10 |
| ATOM | 1639 | CE | LYS | 370 | 76.127 | 25.650 | 17.930 | 1.00 | 27.79 |
| ATOM | 1640 | NZ | LYS | 370 | 77.298 | 25.941 | 18.777 | 1.00 | 30.78 |
| ATOM | 1641 | C | LYS | 370 | 71.033 | 25.875 | 20.705 | 1.00 | 29.27 |
| ATOM | 1642 | O | LYS | 370 | 70.950 | 26.999 | 21.200 | 1.00 | 29.43 |
| ATOM | 1643 | N | VAL | 371 | 70.018 | 25.014 | 20.714 | 1.00 | 29.40 |
| ATOM | 1644 | CA | VAL | 371 | 68.756 | 25.358 | 21.358 | 1.00 | 29.90 |
| ATOM | 1645 | CB | VAL | 371 | 67.687 | 24.237 | 21.218 | 1.00 | 28.75 |
| ATOM | 1646 | CG1 | VAL | 371 | 66.463 | 24.561 | 22.064 | 1.00 | 27.12 |
| ATOM | 1647 | CG2 | VAL | 371 | 67.275 | 24.080 | 19.762 | 1.00 | 29.23 |
| ATOM | 1648 | C | VAL | 371 | 69.075 | 25.573 | 22.832 | 1.00 | 31.39 |
| ATOM | 1649 | O | VAL | 371 | 68.543 | 26.481 | 23.462 | 1.00 | 31.20 |
| ATOM | 1650 | N | THR | 372 | 69.971 | 24.743 | 23.366 | 1.00 | 31.39 |
| ATOM | 1651 | CA | THR | 372 | 70.371 | 24.847 | 24.762 | 1.00 | 31.10 |
| ATOM | 1652 | CB | THR | 372 | 71.282 | 23.664 | 25.170 | 1.00 | 31.59 |
| ATOM | 1653 | OG1 | THR | 372 | 70.554 | 22.441 | 25.008 | 1.00 | 30.60 |
| ATOM | 1654 | CG2 | THR | 372 | 71.720 | 23.795 | 26.625 | 1.00 | 30.14 |
| ATOM | 1655 | C | THR | 372 | 71.071 | 26.186 | 24.994 | 1.00 | 30.76 |
| ATOM | 1656 | O | THR | 372 | 70.711 | 26.935 | 25.910 | 1.00 | 31.45 |
| ATOM | 1657 | N | ASP | 373 | 72.038 | 26.507 | 24.138 | 1.00 | 29.31 |
| ATOM | 1658 | CA | ASP | 373 | 72.744 | 27.772 | 24.252 | 1.00 | 27.32 |
| ATOM | 1659 | CB | ASP | 373 | 73.745 | 27.934 | 23.115 | 1.00 | 27.98 |
| ATOM | 1660 | CG | ASP | 373 | 74.886 | 26.933 | 23.190 | 1.00 | 28.94 |
| ATOM | 1661 | OD1 | ASP | 373 | 75.043 | 26.259 | 24.225 | 1.00 | 31.01 |

FIG. 31A-34

| ATOM | 1662 | OD2 | ASP | 373 | 75.639 | 26.825 | 22.205 | 1.00 | 31.38 |
|------|------|-----|-----|-----|--------|--------|--------|------|-------|
| ATOM | 1663 | C | ASP | 373 | 71.742 | 28.926 | 24.247 | 1.00 | 26.50 |
| ATOM | 1664 | O | ASP | 373 | 71.872 | 29.861 | 25.040 | 1.00 | 27.35 |
| ATOM | 1665 | N | LEU | 374 | 70.711 | 28.826 | 23.412 | 1.00 | 24.17 |
| ATOM | 1666 | CA | LEU | 374 | 69.688 | 29.864 | 23.331 | 1.00 | 23.38 |
| ATOM | 1667 | CB | LEU | 374 | 68.795 | 29.660 | 22.107 | 1.00 | 22.98 |
| ATOM | 1668 | CG | LEU | 374 | 69.361 | 30.183 | 20.786 | 1.00 | 24.45 |
| ATOM | 1669 | CD1 | LEU | 374 | 68.668 | 29.520 | 19.589 | 1.00 | 24.72 |
| ATOM | 1670 | CD2 | LEU | 374 | 69.223 | 31.704 | 20.735 | 1.00 | 22.40 |
| ATOM | 1671 | C | LEU | 374 | 68.839 | 29.964 | 24.589 | 1.00 | 24.31 |
| ATOM | 1672 | O | LEU | 374 | 68.442 | 31.065 | 24.986 | 1.00 | 23.31 |
| ATOM | 1673 | N | ARG | 375 | 68.543 | 28.826 | 25.211 | 1.00 | 25.32 |
| ATOM | 1674 | CA | ARG | 375 | 67.748 | 28.821 | 26.438 | 1.00 | 27.76 |
| ATOM | 1675 | CB | ARG | 375 | 67.455 | 27.392 | 26.908 | 1.00 | 30.82 |
| ATOM | 1676 | CG | ARG | 375 | 66.901 | 26.439 | 25.854 | 1.00 | 38.79 |
| ATOM | 1677 | CD | ARG | 375 | 65.424 | 26.630 | 25.582 | 1.00 | 45.40 |
| ATOM | 1678 | NE | ARG | 375 | 64.709 | 25.360 | 25.620 | 1.00 | 52.61 |
| ATOM | 1679 | CZ | ARG | 375 | 63.800 | 24.967 | 24.726 | 1.00 | 56.89 |
| ATOM | 1680 | NH1 | ARG | 375 | 63.473 | 25.732 | 23.694 | 1.00 | 58.27 |
| ATOM | 1681 | NH2 | ARG | 375 | 63.201 | 23.793 | 24.855 | 1.00 | 58.46 |
| ATOM | 1682 | C | ARG | 375 | 68.563 | 29.542 | 27.512 | 1.00 | 26.98 |
| ATOM | 1683 | O | ARG | 375 | 68.025 | 30.336 | 28.282 | 1.00 | 26.18 |
| ATOM | 1684 | N | MET | 376 | 69.862 | 29.255 | 27.551 | 1.00 | 26.80 |
| ATOM | 1685 | CA | MET | 376 | 70.767 | 29.867 | 28.511 | 1.00 | 29.22 |
| ATOM | 1686 | CB | MET | 376 | 72.172 | 29.270 | 28.379 | 1.00 | 33.70 |
| ATOM | 1687 | CG | MET | 376 | 72.595 | 28.371 | 29.562 | 1.00 | 43.20 |
| ATOM | 1688 | SD | MET | 376 | 73.320 | 29.260 | 31.011 | 1.00 | 52.38 |
| ATOM | 1689 | CE | MET | 376 | 71.843 | 29.854 | 31.913 | 1.00 | 48.11 |
| ATOM | 1690 | C | MET | 376 | 70.804 | 31.384 | 28.339 | 1.00 | 27.54 |
| ATOM | 1691 | O | MET | 376 | 70.792 | 32.126 | 29.323 | 1.00 | 26.96 |
| ATOM | 1692 | N | ILE | 377 | 70.841 | 31.835 | 27.087 | 1.00 | 25.39 |
| ATOM | 1693 | CA | ILE | 377 | 70.847 | 33.264 | 26.767 | 1.00 | 23.26 |
| ATOM | 1694 | CB | ILE | 377 | 70.992 | 33.488 | 25.222 | 1.00 | 22.73 |
| ATOM | 1695 | CG2 | ILE | 377 | 70.560 | 34.909 | 24.819 | 1.00 | 21.81 |
| ATOM | 1696 | CG1 | ILE | 377 | 72.431 | 33.205 | 24.789 | 1.00 | 20.39 |
| ATOM | 1697 | CD1 | ILE | 377 | 72.644 | 33.148 | 23.300 | 1.00 | 18.85 |
| ATOM | 1698 | C | ILE | 377 | 69.558 | 33.900 | 27.309 | 1.00 | 22.91 |
| ATOM | 1699 | O | ILE | 377 | 69.597 | 34.925 | 27.989 | 1.00 | 22.02 |
| ATOM | 1700 | N | GLY | 378 | 68.427 | 33.244 | 27.069 | 1.00 | 22.29 |
| ATOM | 1701 | CA | GLY | 378 | 67.161 | 33.757 | 27.547 | 1.00 | 22.83 |
| ATOM | 1702 | C | GLY | 378 | 67.111 | 33.815 | 29.063 | 1.00 | 25.60 |
| ATOM | 1703 | O | GLY | 378 | 66.546 | 34.752 | 29.630 | 1.00 | 26.25 |
| ATOM | 1704 | N | ALA | 379 | 67.691 | 32.804 | 29.713 | 1.00 | 26.88 |
| ATOM | 1705 | CA | ALA | 379 | 67.744 | 32.707 | 31.175 | 1.00 | 27.19 |
| ATOM | 1706 | CB | ALA | 379 | 68.322 | 31.358 | 31.590 | 1.00 | 26.97 |
| ATOM | 1707 | C | ALA | 379 | 68.606 | 33.827 | 31.738 | 1.00 | 26.13 |
| ATOM | 1708 | O | ALA | 379 | 68.174 | 34.580 | 32.601 | 1.00 | 26.46 |
| ATOM | 1709 | N | CYA | 380 | 69.826 | 33.935 | 31.230 | 1.00 | 27.61 |
| ATOM | 1710 | CA | CYA | 380 | 70.742 | 34.973 | 31.667 | 1.00 | 29.74 |
| ATOM | 1711 | CB | CYA | 380 | 72.070 | 34.865 | 30.923 | 1.00 | 35.44 |

FIG. 31A-35

| ATOM | 1712 | SG | CYA | 380 | 73.081 | 33.458 | 31.417 | 1.00 | 42.61 |
|---|---|---|---|---|---|---|---|---|---|
| ATOM | 1713 | AS | CYA | 380 | 74.829 | 33.691 | 29.945 | 1.00 | 55.91 |
| ATOM | 1714 | C | CYA | 380 | 70.142 | 36.349 | 31.446 | 1.00 | 29.07 |
| ATOM | 1715 | O | CYA | 380 | 70.243 | 37.225 | 32.303 | 1.00 | 29.46 |
| ATOM | 1716 | N | HIS | 381 | 69.494 | 36.538 | 30.304 | 1.00 | 28.29 |
| ATOM | 1717 | CA | HIS | 381 | 68.885 | 37.824 | 30.002 | 1.00 | 26.84 |
| ATOM | 1718 | CB | HIS | 381 | 68.384 | 37.880 | 28.557 | 1.00 | 23.13 |
| ATOM | 1719 | CG | HIS | 381 | 67.597 | 39.113 | 28.259 | 1.00 | 19.84 |
| ATOM | 1720 | CD2 | HIS | 381 | 67.993 | 40.365 | 27.931 | 1.00 | 18.68 |
| ATOM | 1721 | ND1 | HIS | 381 | 66.229 | 39.169 | 28.403 | 1.00 | 19.47 |
| ATOM | 1722 | CE1 | HIS | 381 | 65.817 | 40.407 | 28.190 | 1.00 | 18.64 |
| ATOM | 1723 | NE2 | HIS | 381 | 66.868 | 41.149 | 27.900 | 1.00 | 18.29 |
| ATOM | 1724 | C | HIS | 381 | 67.747 | 38.157 | 30.967 | 1.00 | 26.78 |
| ATOM | 1725 | O | HIS | 381 | 67.560 | 39.314 | 31.337 | 1.00 | 26.39 |
| ATOM | 1726 | N | ALA | 382 | 66.964 | 37.158 | 31.347 | 1.00 | 27.78 |
| ATOM | 1727 | CA | ALA | 382 | 65.867 | 37.395 | 32.269 | 1.00 | 29.45 |
| ATOM | 1728 | CB | ALA | 382 | 65.077 | 36.125 | 32.471 | 1.00 | 29.51 |
| ATOM | 1729 | C | ALA | 382 | 66.425 | 37.904 | 33.604 | 1.00 | 31.74 |
| ATOM | 1730 | O | ALA | 382 | 65.932 | 38.882 | 34.159 | 1.00 | 32.60 |
| ATOM | 1731 | N | SER | 383 | 67.483 | 37.262 | 34.093 | 1.00 | 33.02 |
| ATOM | 1732 | CA | SER | 383 | 68.109 | 37.662 | 35.350 | 1.00 | 34.69 |
| ATOM | 1733 | CB | SER | 383 | 69.212 | 36.677 | 35.733 | 1.00 | 36.18 |
| ATOM | 1734 | OG | SER | 383 | 68.663 | 35.386 | 35.933 | 1.00 | 40.61 |
| ATOM | 1735 | C | SER | 383 | 68.689 | 39.064 | 35.242 | 1.00 | 33.49 |
| ATOM | 1736 | O | SER | 383 | 68.526 | 39.889 | 36.146 | 1.00 | 34.28 |
| ATOM | 1737 | N | ARG | 384 | 69.377 | 39.332 | 34.141 | 1.00 | 32.60 |
| ATOM | 1738 | CA | ARG | 384 | 69.955 | 40.642 | 33.938 | 1.00 | 32.60 |
| ATOM | 1739 | CB | ARG | 384 | 70.926 | 40.638 | 32.762 | 1.00 | 33.60 |
| ATOM | 1740 | CG | ARG | 384 | 71.429 | 42.013 | 32.409 | 1.00 | 36.33 |
| ATOM | 1741 | CD | ARG | 384 | 72.875 | 41.975 | 31.993 | 1.00 | 39.62 |
| ATOM | 1742 | NE | ARG | 384 | 73.760 | 42.260 | 33.114 | 1.00 | 41.76 |
| ATOM | 1743 | CZ | ARG | 384 | 74.587 | 43.301 | 33.179 | 1.00 | 41.92 |
| ATOM | 1744 | NH1 | ARG | 384 | 74.670 | 44.182 | 32.191 | 1.00 | 40.66 |
| ATOM | 1745 | NH2 | ARG | 384 | 75.319 | 43.471 | 34.260 | 1.00 | 44.88 |
| ATOM | 1746 | C | ARG | 384 | 68.862 | 41.694 | 33.758 | 1.00 | 32.28 |
| ATOM | 1747 | O | ARG | 384 | 69.014 | 42.831 | 34.213 | 1.00 | 33.27 |
| ATOM | 1748 | N | PHE | 385 | 67.739 | 41.311 | 33.159 | 1.00 | 29.13 |
| ATOM | 1749 | CA | PHE | 385 | 66.663 | 42.259 | 32.977 | 1.00 | 27.55 |
| ATOM | 1750 | CB | PHE | 385 | 65.552 | 41.687 | 32.105 | 1.00 | 26.89 |
| ATOM | 1751 | CG | PHE | 385 | 64.415 | 42.641 | 31.888 | 1.00 | 25.11 |
| ATOM | 1752 | CD1 | PHE | 385 | 64.495 | 43.630 | 30.918 | 1.00 | 24.94 |
| ATOM | 1753 | CD2 | PHE | 385 | 63.281 | 42.580 | 32.689 | 1.00 | 25.01 |
| ATOM | 1754 | CE1 | PHE | 385 | 63.466 | 44.547 | 30.753 | 1.00 | 25.50 |
| ATOM | 1755 | CE2 | PHE | 385 | 62.244 | 43.495 | 32.531 | 1.00 | 24.06 |
| ATOM | 1756 | CZ | PHE | 385 | 62.338 | 44.482 | 31.563 | 1.00 | 25.44 |
| ATOM | 1757 | C | PHE | 385 | 66.125 | 42.641 | 34.348 | 1.00 | 29.08 |
| ATOM | 1758 | O | PHE | 385 | 65.887 | 43.816 | 34.613 | 1.00 | 27.90 |
| ATOM | 1759 | N | LEU | 386 | 65.972 | 41.658 | 35.231 | 1.00 | 31.19 |
| ATOM | 1760 | CA | LEU | 386 | 65.465 | 41.929 | 36.577 | 1.00 | 33.22 |
| ATOM | 1761 | CB | LEU | 386 | 65.355 | 40.640 | 37.397 | 1.00 | 34.35 |

FIG. 31A-36

| ATOM | 1762 | C | LEU | 386 | 66.362 | 42.940 | 37.279 | 1.00 | 33.52 | |
|---|---|---|---|---|---|---|---|---|---|---|
| ATOM | 1763 | O | LEU | 386 | 65.874 | 43.907 | 37.855 | 1.00 | 32.93 | |
| ATOM | 1764 | N | HIS | 387 | 67.673 | 42.760 | 37.158 | 1.00 | 34.80 | |
| ATOM | 1765 | CA | HIS | 387 | 68.628 | 43.674 | 37.775 | 1.00 | 37.88 | |
| ATOM | 1766 | CB | HIS | 387 | 70.042 | 43.112 | 37.705 | 1.00 | 36.66 | |
| ATOM | 1767 | CG | HIS | 387 | 70.206 | 41.832 | 38.456 | 1.00 | 39.14 | |
| ATOM | 1768 | CD2 | HIS | 387 | 69.307 | 41.080 | 39.144 | 1.00 | 39.28 | |
| ATOM | 1769 | ND1 | HIS | 387 | 71.408 | 41.161 | 38.543 | 1.00 | 40.97 | |
| ATOM | 1770 | CE1 | HIS | 387 | 71.241 | 40.055 | 39.245 | 1.00 | 41.57 | |
| ATOM | 1771 | NE2 | HIS | 387 | 69.980 | 39.984 | 39.618 | 1.00 | 41.45 | |
| ATOM | 1772 | C | HIS | 387 | 68.589 | 45.071 | 37.164 | 1.00 | 40.38 | |
| ATOM | 1773 | O | HIS | 387 | 68.673 | 46.054 | 37.888 | 1.00 | 40.87 | |
| ATOM | 1774 | N | MET | 388 | 68.466 | 45.161 | 35.842 | 1.00 | 43.32 | |
| ATOM | 1775 | CA | MET | 388 | 68.398 | 46.455 | 35.168 | 1.00 | 46.28 | |
| ATOM | 1776 | CB | MET | 388 | 68.170 | 46.286 | 33.665 | 1.00 | 43.30 | |
| ATOM | 1777 | CG | MET | 388 | 69.342 | 45.738 | 32.875 | 1.00 | 43.55 | |
| ATOM | 1778 | SD | MET | 388 | 69.034 | 45.896 | 31.098 | 1.00 | 46.27 | |
| ATOM | 1779 | CE | MET | 388 | 68.208 | 44.370 | 30.709 | 1.00 | 42.36 | |
| ATOM | 1780 | C | MET | 388 | 67.256 | 47.289 | 35.737 | 1.00 | 50.25 | |
| ATOM | 1781 | O | MET | 388 | 67.363 | 48.506 | 35.886 | 1.00 | 49.79 | |
| ATOM | 1782 | N | LYS | 389 | 66.163 | 46.610 | 36.075 | 1.00 | 52.74 | ALTA |
| ATOM | 1783 | CA | LYS | 389 | 64.983 | 47.274 | 36.633 | 1.00 | 56.15 | ALTA |
| ATOM | 1784 | CB | LYS | 389 | 63.770 | 46.334 | 36.565 | 1.00 | 56.87 | ALTA |
| ATOM | 1785 | CG | LYS | 389 | 63.227 | 46.087 | 35.161 | 1.00 | 57.76 | ALTA |
| ATOM | 1786 | CD | LYS | 389 | 62.029 | 45.156 | 35.212 | 1.00 | 55.98 | ALTA |
| ATOM | 1787 | CE | LYS | 389 | 62.426 | 43.796 | 35.778 | 1.00 | 55.48 | ALTA |
| ATOM | 1788 | NZ | LYS | 389 | 61.267 | 43.040 | 36.311 | 1.00 | 55.55 | ALTA |
| ATOM | 1789 | C | LYS | 389 | 65.177 | 47.767 | 38.064 | 1.00 | 56.69 | ALTA |
| ATOM | 1790 | O | LYS | 389 | 64.623 | 48.814 | 38.453 | 1.00 | 58.54 | ALTA |
| ATOM | 1791 | N | VAL | 390 | 65.955 | 47.038 | 38.839 | 1.00 | 55.21 | |
| ATOM | 1792 | CA | VAL | 390 | 66.225 | 47.386 | 40.236 | 1.00 | 51.78 | |
| ATOM | 1793 | CB | VAL | 390 | 66.999 | 46.231 | 40.985 | 1.00 | 50.07 | |
| ATOM | 1794 | CG1 | VAL | 390 | 67.648 | 46.726 | 42.263 | 1.00 | 49.74 | |
| ATOM | 1795 | CG2 | VAL | 390 | 66.037 | 45.093 | 41.317 | 1.00 | 49.06 | |
| ATOM | 1796 | C | VAL | 390 | 67.053 | 48.681 | 40.227 | 1.00 | 49.38 | |
| ATOM | 1797 | O | VAL | 390 | 66.785 | 49.605 | 40.992 | 1.00 | 48.71 | |
| ATOM | 1798 | N | GLU | 391 | 67.974 | 48.778 | 39.272 | 1.00 | 46.71 | |
| ATOM | 1799 | CA | GLU | 391 | 68.866 | 49.919 | 39.142 | 1.00 | 44.88 | |
| ATOM | 1800 | CB | GLU | 391 | 70.156 | 49.488 | 38.438 | 1.00 | 45.24 | |
| ATOM | 1801 | CG | GLU | 391 | 70.793 | 48.207 | 38.997 | 1.00 | 47.65 | |
| ATOM | 1802 | CD | GLU | 391 | 71.461 | 48.388 | 40.358 | 1.00 | 50.29 | |
| ATOM | 1803 | OE1 | GLU | 391 | 71.141 | 49.373 | 41.063 | 1.00 | 50.68 | |
| ATOM | 1804 | OE2 | GLU | 391 | 72.310 | 47.535 | 40.718 | 1.00 | 50.85 | |
| ATOM | 1805 | C | GLU | 391 | 68.324 | 51.174 | 38.458 | 1.00 | 45.28 | |
| ATOM | 1806 | O | GLU | 391 | 68.568 | 52.286 | 38.940 | 1.00 | 46.46 | |
| ATOM | 1807 | N | CYA | 392 | 67.568 | 51.024 | 37.372 | 1.00 | 43.33 | |
| ATOM | 1808 | CA | CYA | 392 | 67.071 | 52.192 | 36.643 | 1.00 | 42.28 | |
| ATOM | 1809 | CB | CYA | 392 | 67.519 | 52.096 | 35.197 | 1.00 | 42.45 | |
| ATOM | 1810 | SG | CYA | 392 | 69.280 | 52.182 | 35.127 | 1.00 | 43.69 | |
| ATOM | 1811 | AS | CYA | 392 | 69.908 | 51.044 | 33.336 | 1.00 | 48.17 | |

FIG. 31A-37

| ATOM | 1812 | C   | CYA | 392 | 65.589 | 52.493 | 36.709 | 1.00 | 42.51 |
|------|------|-----|-----|-----|--------|--------|--------|------|-------|
| ATOM | 1813 | O   | CYA | 392 | 64.792 | 51.634 | 37.070 | 1.00 | 43.30 |
| ATOM | 1814 | N   | PRO | 393 | 65.205 | 53.752 | 36.418 | 1.00 | 42.13 |
| ATOM | 1815 | CD  | PRO | 393 | 66.109 | 54.899 | 36.199 | 1.00 | 40.54 |
| ATOM | 1816 | CA  | PRO | 393 | 63.794 | 54.182 | 36.441 | 1.00 | 42.26 |
| ATOM | 1817 | CB  | PRO | 393 | 63.896 | 55.710 | 36.365 | 1.00 | 41.47 |
| ATOM | 1818 | CG  | PRO | 393 | 65.189 | 55.938 | 35.614 | 1.00 | 41.10 |
| ATOM | 1819 | C   | PRO | 393 | 62.954 | 53.606 | 35.281 | 1.00 | 43.20 |
| ATOM | 1820 | O   | PRO | 393 | 63.463 | 53.452 | 34.163 | 1.00 | 42.61 |
| ATOM | 1821 | N   | THR | 394 | 61.686 | 53.305 | 35.559 | 1.00 | 43.70 |
| ATOM | 1822 | CA  | THR | 394 | 60.764 | 52.755 | 34.564 | 1.00 | 45.50 |
| ATOM | 1823 | CB  | THR | 394 | 59.340 | 52.609 | 35.129 | 1.00 | 47.20 |
| ATOM | 1824 | OG1 | THR | 394 | 59.304 | 53.139 | 36.464 | 1.00 | 50.57 |
| ATOM | 1825 | CG2 | THR | 394 | 58.878 | 51.150 | 35.137 | 1.00 | 47.99 |
| ATOM | 1826 | C   | THR | 394 | 60.682 | 53.583 | 33.283 | 1.00 | 44.58 |
| ATOM | 1827 | O   | THR | 394 | 60.409 | 53.054 | 32.215 | 1.00 | 46.36 |
| ATOM | 1828 | N   | GLU | 395 | 60.899 | 54.888 | 33.396 | 1.00 | 42.88 |
| ATOM | 1829 | CA  | GLU | 395 | 60.842 | 55.790 | 32.246 | 1.00 | 40.54 |
| ATOM | 1830 | CB  | GLU | 395 | 61.096 | 57.234 | 32.699 | 1.00 | 40.69 |
| ATOM | 1831 | C   | GLU | 395 | 61.799 | 55.421 | 31.098 | 1.00 | 38.51 |
| ATOM | 1832 | O   | GLU | 395 | 61.628 | 55.877 | 29.968 | 1.00 | 39.41 |
| ATOM | 1833 | N   | LEU | 396 | 62.828 | 54.640 | 31.402 | 1.00 | 35.60 |
| ATOM | 1834 | CA  | LEU | 396 | 63.795 | 54.220 | 30.386 | 1.00 | 33.11 |
| ATOM | 1835 | CB  | LEU | 396 | 65.169 | 54.003 | 31.027 | 1.00 | 33.60 |
| ATOM | 1836 | CG  | LEU | 396 | 65.831 | 55.230 | 31.660 | 1.00 | 34.54 |
| ATOM | 1837 | CD1 | LEU | 396 | 67.160 | 54.835 | 32.282 | 1.00 | 32.83 |
| ATOM | 1838 | CD2 | LEU | 396 | 66.026 | 56.308 | 30.599 | 1.00 | 35.71 |
| ATOM | 1839 | C   | LEU | 396 | 63.388 | 52.940 | 29.660 | 1.00 | 30.95 |
| ATOM | 1840 | O   | LEU | 396 | 63.950 | 52.605 | 28.624 | 1.00 | 30.90 |
| ATOM | 1841 | N   | PHE | 397 | 62.422 | 52.227 | 30.223 | 1.00 | 30.18 |
| ATOM | 1842 | CA  | PHE | 397 | 61.961 | 50.970 | 29.654 | 1.00 | 28.80 |
| ATOM | 1843 | CB  | PHE | 397 | 61.712 | 49.946 | 30.777 | 1.00 | 28.10 |
| ATOM | 1844 | CG  | PHE | 397 | 62.938 | 49.604 | 31.592 | 1.00 | 28.96 |
| ATOM | 1845 | CD1 | PHE | 397 | 63.403 | 50.472 | 32.591 | 1.00 | 28.39 |
| ATOM | 1846 | CD2 | PHE | 397 | 63.636 | 48.422 | 31.359 | 1.00 | 26.28 |
| ATOM | 1847 | CE1 | PHE | 397 | 64.546 | 50.166 | 33.337 | 1.00 | 28.44 |
| ATOM | 1848 | CE2 | PHE | 397 | 64.784 | 48.107 | 32.103 | 1.00 | 29.21 |
| ATOM | 1849 | CZ  | PHE | 397 | 65.240 | 48.984 | 33.096 | 1.00 | 27.37 |
| ATOM | 1850 | C   | PHE | 397 | 60.683 | 51.093 | 28.836 | 1.00 | 27.54 |
| ATOM | 1851 | O   | PHE | 397 | 59.630 | 51.431 | 29.370 | 1.00 | 26.96 |
| ATOM | 1852 | N   | PRO | 398 | 60.753 | 50.836 | 27.501 | 1.00 | 27.41 |
| ATOM | 1853 | CD  | PRO | 398 | 61.968 | 50.600 | 26.686 | 1.00 | 25.42 |
| ATOM | 1854 | CA  | PRO | 398 | 59.560 | 50.920 | 26.654 | 1.00 | 25.90 |
| ATOM | 1855 | CB  | PRO | 398 | 60.068 | 50.383 | 25.320 | 1.00 | 25.26 |
| ATOM | 1856 | CG  | PRO | 398 | 61.490 | 50.893 | 25.290 | 1.00 | 23.99 |
| ATOM | 1857 | C   | PRO | 398 | 58.494 | 49.995 | 27.272 | 1.00 | 25.86 |
| ATOM | 1858 | O   | PRO | 398 | 58.839 | 48.962 | 27.843 | 1.00 | 25.82 |
| ATOM | 1859 | N   | PRO | 399 | 57.197 | 50.355 | 27.175 | 1.00 | 25.52 |
| ATOM | 1860 | CD  | PRO | 399 | 56.627 | 51.576 | 26.578 | 1.00 | 25.49 |
| ATOM | 1861 | CA  | PRO | 399 | 56.145 | 49.510 | 27.754 | 1.00 | 25.42 |

FIG. 31A-38

| | | | | | | | | | |
|---|---|---|---|---|---|---|---|---|---|
| ATOM | 1862 | CB | PRO | 399 | 54.861 | 50.181 | 27.273 | 1.00 | 26.23 |
| ATOM | 1863 | CG | PRO | 399 | 55.237 | 51.609 | 27.156 | 1.00 | 25.25 |
| ATOM | 1864 | C | PRO | 399 | 56.198 | 48.043 | 27.317 | 1.00 | 26.08 |
| ATOM | 1865 | O | PRO | 399 | 56.132 | 47.131 | 28.159 | 1.00 | 25.45 |
| ATOM | 1866 | N | LEU | 400 | 56.350 | 47.810 | 26.019 | 1.00 | 25.57 |
| ATOM | 1867 | CA | LEU | 400 | 56.406 | 46.440 | 25.509 | 1.00 | 26.27 |
| ATOM | 1868 | CB | LEU | 400 | 56.404 | 46.418 | 23.980 | 1.00 | 25.03 |
| ATOM | 1869 | CG | LEU | 400 | 56.117 | 45.042 | 23.363 | 1.00 | 24.51 |
| ATOM | 1870 | CD1 | LEU | 400 | 54.757 | 44.530 | 23.806 | 1.00 | 23.22 |
| ATOM | 1871 | CD2 | LEU | 400 | 56.173 | 45.149 | 21.862 | 1.00 | 23.70 |
| ATOM | 1872 | C | LEU | 400 | 57.602 | 45.657 | 26.067 | 1.00 | 27.06 |
| ATOM | 1873 | O | LEU | 400 | 57.484 | 44.465 | 26.363 | 1.00 | 27.41 |
| ATOM | 1874 | N | PHE | 401 | 58.736 | 46.339 | 26.231 | 1.00 | 27.16 |
| ATOM | 1875 | CA | PHE | 401 | 59.966 | 45.754 | 26.779 | 1.00 | 27.06 |
| ATOM | 1876 | CB | PHE | 401 | 61.047 | 46.833 | 26.802 | 1.00 | 26.60 |
| ATOM | 1877 | CG | PHE | 401 | 62.408 | 46.351 | 27.217 | 1.00 | 28.08 |
| ATOM | 1878 | CD1 | PHE | 401 | 62.918 | 45.138 | 26.747 | 1.00 | 27.45 |
| ATOM | 1879 | CD2 | PHE | 401 | 63.223 | 47.165 | 28.013 | 1.00 | 27.48 |
| ATOM | 1880 | CE1 | PHE | 401 | 64.220 | 44.746 | 27.055 | 1.00 | 26.95 |
| ATOM | 1881 | CE2 | PHE | 401 | 64.523 | 46.786 | 28.327 | 1.00 | 27.97 |
| ATOM | 1882 | CZ | PHE | 401 | 65.028 | 45.575 | 27.846 | 1.00 | 28.46 |
| ATOM | 1883 | C | PHE | 401 | 59.690 | 45.247 | 28.205 | 1.00 | 27.62 |
| ATOM | 1884 | O | PHE | 401 | 60.046 | 44.125 | 28.570 | 1.00 | 26.24 |
| ATOM | 1885 | N | LEU | 402 | 59.036 | 46.082 | 29.002 | 1.00 | 28.75 |
| ATOM | 1886 | CA | LEU | 402 | 58.692 | 45.719 | 30.366 | 1.00 | 29.58 |
| ATOM | 1887 | CB | LEU | 402 | 58.064 | 46.910 | 31.088 | 1.00 | 30.04 |
| ATOM | 1888 | CG | LEU | 402 | 59.025 | 47.974 | 31.594 | 1.00 | 30.14 |
| ATOM | 1889 | CD1 | LEU | 402 | 58.270 | 49.263 | 31.880 | 1.00 | 29.61 |
| ATOM | 1890 | CD2 | LEU | 402 | 59.734 | 47.438 | 32.827 | 1.00 | 27.99 |
| ATOM | 1891 | C | LEU | 402 | 57.693 | 44.583 | 30.368 | 1.00 | 30.10 |
| ATOM | 1892 | O | LEU | 402 | 57.836 | 43.631 | 31.121 | 1.00 | 29.78 |
| ATOM | 1893 | N | GLU | 403 | 56.688 | 44.683 | 29.510 | 1.00 | 30.49 |
| ATOM | 1894 | CA | GLU | 403 | 55.646 | 43.671 | 29.453 | 1.00 | 32.60 |
| ATOM | 1895 | CB | GLU | 403 | 54.562 | 44.094 | 28.469 | 1.00 | 37.01 |
| ATOM | 1896 | CG | GLU | 403 | 53.329 | 43.218 | 28.520 | 1.00 | 44.01 |
| ATOM | 1897 | CD | GLU | 403 | 52.263 | 43.632 | 27.523 | 1.00 | 48.50 |
| ATOM | 1898 | OE1 | GLU | 403 | 52.516 | 44.525 | 26.677 | 1.00 | 49.66 |
| ATOM | 1899 | OE2 | GLU | 403 | 51.157 | 43.050 | 27.594 | 1.00 | 53.06 |
| ATOM | 1900 | C | GLU | 403 | 56.083 | 42.237 | 29.151 | 1.00 | 32.03 |
| ATOM | 1901 | O | GLU | 403 | 55.627 | 41.304 | 29.816 | 1.00 | 32.58 |
| ATOM | 1902 | N | VAL | 404 | 56.955 | 42.078 | 28.159 | 0.50 | 31.51 | ALTA |
| ATOM | 1903 | CA | VAL | 404 | 57.450 | 40.765 | 27.739 | 0.50 | 30.96 | ALTA |
| ATOM | 1904 | CB | VAL | 404 | 58.108 | 40.849 | 26.333 | 0.50 | 30.32 | ALTA |
| ATOM | 1905 | CG1 | VAL | 404 | 58.616 | 39.489 | 25.889 | 0.50 | 28.72 | ALTA |
| ATOM | 1906 | CG2 | VAL | 404 | 57.115 | 41.388 | 25.328 | 0.50 | 31.67 | ALTA |
| ATOM | 1907 | C | VAL | 404 | 58.465 | 40.149 | 28.696 | 0.50 | 30.45 | ALTA |
| ATOM | 1908 | O | VAL | 404 | 58.549 | 38.926 | 28.822 | 0.50 | 30.10 | ALTA |
| ATOM | 1909 | N | PHE | 405 | 59.224 | 41.002 | 29.369 | 1.00 | 30.16 | |
| ATOM | 1910 | CA | PHE | 405 | 60.266 | 40.549 | 30.263 | 1.00 | 30.65 | |
| ATOM | 1911 | CB | PHE | 405 | 61.577 | 41.221 | 29.863 | 1.00 | 28.92 | |

FIG. 31A-39

| ATOM | 1912 | CG  | PHE | 405 | 62.062 | 40.834 | 28.493 | 1.00 | 26.31 |
|------|------|-----|-----|-----|--------|--------|--------|------|-------|
| ATOM | 1913 | CD1 | PHE | 405 | 62.342 | 41.804 | 27.543 | 1.00 | 25.72 |
| ATOM | 1914 | CD2 | PHE | 405 | 62.269 | 39.500 | 28.166 | 1.00 | 25.92 |
| ATOM | 1915 | CE1 | PHE | 405 | 62.827 | 41.456 | 26.278 | 1.00 | 26.78 |
| ATOM | 1916 | CE2 | PHE | 405 | 62.752 | 39.139 | 26.910 | 1.00 | 25.39 |
| ATOM | 1917 | CZ  | PHE | 405 | 63.034 | 40.122 | 25.962 | 1.00 | 24.39 |
| ATOM | 1918 | C   | PHE | 405 | 60.011 | 40.674 | 31.771 | 1.00 | 32.10 |
| ATOM | 1919 | O   | PHE | 405 | 60.903 | 40.237 | 32.533 | 1.00 | 33.88 |
| ATOM | 1920 | OXT | PHE | 405 | 58.936 | 41.169 | 32.188 | 1.00 | 34.95 |
| ATOM | 1    | O1  | HOH | 501 | 67.542 | 37.066 | 11.311 | 1.00 | 26.83 |
| ATOM | 3    | O1  | HOH | 502 | 68.713 | 41.227 | 12.821 | 1.00 | 23.42 |
| ATOM | 2    | O1  | HOH | 503 | 64.446 | 40.325 | 12.123 | 1.00 | 22.84 |
| ATOM | 4    | O1  | HOH | 504 | 62.236 | 39.752 | 15.941 | 1.00 | 17.97 |
| ATOM | 5    | O1  | HOH | 505 | 48.732 | 20.137 | 5.515  | 1.00 | 50.48 |
| ATOM | 6    | O1  | HOH | 506 | 47.365 | 21.522 | 3.716  | 1.00 | 53.40 |
| ATOM | 7    | O1  | HOH | 507 | 50.211 | 23.203 | 7.900  | 1.00 | 32.66 |
| ATOM | 8    | O1  | HOH | 508 | 51.043 | 20.258 | 8.253  | 1.00 | 21.81 |
| ATOM | 9    | O1  | HOH | 509 | 48.225 | 18.176 | 7.905  | 1.00 | 38.96 |
| ATOM | 10   | O1  | HOH | 510 | 49.569 | 20.871 | 11.586 | 1.00 | 32.97 |
| ATOM | 11   | O1  | HOH | 511 | 53.732 | 17.159 | 10.856 | 1.00 | 47.20 |
| ATOM | 12   | O1  | HOH | 512 | 56.201 | 16.223 | 12.164 | 1.00 | 18.50 |
| ATOM | 13   | O1  | HOH | 513 | 56.653 | 12.298 | 10.528 | 1.00 | 27.71 |
| ATOM | 14   | O1  | HOH | 514 | 58.661 | 10.694 | 9.014  | 1.00 | 46.73 |
| ATOM | 15   | O1  | HOH | 515 | 62.950 | 10.692 | 11.952 | 1.00 | 43.05 |
| ATOM | 16   | O1  | HOH | 516 | 66.411 | 11.552 | 10.897 | 1.00 | 37.36 |
| ATOM | 17   | O1  | HOH | 517 | 68.949 | 13.188 | 12.029 | 1.00 | 39.28 |
| ATOM | 18   | O1  | HOH | 518 | 71.997 | 15.171 | 8.362  | 1.00 | 49.69 |
| ATOM | 19   | O1  | HOH | 519 | 71.946 | 17.928 | 6.743  | 1.00 | 24.50 |
| ATOM | 20   | O1  | HOH | 520 | 75.117 | 15.684 | 9.377  | 1.00 | 35.98 |
| ATOM | 21   | O1  | HOH | 521 | 76.677 | 12.815 | 10.294 | 1.00 | 49.33 |
| ATOM | 22   | O1  | HOH | 522 | 81.421 | 15.415 | 15.139 | 1.00 | 46.74 |
| ATOM | 23   | O1  | HOH | 523 | 78.784 | 21.696 | 17.564 | 1.00 | 49.01 |
| ATOM | 24   | O1  | HOH | 524 | 79.954 | 24.822 | 17.152 | 1.00 | 42.91 |
| ATOM | 25   | O1  | HOH | 525 | 82.199 | 30.253 | 18.821 | 1.00 | 40.27 |
| ATOM | 26   | O1  | HOH | 526 | 82.862 | 33.444 | 21.988 | 1.00 | 46.81 |
| ATOM | 27   | O1  | HOH | 527 | 76.608 | 30.793 | 23.452 | 1.00 | 46.22 |
| ATOM | 28   | O1  | HOH | 528 | 74.726 | 30.483 | 25.469 | 1.00 | 43.76 |
| ATOM | 29   | O1  | HOH | 529 | 77.059 | 28.762 | 20.900 | 1.00 | 33.67 |
| ATOM | 30   | O1  | HOH | 530 | 75.935 | 33.279 | 12.269 | 1.00 | 25.26 |
| ATOM | 31   | O1  | HOH | 531 | 77.402 | 34.447 | 10.087 | 1.00 | 37.04 |
| ATOM | 32   | O1  | HOH | 532 | 74.054 | 29.941 | 9.998  | 1.00 | 26.86 |
| ATOM | 33   | O1  | HOH | 533 | 69.544 | 32.658 | 7.572  | 1.00 | 40.34 |
| ATOM | 34   | O1  | HOH | 534 | 66.709 | 33.618 | 8.477  | 1.00 | 20.63 |
| ATOM | 35   | O1  | HOH | 535 | 68.073 | 35.828 | 8.931  | 1.00 | 23.99 |
| ATOM | 36   | O1  | HOH | 536 | 61.865 | 45.643 | 14.011 | 1.00 | 40.43 |
| ATOM | 37   | O1  | HOH | 537 | 63.662 | 46.881 | 15.670 | 1.00 | 28.04 |
| ATOM | 38   | O1  | HOH | 538 | 63.391 | 49.310 | 13.883 | 1.00 | 39.59 |
| ATOM | 39   | O1  | HOH | 539 | 63.491 | 50.570 | 10.631 | 1.00 | 52.34 |
| ATOM | 40   | O1  | HOH | 540 | 64.592 | 46.849 | 10.299 | 1.00 | 26.63 |
| ATOM | 41   | O1  | HOH | 541 | 55.575 | 41.632 | 10.980 | 1.00 | 38.06 |

FIG. 31A-40

| | | | | | | | |
|---|---|---|---|---|---|---|---|
| ATOM | 42 | O1 | HOH 542 | 51.631 | 42.062 | 17.343 | 1.00 | 45.99 |
| ATOM | 43 | O1 | HOH 543 | 52.755 | 43.156 | 20.209 | 1.00 | 34.17 |
| ATOM | 44 | O1 | HOH 544 | 57.061 | 49.627 | 24.004 | 1.00 | 24.09 |
| ATOM | 45 | O1 | HOH 545 | 61.040 | 50.561 | 21.351 | 1.00 | 30.91 |
| ATOM | 46 | O1 | HOH 546 | 68.533 | 53.616 | 18.390 | 1.00 | 30.91 |
| ATOM | 47 | O1 | HOH 547 | 63.371 | 58.813 | 29.014 | 1.00 | 59.25 |
| ATOM | 48 | O1 | HOH 548 | 57.934 | 52.905 | 31.175 | 1.00 | 40.12 |
| ATOM | 49 | O1 | HOH 549 | 62.364 | 50.496 | 37.543 | 1.00 | 52.28 |
| ATOM | 50 | O1 | HOH 550 | 62.256 | 49.704 | 40.891 | 1.00 | 54.18 |
| ATOM | 51 | O1 | HOH 551 | 61.994 | 46.430 | 40.384 | 1.00 | 43.84 |
| ATOM | 52 | O1 | HOH 552 | 63.675 | 44.459 | 39.268 | 1.00 | 44.73 |
| ATOM | 53 | O1 | HOH 553 | 58.405 | 43.920 | 33.936 | 1.00 | 42.88 |
| ATOM | 54 | O1 | HOH 554 | 62.863 | 39.071 | 34.046 | 1.00 | 45.07 |
| ATOM | 55 | O1 | HOH 555 | 64.426 | 36.925 | 28.676 | 1.00 | 25.36 |
| ATOM | 56 | O1 | HOH 556 | 62.375 | 35.807 | 26.610 | 1.00 | 21.14 |
| ATOM | 57 | O1 | HOH 557 | 63.684 | 33.760 | 25.609 | 1.00 | 33.03 |
| ATOM | 58 | O1 | HOH 558 | 61.542 | 29.906 | 24.568 | 1.00 | 57.37 |
| ATOM | 59 | O1 | HOH 559 | 62.353 | 27.540 | 24.855 | 1.00 | 39.63 |
| ATOM | 60 | O1 | HOH 560 | 62.814 | 28.785 | 27.536 | 1.00 | 58.40 |
| ATOM | 61 | O1 | HOH 561 | 65.531 | 30.642 | 28.821 | 1.00 | 54.44 |
| ATOM | 62 | O1 | HOH 562 | 63.423 | 24.645 | 32.964 | 1.00 | 50.75 |
| ATOM | 63 | O1 | HOH 563 | 64.697 | 21.149 | 28.711 | 1.00 | 51.41 |
| ATOM | 64 | O1 | HOH 564 | 67.100 | 23.370 | 26.900 | 1.00 | 52.36 |
| ATOM | 65 | O1 | HOH 565 | 65.582 | 20.422 | 23.303 | 1.00 | 40.32 |
| ATOM | 66 | O1 | HOH 566 | 61.577 | 18.167 | 23.386 | 1.00 | 65.08 |
| ATOM | 67 | O1 | HOH 567 | 61.022 | 22.649 | 25.573 | 1.00 | 48.85 |
| ATOM | 68 | O1 | HOH 568 | 57.919 | 21.446 | 25.147 | 1.00 | 43.39 |
| ATOM | 69 | O1 | HOH 569 | 59.435 | 20.179 | 28.543 | 1.00 | 51.41 |
| ATOM | 70 | O1 | HOH 570 | 53.860 | 23.216 | 30.984 | 1.00 | 50.28 |
| ATOM | 71 | O1 | HOH 571 | 52.825 | 24.880 | 32.696 | 1.00 | 43.96 |
| ATOM | 72 | O1 | HOH 572 | 48.228 | 29.683 | 30.486 | 1.00 | 44.51 |
| ATOM | 73 | O1 | HOH 573 | 48.925 | 34.467 | 30.521 | 1.00 | 36.28 |
| ATOM | 74 | O1 | HOH 574 | 50.766 | 40.547 | 29.178 | 1.00 | 51.45 |
| ATOM | 75 | O1 | HOH 575 | 57.058 | 32.490 | 30.420 | 1.00 | 31.03 |
| ATOM | 76 | O1 | HOH 576 | 58.075 | 29.544 | 24.664 | 1.00 | 19.54 |
| ATOM | 77 | O1 | HOH 577 | 47.451 | 19.292 | 28.703 | 1.00 | 33.04 |
| ATOM | 78 | O1 | HOH 578 | 53.120 | 15.471 | 17.478 | 1.00 | 35.68 |
| ATOM | 79 | O1 | HOH 579 | 55.101 | 14.146 | 16.095 | 1.00 | 50.46 |
| ATOM | 80 | O1 | HOH 580 | 53.726 | 14.016 | 9.059 | 1.00 | 41.44 |
| ATOM | 81 | O1 | HOH 581 | 57.223 | 13.820 | 1.435 | 1.00 | 48.31 |
| ATOM | 82 | O1 | HOH 582 | 61.169 | 15.688 | 0.210 | 1.00 | 17.60 |
| ATOM | 83 | O1 | HOH 583 | 67.411 | 16.019 | -0.314 | 1.00 | 23.93 |
| ATOM | 84 | O1 | HOH 584 | 67.033 | 17.221 | -2.796 | 1.00 | 26.21 |
| ATOM | 85 | O1 | HOH 585 | 69.893 | 19.520 | -1.582 | 1.00 | 59.67 |
| ATOM | 86 | O1 | HOH 586 | 68.489 | 22.464 | 0.350 | 1.00 | 37.85 |
| ATOM | 87 | O1 | HOH 587 | 65.794 | 23.354 | 0.823 | 1.00 | 27.38 |
| ATOM | 88 | O1 | HOH 588 | 67.550 | 26.810 | 0.937 | 1.00 | 37.18 |
| ATOM | 89 | O1 | HOH 589 | 64.646 | 28.208 | 3.323 | 1.00 | 36.74 |
| ATOM | 90 | O1 | HOH 590 | 67.215 | 31.103 | 3.174 | 1.00 | 30.29 |
| ATOM | 91 | O1 | HOH 591 | 64.164 | 35.667 | 6.220 | 1.00 | 39.72 |

FIG. 31A-41

| ATOM | 92 | O1 | HOH | 592 | 62.810 | 37.518 | 4.836 | 1.00 | 48.48 |
|---|---|---|---|---|---|---|---|---|---|
| ATOM | 93 | O1 | HOH | 593 | 68.105 | 36.898 | 6.110 | 1.00 | 58.00 |
| ATOM | 94 | O1 | HOH | 594 | 57.390 | 37.485 | 2.631 | 1.00 | 37.29 |
| ATOM | 95 | O1 | HOH | 595 | 53.088 | 36.068 | 3.949 | 1.00 | 50.10 |
| ATOM | 96 | O1 | HOH | 596 | 52.974 | 34.676 | 6.758 | 1.00 | 42.52 |
| ATOM | 97 | O1 | HOH | 597 | 58.581 | 31.465 | 2.076 | 1.00 | 32.18 |
| ATOM | 98 | O1 | HOH | 598 | 52.786 | 23.277 | 1.357 | 1.00 | 28.98 |
| ATOM | 99 | O1 | HOH | 599 | 47.501 | 26.551 | 7.672 | 1.00 | 47.83 |
| ATOM | 100 | O1 | HOH | 600 | 46.411 | 35.754 | 14.049 | 1.00 | 53.46 |
| ATOM | 101 | O1 | HOH | 601 | 63.514 | 14.944 | 15.842 | 1.00 | 55.02 |
| ATOM | 102 | O1 | HOH | 602 | 67.943 | 11.792 | 3.438 | 1.00 | 61.21 |
| ATOM | 103 | O1 | HOH | 603 | 62.232 | 9.378 | 3.311 | 1.00 | 35.65 |
| ATOM | 104 | O1 | HOH | 604 | 76.734 | 22.468 | 5.002 | 1.00 | 42.56 |
| ATOM | 105 | O1 | HOH | 605 | 83.589 | 28.967 | 9.626 | 1.00 | 50.64 |
| ATOM | 106 | O1 | HOH | 606 | 82.807 | 43.437 | 17.940 | 1.00 | 39.28 |
| ATOM | 107 | O1 | HOH | 607 | 83.882 | 45.673 | 20.638 | 1.00 | 41.64 |
| ATOM | 108 | O1 | HOH | 608 | 80.215 | 41.021 | 23.441 | 1.00 | 43.16 |
| ATOM | 109 | O1 | HOH | 609 | 79.459 | 46.296 | 31.165 | 1.00 | 32.40 |
| ATOM | 110 | O1 | HOH | 610 | 81.880 | 47.681 | 33.923 | 1.00 | 46.96 |
| ATOM | 111 | O1 | HOH | 611 | 75.594 | 46.142 | 30.384 | 1.00 | 28.64 |
| ATOM | 112 | O1 | HOH | 612 | 77.118 | 40.568 | 32.575 | 1.00 | 34.21 |
| ATOM | 113 | O1 | HOH | 613 | 73.563 | 41.750 | 36.926 | 1.00 | 26.07 |
| ATOM | 114 | O1 | HOH | 614 | 75.955 | 56.565 | 28.863 | 1.00 | 46.31 |
| ATOM | 115 | O1 | HOH | 615 | 79.915 | 59.136 | 15.809 | 1.00 | 50.81 |
| ATOM | 116 | O1 | HOH | 616 | 77.390 | 52.542 | 8.816 | 1.00 | 34.34 |
| ATOM | 117 | O1 | HOH | 617 | 72.726 | 25.005 | 29.671 | 1.00 | 62.84 |
| ATOM | 2038 | C | ACY | 701 | 52.664 | 40.106 | 24.800 | 1.00 | 46.39 |
| ATOM | 2039 | O | ACY | 701 | 53.721 | 39.649 | 24.298 | 1.00 | 47.12 |
| ATOM | 2040 | OXT | ACY | 701 | 51.652 | 40.521 | 24.172 | 1.00 | 46.96 |
| ATOM | 2041 | CH3 | ACY | 701 | 52.600 | 40.162 | 26.329 | 1.00 | 45.99 |
| ATOM | 2050 | C1 | T3 | 1 | 66.961 | 42.243 | 18.491 | 1.00 | 22.34 |
| ATOM | 2051 | C2 | T3 | 1 | 68.748 | 43.593 | 23.015 | 1.00 | 21.84 |
| ATOM | 2052 | C3 | T3 | 1 | 66.873 | 43.557 | 18.970 | 1.00 | 23.43 |
| ATOM | 2053 | C4 | T3 | 1 | 69.252 | 44.540 | 23.871 | 1.00 | 22.31 |
| ATOM | 2054 | C5 | T3 | 1 | 67.638 | 43.989 | 20.011 | 1.00 | 24.83 |
| ATOM | 2055 | C6 | T3 | 1 | 68.851 | 44.553 | 25.178 | 1.00 | 25.16 |
| ATOM | 2056 | C7 | T3 | 1 | 68.541 | 43.108 | 20.632 | 1.00 | 24.65 |
| ATOM | 2057 | C8 | T3 | 1 | 67.895 | 43.567 | 25.639 | 1.00 | 21.93 |
| ATOM | 2058 | C9 | T3 | 1 | 68.665 | 41.792 | 20.183 | 1.00 | 25.09 |
| ATOM | 2059 | C10 | T3 | 1 | 67.427 | 42.654 | 24.733 | 1.00 | 23.66 |
| ATOM | 2060 | C11 | T3 | 1 | 67.878 | 41.380 | 19.117 | 1.00 | 23.12 |
| ATOM | 2061 | C12 | T3 | 1 | 67.829 | 42.624 | 23.384 | 1.00 | 19.67 |
| ATOM | 2062 | C13 | T3 | 1 | 66.055 | 41.788 | 17.371 | 1.00 | 18.97 |
| ATOM | 2063 | C15 | T3 | 1 | 66.721 | 40.956 | 16.295 | 1.00 | 19.32 |
| ATOM | 2064 | C17 | T3 | 1 | 65.901 | 40.829 | 15.051 | 1.00 | 19.02 |
| ATOM | 2065 | I1 | T3 | 1 | 67.393 | 45.986 | 20.621 | 1.00 | 25.29 |
| ATOM | 2066 | I2 | T3 | 1 | 69.483 | 46.066 | 26.432 | 1.00 | 26.49 |
| ATOM | 2067 | I3 | T3 | 1 | 70.019 | 40.450 | 20.975 | 1.00 | 25.67 |
| ATOM | 2068 | N1 | T3 | 1 | 68.131 | 41.337 | 16.037 | 1.00 | 15.12 |
| ATOM | 2069 | O1 | T3 | 1 | 67.542 | 43.587 | 26.966 | 1.00 | 21.79 |

FIG. 31A-42

```
ATOM  2070  O2  T3  1  69.259  43.600  21.682  1.00  22.05
ATOM  2071  O3  T3  1  66.504  40.852  13.963  1.00  20.38
ATOM  2072  O4  T3  1  64.675  40.731  15.192  1.00  20.16
END
```

NUCLEAR RECEPTOR LIGANDS AND LIGAND BINDING DOMAINS

CROSS-REFERENCE TO RELATED APPLICATIONS

This applicatio claims benefit of U.S. provisional Application No. 60/008,540, filed Dec. 13, 1995; U.S. Provisional Application No. 60/008,543, filed Dec. 13, 1995; and U.S. Provisional Application No. 60/008,606, filed Dec. 14, 1995.

This invention was supported in part by grants from the National Institutes of Health grant number 1 R01 DK43787, and 5 R01 Dk 41842. The U.S. Government may have rights in this invention.

INTRODUCTION

1. Technical Field

This invention relates to computational methods for designing ligands that bind to nuclear receptors, crystals of nuclear receptors, synthetic ligands of nuclear receptors and methods of using synthetic ligands.

2. Background

Nuclear receptors represent a superfamily of proteins that specifically bind a physiologically relevant small molecule, such as hormone or vitamin. As a result of a molecule binding to a nuclear receptor, the nuclear receptor changes the ability of a cell to transcribe DNA, i.e. nuclear receptors modulate the transcription of DNA, although they may have transcription independent actions. Unlike integral membrane receptors and membrane associated receptors, the nuclear receptors reside in either the cytoplasm or nucleus of eukaryotic cells. Thus, nuclear receptors comprise a class of intracellular, soluble ligand-regulated transcription factors.

Nuclear receptors include receptors for glucocorticoids (GRs), androgens (ARs), mineralocorticoids (MRs), progestins (PRs), estrogens (ERs), thyroid hormones (TRs), vitamin D (VDRs), retinoids (RARs and RXRs). The so called "orphan receptors" are also part of the nuclear receptor superfamily, as they are structurally homologous to the classic nuclear receptors, such as steroid and thyroid receptors. To date, ligands have not been identified with orphan receptors but it is likely that small molecule ligands will be discovered in the near future for this class of transcription factors. Generally, nuclear receptors specifically bind physiologically relevant small molecules with high affinity and apparent Kd's are commonly in the 0.01–20 nM range, depending on the nuclear receptor/ligand pair.

Development of synthetic ligands that specifically bind to nuclear receptors has been largely guided by the trial and error method of drug design despite the importance of nuclear receptors in a myriad of physiological processes and medical conditions such as hypertension, inflammation, hormone dependent cancers (e.g. breast and prostate cancer), modulation of reproductive organ modulation, hyperthyroidism, hypercholesterolemia and obesity. Previously, new ligands specific for nuclear receptors were discovered in the absence of information on the three dimensional structure of a nuclear receptor with a bound ligand. Before the present invention, researchers were essentially discovering nuclear receptor ligands by probing in the dark and without the ability to visualize how the amino acids of a nuclear receptor held a ligand in its grasp.

Consequently, it would be advantageous to devise methods and compositions for reducing the time required to discover ligands to nuclear receptors, synthesize such compounds and administer such compounds to organisms to modulate physiological processes regulated by nuclear receptors.

SUMMARY OF THE INVENTION

The present invention provides for crystals of nuclear receptor ligand binding domains with a ligand bound to the ligand binding domain (LBD). The crystals of the present invention provide excellent atomic resolution of the amino acids that interact with nuclear receptor ligand, especially thyroid receptor ligands. The three dimensional model of a nuclear receptor LBD with a ligand bound reveals a previously unknown structure for nuclear receptors and shows that the ligand is bound in a water inaccessible binding cavity of the ligand binding domain of the nuclear receptor.

The present invention also provides for computational methods using three dimensional models of nuclear receptors that are based on crystals of nuclear receptor LBDs. Generally, the computational method of designing a nuclear receptor ligand determines which amino acid or amino acids of a nuclear receptor LBD interact with a chemical moiety (at least one) of the ligand using a three dimensional model of a crystallized protein comprising a nuclear receptor LBD with a bound ligand, and selecting a chemical modification (at least one) of the chemical moiety to produce a second chemical moiety with a structure that either decreases or increases an interaction between the interacting amino acid and the second chemical moiety compared to the interaction between the interacting amino acid and the corresponding chemical moiety on the natural hormone.

BRIEF DESCRIPTION OF THE DRAWINGS

FIGS. 3A–3R shows the aligned amino acid sequences of the ligand binding domains of several members of the nuclear receptor superfamily.

FIG. 10 is a diagram comparing agonists and antagonists for several nuclear receptors.

FIG. 15 depicts the chemical structures of several TR ligands.

FIGS. 26A and 26B are stereochemical representations of the TRα LBD with Dimit bound.

FIG. 27–27A-13 is a chart of amino acids that interact with a TR ligand, for TR complexed with Dimit, Triac, IpBr2, and T3.

FIG. 28–28A-45 is a chart of atomic coordinates for the crystal of rat TR-α LBD complexed with Dimit.

FIG. 29–29A-39 is a chart of atomic coordinates for the crystal of rat TR-α LBD complexed with Triac.

FIG. 30–30A-41 is a chart of atomic coordinates for the crystal of rat TR-α LBD complexed with $IpBr_2$.

FIG. 31–31A-42 is a chart of atomic coordinates for the crystal of rat TR-α LBD complexed with $T_3$.

DETAILED DESCRIPTION OF THE INVENTION

Introduction

The present invention provides new methods, particularly computational methods, and compositions for the generation of nuclear receptor synthetic ligands based on the three dimensional structure of nuclear receptors, particularly the thyroid receptor (herein referred to as "TR"). Previously, the lack of three dimensional structural information about the ligand binding domain of a nuclear receptor thwarted the field of nuclear receptor drug discovery, especially the absence of three dimensional structural information relating to a nuclear receptor with a ligand bound.

Figure 1:
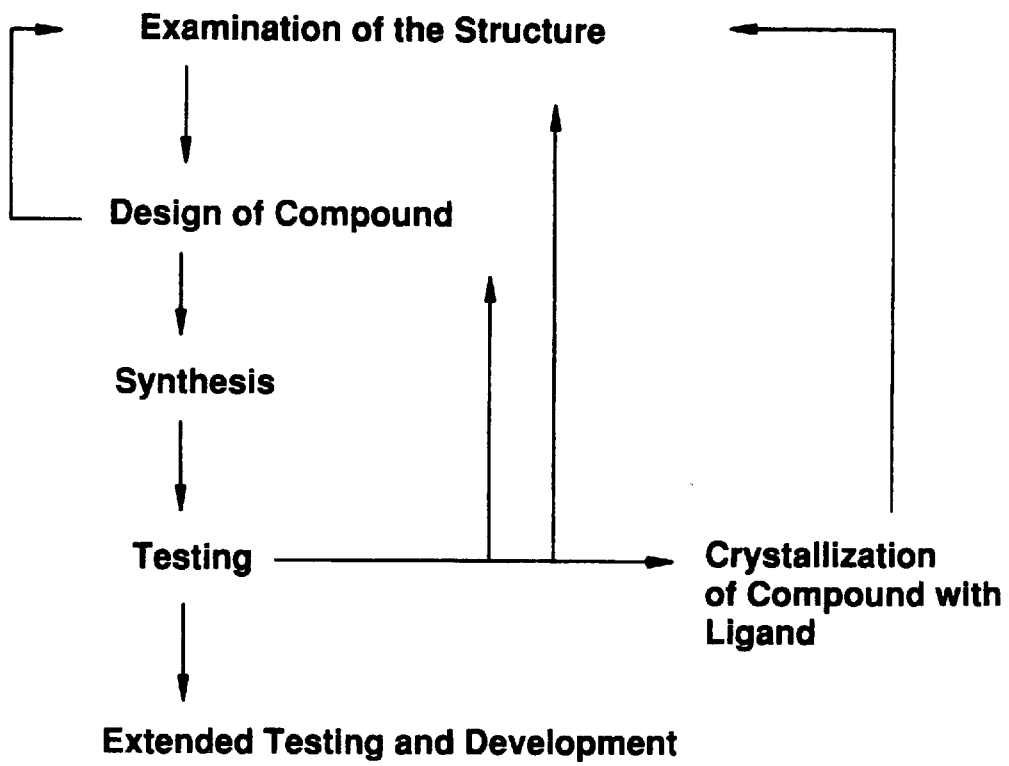
FIG. 1 is a diagram illustrating computational methods for designing ligands that interact with nuclear receptors of the nuclear receptor superfamily.

Described herein for the first time are crystals and three dimensional structural information from a nuclear receptor's ligand binding domain (LBD) with a ligand bound. Such crystals offer superior resolution at the atomic level and the ability to visualize the coordination of nuclear receptor ligands by amino acids that comprise the LBD. The present invention also provides computational methods for designing nuclear receptor synthetic ligands using such crystal and three dimensional structural information to generate synthetic ligands that modulate the conformational changes of a nuclear receptor's LBD. Such synthetic ligands can be designed using the computational methods described herein and shown, in part, in FIG. 1. These computational methods are particularly useful in designing an antagonist or partial agonist to a nuclear receptor, wherein the antagonist or partial agonist has an extended moiety that prevents any one of a number of ligand-induced molecular events that alter the receptor's influence on the regulation of gene expression, such as preventing the normal coordination of the activation domain observed for a naturally occurring ligand or other ligands that mimic the naturally occurring ligand, such as an agonist. As described herein, synthetic ligands of nuclear receptors will be useful in modulating nuclear receptor activity in a variety of medical conditions.

Applicability to Nuclear Receptors

The present invention, particularly the computational methods, can be used to design drugs for a variety of nuclear receptors, such as receptors for glucocorticoids (GRs), androgens (ARs), mineralocorticoids (MRs), progestins (PRs), estrogens (ERs), thyroid hormones (TRs), vitamin D (VDRs), retinoid (RARs and RXRs) and peroxisomal proliferators (PPAP). The present invention can also be applied to the "orphan receptors," as they are structurally homologous in terms of modular domains and primary structure to classic nuclear receptors, such as steroid and thyroid receptors. The amino acid homologies of orphan receptors with other nuclear receptors ranges from very low (<15%) to in the range of 35% when compared to rat RARα and human TR-β receptors, for example. In addition, as is revealed by the X-ray crystallographic structure of the TR and structural analysis disclosed herein, the overall folding of liganded superfamily members is likely to be similar. Although ligands have not been identified with orphan receptors, once such ligands are identified one skilled in the art will be able to apply the present invention to the design and use of such ligands, as their overall structural modular motif will be similar to other nuclear receptors described herein.

Modular Functional Domains Of Nuclear Receptors

The present invention will usually be applicable to all nuclear receptors, as discussed herein, in part, to the patterns of nuclear receptor activation, structure and modulation that have emerged as a consequence of determining the three dimensional structures of nuclear receptors with different ligands bound, notably the three dimensional structures or crystallized protein structure of the ligand binding domains for TR-α and TR-β. Proteins of the nuclear receptor superfamily display substantial regions of amino acid homology, as described herein and known in the art see FIG. 2. Members of this family display an overall structural motif of three modular domains (which is similar to the TR three modular domain motif):

1) a variable amino-terminal domain;
2) a highly conserved DNA-binding domain (DBD); and
3) a less conserved carboxyl-terminal ligand-binding domain (LBD).

The modularity of this superfamily permits different domains of each protein to separately accomplish different functions, although the domains can influence each other. The separate function of a domain is usually preserved when a particular domain is isolated from the remainder of the protein. Using conventional protein chemistry techniques a modular domain can sometimes be separated from the parent protein. Using conventional molecular biology techniques each domain can usually be separately expressed with its original function intact or chimerics of two different nuclear receptors can be constructed, wherein the chimerics retain the properties of the individual functional domains of the respective nuclear receptors from which the chimerics were generated.

Figure 2:
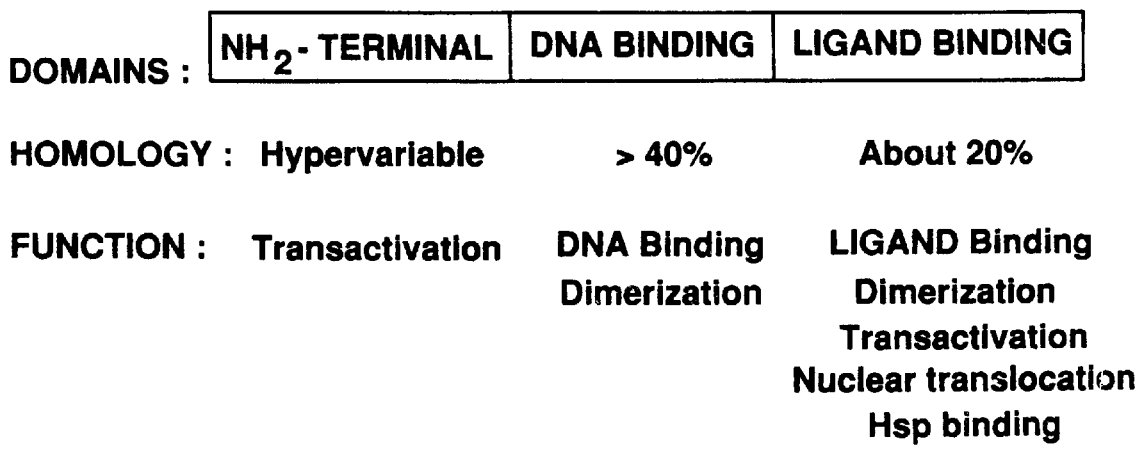
FIG. 2 is a schematic representation of nuclear receptor structures, indicating regions of homology within family members and functions of the various domains.

FIG. 2 provides a schematic representation of family member structures, indicating regions of homology within family members and functions of the various domains.

Amino Terminal Domain

The amino terminal domain is the least conserved of the three domains and varies markedly in size among nuclear receptor superfamily members. For example, this domain contains 24 amino acids in the VDR and 603 amino acids in the MR. This domain is involved in transcriptional activation and in some cases its uniqueness may dictate selective receptor-DNA binding and activation of target genes by specific receptor isoforms. This domain can display synergistic and antagonistic interactions with the domains of the LBD. For example, studies with mutated and/or deleted receptors show positive cooperativity of the amino and carboxy terminal domains. In some cases, deletion of either of these domains will abolish the receptor's transcriptional activation functions.

DNA-Binding Domain

The DBD is the most conserved structure in the nuclear receptor superfamily. It usually contains about 70 amino acids that fold into two zinc finger motifs, wherein a zinc ion coordinates four cysteines. DBDs contain two perpendicularly oriented α-helices that extend from the base of the first and second zinc fingers. The two zinc fingers function in concert along with non-zinc finger residues to direct nuclear receptors to specific target sites on DNA and to align receptor homodimer or heterodimer interfaces. Various amino acids in DBD influence spacing between two half-sites (usually comprised of six nucleotides) for receptor dimer binding. For example, GR subfamily and ER homodimers bind to half-sites spaced by three nucleotides and oriented as palindromes. The optimal spacings facilitate cooperative interactions between DBDs, and D box residues are part of the dimerization interface. Other regions of the DBD facilitate DNA-protein and protein-protein interactions required for RXR homodimerization and heterodimerization on direct repeat elements.

The LBD may influence the DNA binding of the DBD, and the influence can also be regulated by ligand binding. For example, TR ligand binding influences the degree to which a TR binds to DNA as a monomer or diner. Such dimerization also depends on the spacing and orientation of the DNA half sites.

The nuclear receptor superfamily has been subdivided into two subfamilies: 1) GR (GR, AR, MR and PR) and 2) TR (TR, VDR, RAR, RXR, and most orphan receptors) on the basis of DBD structures, interactions with heat shock proteins (hsp), and ability to form heterodimers. GR subgroup members are tightly bound by hsp in the absence of ligand, dimerize following ligand binding and dissociation of hsp, and show homology in the DNA half sites to which they bind. These half sites also tend to be arranged as palindromes. TR subgroup members tend to be bound to DNA or other chromatin molecules when unliganded, can bind to DNA as monomers and dimers, but tend to form heterodimers, and bind DNA elements with a variety of orientations and spacings of the half sites, and also show homology with respect to the nucleotide sequences of the half sites. ER does not belong to either subfamily, since it resembles the GR subfamily in hsp interactions, and the TR subfamily in nuclear localization and DNA-binding properties.

Ligand Binding Domain

The LBD is the second most highly conserved domain in these receptors. Whereas integrity of several different LBD sub-domains is important for ligand binding, truncated molecules containing only the LBD retain normal ligand-binding activity. This domain also participates in other functions, including dimerization, nuclear translocation and transcriptional activation, as described herein. Importantly, this domain binds the ligand and undergoes ligand-induced conformational changes as detailed herein.

Most members of the superfamily, including orphan receptors, possess at least two transcription activation subdomains, one of which is constitutive and resides in the amino terminal domain (AF-1), and the other of which (AF-2 (also referenced as TAU 4)) resides in the ligand-binding domain whose activity is regulated by binding of an agonist ligand. The function of AF-2 requires an activation domain (also called transactivation domain) that is highly conserved among the receptor superfamily (approximately amino acids 1005 to 1022). Most LBDs contain an activation domain. Some mutations in this domain abolish AF-2 function, but leave ligand binding and other functions unaffected. Ligand binding allows the activation domain to serve as an interaction site for essential co-activator proteins that function to stimulate (or in some cases, inhibit) transcription.

The carboxy-terminal activation subdomain, as described herein is in close three dimensional proximity in the LBD to the ligand, so as to allow for ligands bound to the LBD to coordinate (or interact) with amino acid(s) in the activation subdomain. As described herein, the LBD of a nuclear receptor can be expressed, crystallized, its three dimensional structure determined with a ligand bound (either using crystal data from the same receptor or a different receptor or a combination thereof), and computational methods used to design ligands to its LBD, particularly ligands that contain an extension moiety that coordinates the activation domain of the nuclear receptor.

Once a computationally designed ligand (CDL) is synthesized as described herein and known in the art, it can be tested using assays to establish its activity as an agonist, partial agonist or antagonist, and affinity, as described herein. After such testing, the CDLs can be further refined by generating LBD crystals with a CDL bound to the LBD. The structure of the CDL can then be further refined using the chemical modification methods described herein for three dimensional models to improve the activity or affinity of the CDL and make second generation CDLs with improved properties, such as that of a super agonist or antagonist described herein.

Nuclear Receptor Isoforms

The present invention also is applicable to generating new synthetic ligands to distinguish nuclear receptor isoforms. As described herein, CDLs can be generated that distinguish between isoforms, thereby allowing the generation of either tissue specific or function specific synthetic ligands. For instance, GR subfamily members have usually one receptor encoded by a single gene, with the exception that there are two PR isoforms, A and B, translated from the same mRNA by alternate initiation from different AUG codons. This method is especially applicable to the TR subfamily which usually has several receptors that are encoded by two (TR) or three (RAR, RXR, and PPAR) genes or have alternate RNA splicing and such an example for TR is described herein.

Nuclear Receptor Crystals

The invention provides for crystals made from nuclear receptor ligand binding domains with the ligand bound to the receptor. As exemplified in the Examples, TRs are crystallized with a ligand bound to it. Crystals are made from purified nuclear receptor LBDs that are usually expressed by a cell culture, preferably $E.\ coli$. Preferably, different crystals (co-crystals) for the same nuclear receptor are separately made using different ligands, such as a naturally occurring ligand and at least one bromo- or iodo-substituted synthetic ligand that acts as an analog or antagonist of the naturally occurring ligand. Such bromo- and iodo-substitutions act as heavy atom substitutions in nuclear receptor ligands and crystals of nuclear receptor proteins. This method has the advantage for phasing of the crystal in that it bypasses the need for obtaining traditional heavy metal derivatives. After the three dimensional structure is determined for the nuclear receptor LBD with its ligand bound, the three dimensional structure can be used in computational methods to design a synthetic ligand for the nuclear receptor and further activity structure relationships can be determined through routine testing using the assays described herein and known in the art.

Expression and Purification of other Nuclear Receptor LBD Structures

High level expression of nuclear receptor LBDs can be obtained by the techniques described herein as well as others described in the literature. High level expression in $E.\ coli$ of ligand binding domains of TR and other nuclear receptors, including members of the steroid/thyroid receptor superfamily, such as the estrogen (ER), androgen (AR), mineralocorticoid (MR), progesterone (PR), RAR, RXR and vitamin D (VDR) receptors can also be achieved. Yeast and other eukaryotic expression systems can be used with nuclear receptors that bind heat shock proteins as these nuclear receptors are generally more difficult to express in bacteria, with the exception of ER, which can be expressed in bacteria. Representative nuclear receptors or their ligand binding domains have been cloned and sequenced: human RAR-α, human RAR-γ, human RXR-α, human RXR-β, human PPAR-α, human PPAR-β, human PPAR-γ, human VDR, human ER (as described in Seielstad et al., Molecular Endocrinology, vol 9:647–658 (1995), incorporated herein by reference), human GR, human PR, human MR, and human AR. The ligand binding domain of each of these nuclear receptors has been identified and is shown in FIGS. 3A–3R. Using the information in FIGS. 3A–3R in conjunction with the methods described herein and known in the art, one of ordinary skill in the art could express and purify LBDs of any of the nuclear receptors, including those illustrated in FIGS. 3A–3R, bind it to an appropriate ligand, and crystallize the nuclear receptor's LBD with a bound ligand.

FIGS. 3A–3R is an alignment of several members of the steroid/thyroid hormone receptor superfamily that indicates the amino acids to be included in a suitable expression vector.

Extracts of expressing cells are a suitable source of receptor for purification and preparation of crystals of the chosen receptor. To obtain such expression, a vector is constructed in a manner similar to that employed for expression of the rat TR alpha (Apriletti et al. Protein Expression and Purification, 6:368–370 (1995), herein incorporated by reference). The nucleotides encoding the amino acids encompassing the ligand binding domain of the receptor to be expressed, for example the estrogen receptor ligand binding domain (hER-LBD) residues 287 to 549 of SEQ ID NO:12, (corresponding to R at position 725 to L at position 1025 as standardly aligned as shown in the FIGS. 3A–3R), are inserted into an expression vector such as the one employed by Apriletti et al (1995). For the purposes of obtaining material that will yield good crystals it is preferable to include at least the amino acids corresponding to human TR-β positions 725 to 1025 residues 202 to 461 of SEQ ID NO:3. Stretches of adjacent amino acid sequences may be included if more structural information is desired. Thus, an expression vector for the human estrogen receptor can be made by inserting nucleotides encoding amino acids from position 700 to the c-terminus at position 1071 residues 264 to 595 of SEQ ID NO:12. Such a vector gives high yield of receptor in $E.\ coli$ that can bind hormone (Seielstad et al. Molecular Endocrinology Vol 9:647–658 (1995)). However, the c-terminal region beyond position 1025 is subject to variable proteolysis and can advantageously be excluded from the construct, this technique of avoiding variable proteolysis can also be applied to other nuclear receptors.

TR-α And TR-β As Examples of Nuclear receptor LBD Structure and Function TR Expression, Purification And Crystallization As an example of nuclear receptor structure of the ligand binding domain the α- and β-isoforms of TR are crystallized from proteins expressed from expression constructs, preferably constructs that can be expressed in $E.\ coli$. Other expression systems, such as yeast or other eukaryotic expression systems can be used. For the TR, the LBD can be expressed without any portion of the DBD or amino-terminal domain. Portions of the DBD or amino-terminus can be included if further structural information with amino acids adjacent the LBD is desired. Generally, for the TR the LBD used for crystals will be less than 300 amino acids in length. Preferably, the TR LBD will be at least 150 amino acids in length, more preferably at least 200 amino acids in length, and most preferably at least 250 amino acids in length. For example the LBD used for crystallization can comprise amino acids spanning from Met 122 to Val 410 of the rat TR-α, (residues 122 to 410 of SEQ ID NO:1) Glu 202 to Asp 461 of the human TR-β (residues 202 to 461 of SEQ ID NO:3).

Typically TR LBDs are purified to homogeneity for crystallization. Purity of TR LBDs is measured with SDS-PAGE, mass spectrometry and hydrophobic HPLC. The purified TR for crystallization should be at least 97.5% pure or 97.5%, preferably at least 99.0% pure or 99.0% pure, more preferably at least 99.5% pure or 99.5% pure.

Initially purification of the unliganded receptor can be obtained by conventional techniques, such as hydrophobic interaction chromatography (HPLC), ion exchange chromatography (HPLC), and heparin affinity chromatography.

To achieve higher purification for improved crystals of nuclear receptors, especially the TR subfamily and TR, it will be desirable to ligand shift purify the nuclear receptor using a column that separates the receptor according to charge, such as an ion exchange or hydrophobic interaction column, and then bind the eluted receptor with a ligand; especially an agonist. The ligand induces a change in the receptor's surface charge such that when re-chromatographed on the same column, the receptor then elutes at the position of the liganded receptor are removed by the original column run with the unliganded receptor. Usually saturating concentrations of ligand are used in the column and the protein can be preincubated with the ligand prior to passing it over the column. The structural studies detailed herein indicate the general applicability of this technique for obtaining super-pure nuclear receptor LBDs for crystallization.

More recently developed methods involve engineering a "tag" such as with histidine placed on the end of the protein, such as on the amino terminus, and then using a nickle chelation column for purification, Janknecht R., Proc. Natl. Acad. Sci. USA Vol 88:8972–8976 (1991) incorporated by reference.

To determine the three dimensional structure of a TR LBD, or a LBD from another member of the nuclear receptor superfamily, it is desirable to co-crystalize the LBD with a corresponding LBD ligand. In the case of TR LBD, it is preferable to separately co-crystalize it with ligands such as T3, IpBr and Dimit that differ in the heavy atoms which they contain. Other TR ligands such as those encompassed by Formula 1 described herein and known in the prior art, can also be used for the generation of co-crystals of TR LBD and TR ligands. Of the compounds encompassed by Formula 1 it is generally desirable to use at least one ligand that has at least one bromo- or iodo-substitution at the $R_3$, $R_5$, $R_3'$ or $R_5'$ position, preferably such compounds will be have at least two such substitutions and more preferably at least 3 such substitutions. As described herein, such substitutions are advantageously used as heavy atoms to help solve the phase problem for the three dimensional structure of the TR LBD and can be used as a generalized method of phasing using a halogen (e.g. I or Br) substituted ligand, especially for nuclear receptors.

Typically purified LBD, such as TR LBD, is equilibrated at a saturating concentration of ligand at a temperature that preserves the integrity of the protein. Ligand equilibration can be established between 2 and 37° C., although the receptor tends to be more stable in the 2–20° C. range.

Preferably crystals are made with the hanging drop methods detailed herein. Regulated temperature control is desirable to improve crystal stability and quality. Temperatures between 4 and 25° C. are generally used and it is often preferable to test crystallization over a range of temperatures. In the case of TR it is preferable to use crystallization temperatures from 18 to 25° C., more preferably 20 to 23° C., and most preferably 22° C.

Complexes of the TR-α LBD with a variety of agonists, including 3,5,3'-triiodothyronine ($T_3$), 3'-isopropyl-3,5-dibromothyronine ($IpBr_2$), 3'-isopropyl-3,5-dimethylthyronine (Dimit), and 3,5,3'-triiodothyroacetic acid (triac), are prepared with by methods described herein. Cocrystals of the rTR-α LBD, with ligand prebound, are prepared by vapor diffusion at ambient temperature from 15% 2-methyl-2,4-pentanediol (MPD). The crystals are radiation sensitive, and require freezing to measure complete diffraction data. On a rotating anode X-ray source, the crystals diffract to ~3 Å; synchrotron radiation extends the resolution limit significantly, to as high as 2.0 Å for $T_3$ cocrystals. The composition of the thyroid hormone, combined with the ability to prepare and cocrystallize the receptor complexed with a variety of analogs, permitted the unusual phasing strategy. This phasing strategy can be applied to the ligands of the nuclear receptors described therein by generating I and Br substitutions of such ligands. In this strategy, cocrystals of the TR LBD containing four hormone analogs that differ at the 3,5, and 3' positions ($T_3$, $IpBr_2$, Dimit, and triac) provided isomorphous derivatives. For this set of analogs, the halogen substituents (2Br and 3I atoms) function as heavy atoms, while the Dimit cocrystal (3 alkyl groups) acts as the parent. The initial 2.5 Å multiple isomorphous replacement/anomalous scattering/density modified electron density map allowed the LBD to be traced from skeletons created in the molecular graphics program O5 (Jones, T. A. et al. ACTA Cryst, 47:110–119 (1991), incorporated by reference herein). A model of the LBD was built in four fragments, Arg157-Gly184, Trp186-Gly197, Ser199-Pro205, and Val210-Phe405, and refined in XPLOR using positional refinement and simulated annealing protocols. Missing residues were built with the aid of difference density. The final model was refined to $R_{cryst}$=21.8% and $R_{free}$=24.4% for data from 15.0 to 2.2 Å, see Table 3.

This phasing strategy can be applied to the ligands of the nuclear receptors described herein by generating I and Br substitutions of such ligands.

Three Dimensional Structure of TR LBD
Architecture of TR LBD

Figure 4:
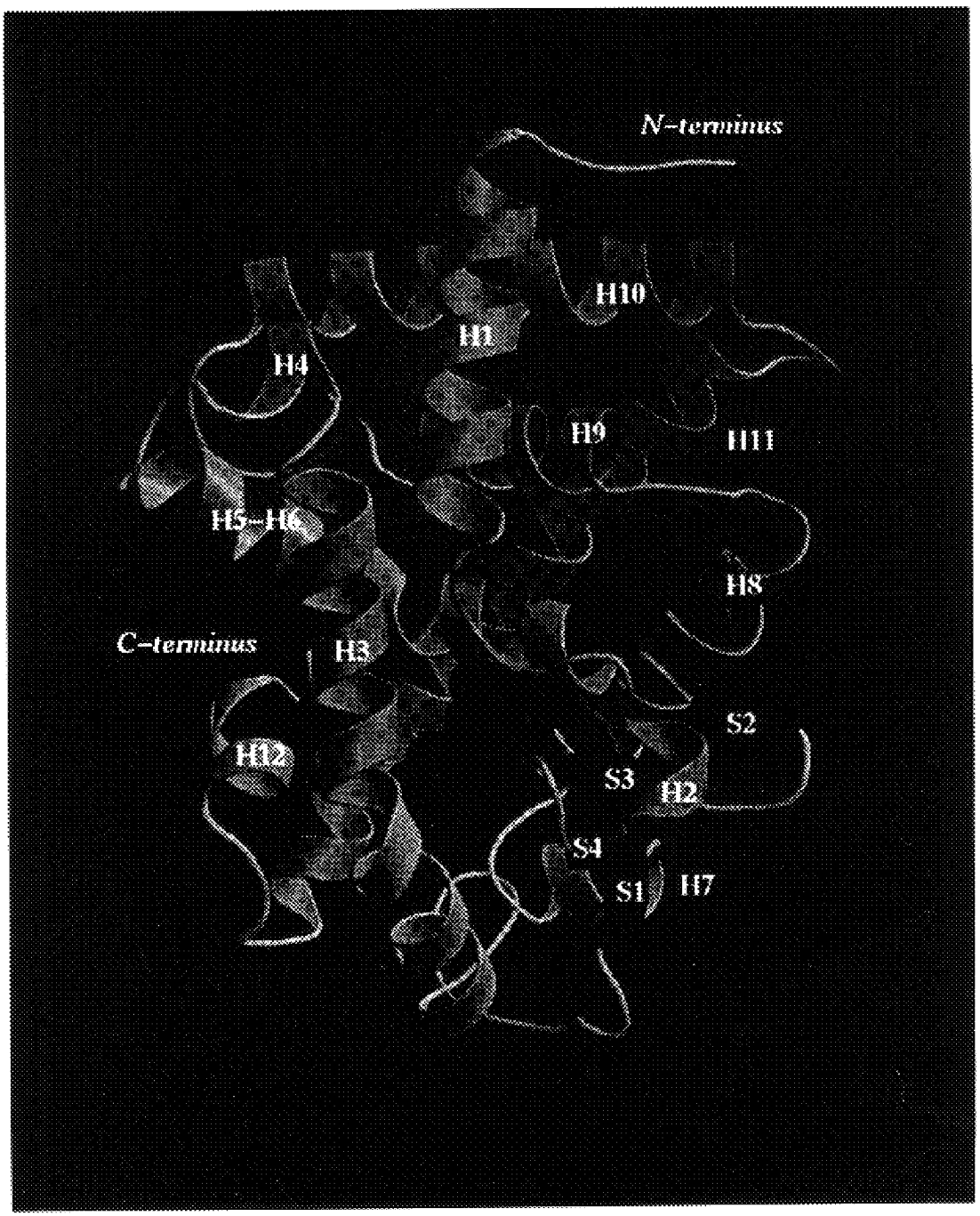
FIG. 4 is a ribbon drawing of the rat TR-α LBD with secondary structure elements labelled. The ligand (magenta) is depicted as a space-filling model. Alpha helices and coil conformations are yellow, beta strands are blue.

As an example of the three dimensional structure of a nuclear receptor, the folding of the TR-$\alpha_1$ LBD is shown in FIG. 4. The TR-α LBD consists of a single structural domain packed in three layers, composed of twelve α-helices, H1-12, and four short β-strands, S1-14, forming a mixed β-sheet. The buried hormone and three antiparallel α-helices, H5-6, H9, and H10, form the central layer of the domain, as shown in FIG. 4. H1, H2, H3 and S1 form one face of the LBD, with the opposite face formed by H7, H8, H11, and H12. The first 35 amino acids of the N-terminus (Met122-Gln156) are not visible in the electron density maps. The three dimensional structure of the heterodimeric RXR:TR DNA-binding domains bound to DNA, amino acids Met122—Gln151 of the TR DBD make extensive contacts with the minor groove of the DNA8. The five disordered amino acids (Arg152-Gln156), which reside between the last visible residue of the TR DBD and the first visible residue of the LBD likely represent the effective "hinge" linking the LBD and the DBD in the intact receptor.

The predominantly helical composition and the layered arrangement of secondary structure is identical to that of the unliganded hRXRα, confirming the existence of a common nuclear receptor fold between two nuclear receptors.

The TR LBD is visible beginning at Arg157, and continues in an extended coil conformation to the start of H1. A turn of α-helix, H2, covers the hormone binding cavity, immediately followed by short β-strand, S1, which forms the edge of the mixed β-sheet, parallel to S4, the outermost of the three antiparallel strands. The chain is mostly irregular until H3 begins, antiparallel to H1. H3 bends at Ile221 and Ile222, residues which contact the ligand. The chain turns almost 90° at the end of H3 to form an incomplete α-helix, H4. The first buried core helix, H5-6, follows, its axis altered by a kink near the ligand at Gly 253. The helix is composed of mostly hydrophobic sidechains interrupted by two striking exceptions: Arg262 is solvent inaccessible and interacts with the ligand carboxylate (1-substituent), and Glu256 meets Arg329 from H9 and Arg375 from H11 in a polar invagination. H5-6 terminates in a short β-strand, S2, of the four strand mixed sheet. S3 and S4 are joined through a left-handed turn, and further linked by a salt bridge between Lys284 and Asp272. Following S4, H7 and H8 form an L, stabilized by a salt bridge between Lys268 and Asp277. The turn between H7 and H8 adopts an unusual conformation, a result of interaction with ligand and its glycine rich sequence. H9 is the second core helix. antiparallel to the neighboring H5-6. Again, two buried polar sidechains are found, Glu315 and Gln320. Glu315 forms a buried salt bridge with His358 and Arg356. The oxygen of Gln320 forms a hydrogen bond with the buried sidechain of His 175. The chain then switches back again to form H10, also antiparallel to H9. H11 extends diagonally across the full length of the molecule. Immediately after H11, the chain forms a type II turn, at approximately 90° to H11. The chain then turns again to form H 12, which packs loosely against H3 and H11 as part of the hormone or ligand binding cavity. The fmal five amino acids at the C-terminus, Glu406 -Val410, are disordered.

TR LBD's Ligand Binding Cavity As An Example Of A Nuclear Receptor's Buried Ligand Cavity The three dimensional structure of the TR LBD leads to the startling finding that ligand binding cavity of the LBD is solvent inaccessible when a T3 or its isostere is bound to the LBD. This surprising result leads to a new model of nuclear receptor three dimensional structure and function, as further described herein, particularly in the sections elucidating the computational methods of ligand design and the application of such methods to designing nuclear receptor synthetic ligands that contain extended positions that prevent normal activation of the activation domain.

Figure 5:
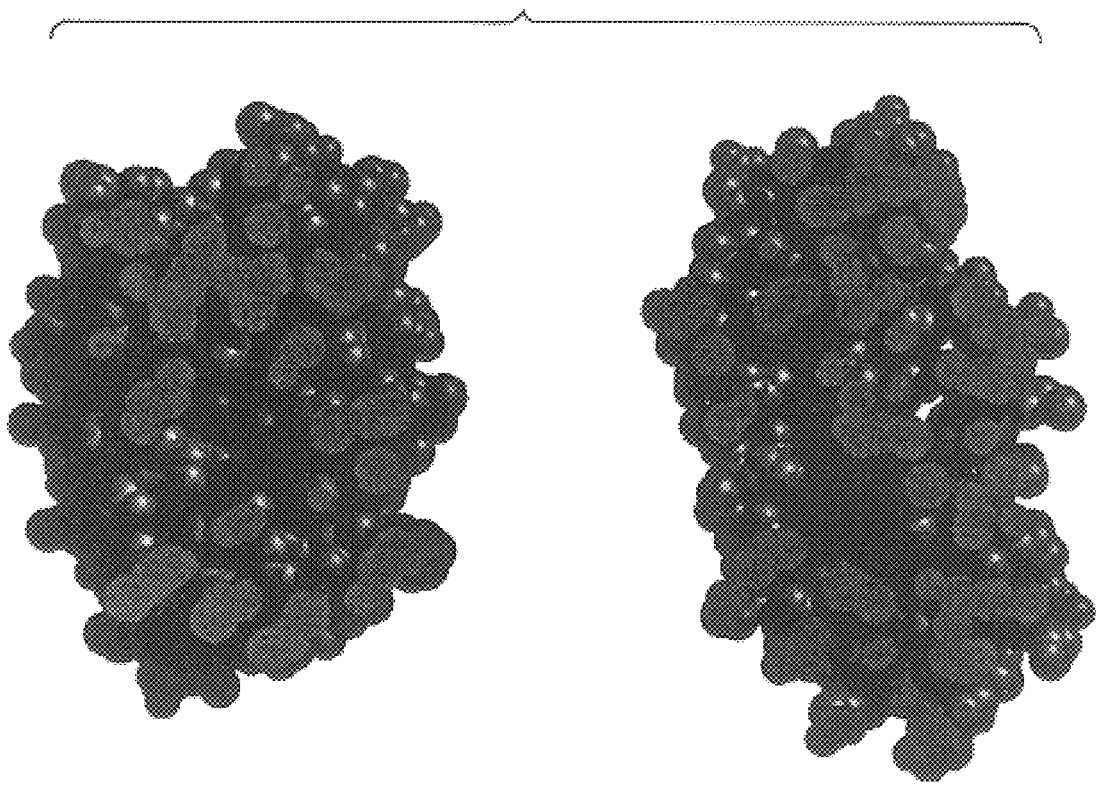
FIG. 5 shows two cross-sections of a space-filling model of rat TR-α exposing the ligand (magenta) tightly packed within the receptor.

Dimit, the ligand bound to the receptor, is an isostere of $T_3$ and a thyroid hormone agonist. Therefore the binding of Dimit should reflect that of $T_3$, and the Dimit-bound receptor is expected to be the active conformation of TR. The ligand is buried within the receptor, providing the hydrophobic core for a subdomain of the protein, as shown in FIG. 5 a and b. H5-6 and H9 comprise the hydrophobic core for the rest of the receptor.

Figure 6:
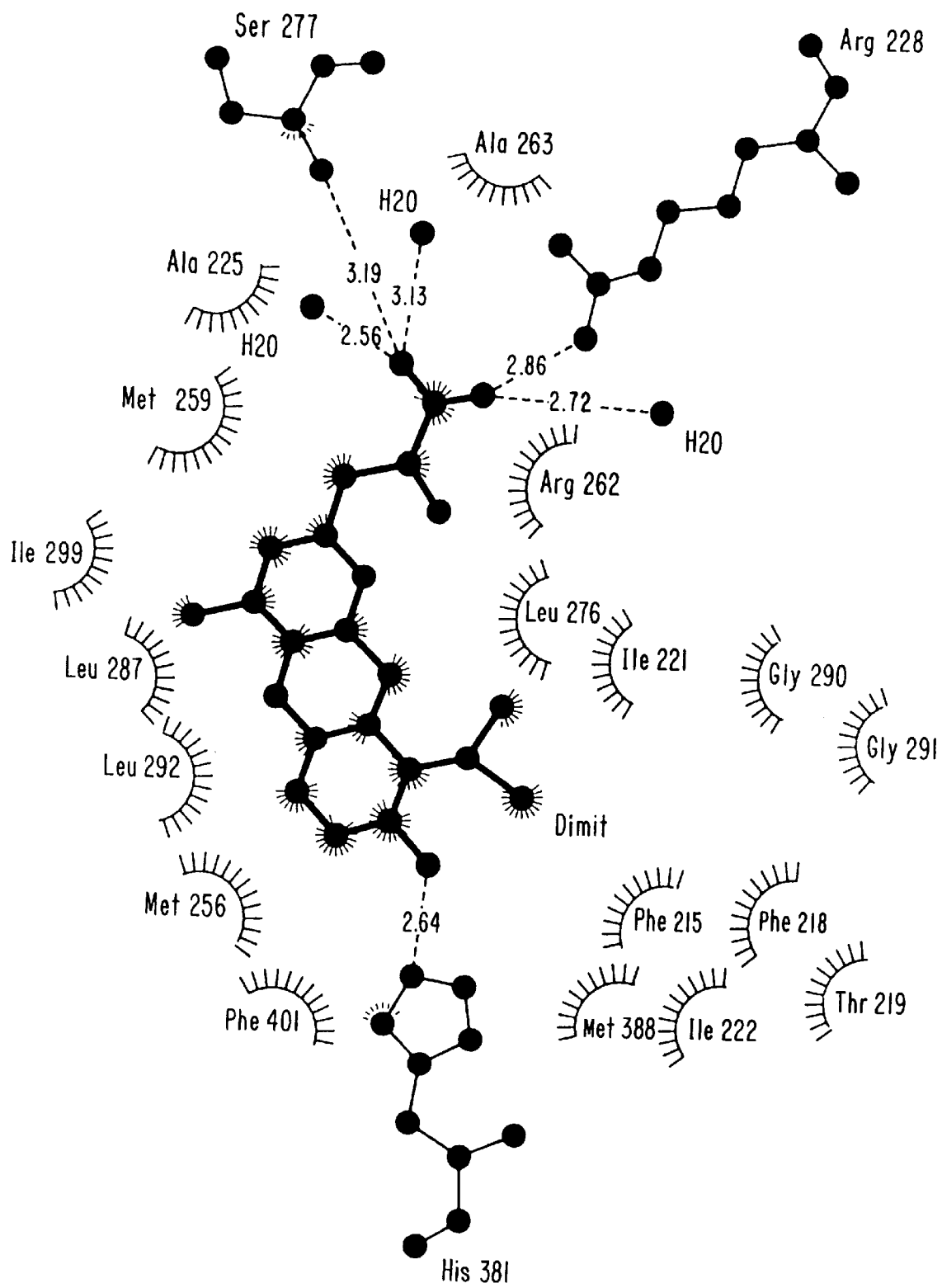
FIG. 6 is a schematic of the ligand binding cavity. Residues which interact with the ligand appear approximately at the site of interaction. Hydrogen bonds are shown as dashed lines between the bonding partners; distances for each bond are listed. Non-bonded contacts are shown as radial spokes which face toward interacting atoms.

An extensive binding cavity is constructed from several structural elements. The cavity is enclosed from above by H5-6 (Met 256- Arg266), from below by H7 and H8 and the intervening loop (Leu287- Ile299), and along the sides by H2 (185-187), by the turn between S3 and S4 (Leu276-Ser277), by H3 (Phe215-Arg228), by H11 (His381-Met388) and by H12 (Phe401-Phe405). The volume of the cavity defined by these elements, calculated by GRASP (Columbia University, USA) (600 Å3), is essentially the volume of the hormone (530 Å). The remaining volume is occupied by water molecules surrounding the amino-propionic acid substituent. FIG. 6 depicts various contacts (or interactions) between TR's LBD and the ligand.

The planes of the inner and outer (prime ring) rings of the ligand are rotated from planarity about 60° with respect to each other, adopting the 3'-distal conformation (in which the 3' substituent of the outer ring projects down and away from the inner ring). The amino-propionic acid and the outer phenolic ring assume the transoid conformation, each on opposite sides of the inner ring. The torsion angle $\chi_1$ for the amino- propionic acid is 300°.

The amino-propionic acid substituent is packed loosely in a polar pocket formed by side chains from H2, H4 and S3. The carboxylate group forms direct hydrogen bonds with the guanidium group of Arg228 and the amino N of Ser277. In addition, Arg262, Arg266 and Asn179 interact with the carboxylate through water-mediated hydrogen bonds. The three arginine residues create a significantly positive local electrostatic potential, which may stabilize the negative charge of the carboxylate. No hydrogen bond is formed by the amino nitrogen. The interactions of the amino-propionic acid substituent are consistent with the fact that triac, which lacks the amino nitrogen, has a binding affinity equal to that of $T_3$, indicating that the amino nitrogen and longer aliphatic chain of $T_3$ do not contribute greatly to binding affinity.

The diphenyl ether, in contrast, is found buried within the hydrophobic core. The inner ring packs in a hydrophobic pocket formed by H3, H5-6, and S3. Pockets for the 3- and 5-methyl substituents are not completely filled, as expected since the van der waals radius of methyl substituent for Dimit is smaller than the iodine substituent provided by the thyroid hormone $T_3$. Such pockets are typically 25 to 100 cubic angstroms (although smaller pocket for substitutes are contemplated in the 40 to 80 cubic angstrom range) and could be filled more tightly with better fitting chemical substitutions, as described herein.

The outer ring packed tightly in a pocket formed by H3, H5-6, H7, H8, H11 and H12, and the loop between H7 and H8. The ether oxygen is found in a hydrophobic environment defined by Phe218, Leu287, Leu276, and Leu292. The absence of a hydrogen bond to the ether oxygen is consistent with its role in establishing the correct stereochemistry of the phenyl rings, as suggested by potent binding of hormone analogs with structurally similar linkages possessing reduced or negligible hydrogen bonding capability. The 3'-isopropyl substituent contacts Gly290 and 291. The presence of glycine at this position in the pocket can explain the observed relationship between activity and the size of 3'-substituents. Activity is highest for 3'-isopropyl, and decreases with added bulk. The only hydrogen bond in the hydrophobic cavity is formed between the phenolic hydroxyl and His381 N∈2. The conformation of His381 is stabilized by packing contacts provided by Phe405, and Met256.

The presence of a 5' substituent larger than hydrogen affects the binding affinity for hormone. The more abundant thyroid hormone, 3,5,3',5'-tetraiodo-L-thyronine ($T_4$), contains an iodine at this position, and binds the receptor with 2% of the affinity of $T_3$. The structure suggests that discrimination against $T_4$ is accomplished through the combination of steric conflict by Met256 and possibly the constraints imposed by the geometry of the hydrogen bond from His381 to the phenolic hydroxyl. The 5' position is a preferred location for introducing a chemical modification of C—H at the 5' of T3 or and TR agonist, as described herein, that produces an extension from the prime ring and results in the creation of an antagonist or partial agonist.

Figure 7:
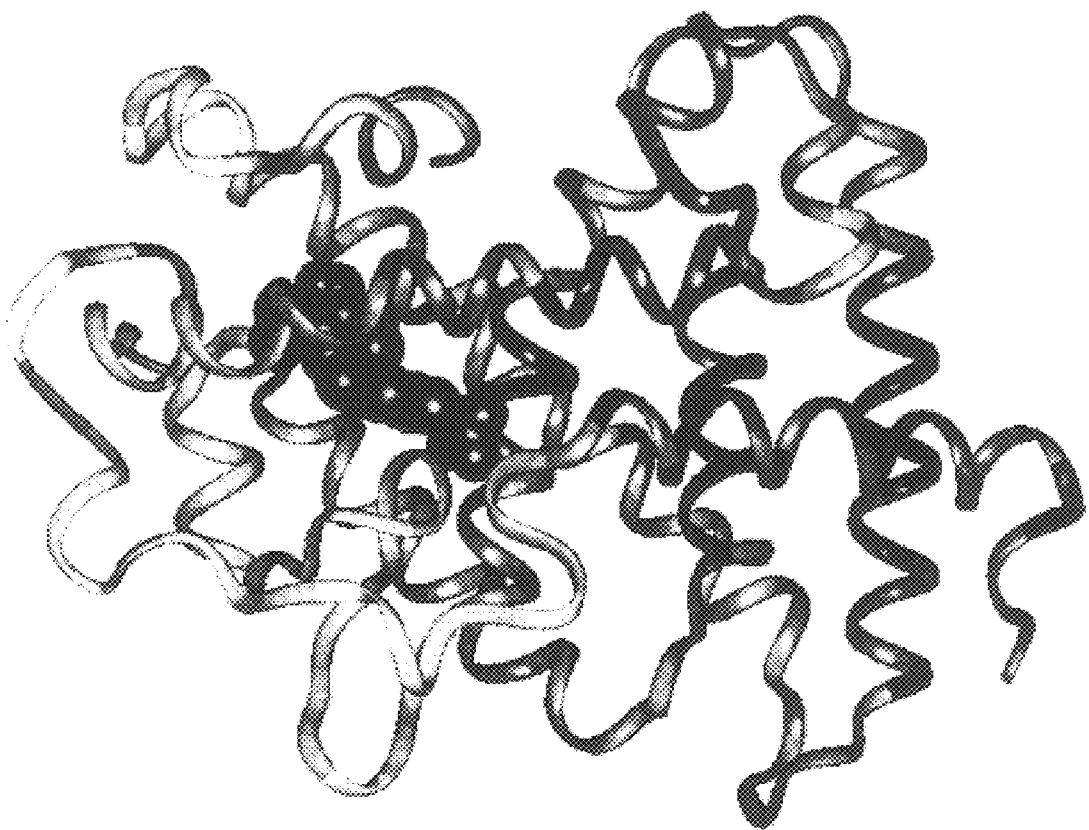
FIG. 7 is the distribution of crystallographic temperature factors in the refined rat TR-α LBD. The distribution is represented as a color gradation ranging from less than 15 (dark blue) to greater than 35 (yellow-green).

Deletion and antibody competition studies suggest the involvement of residues Pro162 to Val202 in ligand binding. The region does not directly contact hormone in the bound structure, although H2 packs against residues forming the polar pocket that interacts with the amino-propionic acid group. One role for H2, then, is to stabilize these residues in the bound state, H2, with β-strands S3 and S4, might also represent a prevalent entry point for ligand, since the amino-propionic acid of the ligand is oriented toward this region. Studies of receptor binding to $T_3$ affinity matrices demonstrate that only a linkage to the amino-propionic acid is tolerated, suggesting that steric hindrance present in other linkages prevent binding. Furthermore, the crystallographic temperature factors suggest the coil and β-strand region is most flexible part of the domain FIG. 7. Participation of this region, part of the hinge domain between the DBD and LBD, in binding hormone may provide structural means for ligand binding to influence DNA binding, since parts of the Hinge domain contact DNA.

TR LBD Transcriptional Activation Helix As An Example Of A Nuclear Receptor Activation Domain In addition to the startling finding that the ligand binding cavity is solvent inaccessible when loaded with a ligand, the activation helix of TR LBD presents a surface to the ligand cavity for interaction between at least one amino acid and the bound ligand. The C-terminal 17 amino acids of the TR, referred to as the activation helix or AF-2 (an example of an LBD activation domain), are implicated in mediating hormone-dependent transcriptional activation. Although, mutations of key residues within the domain decrease ligand-dependent activation it was unclear until the present invention whether such mutations directly affected ligand coordination. Although some mutations of this domain have been noted to reduce or abolish ligand binding, other mutations in more distant sites of the LBD have a similar effect.

Activation domains among nuclear receptors display an analogous three dimensional relationship to the binding cavity, which is a region of the LBD that binds the molecular recognition domain of a ligand, i.e. the activation domain presents a portion of itself to the binding cavity (but necessarily the molecular recognition domain of the ligand). Many nuclear receptors are expected to have such domains, including the retinoid receptors, RAR and RXR, the glucocorticoid receptor GR, and the estrogen receptor ER. Based upon the TR's sequence, the domain is proposed to adopt an amphipathic helical structure. β-sheet or mixed secondary structures, could be present as activation domains in less related nuclear receptors.

Within the activation domain, the highly conserved motif ΦΦXEΦΦ, where Φ represents a hydrophobic residue, is proposed to mediate interactions between the receptors and transcriptional coactivators. Several proteins have been identified which bind the TR in a hormone-dependent fashion. One of these, Trip1, is related to a putative yeast coactivator Sug1, and also interacts with both the C-terminal activation domain and a subset of the basal transcriptional machinery, suggesting a role in transactivation by the TR. Other proteins, such as RIP140, SRC1, (Onate, S. A. et. al., *Science* 270:1354–1357 (1995)) and TF-1 (see also Ledouarim, B., et. al., *EMBO J.* 14:2020–2033 (1995)), also interact with other nuclear receptors in a ligand dependent manner through the C-terminal domain. Binding of these proteins can be modulated using the TR ligands described herein especially those TR ligands with extensions that sterically hinder the interaction between the highly conserved motif and other proteins.

Figure 8:
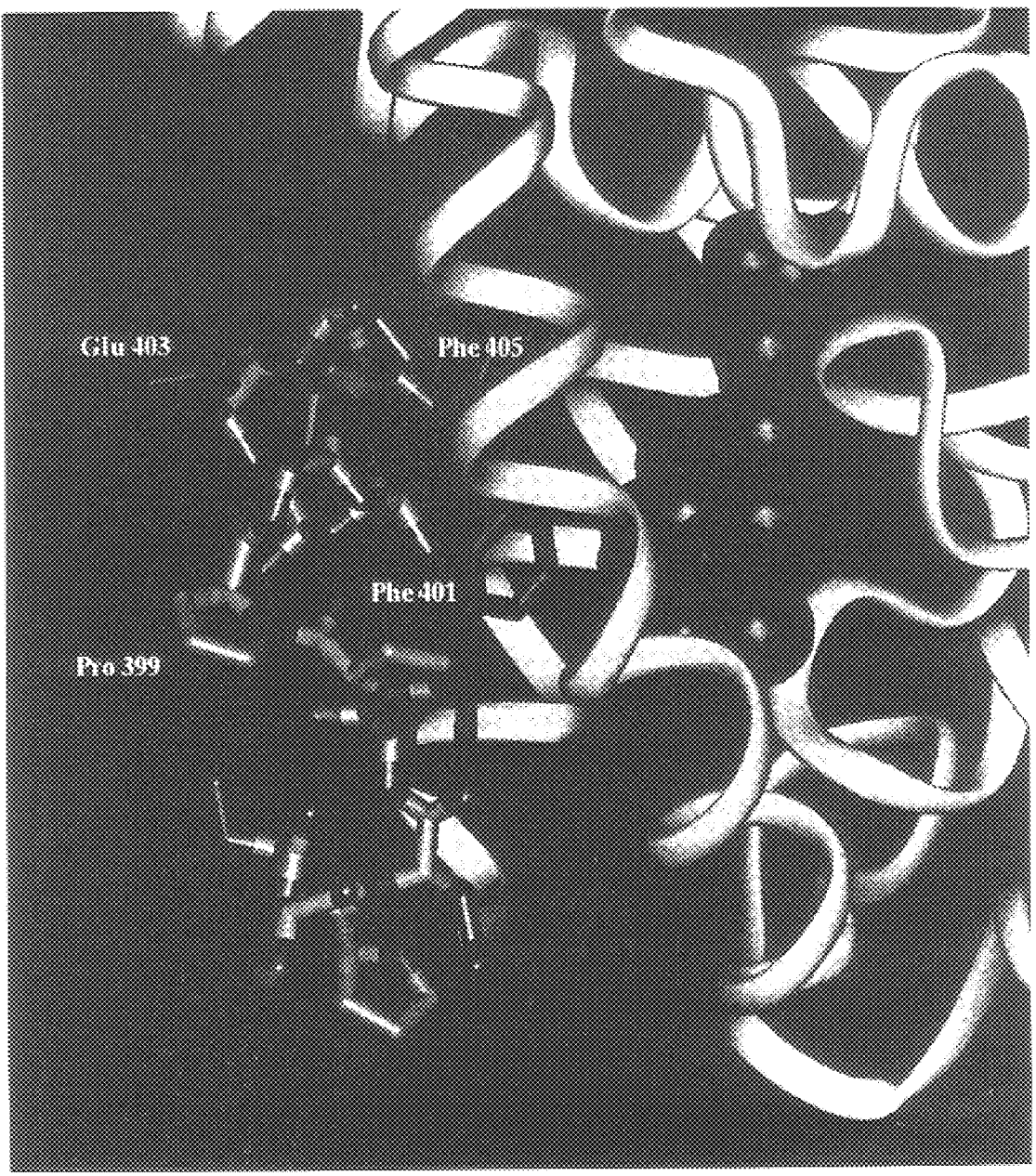
FIG. 8 is a ribbon drawing of the rat TR-α LBD showing the c-terminal activation domain to ligand. Residues which comprise the c-terminal activation domain (Pro393-Phe405) are depicted as a stick representation. Hydrophobic residues, particularly Phe401 and Phe405 (blue) face inwards toward the ligand. Glu403 (red) projects outward into the solvent.
Figure 9:
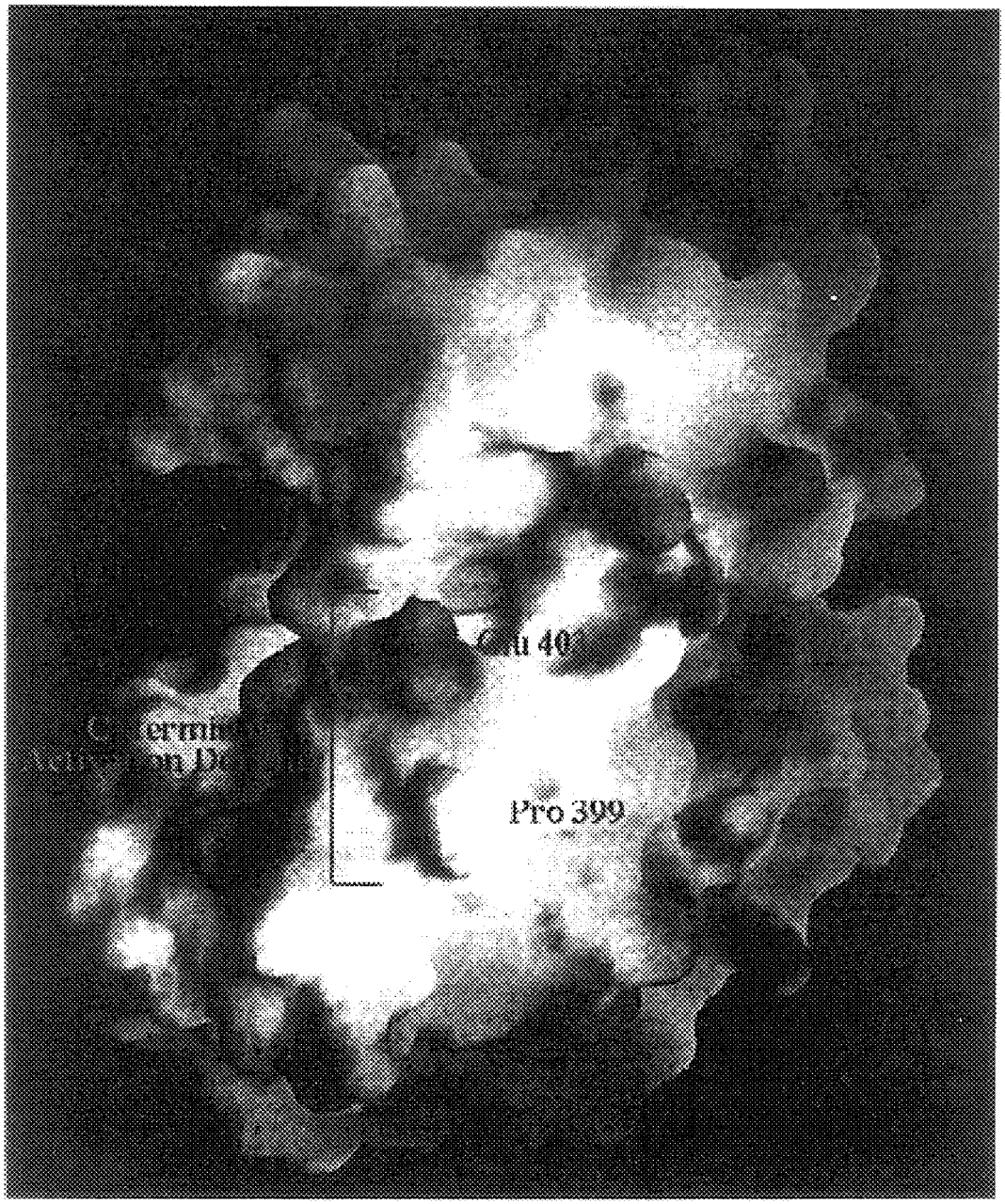
FIG. 9 is an electrostatic potential surface of the rat TR-α LBD, calculated using GRAPH. Negative electrostatic potential is red; positive electrostatic potential is blue. The c-terminal activation domain forms a largely hydrophobic (white). The Glu403 is presented as a singular patch of negative charge (red).

The C-terminal activation domain of the TR forms an amphipathic helix, H12, which nestles loosely against the receptor to form part of the hormone binding cavity. The helix packs with the hydrophobic residues facing inward towards the hormone binding cavity, and the charged residues, including the highly-conserved glutamate, extending into the solvent, as shown in FIG. 8. The activation helix of TR LBD presents Phe 401 to the ligand binding cavity and permits direct coordination with the hormone i.e. such amino acids interact with the ligand forming a van der waals contact with the plane of the outer phenyl ring. Phe 405 also interacts with His 381, perhaps stabilizing its hydrogen bonding conformation, i.e. a favorable hydrogen bond interaction. Participation of Phe 401 and Phe 405 in binding hormone explains how mutation of these residues decreases hormone binding affinity. Furthermore, the impact of these mutations on activation likely derives from a role in stabilizing the domain in the bound structure through increased hydrogen bond interaction of dipole interactions. Glu 403 extends into the solvent, emphasizing its critical role in transactivation. In its observed conformation, presented on the surface as an ordered residue, against a background of predominantly hydrophobic surface, Glu 403 is available to interact with activator proteins described herein, as shown in FIG. 9. The other charged residues, Glu 405 and Asp 406 are disordered, as the helix frays at Phe 405.

Two other sequences in the TR, τ2 and τ3, activate transcription when expressed as fusion proteins with a DNA-binding domain. The sequences, discovered in the TRB, correspond to TR-α residues Pro158-Ile168 in H1 (τ2), and Gly290-Leu319 in H8 and H9 (τ3). Unlike the C-terminal activation domain, τ2 and τ3 do not appear to represent modular structural units in the rat TR-α LBD, nor present a surface for protein-protein interactions: the critical aspartate/glutamate residues of τ3 are located on two separate helices, and do not form a single surface; the charged residues of τ2 are engaged in ion pair interactions with residues of the LBD. Thus, τ2 and τ3 may not function as activation domains in the context of the entire receptor.

Computational Methods For Designing A Nuclear Receptor LBD Ligand

The elucidation of the three dimensional structure of a nuclear receptor ligand binding domain provides an important and useful approach for designing ligands to nuclear receptors using the computational methods described herein. By inspecting the FIGURES it can be determined that the nuclear receptor ligand is bound in a water inaccessible binding cavity in the LBD and that chemical moieties can be added to selected positions on the ligand. Such chemical modifications, usually extensions, can fill up the binding cavity represented in the FIGURES for a tighter fit (or less water) or can be used to disrupt or make contacts with amino acids not in contact with the ligand before the chemical modification was introduced or represented in a figure of the three dimensional model of the LBD. Ligands that interact with nuclear superfamily members can act as agonists, antagonists and partial agonists based on what ligand-induced conformational changes take place.

Agonists induce changes in receptors that place them in an active conformation that allows them to influence transcription, either positively or negatively. There may be several different ligand-induced changes in the receptor's conformation.

Antagonists, bind to receptors, but fail to induce conformational changes that alter the receptor's transcriptional regulatory properties or physiologically relevant conformations. Binding of an antagonist can also block the binding and therefore the actions of an agonist.

Partial agonists bind to receptors and induce only part of the changes in the receptors that are induced by agonists. The differences can be qualitative or quantitative. Thus, a partial agonist may induce some of the conformation changes induced by agonists, but not others, or it may only induce certain changes to a limited extent.

Ligand-induced Conformational Changes

As described herein, the unliganded receptor is in a configuration that is either inactive, has some activity or has repressor activity. Binding of agonist ligands induces conformational changes in the receptor such that the receptor becomes more active, either to stimulate or repress the expression of genes. The receptors may also have non-genomic actions. some of the known types of changes and/or the sequelae of these are listed herein.

Heat Shock Protein Binding

For many of the nuclear receptors ligand binding induces a dissociation of heat shock proteins such that the receptors can form dimers in most cases, after which the receptors bind to DNA and regulate transcription.

Nuclear receptors usually have heat shock protein binding domains that present a region for binding to the LBD and can be modulated by the binding of a ligand to the LBD. Consequently, an extended chemical moiety (or more) from the ligand that stabilizes the binding or contact of the heat shock protein binding domain with the LBD can be designed using the computational methods described herein to produce a partial agonist or antagonist. Typically such extended chemical moieties will extend past and away from the molecular recognition domain on the ligand and usually past the buried binding cavity of the ligand.

Dimerization and Heterodimerization

With the receptors that are associated with the hsp in the absence of the ligand, dissociation of the hsp results in dimerization of the receptors. Dimerization is due to receptor domains in both the DBD and the LBD. Although the main stimulus for dimerization is dissociation of the hsp, the ligand-induced conformational changes in the receptors may have an additional facilitative influence. With the receptors that are not associated with hsp in the absence of the ligand, particularly with the TR, ligand binding can affect the pattern of dimerization/heterodimerization. The influence depends on the DNA binding site context, and may also depend on the promoter context with respect to other proteins that may interact with the receptors. A common pattern is to discourage monomer formation, with a resulting preference for heterodimer formation over dimer formation on DNA.

Nuclear receptor LBDs usually have dimerization domains that present a region for binding to another nuclear receptor and can be modulated by the binding of a ligand to the LBD. Consequently, an extended chemical moiety (or more) from the ligand that disrupts the binding or contact of the dimerization domain can be designed using the computational methods described herein to produce a partial agonist or antagonist. Typically such extended chemical moieties will extend past and away from the molecular recognition domain on the ligand and usually past the buried binding cavity of the ligand.

DNA Binding

In nuclear receptors that bind to hsp, the ligand-induced dissociation of hsp with consequent dimer formation allows, and therefore, promotes DNA binding. With receptors that are not associated (as in the absence of ligand), ligand binding tends to stimulate DNA binding of heterodimers and dimers, and to discourage monomer binding to DNA. However, with DNA containing only a single half site, the ligand tends to stimulate the receptor's binding to DNA. The effects are modest and depend on the nature of the DNA site and probably on the presence of other proteins that may interact with the receptors. Nuclear receptors usually have DBD (DNA binding domains) that present a region for binding to DNA and this binding can be modulated by the binding of a ligand to the LBD. Consequently, an extended chemical moiety (or more) from the ligand that disrupts the binding or contact of the DBD can be designed using the computational methods described herein to produce a partial agonist or antagonist. Typically such extended chemical moieties will extend past and away from the molecular recognition domain on the ligand and usually past the buried binding cavity of the ligand.

Repressor Binding

Receptors that are not associated with hsp in the absence of ligand frequently act as transcriptional repressors in the absence of the ligand. This appears to be due, in part, to transcriptional repressor proteins that bind to the LBD of the receptors. Agonist binding induces a dissociation of these proteins from the receptors. This relieves the inhibition of transcription and allows the transcriptional transactivation functions of the receptors to become manifest.

Transcriptional Transactivation Functions

Ligand binding induces transcriptional activation functions in two basic ways. The first is through dissociation of the hsp from receptors. This dissociation, with consequent dimerization of the receptors and their binding to DNA or other proteins in the nuclear chromatin allows transcriptional regulatory properties of the receptors to be manifest. This may be especially true of such functions on the amino terminus of the receptors.

The second way is to alter the receptor to interact with other proteins involved in transcription. These could be proteins that interact directly or indirectly with elements of the proximal promoter or proteins of the proximal promoter. Alternatively, the interactions could be through other transcription factors that themselves interact directly or indirectly with proteins of the proximal promoter. Several different proteins have been described that bind to the receptors in a ligand-dependent manner. In addition, it is possible that in some cases, the ligand-induced conformational changes do not affect the binding of other proteins to the receptor, but do affect their abilities to regulate transcription.

Nuclear receptors or nuclear receptor LBDs usually have activation domains that present a region for binding to DNA and can be modulated by the binding of a ligand to the LBD. Consequently, an extended chemical moiety (or more) from the ligand that disrupts the binding or contact of the activation domain can be designed using the computational methods described herein to produce a partial agonist or antagonist. Typically such extended chemical moieties will extend past and away from the molecular recognition domain on the ligand and usually past the buried binding cavity of the ligand and in the direction of the activation domain, which is often a helix as seen in the three dimensional model shown in the FIGURES in two dimensions on paper or more conveniently on a computer screen.

Ligand-Induced Conformational Change

Plasma proteins bind hormones without undergoing a conformational change through a static binding pocket formed between monomers or domains. For example, the tetrameric thyroid-binding plasma protein transthyretin forms a solvent-accessible hormone-binding channel at the oligomer interface. The structure of the protein is unchanged upon binding hormone with respect to the appearance of a buried binding cavity with a ligand bound.

However, the structural role for a ligand bound to a nuclear receptor LBD, like rat TR-α LBD, predicts that the receptor would differ in the bound and unbound states. In the absence of hormone, the receptor would possess a cavity at its core, uncharacteristic of a globular protein. A ligand (e.g. hormone) completes the hydrophobic core of the active receptor after it binds to the nuclear receptor. Ligand binding by the receptor is a dynamic process, which regulates receptor function by inducing an altered conformation.

An exact description of the hormone-induced conformational changes requires comparison of the structures of the liganded and the unliganded TR. The structure of the unliganded human RXRα may substitute as a model for the unliganded TR. The rat TR-α LBD and human RXRα LBDs adopt a similar fold, and it is likely that the structural similarity extends to the conformational changes after ligand binding.

There are three major differences between the two structures, which indeed appear to be the result of ligand binding. First, the bound rat TR-α LBD structure is more compact, with the hormone tightly packed within the hydrophobic core of the receptor. By contrast, the unliganded human RXRα LBD contains several internal hydrophobic cavities. The presence of such cavities is unusual in folded proteins, and is likely a reflection of the unliganded state of the receptor. Two of these cavities were proposed as possible binding sites for 9-cis retinoic acid, though these multiple sites only partly overlap with the single buried binding cavity observed in the liganded rat TR-α LBD.

The second difference involves H11 in the rat TR-α LBD, which contributes part of the hormone binding cavity. H11, continuous in the rat TR-α LBD, is broken at Cys 432 in the RXR, forming a loop between H10 and H11 in the hRXRα. This residue corresponds to His381 in the TR, which provides a hydrogen bond to the outer ring hydroxyl of the ligand. Furthermore, the hormone binding cavity occupied by ligand in the rat TR-α LBD is interrupted in the hRXRα by the same loop, forming an isolated hydrophobic pocket in the RXR with H6 and H7. In the bound rat TR-α LBD, the corresponding helices H7 and H8 are contiguous with the binding pocket, and enclose the hormone binding cavity from below.

The third difference between the two receptors is the position of the C-terminal activation domain. While the C-terminal activation domain forms a-helices in both receptors, the domain in the rat TR-α LBD follows a proline-rich turn, and lies against the receptor to contribute part of the binding cavity. In contrast, the activation domain in the unliganded hRXRα, is part of a longer helix which projects into the solvent.

These differences lead to a model for an alternate conformation of the TR LBD assumed in the absence of ligand. In the unliganded TR, the subdomain of the receptor surrounding the hormone binding cavity is loosely packed, with the binding cavity occluded by a partly unstructured H11 providing a partial core for the receptor.

Upon binding hormone, residues which form a coil in the unbound receptor engage the ligand, and continues H11. The ordering of H11 could unblock the hydrophobic cavity, allowing H7 and H8 to interact with hormone. The extended hydrophobic cavity then collapses around the hormone, generating the compact bound structure.

It is possible to predict ligand-induced conformational changes in the C-terminal activation domain that rely, in part, on an extended structure in the unliganded TR that repacks upon ligand binding. The ligand-induced conformation change can be subtle since the amino acid sequence of the rat TR-α in the turn (393-PTELFPP-399) residues 393 to 399 of SEQ ID NO:1 significantly reduces the propensity of the peptide chain of the rat TR-α to form an α-helix and therefore repacking can be accomplished with a minor change in volume.

After the ligand-induced conformational change occurs, it is likely that the conformation of the C-terminal activation domain in the bound structure changes packing compared to the unbound form of the receptor. Binding of the ligand improves the stability of the activation domain. The activation domain packs loosely even in the bound structure, as measured by the distribution of packing interactions for the entire LBD. The packing density for the activation domain, defined as the number of atoms within 4.5 Å, is 1.5 standard deviations below the mean. For comparison, another surface helix, H1, is 0.5 standard deviations below the mean and the most poorly packed part of the structure, the irregular coil from residues Ile196-Asp206, is 2.0 standard deviations below the mean. Moreover, the majority of packing contacts for the C-terminal domain in the bound receptor are provided either by residues which interact with ligand, such as His381, or by the ligand itself. The conformation of these residues can be expected to be different in the bound and unbound receptors, and by extension the conformation of C-terminal activation domain which relies upon these interactions. Without the stabilization provided by a bound ligand, it is likely that the C-terminal activation domain is disordered prior to hormone binding.

The interrelation of ligand-induced conformational changes is evident as described herein. For example, His381 from H11 and Phe405 from H12 interact in the bound structure to provide a specific hydrogen bond to the phenolic hydroxyl. The ligand-induced changes which affect H11 and H12 are reinforcing, and lead to the formation of the compact, bound state.

Computational Methods Using Three Dimensional Models and Extensions of Ligands The three-dimensional structure of the liganded TR receptor is unprecedented, and will greatly aid in the development of new nuclear receptor synthetic ligands, such as thyroid receptor antagonisys. In addition, this receptor superfamily is overall well suited to modern methods including three-dimensional structure elucidation and combinatorial chemistry such as those disclosed in EP 335 628, U.S. Pat. No. 5,463,564, which are incorporated herein by reference. Structure determination using X-ray crystallography is possible because of the solubility properties of the receptors. Computer programs that use crystallography data when practicing the present invention will enable the rational design of ligand to these receptors. Programs such as RASMOL can be used with the atomic coordinates from crystals generated by practicing the invention or used to practice the invention by generating three dimensional models and/or determining the structures involved in ligand binding. Computer programs such as INSIGHT and GRASP allow for further manipulation and the ability to introduce new structures. In addition, high throughput binding and bioactivity assays can be devised using purified recombinant protein and modern reporter gene transcription assays described herein and known in the art in order to refine the activity of a CDL.

Generally the computational method of designing a nuclear receptor synthetic ligand comprises two steps:
1) determining which amino acid or amino acids of a nuclear receptor LBD interacts with a first chemical moiety (at least one) of the ligand using a three dimensional model of a crystallized protein comprising a nuclear receptor LBD with a bound ligand, and
2) selecting a chemical modification (at least one) of the first chemical moiety to produce a second chemical moiety with a structure to either decrease or increase an interaction between the interacting amino acid and the second chemical moiety compared to the interaction between the interacting amino acid and the first chemical moiety.

As shown herein, interacting amino acids form contacts with the ligand and the center of the atoms of the interacting amino acids are usually 2 to 4 angstroms away from the center of the atoms of the ligand. Generally these distances are determined by computer as discussed herein and in McRee 1993, however distances can be determined manually once the three dimensional model is made. Examples of interacting amino acids are described in FIGS. 27–27A-13. See also Wagner et al., Nature 378(6558):670–697 (1995) for stereochemical figures of three dimensional models. More commonly, the atoms of the ligand and the atoms of interacting amino acids are 3 to 4 angstroms apart. The invention can be practiced by repeating steps 1 and 2 to refine the fit of the ligand to the LBD and to determine a better ligand, such as an agonist. As shown in the FIGURES the three dimensional model of TR can be represented in two dimensions to determine which amino acids contact the ligand and to select a position on the ligand for chemical modification and changing the interaction with a particular amino acid compared to that before chemical modification. The chemical modification may be made using a computer, manually using a two dimensional representation of the three dimensional model or by chemically synthesizing the ligand. The three dimensional model may be made using FIGS. 27–27A-13 and the FIGURES. As an additional step, the three dimensional model may be made using atomic coordinates of nuclear receptor LBDs from crystallized protein as known in the art, see McRee 1993 referenced herein.

The ligand can also interact with distant amino acids after chemical modification of the ligand to create a new ligand. Distant amino acids are generally not in contact with the ligand before chemical modification. A chemical modification can change the structure of the ligand to make as new ligand that interacts with a distant amino acid usually at least 4.5 angstroms away from the ligand. Often distant amino acids will not line the surface of the binding cavity for the ligand, as they are too far away from the ligand to be part of a pocket or surface of the binding cavity.

The interaction between an atom of a LBD amino acid and an atom of an LBD ligand can be made by any force or attraction described in nature. Usually the interaction between the atom of the amino acid and the ligand will be the result of a hydrogen bonding interaction, charge interaction, hydrophobic interaction, van der waals interaction or dipole interaction. In the case of the hydrophobic interaction it is recognized that this is not a per se interaction between the amino acid and ligand, but rather the usual result, in part, of the repulsion of water or other hydrophilic group from a hydrophobic surface. Reducing or enhancing the interaction of the LBD and a ligand can be measured by calculating or testing binding energies, computationally or using thermodynamic or kinetic methods as known in the art.

Chemical modifications will often enhance or reduce interactions of an atom of a LBD amino acid and an atom of an LBD ligand. Steric hinderance will be a common means of changing the interaction of the LBD binding cavity with the activation domain. Chemical modifications are preferably introduced at C—H, C— and C—OH position in ligands, where the carbon is part of the ligand structure which remains the same after modification is complete. In the case of C—H, C could have 1, 2 or 3 hydrogens, but usually only one hydrogen will be replaced. The H or OH are removed after modification is complete and replaced with the desired chemical moiety.

Because the thyroid receptor is a member of the larger superfamily of hormone-binding nuclear receptors, the rules for agonist and antagonist development will be recognized by one skilled in the art as useful in designing ligands to the entire superfamily. Examining the structures of known agonists and antagonists of the estrogen and androgen receptors supports the generality of antagonist mechanism of action as shown in FIG. 10.

The overall folding of the receptor based on a comparison of the reported structure of the unliganded RXR and with amino acid sequences of other superfamily members reveals that the overall folding of receptors of the superfamily is similar. Thus, it is predicted from the structure that there is a general pattern of folding of the nuclear receptor around the agonist or antagonist ligand.

The three dimensional structure of a nuclear receptor with a ligand bound leads to the nonobvious observation that a nuclear receptor folds around agonist ligands, as the binding cavity fits the agonist, especially the agonist's molecular recognition domain, and antagonists commonly have chemical structures that extend beyond the ligand, especially the agonist, and would prohibit folding of the receptor around the ligand to form a buried binding cavity or other groups that have the same effect. The location of the extension could affect the folding in various ways as indicated by the structure. Such extensions on antagonists are shown in FIG. 10 for various receptors and compared to the corresponding agonist.

For example, an extension towards the carboxy-terminal activation helix affects the packing/folding of this helix into the body of the receptor. This in turn can affect the ability of this portion of the nuclear receptor to interact with other proteins or other portions of the receptor, including transcriptional transactivation functions on the opposite end of the linear receptor, or the receptor's amino terminus that may interact directly or indirectly with the carboxy-terminal transactivation domain (including helix 12). Extensions in this direction can also affect the packing of helix 11 of TR (or its analogous helix in nuclear receptors) into the body of the receptor and selectively affect dimerization and heterodimerization of receptors. An extension pointing towards helix 1 can affect the relationship of the DNA binding domain and hinge regions of the receptors with the ligand binding domain and selectively or in addition affect the receptors' binding to DNA and/or interactions of receptors with proteins that interact with this region of the receptor. Other extensions towards helix 11 can be made to affect the packing of this helix and helices 1 and 10 and thereby dimerization. Such chemical modifications can be assessed using the computational methods described herein. It is also possible that, in some cases, extensions may protrude through the receptor that is otherwise completely or incompletely folded around the ligand. Such protruding extensions could present a steric blockade to interactions with co-activators or other proteins.

The three dimensional structure with the ligand buried in the binding cavity immediately offers a simple description of a nuclear receptor that has a binding cavity that contains hinges and a lid, composed of one or more structural elements, that move to accommodate and surround the ligand. The ligand to TR can be modified on specific sites with specific classes of chemical groups that will serve to leave the lid and hinge region in open, partially open or closed states to achieve partial agonist or antagonist functions. In these states, the biological response of the TR is different and so the structure can be used to design particular compounds with desired effects.

Knowledge of the three-dimensional structure of the TR-$T_3$ complex leads to a general model for agonist and antagonist design. An important novel feature of the structural data is the fact that the $T_3$ ligand is completely buried within the central hydrophobic core of the protein. Other ligand-receptor complexes belonging to the nuclear receptor superfamily will have a similarly buried ligand binding site and therefore this model will be useful for agonist/antagonist design for the entire superfamily.

When design of an antagonist is desired, one needs either to preserve the important binding contacts of natural hormone agonist while incorporating an "extension group" that interferes with the normal operation of the ligand-receptor complex or to generate the requisite binding affinity through the interactions of the extensions with receptor domains.

The model applied to antagonist design and described herein is called the "Extension Model." Antagonist compounds for nuclear receptors should contain the same or similar groups that facilitate high-affinity binding to the receptor, and in addition, such compounds should contain a side chain which may be large and/or polar. This side chain could be an actual extension, giving it bulk, or it could be a side group with a charge function that differs from the agonist ligand. For example, substitution of a $CH_3$ for $CH_2OH$ at the 21-position, and alteration at the 11-position from an OH group to a keto group of cortisol generates glucocorticoid antagonist activity (Robsseau, G. G., et. al., J. Mol. Biol. 67:99–115 (1972)). However, in most cases effective antagonists have more bulky extensions. Thus, the antiglucocorticoid (and antiprogestin) RU486 contains a bulky side group at the 11-position (Horwitz, K. B. Endocrine Rev. 13: 146–163 (1992)). The antagonist compound will then bind within the buried ligand binding site of the receptor with reasonably high affinity (100 nM), but the extension function will prevent the receptor-ligand complex from adopting the necessary conformation needed for transcription factor function. The antagonism (which could be in an agonist or antagonist) may manifest itself at the molecular level in a number of ways, including by preventing receptor homo/heterodimer formation at the HRE, by preventing coactivator binding to receptor monomers, homodimers or homo/heterodimers, or by a combination of these effects which otherwise prevent transcription of hormone responsive genes mediated by ligand-induced effects on the HRE. There are several antagonist compounds for nuclear receptors in the prior art (see also Horwitz, K. B., Endocrine Rev. 13:146–163 (1992), Raunnaud J. P. et. al., J. Steroid Biochem. 25:811–833 (1986), Keiel S., et. al., Mol. Cell. Biol. 14:287–298 (1994) whose antagonist function can be explained by the extension hypothesis. These compounds are shown in FIG. 10 along with their agonist counterparts. Each of these antagonists contains a large extension group attached to an agonist or agonist analogue core structure. Importantly, these antagonist compounds were discovered by chance and not designed with a structure-function hypothesis such as the extension principle.

One method of design of a thyroid antagonist using the extension hypothesis is provided below as a teaching example. The three-dimensional structure of the TR-αDimit complex combined with structure-activity data published in the prior art, especially those reference herein, can be used to establish the following ligand-receptor interactions which are most critical for high-affinity ligand binding. A physical picture of these interactions is shown in FIG. 6. The figure describes the isolated essential contacts for ligand binding. Because the ligand is buried in the center of the receptor, the structural spacing between these isolated interactions is also important. Thus, our present knowledge of this system dictates that, for this example, a newly designed ligand for the receptor must contain a thyronine structural skeleton, or two substituted aryl groups joined by a one-atom spacer.

The general structure for an antagonist designed by the extension hypothesis is exemplified in the following general description of the substituents of a TR antagonist (referring to Formula 1): R1 can have anionic groups such as a carboxylate, phosphonate, phosphate, sulfate or sulfite and is connected to the ring with a 0 to 3 atom linker, comprising one or more C, O, N, S atoms, and preferably a 2 carbon linker. Such R1 can be optionally substituted with an amine (e.g. —NH2). R3 and R5 are small hydrophobic groups such as —Br, —I, or —CH3. R3 and R5 can be the same substituents or different. $R_3'$ can be a hydrophobic group that may be larger than those of R3 and R5, such as —I, —CH3, -isopropyl, -phenyl, -benzyl, 5 and 6 ring heterocycles. $R_4'$ is a group that can participate in a hydrogen bond as either a donor or acceptor. Such groups include —OH, —$NH_2$, and —SH. $R_5'$ is an important extension group that makes this compound an antagonist. $R_5'$ can be a long chain alkyl (e.g. 1 to 9 carbons, straight chain or branched), aryl (benzyl, phenyl and substituted benzyl and phenyl rings (e.g with halogen, alkyl (1 and 5 carbons) and optionally connected to the ring by a —CH2—), heterocycle (e.g. 5 or 6 atoms, preferably 5 carbons and 1 nitrogen, or five carbons), which can optionally include polar (e.g. —OH, —$NH_2$, and —SH), cationic (e.g. —NH3, N(CH)3), or anionic (carboxylate, phosphonate, phosphate or sulfate) groups. $R_5'$ can also be a polar (e.g. —OH, —$NH_2$, and —SH), cationic (e.g. —NH3, —N(CH3)3), and anionic (carboxylate, phosphonate, phosphate or sulfate) groups. X is the spacer group that appropriately positions the two aromatic rings. This group is usually a one-atom spacer, such as O, S, SO, SO2, NH, NZ where Z is an alkyl, CH2, CHOH, CO, C(CH3)OH, and C(CH3)(CH3). R2, R6, R2' and R6' can be —F, and —Cl and are preferably H.

A TR ligand can also be described as a substituted phenylated 3,5 diiodo tyrosine with substituted R5' and R3' groups. R5' can be a long chain alkyl (e.g. 4 to 9 carbons, straight chain or branched), aryl (benzyl, phenyl and substituted benzyl and phenyl rings (e.g with halogen, alkyl (1 and 5 carbons) and optionally connected to the ring by a —CH2—), heterocycle (e.g. 5 or 6 atoms, preferably 5 carbons and 1 nitrogen, or five carbons), which can optionally include polar (e.g. —OH, —$NH_2$, and —SH), cationic (e.g. —NH3, N(CH)3), or anionic (carboxylate, phosphonate, phosphate or sulfate) groups. R5' can also be a polar (e.g. —OH, —$NH_2$, and —SH), cationic (e.g. —NH3, N(CH)3), and anionic (carboxylate, phosphonate, phosphate or sulfate) groups. R3' can be —IsoPr, halogen, —CH3, alkyl (1 to 6 carbons) or aryl (benzyl, phenyl and substituted benzyl and phenyl rings (e.g with halogen, alkyl (1 and 5 carbons) and optionally connected to the ring by a —CH2—), heterocycle (e.g. 5 or 6 atoms, preferably 5 carbons and 1 nitrogen, or five carbons), which can optionally include polar (e.g. —OH, —$NH_2$, and —SH), cationic (e.g. —NH3, N(CH)3), or anionic (carboxylate, phosphonate, phosphate or sulfate) groups.

A TR antagonist can also be a modified $T_3$ agonist (having a diphenyl structure) wherein $R_5'$ is alkyl, aryl, 5- or 6-membered heterocyclic aromatic, heteroalkyl, heteroaryl, arylalkyl, heteroaryl alkyl, polyaromatic, polyheteroaromatic, polar or charged groups, wherein said $R_5'$ may be substituted with polar or charged groups. The R5' groups are defined, as described herein.

Using these methods the ligands of this example preferably have the following properties:

1. The compounds should bind to the TR with high affinity (for example 100 nM).
2. The compounds should bind the receptor in the same basic orientation as the natural hormone.
3. The extension group R5' should project toward the activation helix (C-terminal helix) of the receptor.
4. The appropriate substituent at R5' should perturb the activation helix from its optimal local structure needed for mediating transcription.

Antagonists may also be designed with multiple extensions in order to block more than one aspect of the folding at any time.

TR ligands (e.g. super agonists) can be designed (and synthesized) to enhance the interaction of at least one amino acid with at least one chemical moiety on the ligand's molecular recognition domain. One method is to enhance the charge and polar interactions by replacing the carboxylate of $T_3$ (R1 position) with phosphonate, phosphate, sulfate or sulfite. This enhances the interaction with Arg 262, Arg 266 and Arg 228. The interaction of at least one amino acid with at least one chemical moiety on the ligand's molecular recognition domain can also be enhanced by increasing the size of R1 group to fill the space occupied by water when Dimit is bound (referring to R1). Preferably the group has a complementary charge and hydrophobicity to the binding cavity.

Another way of improving the interaction of at least one amino acid with at least one chemical moiety on the ligand's molecular recognition domain is to restrict the conformation of the dihedral angle between the two phenyl rings of the thyronine ligand in solution. In solution the planes of two phenyl rings are orthogonal where the dihedral angle is 90°. In the TR Dimit structure, the dihedral angle is close to 60°. A TR ligand design that fixes the angle between the two phenyl rings will lead to tighter binding. Such a ligand may be made by connecting the R6' and the R5 positions of a thyronine or a substituted thyronine-like diphenyl. The size of the cyclic connection can fix the angle between the two phenyl rings. Referring specifically to Formula 1, the following cyclic modifications are preferred: 1) $R_5$ is connected to $R_6'$, 2) $R_3$ is connected to $R_2'$ or 3) $R_5$ is connected to $R_6'$ and $R_3$ is connected to R2'. The connections can be made by an alkyl or heteroalkyl chain having between 1 to 6 atoms and preferably from 2 to 4 carbon atoms or other atoms. Any position of the heteroalkyl chain can be N, O, P or S. The S and P heteroatoms along said heteroalkyl chain are in any of their possible oxidative states. The N heteroatom or any carbon along the alkyl or heteroalkyl chain may have one or more Z substituents, wherein Z is alkyl, heteroalkyl, aryl, heteroaryl, 5- or 6-membered heterocyclic aromatic. These compounds can be claimed with the proviso that Formula 1 does not include any prior art compound as of the filing date of this application.

The interaction of at least one amino acid with at least one chemical moiety on the ligand's molecular recognition domain can also be enhanced by selecting a chemical modification that fills the unfilled space between a TR ligand and the LBD in the area of the bridging oxygen (such as in T3, triac or Dimit). Thus, a slighter larger moiety that replaces the ether oxygen can enhance binding. Such a linker may be a mono- or geminal-disubstituted carbon group. A group approximately the same size as oxygen but with greater hydrophobicity is preferred as well as small, hydrophobic groups for the disubstituted carbon.

TR-α and Selectivity for the Thyroid Hormone Receptor

Using the method described herein ligands can be designed that selectively bind to the alpha more than the beta TR. The X-ray crystallographic structure of the rat TR-a LBD provides insight into design of such ligands.

The three dimensional structure reveals that the major difference between the TR-α and TR-β in the ligand binding cavity resides in amino acid Ser 277 (with the side group —CH2OH) in the rat TR-a and whose corresponding residue is 331, asparagine (with the side group —CH2CONH2), in the human TR-β. The side chain in human TR-β is larger, charged and has a different hydrogen bonding potential, which would allow the synthesis of compounds that discriminate between this difference.

For example, in the complex of TRα with triac, Ser277 does not participate in ligand binding. The absence of a role for Ser277 (Asn331 in beta) is consistent with the equal affinity of triac for the alpha and beta isoforms, and indirectly supports the contention that alpha/beta selectivity resides in the amino acid substitution Ser277 to Asn331 and its interaction with Arg228.

In terms of ligand design, these differences mean that for β-selective ligands, some or all of the following differences should be exploited:

1. The presence of a larger side chain asparagine.
2. The ability of the carbonyl group on the side chain to provide a strong hydrogen bond acceptor.
3. The ability of the amido group on the side chain to provide a two hydrogen bond donors.
4. Adjustment of polarity to reorganize the trapped water in the T3 pocket.

In terms of pharmaceutical design, these differences mean that for α-selective ligands, some or all of the following differences should be exploited:

1. The presence of a smaller side group.
2. The ability of the hydroxyl on the —CH2OH side group carbonyl group on the side chain to provide a weak hydrogen donor.
3. Adjustment of polarity to reorganize the trapped water in the T3 pocket.

In both cases these differences can be exploited in a number of ways. For example, they can also be used with a software set for construction of novel organic molecules such as LUDI from Biosym-MSI.

Methods of Treatment

The compounds of Formula 1 can be useful in medical treatments and exhibit biological activity which can be demonstrated in the following tests:

(i) the induction of mitochondrial α-glycerophosphate dehydrogenase (GPDH:EC 1.1.99.5). This assay is particularly useful since in certain species e.g. rats it is induced specifically by thyroid hormones and thyromimetics in a close-related manner in responsive tissues e.g. liver, kidney and the heart (Westerfield, W. W., Richert, D. A. and Ruegamer, W. R., Endocrinology, 1965, 77, 802). The assay allows direct measurement in rates of a thyroid hormone-like effect of compounds and in particular allows measurement of the direct thyroid hormone-like effect on the heart;

(ii) the elevation of basal metabolic rate as measured by the increase in whole body oxygen consumption (see e.g., Barker et al., Ann. N. Y. Acad. Sci., 86:545–562 (1960));

(iii) the stimulation of the rate of beating of atria isolated from animals previously dosed with thyromimetrics (see e.g., Stephan et al., Biochem. Pharmacol. (1992) 13:1969–1974; Yokoyama et al., J. Med. Chem. 38:695–707 (1995));

(iv) the change in total plasma cholesterol levels as determined using a cholesterol oxidase kit (for example, the Merck CHOD iodine colorimetric kit. see also, Stephan et al. (1992));

(v) the measurement of LDL (low density lipoprotein) and HDL (high density lipoprotein) cholesterol in lipoprotein fractions separated by ultracentrifugation; and p (vi) the change in total plasma triglyceride levels as determined using enzymatic color tests, for example the Merck System GPO-PAP method.

The compounds of Formula 1 can be found to exhibit selective thyromimetic activity in these tests, (a) by increasing the metabolic rate of test animals, and raising hepatic GPDH levels at doses which do not significantly modify cardiac GPDH levels.

(b) by lowering plasma cholesterol and triglyceride levels, and the ratio of LDL to HDL cholesterol at doses which do not significantly modify cardiac GPDH levels.

The compounds of Formula 1 may therefore be used in therapy, in the treatment of conditions which can be alleviated by compounds which selectively mimic the effects of thyroid hormones in certain tissues whilst having little or no direct thyromimetic effect on the heart. For example, compounds of Formula 1 which raise hepatic GPDH levels and metabolic rate at doses which do not significantly modify cardiac GPDH levels are indicated in the treatment of obesity.

Agonists of Formula 1 will lower total plasma cholesterol, the ratio of LDL-cholesterol to HDL-cholesterol and triglyceride levels at doses which do not significantly modify cardiac GPDH levels are indicated for use as general anti-hyperlipidaemic (antihyperlipoproteinaemic) agents i.e. in the treatment of patients having elevated plasma lipid (cholesterol and triglyceride) levels. In addition, in view of this effect on plasma cholesterol and triglyceride, they are also indicated for use as specific anti-hypercholesterolemic and anti-hypertriglyceridaemic agents.

Patients having elevated plasma lipid levels are considered at risk of developing coronary heart disease or other manifestations of atherosclerosis as a result of their high plasma cholesterol and/or triglyceride concentrations. Further, since LDL-cholesterol is believed to be the lipoprotein which induces atherosclerosis, and HDL-cholesterol believed to transport cholesterol from blood vessel walls to the liver and to prevent the build up of atherosclerotic plaque, anti-hyperlipidemic agents which lower the ratio of LDL-cholesterol to HDL cholesterol are indicated as anti-atherosclerotic agents, herein incorporated by reference U.S. Pat. Nos. 4,826,876 and 5,466,861.

The present invention also provides a method of producing selective thyromimetic activity in certain tissues except the heart which comprises administering to an animal in need thereof an effective amount to produce said activity of a compound of Formula 1 or a pharmaceutically acceptable salt thereof.

The present invention also relates to a method of lowering plasma lipid levels and a method of lowering the ratio of LDL-cholesterol to HDL-cholesterol levels by suitably administering a compound of this invention or a pharmaceutically acceptable sale thereof.

In addition, compounds of Formula 1 may be indicated in thyroid hormone replacement therapy in patients with compromised cardiac function.

In therapeutic use the compounds of the present invention are usually administered in a standard pharmaceutical composition.

The present invention therefore provides in a further aspect pharmaceutical compositions comprising a compound of Formula 1 or a pharmaceutically acceptable salt thereof and a pharmaceutically acceptable carrier. Such compositions include those suitable for oral, parenteral or rectal administration.

Pharmaceutical Compositions

Compounds of Formula 1 and their pharmaceutically acceptable salts which are active when given orally can be formulated as liquids for example syrups, suspensions or emulsions, tablets, capsules and lozenges.

A liquid composition will generally consist of a suspension or solution of the compound or pharmaceutically acceptable salt in a suitable liquid carrier(s), for example ethanol, glycerine, sorbitol, non-aqueous solvent such as polyethylene glycol, oils or water, with a suspending agent, preservative, surfactant, wetting agent, flavoring or coloring agent. Alternatively, a liquid formulation can be prepared from a reconstitutable powder.

For example a powder containing active compound, suspending agent, sucrose and a sweetener can be reconstituted with water to form a suspension; and a syrup can be prepared from a powder containing active ingredient, sucrose and a sweetener.

A composition in the form of a tablet can be prepared using any suitable pharmaceutical carrier(s) routinely used for preparing solid compositions. Examples of such carriers include magnesium stearate, starch, lactose, sucrose, microcrystalline cellulose and binders, for example polyvinylpyrrolidone. The tablet can also be provided with a color film coating, or color included as part of the carrier(s). In addition, active compound can be formulated in a controlled release dosage form as a tablet comprising a hydrophilic or hydrophobic matrix.

A composition in the form of a capsule can be prepared using routine encapsulation procedures, for example by incorporation of active compound and excipients into a hard gelatin capsule. Alternatively, a semi-solid matrix of active compound and high molecular weight polyethylene glycol can be prepared and filled into a hard gelatin capsule; or a solution of active compound in polyethylene glycol or a suspension in edible oil, for example liquid paraffin or fractionated coconut oil can be prepared and filled into a soft gelatin capsule. Compound of Formula 1 and their pharmaceutically acceptable salts which are active when given parenterally can be formulated for intramuscular or intravenous administration.

A typical composition for intramuscular administration will consist of a suspension or solution of active ingredient in an oil, for example arachis oil or sesame oil. A typical composition for intravenous administration will consist of a sterile isotonic aqueous solution containing, for example active ingredient, dextrose, sodium chloride, a co-solvent, for example polyethylene glycol and, optionally, a chelating agent, for example ethylenediamine tetracetic acid and an anti-oxidant, for example, sodium metabisulphite.

Alternatively, the solution can be freeze dried and then reconstituted with a suitable solvent just prior to administration.

Compounds of structure (1) and their pharmaceutically acceptable salts which are active on rectal administration can be formulated as suppositories. A typical suppository formulation will generally consist of active ingredient with a binding and/or lubricating agent such as a gelatin or cocoa butter or other low melting vegetable or synthetic wax or fat.

Compounds of Formula 1 and their pharmaceutically acceptable salts which are active on topical administration can be formulated as transdermal compositions. Such compositions include, for example, a backing, active compound reservoir, a control membrane, liner and contact adhesive.

The typical daily dose of a compound of Formula 1 varies according to individual needs, the condition to be treated and with the route of administration. Suitable doses are in the general range of from 0.001 to 10 mg/kg bodyweight of the recipient per day.

Within this general dosage range, doses can be chosen at which the compounds of Formula 1 lower plasma cholesterol levels and raise metabolic rate with little or no direct effect on the heart. In general, but not exclusively, such doses will be in the range of from 0.5 to 10 mg/kg.

In addition, within the general dose range, doses can be chosen at which the compounds of Formula 1 lower plasma cholesterol levels and have little or no effect on the heart without raising metabolic rate. In general, but not exclusively, such doses will be in the range of from 0.001 to 0.5 mg/kg.

It is to be understood that the 2 sub ranges noted above are not mutually exclusive and that the particular activity encountered at a particular dose will depend on the nature of the compound of Formula 1 used.

Preferably, the compound of Formula 1 is in unit dosage form, for example, a tablet or a capsule so that the patient may self-administer a single dose. In general, unit doses contain in the range of from 0.05–100 mg of a compound of Formula 1. Preferred unit doses contain from 0.05 to 10 mg of a compound of Formula 1.

The active ingredient may be administered from 1 to 6 times a day. Thus daily doses are in general in the range of from 0.05 to 600 mg per day. Preferably, daily doses are in the range of from 0.05 to 100 mg per day. Most preferably from 0.05 to 5 mg per day.

EXAMPLES

Example 1

Synthesis of TR Ligands

Many TR ligands are known in the art, including T4 (thyroxine), T3, T2 and TS-9. See Jorgensen, Thyroid Hormones and Analogs, in 6 *Hormonal Proteins and Peptides, Thyroid Hormones* 107–204 (Choh Hao Li ed., 1978), incorporated by reference herein.

The syntheses of several TR ligands are described below.
Synthesis of TS1, TS2, TS3, TS4, TS5

Figure 11:
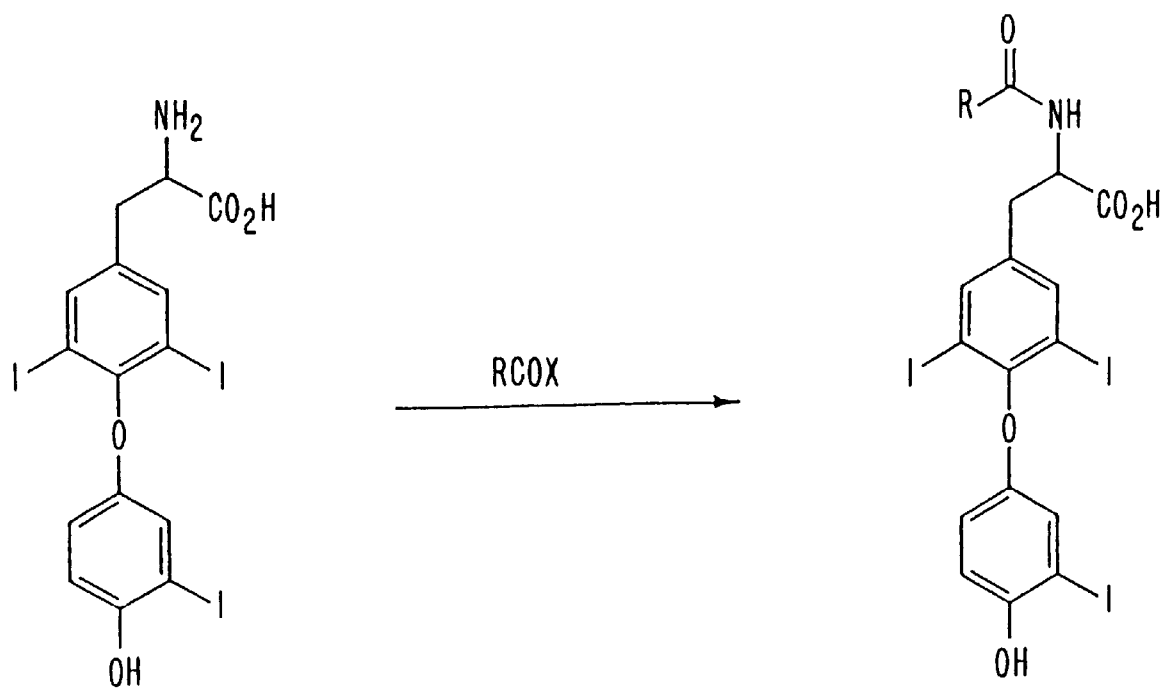
FIG. 11 is the synthetic scheme for preparation of TS1, TS2, TS3, TS4 and TS5.

TS1, TS2, TS3, TS4 and TS5 and analogs thereof can all be prepared by simple acylation of the nitrogen atom of any thyronine analog, including T3 (3,5,3'-triiodo-L-thyronine), T4 (thyroxine) and 3,5-diiodothyronine. TS1 and TS2 are synthesized by reacting T3 with $Ph_2CHCO_2NHS$ (N-hydroxy succinimide-2,2-diphenylacetate) and $C_{16}H_{33}CO_2NHS$, respectively. TS3 is synthesized by reacting T3 with FMOC—Cl (fluorenylmethyloxycarbonylchloride). TS4 is synthesized by reacting T3 with $tBOC_2O$ (tBOC anhydride or di-t-butyldicarbonate). TS5, which differs from TS1-4 by having a —H instead of an —I at the $R^1_3$ position, is synthesized by reacting 3,5-diiodothyronine with $tBOC_2O$. The general reaction scheme for TS1, TS2, TS3, TS4 and TS5 is depicted in FIG. 11. It should be noted that in the reaction scheme, both TS5 and its precursor both have a hydrogen rather than an iodine at the $R^1_3$ position.

Synthesis of TS6 and TS7

Figure 12:
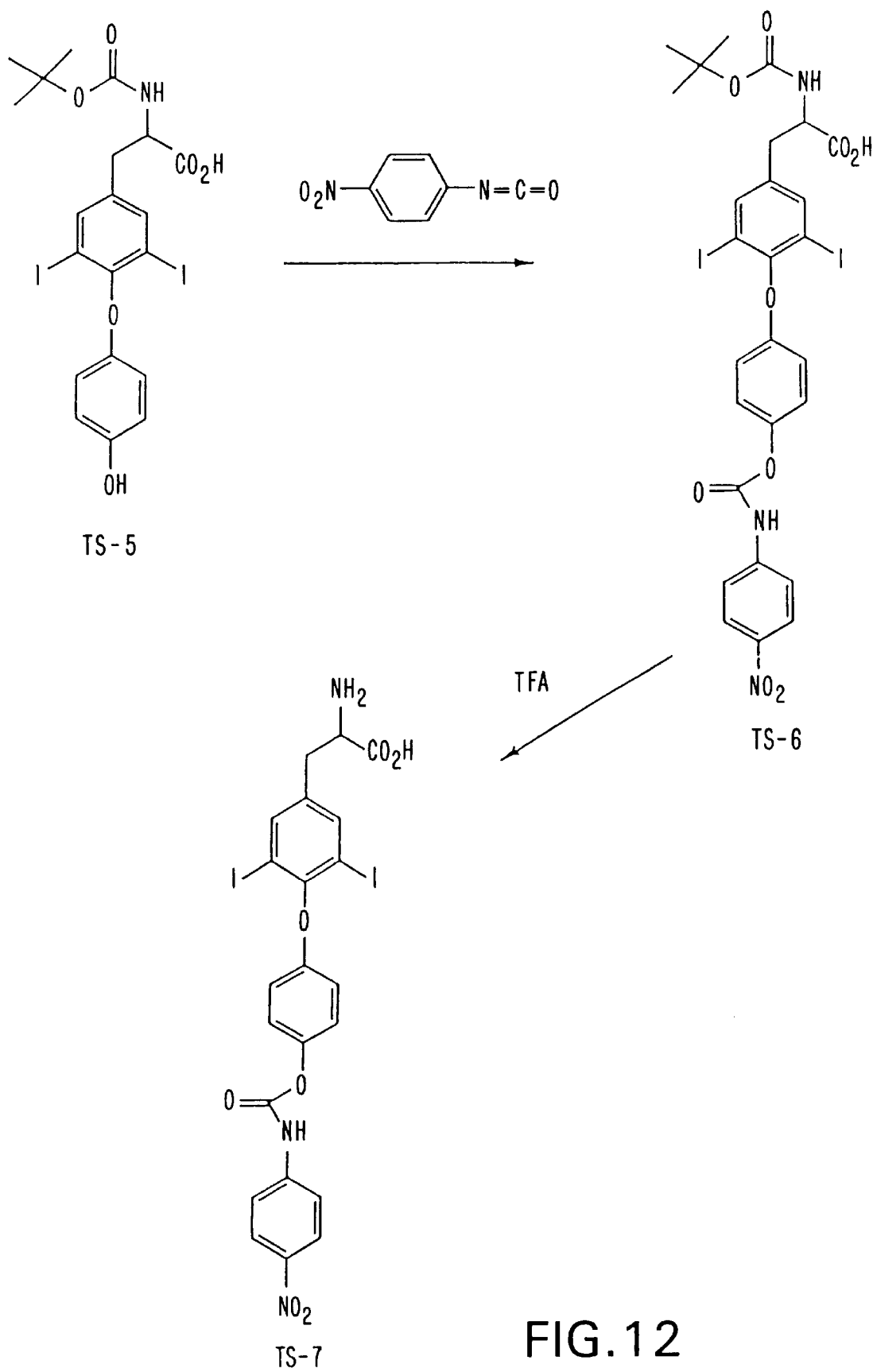
FIG. 12 is the synthetic scheme for preparation of TS6 and TS7.

TS6 is synthesized by reacting TS5 with paranitrophenylisocyanate. TS7 is synthesized by reacting TS6 with TFA (trifluoroacetic acid), which cleaves the tBOC group. These reactions are simple organic synthesis reactions that can be performed by anyone of ordinary skill in the art. The synthetic scheme for TS6 and TS7 is diagrammed in FIG. 12.

Synthesis of TS8

Figure 13:
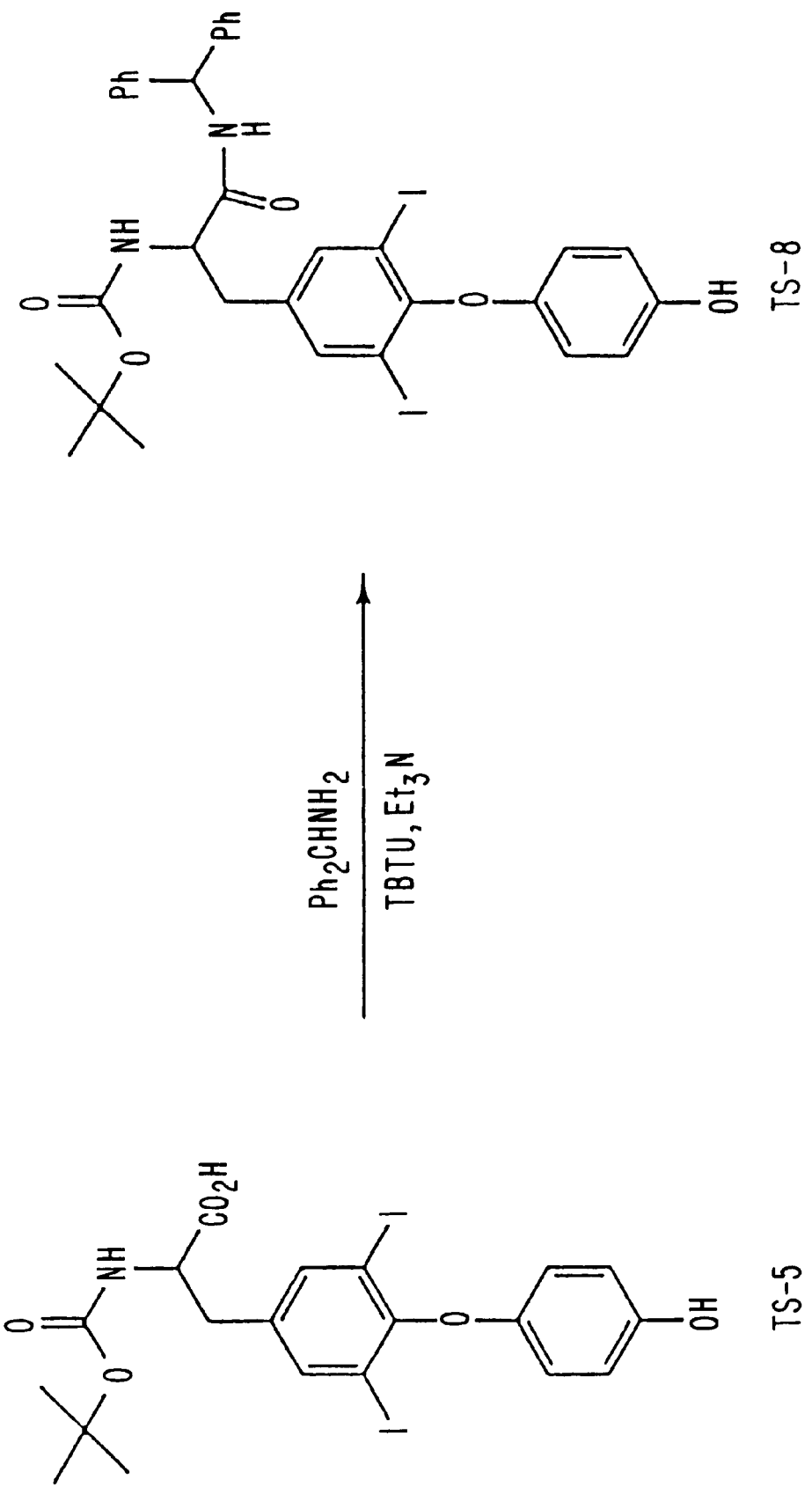
FIG. 13 is the synthetic scheme for preparation of TS8.

TS8 is synthesized by reacting TS5 with $Ph_2CHNH_2$ (diphenylmethylamine) in the presence of triethylamine and any amide forming condensing reagent, such as TBTU (hydroxybenztriazoleuronium tetrafluoroborate) or HBTU (hydroxybenztriazoleuronium hexafluorophosphate). The synthesis scheme for TS8 is depicted in FIG. 13.

Synthesis of Diiodo Isopropylthyronne Derivatives

For designing a class of antagonists, it is important to have a hydrophobic group at the 3' position as well as an extension at the 5' position. Preferred hydrophobic groups at the 3' position include: methyl, benzyl, phenyl, iodo, and heterocyclic structures. The synthesis of a 3,5-diiodo-3'-isopropyl-5'-substituted thyronine is described below. The example provided describes the specific steps for synthesizing the TS10 compound, but this general reaction scheme can be used by one of ordinary skill in the art to synthesize any number of 3,5,-diiodo-3'-isopropyl-5'-substituted thyronine derivatives, which are characterized by having an extension at the 5' position. Additional compounds of this class can be synthesized using known organic synthesis techniques.

Figure 14A:
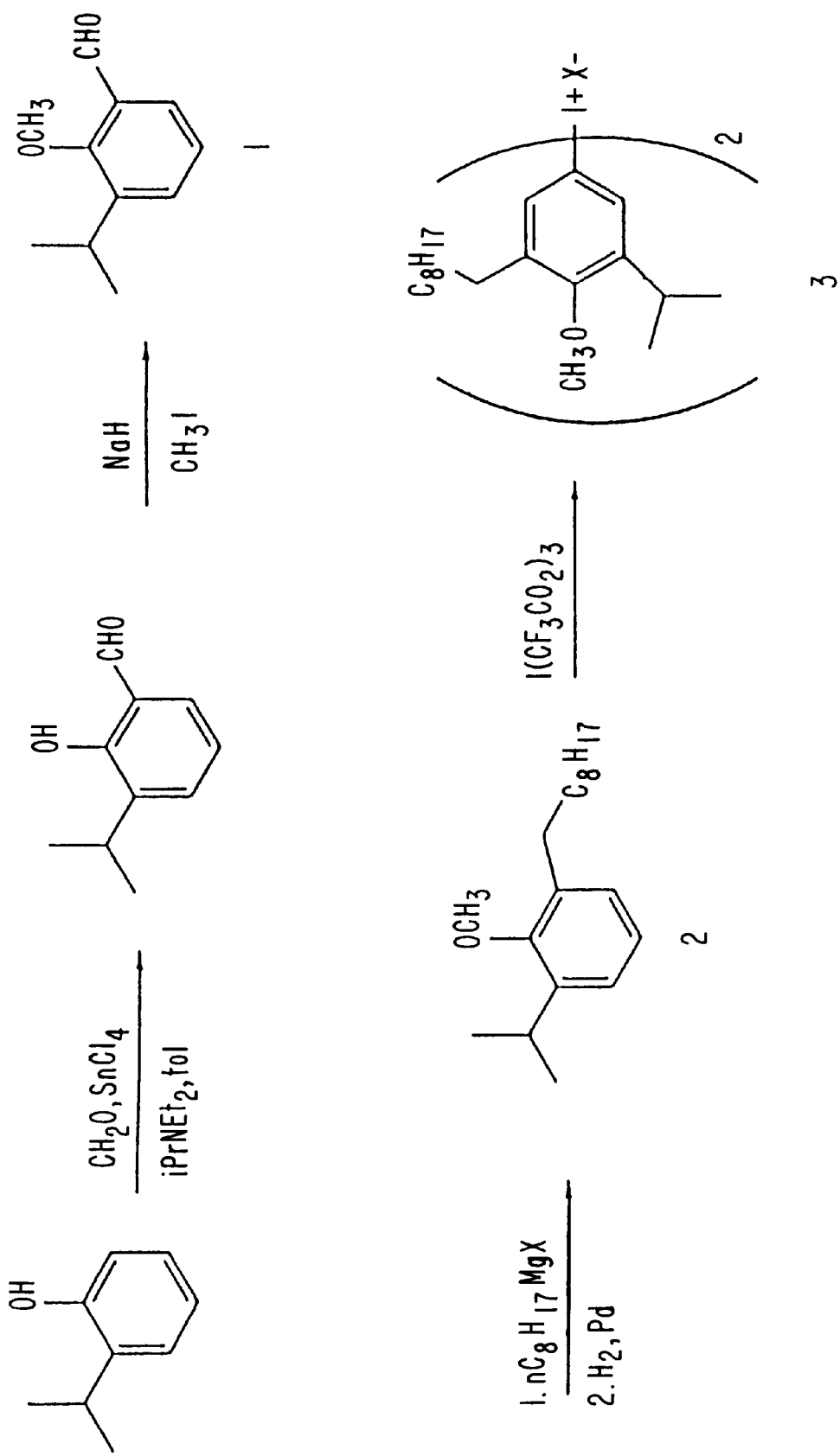
FIGS. 14A–14B is the synthetic scheme for preparation of TS10.
Figure 14B:
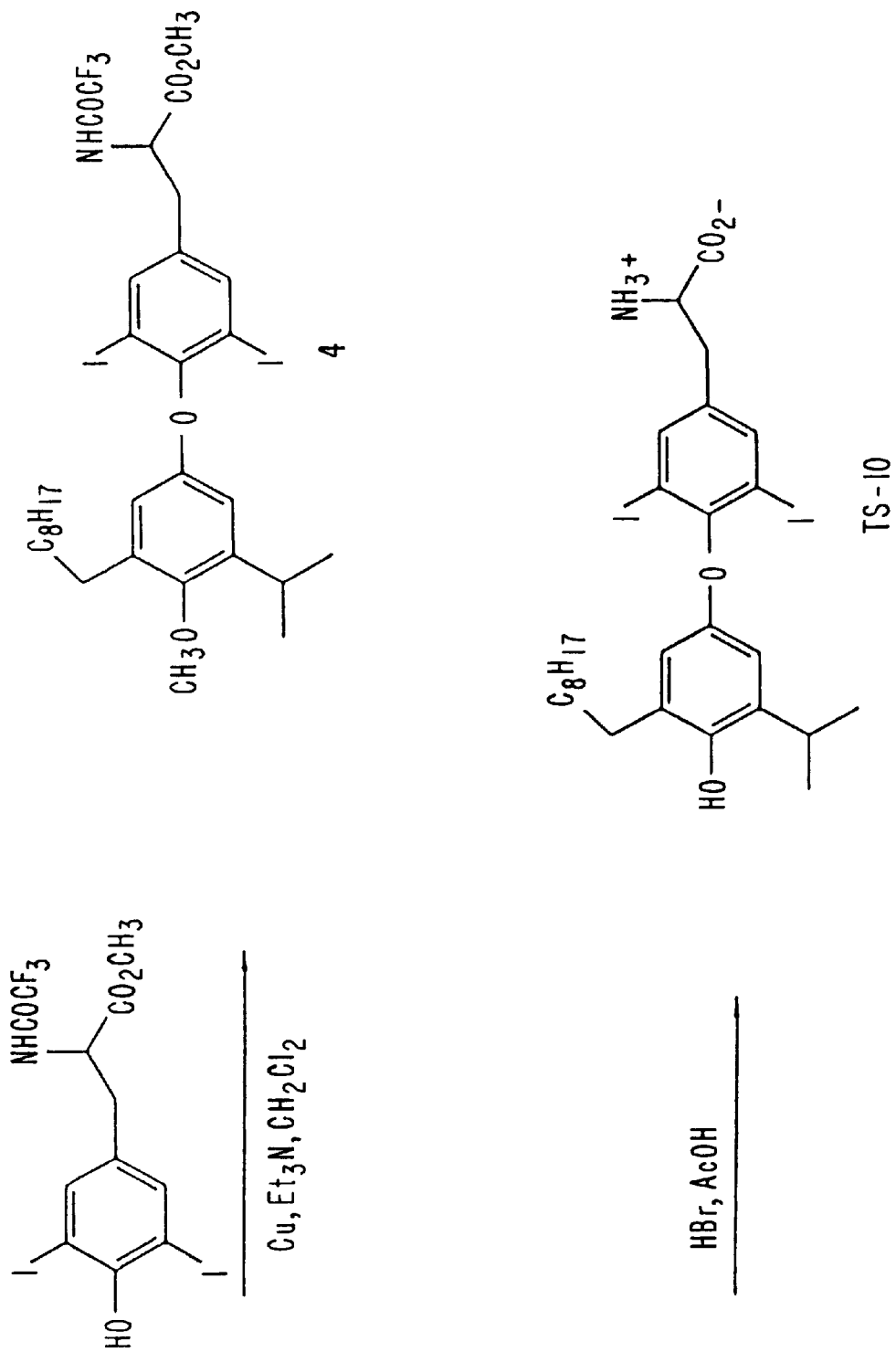

The synthesis of TS10 is described below and is depicted in FIGS. 14A–14B. Numbers used in the reaction scheme for TS10 indicating the reaction product for each step are in parentheses.

2-Formyl-6-isopropylanisole (1): 2-formyl-6-isopropylanisole (10.0 g, 61 mmol), as made by Casiraghi, et al. J C S Perkin I, 1862 (1980) (incorporated by reference), is added dropwise to a suspension of sodium hydride (3.7 g, 153 mmol) in 50 ML THF and 50 mL of DMF in a round bottom flask. The addition generates an exothermic reaction and formation of a gray solid. Methyl iodide (26.0 g, 183 mmol) is then added dropwise and the reaction mixture is stirred at room temperature for 5 hours. The reaction mixture is quenched with 20 mL of water, then poured into 500 mL of water, and is extracted with ether (2×300 mL). The ether layers are combined, washed with water (5×1000 mL), dried over magnesium sulfate and concentrated in vacuo to provide 10.2 g (94%) of the title compound, with the following $^1$H NMR ($CDCl_3$) properties: d 10.30 (s, 1H), 7.63 (d, 1H, J=3 Hz), 7.50 (d, 1H, J=3 Hz), 7.13 (t, 1H, J=3 Hz), 3.81 (s, 3H), 3.31 (heptet, 1H, J=7.5 Hz), 1.19 (d, 6H, J=7.5 Hz).

2-(2-Hydroxynonyl)-6-isopropylanisole (not shown in scheme): Octylmagnesium chloride (8.4 mL, 16.9 mmol, 2.0 M) is added dropwise to a solution of 1 (1.5 g, 8.4 mmol) in 10 mL THF at −78° C. The reaction mixture is stirred for 2 hours with warming to room temperature. The reaction mixture is diluted with 50 ML ether and poured into 50 mL water. The ether layer is washed with brine (1×50 mL), dried over sodium sulfate, and concentrated in vacuo. Flash chromatography (silica gel, 10% ether/hexane→15% ether/hexane) provides 734 mg (30%) of the title compound with the following $^1$H NMR (CDCl$_3$) properties: d 7.33–7.10 (m, 3H), 5.00 (br. s, 1H), 3.81 (s, 3H), 3.33 (heptet, 1H, J=7 Hz) 1.90–1.19 (m, 14H), 0.86 (t, 3H, J=6.5 Hz); HRMS (EI), found: 292.2404; calc'd: 292.2402.

2-nonyl-6-isopropylanisole (2): Compound 2 (663 mg, 2.3 mmol) is dissolved in solution of 5 mL ethanol and 5 mL acetic acid, and a spatula tip of palladium on carbon catalyst is added. The reaction mixture is then charged with hydrogen gas (using a simple balloon and needle) and the mixture is stirred at room temperature overnight. The next day, the reaction mixture is poured into ether (100 mL) and the ether layer is extracted with saturated sodium bicarbonate (3×100 mL). The ether layer is dried over sodium sulfate and concentrated in vacuo to provide 581 mg (91%) of (2) with the following $^1$H NMR (CDCl$_3$) properties: d 7.14–7.00 (m, 3H), 3.75 (s, 3H), 3.36 (heptet, 1H, J=6.8 Hz), 2.63 (t, 2H, J=7.5 Hz), 1.68–1.15 (m, 14H), 0.86 (t, 3H, J=5.5 Hz); HRMS (EI), mass found: 276.2459; calculated: 276.2453.

Thyronine adduct (4): Fuming nitric acid (0.071 mL) is added to 0.184 mL acetic anhydride chilled to −5° C. Iodine (66 mg) is added to this mixture followed by trifluoroacetic acid (0.124 mL). This mixture is stirred for 1 hour with warming to room temperature, at which point all of the iodine is dissolved. The reaction mixture was then concentrated in vacuo to provide an oily semi-solid material. The residue was dissolved in 0.7 mL of acetic anhydride and cooled to −20° C. A solution of anisole (2) (581 mg, 2.1 mmol) in 1.2 mL acetic anhydride and 0.58 mL TFA is added dropwise. The reaction mixture is stirred at −20° for 1 hour, then stirred overnight with warming to room temperature. The reaction mixture is partitioned between water and methylene chloride. The methylene chloride layer is dried over sodium sulfate and concentrated in vacuo to provide the iodonium salt (3) as an oil. This material is not purified or characterized, and is directly introduced into the coupling reaction.

N-Trifluoroacetyl-3,5-diiodotyrosine methyl ester (552 mg, 1.0 mmol) prepared according to the procedure of N. Lewis and P. Wallbank, *Synthesis* 1103 (1987) (incorporated by reference) and all of the crude iodonium salt (3) from above is dissolved in 5 mL of anhydrous methanol. Diazabicyclo[5.4.0]undecane (DBU) (183 mg, 1.2 mmol) and a spatula tip of copper-bronze are added and the resulting mixture is stirred at room temperature overnight. The next day, the reaction mixture is filtered, and the filtrate is concentrated in vacuo. The crude residue is purified by flash chromatography (silica gel, 10% ethyl acetate/hexane) to provide 30 mg (4%) of the protected thyronine adduct (4).

Deprotected thyronine (TS10): The protected thyronine 4 (30 mg, 0.04 mmol) is dissolved in a mixture of 2.25 mL acetic acid and 2.25 mL 49% hydrobromic acid. The reaction mixture is heated to reflux for 5 hours. The reaction mixture is cooled to room temperature, and the solvents are removed in vacuo. Water is added to triturate the oily residue into a gray solid. This solid material is filtered, washed with water, and dried over P$_2$O$_5$ in vacuo to provide 24 mg (81%) of the title compound, TS10, with the following $^1$H NMR (CDCl$_3$) properties: d 7.57 (s, 1H), 6.86 (s, 1H), 6.45 (s, 1H), 6.34 (s, 1H), 4.8 (m, 1H), 3.86 (s, 3H), 3.71 (s, 3H), 3.33–3.05 (m, 3H), 2.58–2.47 (m, 2H), 1.62–0.76 (m, 23H); MS (LSIMS): M$^+$=817.0.

As mentioned above, this reaction scheme can be modified by one of ordinary skill in the art to synthesize a class of compounds characterized by 3,5-diiodo-3'isopropylthyronine derivatives, wherein (1) the 3' isopropyl group can be replaced with a hydrophobic group, including methyl, benzyl, phenyl, iodo, and heterocyclic structures, and (2) a wide variety of chemical structures can be incorporated at the 5' position, including alkyl groups, planar aryl, heterocyclic groups, or polar and/or charged groups.

The aldehyde (1) in the above reaction scheme is a versatile synthetic intermediate which allows for the attachment of a variety of chemical moieties to the 5' position of the final thyronine derivative. In addition, a variety of chemical reactions can be used to attach the chemical moieties. These reactions are well known in the art and include organometallic additions to the aldehyde (including Grignard reagents, organolithiums, etc.), reductive amination reactions of the aldehyde with a primary or secondary amine, and Wittig olefination reactions with a phosphorous ylid or stabilized phosphonate anion. Other possibilities include reduction of the aldehyde to a benzyl alcohol allowing for etherification reactions at the 5' position. As mentioned above, these methods allow for a wide variety of chemical structures to be incorporated at the 5' position of the final thyronine derivative, including alkyl groups, planar aryl, heterocyclic groups or polar and/or charged groups. Synthesis of 3,5-dibromo-4-(3',5'-diisopropyl-4'-hydroxyphenoxy) Benzoic Acid (Compound 11).

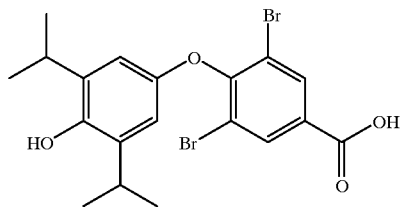

(a) A mixture of 2,6-diisopropyl phenol (20 g, 0.11 mol), potassium carbonate (62 g, 0.45 mol), acetone (160 ml) and methyl iodide (28 ml, 0.45 mole) is refluxed for three days. The reaction mixture is filtered through celite, evaporated, dissolved in ether, washed twice with 1M sodium hydroxide, dried over magnesium sulphate and concentrated to afford 15.1 g (0.08 mol, 70%) of 2,6-diisopropyl anisole as a slightly yellow oil.

(b) Fuming nitric acid (12.4 ml, 265 mmol) is added dropwise to 31.4 ml of acetic anhydride which is cooled in a dry ice/carbon tetrachloride bath. Iodine 11.3 g, 44.4 mmol) is added in one portion followed by dropwise addition of trifluoroacetic acid (20.5 ml, 266 mmole). The reaction mixture is stirred at room temperature until all the iodine is dissolved. Nitrogen oxides are removed by flushing nitrogen into the vessel. The reaction mixture is concentrated, the residue is dissolved in 126 ml of acetic anhydride and is cooled in a dry ice/carbon tetrachloride bath. To the stirred solution 2,6-diisopropylanisole (51 g, 266 mmol) in 150 ml of acetic anhydride and 22.6 ml of trifluoroacetic acid is added dropwise. The reaction mixture is left to stand at room temperature over night and then is concentrated. The residue is taken up in 150 ml of methanol and treated with 150 ml of 10% aqueous sodium bisulfite solution and 1 liter of 2M sodium borotetrafluoride solution. After the precipitate aggregates, petroleum ether is added and the supernatant is decanted. The precipitate is triturated with petroleum ether, filtered, washed with petroleum ether and dried at room temperature in vacuo. This affords 34 g (57 mmol, 65%) of bis(3,5-diisopropyl-4-methoxyphenyl)iodonium tetrafluoroborate as a white solid.

(c) To a stirred solution of 3,5-dibromo-4-hydroxybenzoic acid (12 g, 40.5 mmol) in 250 ml of methanol, thionyl chloride (3 ml) is added dropwise. The reaction mixture is refluxed for five days, water is added and the precipitated product is filtered off. The residue is dissolved in ethyl acetate. From the aqueous phase, methanol is removed by concentration. The aqueous phase is then saturated with sodium chloride, and extracted with ethyl acetate. The combined organic phases are dried over magnesium sulphate, filtered and concentrated.

TABLE 1 and FIG. 15 depict the structures of several TR ligands.

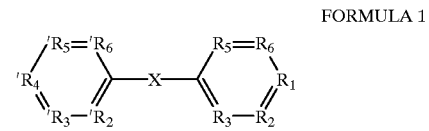

FORMULA 1

TABLE 1

| Cmpd | $R_3$ | $R_4$ | $R_5$ | $R^1_3$ | $R^1_4$ | $R^1_5$ | $R_1$ |
|---|---|---|---|---|---|---|---|
| $T_3$ | —I | —O— | —I | —I | —OH | —H | —CH$_2$CH(NH$_2$)CO$_2$H |
| $T_4$ | —I | —O— | —I | —I | —OH | —I | —CH$_2$CH(NH$_2$)CO$_2$H |
| TS1 | —I | —O— | —I | —I | —OH | —H | —CH$_2$CH[NHCOCHØ$_2$]CO$_2$H |
| TS2 | —I | —O— | —I | —I | —OH | —H | —CH$_2$CH[NHCO(CH$_2$)$_{15}$CH$_3$]CO$_2$H |
| TS3 | —I | —O— | —I | —I | —OH | —H | —CH$_2$CH[NH—FMOC]CO$_2$H |
| TS4 | —I | —O— | —I | —I | —OH | —H | —CH$_2$CH[NH—tBOC]CO$_2$H |
| TS5 | —I | —O— | —I | —H | —OH | —H | —CH$_2$CH[NH—tBOC]CO$_2$H |
| TS6 | —I | —O— | —I | —H | —OC(O)NH=Ø$_p$NO$_2$ | —H | —CH$_2$CH[NH—tBOC]CO$_2$H |
| TS7 | —I | —O— | —I | —I | —OC(O)NH=NHØNO$_2$ | —H | —CH$_2$CH(NH$_2$)CO$_2$H |
| TS8 | —I | —O— | —I | —H | —NH—CHØØ | —H | —CH$_2$CH[NH—tBOC]CO$_2$H |
| TS9 | —I | —O— | —I | —IsoPr | —OH | —H | —CH$_2$CH(NH$_2$)CO$_2$H |
| TS10 | —I | —O— | —I | —IsoPr | —OH | —(CH)$_8$—CH$_3$ | —CH$_2$CH(NH$_2$)CO$_2$H |

*Prior Art Compound From SKF
—Ø: phenyl
—ØpNO$_2$: para nitro phenyl

This gives 12.5 g (40.5 mmol, 100%) of 3,5-dibromo-4-hydroxymethyl benzoate as a white crystalline solid.

(d) The products obtained in steps b and c are reacted with each other according to the following protocol. To bis(3,5-diisopropyl-4-methoxyphenyl)iodonium tetrafluoroborate (2.86 g, 4.8 mmole) and copper bronze (0.42 g, 6.4 mmole) in 7 ml. of dichloromethane at 0° C. is added dropwise a solution of 3,5-dibromo4-hydroxymethyl benzoate (1.0 g, 3.2 mmole) and triethylamine (0.36 g, 3.5 mmole) in 5 ml of dichloromethane. The reaction mixture is stirred in the dark for eight days and then is filtered through celite. The filtrate is concentrated and the residue is purified by column chromatography (silica gel, 97:3 petroleum ether/ethyl acetate) to give 0.62 g (1.2 mmole, 39%) of 3,5-dibromo-4-(3',5'-diisopropyl-4'-methoxyphenoxy) methyl benzoate as a solid.

(e) The product from step d (0.2 g, 0.4 mmole) is dissolved in 2 ml. dichloromethane, is put under nitrogen and is cooled at −40° C. To the stirred solution is added 1M BBr$_3$ (1.2 ml, 1.2 mmole) dropwise. The reaction mixture is allowed to reach room temperature and then is left over night. It is cooled to 0° C. and then hydrolyzed with water. Dichloromethane is removed by concentration and the aqueous phase is extracted with ethyl acetate. The organic phase is washed with 1M hydrochloric acid and brine. Then it is dried over magnesium sulphate, filtered and concentrated. The residue is chromatographed (silica, 96:3.6:0.4 dichloromethane/methanol/acetic acid) producing 93 mg (0.2 mmole, 51%) of 3,5-dibromo-4-(3',5'-diisopropyl-4'-hydroxyphenoxy)benzoic acid as a white solid. $^1$H nmr (CDCl$_3$) δ 1.23 (d, 12H, methyl), 3.11 (m, 2H, CH), 6.50 (s, 2H, 2,6-H) 8.33 (s, 2H, 2',6'-H).

Example 2

Receptor Bindind Assays of TR Ligands

To test the ability of synthesized TR ligands to bind to a thyroid receptor (TR), the binding affinity of a TR ligand for TR is assayed using TR's prepared from rat liver nuclei and $125_I$ T$_3$ as described in J. D. Apriletti, J. B. Baxter, and T. N. Lavin, J. Biol. Chem., 263: 9409–9417 (1988). The apparent Kd's are calculated using the method described by Apriletti (1995) and Apriletti (1988). The apparent Kd's are presented in TABLE 2. The apparent Kd's (App.Kd) are determined in the presence of the sample to be assayed, 1 nM [$^{125}$I]T$_3$, and 50 μg/ml core histones, in buffer E (400 mM KCl, 200 mM potassium phosphate, pH 8.0, 0.5 mM EDTA, 1 mM MgCl$_2$, 10% glycerol, 1 mM DTT) in a volume of 0.21 ml. After incubation overnight at 4° C., 0.2 ml of the incubation mixture is loaded onto a Quick-Sep Sephadex G-25 column (2.7×0.9 cm, 1.7 ml bed volume) equilibrated with buffer E. The excluded peak of protein-bound [$^{125}$I]T$_3$ is eluted with 1 ml of buffer E, collected in a test tube, and counted. Specific T$_3$ binding is calculated by subtracting nonspecific binding from total binding.

TABLE 2

| Compound | App.Kd(nM) | Coactivation Assay RIP-140 | EC$_{50}$(M) |
|---|---|---|---|
| T$_3$ | 0.06 | + | 10$^{-10}$ |
| T$_4$ | 2 | + | 10$^{-9}$ |
| TS1 | 4 | + | 10$^{-7}$ |
| TS2 | 1400 | nd | nd |
| TS3 | 4 | + | 10$^{-8}$ |
| TS4 | 8 | + | nd |
| TS5 | 220 | + | 10$^{-6}$ |
| TS6 | >10000 | nd | nd |

TABLE 2-continued

| Compound | App.Kd(nM) | Coactivation Assay RIP-140 | $EC_{50}(M)$ |
|---|---|---|---|
| TS7 | 260 | + | $10^{-7}$ |
| TS8 | 6000 | nd | nd |
| TS9 | 1 | + | $10^{-10}$ |
| TS10 | 400 | + | $10^{-6}$ |

+: RIP-140 Binding
−: RIP-140 Binding
nd: Not Determined

Example 3
Increased Nuclear Protein Coactivation by TR Ligands

To test the ability of TR ligands to activate the binding of TR to the nuclear activation protein RIP-140 (a nuclear protein that can bind to nuclear receptors, such as the estrogen receptor), a TR ligand is liganded to TR and then incubated with RIP-140 as described in V. Cavailles, et al., *EMBO J.*, 14(15):3741–3751 (1995), which is incorporated by reference herein. In this assay, $35_S$-RIP-140 protein binds to liganded TR but not unliganded TR. Many TR $35_S$ ligands can activate RIP-140 binding as shown in TABLE 2.

Example 4
TR Ligand Binding and TR Activation in Cultured Cells

To test TR activation of transcription in a cellular environment, TR ligands are assayed for their ability to activate a reporter gene, chloramphenicol transferase ("CAT"), which has a TR DNA binding sequence operatively linked to it. Either GC or L937 cells (available from the ATCC) can be used, respectively). In such assays, a TR ligand crosses the cell membrane, binds to the TR, and activates the TR, which in turn activates gene transcription of the CAT by binding the TR DNA binding region upstream of the CAT gene. The effective concentration for half maximal gene activation ($EC_{50}$) is determined by assaying CAT gene activation at various concentrations as described herein and in the literature. The results of CAT gene activation experiments are shown in TABLE 2.

CAT Gene Activation Assays

Functional response to thyroid hormone (3,5,3'-triiodo-L-thyronine, $T_3$) and TR ligands is assessed either in a rat pituitary cell line, GC cells, that contain endogenous thyroid hormone receptors (TRs) or U937 cells that contain exogenous TRs expressed as known in the art. GC cells are grown in 10-cm dishes in RPMI 1640 with 10% newborn bovine serum, 2 mM glutamine, 50 units/ml penicillin and 50 μg/ml streptomycin. For transfections, cells are trypsinized, resuspended in buffer (PBS, 0.1% glucose) and mixed with a TREtkCAT plasmid (10 mg) or phage in 0.5 ml buffer (15±5 million cells) and electroporated using a Bio-Rad gene pulser at 0.33 kvolts and 960 mF. The TREtkCAT plasmid contains two copies of a $T_3$ response element (AGGTCAcaggAGGTCA) cloned in the Hind III site of the pUC19 polylinker immediately upstream of a minimal (−32/+45) thymidine kinase promoter linked to CAT (tkCAT) coding sequences. After electroporation, cells are pooled in growth medium (RPMI with 10% charcoal-treated, hormone stripped, newborn bovine serum), plated in 6-well dishes and treated with either ethanol or hormone. CAT activity is determined 24 hours later as described D. C. Leitman, R. C. J. Ribeiro, E. R. Mackow, J. D. Baxter, B. L. West, *J. Biol. Chem.* 266, 9343 (1991), which is incorporated by reference herein.

Effect of TS-10 on the Ranscriptional Regulation of the DR4-ALP Reporter Gene in the Presence or Absence of T3.

Characteristics of the TRAF cells: TRAFa1 are CHO K1 cells stably transformed with an expression vector encoding the human thyroid hormone receptor α 1 and a DR4,ALP reporter vector; TRAFb1 are CHO K1 cells stably transformed with an expression vector encoding the human thyroid hormone receptor β1 and a DR4-ALP reporter vector.

Interpretation of the Effect of Compound TS-10 on the Transcriptional Regulation of the DR4-ALP Reporter Gene in the Presence or Absence of T3.

TRAFa1 reporter cells: TS-10 alone (open circles) induces a partial activation of the expression of the ALP reporter protein amounting to approximately 27% of the maximal effect by the natural thyroid hormone T3. In the presence of T3 (filled circles), TS-10 has a weak antagonistic effect. The EC50 concentration for the agonistic effect of TS-10 and the EC50 concentration for its T3 antagonistic effect, respectively, is indicated in FIG. 18.

Figure 18:
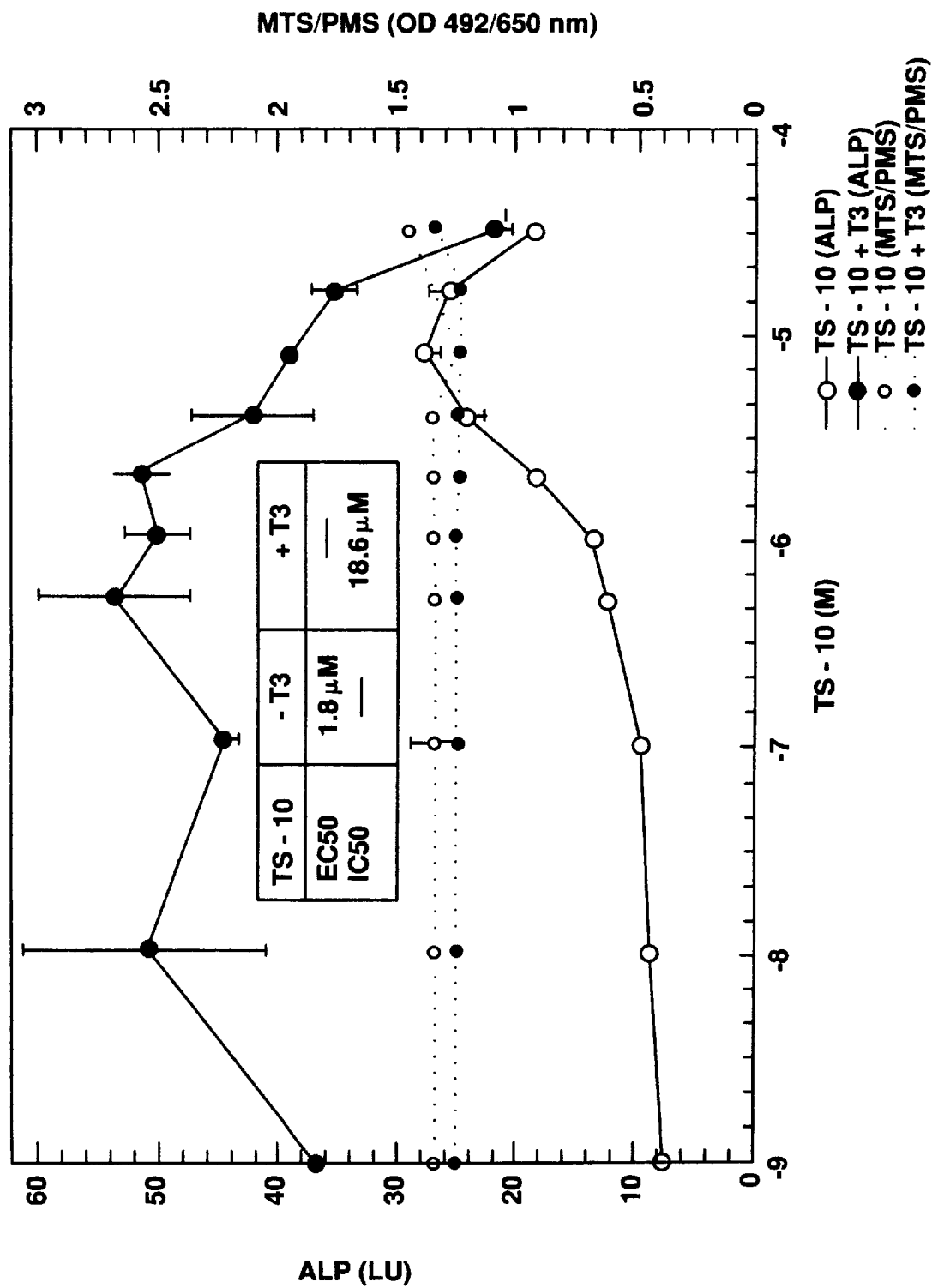
FIG. 18 is a chart showing the effect of TS-10 on the transcriptional regulation of the DR4-ALP reporter gene in the presence or absence of T3 as assayed in TRAFα1 reporter cells.

In FIG. 18, open and filled circles with dotted lines show the dose-dependent effect of TS-10/T3 on the toxicity marker (MTS/PMS), reduction of tetrazolium salt in the mitochondria, displayed on the right y-axis as optical density. There is no obvious toxic effect of TS-10 on the MTS-PMS marker but there is a clear effect on the morphology of the cells, as can be seen under the light microscope, at the highest concentration of TS-10 (32 mM) both in the absence and presence of T3, respectively (not shown in the figure).

Figure 19:
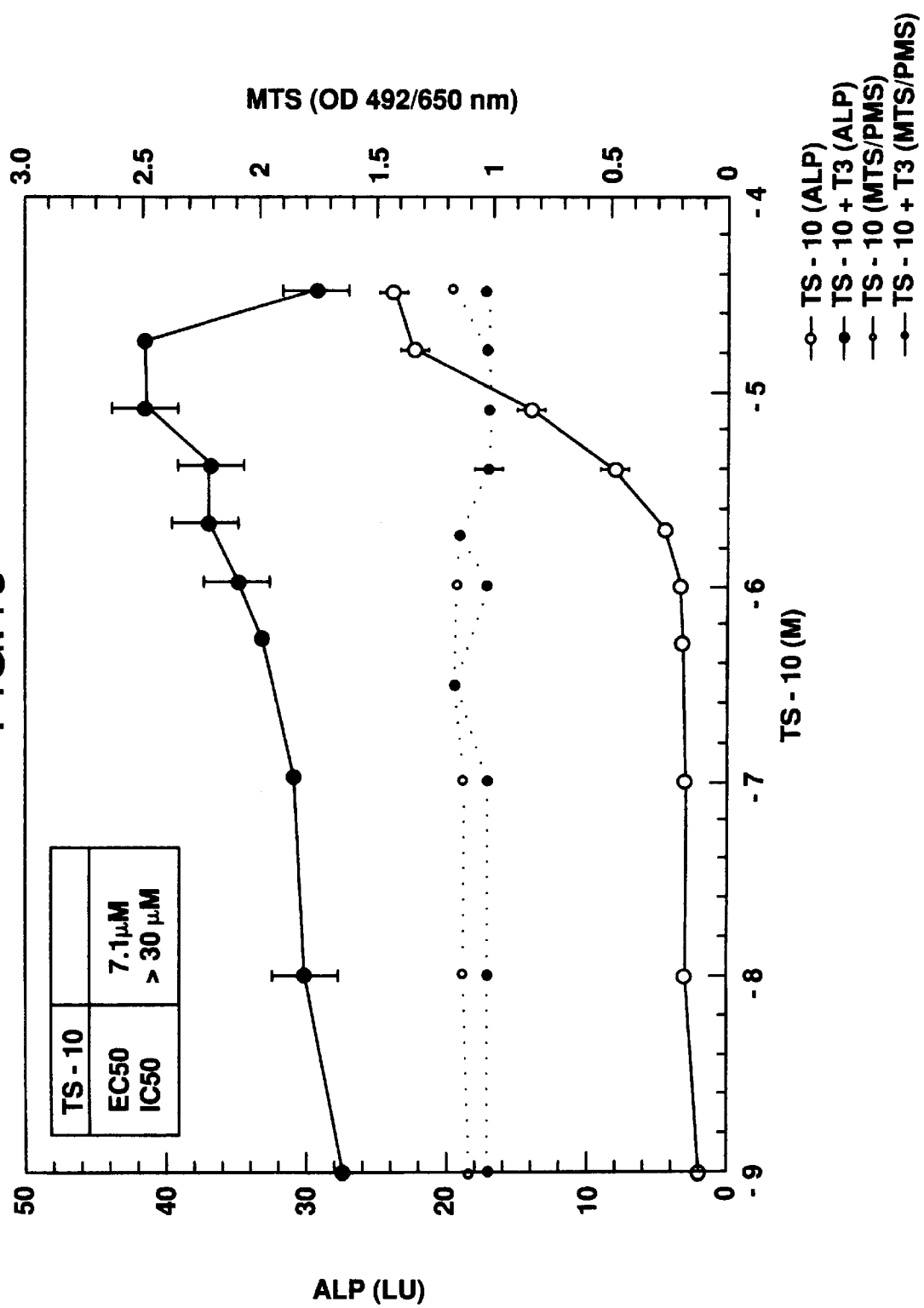
FIG. 19 is a chart showing the effect of TS-10 on the transcriptional regulation of the DR4-ALP reporter gene in the presence or absence of T3 as assayed in TRAFβ1 reporter cells.

TRAFb1 reporter cells: TS-10 alone (open circles) induces a partial activation of the expression of the ALP reporter protein amounting to approximately 35% of the maximal effect by T3. The EC50 concentration for the agonistic effect of TS-10 is indicated in FIG. 19. In the presence of T3 (filled circles), TS-10 shows, if anything, a slight potentiation of the T3 effect on the expression of the ALP reporter protein. The T3 inhibitory effect of TS-10 at its highest concentration used (32 mM) is a toxic effect rather than T3 antagonism.

In FIG. 19, open and filled circles with dotted lines show the dose-dependent effect of TS-10/T3 on the toxicity marker (MTS/PMS), reduction of tetrazolium salt in the mitochondria, displayed on the right y-axis as optical density. There is no obvious toxic effect of TS-10 on the MTS-PMS marker but a clear effect on the morphology of the cells can be observed, under the light microscope, at the highest concentration of TS-10 (32 mM) both in the absence and presence of T3, respectively (not shown in the figure).

Figure 20:
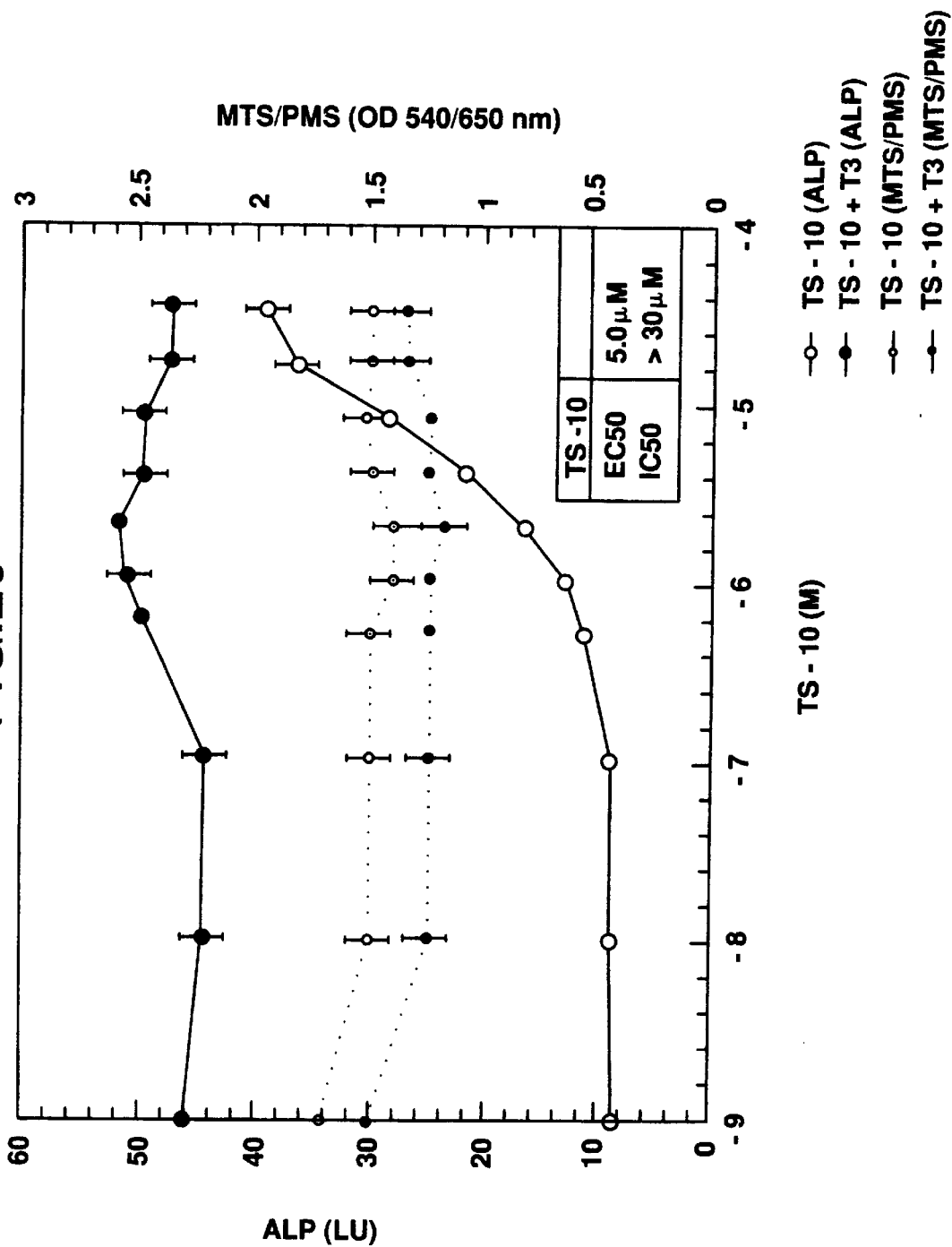
FIG. 20 is a chart showing the effect of TS-10 on the transcriptional regulation of the DR4-ALP reporter gene in the presence or absence of T3 as assayed in HepG2, a liver reporter cell line.

HepG2 (HAF18) reporter cells: TS-10 alone (open circles) induces a partial activation of the expression of the ALP reporter protein amounting to slightly more than 50% of the maximal effect by T3. The EC50 concentration for the agonistic effect of TS-10 is indicated in FIG. 20. In the presence of T3 (filled circles), TS-10 shows no effect i.e. no T3 antagonism nor potentiation/additive effect to T3. Open and filled circles with dotted lines show the dose-dependent effect of TS-10/T3 on the toxicity marker (MTS/PMS), reduction of tetrazolium salt in the mitochondria, displayed on the right y-axis as optical density. There is no obvious toxic effect of TS-10 on the MTS/PMS marker or on the morphology of the cells, as can be observed using a light microscope, at any concentration of TS-10/T3 used.

Figure 16:
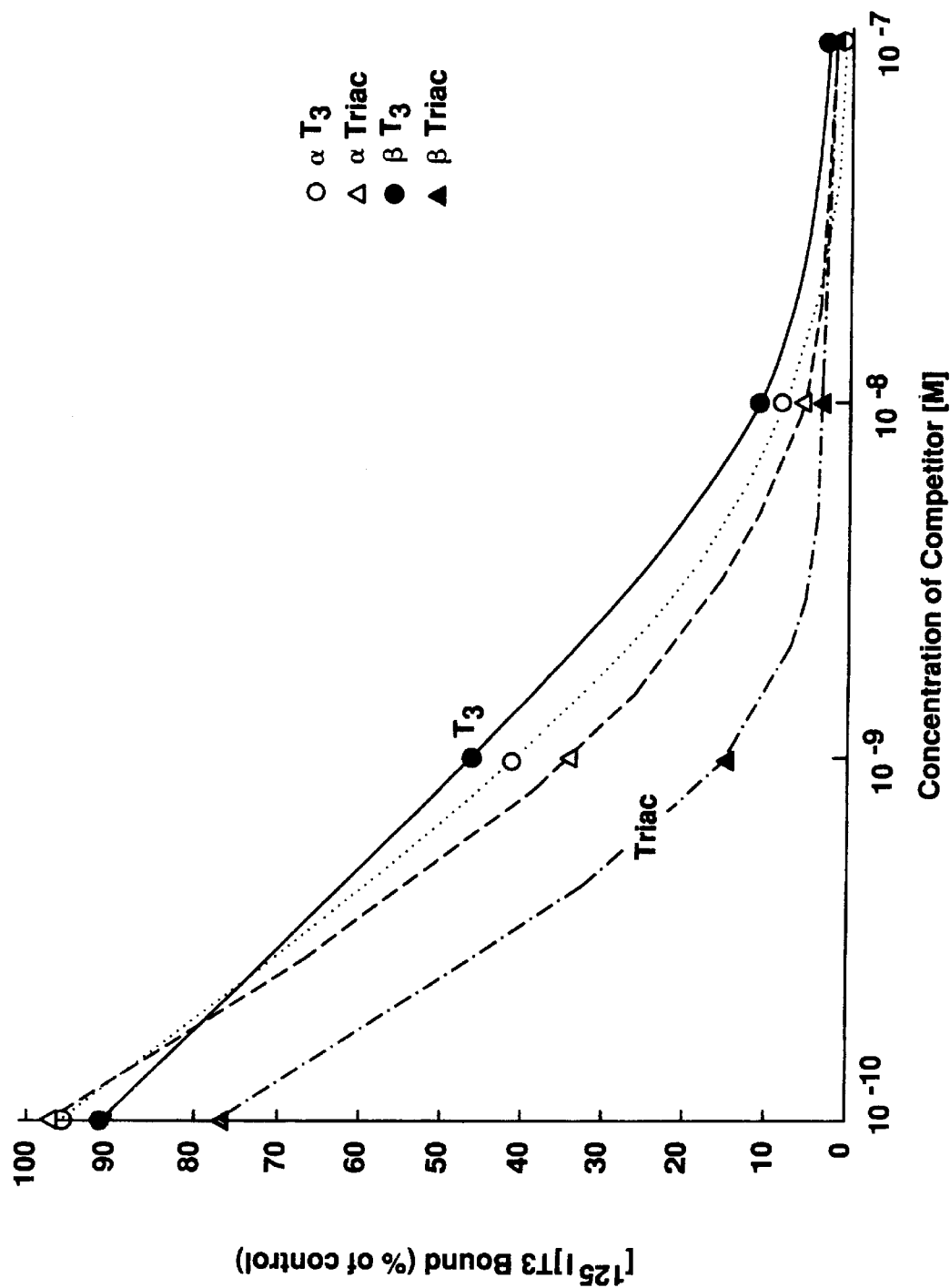
FIG. 16 is a graph illustrating competition assays in which $T_3$ and triac compete with labeled $T_3$ for binding to human TR-α or human TR-β.

Example 5
Comparisons of Human TR-α and Human TR-β
Competition for [$^{125}$I]$T_3$ binding to TR LBD by $T_3$ and Triac The drug, triac, is a thyroid hormone agonist. Triac is 3,5,3'-triiodothyroacetic acid and is described in Jorgensen, Thyroid Hormones and Analogs in 6 *Hormonal Proteins and Peptides, Thyroid Hormones* at 150–151 (1978). Another compound that can be used in place of triac is 3,5-diiodo- 3'-isopropylthyroacetic acid. Competition assays are performed to compare the displacement of [$^{125}$I]T$_3$ from binding with human TR-α LBD or human TR-β LBD by unlabeled T$_3$ or triac. The results of such assays are depicted in FIG. 16.

Standard binding reactions are prepared containing 1 nM [$^{125}$I]T$_3$, 30 fmol of human TR-α (empty symbols) or β (solid symbols), and various concentrations of competing unlabeled T$_3$ (circles) or triac (triangles). Assays are performed in duplicate.

Scatchard Analysis of [$^{125}$I]T$_3$ Binding to TR

Figure 17A:
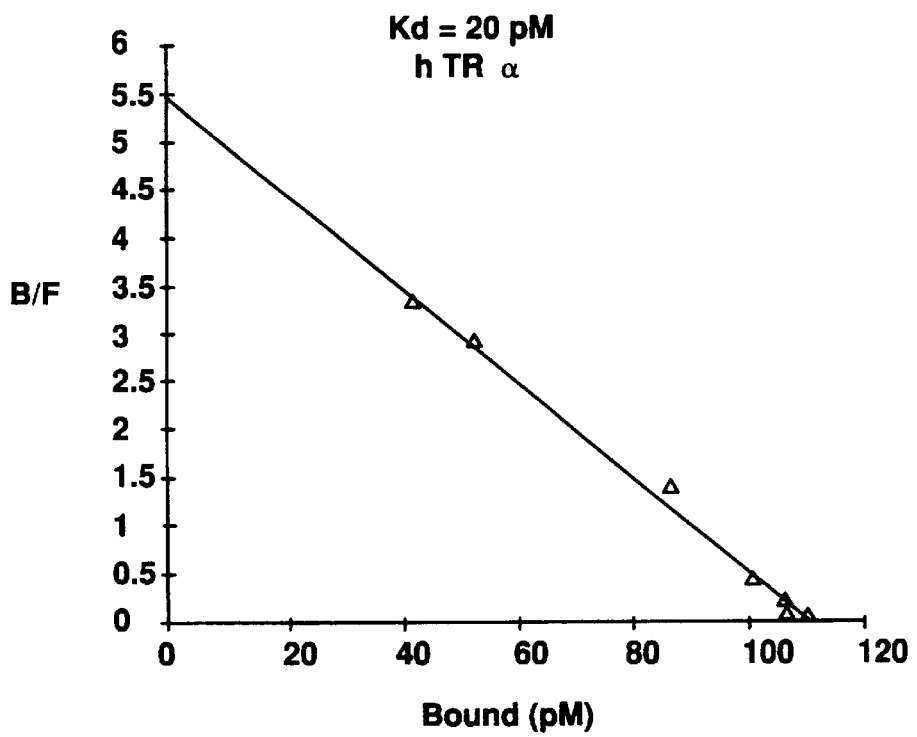
FIGS. 17A–17B depicts a Scatchard analysis of labelled $T_3$ binding to TR-α and TR-β.
Figure 17B:
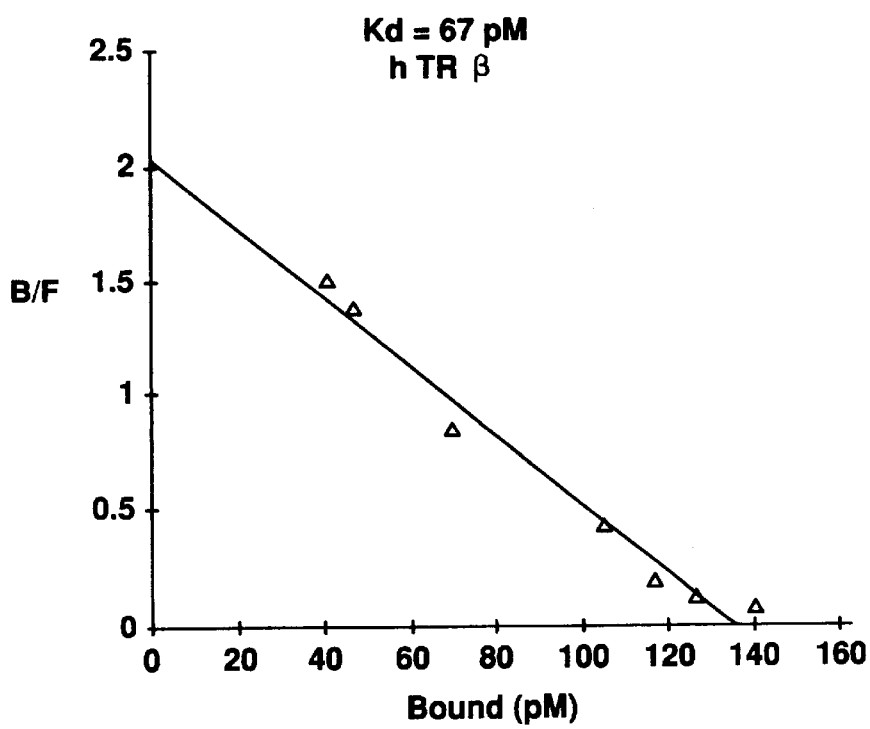

Human TR-α (left panel) or human TR-β (right panel) is assayed for T$_3$ binding in the presence of increasing concentrations of [$^{125}$I]T$_3$. The apparent equilibrium dissociation constant (20 pM for α and 67 pM for β) is calculated by linear regression analysis and is depicted in FIGS. 17A–17B.

3,5-DIBROMO-4-(3',5'-DIISOPROPYL-4'-HYDROXYPHENOXY) BENZOIC ACID IS A TR-A SELECTIVE SYNTHETIC LIGAND.

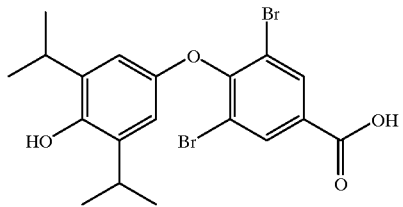

3,5-dibromo-4-(3',5'-diisopropyl-4'-hydroxyphenoxy) benzoic acid (Compound 11), the structure of which is drawn above, is assayed for binding to the two different isoforms of the TR, TRα and TRβ. Compound 11 exhibits an IC50 of 1.6 μM for binding to TRα and an IC50 of 0.91 μM for binding to TRβ. Assays for determining selective binding to the TRα or TRβ LBD can include reporter assays, as described herein. See also Hollenberg, et al., J. Biol. Chem., 270(24)14274–14280 (1995).

Example 6
Preparation and Purification of A TR-A LBD

Rat TR-α LBD, residues Met122-Val410 (residues 122 to 410 of SEQ ID NO:1), is purified from E. coli ("LBD-122/410"). The expression vector encoding the rat TR-α LBD is freshly transfected into E. coli strain BL21(DE3) and grown at 22° C. in a 50-liter fermenter using 2× LB medium. At an A$_{600}$ of 2.5–3, IPTG is added to 0.5 mM and growth is continued for 3 h before harvesting. The bacterial pellet is quickly frozen in liquid nitrogen and stored at −70° C. until processed. Extraction and purification steps are carried out at 4° C. The bacteria are thawed in extraction buffer (20 MM Hepes, pH 8.-, 1 mM EDTA, 0.1% MTG, 0.1 mM PMSF, and 10% glycerol) at a ratio of 10 ml buffer/g bacteria. Bacteria are lysed by incubation for 15 min. with 0.2 mg/ml lysozyme and sonicated at maximum power while simultaneously homogenized with a Brinkmann homogenizer (Model PT 10/35 with generator PTA 35/2) until the solution loses its viscosity. After centrifugation for 10 min at 10,000 g, the supernatant is adjusted to 0.4 M KCl, treated with 0.6% PEI to precipitate fragmented DNA, and centrifuged for 10 min at 10,000 g. The rat TR-α LBD in the supernatant is then precipitated with 50% ammonium sulfate and centrifuged for 10 min at 10,000 g. The precipitate is resuspended with buffer B (20 mM Hepes, pH 8.0, 1 mM EDTA, 1 mM DTT, 0.1 mM PMSF, 0.01% Lubrol, and 10% glycerol) to a final conductivity of 9 mS/cm (approx. 0.7 M ammonium sulfate) and centrifuged 1 h at 100,000g. The supernatant is frozen in liquid nitrogen and stored at −70° C.

The crude extract is thawed, bound with a tracer amount of [$^{125}$I]T$_3$, and loaded directly onto a phenyl-Toyopearl hydrophobic interaction column (2.6×18 cm, 95 ml bed volume) at 1.5 ml/min. The column is eluted with a 2-h gradient from 0.7 ammonium sulfate, no glycerol to no salt, 20% glycerol in buffer C (20 mM Hepes, pH 8.0, 0.5 mM EDTA, 1 mM DTT, 0.2 mM PMSF). The rat TR-α LBD prebound to tracer [$^{125}$I]T$_3$ (less than 0.005% of total rat TR-α LBD) is detected using a flow-through gamma emission detector, whereas unliganded rat TR-α LBD is assayed by postcolumn [$^{125}$I]T$_3$ binding assays (described herein).

The phenyl-Toyopearl unliganded rat TR-α LBD peak fractions are pooled, diluted with buffer B to a conductivity of 0.5 mS/cm (equivalent to approx. 20 mM ammonium sulfate), loaded onto a TSK-DEAE anion-exchange column (2×15 cm, 47 ml bed volume) at 4 ml/min, and eluted with a 60-min gradient from 50 to 200 mM NaCl in buffer B.

The unliganded rat TR-α LBD peak fractions from TSK-DEAE are pooled, diluted twofold with buffer B, loaded at 0.75 ml/min on a TSK-heparin HPLC column (0.8×7.5 cm, 3 ml bed volume), and eluted with a 50 to 400 mM NaCl gradient in buffer B.

The pool of unliganded rat TR-α LBD peak fractions from the TSK-heparin column is adjusted to 0.7 M ammonium sulfate, loaded at 0.75 ml/min on a TSK-phenyl HPLC column (0.8×7.5 cm, 3 ml bed volume), and eluted with a 60-min gradient from 0.7 M ammonium sulfate without glycerol to no salt with 20% glycerol in buffer C. The fractions containing unliganded rat TR-α LBD are pooled and incubated with a five fold excess of hormone for 1 h, the salt concentration is adjusted to 0.7 M ammonium sulfate, and the sample is reloaded and chromatographed on the same column as described above.

Example 7
Crystalization of Liganded TR-α LBD

Material from a single LBD-122/410 preparation is divided into batches, and quantitatively bound with one of the following ligands: Dimit, T$_3$, or triac IpBr$_2$ (3,5dibromo-3'isopropylthyronine) for the final purification step.

To maintain full saturation of rat TR-α LBD with a ligand, and to prepare the complex for crystallization, the ligand-bound rat TR-α LBD is concentrated and desalted in an Amicon Centricon-10 microconcentrator (McGrath et al, Biotechniques, 7:246–247 (1989), incorporated by reference herein), using 10 mM Hepes (pH 7.0), 3.0 mM DTT, and 1.0 nM to 10 nM ligand.

Factorial crystallization screening trials (Jancarik & Kim, J. Appl. Crystallogr. 24:409–411 (1991) incorporated by reference herein) are carried out for rat TR-α LBD bound to selected ligands using hanging-drop vapor diffusion at 17° C. (with 1 μl protein solution, 1 μl precipitant solution and a 0.5 ml reservoir using silanized coverslip: (McPherson, Preparation and Analysis of Protein Crystals (1982), incorporated by reference herein). Rat TR-α LBD is not stable at 4° C. and is stored at −80° C., where it maintains its avidity for hormone and its crystallizability for approximately two to three months. These procedures are carried out as described in McGrath, M. E. et al. J. Mol. Biol. 237:236–239 (1994) (incorporated by reference).) Crystals are obtained in condition 21 of the screening trials (Jancarik & Kim 1991) and conditions are then optimized. Wedge-shaped crystals are reproducibly obtained with hanging-drop vapor fusion at 22° C. with 15% 2-methyl-2,4-pentanediol (MPD), 0.2 M ammonium acetate and 0.1 M sodium cacodylate (pH 6.7), 3 mM DTT, with 2 µl protein solution, 1 µl precipitant solution and a 0.6 ml reservoir using silanized coverslip, and with 8.7 mg/ml (Dimit), 5.5 mg/ml (IpBr$_2$), 5 mg/ml (triac), or 2.3 mg/ml (T$_3$) over a period of three days. Under these conditions, diffraction quality crystals (dimension 0.5×0.2× 0.0075 mm$^3$) can be grown at ambient temperature (22° C.). The best crystals have a limiting dimension of approximately 100 µm and are obtained at a protein concentration between 2.3 and 8.7 mg/ml in the presence of 3 mM DTT. The crystals are of the monoclinic space group C2, with one monomer in the asymmetric unit.

Example 8
Crystalization of Human TR-β LBD Complexed with T$_3$ or Triac

Human TR-β LBD complexed with T$_3$ and human TR-β LBD complexed with triac are purified according to the same procedures described above for the rat TR-α LBD, with the following modifications.

The expression of human TR-β LBD differs from the rat TR-α LBD in that the human TR-β LBD residues extend from the amino acid at position 716 through the amino acid at position 1022 (residues 202 to 461 of SEQ ID NO:3), according to the amino acid numbering scheme for the various nuclear receptor LBDs depicted in FIGS. 3A–3B. FIGS. 3A–3R illustrates a numbering scheme applicable to all of the nuclear receptors listed as well as to any additional homologous nuclear receptors. The vertical lines on FIGS. 3A–3R at position 725 and at position 1025 delineate the preferred minimum amino acid sequence necessary to obtain adequate binding of ligand. The amino acid sequence from position 716 to position 1022 according to the numbering scheme of FIGS. 3A–3R corresponds to the amino acid positions 202 to 461 according to the conventional numbering of the amino acid sequence of human TR-β which is publicly available. Also, the human TR-β LBD is expressed with a histidine tag, as described in Crowe et al., Methods in Molecular Biology 31:371–387 (1994), incorporated by reference herein.

The purification of human TR-β LBD is the same as that described above for the rat TR-α LBD with the following exceptions. First, before the purification step using the hydrophobic interaction column, a step is added in which the expressed human TR-β LBD is purified using a nickel NTA column (commercially available from Qiagen, Chatsworth, Calif.) according to manufacturer's instructions, and eluted with 200 mM imidazole. The second difference is that in the purification of the human TR-β LBD, the purification step using a heparin column is omitted.

The crystallization of human TR-β LBD bound to T$_3$ or triac is as follows. Crystals are obtained in condition 7 of the factorial screen using hanging drops as before at ambient temperature (22° C.) using the factorial crystallization screening trials of Jancarik & Kim (1991) and using the commercially available product from Hampton Research, Riverside). The following are optimum conditions: hexagonal bipyrimidal crystals are grown at 4° C. for 2–3 days from hanging drops containing 1.0–1.2 M sodium acetate (pH unadjusted) and 0.1 M sodium cacodylate (pH 7.4), 3 mM DTT, with either a 1 µl protein solution, 1 µl precipitant solution or 2 µl protein solution, 1 µl precipitant solution and a 0.6 ml reservoir using silanized coverslip, at a protein concentration of 7–10 mg/ml. The best crystals have a limiting dimension of 200 µm.

The crystal system for human TR-β LBD bound to T$_3$ or triac is trigonal with the space group p3$_1$21. The unit cell dimensions are cell length a=cell length b=68.448 angstroms, cell length c=130.559 angstroms. The angles are α=90°, β=90°, gamma=120°.

Example 9
Determination of Liganded TR-α LBD Crystal Structure

Data from each of three cocrystals (Rat TR-α LBD with Dimit, T3 and IpBr$_2$) is measured on a Mar area detector at Stanford Synchrotron Radiation Laboratory beamline 7-1 (λ=1.08 angstroms) using 1.2° oscillations.

Data from the T$_3$ cocrystal is measured with the b* axis approximately parallel with the spindle. The crystals are flash frozen at −178° C. in a nitrogen gas stream with the MPD mother liquor serving as the cryosolvent. An orientation matrix for each crystal is determined using REFIX (Kabsch, W., J. Appl. Crystallogr. 26:795–800 (1993) incorporated by reference). Reflections are integrated with DENZO (commercially available from Molecular Structure Corp., The Woodlands, Texas), and are scaled with SCALEPACK (as described in Otwinowski, Z, Proceedings of the CCP4 Study Weekend: "Data Collection and Processing," 56–62 (SERC Daresbury Laboratory, Warrington, UK 1993) incorporated by reference).

For the T$_3$ data set, Bijvoet pairs are kept separate, and are locally scaled using MADSYS (W. Hendrickson (Columbia University) and W. Weis (Stanford University)).

Cocrystals prepared from the three isosteric ligands are isomorphous. MIR analysis is performed using programs from the CCP4 suite (Collaborative Computational Project, N.R. Acta Crystallogr. D50:760–763 (1994), incorporated by reference herein). Difference Pattersons is calculated for both T$_3$ and IpBr$_2$, taking the Dimit cocrystal as the parent. The positions of the three iodine atoms in the T$_3$ difference Patterson are unambiguously determined from the Harker section of the density map as peaks of 11σ above background. The positions for the two bromine atoms in the IpBr$_2$ cocrystals, are located independently, as peaks 8σ above the noise level. Phases for the LBD-122/410 are calculated from the solution to the IpBr$_2$ difference Patterson, and are used to confirm the location of the unique third iodine of the T$_3$ cocrystal. Halogen positions are refined with MLPHARE, including the anomalous contributions from the iodine atoms (Otwinowski, Z, Proceedings of the CCPR Study Weekend 80–86 (SERC Daresbury Laboratory, Warrington, UK 1991)). The MIRAS phases are improved through solvent flattening/histogram matching using DM (Cowtan, K., Joint CCP4 and ESF-EACBM Newsletter on Protein Crystallography 31: 34–38 (1994), incorporated by reference herein).

A model of the LBD-122/410 with Dimit bound is built with the program O from the solvent flattened MIRAS 2.5 angstrom electron density map (Jones et al., Acta Crystallogr. A 47:110–119 (1991), incorporated by reference herein). The initial model, without ligand, (Rcryst=40.1%), is refined using least-squares protocols with XPLOR. The Dimit ligand is built into unambiguous Fo-Fc difference density during the following round. Subsequent refinement employs both least-squares and simulated annealing protocols with XPLOR (Brunger et al., Science 235:458–460 (1987), incorporated by reference herein). Individual atomic B-factors are refined isotropically. As defined in PROCHECK, all residues are in allowed main-chain torsion angle regions as described in Laskowski et al., J. Appl. Crystallogr. 26:283–291 (1993), incorporated by reference herein. The current model is missing 34 residues (Met$_{122}$-Gln$_{156}$) at the N-terminus, and 5 residues (Glu$_{406}$-Val$_{410}$) at the C-terminus.

In addition, the following residues are not modeled beyond Cβ due to poor density: 184, 186, 190, 198, 206, 209, 240, 301, 330, 337, 340, 343, 359, and 395. The average B-value for protein atoms is 34.5 Å². The final model consists of the LBD-122/410, residues $Arg_{157}$-$Ser_{183}$, $Trp_{185}$-$Gly_{197}$, $Ser_{199}$-$Asp_{206}$ and $Asp_{208}$-$Phe_{405}$; three cacodylate-modified cysteines: $Cys_{334}$, $Cys_{380}$ and $Cys_{392}$; and 73 solvent molecules modeled as water (2003 atoms).

\*$R_{sym}=100\times\Sigma_{hkl}\Sigma_i|I_i-\bar{I}_i|/\Sigma_{hkl}\Sigma_i I_i$ †$R_{der}=100\times\Sigma_{hkl}|F_{PH}-F_H|/\Sigma_{hkl}|F_P|$ The occupancy for the two bromine sites is set to 35 electrons. The occupancies of the iodine sites are relative to this value.

§Phasing power=(FH)/(∈), where (FH) is the mean calculated heavy atom structure factor amplitude and (∈) is the mean estimated lack of closure.

||Rcullis=(∈)/(iso), where (∈) is the mean estimated lack of closure and (iso) is the isomorphous difference.

¶Rcryst=$100\times\Sigma_{hkl}|F_o-Fc|/\Sigma_{hkl}|F_o|$ where $F_o$ and $F_c$ are the observed and calculated structure factor amplitudes (for data F/σ>2). The Rfree was calculated using 3% of the data, chosen randomly, and omitted from the refinement.

§ Correlation coefficient=$\Sigma_{hkl}(|F_o|-|\bar{I}_o|)\times(|F_c|-|F_c|)/\Sigma_{hkl}(|F_o|-|F_o|)^2\times\Sigma_{hkl}(|F_c|-|F_c|)^2$

Example 10

Phasing of the rTRα LBD Complex with Triac

Due to the possible non-isomorphism of the rTRα LBD complex with Triac, a molecular replacement solution is determined using AMORE (Navaza, J., Acta Crystallographica Section A-Fundamentals of Crystallography 50:157–63 (1994) from a starting model consisting of rTRα LBD complex with $T_3$, but with the ligand, all water molecules, and the following residues omitted: Asn 179, Arg228, Arg262, Arg266, and Ser 277. Strong peaks are obtained in both the rotation and translation searches, with no significant (>0.5 times the top peak) false solutions observed (Table 3). Strong positive density present in both the anomalous and conventional difference Fourier maps confirm the solution. Maps are calculated using sigma-A weighted coefficients output by REFMAC (Murshudov, et al. "Application of Maximum Likelihood Refinements," in the Refinement of Protein Structures, Proceedings of Daresbury Study Weekend (1996)) after 15 cycles of maximum likelihood refinement. Triac, the omitted residues, and water molecules 503, 504, 534 (following the numbering convention for the TR complex with T3) are built into the resulting difference density using O (Jones et. al.); the conformations of these residues are further confirmed in a simulated-annealing omit map (Brunger et. al.). The complete model is then refined using positional least-squares, simulated annealing, and restrained, grouped B factor refinement in XPLOR to an Rcryst of 23.6% and an Rfree of 24.1%

Example 11

Connecting QSAR with Structure in the Thyroid Hormone Receptor

The conclusions of classic thyroid hormone receptor quantitative structure-activity relationships may be summarized as follows:

1) the $R_4$'-hydroxyl group functions as a hydrogen bond donor;
2) the amino-propionic acid interacts electrostatically through the carboxylate anion with a positively charged residue from the receptor;
3) the preferences of $R_3/R_5$ substituent are I>Br>Me>>H;
4) the preferences of the $R_3$'-substituent are Ipr>I>Br>Me>>H.

The structure of the thyroid hormone receptor ligand binding domain complexed with the agonists 3,5,3'-triiodothyronine ($T_3$), 3,5-dibromo-3'-isopropylthyronine ($IpBr_2$), 3,5-dimethyl-3'-isopropylthyronine (Dimit), and 3,5,3'-triiodothyroacetic acid (Triac), as provided herein, permits:

1) the identification of receptor determinants of binding at the level of the hydrogen bond;
2) the association of these determinants with the predictions of classic thyroid hormone receptor QSAR; and
3) prediction as to which determinants of binding are rigid, and which are flexible, for both the ligand and the receptor.

This classification for the agonists of the type ($R_1$=aminopropionic, acetic acid; $R_3,R_5$=I,Br,Me; $R_3$'=Ipr,I) is given below (for the representative ligand $T_3$);

F=Fiducial (always satisfied)
A=Adjustable

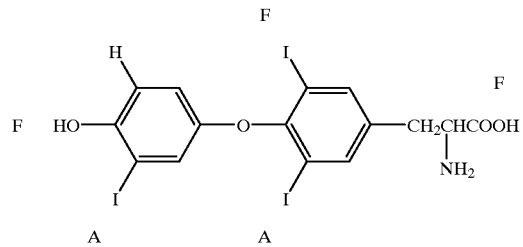

Figure 21:
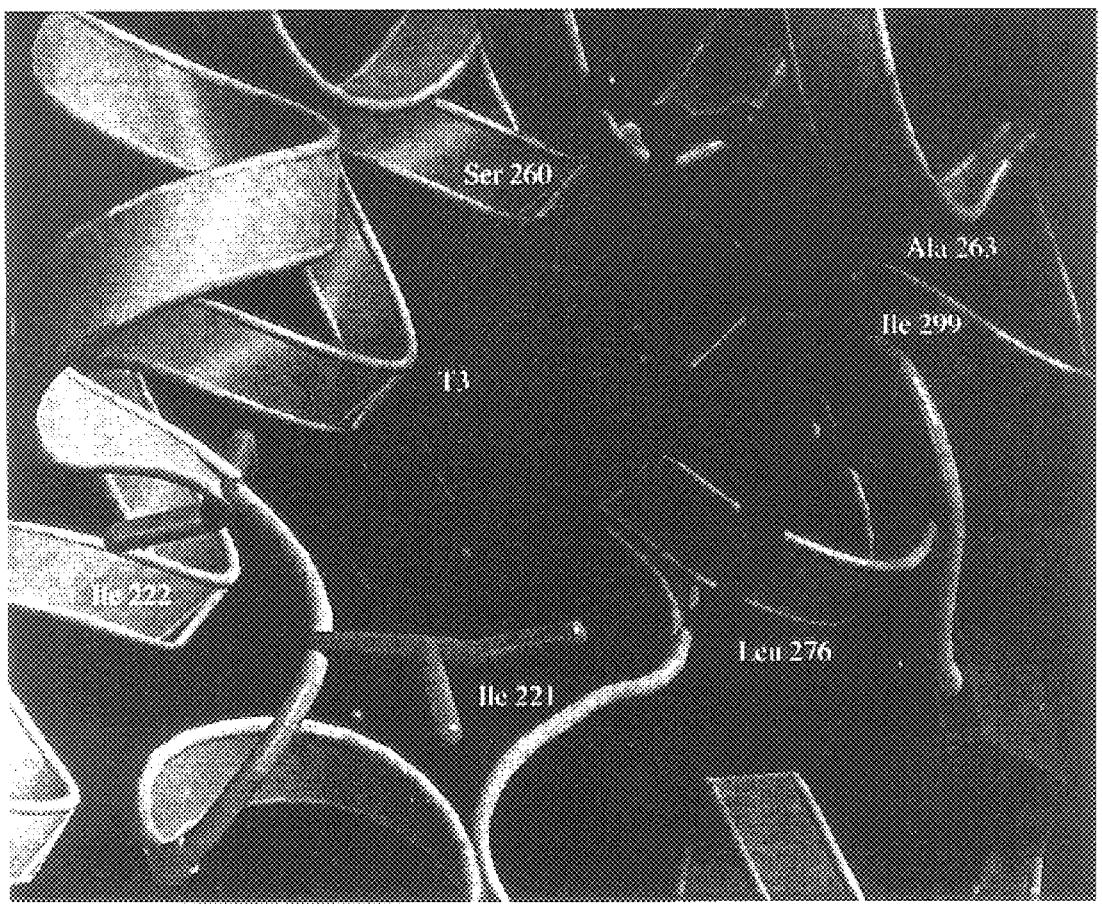
FIG. 21 is a partial ribbon drawing of TR-α LBD with T3 in the ligand binding cavity. Selected interacting amino acids are labelled, including Ile221, Ile222 and Ser260, Ala263, Ile299 and Leu 276.
Figure 22:
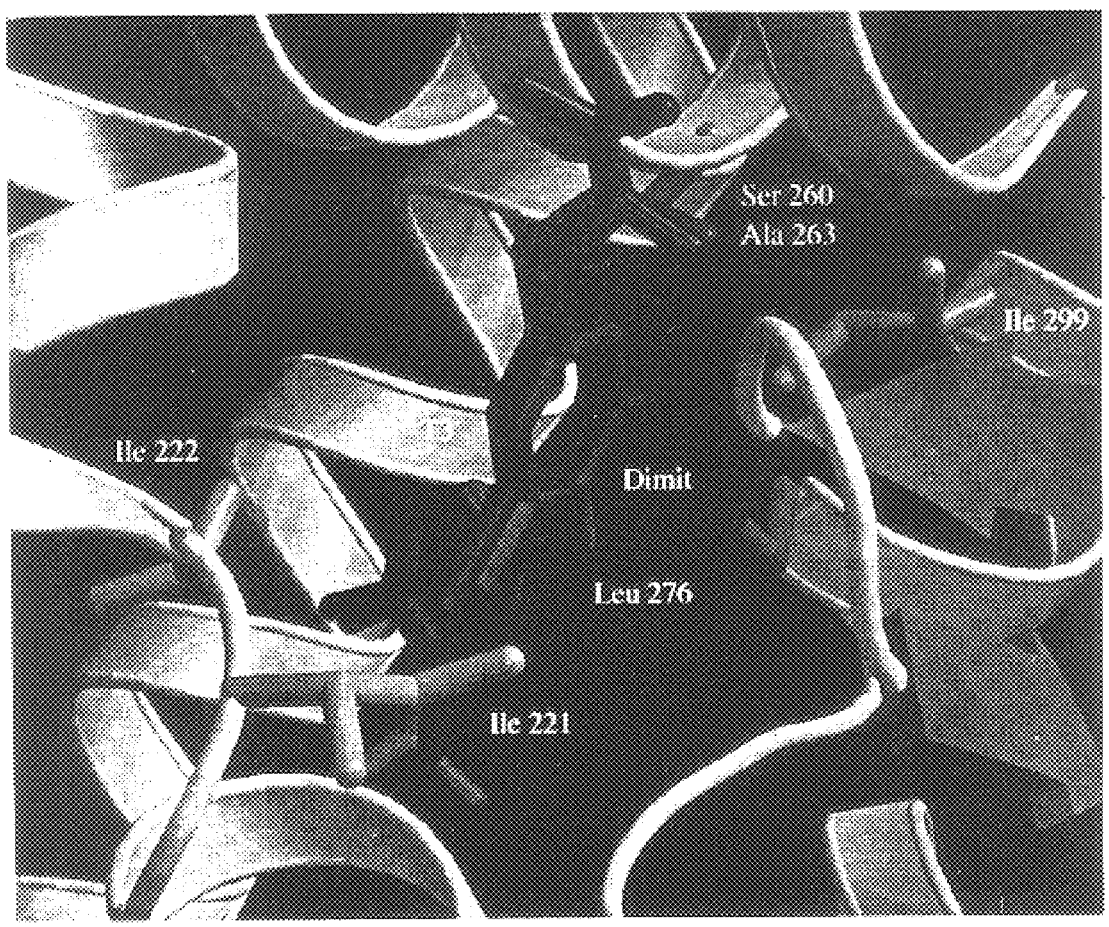
FIG. 22 is a partial ribbon drawing of TR-α LBD with T3 and Dimit superimposed in the ligand binding cavity. Interactions with Ile221, Ile222, Ala260, Ile 299 and Leu276 are labelled.
Figure 23:
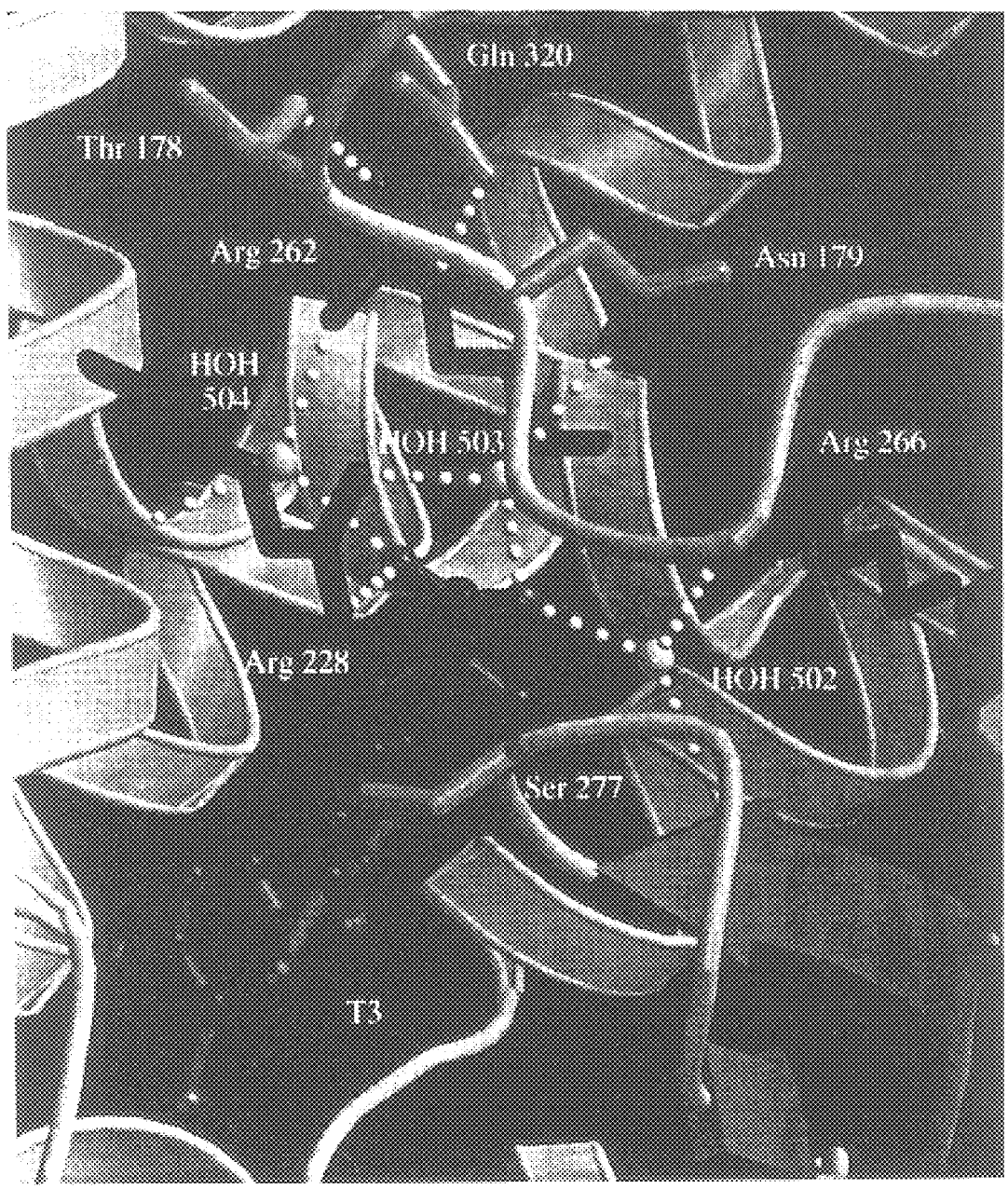
FIG. 23 is a partial ribbon drawing of TR-α LBD with T3, illustrating the three Arginine residues (Arg228, Arg262 and Arg 266 (dark stick figures)) of the polar pocket, three water molecules HOH502, HOH503 and HOH504, with hydrogen bonds indicated by dotted lines.
Figure 24:
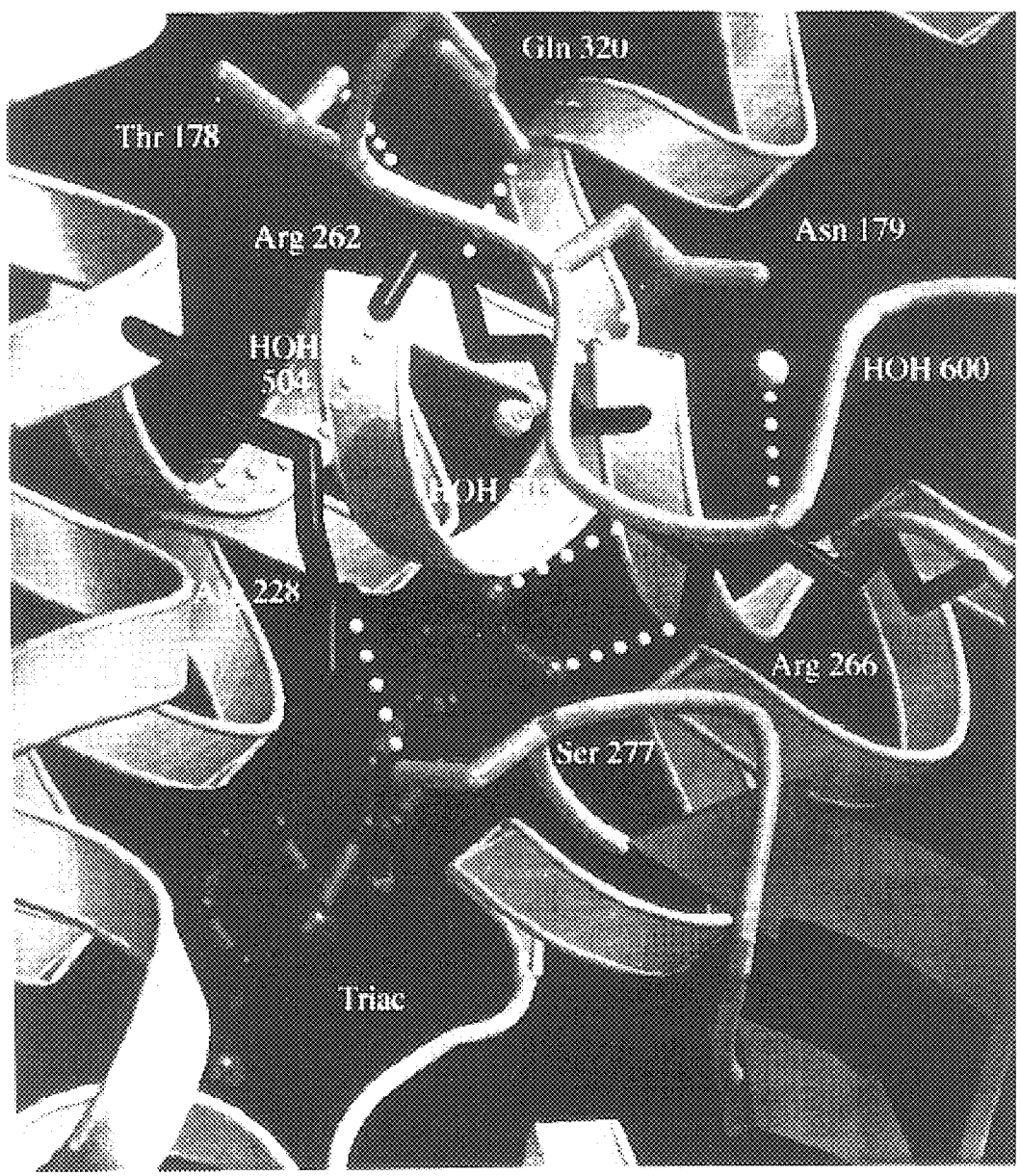
FIG. 24 is a partial ribbon drawing of TR-α LBD with triac, illustrating the three Arginine residues (dark stick figures) of the polar pocket, water molecules (HOH503, HOH504 and HOH600), with hydrogen bonds indicated by dotted lines.
Figure 25:
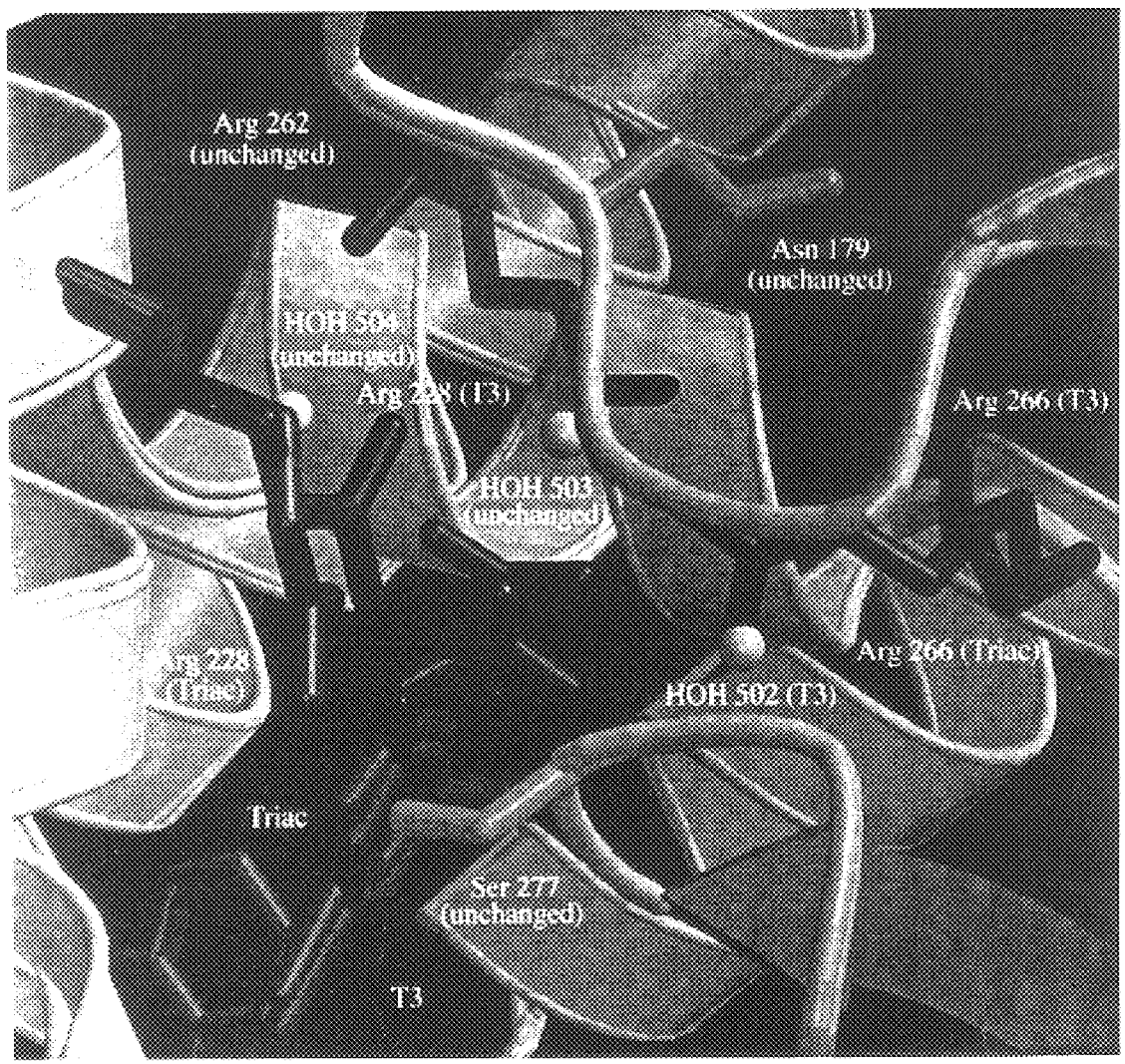
FIG. 25 is a partial ribbon drawing of the TR-α LBD with T3 and triac superimposed in the ligand binding cavity. The drawing shows several interacting amino acid residues in the polar pocket that remain unchanged whether T3 or triac occupies the ligand binding cavity: Arg262, Asn179, HOH503 and HOH504, and Ser277. Both Arg228 and Arg 266 occupy two different positions, depending on whether T3 or triac is bound.
Figure 26A:
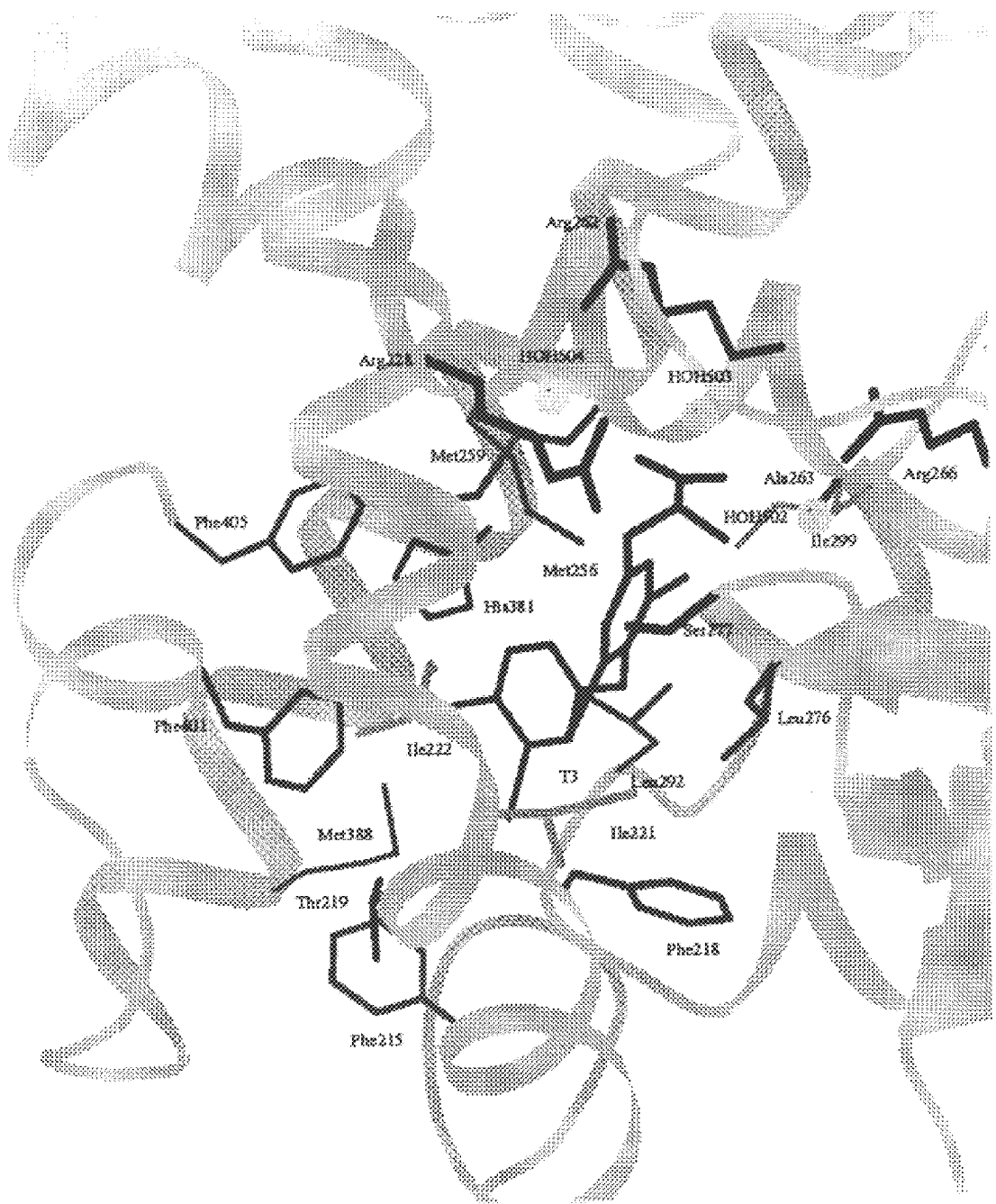

Based upon the methods and data described herein, the following is an embodiment of the computational methods of the invention, which permit design of nuclear receptor ligands based upon interactions between the structure of the amino acid residues of the receptor LBD and the four different ligands described herein. The small molecule structures for the ligands can be obtained from Cambridge Structural Database (CSD), and three dimensional models can be constructed using the methods described throughout the specification. The following are factors to consider in designing synthetic ligands:

1) Histidine 381 acts as a hydrogen bond acceptor for the $R_4$' hydroxyl, with the optimal tautomer maintained by water molecules. See FIG. 23 and FIG. 24. Histidine is the only hydrophilic residue in this hydrophobic pocket that surrounds the $R_4$' substituent. Histidine can be either a hydrogen bond acceptor or donor, depending on its tautomeric state. It is preferably a hydrogen bond donor, but can tolerate being a hydrogen bond acceptor, as for example, when there is a methoxy at the $R_4$' position of the ligand;

2) Arginines 228, 262, and 266 interact directly and through water-mediated hydrogen bonds with the $R_1$-substituent, with the electrostatic interaction provided by Arginine 266 (as in the Triac complex). This polar pocket is illustrated by FIG. 23–FIG. 25. FIG. 23 depicts $T_3$ in the TRα ligand binding cavity, where T3's amino-propionic R1-substituent interacts with Arg 228, HOH502, H9H503 and HOH504 via hydrogen bonds. FIG. 24 depicts triac in the ligand binding cavity, with its —COOH $R_1$ substituent in the polar pocket. In FIG. 24, Arg 228 no longer shares a hydrogen bond with the ligand, but the —COOH $R_1$ substituent forms hydrogen bonds with Arg 266. FIG. 25 superimposes $T_3$ and triac in the ligand binding cavity and shows several positionally unchanged amino acids and water molecules, and selected changed interacting amino acids and water molecules. The three figures illustrate parts of the polar pocket that can change and those parts that do not move upon binding of different ligands. For example, the Arg 262 at the top of the polar pocket does not move, even when the $R_1$ substituent has changed from a —COOH to an aminopropionic acid group. However, the other two Arginines, Arg 228 and Arg 266, demonstrate flexibility in the polar pocket to respond to the change in the size or chemical naure of the $R_1$ substituent.;

3) Inner and outer pockets for the $R_3/R_5$ substituents are formed by Ser260, Ala263, Ile299; and Phe 218, Ile221, Ile222, respectively. See FIGS. 21 and 22. The inner pocket is filled by either the $R_3$ or the $R_5$ substituent, regardless of the size of the substituent, and may act as a binding determinant by positioning the ligand in the receptor. Optimally, the inner pocket amino acids interact with an R3 or R5 substituent that is no larger than an iodo group. If the inner pocket is filled by the $R_3$ substituent, then the outer pocket interacts with the $R_5$ substituent and vice versa. The outer pocket can adjust to the size of its substituent through main chain motion centered at the break in helix 3 (Lys220-Ile221), suggesting that the bending of H3, and motion of the N-terminal portion of H3, may represent a conformational change induced on ligand binding. The outer pocket has greater flexibility than does the inner pocket in terms of accommodating a larger substituent group.

4) A pocket for the $R_3$'-substituent is formed by Phe 215, Gly290, Met388. The pocket is incompletely filled by the $R_3$'-iodo substituent, and accommodates the slightly larger 3'-isopropyl substituent by movement of the flexible Met388 side chain and the H7/H8 loop. This pocket can accommodate $R_3$' substituents that are even larger than isopropyl, for example, a phenyl group.

The above information will facilitate the design of high affinity agonists and antagonists by improving automated QSAR methodologies and informing manual modeling of pharmaceutical lead compounds. For example, the inclusion of discrete water molecules provides a complete description of hydrogen bonding in the polar pocket for use with pharmacophore development: also, the identification of mobile and immobile residues within the receptor suggests physically reasonable constraints for use in molecular mechanics/dynamics calculations.

Example 12
Design of an Increased Affinity Ligand

Direct interaction between the receptor and the ligand is limited in the polar pocket, which interacts with the $R_1$ substituent. While the lack of complementarity may contain implications for biological regulation, it also provides an opportunity for increasing affinity by optimizing the interaction between the amino acids of the polar pocket and the $R_1$ substituent of a synthetic ligand. The structure of the receptor-ligand interactions described herein enables design of an increased affinity synthetic ligand having two complementary modifications:

1) Remove the positively charged amine. The strongly positive electrostatic potential predicted for the polar pocket suggests that the positively charged amine of the aminopropionic acid $R_1$ substituent may be detrimental to binding. Suitable groups for substitution are suggested by the nature of nearby hydrogen bond partners: for example, Thr 275 O or Ser 277 N. See e.g. Tables in FIGS. 27–27A-13. For example, any any negatively charged substituent would be compatible for interacting with the amino acids of the polar pocket, including carboxylates, carbonyl, phosphonates, and sulfates, comprising 0 to 4 carbons. Another example of an $R_1$ substitution is an oxamic acid that replaces the amine of the naturally occurring ligand with one or more carbonyl groups.

2) Incorporate hydrogen bond acceptor and donor groups into the $R_1$-substituent to provide broader interactions with the polar pocket scaffold. Such hydrogen bond acceptor and donor groups incorporated into the R1-substituent will allow interactions that would otherwise occur with water molecules in the polar pocket. Specific waters include HOH 504 (hydrogen-bonds with Ala 225 O and Arg 262 NH); and HOH 503 hydrogen bonds with Asn 179 OD1, Ala 180 N), both of which are present in all four complexes (TR LBD complexed with T3, TR LBC complexed with $IpBr_2$, TR LBD complexed with Dimit and TR LBD complexed with Triac). Analysis of the hydrogen bonding network in the polar pocket suggests replacement of HOH 504 with a hydrogen bond acceptor, and HOH 503 with an hydrogen bond donor (although the chemical nature of asparagine probably permits flexibility at this site). Thus, incorporating a hydrogen bond acceptor in an R1 substituent that could take the place of the HOH504 or incorporating a hydrogen bond acceptor in an R1 substituent that could positionally replace the HOH503, or a combination thereof, are methods of designing novel synthetic TR ligands.

These two design approaches can be used separately or in combination to design synthetic ligands, including those in Table 4 (below).

A corollary to this approach is to design specific interactions to the residues Arg262 and Asn 179. The goal is to build in interactions to these residues by designing ligands that have $R_1$ substituents that form hydrogen bonds with water molecules or charged residues in the polar pocket.

TABLE 4

Synthetic TR Ligands

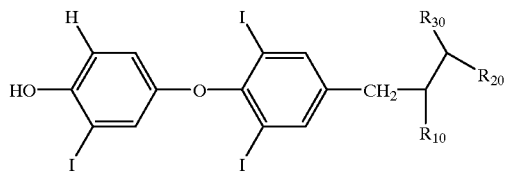

| R1 | R2 | R3 | R5 | R6 | X | R'2 | R'3 | R'4 | R'5 | R'6 |
|---|---|---|---|---|---|---|---|---|---|---|
| CO2H | H | Me | Me | H | O | H | Me | OH | Me | H |
| CH2CO2H | | I | I | | S | | Et | SH | Et | |
| CH2CH2CO2H | | Br | Br | | | | nPr | NH2 | nPr | |
| CH2CH(NH2)CO2H | | Cl | Cl | | | | iPr | | ipr | |
| OCH2CO2H | | Et | Et | | | | Ph | | nBu | |
| OCH2CH2CO2H | | OH | OH | | | | I | | nPen | |
| NHCH2CO2H | | NH2 | NH2 | | | | Br | | nHex | |
| NHCH2CH2CO2H | | SH | SH | | | | Cl | | Ph | |
| CH2COCOCO2H | | | | | | | | | heterocycle | |
| NHCOCOCO2H | | | | | | | | | aryl | |
| COCO2H | | | | | | | | | | |
| CF2CO2H | | | | | | | | | | |
| COCH2CO2H | | | | | | | | | | |

Any combination of the above substituents in the biphenyl ether scaffold structure shown above may result in a potentially pharmacologically useful ligand for the thyroid hormone receptor. These novel ligands may be antagonists of the thyroid receptor.

A strategy for designing synthetic ligands using the computational methods described herein is summed below:

For example,

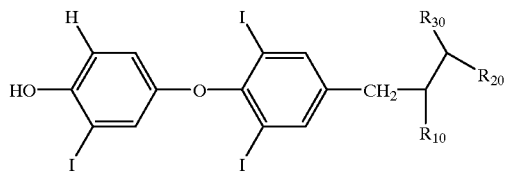

-continued

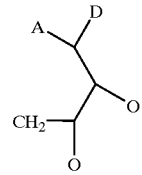

A=Hydrogen Bond Acceptor

D=Hydrogen Bond Donor

O=—OH, —CO

R10 can be —OH, —CO

R20 can be —CO

R30 can be —COOH, —CONH2

See also Table of synthetic TR Ligands

TABLE 3

| | LBD-122/410 | | | |
|---|---|---|---|---|
| | Dimit | T3 | IpBr$_2$ | Triac |
| Data collection | | | | |
| Cell dimensions | | | | |
| a (Å) | 117.16 | 117.19 | 117.18 | 118.19 |
| b (Å) | 80.52 | 80.20 | 80.12 | 81.37 |
| c (Å) | 63.21 | 63.23 | 63.13 | 63.73 |
| β (°) | 120.58 | 120.60 | 120.69 | 121.00 |
| Resolution (Å) | 2.2 | 2.0 | 2.1 | 2.45 |

TABLE 3-continued

LBD-122/410

| | Dimit | T3 | IpBr₂ | Triac |
|---|---|---|---|---|
| Obs. Reflections, (no.) | 57031 | 64424 | 66877 | 83573 |
| Unique Reflections, (no.) | 22327 | 21023 | 23966 | 18453 |
| Completeness, (%) | 87.0 | 82.4 | 93.7 | 96.0 |
| *$R_{sym}$ (%) | 3.9 | 3.5 | 4.5 | 7.5 |
| Phasing (15.0–2.5Å) | | | | |
| †$R_{der}$ (%) | — | 19.6 | 11.6 | |
| No. of sites | — | 3 | 2 | |
| ‡Occupancy | — | 44.6 (19.8) | 35.0 | |
| (Anomalous) | — | 50.2 (23.7) | 35.0 | |
| | | 39.2 (22.3) | | |
| §$F_H$/E | | | | |
| centric (acentric) | | | | |
| 15.0–5.0 Å | — | 3.67 (4.61) | 2.25 (3.09) | |
| 5.0–3.0 Å | — | 2.23 (2.75) | 1.25 (1.85) | |
| 3.0–2.5 Å | — | 1.64 (1.99) | 1.15 (1.57) | |
| ‖$R_{Cullis}$(%) | | | | |
| 15.0–5.0 Å | — | 33 | 44 | |
| 5.0–3.0 Å | — | 45 | 63 | |
| 3.0–2.5 Å | — | 60 | 65 | |
| Mean figure of merit | 0.62 | — | — | |
| MR Phasing (10–3.5Å) | | | | |
| Rotation Search: | | | | $\Theta_1$ = 309.37 |
| Eyler Angles (°) | | | | $\Theta_2$ = 48.96 |
| | | | | $\Theta_3$ = 127.28 |
| § correlation coefficient | | | | 34.3 |
| Translation Search: Fractional coordinates | | | | x = 0.1571 |
| | | | | y = 0.000 |
| | | | | z = 0.3421 |
| § correlation Coefficient | | | | 65.8 |
| 'R factor | | | | 31.2 |
| Refinement Resolution (Å) | 15.0–2.2 | 5.0–2.0 | 15.0–2.2 | 25–2.5 |
| ¶$R_{cryst}$ (%) | 20.5 | 22.1 | 21.4 | 23.6 |
| $R_{free}$ (%) | 22.7 | 24.0 | 22.4 | 24.1 |

All publications and patent applications mentioned in this specification are herein incorporated by reference to the same extent as if each individual publication or patent application was specifically and individually indicated to be incorporated by reference. The nuclear receptor ligands, particularly the TR ligands, of these references are herein incorporated by reference and can be optionally excluded from the claimed compounds with a proviso.

Headings and subheadings are presented only for the convenience of the reader and should not be used to construe the meaning of terms used within such headings and subheadings.

The invention now being fully described, it will be apparent to one of ordinary skill in the art that many changes and modifications can be made thereto without departing from the spirit or scope of the appended claims.

APPENDIX 1

Andrea, T. A., et al. *J Med Chem* 22, 221–232 (1979).
Andrews et al, U.S. Pat. No. 4,741,897, issued May 3, 1989.
Apriletti, J. W., Baxter, J. D., Lau, K. H & West, B. L. *Protein Expression and Purification* 6, 363–370 (1995).
Apriletti, J. W., Baxter, J. D. & Lavin, T. N. *J. Biol. Chem.* 263, 9409–9417 (1988).
Au-Fliegner, M., Helmer, E., Casanova, J., Raaka, B. M. & Samuels, H. H. *Mol Cell Biol* 13, 5725–5737 (1993).
Baniahmad, A., et al. *Mol Cell Biol* 15, 76–86 (1995).
Barettino, D., Vivanco Ruiz, M. M. & Stunnenberg, H. G. *Embo J* 13, 3039–3049 (1994).
Beck-Peccoz, P., et al. *J Clin Endocrinol Metab* 78, 990–993 (1994).
Bhat, M. K., McPhie, P. & Cheng, S. Y. *Biochem Biophys Res Commun* 210, 464–471 (1995).
Blake, C. C. & Oatley, S. J. *Nature* 268, 115–120 (1977).
Blake, C. C., Geisow, M. J., Oatley, S. J., Rerat, B. & Rerat, C. *J Mol Biol* 121, 339–356 (1978).
Bourguet, W., Ruff, M., Chambon, P., Gronemeyer, H. & Moras, D. *Nature* 375, 377–382 (1995).
Brent, G. A. *N Engl J Med* 331, 847–853 (1994).
Brunger, A. T., Kuriyan, J. & Karplus, M. *Science* 235, 458–460 (1987).
Casanova, J., et al. *Mol Cell Biol* 14, 5756–5765 (1994).
Cavailles, V., et al. *Embo J* 14, 3741–3751 (1995).
Chin et al, U.S. Pat. No. 5,284,999, issued Feb. 8, 1994.
Collaborative Computational Project, N.4. *Acta Crystallogr.* D50, 760–763 (1994).

Collingwood, T. N., Adams, M., Tone, Y & Chatterjee, V. K. *Mol Endocrinol* 8, 1262–1277 (1994).

Cowtan, K. *Joint CCP4 and ESF-EACBM Newsletter on Protein Crystallography* 31, 34–38 (1994).

Damm, K. & Evans, R. M. *Proc Natl Acad Sci USA* 90, 10668–10672 (1993).

Danielian, P. S., White, R., Lees, J. A. & Parker, M. G. *Embo J* 11, 1025–1033 (1992).

Davies et al, U.S. Pat. No. 5,322,933, issued Jun. 21, 1994.

Dawson et al, U.S. Pat. No. 5,466,861, issued Nov. 14, 1995.

DeGroot et al, U.S. Pat. No. 5,438,126, issued Aug. 1, 1995.

Dietrich, S. W., Bolger, M. B., Kollman, P. A. & Jorgensen, E. C. *J Med Chem* 20, 863–880 (1977).

Durand, B., et al. *Embo J* 13, 5370–5382 (1994).

Ellis et al, U.S. Pat. No. 4,766,121, issued Aug. 23, 1988.

Ellis et al, U.S. Pat. No. 4,826,876, issued May 2, 1989.

Ellis et al, U.S. Pat. No. 4,910,305, issued Mar. 20, 1990.

Emmett et al, U.S. Pat. No. 5,061,798, issued Oct. 29, 1991.

Evans, R. M. *Science* 240, 889–895 (1988).

Evans et al, U.S. Pat. No. 5,171,671, issued Dec. 15, 1992.

Evans et al, U.S. Pat. No. 5,312,732, issued May 17, 1994.

Fawell, S. E., Lees, J. A., White, R. & Parker, M. G. *Cell* 60, 953–962 (1990).

Forman, B. M. & Samuels, H. H. *Mol. Endocrinol.* 4, 1293–1301 (1990).

Gewirth, D. T. & Sigler, P. B. *Nature Structural Biology* 2, 386–394 (1995).

Glass, C. K. *Endocr Rev* 15, 391–407 (1994).

Hayashi, Y. Sunthornthepvarakul, T. & Refetoff, S. *J Clin Invest* 94, 607–615 (1994).

Jones, T. A., Zou, J. Y., Cowan, S. W. & Kjeldgaard. *Acta Crystallogr* A 47, 110–119 (1991).

Jorgensen, E. C. in *Hormonal Peptides and Proteins (eds. Li, C. H.)* 107–204 (Academic Press, New York, 1978).

Kabsch, W. *J Appl. Crystallogr.* 26, 795–800 (1993).

Kabsch, W. & Sander, C. *Biopolymers* 22, 2577–2637 (1983).

Laskowski, R. A., Macarthur, M. W., Moss, D. S. & Thornton, J. M. *J Appl. Crystallogr.* 26, 283–291 (1993).

Latham, K. R., Apriletti, J. W., Eberhardt, N. L. & Baxter, J. D. *J Biol Chem* 256, 12088–12093 (1981).

Laudet, V., Hanni, C., Coll, J., Catzeflis, F. & Stehelin, D. *Embo J* 11, 1003–1013 (1992).

LeDouarin, B., et al. *Embo J* 14, 2020–2033 (1995).

Lee, J. W., Ryan, F., Swaffield, J. C., Johnston, S. A. & Moore, D. D. *Nature* 374, 91–94 (1995).

Lee, J. W., Choi, H. S., Gyuris, J., Brent, R. & Moore, D. D. *Molec. Endocrinol.* 9, 243–254 (1995).

Leeson, P. D., Emmett, J. C., Shah, V. P., Showell, G. A., Novelli, R., Prain, H. D., Benson, M. G., Ellis, D., Pearce, N. J. & Underwood, A. H. *J Med Chem.* 32, 320–336 (1989).

Leeson, P. D., Ellis, D., Emmett, J. D., Shah, V. P., Showell, G. A. & Underwood, A. H. J. Leng, X, et al. *Mol Cell Biol* 15, 255–263 (1995).

Leng, X., Tsai, S. Y., O'Malley, B. W. & Tsai, M. J. *J Steroid Biochem Mol Biol* 46, 643–661 (1993).

Lin, K. H., Parkison, C., McPhie, P. & Cheng, S. Y. *Mol. Endocrinol.* 5, 485–492 (1991).

Luisi, B. F., et al. *Nature* 352, 497–505 (1991).

McGrath, M. E., et al. *J. Mol. Biol.* 237, 236–239 (1994).

McRee, D. E., *Practical Protein Crystallography*, Academic Press, N.Y. (1993), especially chapters 1, 2 and 3.

Meier, C. A., et al. *Mol. Endocrinol.* 6, 248–258 (1992).

Miura et al, U.S. Pat. No. 5,116,828, issued May 26, 1992.

Monaco, H. L., Rizzi, M. & Coda, A. *Science* 268, 1039–1041 (1995).

Nicholls, A., Sharp, K. A. & Honig, B. *Proteins* 11, 281–296 (1991).

O'Donnell, A. L., Rosen, E. D., Darling, D. S. & Koenig, R. J. *Mol. Endocrinol.* 5, 94–99 (1991).

Otwinowski, Z. *Proceedings of the CCP4 Study Weekend* 80–86 (SERC Daresbury Laboratory, Warrington, UK, 1991).

Otwinowski, Z. *Proceedings of the CCP4 Study Weekend: "Data Collection and Processing"* 56–62 (SERC Daresbury Laboratory, Warrington, U.K., 1993).

Ozato, U.S. Pat. No. 5,403,925, issued Apr. 4, 1995.

Rastinejad, R., Perlmann, T., Evans, R. M. & Sigler, P. B. *Nature* 375, 203–211 (1995).

Refetoff, S., Weiss, R. E. & Usala, S. J. *Endocr. Rev.* 14, 348–399 (1993).

Ribeiro, R. C. J., Kushner, P. J. & Baxter, J. D. *Annu. Rev. Med.* 46, 443–453 (1995).

Ribeiro, R. C. J., et al. *Ann. N. Y. Acad. Sci.* 758, 366–389 (1995).

Ribeiro, R. C., Kushner, P. J., Apriletti, J. W., West, B. L. & Baxter, J. D. *Mol. Endocrinol.* 6, 1142–1152 (1992).

Saatcioglu, F., Bartunek, P., Deng, T., Zenke, M. & Karin, M. *Mol. Cell Biol.* 13, 3675–3685 (1993).

Schwabe, J. W., Chapman, L., Finch, J. T. & Rhodes, D. *Cell* 75, 567–578 (1993).

Selmi, S. & Samuels, H. H. *J. Biol. Chem.* 266, 11589–11593 (1991).

Swaffield, J. C., Melcher, K. & Johnston, S. A. *Nature* 374, 88–91 (1995).

Toney, J. H. et al. *Biochemistry* 32, 2–6 (1993).

Tsai, M. J. & O'Malley, B. W. *Annu. Rev. Biochem.* 63, 451–486 (1994).

Zenke, M., Munoz, A., Sap, J., Vennstrom, B. & Beug, H. *Cell* 61, 1035–1049 (1990).

What is claimed is:

1. A method of designing a nuclear receptor synthetic ligand comprising:

1) generating a three dimensional model of a protein comprising a nuclear receptor ligand binding domain (LBD) with a bound ligand utilizing data from FIGS. 28, 29, 30, or 31 and a computer programmed for generating said model from said data;

2) determining at least one interacting amino acid of said nuclear receptor LBD that interacts with at least one first chemical moiety of said bound ligand in said three dimensional model;

3) selecting at least one chemical modification of said first chemical moiety to produce a second chemical moiety;

4) measuring the reduction or enhancement of the interaction between said interacting amino acid and said second chemical moiety compared to the interaction between said interacting amino acid and said first chemical moiety;

5) generating a designed nuclear receptor synthetic ligand wherein said first chemical moiety is replaced with said second chemical moiety.

2. The method of claim 1, wherein steps 2, 3 and 4 are repeated.

3. The method of claim 1, wherein said three dimensional model comprises a thyroid hormone receptor (TR) LBD with a bound TR ligand.

4. The method of claim 3, wherein said selecting uses said first chemical moiety that interacts with at least one of the said interacting amino acids listed in FIG. 27.

5. The method of claim 4, wherein said enhancement of the interaction is enhancement of hydrogen bonding interaction, charge interaction, hydrophobic interaction, Van Der Waals interaction or dipole interaction.

6. The method of claim 4, wherein said reduction of the interaction is reduction of hydrogen bonding interaction, charge interaction, hydrophobic interaction, Van Der Waals interaction or dipole interaction.

7. The method of claim 5 wherein said measuring and replacing are performed using a computer program to represent chemical structures of said interacting amino acid and ligand.

8. The method of claim 6, wherein said TR ligand is a thyronine derivative of the formula

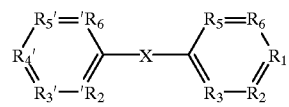

and said chemical modification is at the R5' position of said thyronine derivative.

9. The method of claim 1 wherein said protein is a nuclear receptor other than TR.

10. A method of designing a nuclear receptor antagonist from a nuclear receptor agonist comprising:

1) determining a structure of a molecular recognition domain of said agonist using a three dimensional model of a protein comprising a nuclear receptor ligand binding domain (LBD) generated from data from FIGS. 28, 29, 30, or 31 and a computer programmed for generating said model when supplied with said data as input data;

2) selecting at least one chemical modification of a first chemical moiety to produce a second chemical moiety that extends beyond a binding site for said agonist and in the direction of at least one protein domain selected from the group consisting of a transcription activation domain of said LBD, a repressor binding domain of said LBD, a DNA binding domain of said nuclear receptor, a heat shock protein binding domain of said nuclear receptor, a dimerization domain of said LBD, and a hinge region to said DNA binding domain; and 3) generating a designed nuclear receptor antagonist wherein said first chemical moiety is replaced with said second chemical moiety.

11. The method of claim 10, wherein said protein comprises said nuclear receptor LBD bound to a nuclear receptor ligand.

12. The method of claim 11, wherein said nuclear receptor LBD bound to a nuclear receptor ligand comprises a thyroid hormone receptor (TR) LBD with a bound TR ligand.

13. The method of claim 12, wherein said bound TR ligand is a thyronine derivative of the formula:

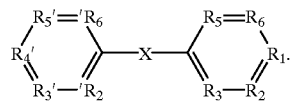

14. The method of claim 11, wherein said LBD is from a receptor selected from a group consisting of glucocorticoid receptor, estrogen receptor, retinoid receptor and vitamin D receptor.

15. A method of designing a nuclear receptor super agonist or antagonist comprising:

1) generating a three dimensional model of a protein comprising a nuclear receptor ligand binding domain (LBD) with a bound ligand utilizing data from FIGS. 28, 29, 30, or 31 and a computer programmed for generating said model from said data;

2) determining at least one interacting amino acid of said nuclear receptor LBD that interacts with at least one first chemical moiety of said ligand using said three dimensional model;

3) selecting at least one chemical modification of said first chemical moiety to produce a second chemical moiety;

4) measuring the reduction or enhancement of the interaction between said interacting amino acid and said second chemical moiety compared to the interaction between said interacting amino acid and said first chemical moiety; and 5) generating a designed nuclear receptor super agonist or antagonist wherein said first chemical moiety is replaced with said second chemical moiety.

16. The method of claim 15, wherein said enhancement of the interaction is enhancement of hydrogen bonding interaction, electrostatic interaction, charge interaction, hydrophobic interaction, Van Der Waals interaction or dipole interaction.

17. The method of claim 16, wherein said chemical modification changes a carboxylate moiety of said first chemical moiety to a chemical moiety selected from the group consisting of phosphonate and phosphate.

18. The method of claim 17, wherein said nuclear receptor is a thyroid hormone receptor (TR) and said chemical modification enhances said interaction between said second chemical moiety and at least one of the following arginines: Arg 262, Arg 266 or Arg 228 of the rat α-TR (SEQ ID NO: 1) or an arginine of human α-TR or β-TR that corresponds in its three dimensional position in said three dimensional model to said arginines: Arg 262, Arg 266 or Arg 228.

19. A method of designing a nuclear receptor ligand comprising:

1) providing atomic coordinate data of FIGS. 28, 29, 30, or 31 to a computer having a computer program capable of generating an atomic model of a molecule from atomic coordinate data of said molecule;

2) generating with said computer an atomic model of a protein comprising a nuclear receptor ligand binding domain (LBD) or portion thereof with a bound ligand;

3) determining a first chemical moiety of said bound ligand that interacts with an amino acid of said LBD;

4) selecting at least one chemical modification of said first chemical moiety to produce a second chemical moiety;

5) measuring the reduction or enhancement of the interaction between said interacting amino acid and said second chemical moiety compared to the interaction between said interacting amino acid and said first chemical moiety; and 6) generating a designed nuclear receptor ligand having altered interaction with said amino acid of said LBD wherein said first chemical moiety is replaced with said second chemical moiety.

20. The method of claim 19, wherein said bound ligand comprises the formula:

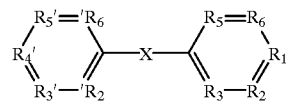

21. The method of claim 19, wherein said nuclear receptor LBD comprises a thyroid hormone receptor (TR) LBD.

22. The method of claim 19, wherein said nuclear receptor ligand comprises the formula:

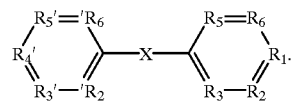

* * * * *

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
      (A) LENGTH: 410 amino acids
      (B) TYPE: amino acid
      (C) STRANDEDNESS:
      (D) TOPOLOGY: linear (ii) MOLECULE TYPE: protein (xi) SEQUENCE DESCRIPTION: SEQ ID NO:1:

```
Met Glu Gln Lys Pro Ser Lys Val Glu Cys Gly Ser Asp Pro Glu Glu
1               5                   10                  15

Asn Ser Ala Arg Ser Pro Asp Gly Lys Arg Lys Arg Lys Asn Gly Gln
            20                  25                  30

Cys Pro Leu Lys Ser Ser Met Ser Gly Tyr Ile Pro Ser Tyr Leu Asp
            35                  40                  45

Lys Asp Glu Gln Cys Val Val Cys Gly Asp Lys Ala Thr Gly Tyr His
        50                  55                  60

Tyr Arg Cys Ile Thr Cys Glu Gly Cys Lys Gly Phe Phe Arg Arg Thr
65                  70                  75                  80

Ile Gln Lys Asn Leu His Pro Thr Tyr Ser Cys Lys Tyr Asp Ser Cys
                85                  90                  95

Cys Val Ile Asp Lys Ile Thr Arg Asn Gln Cys Gln Leu Cys Arg Phe
            100                 105                 110

Lys Lys Cys Ile Ala Val Gly Met Ala Met Asp Leu Val Leu Asp Asp
            115                 120                 125

Ser Lys Arg Val Ala Lys Arg Lys Leu Ile Glu Gln Asn Arg Glu Arg
130                 135                 140

Arg Arg Lys Glu Glu Met Ile Arg Ser Leu Gln Gln Arg Pro Glu Pro
145                 150                 155                 160

Thr Pro Glu Glu Trp Asp Leu Ile His Val Ala Thr Glu Ala His Arg
                165                 170                 175

Ser Thr Asn Ala Gln Gly Ser His Trp Lys Gln Arg Arg Lys Phe Leu
            180                 185                 190

Pro Asp Asp Ile Gly Gln Ser Pro Ile Val Ser Met Pro Asp Gly Asp
            195                 200                 205

Lys Val Asp Leu Glu Ala Phe Ser Glu Phe Thr Lys Ile Ile Thr Pro
        210                 215                 220

Ala Ile Thr Arg Val Val Asp Phe Ala Lys Lys Leu Pro Met Phe Ser
225                 230                 235                 240

Glu Leu Pro Cys Glu Asp Gln Ile Ile Leu Leu Lys Gly Cys Cys Met
                245                 250                 255

Glu Ile Met Ser Leu Arg Ala Ala Val Arg Tyr Asp Pro Glu Ser Asp
            260                 265                 270

Thr Leu Thr Leu Ser Gly Glu Met Thr Val Lys Arg Lys Gln Leu Lys
            275                 280                 285

Asn Gly Gly Leu Gly Val Val Ser Asp Ala Ile Phe Glu Leu Gly Lys
290                 295                 300

Ser Leu Ser Ala Phe Asn Leu Asp Asp Thr Glu Val Ala Leu Leu Gln
305                 310                 315                 320

Ala Val Leu Leu Met Ser Thr Asp Arg Ser Gly Leu Leu Cys Val Asp
                325                 330                 335

Lys Ile Glu Lys Ser Gln Glu Ala Tyr Leu Leu Ala Phe Glu His Tyr
            340                 345                 350

Val Asn His Arg Lys His Asn Ile Pro His Phe Trp Pro Lys Leu Leu
            355                 360                 365

Met Lys Val Thr Asp Leu Arg Met Ile Gly Ala Cys His Ala Ser Arg
        370                 375                 380

Phe Leu His Met Lys Val Glu Cys Pro Thr Glu Leu Phe Pro Pro Leu
385                 390                 395                 400
```

```
Phe Leu Glu Val Phe Glu Asp Gln Glu Val
                405                 410

(2) INFORMATION FOR SEQ ID NO:2:

(i) SEQUENCE CHARACTERISTICS:
        (A) LENGTH: 410 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:2:

Met Glu Gln Lys Pro Ser Lys Val Glu Cys Gly Ser Asp Pro Glu Glu
1               5                   10                  15

Asn Ser Ala Arg Ser Pro Asp Gly Lys Arg Lys Arg Lys Asn Gly Gln
                20                  25                  30

Cys Ser Leu Lys Thr Ser Met Ser Gly Tyr Ile Pro Ser Tyr Leu Asp
            35                  40                  45

Lys Asp Glu Gln Cys Val Val Cys Gly Asp Lys Ala Thr Gly Tyr His
50                  55                  60

Tyr Arg Cys Ile Thr Cys Glu Gly Cys Lys Gly Phe Phe Arg Arg Thr
65                  70                  75                  80

Ile Gln Lys Asn Leu His Pro Thr Tyr Ser Cys Lys Tyr Asp Ser Cys
                85                  90                  95

Cys Val Ile Asp Lys Ile Thr Arg Asn Gln Cys Gln Leu Cys Arg Phe
            100                 105                 110

Lys Lys Cys Ile Ala Val Gly Met Ala Met Asp Leu Val Leu Asp Asp
        115                 120                 125

Ser Lys Arg Val Ala Lys Arg Lys Leu Ile Glu Gln Asn Arg Glu Arg
130                 135                 140

Arg Arg Lys Glu Glu Met Ile Arg Ser Leu Gln Gln Arg Pro Glu Pro
145                 150                 155                 160

Thr Pro Glu Glu Trp Asp Leu Ile His Ile Ala Thr Glu Ala His Arg
                165                 170                 175

Ser Thr Asn Ala Gln Gly Ser His Trp Lys Gln Arg Arg Lys Phe Leu
            180                 185                 190

Pro Asp Asp Ile Gly Gln Ser Pro Ile Val Ser Met Pro Asp Gly Asp
        195                 200                 205

Lys Val Asp Leu Glu Ala Phe Ser Glu Phe Thr Lys Ile Ile Thr Pro
210                 215                 220

Ala Ile Thr Arg Val Val Asp Phe Ala Lys Lys Leu Pro Met Phe Ser
225                 230                 235                 240

Glu Leu Pro Cys Glu Asp Gln Ile Ile Leu Leu Lys Gly Cys Cys Met
                245                 250                 255

Glu Ile Met Ser Leu Arg Ala Ala Val Arg Tyr Asp Pro Glu Ser Asp
            260                 265                 270

Thr Leu Thr Leu Ser Gly Glu Met Ala Val Lys Arg Glu Gln Leu Lys
        275                 280                 285

Asn Gly Gly Leu Gly Val Val Ser Asp Ala Ile Phe Glu Leu Gly Lys
290                 295                 300

Ser Leu Ser Ala Phe Asn Leu Asp Asp Thr Glu Val Ala Leu Leu Gln
305                 310                 315                 320

Ala Val Leu Leu Met Ser Thr Asp Arg Ser Gly Leu Leu Cys Val Asp
                325                 330                 335
```

-continued

```
Lys Ile Glu Lys Ser Gln Glu Ala Tyr Leu Ala Phe Glu His Tyr
                340                 345                 350

Val Asn His Arg Lys His Asn Ile Pro His Phe Trp Pro Lys Leu Leu
            355                 360                 365

Met Lys Val Thr Asp Leu Arg Met Ile Gly Ala Cys His Ala Ser Arg
        370                 375                 380

Phe Leu His Met Lys Val Glu Cys Pro Thr Glu Leu Phe Pro Pro Leu
385                 390                 395                 400

Phe Leu Glu Val Phe Glu Asp Gln Glu Val
                405                 410

(2) INFORMATION FOR SEQ ID NO:3:

(i) SEQUENCE CHARACTERISTICS:
        (A) LENGTH: 461 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:3:

Met Thr Pro Asn Ser Met Thr Glu Asn Gly Leu Thr Ala Trp Asp Lys
1               5                   10                  15

Pro Lys His Cys Pro Asp Arg Glu His Asp Trp Lys Leu Val Gly Met
                20                  25                  30

Ser Glu Ala Cys Leu His Arg Lys Ser His Ser Glu Arg Arg Ser Thr
            35                  40                  45

Leu Lys Asn Glu Gln Ser Ser Pro His Leu Ile Gln Thr Thr Trp Thr
        50                  55                  60

Ser Ser Ile Phe His Leu Asp His Asp Val Asn Asp Gln Ser Val
65                  70                  75                  80

Ser Ser Ala Gln Thr Phe Gln Thr Glu Glu Lys Lys Cys Lys Gly Tyr
                85                  90                  95

Ile Pro Ser Tyr Leu Asp Lys Asp Glu Leu Cys Val Val Cys Gly Asp
            100                 105                 110

Lys Ala Thr Gly Tyr His Tyr Arg Cys Ile Thr Cys Glu Gly Cys Lys
        115                 120                 125

Gly Phe Phe Arg Arg Thr Ile Gln Lys Asn Leu His Pro Ser Tyr Ser
130                 135                 140

Cys Lys Tyr Glu Gly Lys Cys Val Ile Asp Lys Val Thr Arg Asn Gln
145                 150                 155                 160

Cys Gln Glu Cys Arg Phe Lys Lys Cys Ile Tyr Val Gly Met Ala Thr
                165                 170                 175

Asp Leu Val Leu Asp Asp Ser Lys Arg Leu Ala Lys Arg Lys Leu Ile
            180                 185                 190

Glu Glu Asn Arg Glu Lys Arg Arg Arg Glu Glu Leu Gln Lys Ser Ile
        195                 200                 205

Gly His Lys Pro Glu Pro Thr Asp Glu Glu Trp Glu Leu Ile Lys Thr
210                 215                 220

Val Thr Glu Ala His Val Ala Thr Asn Ala Gln Gly Ser His Trp Lys
225                 230                 235                 240

Gln Lys Pro Lys Phe Leu Pro Glu Asp Ile Gly Gln Ala Pro Ile Val
                245                 250                 255

Asn Ala Pro Glu Gly Gly Lys Val Asp Leu Glu Ala Phe Ser His Phe
            260                 265                 270
```

```
Thr Lys Ile Ile Thr Pro Ala Ile Thr Arg Val Val Asp Phe Ala Lys
            275                 280                 285
Lys Leu Pro Met Phe Cys Glu Leu Pro Cys Glu Asp Gln Ile Ile Leu
        290                 295                 300
Leu Lys Gly Cys Cys Met Glu Ile Met Ser Leu Arg Ala Ala Val Arg
305                 310                 315                 320
Tyr Asp Pro Glu Ser Glu Thr Leu Thr Leu Asn Gly Glu Met Ala Val
                325                 330                 335
Ile Arg Gly Gln Leu Lys Asn Gly Gly Leu Gly Val Val Ser Asp Ala
            340                 345                 350
Ile Phe Asp Leu Gly Met Ser Leu Ser Ser Phe Asn Leu Asp Asp Thr
            355                 360                 365
Glu Val Ala Leu Leu Gln Ala Val Leu Leu Met Ser Ser Asp Arg Pro
        370                 375                 380
Gly Leu Ala Cys Val Glu Arg Ile Glu Lys Tyr Gln Asp Ser Phe Leu
385                 390                 395                 400
Leu Ala Phe Glu His Tyr Ile Asn Tyr Arg Lys His His Val Thr His
                405                 410                 415
Phe Trp Pro Lys Leu Leu Met Lys Val Thr Asp Leu Arg Met Ile Gly
            420                 425                 430
Ala Cys His Ala Ser Arg Phe Leu His Met Lys Val Glu Cys Pro Thr
            435                 440                 445
Glu Leu Leu Pro Pro Leu Phe Leu Glu Val Phe Glu Asp
        450                 455                 460

(2) INFORMATION FOR SEQ ID NO:4:

(i) SEQUENCE CHARACTERISTICS:
        (A) LENGTH: 416 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:4:

Pro Asn Ser Asn His Val Ala Ser Gly Ala Gly Glu Ala Ala Ile Glu
1               5                  10                  15
Thr Gln Ser Ser Ser Glu Glu Ile Val Pro Ser Pro Pro Ser Pro Pro
            20                  25                  30
Pro Pro Leu Pro Arg Ile Tyr Lys Pro Cys Phe Val Cys Gln Asp Lys
        35                  40                  45
Ser Ser Gly Tyr His Tyr Gly Val Ser Ala Cys Glu Gly Cys Lys Gly
    50                  55                  60
Phe Phe Arg Arg Ser Ile Gln Lys Asn Met Val Tyr Thr Cys His Arg
65                  70                  75                  80
Asp Lys Asn Cys Ile Ile Asn Lys Val Thr Arg Asn Arg Cys Gln Tyr
                85                  90                  95
Cys Arg Leu Gln Lys Cys Phe Glu Val Gly Met Ser Lys Glu Ser Val
            100                 105                 110
Arg Asn Asp Arg Asn Lys Lys Lys Lys Glu Val Pro Lys Pro Glu Cys
        115                 120                 125
Ser Glu Ser Tyr Thr Leu Thr Pro Glu Val Gly Glu Leu Ile Glu Lys
    130                 135                 140
Val Arg Lys Ala His Gln Glu Thr Phe Pro Ala Leu Cys Gln Leu Gly
145                 150                 155                 160
```

```
Lys Tyr Thr Thr Asn Asn Ser Ser Glu Gln Arg Val Ser Leu Asp Ile
                165                 170                 175
Asp Leu Trp Asp Lys Phe Ser Glu Leu Ser Thr Lys Cys Ile Ile Lys
            180                 185                 190
Thr Val Glu Phe Ala Lys Gln Leu Pro Gly Phe Thr Thr Leu Thr Ile
        195                 200                 205
Ala Asp Gln Ile Thr Leu Leu Lys Ala Ala Cys Leu Asp Ile Leu Ile
    210                 215                 220
Leu Arg Ile Cys Thr Arg Tyr Thr Pro Glu Gln Asp Thr Met Thr Phe
225                 230                 235                 240
Ser Asp Gly Leu Thr Leu Asn Arg Thr Gln Met His Asn Ala Gly Phe
                245                 250                 255
Gly Pro Leu Thr Asp Leu Val Phe Ala Phe Ala Asn Gln Leu Leu Pro
            260                 265                 270
Leu Glu Met Asp Asp Ala Glu Thr Gly Ile Leu Ser Ala Ile Cys Leu
        275                 280                 285
Ile Cys Gly Asp Arg Gln Asp Leu Glu Gln Pro Asp Arg Val Asp Met
    290                 295                 300
Leu Gln Glu Pro Leu Leu Glu Ala Leu Lys Val Tyr Val Arg Lys Arg
305                 310                 315                 320
Arg Pro Ser Arg Pro His Met Phe Pro Lys Met Leu Met Lys Ile Thr
                325                 330                 335
Asp Leu Arg Ser Ile Ser Ala Lys Gly Ala Glu Arg Val Ile Thr Leu
            340                 345                 350
Lys Met Glu Ile Pro Gly Ser Met Pro Pro Leu Ile Gln Glu Met Leu
        355                 360                 365
Glu Asn Ser Glu Gly Leu Asp Thr Leu Ser Gly Gln Pro Gly Gly Gly
    370                 375                 380
Gly Arg Asp Gly Gly Gly Leu Ala Pro Pro Pro Gly Ser Cys Ser Pro
385                 390                 395                 400
Ser Leu Ser Pro Ser Ser Asn Arg Ser Ser Pro Ala Thr His Ser Pro
                405                 410                 415

(2) INFORMATION FOR SEQ ID NO:5:

(i) SEQUENCE CHARACTERISTICS:
        (A) LENGTH: 454 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:5:

Met Ala Thr Asn Lys Glu Arg Leu Phe Ala Ala Gly Ala Leu Gly Pro
1               5                   10                  15
Gly Ser Gly Tyr Pro Gly Ala Gly Phe Pro Phe Ala Phe Pro Gly Ala
                20                  25                  30
Leu Arg Gly Ser Pro Pro Phe Glu Met Leu Ser Pro Ser Phe Arg Gly
            35                  40                  45
Leu Gly Gln Pro Asp Leu Pro Lys Glu Met Ala Ser Leu Ser Val Glu
    50                  55                  60
Thr Gln Ser Thr Ser Ser Glu Glu Met Val Pro Ser Ser Pro Ser Pro
65                  70                  75                  80
Pro Pro Pro Pro Arg Val Tyr Lys Pro Cys Phe Val Cys Asn Asp Lys
                85                  90                  95
```

```
Ser Ser Gly Tyr His Tyr Gly Val Ser Ser Cys Glu Gly Cys Lys Gly
            100                 105                 110

Phe Phe Arg Arg Ser Ile Gln Lys Asn Met Val Tyr Thr Cys His Arg
            115                 120                 125

Asp Lys Asn Cys Ile Ile Asn Lys Val Thr Arg Asn Arg Cys Gln Tyr
            130                 135             140

Cys Arg Leu Gln Lys Cys Phe Glu Val Gly Met Ser Lys Glu Ala Val
145                 150                 155                 160

Arg Asn Asp Arg Asn Lys Lys Lys Glu Val Lys Glu Glu Gly Ser
                165                 170                 175

Pro Asp Ser Tyr Glu Leu Ser Pro Gln Leu Glu Glu Leu Ile Thr Lys
            180                 185                 190

Val Ser Lys Ala His Gln Glu Thr Phe Pro Ser Leu Cys Gln Leu Gly
        195                 200                 205

Lys Tyr Thr Thr Asn Ser Ser Ala Asp His Arg Val Gln Leu Asp Leu
        210                 215                 220

Gly Leu Trp Asp Lys Phe Ser Glu Leu Ala Thr Lys Cys Ile Ile Lys
225                 230                 235                 240

Ile Val Glu Phe Ala Lys Arg Leu Pro Gly Phe Thr Gly Leu Ser Ile
                245                 250                 255

Ala Asp Gln Ile Thr Leu Leu Lys Ala Ala Cys Leu Asp Ile Leu Met
            260                 265                 270

Leu Arg Ile Cys Thr Arg Tyr Thr Pro Glu Gln Asp Thr Met Thr Phe
        275                 280                 285

Ser Asp Gly Leu Thr Leu Asn Arg Thr Gln Met His Asn Ala Gly Phe
        290                 295                 300

Gly Pro Leu Thr Asp Leu Val Phe Ala Phe Ala Gly Gln Leu Leu Pro
305                 310                 315                 320

Leu Glu Met Asp Asp Thr Glu Thr Gly Leu Leu Ser Ala Ile Cys Leu
                325                 330                 335

Ile Cys Gly Asp Arg Met Asp Leu Glu Glu Pro Glu Lys Val Asp Lys
            340                 345                 350

Leu Gln Glu Pro Leu Leu Glu Ala Leu Arg Leu Tyr Ala Arg Arg Arg
        355                 360                 365

Arg Pro Ser Gln Pro Tyr Met Phe Pro Arg Met Leu Met Lys Ile Thr
        370                 375                 380

Asp Leu Arg Gly Ile Ser Thr Lys Gly Ala Glu Arg Ala Ile Thr Leu
385                 390                 395                 400

Lys Met Glu Ile Pro Gly Pro Met Pro Pro Leu Ile Arg Glu Met Leu
                405                 410                 415

Glu Asn Pro Glu Met Phe Glu Asp Asp Ser Ser Gln Pro Gly Pro His
            420                 425                 430

Pro Asn Ala Ser Ser Glu Asp Glu Val Pro Gly Gly Gln Gly Lys Gly
        435                 440                 445

Gly Leu Lys Ser Pro Ala
    450
```

(2) INFORMATION FOR SEQ ID NO:6:

(i) SEQUENCE CHARACTERISTICS:
        (A) LENGTH: 462 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:6:

```
Met Asp Thr Lys His Phe Leu Pro Leu Asp Phe Ser Thr Gln Val Asn
1               5                   10                  15

Ser Ser Leu Thr Ser Pro Thr Gly Arg Gly Ser Met Ala Ala Pro Ser
            20                  25                  30

Leu His Pro Ser Leu Gly Pro Gly Ile Gly Ser Pro Gly Gln Leu His
            35                  40                  45

Ser Pro Ile Ser Thr Leu Ser Ser Pro Ile Asn Gly Met Gly Pro Pro
50                  55                  60

Phe Ser Val Ile Ser Ser Pro Met Gly Pro His Ser Met Ser Val Pro
65                  70                  75                  80

Thr Thr Pro Thr Leu Gly Phe Ser Thr Gly Ser Pro Gln Leu Ser Ser
            85                  90                  95

Pro Met Asn Pro Val Ser Ser Glu Asp Ile Lys Pro Pro Leu Gly
            100                 105                 110

Leu Asn Gly Val Leu Lys Val Pro Ala His Pro Ser Gly Asn Met Ala
            115                 120                 125

Ser Phe Thr Lys His Ile Cys Ala Ile Cys Gly Asp Arg Ser Ser Gly
            130                 135                 140

Lys His Tyr Gly Val Tyr Ser Cys Glu Gly Cys Lys Gly Phe Phe Lys
145                 150                 155                 160

Arg Thr Val Arg Lys Asp Leu Thr Tyr Thr Cys Arg Asp Asn Lys Asp
                165                 170                 175

Cys Leu Ile Asp Lys Arg Gln Arg Asn Arg Cys Gln Tyr Cys Arg Tyr
            180                 185                 190

Gln Lys Cys Leu Ala Met Gly Met Lys Arg Glu Ala Val Gln Glu Glu
            195                 200                 205

Arg Gln Arg Gly Lys Asp Arg Asn Glu Asn Glu Val Glu Ser Thr Ser
            210                 215                 220

Ser Ala Asn Glu Asp Met Pro Val Glu Arg Ile Leu Glu Ala Glu Leu
225                 230                 235                 240

Ala Val Glu Pro Lys Thr Glu Thr Tyr Val Glu Ala Asn Met Gly Leu
                245                 250                 255

Asn Pro Ser Ser Pro Asn Asp Pro Val Thr Asn Ile Cys Gln Ala Ala
            260                 265                 270

Asp Lys Gln Leu Phe Thr Leu Val Glu Trp Ala Lys Arg Ile Pro His
            275                 280                 285

Phe Ser Glu Leu Pro Leu Asp Asp Gln Val Ile Leu Leu Arg Ala Gly
290                 295                 300

Trp Asn Glu Leu Leu Ile Ala Ser Phe Ser His Arg Ser Ile Ala Val
305                 310                 315                 320

Lys Asp Gly Ile Leu Leu Ala Thr Gly Leu His Val His Arg Asn Ser
                325                 330                 335

Ala His Ser Ala Gly Val Gly Ala Ile Phe Asp Arg Val Leu Thr Glu
            340                 345                 350

Leu Val Ser Lys Met Arg Asp Met Gln Met Asp Lys Thr Glu Leu Gly
            355                 360                 365

Cys Leu Arg Ala Ile Val Leu Phe Asn Pro Asp Ser Lys Gly Leu Ser
            370                 375                 380

Asn Pro Ala Glu Val Glu Ala Leu Arg Glu Lys Val Tyr Ala Ser Leu
385                 390                 395                 400
```

```
Glu Ala Tyr Cys Lys His Lys Tyr Pro Glu Gln Pro Gly Arg Phe Ala
            405                 410                 415

Lys Leu Leu Arg Leu Pro Ala Leu Arg Ser Ile Gly Leu Lys Cys
            420                 425                 430

Leu Glu His Leu Phe Phe Lys Leu Ile Gly Asp Thr Pro Ile Asp
            435                 440                 445

Thr Phe Leu Met Glu Met Leu Glu Ala Pro His Gln Met Thr
450                 455                 460

(2) INFORMATION FOR SEQ ID NO:7:

(i) SEQUENCE CHARACTERISTICS:
        (A) LENGTH: 525 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:7:

Met Ser Trp Ala Ala Arg Pro Pro Phe Leu Pro Gln Arg His Ala Glu
1               5                   10                  15

Gly Ser Val Gly Arg Trp Gly Ala Lys Glu Cys Ile Val Gly Ser Ala
            20                  25                  30

Thr Ala Leu Ala Gly Ser Arg Ser Gly Gly Gly Gly Gly Gly Arg
            35                  40                  45

Arg Arg Thr Thr Asn Pro Gly Ala Gly Ala Arg Gly Trp Thr Gly Arg
50                  55                  60

Asp Gly Arg His Gly Arg Asp Ser Arg Ser Pro Asp Ser Ser Ser Pro
65                  70                  75                  80

Asn Pro Leu Pro Gln Gly Val Pro Pro Ser Pro Pro Gly Pro Pro
            85                  90                  95

Leu Pro Pro Ser Thr Ala Pro Thr Leu Gly Gly Ser Gly Ala Pro Pro
            100                 105                 110

Pro Pro Pro Met Pro Pro Pro Leu Gly Ser Pro Phe Pro Val Ile
            115                 120                 125

Ser Ser Ser Met Gly Ser Pro Gly Leu Pro Pro Ala Pro Pro Gly
            130                 135                 140

Phe Ser Gly Pro Val Ser Ser Pro Gln Ile Asn Ser Thr Val Ser Leu
145                 150                 155                 160

Pro Gly Gly Gly Ser Gly Pro Pro Glu Asp Val Lys Pro Pro Val Leu
            165                 170                 175

Gly Val Arg Gly Leu His Cys Pro Pro Pro Gly Gly Pro Gly Ala
            180                 185                 190

Gly Lys Arg Leu Cys Ala Ile Cys Gly Asp Arg Ser Ser Gly Lys His
            195                 200                 205

Tyr Gly Val Tyr Ser Cys Glu Gly Cys Lys Gly Phe Phe Lys Arg Thr
            210                 215                 220

Ile Arg Lys Asp Leu Thr Tyr Ser Cys Arg Asp Asn Lys Asp Cys Thr
225                 230                 235                 240

Val Asp Lys Arg Gln Arg Asn Arg Cys Gln Tyr Cys Arg Tyr Gln Lys
            245                 250                 255

Cys Leu Ala Thr Gly Met Lys Arg Glu Ala Val Gln Glu Glu Arg Gln
            260                 265                 270

Arg Gly Lys Asp Lys Asp Gly Asp Gly Glu Cys Ala Gly Gly Ala Pro
            275                 280                 285
```

-continued

```
Glu Glu Met Pro Val Asp Arg Ile Leu Glu Ala Glu Leu Ala Val Glu
    290                 295                 300

Gln Lys Ser Asp Gln Gly Val Glu Gly Pro Gly Gly Thr Gly Gly Ser
305                 310                 315                 320

Gly Ser Ser Pro Asn Asp Pro Val Thr Asn Ile Cys Gln Ala Ala Asp
                325                 330                 335

Lys Gln Leu Phe Thr Leu Val Glu Trp Ala Lys Arg Ile Pro His Phe
                340                 345                 350

Ser Ser Leu Pro Leu Asp Asp Gln Val Ile Leu Leu Arg Ala Gly Trp
                355                 360                 365

Asn Glu Leu Leu Ile Ala Ser Phe Ser His Arg Ser Ile Asp Val Arg
    370                 375                 380

Asp Gly Ile Leu Leu Ala Thr Gly Leu His Val His Arg Asn Ser Ala
385                 390                 395                 400

His Ser Ala Gly Val Gly Ala Ile Phe Asp Arg Val Leu Thr Glu Leu
                405                 410                 415

Val Ser Lys Met Arg Asp Met Arg Met Asp Lys Thr Glu Leu Gly Cys
                420                 425                 430

Leu Arg Ala Ile Ile Leu Phe Asn Pro Asp Ala Lys Gly Leu Ser Asn
    435                 440                 445

Pro Ser Glu Val Glu Val Leu Arg Glu Lys Val Tyr Ala Ser Leu Glu
    450                 455                 460

Thr Tyr Cys Lys Gln Lys Tyr Pro Glu Gln Gln Gly Arg Phe Ala Lys
465                 470                 475                 480

Leu Leu Leu Arg Leu Pro Ala Leu Arg Ser Ile Gly Leu Lys Cys Leu
                485                 490                 495

Glu His Leu Phe Phe Phe Lys Leu Ile Gly Asp Thr Pro Ile Asp Thr
                500                 505                 510

Phe Leu Met Glu Met Leu Glu Ala Pro His Gln Leu Ala
                515                 520                 525
```

(2) INFORMATION FOR SEQ ID NO:8:

(i) SEQUENCE CHARACTERISTICS:
        (A) LENGTH: 468 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:8:

```
Met Val Asp Thr Glu Ser Pro Leu Cys Pro Leu Ser Pro Leu Glu Ala
1               5                   10                  15

Gly Asp Leu Glu Ser Pro Leu Ser Glu Glu Phe Leu Gln Glu Met Gly
                20                  25                  30

Asn Ile Gln Glu Ile Ser Gln Ser Ile Gly Glu Asp Ser Ser Gly Ser
                35                  40                  45

Phe Gly Phe Thr Glu Tyr Gln Tyr Leu Gly Ser Cys Pro Gly Ser Asp
    50                  55                  60

Gly Ser Val Ile Thr Asp Thr Leu Ser Pro Ala Ser Ser Pro Ser Ser
65                  70                  75                  80

Val Thr Tyr Pro Val Val Pro Gly Ser Val Asp Glu Ser Pro Ser Gly
                85                  90                  95

Ala Leu Asn Ile Glu Cys Arg Ile Cys Gly Asp Lys Ala Ser Gly Tyr
                100                 105                 110
```

```
His Tyr Gly Val His Ala Cys Glu Gly Cys Lys Gly Phe Phe Arg Arg
            115                 120                 125

Thr Ile Arg Leu Lys Leu Val Tyr Asp Lys Cys Asp Arg Ser Cys Lys
        130                 135                 140

Ile Gln Lys Lys Asn Arg Asn Lys Cys Gln Tyr Cys Arg Phe His Lys
145                 150                 155                 160

Cys Leu Ser Val Gly Met Ser His Asn Ala Ile Arg Phe Gly Arg Met
                165                 170                 175

Pro Arg Ser Glu Lys Ala Lys Leu Lys Ala Glu Ile Leu Thr Cys Glu
                180                 185                 190

His Asp Ile Glu Asp Ser Glu Thr Ala Asp Leu Lys Ser Leu Ala Lys
            195                 200                 205

Arg Ile Tyr Glu Ala Tyr Leu Lys Asn Phe Asn Met Asn Lys Val Lys
        210                 215                 220

Ala Arg Val Ile Leu Ser Gly Lys Ala Ser Asn Asn Pro Pro Phe Val
225                 230                 235                 240

Ile His Asp Met Glu Thr Leu Cys Met Ala Glu Lys Thr Leu Val Ala
                245                 250                 255

Lys Leu Val Ala Asn Gly Ile Gln Asn Lys Glu Val Glu Val Arg Ile
                260                 265                 270

Phe His Cys Cys Gln Cys Thr Ser Val Glu Thr Val Thr Glu Leu Thr
            275                 280                 285

Glu Phe Ala Lys Ala Ile Pro Ala Phe Ala Asn Leu Asp Leu Asn Asp
290                 295                 300

Gln Val Thr Leu Leu Lys Tyr Gly Val Tyr Glu Ala Ile Phe Ala Met
305                 310                 315                 320

Leu Ser Ser Val Met Asn Lys Asp Gly Met Leu Val Ala Tyr Gly Asn
                325                 330                 335

Gly Phe Ile Thr Arg Glu Phe Leu Lys Ser Leu Arg Lys Pro Phe Cys
                340                 345                 350

Asp Ile Met Glu Pro Lys Phe Asp Phe Ala Met Lys Phe Asn Ala Leu
            355                 360                 365

Glu Leu Asp Asp Ser Asp Ile Ser Leu Phe Val Ala Ala Ile Ile Cys
        370                 375                 380

Cys Gly Asp Arg Pro Gly Leu Leu Asn Val Gly His Ile Glu Lys Met
385                 390                 395                 400

Gln Glu Gly Ile Val His Val Leu Arg Leu His Leu Gln Ser Asn His
                405                 410                 415

Pro Asp Asp Ile Phe Leu Phe Pro Lys Leu Leu Gln Lys Met Ala Asp
                420                 425                 430

Leu Arg Gln Leu Val Thr Glu His Ala Gln Leu Val Gln Ile Ile Lys
        435                 440                 445

Lys Thr Glu Ser Asp Ala Ala Leu His Pro Leu Leu Gln Glu Ile Tyr
450                 455                 460

Arg Asp Met Tyr
465

(2) INFORMATION FOR SEQ ID NO:9:

(i) SEQUENCE CHARACTERISTICS:
        (A) LENGTH: 441 amino acids
        (B) TYPE: amino acid
        (C) STRANDEDNESS:
        (D) TOPOLOGY: linear (ii) MOLECULE TYPE: protein
```

(xi) SEQUENCE DESCRIPTION: SEQ ID NO:9:

```
Met Glu Gln Pro Gln Glu Ala Pro Glu Val Arg Glu Glu Glu
 1               5                  10                  15

Lys Glu Glu Val Ala Glu Ala Glu Gly Ala Pro Glu Leu Asn Gly Gly
                 20                  25                  30

Pro Gln His Ala Leu Pro Ser Ser Tyr Thr Asp Leu Ser Arg Ser
             35                  40                  45

Ser Ser Pro Pro Ser Leu Leu Asp Gln Leu Gln Met Gly Cys Asp Gly
     50                  55                  60

Ala Ser Cys Gly Ser Leu Asn Met Glu Cys Arg Val Cys Gly Asp Lys
 65                  70                  75                  80

Ala Ser Gly Phe His Tyr Gly Val His Ala Cys Glu Gly Cys Lys Gly
                 85                  90                  95

Phe Phe Arg Arg Thr Ile Arg Met Lys Leu Glu Tyr Glu Lys Cys Glu
            100                 105                 110

Arg Ser Cys Lys Ile Gln Lys Lys Asn Arg Asn Lys Cys Gln Tyr Cys
            115                 120                 125

Arg Phe Gln Lys Cys Leu Ala Leu Gly Met Ser His Asn Ala Ile Arg
130                 135                 140

Phe Gly Arg Met Pro Glu Ala Glu Lys Arg Lys Leu Val Ala Gly Leu
145                 150                 155                 160

Thr Ala Asn Glu Gly Ser Gln Tyr Asn Pro Gln Val Ala Asp Leu Lys
            165                 170                 175

Ala Phe Ser Lys His Ile Tyr Asn Ala Tyr Leu Lys Asn Phe Asn Met
            180                 185                 190

Thr Lys Lys Lys Ala Arg Ser Ile Leu Thr Gly Lys Ala Ser His Thr
            195                 200                 205

Ala Pro Phe Val Ile His Asp Ile Glu Thr Leu Trp Gln Ala Glu Lys
            210                 215                 220

Gly Leu Val Trp Lys Gln Leu Val Asn Gly Leu Pro Pro Tyr Lys Glu
225                 230                 235                 240

Ile Ser Val His Val Phe Tyr Arg Cys Gln Cys Thr Thr Val Glu Thr
            245                 250                 255

Val Arg Glu Leu Thr Glu Phe Ala Lys Ser Ile Pro Ser Phe Ser Ser
            260                 265                 270

Leu Phe Leu Asn Asp Gln Val Thr Leu Leu Lys Tyr Gly Val His Glu
            275                 280                 285

Ala Ile Phe Ala Met Leu Ala Ser Ile Val Asn Lys Asp Gly Leu Leu
            290                 295                 300

Val Ala Asn Gly Ser Gly Phe Val Thr Arg Glu Phe Leu Arg Ser Leu
305                 310                 315                 320

Arg Lys Pro Phe Ser Asp Ile Ile Glu Pro Lys Phe Glu Phe Ala Val
            325                 330                 335

Lys Phe Asn Ala Leu Glu Leu Asp Asp Ser Asp Leu Ala Leu Phe Ile
            340                 345                 350

Ala Ala Ile Ile Leu Cys Gly Asp Arg Pro Gly Leu Met Asn Val Pro
            355                 360                 365

Arg Val Glu Ala Ile Gln Asp Thr Ile Leu Arg Ala Leu Glu Phe His
            370                 375                 380

Leu Gln Ala Asn His Pro Asp Ala Gln Tyr Leu Phe Pro Lys Leu Leu
385                 390                 395                 400

Gln Lys Met Ala Asp Leu Arg Gln Leu Val Thr Glu His Ala Gln Met
```

```
                    405                 410                 415
Met Gln Arg Ile Lys Lys Thr Glu Thr Glu Thr Ser Leu His Pro Leu
                420                 425                 430

Leu Gln Glu Ile Tyr Lys Asp Met Tyr
            435                 440
```

(2) INFORMATION FOR SEQ ID NO:10:

(i) SEQUENCE CHARACTERISTICS:
        (A) LENGTH: 475 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:10:

```
Met Val Asp Thr Glu Met Pro Phe Trp Pro Thr Asn Phe Gly Ile Ser
1               5                   10                  15

Ser Val Asp Leu Ser Met Met Asp Asp His Ser His Ser Phe Asp Ile
            20                  25                  30

Lys Pro Phe Thr Thr Val Asp Phe Ser Ser Ile Ser Ala Pro His Tyr
        35                  40                  45

Glu Asp Ile Pro Phe Thr Arg Ala Asp Pro Met Val Ala Asp Tyr Lys
    50                  55                  60

Tyr Asp Leu Lys Leu Gln Glu Tyr Gln Ser Ala Ile Lys Val Glu Pro
65                  70                  75                  80

Ala Ser Pro Pro Tyr Tyr Ser Glu Lys Ala Gln Leu Tyr Asn Arg Pro
                85                  90                  95

His Glu Glu Pro Ser Asn Ser Leu Met Ala Ile Glu Cys Arg Val Cys
            100                 105                 110

Gly Asp Lys Ala Ser Gly Phe His Tyr Gly Val His Ala Cys Glu Gly
        115                 120                 125

Cys Lys Gly Phe Phe Arg Arg Thr Ile Arg Leu Lys Leu Ile Tyr Asp
    130                 135                 140

Arg Cys Asp Leu Asn Cys Arg Ile His Lys Lys Ser Arg Asn Lys Cys
145                 150                 155                 160

Gln Tyr Cys Arg Phe Gln Lys Cys Leu Ala Val Gly Met Ser His Asn
                165                 170                 175

Ala Ile Arg Phe Gly Arg Met Pro Gln Ala Glu Lys Glu Lys Leu Leu
            180                 185                 190

Ala Glu Ile Ser Ser Asp Ile Asp Gln Leu Asn Pro Glu Ser Ala Asp
        195                 200                 205

Leu Arg Ala Leu Ala Lys His Leu Tyr Asp Ser Tyr Ile Lys Ser Phe
    210                 215                 220

Pro Leu Thr Lys Ala Lys Ala Arg Ala Ile Leu Thr Gly Lys Thr Thr
225                 230                 235                 240

Asp Lys Ser Pro Phe Val Ile Tyr Asp Met Asn Ser Leu Met Met Gly
                245                 250                 255

Glu Asp Lys Ile Lys Phe Lys His Ile Thr Pro Leu Gln Glu Gln Ser
            260                 265                 270

Lys Glu Val Ala Ile Arg Ile Phe Gln Gly Cys Gln Phe Arg Ser Val
        275                 280                 285

Glu Ala Val Gln Glu Ile Thr Glu Tyr Ala Lys Asn Ile Pro Gly Phe
    290                 295                 300

Ile Asn Leu Asp Leu Asn Asp Gln Val Thr Leu Leu Lys Tyr Gly Val
```

-continued

```
             305                 310                 315                 320
His Glu Ile Ile Tyr Thr Met Leu Ala Ser Leu Met Asn Lys Asp Gly
                 325                 330                 335

Val Leu Ile Ser Glu Gly Gln Gly Phe Met Thr Arg Glu Phe Leu Lys
                 340                 345                 350

Ser Leu Arg Lys Pro Phe Gly Asp Phe Met Glu Pro Lys Phe Glu Phe
                 355                 360                 365

Ala Val Lys Phe Asn Ala Leu Glu Leu Asp Asp Ser Asp Leu Ala Ile
                 370                 375                 380

Phe Ile Ala Val Ile Ile Leu Ser Gly Asp Arg Pro Gly Leu Leu Asn
385                  390                 395                 400

Val Lys Pro Ile Glu Asp Ile Gln Asp Asn Leu Leu Gln Ala Leu Glu
                 405                 410                 415

Leu Gln Leu Lys Leu Asn His Pro Glu Ser Ser Gln Leu Phe Ala Lys
                 420                 425                 430

Val Leu Gln Lys Met Thr Asp Leu Arg Gln Ile Val Thr Glu His Val
                 435                 440                 445

Gln Leu Leu His Val Ile Lys Lys Thr Glu Thr Asp Met Ser Leu His
                 450                 455                 460

Pro Leu Leu Gln Glu Ile Tyr Lys Asp Leu Tyr
465                  470                 475

(2) INFORMATION FOR SEQ ID NO:11:

(i) SEQUENCE CHARACTERISTICS:
           (A) LENGTH: 427 amino acids
           (B) TYPE: amino acid
           (C) STRANDEDNESS:
           (D) TOPOLOGY: linear (ii) MOLECULE TYPE: protein (xi) SEQUENCE DESCRIPTION: SEQ ID NO:11:

Met Glu Ala Met Ala Ala Ser Thr Ser Leu Pro Asp Pro Gly Asp Phe
1                5                  10                  15

Asp Arg Asn Val Pro Arg Ile Cys Gly Val Cys Gly Asp Arg Ala Thr
                 20                  25                  30

Gly Phe His Phe Asn Ala Met Thr Cys Glu Gly Cys Lys Gly Phe Phe
                 35                  40                  45

Arg Arg Ser Met Lys Arg Lys Ala Leu Phe Thr Cys Pro Phe Asn Gly
50                   55                  60

Asp Cys Arg Ile Thr Lys Asp Asn Arg Arg His Cys Gln Ala Cys Arg
65                   70                  75                  80

Leu Lys Arg Cys Val Asp Ile Gly Met Met Lys Glu Phe Ile Leu Thr
                 85                  90                  95

Asp Glu Glu Val Gln Arg Lys Arg Glu Met Ile Leu Lys Arg Lys Glu
                 100                 105                 110

Glu Glu Ala Leu Lys Asp Ser Leu Arg Pro Lys Leu Ser Glu Glu Gln
                 115                 120                 125

Gln Arg Ile Ile Ala Ile Leu Leu Asp Ala His His Lys Thr Tyr Asp
                 130                 135                 140

Pro Thr Tyr Ser Asp Phe Cys Gln Phe Arg Pro Pro Val Arg Val Asn
145                  150                 155                 160

Asp Gly Gly Gly Ser His Pro Ser Arg Pro Asn Ser Arg His Thr Pro
                 165                 170                 175

Ser Phe Ser Gly Asp Ser Ser Ser Ser Cys Ser Asp His Cys Ile Thr
```

```
                    180                 185                 190
Ser Ser Asp Met Met Asp Ser Ser Phe Ser Asn Leu Asp Leu Ser
                195                 200                 205
Glu Glu Asp Ser Asp Pro Ser Val Thr Leu Glu Leu Ser Gln Leu
    210                 215                 220
Ser Met Leu Pro His Leu Ala Asp Leu Val Ser Tyr Ser Ile Gln Lys
225                 230                 235                 240
Val Ile Gly Phe Ala Lys Met Ile Pro Gly Phe Arg Asp Leu Thr Ser
                245                 250                 255
Glu Asp Gln Ile Val Leu Leu Lys Ser Ser Ala Ile Glu Val Ile Met
        260                 265                 270
Leu Arg Ser Asn Glu Ser Phe Thr Met Asp Asp Met Ser Trp Thr Cys
            275                 280                 285
Gly Asn Gln Asp Tyr Lys Tyr Arg Val Ser Asp Val Thr Lys Ala Gly
        290                 295                 300
His Ser Leu Glu Leu Ile Glu Pro Leu Ile Lys Phe Gln Val Gly Leu
305                 310                 315                 320
Lys Lys Leu Asn Leu His Glu Glu His Val Leu Leu Met Ala Ile
                325                 330                 335
Cys Ile Val Ser Pro Asp Arg Pro Gly Val Gln Asp Ala Ala Leu Ile
                340                 345                 350
Glu Ala Ile Gln Asp Arg Leu Ser Asn Thr Leu Gln Thr Tyr Ile Arg
            355                 360                 365
Cys Arg His Pro Pro Gly Ser His Leu Leu Tyr Ala Lys Met Ile
    370                 375                 380
Gln Lys Leu Ala Asp Leu Arg Ser Leu Asn Glu Glu His Ser Lys Gln
385                 390                 395                 400
Tyr Arg Cys Leu Ser Phe Gln Pro Glu Cys Ser Met Lys Leu Thr Pro
                405                 410                 415
Leu Val Leu Glu Val Phe Gly Asn Glu Ile Ser
                420                 425

(2) INFORMATION FOR SEQ ID NO:12:

(i) SEQUENCE CHARACTERISTICS:
        (A) LENGTH: 595 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:12:

Met Thr Met Thr Leu His Thr Lys Ala Ser Gly Met Ala Leu Leu His
1               5                   10                  15
Gln Ile Gln Gly Asn Glu Leu Glu Pro Leu Asn Arg Pro Gln Leu Lys
                20                  25                  30
Ile Pro Leu Glu Arg Pro Leu Gly Glu Val Tyr Leu Asp Ser Ser Lys
            35                  40                  45
Pro Ala Val Tyr Asn Tyr Pro Glu Gly Ala Ala Tyr Glu Phe Asn Ala
    50                  55                  60
Ala Ala Ala Ala Asn Ala Gln Val Tyr Gly Gln Thr Gly Leu Pro Tyr
65                  70                  75                  80
Gly Pro Gly Ser Glu Ala Ala Ala Phe Gly Ser Asn Gly Leu Gly Gly
                85                  90                  95
Phe Pro Pro Leu Asn Ser Val Ser Pro Ser Pro Leu Met Leu Leu His
```

-continued

```
                100                 105                 110
Pro Pro Pro Gln Leu Ser Pro Phe Leu Gln Pro His Gly Gln Gln Val
        115                 120                 125
Pro Tyr Tyr Leu Glu Asn Glu Pro Ser Gly Tyr Thr Val Arg Glu Ala
130                 135                 140
Gly Pro Pro Ala Phe Tyr Arg Pro Asn Ser Asp Asn Arg Arg Gln Gly
145                 150                 155                 160
Gly Arg Glu Arg Leu Ala Ser Thr Asn Asp Lys Gly Ser Met Ala Met
                165                 170                 175
Glu Ser Ala Lys Glu Thr Arg Tyr Cys Ala Val Cys Asn Asp Tyr Ala
            180                 185                 190
Ser Gly Tyr His Tyr Gly Val Trp Ser Cys Glu Gly Cys Lys Ala Phe
        195                 200                 205
Phe Lys Arg Ser Ile Gln Gly His Asn Asp Tyr Met Cys Pro Ala Thr
    210                 215                 220
Asn Gln Cys Thr Ile Asp Lys Asn Arg Arg Lys Ser Cys Gln Ala Cys
225                 230                 235                 240
Arg Leu Arg Lys Cys Tyr Glu Val Gly Met Met Lys Gly Gly Ile Arg
                245                 250                 255
Lys Asp Arg Arg Gly Gly Arg Met Leu Lys His Lys Arg Gln Arg Asp
            260                 265                 270
Asp Gly Glu Gly Arg Gly Glu Val Gly Ser Ala Gly Asp Met Arg Ala
        275                 280                 285
Ala Asn Leu Trp Pro Ser Pro Leu Met Ile Lys Arg Ser Lys Lys Asn
    290                 295                 300
Ser Leu Ala Leu Ser Leu Thr Ala Asp Gln Met Val Ser Ala Leu Leu
305                 310                 315                 320
Asp Ala Glu Pro Pro Ile Leu Tyr Ser Glu Tyr Asp Pro Thr Arg Pro
                325                 330                 335
Phe Ser Glu Ala Ser Met Met Gly Leu Leu Thr Asn Leu Ala Asp Arg
            340                 345                 350
Glu Leu Val His Met Ile Asn Trp Ala Lys Arg Val Pro Gly Phe Val
        355                 360                 365
Asp Leu Thr Leu His Asp Gln Val His Leu Leu Glu Cys Ala Trp Leu
    370                 375                 380
Glu Ile Leu Met Ile Gly Leu Val Trp Arg Ser Met Glu His Pro Gly
385                 390                 395                 400
Lys Leu Leu Phe Ala Pro Asn Leu Leu Leu Asp Arg Asn Gln Gly Lys
                405                 410                 415
Cys Val Glu Gly Met Val Glu Ile Phe Asp Met Leu Leu Ala Thr Ser
            420                 425                 430
Ser Arg Phe Arg Met Met Asn Leu Gln Gly Glu Glu Phe Val Cys Leu
        435                 440                 445
Lys Ser Ile Ile Leu Leu Asn Ser Gly Val Tyr Thr Phe Leu Ser Ser
    450                 455                 460
Thr Leu Lys Ser Leu Glu Glu Lys Asp His Ile His Arg Val Leu Asp
465                 470                 475                 480
Lys Ile Thr Asp Thr Leu Ile His Leu Met Ala Lys Ala Gly Leu Thr
                485                 490                 495
Leu Gln Gln Gln His Gln Arg Leu Ala Gln Leu Leu Leu Ile Leu Ser
            500                 505                 510
His Ile Arg His Met Ser Asn Lys Gly Met Glu His Leu Tyr Ser Met
        515                 520                 525
```

```
Lys Cys Lys Asn Val Val Pro Leu Tyr Asp Leu Leu Leu Glu Met Leu
    530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
                580                 585                 590

Ala Thr Val
        595

(2) INFORMATION FOR SEQ ID NO:13:

(i) SEQUENCE CHARACTERISTICS:
        (A) LENGTH: 777 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:13:

Met Asp Ser Lys Glu Ser Leu Thr Pro Gly Arg Glu Glu Asn Pro Ser
1               5                   10                  15

Ser Val Leu Ala Gln Glu Arg Gly Asp Val Met Asp Phe Tyr Lys Thr
                20                  25                  30

Leu Arg Gly Gly Ala Thr Val Lys Val Ser Ala Ser Ser Pro Ser Leu
            35                  40                  45

Ala Val Ala Ser Gln Ser Asp Ser Lys Gln Arg Arg Leu Leu Val Asp
        50                  55                  60

Phe Pro Lys Gly Ser Val Ser Asn Ala Gln Gln Pro Asp Leu Ser Lys
65                  70                  75                  80

Ala Val Ser Leu Ser Met Gly Leu Tyr Met Gly Glu Thr Glu Thr Lys
                85                  90                  95

Val Met Gly Asn Asp Leu Gly Phe Pro Gln Gln Gly Gln Ile Ser Leu
                100                 105                 110

Ser Ser Gly Glu Thr Asp Leu Lys Leu Leu Glu Glu Ser Ile Ala Asn
            115                 120                 125

Leu Asn Arg Ser Thr Ser Val Pro Glu Asn Pro Lys Ser Ser Ala Ser
130                 135                 140

Thr Ala Val Ser Ala Ala Pro Thr Glu Lys Glu Phe Pro Lys Thr His
145                 150                 155                 160

Ser Asp Val Ser Ser Glu Gln Gln His Leu Lys Gly Gln Thr Gly Thr
                165                 170                 175

Asn Gly Gly Asn Val Lys Leu Tyr Thr Thr Asp Gln Ser Thr Phe Asp
                180                 185                 190

Ile Leu Gln Asp Leu Glu Phe Ser Ser Gly Ser Pro Gly Lys Glu Thr
            195                 200                 205

Asn Glu Ser Pro Trp Arg Ser Asp Leu Leu Ile Asp Glu Asn Cys Leu
        210                 215                 220

Leu Ser Pro Leu Ala Gly Glu Asp Asp Ser Phe Leu Leu Glu Gly Asn
225                 230                 235                 240

Ser Asn Glu Asp Cys Lys Pro Leu Ile Leu Pro Asp Thr Lys Pro Lys
                245                 250                 255

Ile Lys Asp Asn Gly Asp Leu Val Leu Ser Ser Pro Ser Asn Val Thr
                260                 265                 270
```

-continued

```
Leu Pro Gln Val Lys Thr Glu Lys Glu Asp Phe Ile Glu Leu Cys Thr
        275                 280                 285
Pro Gly Val Ile Lys Gln Glu Lys Leu Gly Thr Val Tyr Cys Gln Ala
        290                 295                 300
Ser Phe Pro Gly Ala Asn Ile Ile Gly Asn Lys Met Ser Ala Ile Ser
305                 310                 315                 320
Val His Gly Val Ser Thr Ser Gly Gly Gln Met Tyr His Tyr Asp Met
                325                 330                 335
Asn Thr Ala Ser Leu Ser Gln Gln Gln Asp Gln Lys Pro Ile Phe Asn
            340                 345                 350
Val Ile Pro Pro Ile Pro Val Gly Ser Glu Asn Trp Asn Arg Cys Gln
            355                 360                 365
Gly Ser Gly Asp Asp Asn Leu Thr Ser Leu Gly Thr Leu Asn Phe Pro
        370                 375                 380
Gly Arg Thr Val Phe Ser Asn Gly Tyr Ser Ser Pro Ser Met Arg Pro
385                 390                 395                 400
Asp Val Ser Ser Pro Ser Ser Ser Thr Ala Thr Thr Gly Pro
                405                 410                 415
Pro Pro Lys Leu Cys Leu Val Cys Ser Asp Glu Ala Ser Gly Cys His
            420                 425                 430
Tyr Gly Val Leu Thr Cys Gly Ser Cys Lys Val Phe Phe Lys Arg Ala
        435                 440                 445
Val Glu Gly Gln His Asn Tyr Leu Cys Ala Gly Arg Asn Asp Cys Ile
        450                 455                 460
Ile Asp Lys Ile Arg Arg Lys Asn Cys Pro Ala Cys Arg Tyr Arg Lys
465                 470                 475                 480
Cys Leu Gln Ala Gly Met Asn Leu Glu Ala Arg Lys Thr Lys Lys Lys
                485                 490                 495
Ile Lys Gly Ile Gln Gln Ala Thr Thr Gly Val Ser Gln Glu Thr Ser
            500                 505                 510
Glu Asn Pro Gly Asn Lys Thr Ile Val Pro Ala Thr Leu Pro Gln Leu
            515                 520                 525
Thr Pro Thr Leu Val Ser Leu Leu Glu Val Ile Glu Pro Glu Val Leu
        530                 535                 540
Tyr Ala Gly Tyr Asp Ser Ser Val Pro Asp Ser Thr Trp Arg Ile Met
545                 550                 555                 560
Thr Thr Leu Asn Met Leu Gly Gly Arg Gln Val Ile Ala Ala Val Lys
                565                 570                 575
Trp Ala Lys Ala Ile Pro Gly Phe Arg Asn Leu His Leu Asp Asp Gln
            580                 585                 590
Met Thr Leu Leu Gln Tyr Ser Trp Met Phe Leu Met Ala Phe Ala Leu
            595                 600                 605
Gly Trp Arg Ser Tyr Arg Gln Ser Ser Ala Asn Leu Leu Cys Phe Ala
        610                 615                 620
Pro Asp Leu Ile Ile Asn Glu Gln Arg Met Thr Leu Pro Cys Met Tyr
625                 630                 635                 640
Asp Gln Cys Lys His Met Leu Tyr Val Ser Ser Glu Leu His Arg Leu
                645                 650                 655
Gln Val Ser Tyr Glu Glu Tyr Leu Cys Met Lys Thr Leu Leu Leu Leu
            660                 665                 670
Ser Ser Val Pro Lys Asp Gly Leu Lys Ser Gln Glu Leu Phe Asp Glu
            675                 680                 685
```

```
Ile Arg Met Thr Tyr Ile Lys Glu Leu Gly Lys Ala Ile Val Lys Arg
    690                 695                 700

Glu Gly Asn Ser Ser Gln Asn Trp Gln Arg Phe Tyr Gln Leu Thr Lys
705                 710                 715                 720

Leu Leu Asp Ser Met His Glu Val Val Glu Asn Leu Leu Asn Tyr Cys
                725                 730                 735

Phe Gln Thr Phe Leu Asp Lys Thr Met Ser Ile Glu Phe Pro Glu Met
            740                 745                 750

Leu Ala Glu Ile Ile Thr Asn Gln Ile Pro Lys Tyr Ser Asn Gly Asn
        755                 760                 765

Ile Lys Lys Leu Leu Phe His Gln Lys
770                 775

(2) INFORMATION FOR SEQ ID NO:14:

(i) SEQUENCE CHARACTERISTICS:
        (A) LENGTH: 933 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:14:

Met Thr Glu Leu Lys Ala Lys Gly Pro Arg Ala Pro His Val Ala Gly
1               5                   10                  15

Gly Pro Pro Ser Pro Glu Val Gly Ser Pro Leu Leu Cys Arg Pro Ala
                20                  25                  30

Ala Gly Pro Phe Pro Gly Ser Gln Thr Ser Asp Thr Leu Pro Glu Val
            35                  40                  45

Ser Ala Ile Pro Ile Ser Leu Asp Gly Leu Leu Phe Pro Arg Pro Cys
50                  55                  60

Gln Gly Gln Asp Pro Ser Asp Glu Lys Thr Gln Asp Gln Gln Ser Leu
65                  70                  75                  80

Ser Asp Val Glu Gly Ala Tyr Ser Arg Ala Glu Ala Thr Arg Gly Ala
                85                  90                  95

Gly Gly Ser Ser Ser Ser Pro Pro Glu Lys Asp Ser Gly Leu Leu Asp
            100                 105                 110

Ser Val Leu Asp Thr Leu Leu Ala Pro Ser Gly Pro Gly Gln Ser Gln
        115                 120                 125

Pro Ser Pro Pro Ala Cys Glu Val Thr Ser Ser Trp Cys Leu Phe Gly
130                 135                 140

Pro Glu Leu Pro Glu Asp Pro Pro Ala Ala Pro Ala Thr Gln Arg Val
145                 150                 155                 160

Leu Ser Pro Leu Met Ser Arg Ser Gly Cys Lys Val Gly Asp Ser Ser
                165                 170                 175

Gly Thr Ala Ala Ala His Lys Val Leu Pro Arg Gly Leu Ser Pro Ala
            180                 185                 190

Arg Gln Leu Leu Leu Pro Ala Ser Glu Ser Pro His Trp Ser Gly Ala
        195                 200                 205

Pro Val Lys Pro Ser Pro Gln Ala Ala Ala Val Glu Val Glu Glu Glu
210                 215                 220

Asp Ser Ser Glu Ser Glu Glu Ser Ala Gly Pro Leu Leu Lys Gly Lys
225                 230                 235                 240

Pro Arg Ala Leu Gly Gly Ala Ala Ala Gly Gly Gly Ala Ala Ala Cys
                245                 250                 255
```

-continued

```
Pro Pro Gly Ala Ala Gly Gly Val Ala Leu Val Pro Lys Glu Asp
        260                 265                 270

Ser Arg Phe Ser Ala Pro Arg Val Ala Leu Val Glu Gln Asp Ala Pro
        275                 280                 285

Met Ala Pro Gly Arg Ser Pro Leu Ala Thr Thr Val Met Asp Phe Ile
290                 295                 300

His Val Pro Ile Leu Pro Leu Asn His Ala Leu Leu Ala Ala Arg Thr
305                 310                 315                 320

Arg Gln Leu Leu Glu Asp Glu Ser Tyr Asp Gly Gly Ala Gly Ala Ala
                325                 330                 335

Ser Ala Phe Ala Pro Pro Arg Thr Ser Pro Cys Ala Ser Ser Thr Pro
                340                 345                 350

Val Ala Val Gly Asp Phe Pro Asp Cys Ala Tyr Pro Pro Asp Ala Glu
                355                 360                 365

Pro Lys Asp Asp Ala Tyr Pro Leu Tyr Ser Asp Phe Gln Pro Pro Ala
        370                 375                 380

Leu Lys Ile Lys Glu Glu Glu Gly Ala Glu Ala Ser Ala Arg Ser
385                 390                 395                 400

Pro Arg Ser Tyr Leu Val Ala Gly Ala Asn Pro Ala Ala Phe Pro Asp
                405                 410                 415

Phe Pro Leu Gly Pro Pro Pro Leu Pro Pro Arg Ala Thr Pro Ser
                420                 425                 430

Arg Pro Gly Glu Ala Ala Val Thr Ala Ala Pro Ala Ser Ala Ser Val
        435                 440                 445

Ser Ser Ala Ser Ser Ser Gly Ser Thr Leu Glu Cys Ile Leu Tyr Lys
450                 455                 460

Ala Glu Gly Ala Pro Pro Gln Gln Gly Pro Phe Ala Pro Pro Pro Cys
465                 470                 475                 480

Lys Ala Pro Gly Ala Ser Gly Cys Leu Leu Pro Arg Asp Gly Leu Pro
                485                 490                 495

Ser Thr Ser Ala Ser Ala Ala Ala Gly Ala Ala Pro Ala Leu Tyr
                500                 505                 510

Pro Ala Leu Gly Leu Asn Gly Leu Pro Gln Leu Gly Tyr Gln Ala Ala
        515                 520                 525

Val Leu Lys Glu Gly Leu Pro Gln Val Tyr Pro Pro Tyr Leu Asn Tyr
        530                 535                 540

Leu Arg Pro Asp Ser Glu Ala Ser Gln Ser Pro Gln Tyr Ser Phe Glu
545                 550                 555                 560

Ser Leu Pro Gln Lys Ile Cys Leu Ile Cys Gly Asp Glu Ala Ser Gly
                565                 570                 575

Cys His Tyr Gly Val Leu Thr Cys Gly Ser Cys Lys Val Phe Phe Lys
                580                 585                 590

Arg Ala Met Glu Gly Gln His Asn Tyr Leu Cys Ala Gly Arg Asn Asp
        595                 600                 605

Cys Ile Val Asp Lys Ile Arg Arg Lys Asn Cys Pro Ala Cys Arg Leu
610                 615                 620

Arg Lys Cys Cys Gln Ala Gly Met Val Leu Gly Gly Arg Lys Phe Lys
625                 630                 635                 640

Lys Phe Asn Lys Val Arg Val Val Arg Ala Leu Asp Ala Val Ala Leu
                645                 650                 655

Pro Gln Pro Leu Gly Val Pro Asn Glu Ser Gln Ala Leu Ser Gln Arg
        660                 665                 670

Phe Thr Phe Ser Pro Gly Gln Asp Ile Gln Leu Ile Pro Pro Leu Ile
```

-continued

```
                675                 680                 685
Asn Leu Leu Met Ser Ile Glu Pro Asp Val Ile Tyr Ala Gly His Asp
            690                 695                 700
Asn Thr Lys Pro Asp Thr Ser Ser Leu Leu Thr Ser Leu Asn Gln
705                 710                 715                 720
Leu Gly Glu Arg Gln Leu Leu Ser Val Val Lys Trp Ser Lys Ser Leu
                725                 730                 735
Pro Gly Phe Arg Asn Leu His Ile Asp Asp Gln Ile Thr Leu Ile Gln
            740                 745                 750
Tyr Ser Trp Met Ser Leu Met Val Phe Gly Leu Gly Trp Arg Ser Tyr
                755                 760                 765
Lys His Val Ser Gly Gln Met Leu Tyr Phe Ala Pro Asp Leu Ile Leu
770                 775                 780
Asn Glu Gln Arg Met Lys Glu Ser Ser Phe Tyr Ser Leu Cys Leu Thr
785                 790                 795                 800
Met Trp Gln Ile Pro Gln Glu Phe Val Lys Leu Gln Val Ser Gln Glu
                805                 810                 815
Glu Phe Leu Cys Met Lys Val Leu Leu Leu Leu Asn Thr Ile Pro Leu
                820                 825                 830
Glu Gly Leu Arg Ser Gln Thr Gln Phe Glu Glu Met Arg Ser Ser Tyr
                835                 840                 845
Ile Arg Glu Leu Ile Lys Ala Ile Gly Leu Arg Gln Lys Gly Val Val
850                 855                 860
Ser Ser Ser Gln Arg Phe Tyr Gln Leu Thr Lys Leu Leu Asp Asn Leu
865                 870                 875                 880
His Asp Leu Val Lys Gln Leu His Leu Tyr Cys Leu Asn Thr Phe Ile
                885                 890                 895
Gln Ser Arg Ala Leu Ser Val Glu Phe Pro Glu Met Met Ser Glu Val
                900                 905                 910
Ile Ala Ala Gln Leu Pro Lys Ile Leu Ala Gly Met Val Lys Pro Leu
                915                 920                 925
Leu Phe His Lys Lys
            930

(2) INFORMATION FOR SEQ ID NO:15:

(i) SEQUENCE CHARACTERISTICS:
        (A) LENGTH: 984 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:15:

Met Glu Thr Lys Gly Tyr His Ser Leu Pro Glu Gly Leu Asp Met Glu
1               5                   10                  15
Arg Arg Trp Gly Gln Val Ser Gln Ala Val Glu Arg Ser Ser Leu Gly
                20                  25                  30
Pro Thr Glu Arg Thr Asp Glu Asn Asn Tyr Met Glu Ile Val Asn Val
            35                  40                  45
Ser Cys Val Ser Gly Ala Ile Pro Asn Asn Ser Thr Gln Gly Ser Ser
        50                  55                  60
Lys Glu Lys Gln Glu Leu Leu Pro Cys Leu Gln Gln Asp Asn Asn Arg
65                  70                  75                  80
Pro Gly Ile Leu Thr Ser Asp Ile Lys Thr Glu Leu Glu Ser Lys Glu
```

-continued

```
                85                  90                  95
Leu Ser Ala Thr Val Ala Glu Ser Met Gly Leu Tyr Met Asp Ser Val
                100                 105                 110
Arg Asp Ala Asp Tyr Ser Tyr Glu Gln Gln Asn Gln Gln Gly Ser Met
                115                 120                 125
Ser Pro Ala Lys Ile Tyr Gln Asn Val Glu Gln Leu Val Lys Phe Tyr
                130                 135                 140
Lys Gly Asn Gly His Arg Pro Ser Thr Leu Ser Cys Val Asn Thr Pro
145                 150                 155                 160
Leu Arg Ser Phe Met Ser Asp Ser Gly Ser Val Asn Gly Gly Val
                165                 170                 175
Met Arg Ala Ile Val Lys Ser Pro Ile Met Cys His Glu Lys Ser Pro
                180                 185                 190
Ser Val Cys Ser Pro Leu Asn Met Thr Ser Ser Val Cys Ser Pro Ala
                195                 200                 205
Gly Ile Asn Ser Val Ser Ser Thr Ala Ser Phe Gly Ser Phe Pro
                210                 215                 220
Val His Ser Pro Ile Thr Gln Gly Thr Pro Leu Thr Cys Ser Pro Asn
225                 230                 235                 240
Ala Glu Asn Arg Gly Ser Arg Ser His Ser Pro Ala His Ala Ser Asn
                245                 250                 255
Val Gly Ser Pro Leu Ser Ser Pro Leu Ser Ser Met Lys Ser Ser Ile
                260                 265                 270
Ser Ser Pro Pro Ser His Cys Ser Val Lys Ser Pro Val Ser Ser Pro
                275                 280                 285
Asn Asn Val Thr Leu Arg Ser Ser Val Ser Ser Pro Ala Asn Ile Asn
                290                 295                 300
Asn Ser Arg Cys Ser Val Ser Ser Pro Ser Asn Thr Asn Asn Arg Ser
305                 310                 315                 320
Thr Leu Ser Ser Pro Ala Ala Ser Thr Val Gly Ser Ile Cys Ser Pro
                325                 330                 335
Val Asn Asn Ala Phe Ser Tyr Thr Ala Ser Gly Thr Ser Ala Gly Ser
                340                 345                 350
Ser Thr Leu Arg Asp Val Val Pro Ser Pro Asp Thr Gln Glu Lys Gly
                355                 360                 365
Ala Gln Glu Val Pro Phe Pro Lys Thr Glu Glu Val Glu Ser Ala Ile
                370                 375                 380
Ser Asn Gly Val Thr Gly Gln Leu Asn Ile Val Gln Tyr Ile Lys Pro
385                 390                 395                 400
Glu Pro Asp Gly Ala Phe Ser Ser Ser Cys Leu Gly Gly Asn Ser Lys
                405                 410                 415
Ile Asn Ser Asp Ser Ser Phe Ser Val Pro Ile Lys Gln Glu Ser Thr
                420                 425                 430
Lys His Ser Cys Ser Gly Thr Ser Phe Lys Gly Asn Pro Thr Val Asn
                435                 440                 445
Pro Phe Pro Phe Met Asp Gly Ser Tyr Phe Ser Phe Met Asp Asp Lys
                450                 455                 460
Asp Tyr Tyr Ser Leu Ser Gly Ile Leu Gly Pro Pro Val Pro Gly Phe
465                 470                 475                 480
Asp Gly Asn Cys Glu Gly Ser Gly Phe Pro Val Gly Ile Lys Gln Glu
                485                 490                 495
Pro Asp Asp Gly Ser Tyr Tyr Pro Glu Ala Ser Ile Pro Ser Ser Ala
                500                 505                 510
```

```
Ile Val Gly Val Asn Ser Gly Gly Gln Ser Phe His Tyr Arg Ile Gly
    515                 520                 525

Ala Gln Gly Thr Ile Ser Leu Ser Arg Ser Ala Arg Asp Gln Ser Phe
    530                 535                 540

Gln His Leu Ser Ser Phe Pro Pro Val Asn Thr Leu Val Glu Ser Trp
545                 550                 555                 560

Lys Ser His Gly Asp Leu Ser Ser Arg Ser Asp Gly Tyr Pro Val
                565                 570                 575

Leu Glu Tyr Ile Pro Glu Asn Val Ser Ser Ser Thr Leu Arg Ser Val
            580                 585                 590

Ser Thr Gly Ser Ser Arg Pro Ser Lys Ile Cys Leu Val Cys Gly Asp
        595                 600                 605

Glu Ala Ser Gly Cys His Tyr Gly Val Val Thr Cys Gly Ser Cys Lys
    610                 615                 620

Val Phe Phe Lys Arg Ala Val Glu Gly Gln His Asn Tyr Leu Cys Ala
625                 630                 635                 640

Gly Arg Asn Asp Cys Ile Ile Asp Lys Ile Arg Arg Lys Asn Cys Pro
                645                 650                 655

Ala Cys Arg Leu Gln Lys Cys Leu Gln Ala Gly Met Asn Leu Gly Ala
            660                 665                 670

Arg Lys Ser Lys Lys Leu Gly Lys Leu Lys Gly Ile His Glu Glu Gln
        675                 680                 685

Pro Gln Gln Gln Gln Pro Pro Pro Pro Pro Pro Pro Gln Ser Pro
    690                 695                 700

Glu Glu Gly Thr Thr Tyr Ile Ala Pro Ala Lys Glu Pro Ser Val Asn
705                 710                 715                 720

Thr Ala Leu Val Pro Gln Leu Ser Thr Ile Ser Arg Ala Leu Thr Pro
                725                 730                 735

Ser Pro Val Met Val Leu Glu Asn Ile Glu Pro Glu Ile Val Tyr Ala
            740                 745                 750

Gly Tyr Asp Ser Ser Lys Pro Asp Thr Ala Glu Asn Leu Leu Ser Thr
        755                 760                 765

Leu Asn Arg Leu Ala Gly Lys Gln Met Ile Gln Val Val Lys Trp Ala
770                 775                 780

Lys Val Leu Pro Gly Phe Lys Asn Leu Pro Leu Glu Asp Gln Ile Thr
785                 790                 795                 800

Leu Ile Gln Tyr Ser Trp Met Cys Leu Ser Ser Phe Ala Leu Ser Trp
                805                 810                 815

Arg Ser Tyr Lys His Thr Asn Ser Gln Phe Leu Tyr Phe Ala Pro Asp
            820                 825                 830

Leu Val Phe Asn Glu Glu Lys Met His Gln Ser Ala Met Tyr Glu Leu
        835                 840                 845

Cys Gln Gly Met His Gln Ile Ser Leu Gln Phe Val Arg Leu Gln Leu
    850                 855                 860

Thr Phe Glu Glu Tyr Thr Ile Met Lys Val Leu Leu Leu Leu Ser Thr
865                 870                 875                 880

Ile Pro Lys Asp Gly Leu Lys Ser Gln Ala Ala Phe Glu Glu Met Arg
                885                 890                 895

Thr Asn Tyr Ile Lys Glu Leu Arg Lys Met Val Thr Lys Cys Pro Asn
            900                 905                 910

Asn Ser Gly Gln Ser Trp Gln Arg Phe Tyr Gln Leu Thr Lys Leu Leu
        915                 920                 925
```

-continued

```
Asp Ser Met His Asp Leu Val Ser Asp Leu Leu Glu Phe Cys Phe Tyr
    930             935             940
Thr Phe Arg Glu Ser His Ala Leu Lys Val Glu Phe Pro Ala Met Leu
945             950             955             960
Val Glu Ile Ile Ser Asp Gln Leu Pro Lys Val Glu Ser Gly Asn Ala
                965             970             975
Lys Pro Leu Tyr Phe His Arg Lys
            980
```

(2) INFORMATION FOR SEQ ID NO:16:

(i) SEQUENCE CHARACTERISTICS:
        (A) LENGTH: 452 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:16:

```
Gly Gly Gly Gly Gly Glu Ala Gly Ala Val Ala Pro Tyr Gly Tyr Thr
1               5                   10                  15
Arg Pro Pro Gln Gly Leu Ala Gly Gln Glu Ser Asp Phe Thr Ala Pro
                20                  25                  30
Asp Val Trp Tyr Pro Gly Gly Met Val Ser Arg Val Pro Tyr Pro Ser
            35                  40                  45
Pro Thr Cys Val Lys Ser Glu Met Gly Pro Trp Met Asp Ser Tyr Ser
        50                  55                  60
Gly Pro Tyr Gly Asp Met Arg Leu Glu Thr Ala Arg Asp His Val Leu
65                  70                  75                  80
Pro Ile Asp Tyr Tyr Phe Pro Pro Gln Lys Thr Cys Leu Ile Cys Gly
                85                  90                  95
Asp Lys Ala Ser Gly Cys His Tyr Gly Ala Leu Thr Cys Gly Ser Cys
            100                 105                 110
Lys Val Phe Phe Lys Arg Ala Ala Glu Gly Lys Gln Lys Tyr Leu Cys
        115                 120                 125
Ala Ser Arg Asn Asp Cys Thr Ile Asp Lys Phe Arg Arg Lys Asn Cys
130                 135                 140
Pro Ser Cys Arg Leu Arg Lys Cys Tyr Glu Ala Gly Met Thr Leu Gly
145                 150                 155                 160
Ala Arg Lys Leu Lys Lys Leu Gly Asn Leu Lys Leu Gln Glu Glu Gly
                165                 170                 175
Glu Ala Ser Ser Thr Thr Ser Pro Thr Glu Glu Thr Thr Gln Lys Leu
            180                 185                 190
Thr Val Ser His Ile Glu Gly Tyr Glu Cys Gln Pro Ile Phe Leu Asn
        195                 200                 205
Val Leu Glu Ala Ile Glu Pro Gly Val Val Cys Ala Gly His Asp Asn
210                 215                 220
Asn Gln Pro Asp Ser Phe Ala Ala Leu Leu Ser Ser Leu Asn Glu Leu
225                 230                 235                 240
Gly Glu Arg Gln Leu Val His Val Val Lys Trp Ala Lys Ala Leu Pro
                245                 250                 255
Gly Phe Arg Asn Leu His Val Asp Asp Gln Met Ala Val Ile Gln Tyr
            260                 265                 270
Ser Trp Met Gly Leu Met Val Phe Ala Met Gly Trp Arg Ser Phe Thr
        275                 280                 285
```

```
-continued

Asn Val Asn Ser Arg Met Leu Tyr Phe Ala Pro Asp Leu Val Phe Asn
    290             295             300

Glu Tyr Arg Met His Lys Ser Arg Met Tyr Ser Gln Cys Val Arg Met
305             310             315                     320

Arg His Leu Ser Gln Glu Phe Gly Trp Leu Gln Ile Thr Pro Gln Glu
                325             330                 335

Phe Leu Cys Met Lys Ala Leu Leu Leu Phe Ser Ile Ile Pro Val Asp
            340             345                 350

Gly Leu Lys Asn Gln Lys Phe Phe Asp Glu Leu Arg Met Asn Tyr Ile
        355             360             365

Lys Glu Leu Asp Arg Ile Ile Ala Cys Lys Arg Lys Asn Pro Thr Ser
    370             375             380

Cys Ser Arg Arg Phe Tyr Gln Leu Thr Lys Leu Leu Asp Ser Val Gln
385             390             395                     400

Pro Ile Ala Arg Glu Leu His Gln Phe Thr Phe Asp Leu Leu Ile Lys
            405             410             415

Ser His Met Val Ser Val Asp Phe Pro Glu Met Met Ala Glu Ile Ile
            420             425             430

Ser Val Gln Val Pro Lys Ile Leu Ser Gly Lys Val Lys Pro Ile Tyr
        435             440             445

Phe His Thr Gln
    450
```